(12) United States Patent
Habib et al.

(10) Patent No.: US 12,221,720 B2
(45) Date of Patent: Feb. 11, 2025

(54) METHODS FOR DETERMINING SPATIAL AND TEMPORAL GENE EXPRESSION DYNAMICS DURING ADULT NEUROGENESIS IN SINGLE CELLS

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Naomi Habib, Cambridge, MA (US); Aviv Regev, Cambridge, MA (US); Eugene Drokhlyansky, Cambridge, MA (US); Anindita Basu, Cambridge, MA (US); Inbal Avraham-Davidi, Cambridge, MA (US); Orit Rozenblatt-Rosen, Cambridge, MA (US); David A. Weitz, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 963 days.

(21) Appl. No.: 16/763,681

(22) PCT Filed: Nov. 13, 2018

(86) PCT No.: PCT/US2018/060860
§ 371 (c)(1),
(2) Date: May 13, 2020

(87) PCT Pub. No.: WO2019/094984
PCT Pub. Date: May 16, 2019

(65) Prior Publication Data
US 2021/0395821 A1    Dec. 23, 2021

Related U.S. Application Data

(60) Provisional application No. 62/734,988, filed on Sep. 21, 2018, provisional application No. 62/723,425, (Continued)

(51) Int. Cl.
*C40B 50/06*    (2006.01)
*A61K 35/30*    (2015.01)
(Continued)

(52) U.S. Cl.
CPC .............. *C40B 30/06* (2013.01); *A61K 35/30* (2013.01); *C12N 5/0619* (2013.01);
(Continued)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |

(Continued)

FOREIGN PATENT DOCUMENTS

| | | |
|---|---|---|
| EP | 0 264 166 A1 | 4/1988 |
| EP | 2 047 910 A2 | 4/2009 |

(Continued)

OTHER PUBLICATIONS

Dennis et al. (Jan. 2016) Trends in Developmental Biology vol. 9 pp. 77 to 90.*

(Continued)

*Primary Examiner* — Christian C Boesen
(74) *Attorney, Agent, or Firm* — Foley & Lardner LLP; Sunit Talapatra

(57) ABSTRACT

Techniques Nuc-seq, Div-Seq, and Dronc-Seq are allow for unbiased analysis of any complex tissue. Nuc-Seq, a scalable single nucleus RNA-Seq method, can sensitively identify closely related cell types, including within the adult hippocampus. Div-seq combines Nuc-Seq with EdU-medi- (Continued)

ated labeling of proliferating cells, allowing tracking of transcriptional dynamics of newborn neurons in an adult neurogenic region in the hippocampus. Dronc-Seq uses a microfluidic device to co-encapsulate individual nuclei in reverse emulsion aqueous droplets in an oil medium together with one uniquely barcoded mRNA-capture bead.

13 Claims, 179 Drawing Sheets

Specification includes a Sequence Listing.

Related U.S. Application Data filed on Aug. 27, 2018, provisional application No. 62/585,529, filed on Nov. 13, 2017.

(51) Int. Cl.
| | | |
|---|---|---|
| *C12N 5/0793* | | (2010.01) |
| *C12N 5/0797* | | (2010.01) |
| *C12Q 1/6806* | | (2018.01) |
| *C12Q 1/6881* | | (2018.01) |
| *C40B 30/06* | | (2006.01) |
| *C12N 5/00* | | (2006.01) |

(52) U.S. Cl.
CPC ......... *C12N 5/0623* (2013.01); *C12Q 1/6806* (2013.01); *C12Q 1/6881* (2013.01); *C12N 5/0081* (2013.01); *C12Q 2600/158* (2013.01)

(56) References Cited

U.S. PATENT DOCUMENTS

| | | | |
|---|---|---|---|
| 4,873,316 | A | 10/1989 | Meade et al. |
| 5,543,158 | A | 8/1996 | Gref et al. |
| 5,843,657 | A | 12/1998 | Liotta et al. |
| 5,846,946 | A | 12/1998 | Huebner et al. |
| 5,855,913 | A | 1/1999 | Hanes et al. |
| 5,859,699 | A | 1/1999 | Baer et al. |
| 5,869,326 | A | 2/1999 | Hofmann |
| 5,985,085 | A | 11/1999 | Baer et al. |
| 5,985,309 | A | 11/1999 | Edwards et al. |
| 6,007,845 | A | 12/1999 | Domb et al. |
| 6,479,626 | B1 | 11/2002 | Kim et al. |
| 6,534,261 | B1 | 3/2003 | Cox et al. |
| 6,607,882 | B1 | 8/2003 | Cox et al. |
| 6,746,838 | B1 | 6/2004 | Choo et al. |
| 6,750,059 | B1 | 6/2004 | Blakesley et al. |
| 6,794,136 | B1 | 9/2004 | Eisenberg et al. |
| 6,824,978 | B1 | 11/2004 | Cox et al. |
| 6,866,997 | B1 | 3/2005 | Choo et al. |
| 6,903,185 | B2 | 6/2005 | Kim et al. |
| 6,933,113 | B2 | 8/2005 | Case et al. |
| 6,979,539 | B2 | 12/2005 | Cox et al. |
| 7,013,219 | B2 | 3/2006 | Case et al. |
| 7,030,215 | B2 | 4/2006 | Liu et al. |
| 7,041,481 | B2 | 5/2006 | Anderson et al. |
| 7,220,719 | B2 | 5/2007 | Case et al. |
| 7,241,573 | B2 | 7/2007 | Choo et al. |
| 7,241,574 | B2 | 7/2007 | Choo et al. |
| 7,259,015 | B2 | 8/2007 | Kingsman et al. |
| 7,303,910 | B2 | 12/2007 | Bebbington et al. |
| 7,351,585 | B2 | 4/2008 | Mitrophanous et al. |
| 7,585,849 | B2 | 9/2009 | Liu et al. |
| 7,595,376 | B2 | 9/2009 | Kim et al. |
| 7,708,949 | B2 | 5/2010 | Stone et al. |
| 7,776,321 | B2 | 8/2010 | Cascalho et al. |
| RE41,780 | E | 9/2010 | Anderson et al. |
| 8,021,867 | B2 | 9/2011 | Smith et al. |
| 8,119,361 | B2 | 2/2012 | Smith et al. |
| 8,119,381 | B2 | 2/2012 | Smith et al. |
| 8,124,369 | B2 | 2/2012 | Smith et al. |
| 8,129,134 | B2 | 3/2012 | Smith et al. |
| 8,133,697 | B2 | 3/2012 | Smith et al. |
| 8,163,514 | B2 | 4/2012 | Smith et al. |
| 8,404,658 | B2 | 3/2013 | Hajjar et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,454,972 | B2 | 6/2013 | Nabel et al. |
| 8,697,359 | B1 | 4/2014 | Zhang |
| 8,709,843 | B2 | 4/2014 | Shakuda |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,301,923 | B2 | 4/2016 | Baryza et al. |
| 9,790,490 | B2 | 10/2017 | Zhang et al. |
| 2002/0150626 | A1 | 10/2002 | Kohane et al. |
| 2004/0013648 | A1 | 1/2004 | Kingsman et al. |
| 2004/0171156 | A1 | 9/2004 | Hartley et al. |
| 2005/0123596 | A1 | 6/2005 | Kohane et al. |
| 2005/0172476 | A1 | 8/2005 | Stone et al. |
| 2006/0163385 | A1 | 7/2006 | Link et al. |
| 2006/0281180 | A1 | 12/2006 | Radcliffe et al. |
| 2007/0003442 | A1 | 1/2007 | Link et al. |
| 2007/0025970 | A1 | 2/2007 | Kingsman et al. |
| 2007/0054961 | A1 | 3/2007 | Maden et al. |
| 2007/0184489 | A1 | 8/2007 | Griffiths et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2009/0005254 | A1 | 1/2009 | Griffiths et al. |
| 2009/0007284 | A1 | 1/2009 | Radcliffe et al. |
| 2009/0017543 | A1 | 1/2009 | Wilkes et al. |
| 2009/0111106 | A1 | 4/2009 | Mitrophanous et al. |
| 2009/0131543 | A1 | 5/2009 | Weitz et al. |
| 2010/0002241 | A1 | 1/2010 | Hirose |
| 2010/0022414 | A1 | 1/2010 | Link et al. |
| 2010/0129793 | A1 | 5/2010 | Mirkin et al. |
| 2010/0137163 | A1 | 6/2010 | Link et al. |
| 2010/0172803 | A1 | 7/2010 | Stone et al. |
| 2010/0317109 | A1 | 12/2010 | Maden et al. |
| 2011/0027239 | A1 | 2/2011 | Paek |
| 2011/0117189 | A1 | 5/2011 | Mazzone et al. |
| 2011/0212179 | A1 | 9/2011 | Liu |
| 2011/0265198 | A1 | 10/2011 | Gregory et al. |
| 2011/0293571 | A1 | 12/2011 | Widdowson et al. |
| 2012/0003201 | A1 | 1/2012 | Nicholas et al. |
| 2012/0017290 | A1 | 1/2012 | Cui et al. |
| 2012/0088812 | A1 | 4/2012 | Song et al. |
| 2012/0219947 | A1 | 8/2012 | Yurkovetsky et al. |
| 2012/0276068 | A1 | 11/2012 | Sabaawy |
| 2012/0295960 | A1 | 11/2012 | Palfi et al. |
| 2013/0236946 | A1 | 9/2013 | Gouble |
| 2013/0302401 | A1 | 11/2013 | Ma et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0256595 | A1 | 9/2014 | Link et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |

(56) References Cited

U.S. PATENT DOCUMENTS

| | | |
|---|---|---|
| 2014/0287938 A1 | 9/2014 | Zhang et al. |
| 2014/0301951 A1 | 10/2014 | Liu et al. |
| 2014/0308304 A1 | 10/2014 | Manoharan et al. |
| 2014/0310830 A1 | 10/2014 | Zhang et al. |
| 2014/0328759 A1 | 11/2014 | Cullis et al. |
| 2014/0348900 A1 | 11/2014 | Zhu |
| 2015/0105538 A1 | 4/2015 | Chromy et al. |
| 2015/0184139 A1 | 7/2015 | Zhang et al. |
| 2015/0232883 A1 | 8/2015 | Dahlman et al. |
| 2015/0250725 A1 | 9/2015 | Bader et al. |
| 2016/0174546 A1 | 6/2016 | Berg et al. |
| 2016/0367686 A1 | 12/2016 | Anderson et al. |
| 2017/0079916 A1 | 3/2017 | Khan et al. |

FOREIGN PATENT DOCUMENTS

| | | |
|---|---|---|
| EP | 2 764 103 A2 | 8/2014 |
| EP | 2 771 468 A1 | 9/2014 |
| EP | 3 009 511 A2 | 4/2016 |
| WO | WO-97/49450 A1 | 12/1997 |
| WO | WO-98/52609 A1 | 11/1998 |
| WO | WO-01/89788 A2 | 11/2001 |
| WO | WO-2004/002627 A2 | 1/2004 |
| WO | WO-2004/091763 A2 | 10/2004 |
| WO | WO-2005/021151 A1 | 3/2005 |
| WO | WO-2006/040551 A2 | 4/2006 |
| WO | WO-2006/040554 A1 | 4/2006 |
| WO | WO-2006/096571 A2 | 9/2006 |
| WO | WO-2007/081385 A2 | 7/2007 |
| WO | WO-2007/089541 A2 | 8/2007 |
| WO | WO-2007/133710 A2 | 11/2007 |
| WO | WO-2008/063227 A2 | 5/2008 |
| WO | WO-2011/028929 A2 | 3/2011 |
| WO | 2011/046570 A1 | 4/2011 |
| WO | WO-2011/079176 A2 | 6/2011 |
| WO | WO-2014/018423 A2 | 1/2014 |
| WO | 2014/085802 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/118272 A1 | 8/2014 |
| WO | 2014/210353 A2 | 12/2014 |
| WO | WO-2014/204723 A1 | 12/2014 |
| WO | WO-2014/204724 A1 | 12/2014 |
| WO | WO-2014/204725 A1 | 12/2014 |
| WO | WO-2014/204726 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/089351 A1 | 6/2015 |
| WO | WO-2015/089354 A1 | 6/2015 |
| WO | WO-2015/089364 A1 | 6/2015 |
| WO | WO-2015/089419 A1 | 6/2015 |
| WO | WO-2015/089419 A2 | 6/2015 |
| WO | WO-2015/089427 A1 | 6/2015 |
| WO | WO-2015/089462 A1 | 6/2015 |
| WO | WO-2015/089465 A1 | 6/2015 |
| WO | WO-2015/089473 A1 | 6/2015 |
| WO | WO-2015/089486 A1 | 6/2015 |
| WO | 2016/040476 A1 | 3/2016 |
| WO | WO-2016/049258 A1 | 3/2016 |
| WO | WO-2016/094867 A1 | 6/2016 |
| WO | WO-2016/094872 A1 | 6/2016 |
| WO | WO-2016/094874 A1 | 6/2016 |
| WO | WO-2016/106244 A1 | 6/2016 |
| WO | 2016/161516 A1 | 10/2016 |
| WO | 2016/168584 A1 | 10/2016 |
| WO | 2017/164936 A1 | 9/2017 |
| WO | 2019/094984 A1 | 5/2019 |

OTHER PUBLICATIONS

Dulken, et al., "Single-Cell Transcriptomic Analysis Defines Heterogeneity and Transcriptional Dynamics in the Adult Neural Stem Cell Lineage", Cell Rep., vol. 18, Jan. 17, 2017, pp. 777-790.

Habib, et al., "Div-Seq: Single-Nucleus RNA-Seq Reveals Dynamics of Rare Adult Newborn Neurons", Science, vol. 353, Jul. 28, 2016, pp. 925-928.

Schnell, et al., "The Nuclear Receptor REV-ERB alpha Regulates Fabp7 and Modulates Adult Hippocampal Neurogenesis", PLoS One, vol. 9, Jun. 16, 2014, pp. 1-14.

The Broad Institute, Inc., et al., "Notification of Transmittal of the International Search Report and the Written Opinion of the International Searching Authority, or the Declaration", PCT/US2018/060860, Mar. 5, 2019, 19 pages.

Miller, et al., "Conserved Molecular Signatures of Neurogenesis in the Hippocampal Subgranular Zone of Rodents and Primates", Development, vol. 140, No. 22, Nov. 2013, 4633-4644.

Ming, et al., "Adult Neurogenesis in the Mammalian Brain: Significant Answers and Significant Questions", Neuron, vol. 70, No. 4, May 26, 2011, 687-702.

Moore, et al., "A Mechanism for the Segregation of Age in Mammalian Neural Stem Cells", Science, vol. 349, No. 6254, Sep. 18, 2015, 1334-1338.

Moran, P. A.P.., "Notes on Continuous Stochastic Phenomena", Biometrika, vol. 37, No. (1-2), Jun. 1950, 17-23.

Paix, et al., "High Efficiency, Homology-Directed Genome Editing in Caenorhabditis Elegans using CRISPR-Cas9 Ribonucleoprotein Complexes" Genetics, vol. 201, No. 1, Sep. 2015, 47-54.

Paul, et al., "The Nissl Stain: A Stain for Cell Bodies in Brain Sections", Cold Spring Harbor Protocols, vol. 3, Issue 9, Sep. 1, 2008, 2 pages.

Petryniak, et al., "Dlx1 and Dlx2 Control Neuronal Versus Oligodendroglial Cell Fate Acquisition in the Developing Forebrain", Neuron, vol. 55, No. 3, Aug. 2, 2007, 417-433.

Picelli, et al., "Full-Length RNA-Seq from Single Cells using Smart-seq2", Nature Protocols, vol. 9, No. 1, Jan. 2, 2014, 171-181.

Picelli, et al., "Smart-Seq2 for Sensitive Full-Length Transcriptome Profiling in Single Cells", Nature methods, vol. 10, Issue 11, Sep. 22, 2013, 5 pages.

Robinson, et al., "edger: A Bioconductor Package for Differential Expression Analysis of Digital Gene Expression Data", Bioinformatics, vol. 26, No. 1, Jan. 1, 2010, 139-140.

Robinson, et al., "Integrative Genomics Viewer", Nature Biotechnology, vol. 29, No. 1, Jan. 2011, 6 pages.

Zhao, et al., "Fluorescent Labeling of Newborn Dentate Granule Cells in Gad67-GFP Transgenic Mice: A Genetic Tool for the Study of Adult Neurogenesis," PLoS One, vol. 5, No. 9, Sep. 2, 2010, 12 pages.

Rodriguez, et al., "Clustering by Fast Search and find of Density Peaks", Science, vol. 344, Issue 6191, Jun. 27, 2014, 1492-1496.

Roques, et al., "Inhibiting the Breakdown of Endogenous Opioids and Cannabinoids to Alleviate Pain", Nature Reviews Drug Discovery, vol. 11, No. 4, Apr. 2012, 292-310.

Rosenberg, et al., "Scaling Single Cell Transcriptomics Through Split Pool Barcoding", Science, vol. 360, No. 6385, Feb. 2, 2017, 13 pages.

Rottkamp, et al., "Pbx3 is Required for Normal Locomotion and Dorsal Horn Development", Developmental Biology, vol. 314, No. 1, Feb. 1, 2008, 23-39.

Rousseeuw, et al., "Alternatives to the Median Absolute Deviation", Journal of the American Statistical Association, vol. 88, No. 424, Dec. 1993, 1273-1283.

Roweis, et al., "Nonlinear Dimensionality Reduction by Locally Linear Embedding", Science, vol. 290, No. 5500, Dec. 22, 2000, 2323-2326.

Ryan, et al., "Single-Cell Assays", Biomicrofluidics, vol. 5, No. 021501, Jun. 2011, 9 pages.

(56) References Cited

OTHER PUBLICATIONS

Satija, et al., "Spatial Reconstruction of Single-Cell Gene Expression Data", Nature Biotechnology, vol. 33, No. 5, May 2015, 495-502.
Zilionis, et al., "Single-cell Barcoding and Sequencing Using Droplet Microfluidics", Nature Protocols, vol. 12, No. 1, Jan. 2017, 44-73.
Schouten, et al., "New Neurons in Aging Brains: Molecular Control by Small Non-Coding RNAs", Frontiers in Neuroscience, vol. 6, Article 25, Feb. 2012, 13 pages.
Sengupta, et al., "Value Proposition Framework: Implications for Employer Branding", Decision, vol. 42, No. 3, Sep. 2015, 307-323.
Shalek, et al., "Single-Cell RNA-Seq Reveals Dynamic Paracrine Control of Cellular Variation", Nature, vol. 510, Jun. 19, 2014, 363-369.
Shalek, et al., "Single-Cell Transcriptomics Reveals Bimodality in Expression and Splicing in Immune Cells", Nature, vol. 498, No. 7453, Jun. 13, 2013, 236-240.
Shechter, et al., "New GABAergic Interneurons Supported by Myelin-specific T Cells are Formed in Intact Adult Spinal Cord", Stem Cells, vol. 25, No. 9, Sep. 2007, 2277-2282.
Shin, et al., Single-Cell RNA-Seq with Waterfall Reveals Molecular Cascades underlying Adult Neurogenesis, Cell Stem Cell, vol. 17, No. 3, Sep. 3, 2015, 360-372.
Simone, et al., "Laser-capture Microdissection: Opening the Microscopic Frontier to Molecular Analysis", Trends in Genetics, vol. 14, Issue 7, Jul. 1998, 272-276.
Steiner, et al., "Cell-type-specific Nuclei Purification from Whole Animals for Genome-wide Expression and Chromatin Profiling", Genome Research, vol. 22, No. 4, Apr. 2012, 766-777.
Strange, et al., "Functional Organization of the Hippocampal Longitudinal Axis", Nature Reviews Neuroscience, vol. 15, No. 10, Oct. 2014, 655-669.
Suarez-Quian, et al., "Laser Capture Microdissection of Single Cells from Complex Tissues", BioTechniques, vol. 26, No. 2, Feb. 1999, 328-335.
Subramanian, et al., "Gene Set Enrichment Analysis: A Knowledge-Based Approach for Interpreting Genome-Wide Expression Profiles", Proceedings of the National Academy of Sciences, vol. 102, No. 43, Oct. 2005, 15545-15550.
Swiech, et al., "In Vivo Interrogation of Gene Function in the Mammalian Brain Using CRISPR-Cas9", Nature Biotechnology, vol. 33, No. 1, Jan. 2015, 102-106.
Tasic, et al., "Adult Mouse Cortical Cell Taxonomy Revealed by Single Cell Transcriptomics", Nature Neuroscience, vol. 19, No. 2, Feb. 2016, 41 pages.
Telley, et al., "Sequential Transcriptional Waves Direct The Differentiation of Newborn Neurons in the Mouse Neocortex", Science, vol. 351, No. 6280, Mar. 25, 2016, 1443-1446.
Thomsen, et al., "Fixed Single-cell Transcriptomic Characterization of Human Radial Glial Diversity", Nature Methods, vol. 13, No. 1, Jan. 2016, 24 pages.
Trapnell, et al., "The Dynamics and Regulators of Cell Fate Decisions are Revealed by Pseudotemporal Ordering of Single Cells", Nature Biotechnology, vol. 32, No. 4, Apr. 2014, 381-386.
Trapnell, et al., "Tophat: Discovering Splice Junctions with RNA-Seq", Bioinformatics, vol. 25, No. 9, May 1, 2009, 1105-1111.
Trapnell, et al., "Transcript Assembly and Quantification by RNA-Seq Reveals Unannotated Transcripts and Isoform Switching During Cell Differentiation", Nature Biotechnology, vol. 28, No. 5, May 2010, 20 pages.
Trombetta, et al., "Preparation of Single-Cell RNA-Seq Libraries for Next Generation Sequencing", Current Protocols in Molecular Biology, vol. 107, Issue 1, Jul. 2014, 4.22.1-4.22.17.
Usoskin, et al., "Unbiased Classification of Sensory Neuron Types by Large-Scale Single-cell RNA Sequencing", Nature Neuroscience, vol. 18, No. 1, Jan. 2015, 145-153.
Van Der Maaten, et al., "Visualizing Data Using t-SNE", Journal of Machine Learning Research, vol. 9, Nov. 2008, 2579-2605.
Vander Maaten,"Laurens Accelerating t-SNE using Tree-Based Algorithms", Journal of Machine Learning Research, vol. 15, No. 1, Oct. 2014, 3221-3245.
Wang, et al., "One-Step Generation of Mice Carrying Mutations in Multiple Genes by CRISPR/Cas-Mediated Genome Engineering", Cell, vol. 153, No. 4, May 9, 2013, 13 pages.
Wu, et al., "Regulation of Dendritic Development by Neuron-specific Chromatin Remodeling Complexes", Neuron, vol. 56, No. 1, Oct. 4, 2007, 94-108.
Yianilos, et al., "Data Structures and Algorithms for Nearest Neighbor Search in General Metric Spaces", Proceedings of the fourth annual ACM-SIAM symposium on Discrete algorithms, vol. 93, Jan. 1993, 311-321.
Zeisel, et al., "Cell Types in the Mouse Cortex and Hippocampus Revealed by Single-cell RNA-seq", Science, vol. 347, No. 6226, Mar. 6, 2015, 8 pages.
Zhang, et al., "An RNA-Sequencing Transcriptome and Splicing Database of Glia, Neurons, and Vascular Cells of the Cerebral Cortex", The Journal of Neuroscience, vol. 34, No. 36, Sep. 3, 2014, 11929-11947.
Venteicher et al., "Decoupling genetics, lineages, and microenvironment in IDH-mutant gliomas by single-cell RNA-seq", Science, 355, 2017, 13 pages.
Maruyama, Yuzo.,"An Alternative to Moran's for Spatial Autocorrelation" Center for Spatial Information Science, University of Tokyo, Jan. 26, 2015, 6 pages.
Agoston, et al., "Meis2 is a Pax6 Co-factor in Neurogenesis and Dopaminergic Periglomerular Fate Specification in the Adult Olfactory Bulb", Development , vol. 141, 2014, 28-38.
Amir, et al., "viSNE Enables Visualization of High Dimensional Single-Cell Data and Reveals Phenotypic Heterogeneity of Leukemia", Nature Biotechnology, vol. 31, No. 6, Jun. 2013, 25 pages.
Anders, et al., "Differential Expression Analysis for Sequence Count Data", Genome Biology, vol. 11, No. 10, 2010, 12 pages.
Ashburner, et al., "Gene Ontology: Tool for the Unification of Biology. The Gene Ontology Consortium", Nature Genetics, vol. 25, No. 1, May 2000, 9 pages.
Bendall, et al., "Single-cell Trajectory Detection Uncovers Progression and Regulatory Coordination in Human B Cell", Development Cell, vol. 157, No. 3, Apr. 24, 2014, 714-725.
Benjamini, et al.,"Controlling the False Discovery Rate: A Practical and Powerful Approach to Multiple Testing", Journal of the Royal Statistical Society, Series B, vol. 57, No. 1, 1995, 289-300.
Bonner, et al., "Laser Capture Microdissection: Molecular Analysis of Tissue", Science, vol. 278, No. 5342, Nov. 21, 1997, 1481-1483.
Zhang, et al., "Ezh2 Regulates Adult Hippocampal Neurogenesis and Memory", The Journal of Neuroscience, vol. 34, No. 15, Apr. 9, 2014, 5184-5199.
Botev, et al., "Kernel Density Estimation Via Diffusion", The Annals of Statistics, vol. 38, No. 5, Nov. 11, 2010, 44 pages.
Brennecke, et al.,"Accounting for Technical Noise in Single-Cell RNA-seq Experiments", Nature methods, vol. 10, Issue 11, Sep. 22, 2013, 1093-1095.
Busskamp, et al., "Rapid Neurogenesis Through Transcriptional Activation in Human Stem Cells", Molecular Systems Biology, vol. 10, No. 760, Nov. 17, 2014, 21 pages.
Cao, et al., "Comprehensive Single Cell Transcriptional Profiling of a Multicellular Organism by Combinatorial Indexing", Science, vol. 357, No. 6352, Aug. 17, 2018, 25 pages.
Cembrowski, et al., "Spatial Gene-Expression Gradients Underlie Prominent Heterogeneity of CA1 Pyramidal Neurons", Neuron, vol. 89, No. 2, Jan. 20, 2016, 351-368.
Chu, et al., "Efficient Generation of Rosa26 Knock-in Mice using Crispr/cas9 in C57bl/6 Zygotes", BMC Biotechnology, vol. 16, No. 4, Jan. 16, 2016, 15 pages.
Darmanis, et al., "A Survey of Human Brain Transcriptome Diversity at the Single Cell Level", Proceedings of the National Academy of Sciences, vol. 112, No. 23, Jun. 9, 2015, 7285-7290.
De Luca, et al., "RNA-SeQC: RNA-seq Metrics for Quality Control and Process Optimization", Bioinformatics, vol. 28, No. 11, Jun. 1, 2012, 1530-1532.

(56) References Cited

OTHER PUBLICATIONS

Macosko, et al., "Highly Parallel Genome-Wide Expression Profiling of Individual Cells Using Nanoliter Droplets", Cell, vol. 161, No. 5, May 21, 2015, 1202-1214.
Dunn, J. C.,"Well-Separated Clusters and Optimal Fuzzy Partitions", Journal of Cybernetics, vol. 4, Issue 1, 1974 95-104.
Edelman, et al., "Random Matrix Theory", Acta Numerica, 2005, pp. 1-65.
Eden, et al., "Discovering Motifs in Ranked Lists of DNA Sequences", PLoS Computational Biology, vol. 3, Issue 3, Mar. 2007, 0508-0522.
Fan, et al., "Liblinear: A Library for Large Linear Classification", Journal of Machine Learning Research, vol. 9, No. 9, Aug. 2008, 1871-1874.
Feliciano, et al., "Noncanonical Sites of Adult Neurogenesis in the Mammalian Brain", Cold Spring Harbor Perspectives in Biology, vol. 7, No. 10, Sep. 18, 2015, 14 pages.
Ge, et al., "GABA Regulates Synaptic Integration of Newly Generated Neurons in the Adult Brain", Nature, vol. 439, No. 7076, Feb. 2, 2006, 10 pages.
Grindberg, et al., "RNA-sequencing from Single Nuclei", Proceedings of the National Academy of Sciences of the United States of America, vol. 110, No. 49, Dec. 3, 2013, 19802-19807.
Guo, et al., "Droplet Microfluidics for High-throughput Biological Assays", Lab on a Chip, vol. 12, No. 12, Jun. 21, 2012, 10 pages.
Love, et al., "Moderated Estimation of Fold Change and Dispersion for RNA-seq Data with DESeq2", Genome Biology, vol. 15, No. 12, 2014, 21 pages.
Habib, et al., "Massively Parallel Single-Nucleus RNA-seq with DroNc-seq", Nature Methods, vol. 14, No. 10, Oct. 2017, 18 pages.
Hagihara, et al., "Dissection of Hippocampal Dentate Gyrus from Adult Mouse", Journal of Visualized Experiments, vol. 33, No. 1543, Nov. 2009, 6 pages.
Helsgaun, Keld, "An Effective Implementation of the Lin-Kernighan Traveling Salesman Heuristic", Department of Computer Science, Roskilde University,DK-4000 Roskilde, Denmark, 2000, 71 pages.
Helsgaun, Keld, "General K-opt Submoves for the Lin-Kernighan TSP Heuristic", Mathematical Programming Computation, vol. 1, Jul. 1, 2009, 119-163.
Hempel, et al., "A Manual Method for the Purification of Fluorescently Labeled Neurons from the Mammalian Brain", Nature Protocols, vol. 2, No. 11, Nov. 8, 2007, 2924-2929.
Henry, et al.,"A Common Pesticide Decreases Foraging Success and Survival in Honey Bees", Science, vol. 336, No. 6079, Apr. 20, 2012, 348-350.
Horner, et al., "Proliferation and Differentiation of Progenitor Cells Throughout the Intact Adult Rat Spinal Cord", The Journal of Neuroscience, vol. 20, No. 6, Mar. 15, 2000, 2218-2228.
Hsiao, et al., "Microbiota Modulate Behavioral and Physiological Abnormalities Associated with Neurodevelopmental Disorders", Cell, vol. 155, No. 7, Dec. 19, 2013, 1451-1463.
Hu, et al., "Fast-spiking, Parvalbumin(+) Gabaergic Interneurons: from Cellular Design to Microcircuit Function", Science, vol. 345, Issue 6196, Aug. 1, 2014, 1255263-1-1255263-13.
Kharchenko, et al., "Bayesian Approach to Single-Cell Differential Expression Analysis", Nature Methods, vol. 11, Issue 7, Jul. 2014, 11 pages.
Kim, et al., "Highly Efficient Rna-guided Genome Editing in Human Cells via Delivery of Purified Cas9 Ribonucleoproteins", Genome Research, vol. 24, No. 6, Jun. 24, 2014, 1012-1019.
Klein, et al., "Droplet Barcoding for Single-Cell Transcriptomics Applied to Embryonic Stem Cells", Cell, vol. 161, No. 5, May 21, 2015, 24 pages.
Knobloch, et al., "Metabolic Control of Adult Neural Stem Cell Activity by Fasn-dependent Lipogenesis", Nature, vol. 493, Jan. 10, 2013, 226-230.
Krishnaswami, et al., "Using Single Nuclei for RNA-seq to Capture the Transcriptome of Postmortem Neurons", Nature Protocols, vol. 11, No. 3, Mar. 2016, 51 pages.
Lacar, et al., "Nuclear RNA-seq of Single Neurons Reveals Molecular Signatures of Activation" Nature Communications, vol. 7, No. 11022, Apr. 19, 2016, 11 pages.
Langmead, et al., "Fast Gapped-Read Alignment with Bowtie 2", Nature Methods, vol. 9, No. 4, Mar. 2012, 8 pages.
Lason, et al., "The Effects of Excitatory Amino Acids on Proenkephalin and Prodynorphin mRNA Levels in the Hippocampal Dentate Gyrus of the Rat; An In Situ Hybridization Study", Molecular Brain Research, vol. 12, No. (1-3), Jan. 1992, 243-247.
Lein, et al., "Genome-wide Atlas of Gene Expression in the Adult Mouse Brain", Nature, vol. 445, No. 7124, Jan. 11, 2007, 168-176.
Li, et al. "RNA-seq Gene Expression Estimation with Read Mapping Uncertainty", Bioinformatics, vol. 26, No. 4, Feb. 15, 2010, 493-500.
Llorens-Bobadilla, et al., "Single-Cell Transcriptomics Reveals a Population of Dormant Neural Stem Cells that Become Activated upon Brain Injury", Cell Stem Cell, vol. 17, No. 3, Sep. 3, 2015, 329-340.
Zheng, et al., "Massively Parallel Digital Transcriptional Profiling of Single Cells", Nature Communications, vol. 8, No. 14049, Jan. 16, 2017, 12 pages.
Zheng, et al., "Haplotyping Germline and Cancer Genomes with High-Throughput Linked-Read Sequencing", Nature Biotechnology, vol. 34, No. 3, Mar. 2016, 303-311.
The Broad Institute, Inc., "Notification Concerning Transmittal of International Preliminary Report on Patentability for PCT/US2018/060860", May 28, 2020, 14 pages.
Abudayyeh et al., C2c2 is a single-component programmable RNA-guided RNA targeting CRISPR effector, Science, Aug. 5, 2016, vol. 353, No. 6299 (23 pages).
Ahmad et al., "In silico modelling of drug-polymer interactions for pharmaceutical formulations," Journal of the Royal Society Interface, 2010, vol. 7 (pp. S423-S433).
Akinc et al., "Targeted Delivery of RNAi Therapeutics With Endogenous and Exogenous Ligand-Based Mechanisms," Molecular Therapy, Jul. 2010, vol. 18, No. 7 (1357-1364).
Alabi et al., "Multiparametric approach for the evaluation of lipid nanoparticles for siRNA delivery," Proceedings of the National Academy of Sciences, USA, Aug. 6, 2013, vol. 110, No. 32 (pp. 12881-12886).
Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).
Altinoglu et al., "Intracellular delivery of the PTEN protein using cationic lipidoids for cancer therapy," Biomaterial Science, Nov. 15, 2016, vol. 4, No. 12 (pp. 1773-1780) ** Electronic Supplementary Material (ESI) for Biomaterials Science.
Amann et al., "Tightly regulated tac promoter vectors useful for the expression of unfused and fused proteins in *Escherichia coli*," Gene, Jun. 15, 1988, vol. 69 (pp. 301-315).
Ausubel, "A botanical macroscope" Proceedings of the National Academy of Sciences, Aug. 4, 2009, vol. 106, No. 31 (pp. 12569-12570).
Balaggan et al., "Stable and efficient intraocular gene transfer using pseudotyped EIAV lentiviral vectors," The Journal of Gene Medicine, Mar. 2006, vol. 8, No. 3 (pp. 275-285).
Baldari et al., "A novel leader peptide which allows efficient secretion of a fragment of human interleukin 1 beta in *Saccharomyces cerevisiae*", EMBO Journal, Jan. 1, 1987, vol. 6, No. 1 (pp. 229-234).
Banerji et al., "A lymphocyte-specific cellular enhancer is located downstream of the joining region in immunoglobulin heavy chain genes," Cell, Jul. 1983, vol. 33, No. 3 (pp. 729-740).
Barany, "Genetic disease detection and DNA amplification using cloned thermostable ligase," Proceedings of the National Academy of Sciences, USA, Jan. 1991, vol. 8 (pp. 189-193).
Basha et al., "Influence of cationic lipid composition on gene silencing properties of lipid nanoparticle formulations of siRNA in antigen-presenting cells," Molecular Therapy, Dec. 2011, vol. 19, No. 12 (pp. 2186-2200).

(56) References Cited

OTHER PUBLICATIONS

Binley et al., "Safety and Biodistribution of an Equine Infectious Anemia Virus-Based Gene Therapy, RetinoStat, for Age-Related Macular Degeneration," Human Gene Therapy, Jun. 2012, vol. 23, No. 9 (pp. 980-991).
Birrell et al., "A genome-wide screen in *Saccharomyces cerevisiae* for genes affecting UV radiation sensitivity," Proceedings of the National Academy of Sciences, USA, Oct. 23, 2001, vol. 98, No. 22 (pp. 12608-12613).
Boch et al., "Breaking the Code of DNA Binding Specificity of T AL-Type III Effectors," Science, Dec. 11, 2009 vol. 326, No. 5959 (pp. 1509-1512).
Boshart et al., "A Very Strong Enhancer is Located Upstream of an Immediate Early Gene of Human Cytomegalovirus", Cell, Jun. 1985 vol. 41 (pp. 521-530).
Bramsen et al., "Development of Therapeutic-Grade Small Interfering RNAs by Chemical Engineering," Frontiers in Genetics, Aug. 20, 2012, vol. 3, Article 154 (pp. 1-22).
Byrne et al., "Multiplex gene regulation: a two-tiered approach to transgene regulation in transgenic mice," Proceedings of the National Academy of Sciences, USA, Jul. 1989, vol. 86 (pp. 5473-5477).
Calame et al., "Transcriptional Controlling Elements in the Immunoglobulin and T Cell Receptor Loci," Advances in Immunology, 1988, vol. 43, (pp. 235-275).
Camper et al., "Postnatal repression of the alpha-fetoprotein gene is enhancer independent elements," Genes and Development, 1989, vol. 3 (pp. 537-546).
Canver et al., "BCL11A enhancer dissection by Cas9-mediated in situ saturating mutagenesis," Nature, vol. 527, 2015 (pp. 192-197) [including Supplementary Material].
Carr et al., "Genome Engineering," Nature Biotechnology, Dec. 2009, vol. 27, No. 12 (pp. 1151-1162).
CBOL Plant Working Group, "A DNA barcode for land plants," Proceedings of the National Academy of Sciences, Aug. 4, 2009, vol. 106, No. 31 (pp. 12794-12797).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Chen et al., "Dynamic Imaging of Genomic Loci in Living Human Cells by an Optimized CRISPR/Cas System," Cell, 2013, vol. 155 (pp. 1479-1491).
Chen et al., "Genome-wide CRISPR Screen in a Mouse Model of Tumor Growth and Metastasis," Cell, 2015 vol. 160 (pp. 1-15).
Cho et al., "Lipid-like nanoparticles for small interfering RNA delivery to endothelial cells," Advanced Functional Materials, Oct. 9, 2009, vol. 19, No. 19 (pp. 1-15).
Chung et al., "Structural and molecular interrogation of intact biological systems," Nature, May 16, 2013, vol. 497 (pp. 332-337).
Coelho et al., "Safety and efficacy of RNAi therapy for transthyretin amyloidosis," New England Journal of Medicine, Aug. 29, 2013, vol. 369, No. 9 (pp. 819-829).
Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].
Dahlman et al., "In vivo endothelial siRNA delivery using polymeric nanoparticles with low molecular weight," Nature Nanotechnology, 2014, vol. 9 (pp. 648-655).
Datlinger et al., "Pooled CRISPR Screening with Single-Cell Transcriptome Read-Out", Nature Methods, Mar. 2017, vol. 14, No. 3, (20 pages).
Dellinger et al., "Streamlined process for the chemical synthesis of RNA using 2'-O-thionocarbamate-protected nucleoside phosphoramidites in the solid phase," Journal of the American Chemical Society, Aug. 3, 2011, vol. 133, No. 30 (pp. 11540-11556).
Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).

Digiusto et al., "RNA-Based Gene Therapy for HIV with Lentiviral Vector-Modified CD34(+) Cells in Patients Undergoing Transplantation for AIDS-Related Lymphoma," Science Translational Medicine, Jun. 16, 2010, vol. 2, No. 36 (pp. 1-18).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Doyon et al., "Heritable targeted gene disruption in zebrafish using designed zinc-finger nucleases," Nature Biotechnology, Jun. 2008, vol. 26, No. 6 (pp. 702-708).
Dumitrache et al., "Trex2 Enables Spontaneous Sister Chromatid Exchanges Without Facilitating DNA Double-Strand Break Repair," Genetics, vol. 188, Aug. 2011 (pp. 787-797).
Edd et al., "Controlled encapsulation of single-cells into monodisperse picolitre drops," Lab Chip, 2008, vol. 8, No. 8 (pp. 1262-1264).
Edlund et al., "Cell-Specific Expression of the Rat Insulin Gene: Evidence for Role of Two Distinct 5' Flanking Elements," Science, Nov. 22, 1985, vol. 230, No. 4728 (pp. 912-916).
El-Andaloussi et al., "Exosome-mediated delivery of siRNA in vitro and in vivo," Nature Protocols, Dec. 2012, vol. 7, No. 12 (pp. 2112-2126).
Empedocles et al., "Three-dimensional orientation measurements of symmetric single chromophores using polarization microscopy," Nature, 1999, vol. 399 (pp. 126-130).
Gao et al., "Engineered Cpf1 enzymes with altered PAM specificities," bioRxiv preprint, Dec. 4, 2016 [pp. 1/14-14/14, pp. 1/3-3/3 of Figs, and pp. S1-S8 (25 pages)].
Garrett et al., "Exploring uptake mechanisms of oral nanomedicines using multimodal nonlinear optical microscopy," Journal of Biophotonics, 2012, vol. 5, Nos. 5-6 (pp. 458-468).
Garrett et al., "Label-free imaging of polymeric nanomedicines using coherent anti-stokes Raman scattering microscopy," Journal of Raman Spectroscopy, 2012, vol. 43, No. 5 (pp. 681-688).
Giaever et al., "Functional profiling of the *Saccharomyces cerevisiae* genome," Nature, vol. 418, Jul. 25, 2002 (pp. 387-391).
Grimm et al., "In vitro and in vivo gene therapy vector evolution via multispecies interbreeding and retargeting of adeno-associated viruses," Journal of Virology, 2008, vol. 82, No. 12 (pp. 5887-5911).
Groenen et al., "Nature of DNA polymorphism in the direct repeat cluster of *Mycobacterium tuberculosis*; application for strain differentiation by a novel typing method," Molecular Microbiology, Dec. 1993, vol. 10, No. 5 (pp. 1057-1065).
Gruber et al., "The Vienna RNA Websuite," Nucleic Acids Research, Apr. 19, 2008, vol. 36 (pp. W70-W74).
Hendel et al., "Chemically modified guide RNAs enhance CRISPR-Cas genome editing in human primary cells," Nature Biotechnology Sep. 2015, vol. 33, No. 9 (pp. 985-989).
Hicke et al., "Escort aptamers: a delivery service for diagnosis and therapy," The Journal of Clinical Investigation, Oct. 2000, vol. 106, No. 8 (pp. 923-928).
Hoe et al., "Rapid Molecular Genetic Subtyping of Serotype M1 Group A *Streptococcus* Strains," Emerging Infectious Diseases, Mar.-Apr. 1999, vol. 5, No. 2 (pp. 254-263).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases", Nature Biotechnology, Sep. 2013, vol. 31, No. 9 (pp. 827-832).
Hur et al., "Targeted mutagenesis in mice by electroporation of Cpf1 ribonucleoproteins," Nature Biotechnology, Jun. 2016, vol. 34 (pp. 807-808).
Inoue et al., "An inducible translocation strategy to rapidly activate and inhibit small GTPase signaling pathways," Nature Methods, Jun. 2005, vol. 2, No. 6 (pp. 415-418).
Ishino et al., "Nucleotide sequence of the iap gene, responsible for alkaline phosphatase isozyme conversion in *Escherichia coli*, and identification of the gene product," Journal Bacteriology, Dec. 1987, vol. 169 (pp. 5429-5433).
Jansen et al., "Identification of a novel family of sequence repeats among prokaryotes," OMICS, A Journal of Integrative Biology, 2002, vol. 6, No. 1 (pp. 23-33).

(56) References Cited

OTHER PUBLICATIONS

Jansen et al., "Identification of genes that are associated with DNA repeats in prokaryotes", Molecular Microbiology, Mar. 2002, vol. 43, No. 6 (pp. 1565-1575).
Jiang et al., "Lipidoid-coated iron oxide nanoparticles for efficient DNA and siRNA delivery," Nano Letters, Mar. 13, 2013, vol. 13, No. 3 (pp. 1059-1064).
Jiang et al., "RNA-guided editing of bacterial genomes using CRISPR-Cas systems," Nature Biotechnology, Mar. 2013, vol. 31 [30 pages, including supplementary information] (pp. 233-239).
Karagiannis et al., "Rationally designed tumor-penetrating nanocomplexes," ACS Nano 2012, vol. 6, No. 10 (pp. 8484-8487).
Kaufman et al., "Translational efficiency of polycistronic mRNAs and their utilization to express heterologous genes in mammalian cells," EMBO Journal, 1987, vol. 6, No. 1 (pp. 187-195).
Keefe et al., "Aptamers as therapeutics," Nature Reviews, Jul. 2010, vol. 9 (pp. 537-550).
Kelley et al., "Versatility of chemically synthesized guide RNAs for CRISPR-Cas9 genome editing," Journal of Biotechnology, Sep. 2016, vol. 233, 10 (pp. 74-83).
Kessel et al., "Murine developmental control genes," Science, Jul. 1990, vol. 249 (pp. 374-379).
Kim et al., "Chimeric restriction endonuclease," Proceedings of the National Academy of Sciences, USA, Biochemistry, Feb. 1994, vol. 91 (pp. 883-887).
Kim et al., "Hybrid restriction enzymes: Zinc finger fusions to Fok I cleavage domain," Proceedings of the National Academy of Science, USA, Feb. 1996, vol. 93, No. 3 (pp. 1156-1160).
Kleinstiver et al., "Engineered CRISPR-Cas9 nucleases with altered PAM specificities," Nature, Jul. 23, 2015, vol. 523, No. 7561 (pp. 481-485).
Koch, "Combining morphology and DNA barcoding resolves the taxonomy of Western Malagasy Liotrigona Moure, 1961," African Invertebrates, Dec. 2010, vol. 51, No. 2 (pp. 413-421).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Kress et al., "DNA barcodes: Genes, genomics, and bioinformatics," Proceedings of the National Academy of Sciences, Feb. 26, 2008, vol. 105, No. 8 (pp. 2761-2762).
Kress et al., "Use of DNA barcodes to identify flowering plants" Proceedings of the National Academy of Sciences, USA, vol. 102, No. 23 (pp. 8369-8374).
Kurjan et al., "Structure of a yeast pheromone gene (MF alpha): a putative alpha-factor precursor contains four tandem copies of mature alpha-factor," Cell, Oct. 1982, vol. 30, No. 3 (pp. 933-943).
Lacoste et al. "Ultrahigh-resolution multicolor colocalization of single fluorescent probes," Proceedings of the National Academy of Sciences, USA, Aug. 15, 2000, vol. 97, No. 17 (pp. 9461-9466).
Lahaye et al., "DNA barcoding the floras of biodiversity hotspots," Proceedings of the National Academy of Sciences, USA, Feb. 26, 2008, vol. 105, No. 8 (pp. 2923-2928).
Lalatsa et al., "A prodrug nanoparticle approach for the oral delivery of a hydrophilic peptide, leucine(5)-enkephalin, to the brain," Molecular Pharmaceutics, Jun. 4, 2012, vol. 9, No. 6 (pp. 1665-1680).
Lalatsa et al., "Amphiphilic poly(L-amino acids)—new materials for drug delivery," Journal of Control Release, Jul. 20, 2012, vol. 161, No. 2 (pp. 523-236).
Lalatsa et al., "Delivery of peptides to the blood and brain after oral uptake of quaternary ammonium palmitoyl glycol chitosan nanoparticles," Molecular Pharmaceutics, Jun. 4, 2012, vol. 9, No. 6 (pp. 1764-1774).
Lamb et al., "The Connectivity Map: Using Gene-Expression Signatures to Connect Small Molecules, Genes, and Disease," Science, Sep. 29, 2006, vol. 313, Issue 5795 (pp. 1929-1935).
Lamb, "The Connectivity Map: A New Tool for Biomedical Research," Nature Reviews, Cancer, Jan. 2007, vol. 7, No. 1 (pp. 54-60).
Lee et al., "Molecularly self-assembled nucleic acid nanoparticles for targeted in vivo siRNA delivery," Nature Nanotechnology, Jun. 3, 2012, vol. 7, No. 6 (pp. 389-393).
Lee et al., "Synthetically modified guide RNA and donor DNA are a versatile platform for CRISPR-Cas9 engineering," Elife, May 2, 2017, vol. 6 e25312 (17 pages).
Levy-Nissenbaum et al., Nanotechnology and aptamers: applications in drug delivery, Trends in Biotechnology, Aug. 2008, vol. 26, No. 8 (pp. 442-449).
Li et al., "Engineering CRISPR-Cpf1 crRNAs and mRNAs to maximize genome editing efficiency," Nature Biomedical Engineering, May 2017, vol. 1, No. 5 (21 pages).
Liang et al., "CRISPR/Cas9-mediated gene editing in human tripronuclear zygotes," Protein Cell, 2015, vol. 6, No. 5 (pp. 363-372).
Luckow et al. "High Level Expression of Nonfused Foreign Genes with *Autographa californica* Nuclear Polyhedrosis Virus Expression Vectors," Virology, May 1989, vol. 170 (pp. 31-39).
Masepohl et al., "Long tandemly repeated repetitive (LTRR) sequences in the filamentous cyanobacterium *Anabaena* sp. PCC 7120," Biochimica et Biophysica Acta (BBA)—Gene Structure and Expression, Jun. 3, 1996, vol. 1307, No. (pp. 26-30).
Matsuda et al., "Controlled expression of transgenes introduced by in vivo electroporation," Proceedings of the National Academy of Sciences, Jan. 16, 2007, vol. 104, No. 3 (pp. 1027-1032).
Mazza et al., "Nanofiber-Based Delivery of Therapeutic Peptides to the Brain," ACS Nano, Jan. 4, 2013, vol. 7, No. 2 (pp. 1016-1026).
Miyamoto et al., "Rapid and orthogonal logic gating with a gibberellin-induced dimerization system," Nature Chemical Biology, 2012, vol. 8, No. 5 (pp. 465-470).
Mojica et al., "Biological significance of a family of regularly spaced repeats in the genomes of Archaea, Bacteria and mitochondria," Molecular Microbiology, vol. 36, 2000 (pp. 244-246).
Mojica et al., "Long stretches of short tandem repeats are present in the largest replicons of the Archaea Haloferax mediterranei and Haloferax volcanii and could be involved in replicon partitioning," Molecular Microbiology, Jul. 1995, vol. 17, No. 1 (pp. 85-93).
Morocz et al., "Brain edema development after MRI-guided focused ultrasound treatment," Journal of Magnetic Resonance Imaging, Jan.-Feb. 1998, vol. 8, No. 1 (pp. 136-142).
Moscou, et al., "A Simple Cipher Governs DNA Recognition by TAL Effectors," Science, Dec. 11, 2009, vol. 326, No. 11 (p. 1501).
Moussatov et al., "A Possible Approach to the Treatment of Polycystic Ovarian Syndrome Using Focused Ultrasound," Ultrasonics, 1998, vol. 36, No. 8 (pp. 893-900).
Nair et al., "Multivalent N-acetylgalactosamine-conjugated siRNA localizes in hepatocytes and elicits robust RNAi-mediated gene silencing," Journal of the American Chemical Society, Dec. 1, 2014, vol. 136 (pp. 16958-16961).
Nakamura et al., "Codon usage tabulated from the international DNA sequence databases: status for the year 2000," Nucleic Acids Research, 2000, vol. 28, No. 1 (p. 292).
Nakata et al., "Unusual Nucleotide Arrangement with Repeated Sequences in the *Escherichia coli* K-12 Chromosome," Journal of Bacteriology, Jun. 1989, vol. 171, No. 6 (pp. 3553-3556).
Nishimasu et al., "Crystal Structure of Cas9 in Complex with Guide RNA and Target DNA," Cell, Feb. 27, 2014, vol. 156 (pp. 935-949).
Nishimasu et al.,"Crystal Structure of *Staphylococcus aureus* Cas9", Cell, 2015, vol. 162 (pp. 1113-1126) [with Supplemental Information].
O'Hare et al., "Transformation of mouse fibroblasts to methotrexate resistance by a recombinant plasmid expressing a prokaryotic dihydrofolate reductase," Proceedings of the National Academy of Sciences, USA, Mar. 1981, vol. 78, No. 3 (pp. 1527-1531).
Ostergaard et al., "Efficient Synthesis and Biological Evaluation of 5'-GalNAc Conjugated Antisense Oligonucleotides," Bioconjugate Chemistry, 2015 vol. 26, No. 8 (pp. 1451-1455).
Paige et al., "RNA mimics of green fluorescent protein," Science, Jul. 29, 2011, vol. 333, No. 6042 (pp. 642-646).

(56) References Cited

OTHER PUBLICATIONS

Parnas et al., "A Genome-Wide CRISPR Screen in Primary Immune Cells to Dissect Regulatory Networks," 2015, vol. 162 (pp. 675-686) [with Supplementary Information].
Pinkert et al., "An albumin enhancer located 10 kb upstream functions along with its promoter to direct efficient, liver-specific expression in transgenic mice," Genes Development, May 1987, vol. 1 (pp. 268-276).
Platt et al, "CRISPR-Cas9 Knockin Mice for Genome Editing and Cancer Modeling," Cell, 2014, vol. 159 (pp. 440-455).
Qu et al., "Carbohydrate-based micelle clusters which enhance hydrophobic drug bioavailability by up to 1 order of magnitude," Biomacromolecules, Nov. 7, 2006, vol. 7, No. 12 (pp. 3452-3459).
Queen et al., "Immunoglobulin gene transcription is activated by downstream sequence elements," Cell, Jul. 1983, vol. 33, No. 3 (pp. 741-748).
Rahdar et al., "Synthetic CRISPR RNA-Cas9-guided genome editing in human cells," Proceedings of the American Academy of Sciences, U.S.A. Nov. 16, 2015 (pp. E7110-E7117).
Ramanan et al., "CRISPR-Cas9 cleavage of viral DNA efficiently suppresses hepatitis B virus," Nature/Scientific Reports, Jun. 2015 (9 pages).
Ran et al., "Double Nicking by RNA-guided CRISPR Cas9 for enhanced genome editing specificity", Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Ran et al., "In vivo genome editing using *Staphylococcus aureus* Cas9," Nature, Apr. 9, 2015, vol. 520, No. 7546 (pp. 186-203).
Reichert et al., "Chip-Based Optical Detection of DNA Hybridization by Means of Nanobead Labeling," Analytical Chemistry, Dec. 15, 2000, vol. 72, No. 24 (pp. 6025-6029).
Scaringe et al., "Advanced 5'-silyl-2'-orthoester approach to RNA oligonucleotide synthesis," Methods in Enzymology, 2000, vol. 317 (pp. 3-18).
Scaringe et al., "Novel RNA Synthesis Method Using 5'-O-Silyl-2'-O-orthoester Protecting Groups," Journal of the American Chemical Society, 1998, vol. 120, No. 45 (pp. 11820-11821).
Schroeder et al., "Lipid-based nanotherapeutics for siRNA delivery," Journal of Internal Medicine, Jan. 2010, vol. 267, No. 1 (pp. 9-21).
Schultz et al., "Expression and secretion in yeast of a 400-kDa envelope glycoprotein derived from Epstein-Barr virus," Gene, Mar. 2, 1987, vol. 54 (pp. 113-123).
Seberg et al., "How many loci does it take to DNA barcode a crocus?" PLoS One, Feb. 2009, vol. 4, No. 2 e4598 (pp. 1-6).
Seed, B., "An LFA-3 cDNA encodes a phospholipid-linked membrane protein homologous to its receptor CD2," Nature, Oct. 1987, vol. 329 (pp. 840-842).
Shalem et al., "Genome-Scale CRISPR-Cas9 Knockout Screening in Human Cells," Science, Jan. 3, 2014, vol. 343 (pp. 84-87).
Shalem et al., "High-throughput functional genomics using CRISPR-Cas9" Nature Review Genetics, 2015, vol. 16, No. 5 (pp. 299-311).
Sharma et al., "Antisense oligonucleotides: modifications and clinical trials," Medical Chemistry Journal, 2014, 5 (pp. 1454-1471).
Shmakov et al., "Discovery and Functional Characterization of Diverse Class 2 CRISPR-Cas Systems," Molecular Cell, Nov. 1, 2015, vol. 60, No. 3 (pp. 385-397).
Siew et al., "Enhanced oral absorption of hydrophobic and hydrophilic drugs using quaternary ammonium palmitoyl glycol chitosan nanoparticles," Molecular Pharmaceutics, Jan. 1, 2012, vol. 9, No. 1 (pp. 14-28).
Slaymaker et al., "Rationally engineered Cas9 nucleases with improved specificity," Science, Dec. 1, 2015, vol. 351, No. 6268 (pp. 84-88).
Smith et al., "Single-step purification of polypeptides expressed in *Escherichia coli* as fusions with glutathione S-transferase," Gene, Mar. 16, 1988, vol. 67 (pp. 31-40).

Smith et al., "Production of Human Beta Interferon in Insect Cells Infected with a Baculovirus Expression Vector," Molecular and Cellular Biology, vol. 3, No. 12, Dec. 1983 (pp. 2156-2165).
Soininen et al., "Analysing diet of small herbivores: the efficiency of DNA barcoding coupled with high-throughput pyrosequencing for deciphering the composition of complex plant mixtures," Frontiers in Zoology, Aug. 2009, vol. 6, No. 16 (pp. 1-9).
Stanley et al., "Radio-Wave Heating of Iron Oxide Nanoparticles Can Regulate Plasma Glucose in Mice," Science, May 4, 2012 vol. 336, No. 6081 (pp. 604-608).
Stegmaier et al., "Gene expression-based high-throughput screening (GE-HTS) and application to leukemia differentiation," Nature Genetics, 2004, vol. 36 (pp. 257-263).
Su et al., "In vitro and in vivo mRNA delivery using lipid-enveloped pH-responsive polymer nanoparticles," Molecular Pharmaceutics, Jun. 6, 2011 vol. 8, No. 3 (pp. 774-787).
Tabernero et al., "First-in-humans trial of an RNA interference therapeutic targeting VEGF and KSP in cancer patients with liver involvement," Cancer Discovery, Apr. 2013 (pp. 406-417).
Takebe et al., "SR alpha promoter: an efficient and versatile mammalian cDNA expression system composed of the simian virus 40 early promoter and the R-U5 segment of human T-cell leukemia virus type 1 long terminal repeat," Molecular and Cellular Biology, Jan. 1988, vol. 8, No. 1 (pp. 466-472).
Takeda et al., "Synthetic and nature-derived lipid nanoparticles for neural regeneration," Neural Regeneration Research, May 2015, vol. 10, No. 5 (pp. 689-690).
Tran-Huu-Hue et al., "Practical Systems for the Generation of High Power Continuous Wave-Non Focused Ultrasound in the MHz Range," Acustica, acta acustica, 1997, vol. 83 (pp. 1103-1106).
Tsai et al., "Dimeric CRISPR RNA-guided FokI nucleases for highly specific genome editing," Nature Biotechnology, 2014, vol. 32, No. 6 (pp. 569-576).
Tuerk et al., "Systematic evolution of ligands by exponential enrichment: RNA ligands to bacteriophage T4 DNA polymerase," Science, Aug. 3, 1990, vol. 249, No. 4968 (pp. 505-510).
Uchegbu et al., "Quaternary ammonium palmitoyl glycol chitosan—a new polysoap for drug delivery," International Journal of Pharmaceutics, Aug. 14, 2001, vol. 224, Nos. 1-2 (pp. 185-199).
Uchegbu, I.F., "Pharmaceutical nanotechnology: polymeric vesicles for drug and gene delivery," Expert Opinion on Drug Delivery, Sep. 2006, vol. 3, No. 5 (pp. 629-640).
Uno et al., "High-Density Lipoprotein Facilitates In Vivo Delivery of a-Tocopherol-Conjugated Short-Interfering RNA to the Brain," Human Gene Therapy, Jun. 2011, vol. 22 (pp. 711-719).
Van Embden et al. "Genetic variation and evolutionary origin of the direct repeat locus of *Mycobacterium tuberculosis* complex bacteria," Journal of Bacteriology, May 2000, vol. 182, No. 9 (pp. 2393-2401).
Wang et al., "Combinatorially designed lipid-like nanoparticles for intracellular delivery of cytotoxic protein for cancer therapy," Angewandte Chemie, International Edition, England, Mar. 10, 2014, vol. 53, No. 11 (pp. 2893-2898).
Wang et al., "Efficient delivery of genome-editing proteins using bioreducible lipid nanoparticles," Proceedings of the National Academy of Sciences, USA, Mar. 15, 2016, vol. 113, No. 11 (pp. 2868-2873).
Wang et al., "Enhanced intracellular siRNA delivery using bioreducible lipid-like nanoparticles," Advanced Healthcare Materials, Sep. 2014, vol. 3 (pp. 1398-1403).
Wang et al., "Genetic Screens in Human Cells Using the CRISPR-Cas9 System", Science, 2014, vol. 343 (pp. 80-84).
Wang et al., "Hyaluronic acid modification of RNase A and its intracellular delivery using lipid-like nanoparticles," Journal of Controlled Release, Oct. 10, 2017, vol. 263 (pp. 39-45).
Wang et al., "Integrating Protein Engineering and Bioorthogonal Click Conjugation for Extracellular Vesicle Modulation and Intracellular Delivery," PLoS One, Nov. 3, 2015, vol. 10, No. 11 (pp. 1-12).
Whitehead et al., "In vitro-in vivo translation of lipid nanoparticles for hepatocellular siRNA delivery," ACS Nano, Aug. 28, 2012, vol. 6, No. 8 (pp. 6922-6929).

(56) References Cited

OTHER PUBLICATIONS

Winoto et al., "A novel, inducible and T cell-specific enhancer located at the 3' end of the T cell receptor a locus," EMBO Journal, Mar. 1989, vol. 8, No. 3 (pp. 729-733).

Winzeler et al., "Functional characterization of the S. cerevisiae genome by gene deletion and parallel analysis," Science, Aug. 6, 1999, vol. 285, No. 5429 (pp. 901-906).

Wu et al., "Genome-wide binding of the CRISPR endonuclease Cas9 in mammalian cells," Nature Biotechnology, 2014, Including Supplemental information, 2 pages, (pp. 1-9).

Xu et al., "Design of 240,000 orthogonal 25mer DNA barcode probes," Proceedings of the National Academy of Sciences, USA, Feb. 17, 2009, vol. 106, No. 7 (pp. 2289-2294).

Xu et al., "Sequence determinants of improved CRISPR sgRNA design," Genome Research, Aug. 2015, vol. 25 (pp. 1147-1157).

Zetsche at el., "Cpf1 is a Single RNA-Guided Endonuclease of a Class 2 CRISPR-Cas System," Cell, Oct. 22, 2015, vol. 163, No. 3 (pp. 759-771).

Zetsche et al., "A split-Cas9 architecture for inducible genome editing and transcription modulation", Nature Biotechnology, Feb. 2015, vol. 33, No. 2 (pp. 139-142).

Zhang et al., "Efficient Construction of Sequence-Specific TAL Effectors for Modulating Mammalian Transcription," Nature Biotechnology, Feb. 2011 (published on-line Jan. 19, 2011), Feb. 2011 (published on-line Jan. 19, 2011), vol. 29, No. 2 (pp. 149-153).

Zhang, X., "Broadband Terahertz Wave Deflection Based on C-shape Complex Metamaterials with Phase Discontinuities," Advanced Materials, Sep. 2013, vol. 25, No. 33 (pp. 4641-4645).

Zhou et al., "Aptamer-targeted cell-specific RNA interference," Silence, Feb. 1, 2010, vol. 1, No. 4 (10 pages).

Zou et al., Intrathecal Lentiviral-Mediated RNA Interference Targeting PKC-gamma Attenuates Chronic Constriction Injury-Induced Neuropathic Pain in Rats, Human Gene Therapy, Nov. 19, 2010, vol. 22, No. 4 (pp. 465-475).

Zuker et al., "Optimal computer folding of large RNA sequences using thermodynamics and auxiliary information," Nucleic Acids Research, Jan. 10, 1981, vol. 9, No. 1 (pp. 133-148).

\* cited by examiner

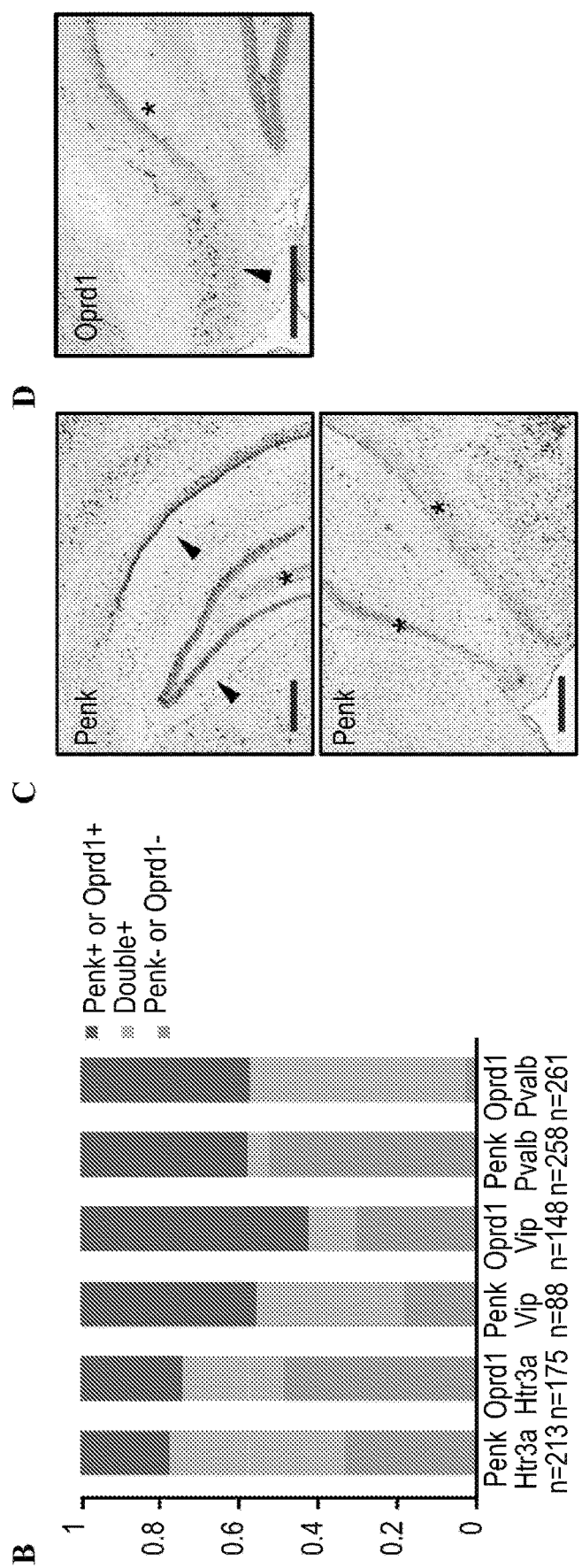
FIG. 21B-D

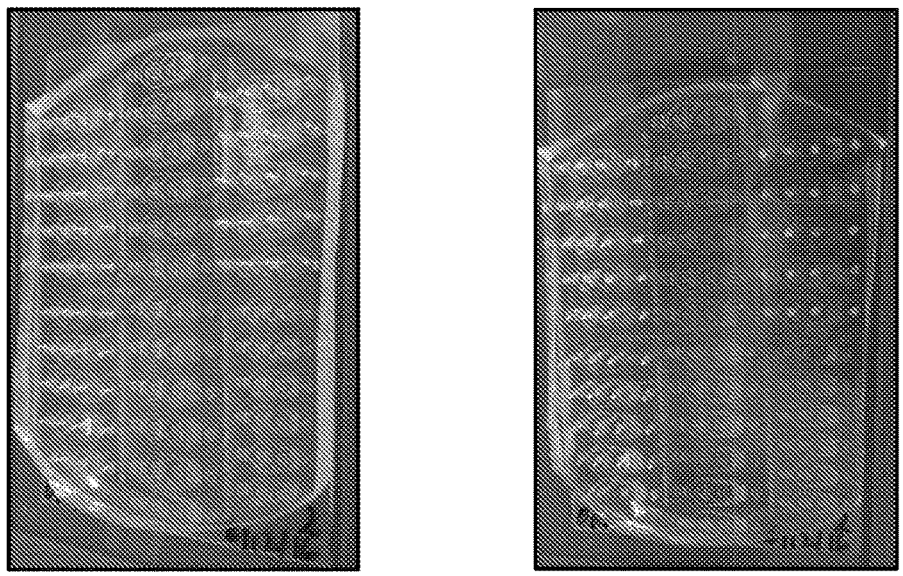
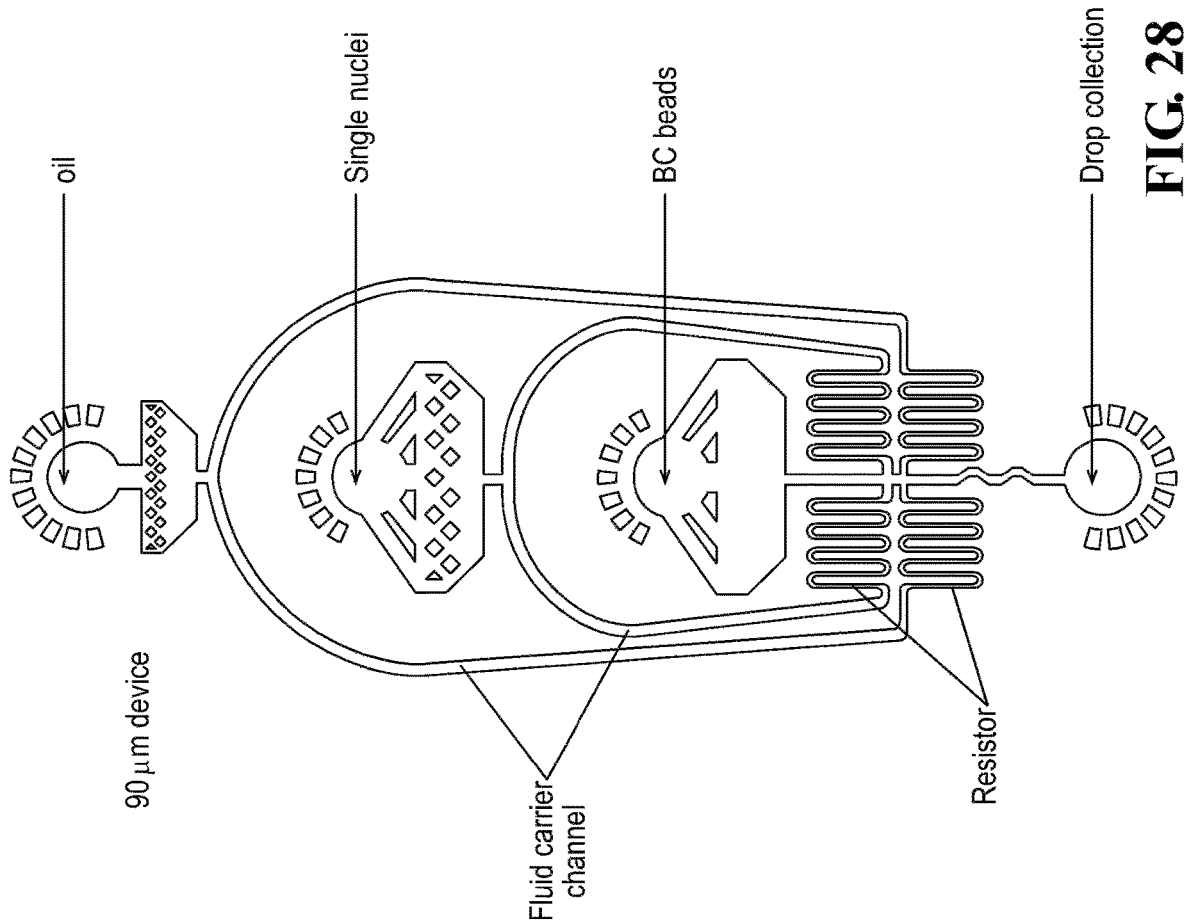
FIG. 28

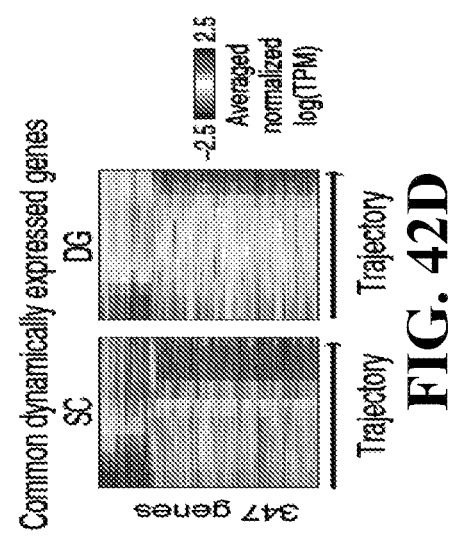
FIG. 42D
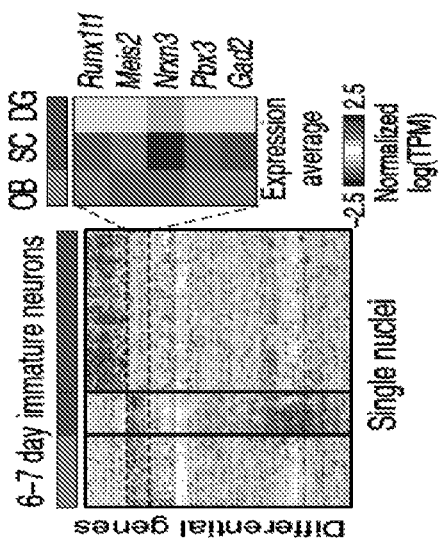
FIG. 42F
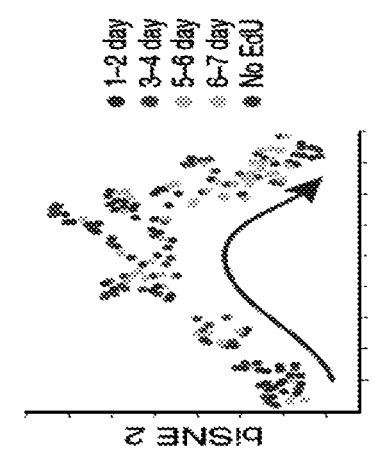
FIG. 42C
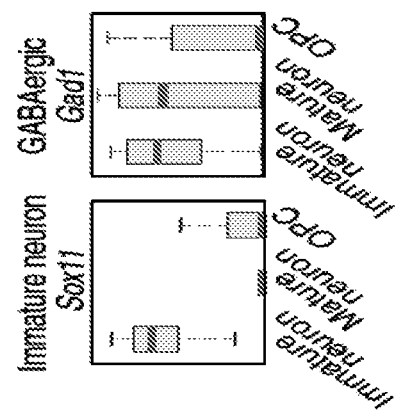
FIG. 42E
FIG. 42A
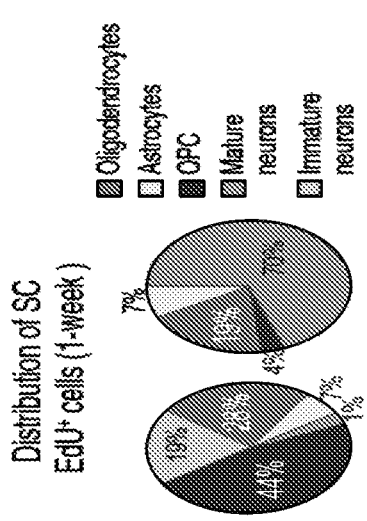
FIG. 42B

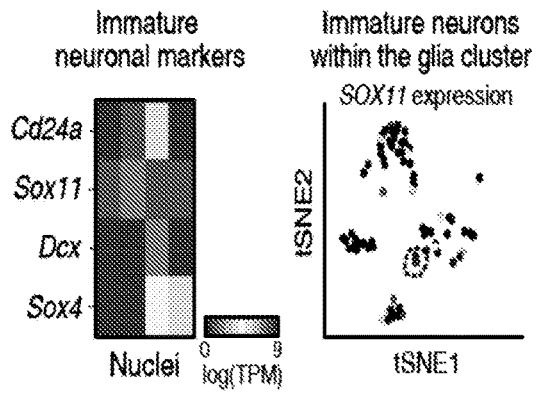
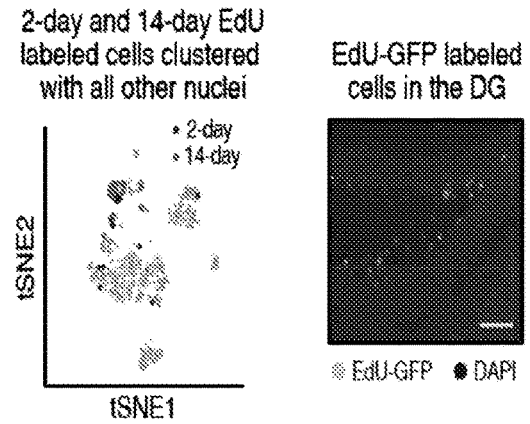
FIG. 43A  FIG. 43B  FIG. 43C
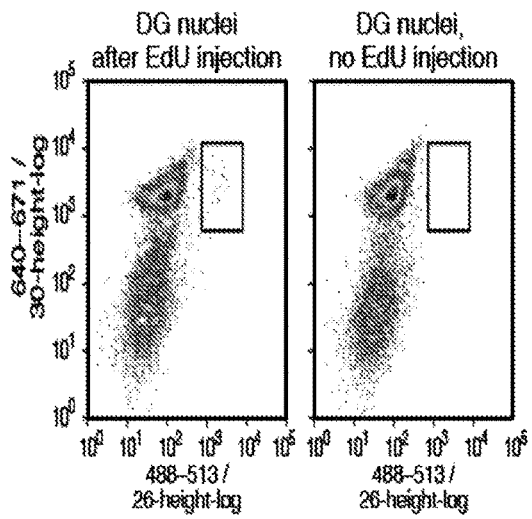
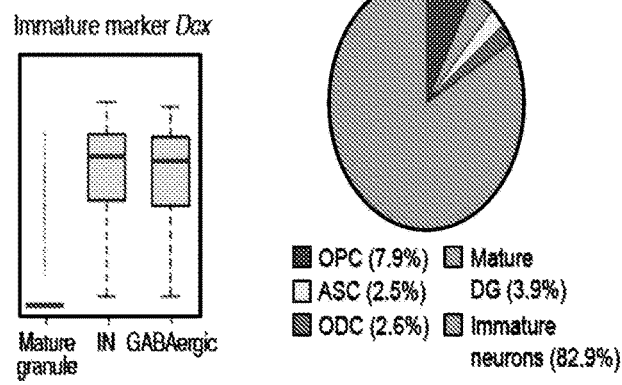
FIG. 43D  FIG. 43E  FIG. 43F
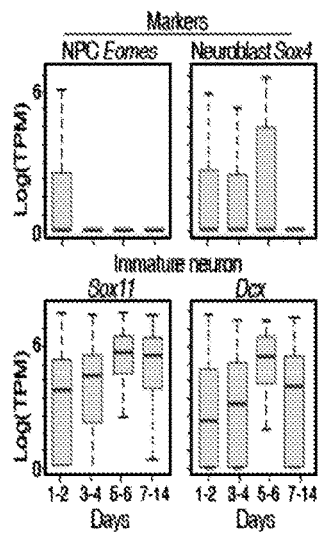
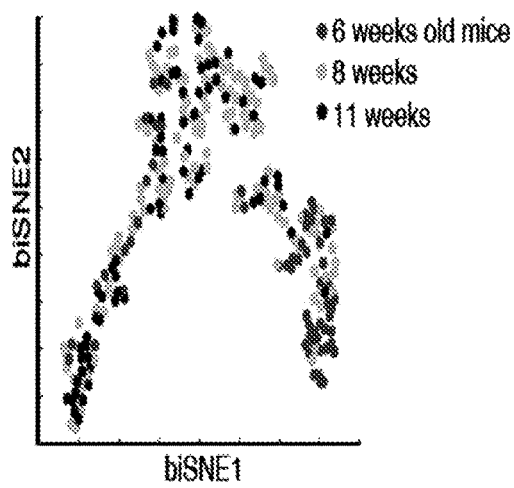
FIG. 43G  FIG. 43H

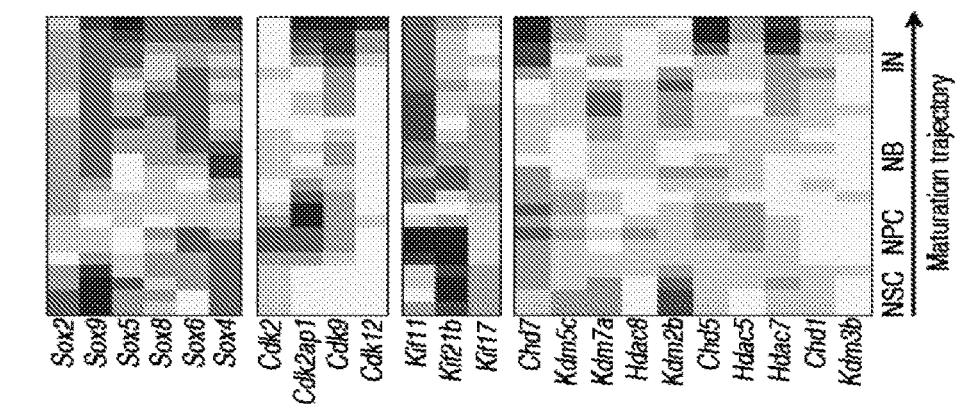
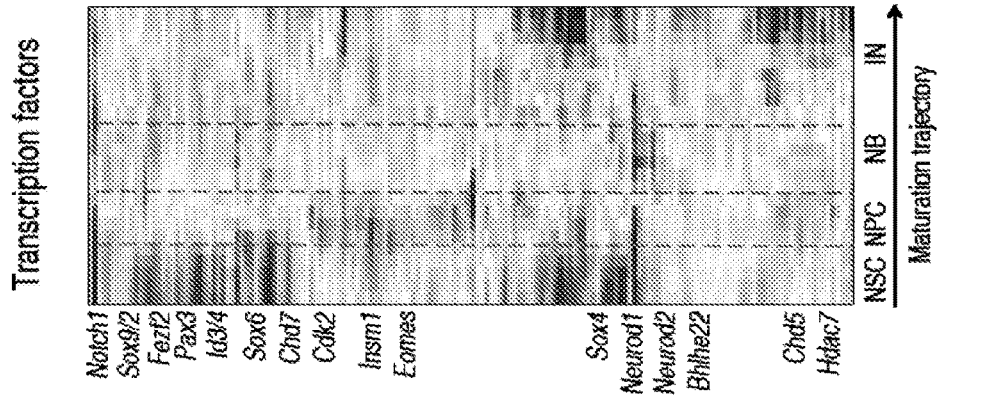
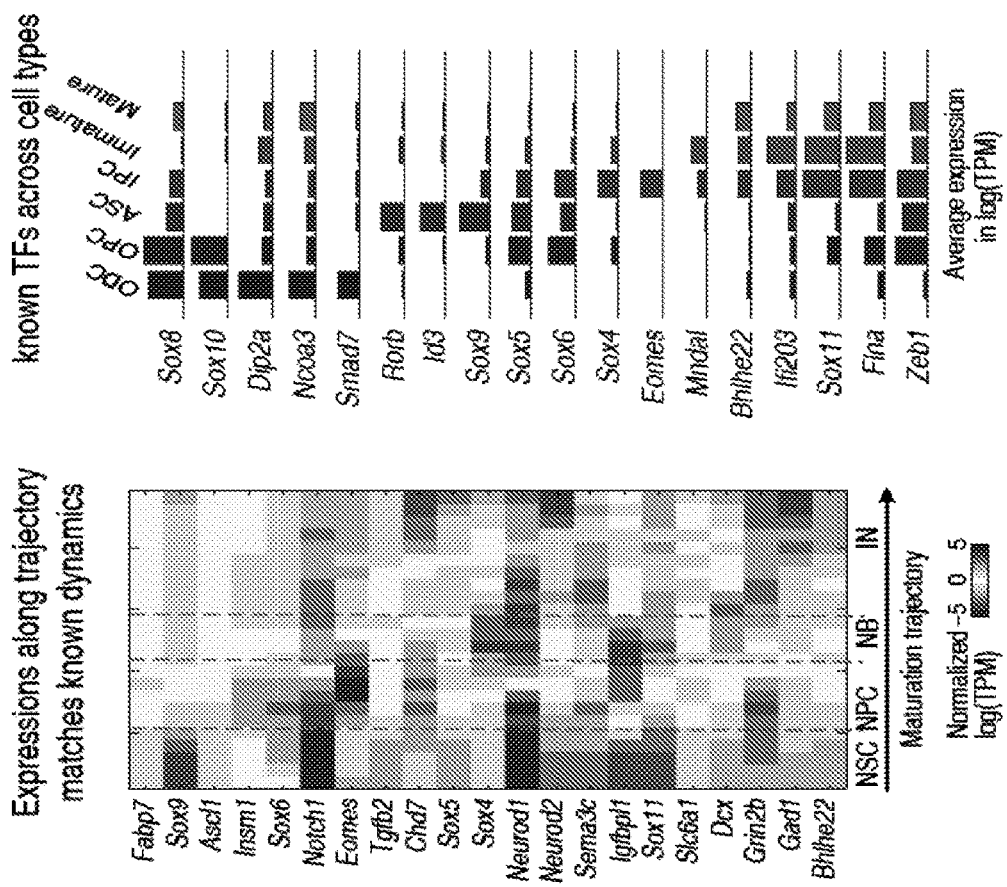
FIG. 44A  FIG. 44B  FIG. 44C  FIG. 44D

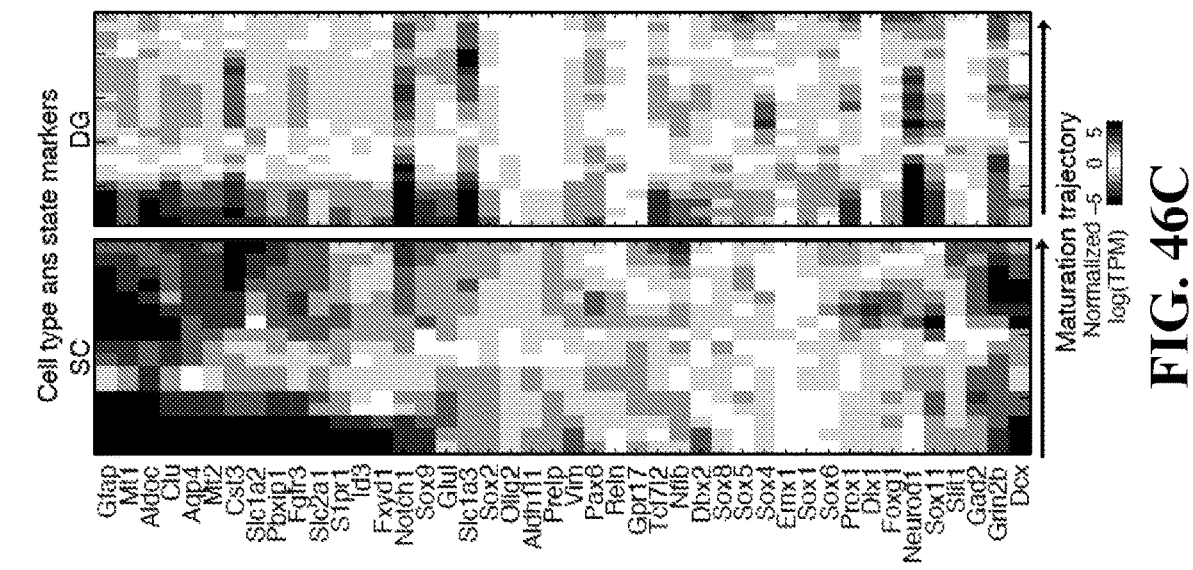
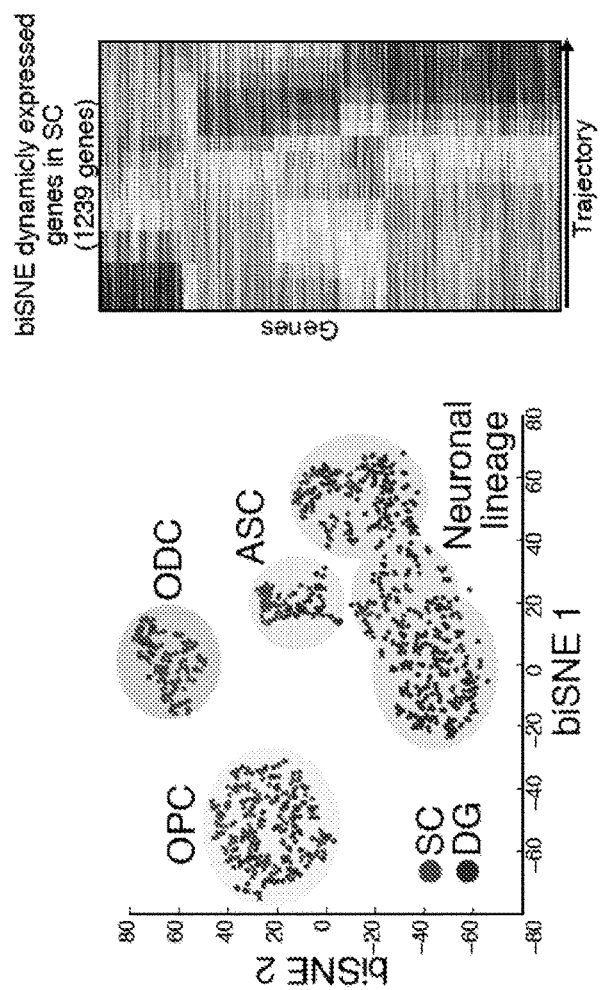
FIG. 46A
FIG. 46B
FIG. 46C

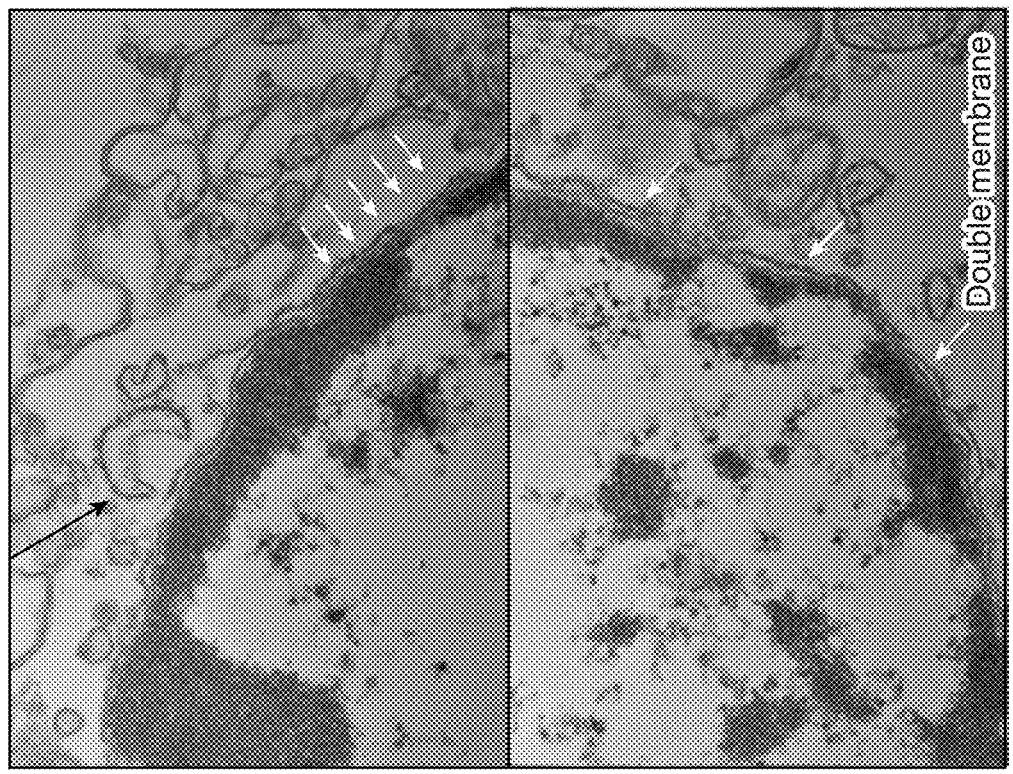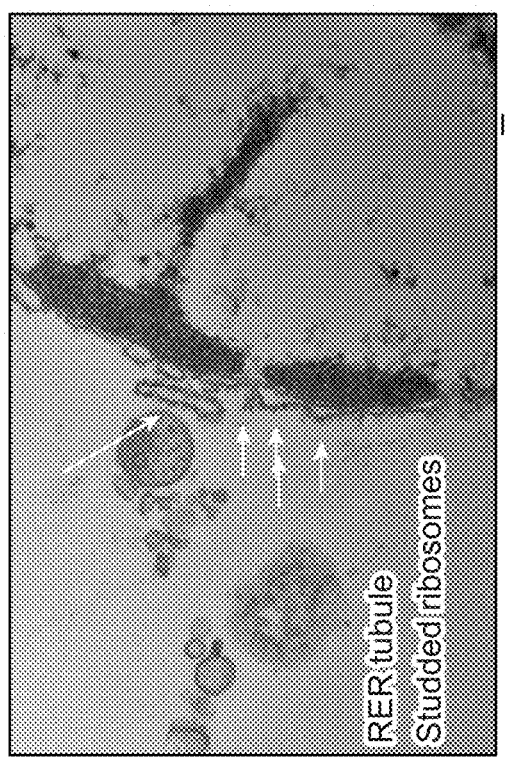
FIG. 57

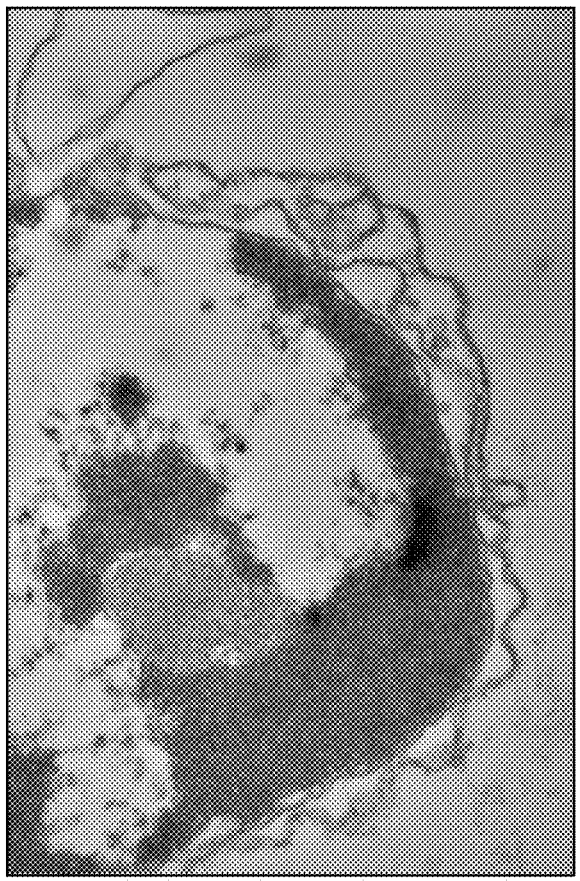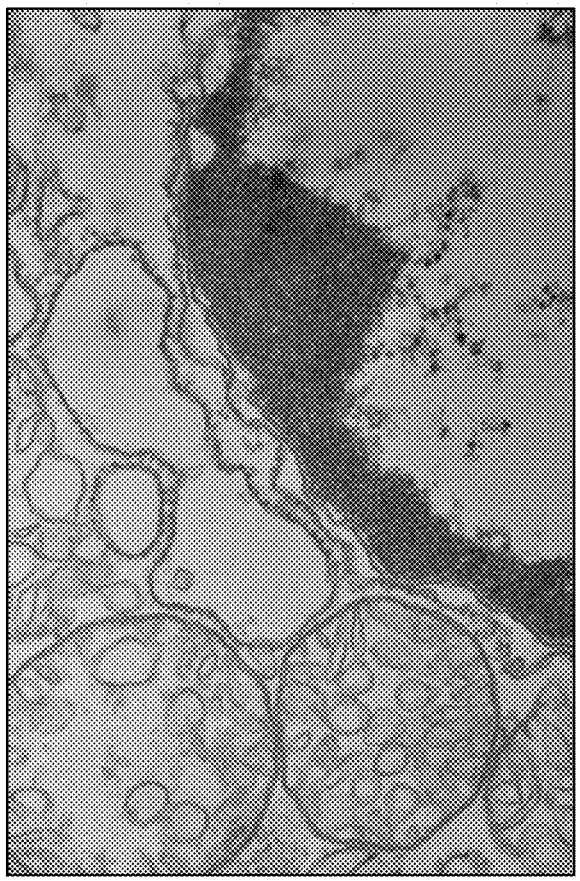
FIG. 59

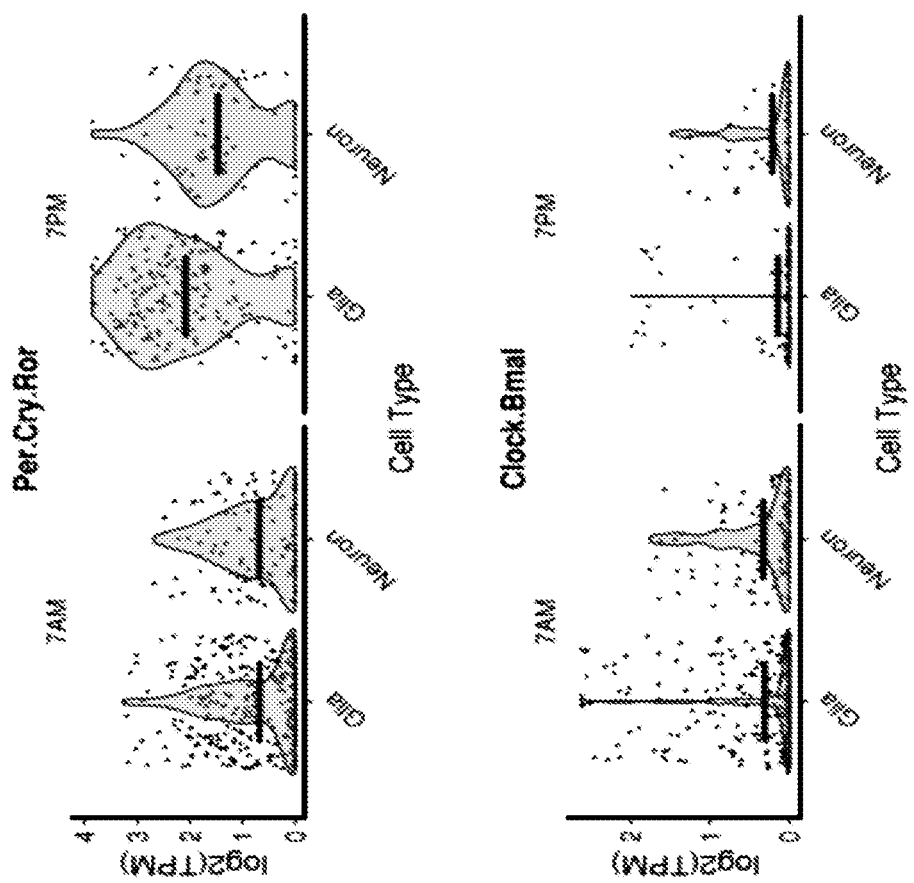
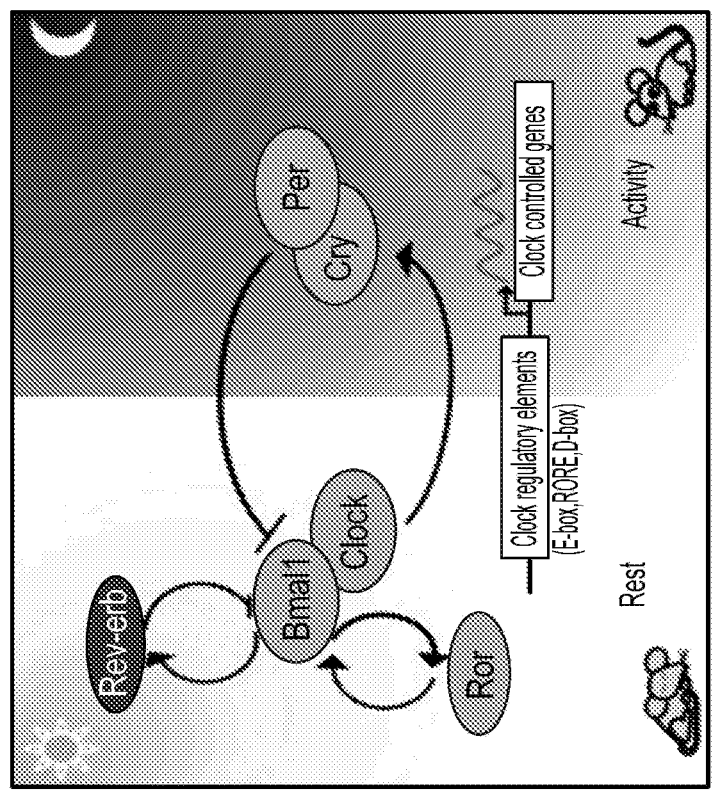
FIG. 63C

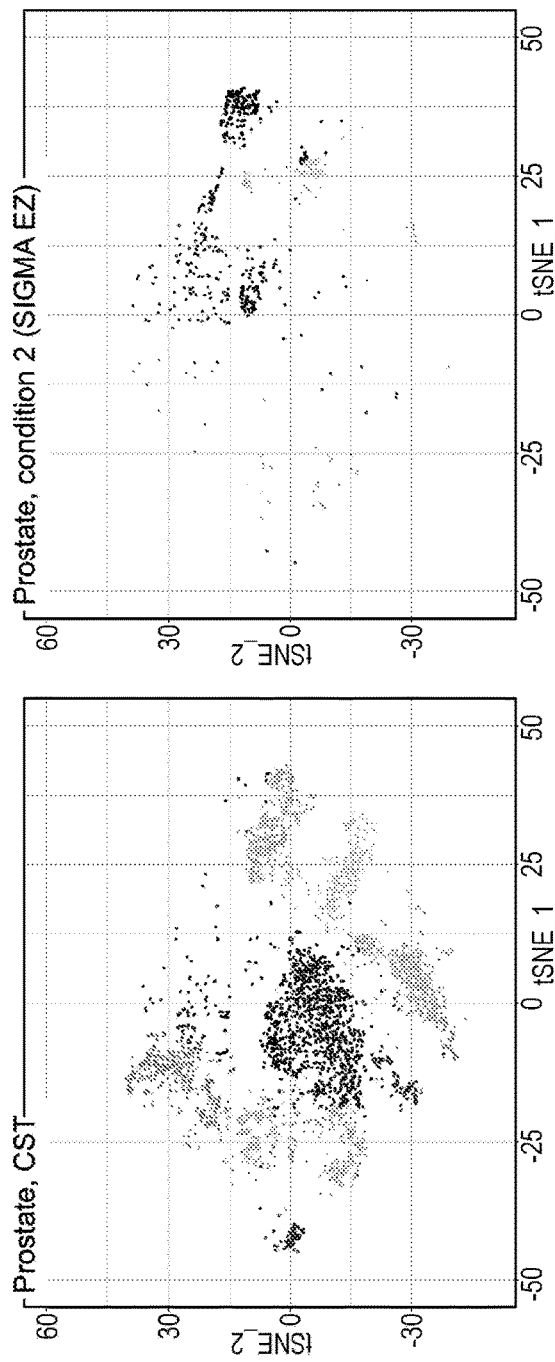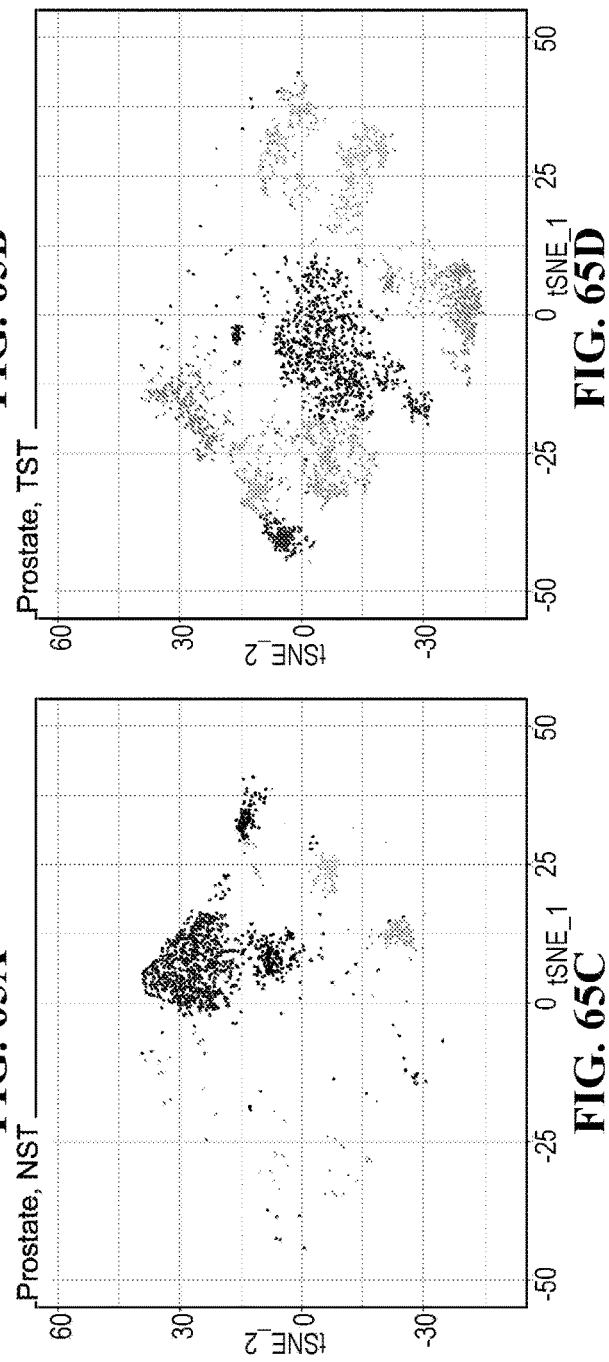

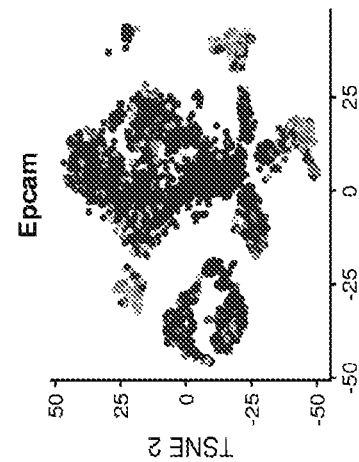
FIG. 66C
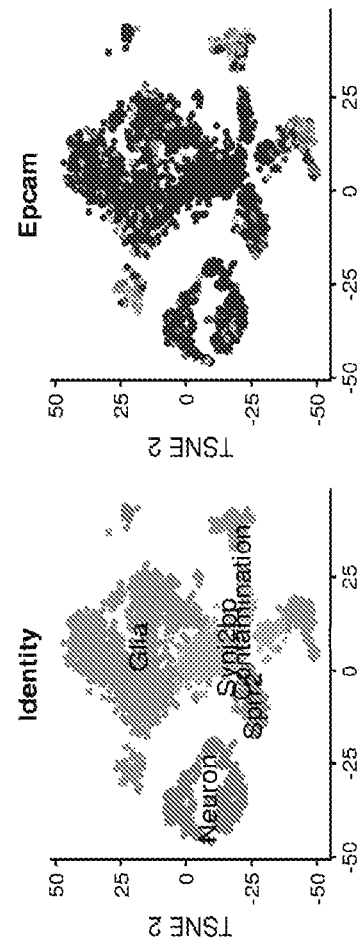
FIG. 66B
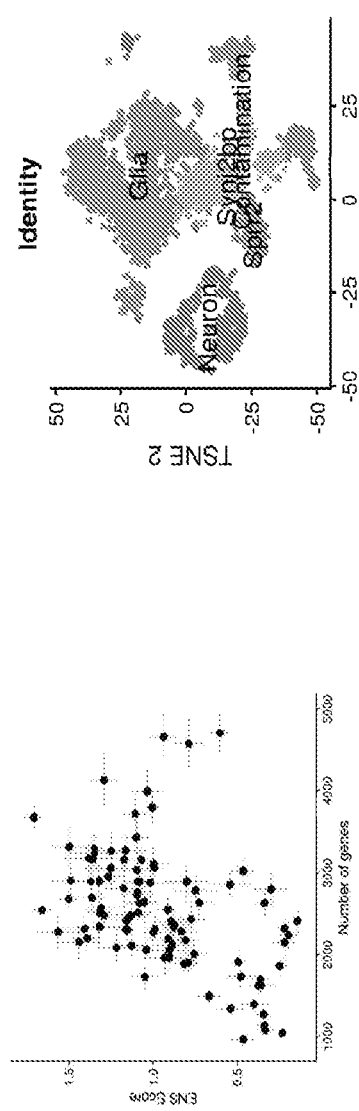
FIG. 66A
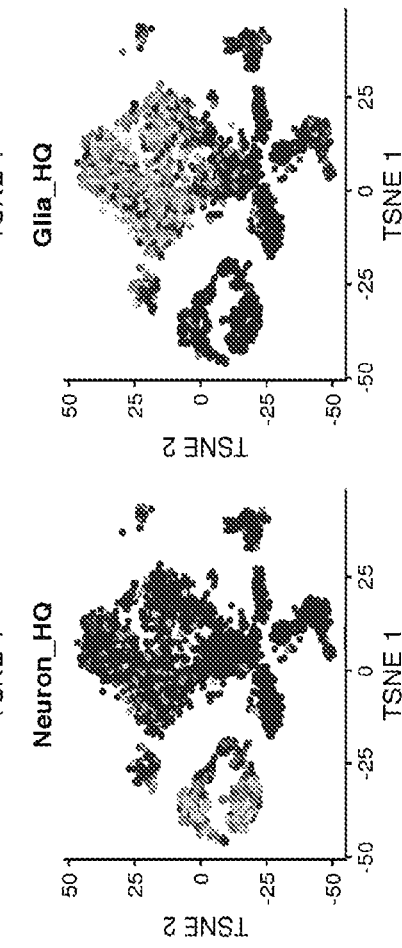
FIG. 66F
FIG. 66E
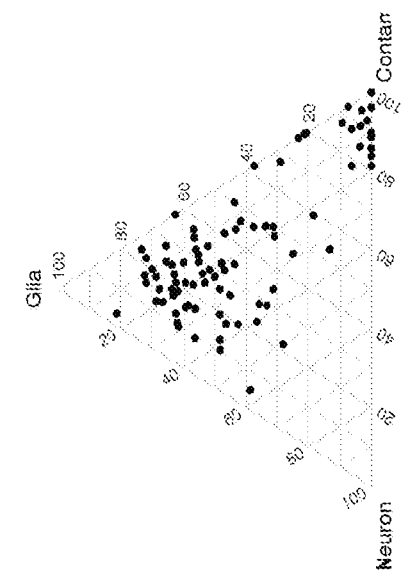
FIG. 66D

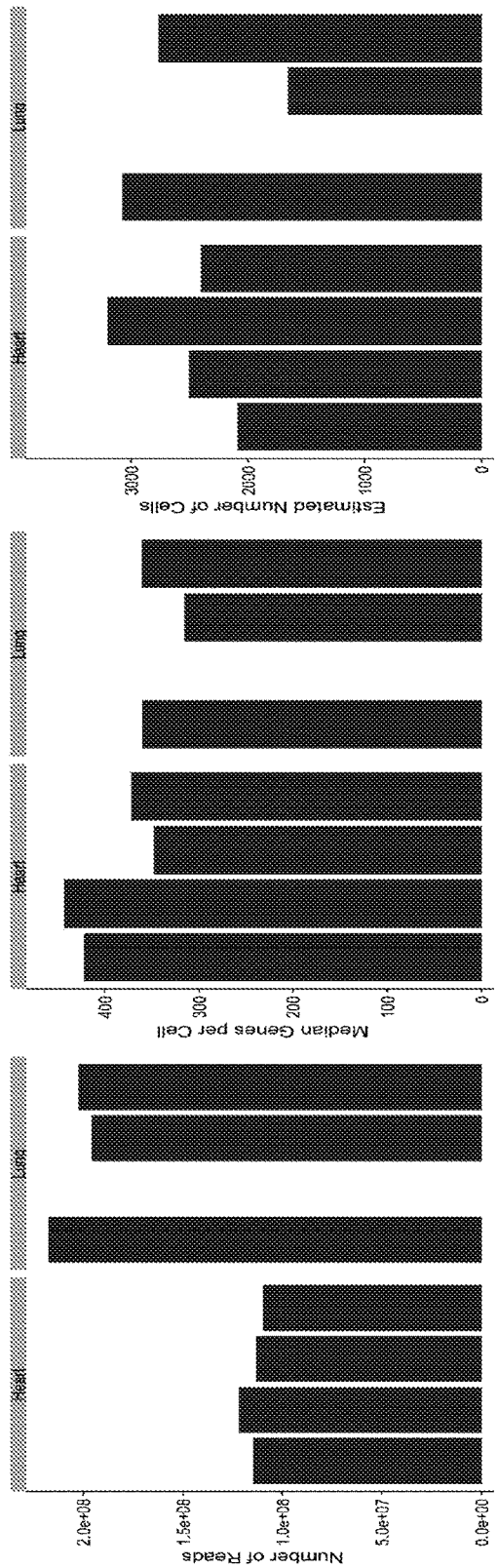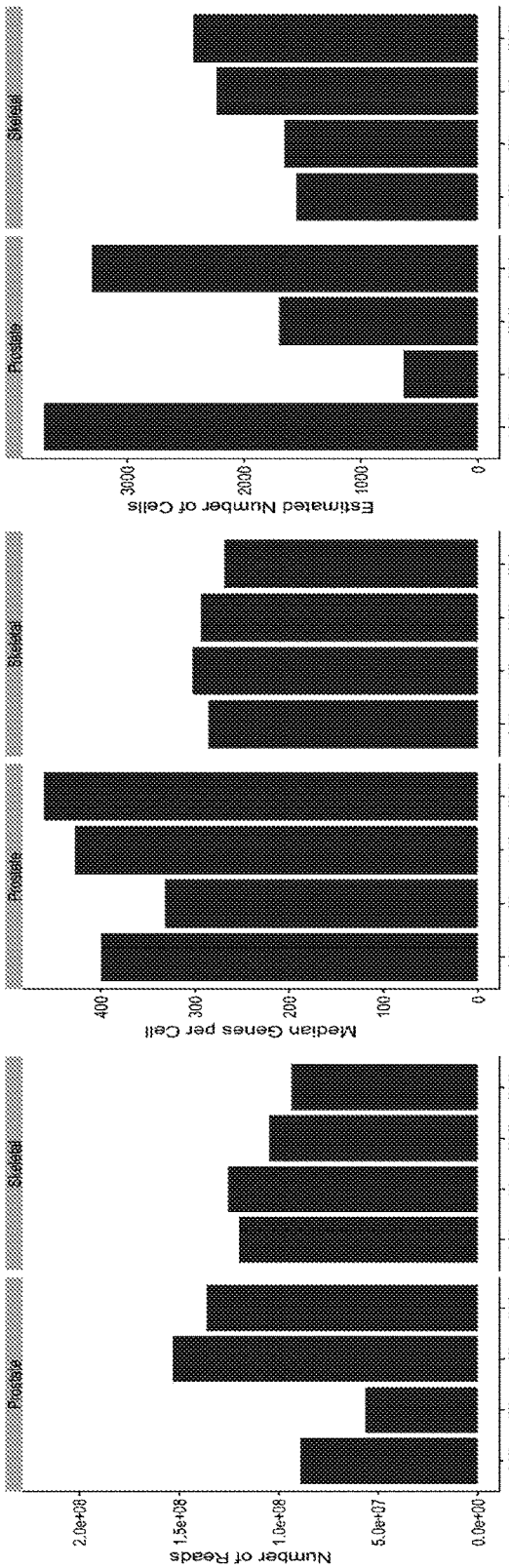

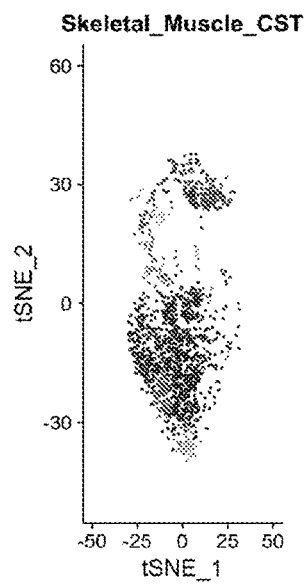 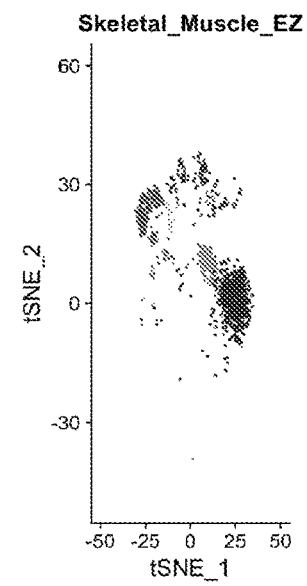 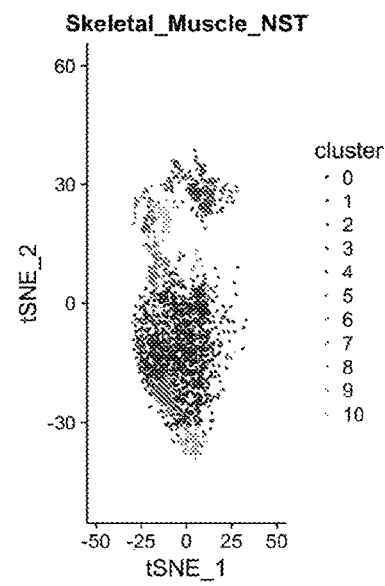
FIG. 77A  FIG. 77B  FIG. 77C
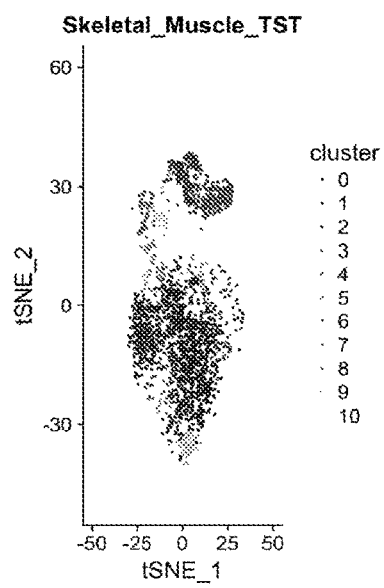 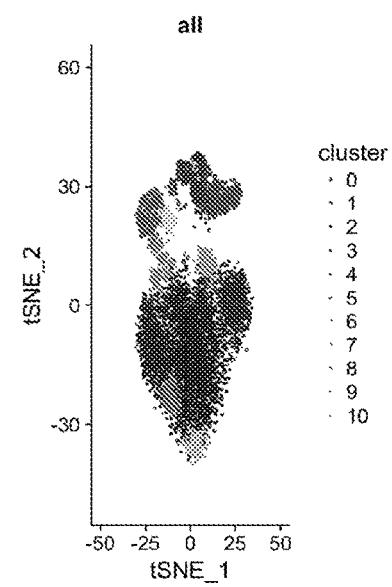
FIG. 77D  FIG. 77E

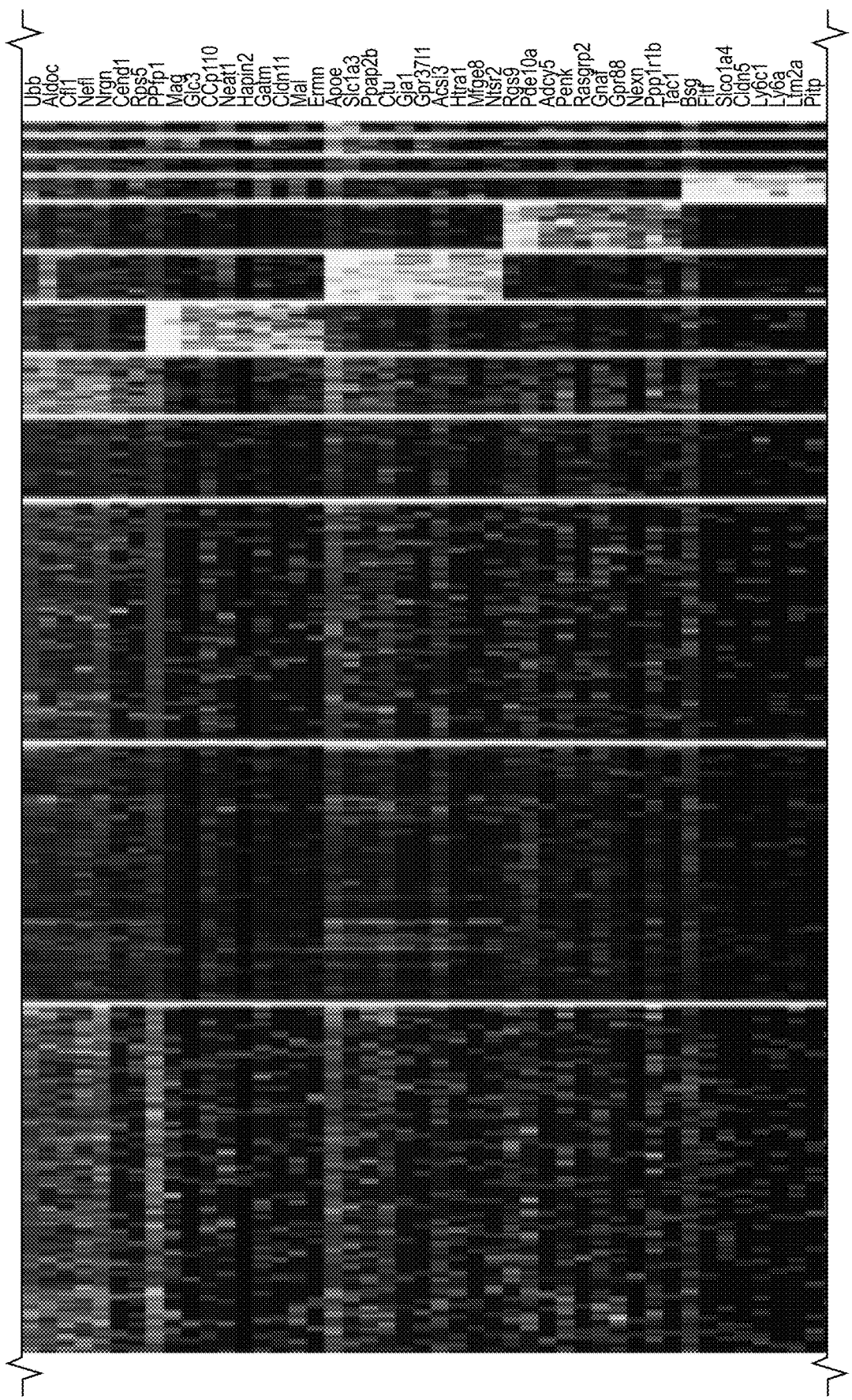
FIG. 84 (Cont. 1)

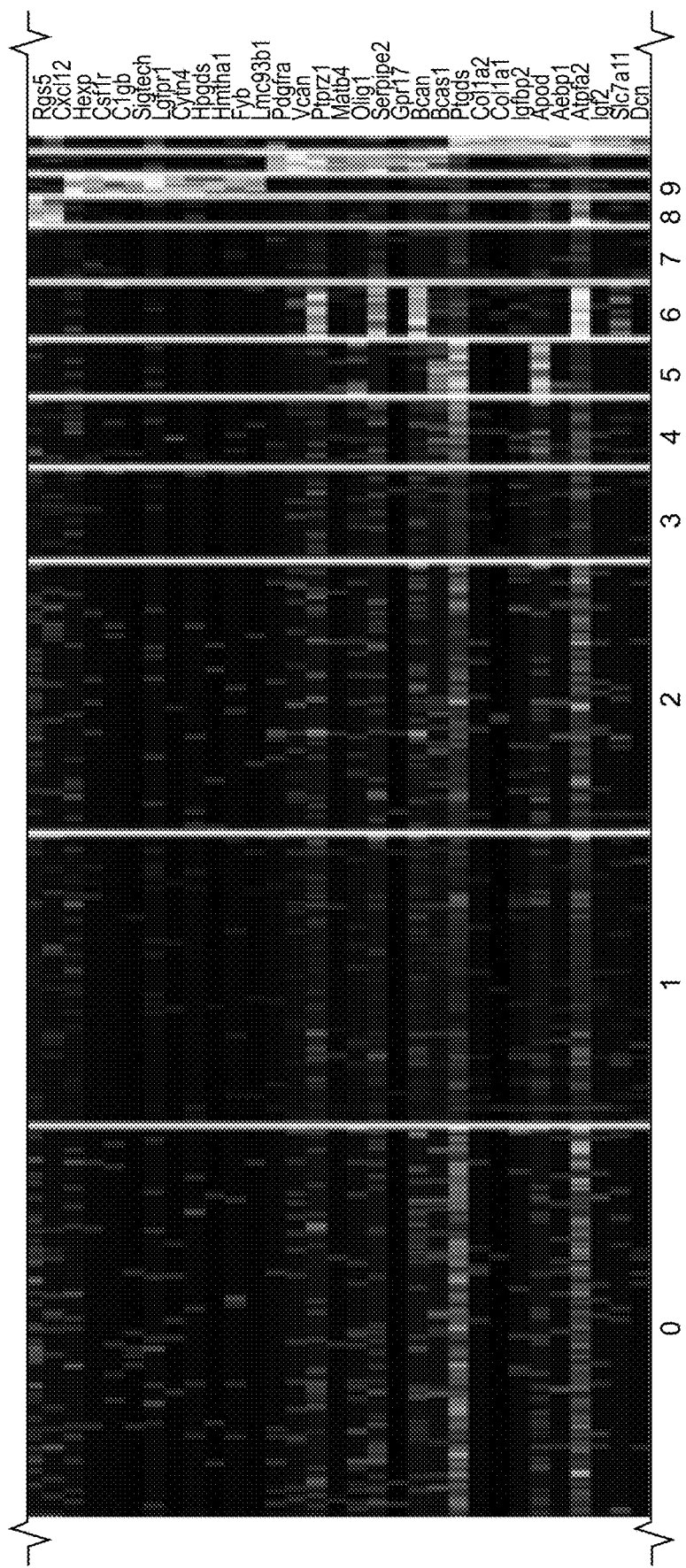
FIG. 84 (Cont. 2)

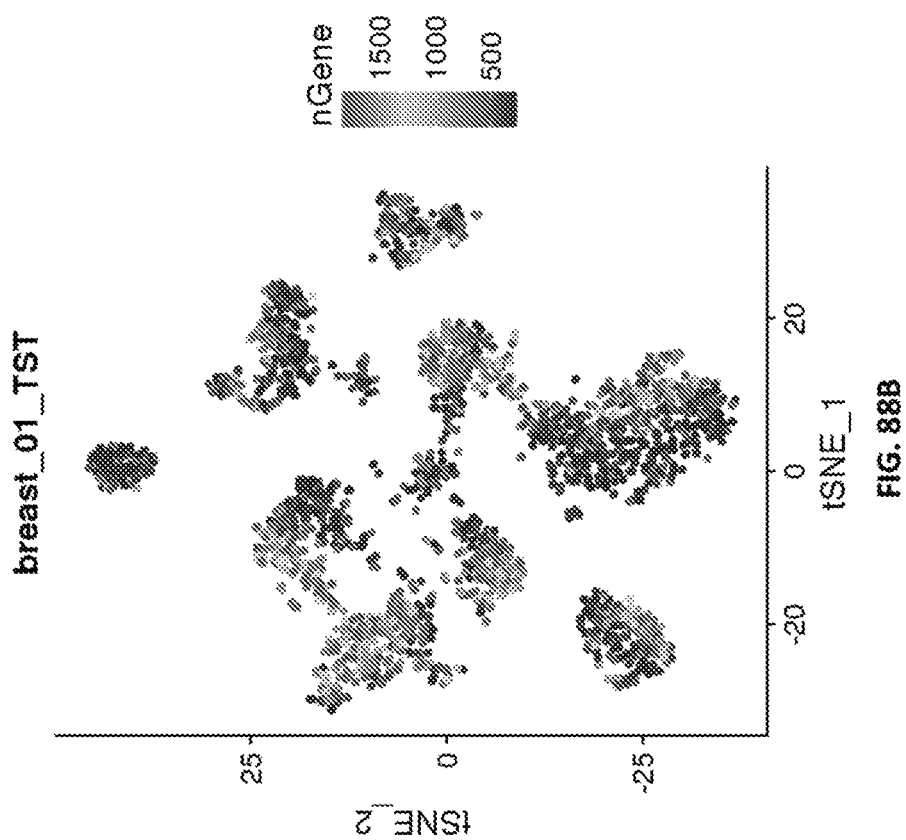
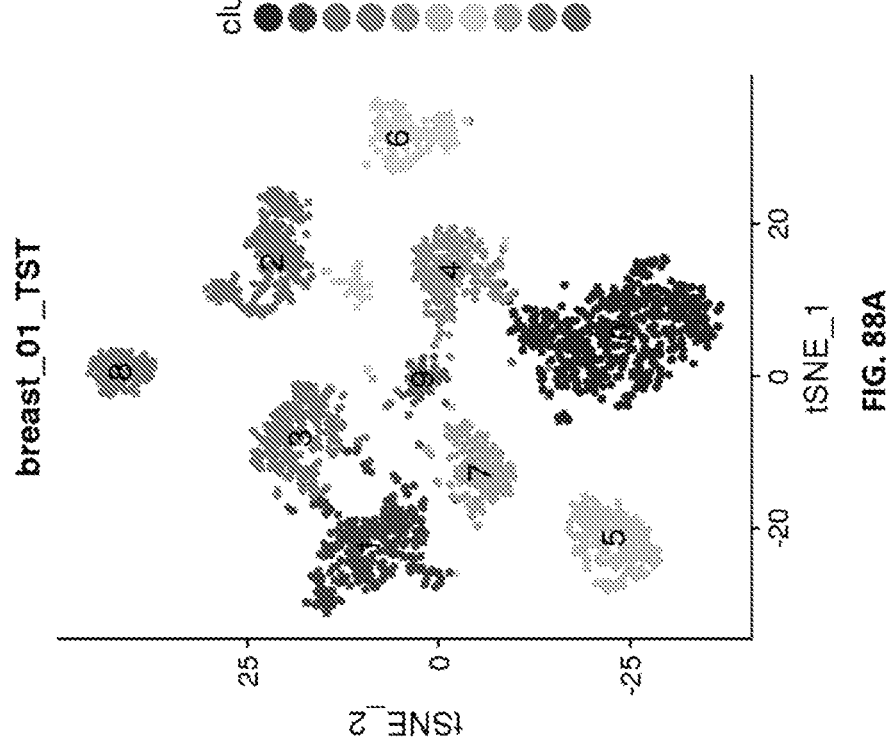
FIG. 88A
FIG. 88B

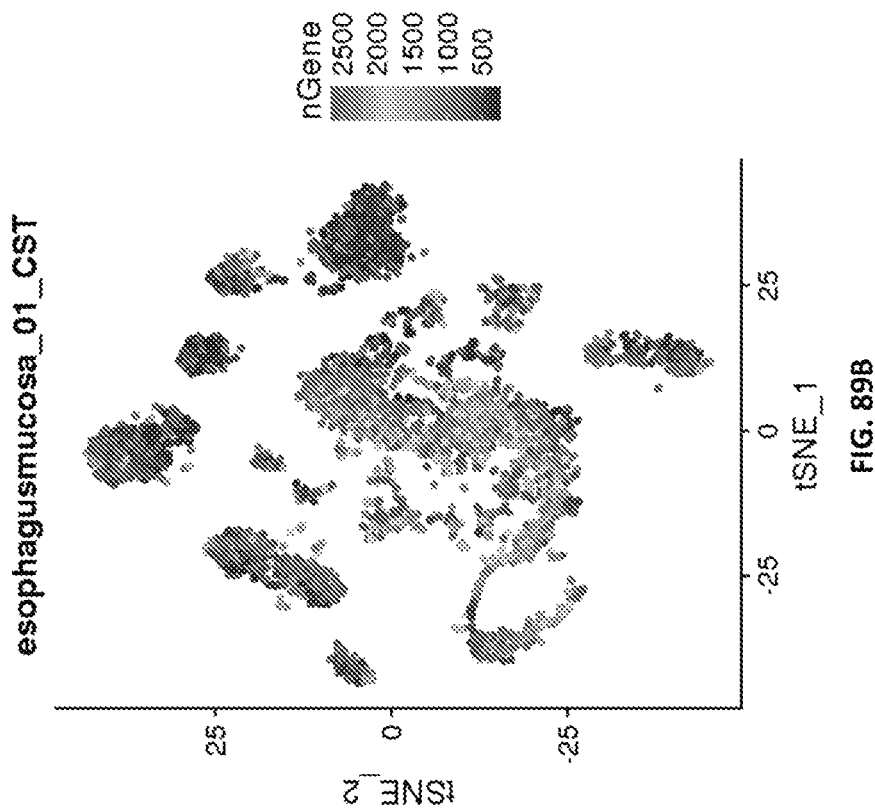
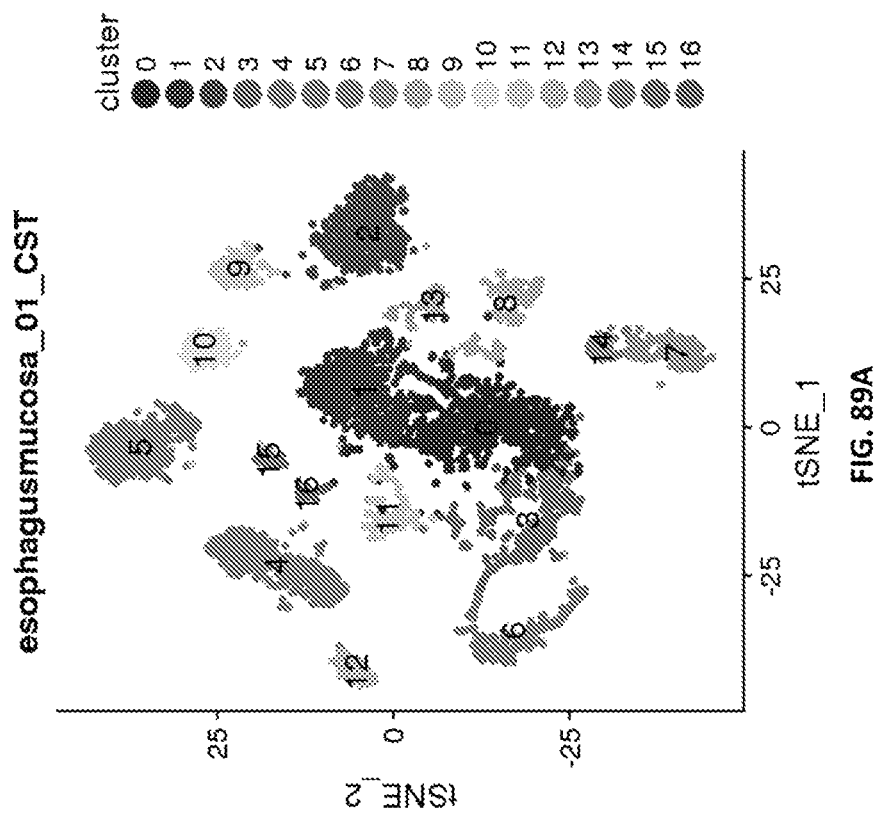
FIG. 89A
FIG. 89B

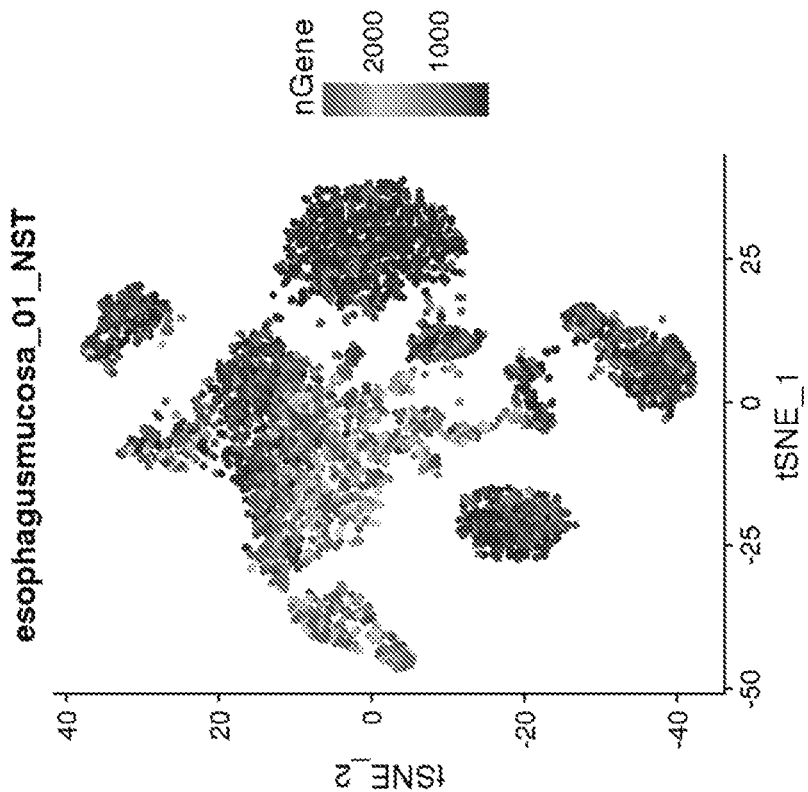
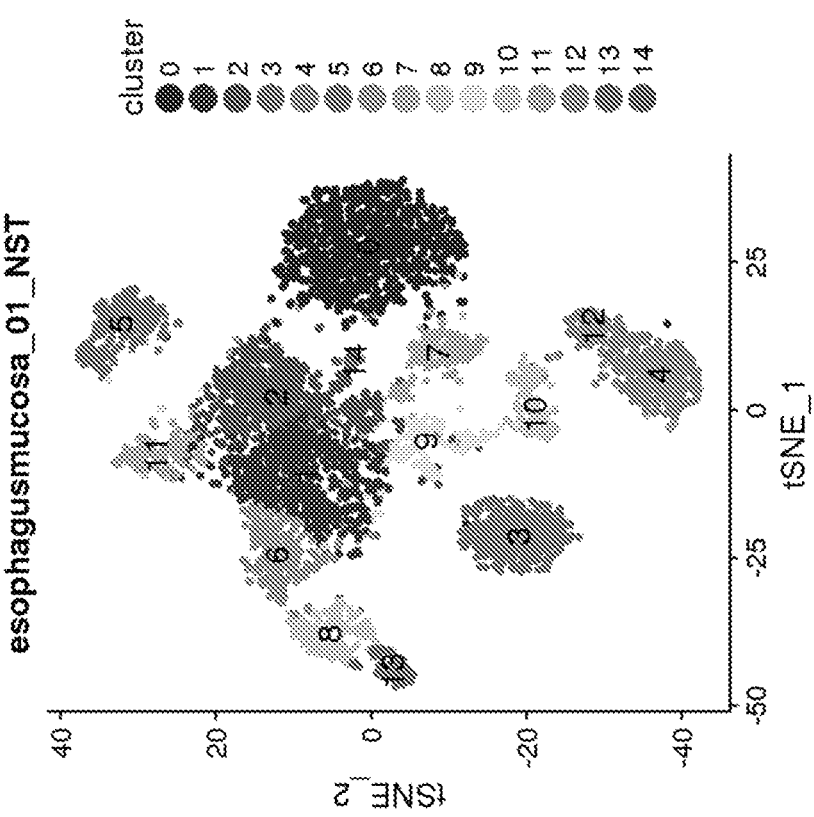
FIG. 91B
FIG. 91A

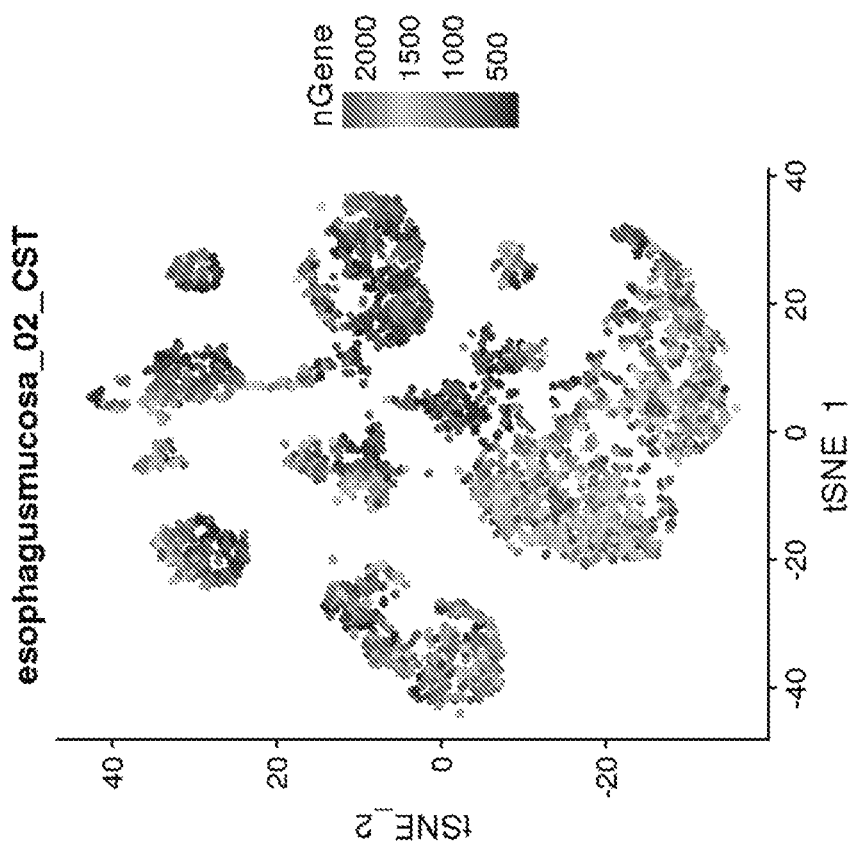
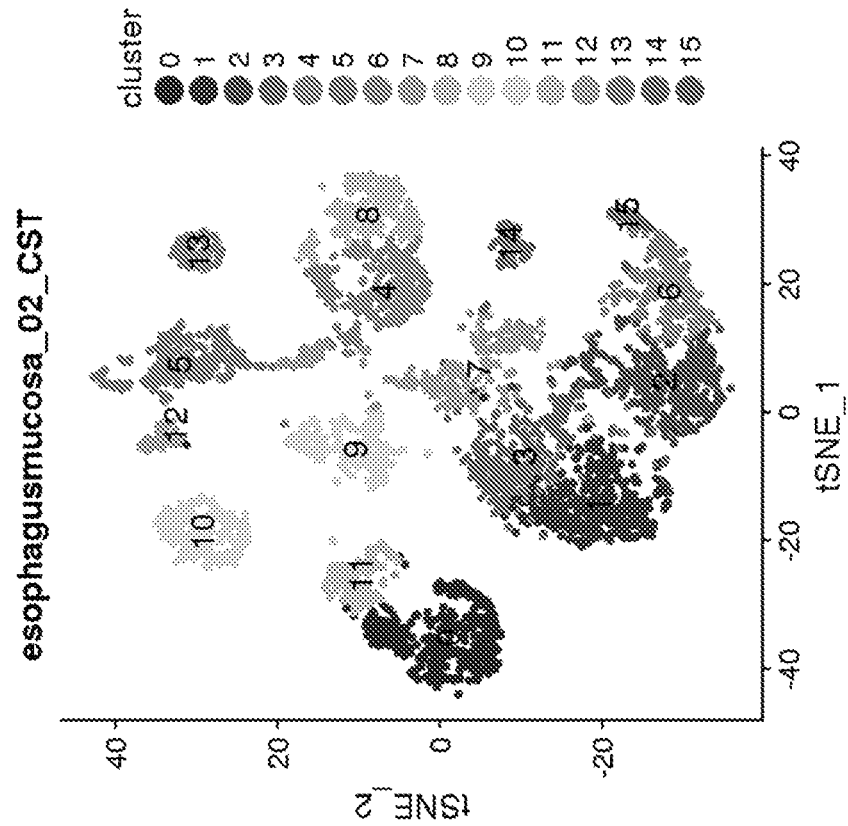
FIG. 93A
FIG. 93B

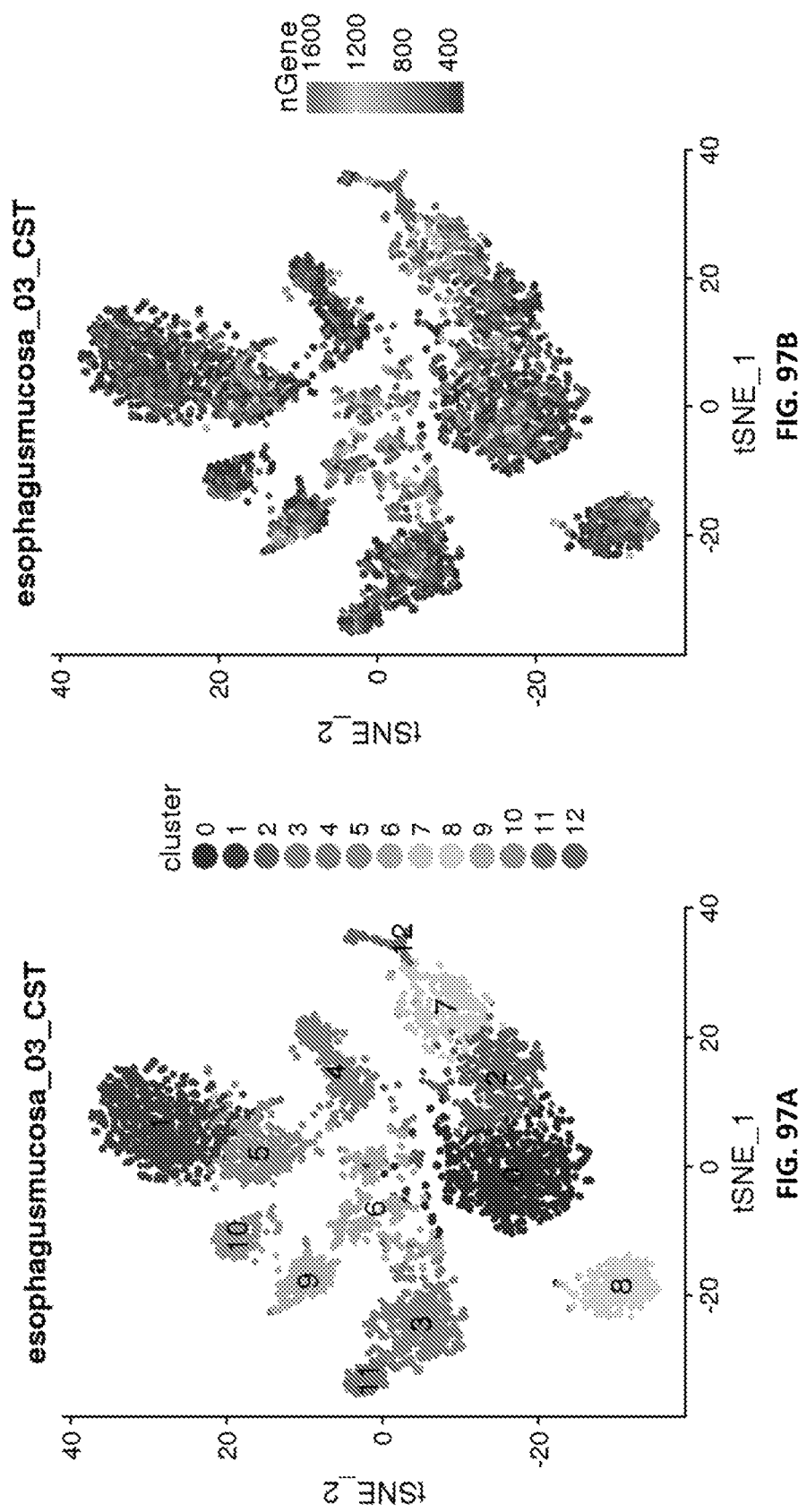

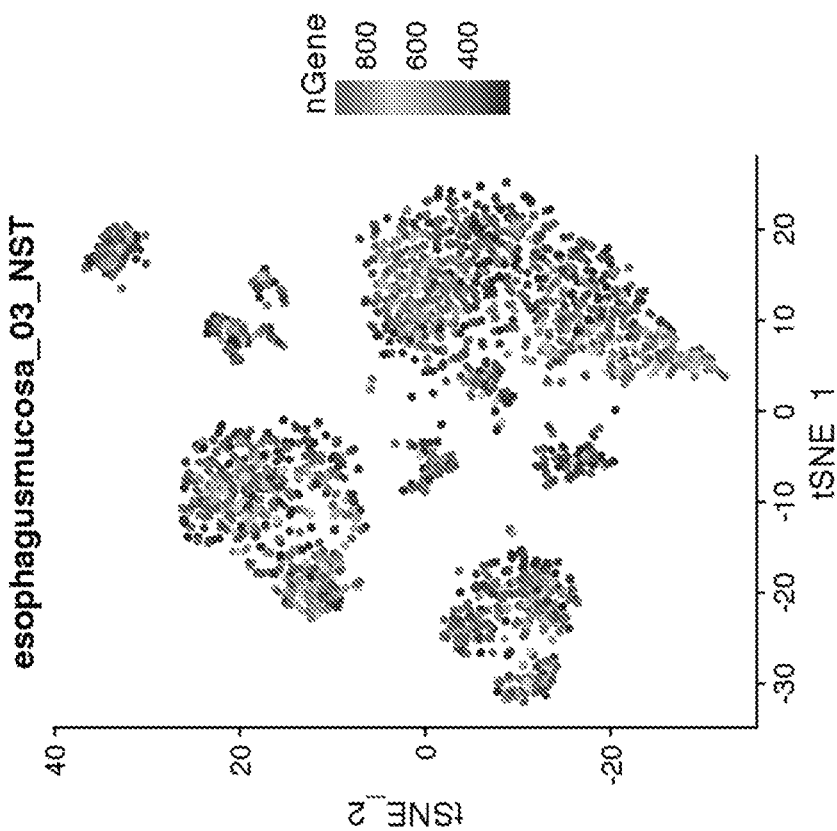
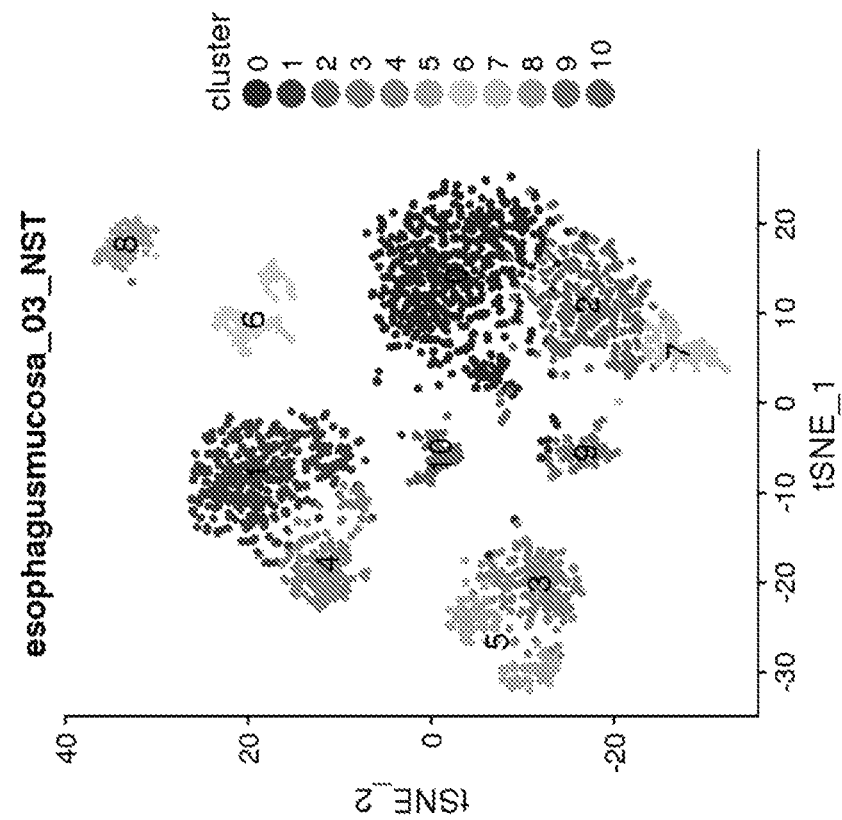
FIG. 99B
FIG. 99A

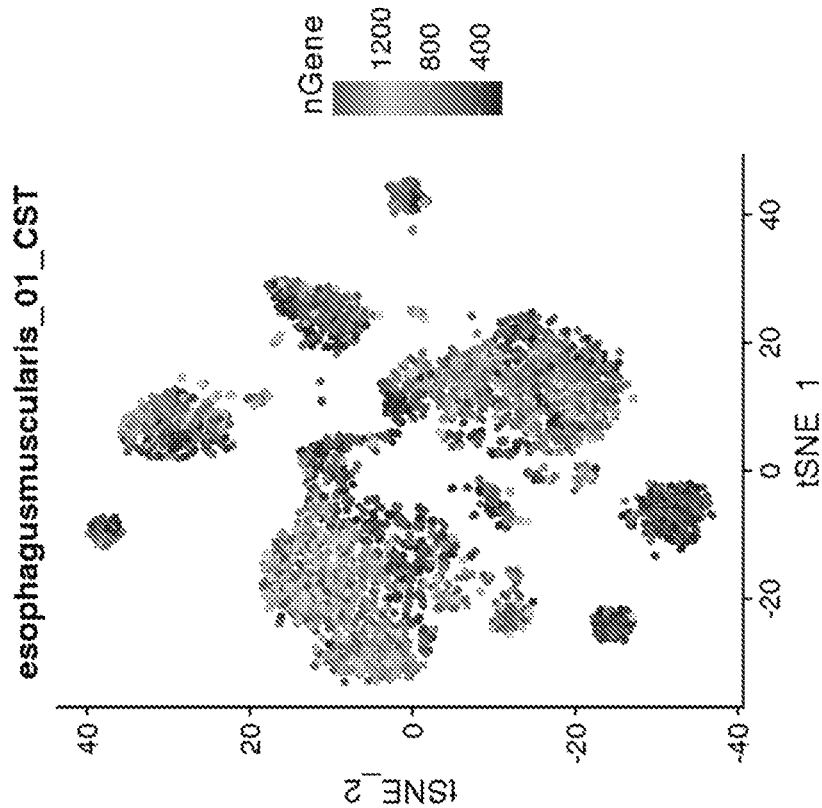
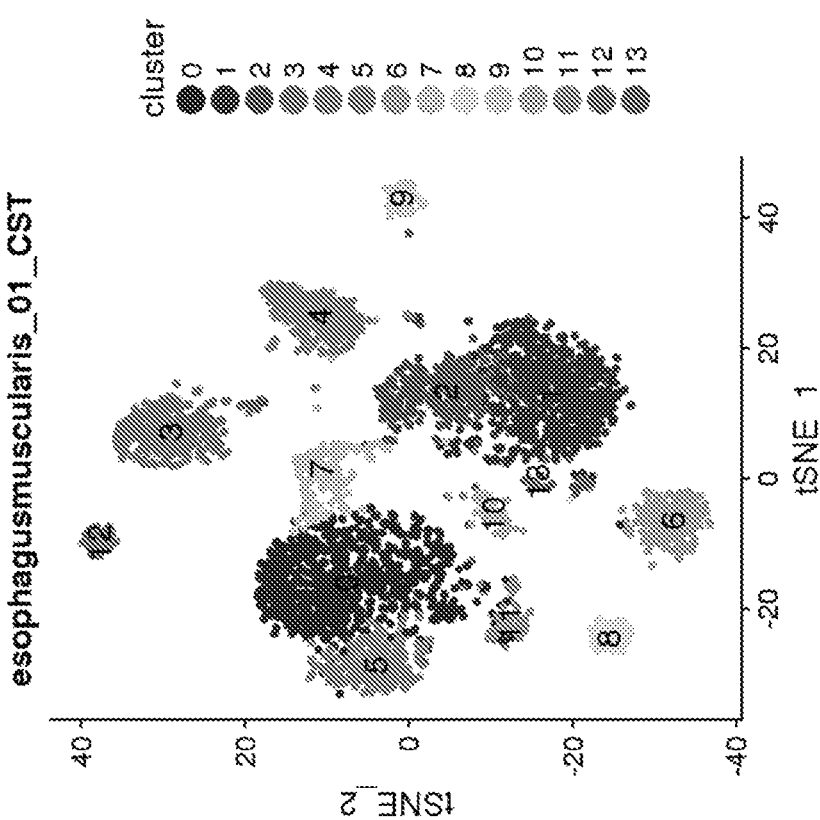
FIG. 101A
FIG. 101B

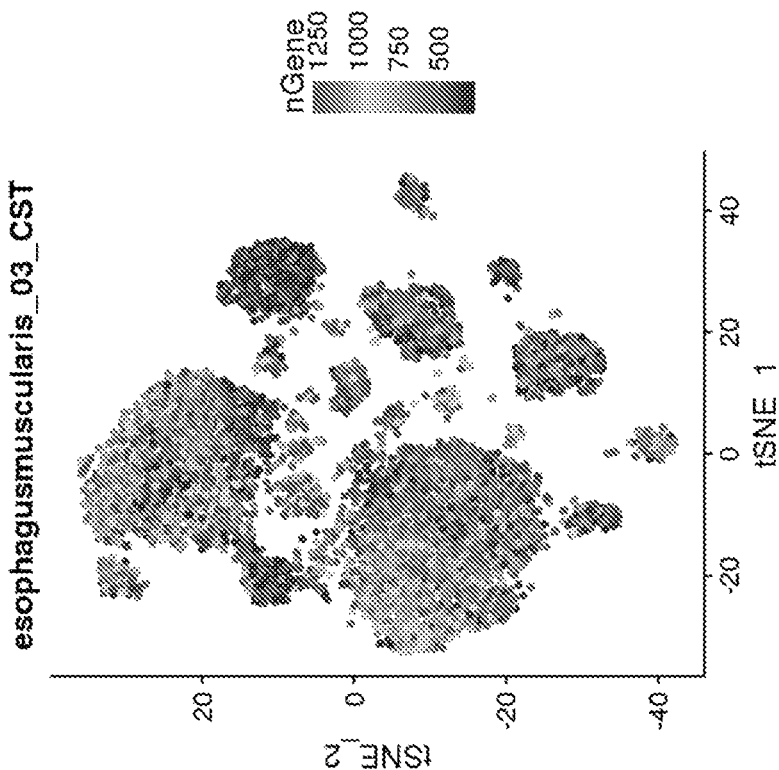
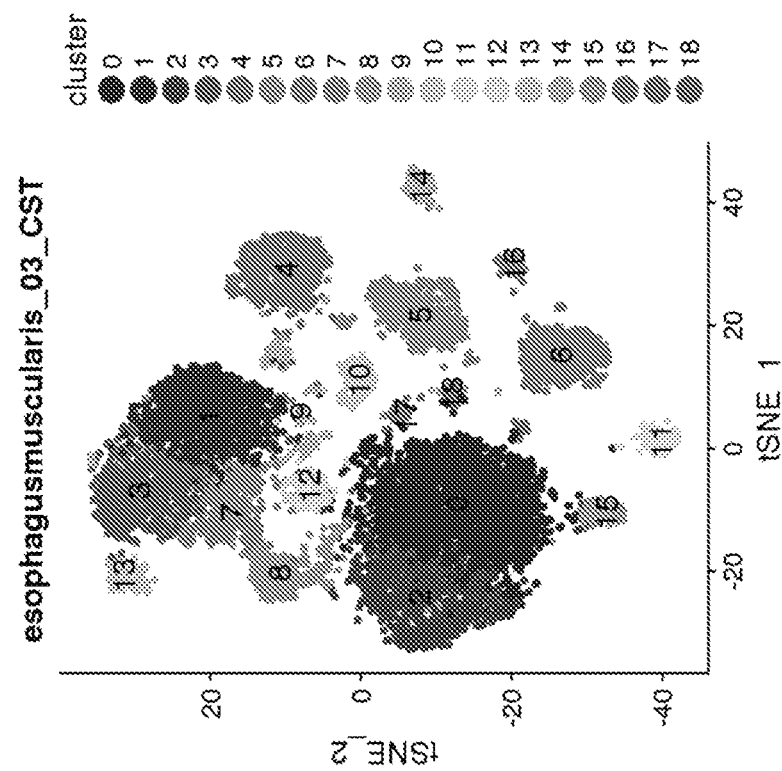
FIG. 109A
FIG. 109B

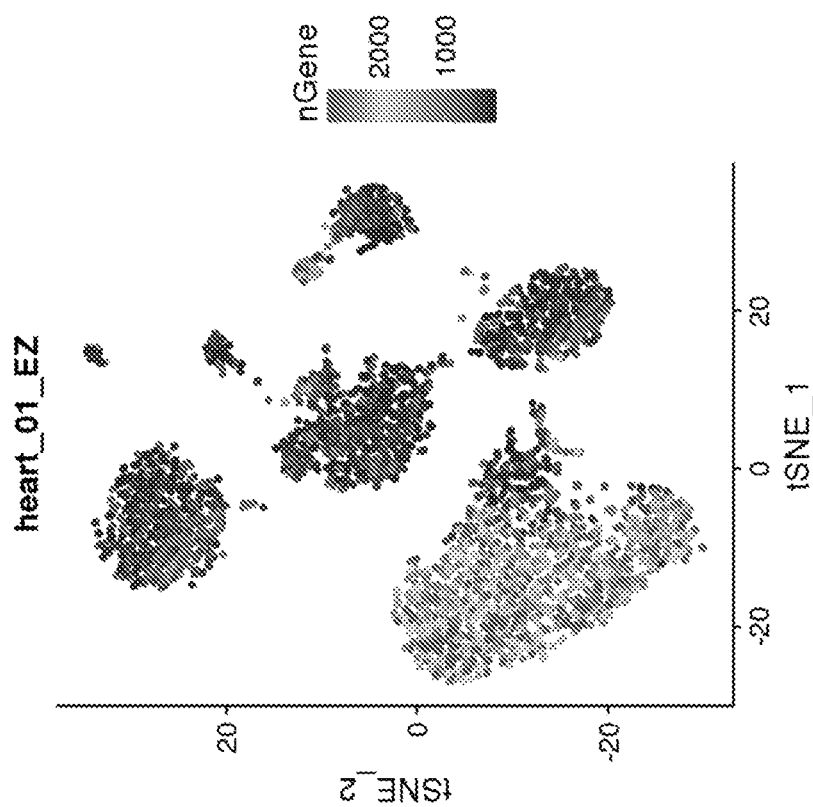
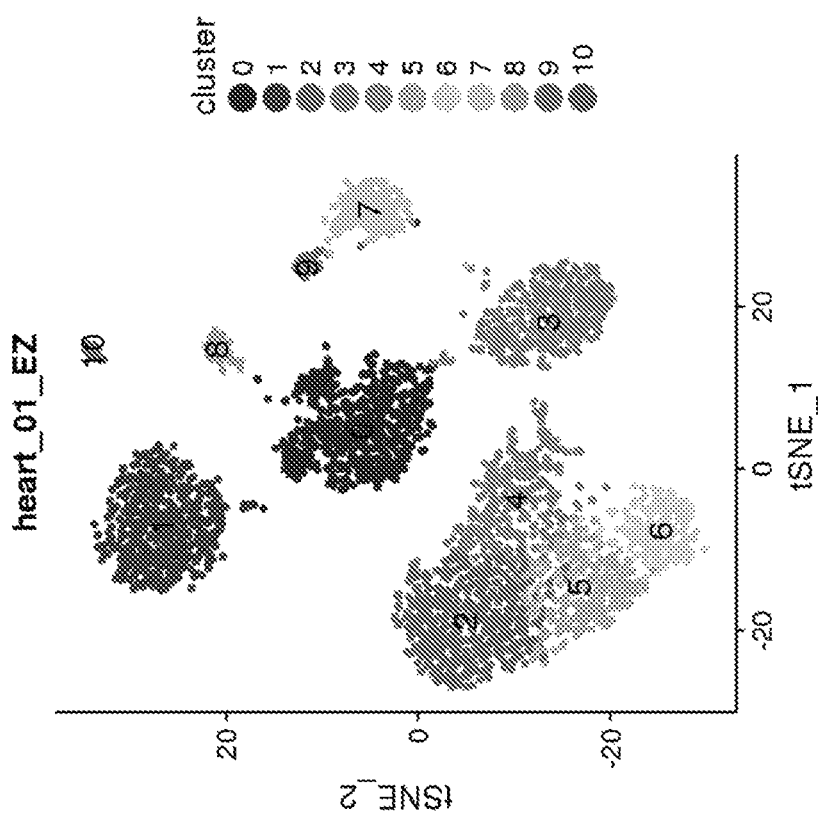
FIG. 114B
FIG. 114A

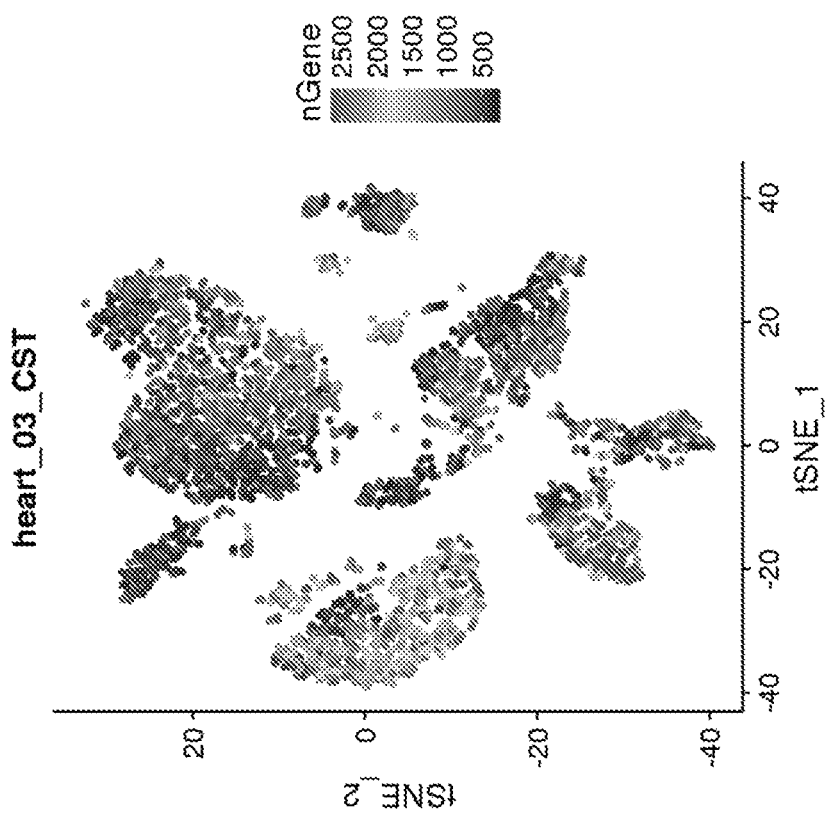
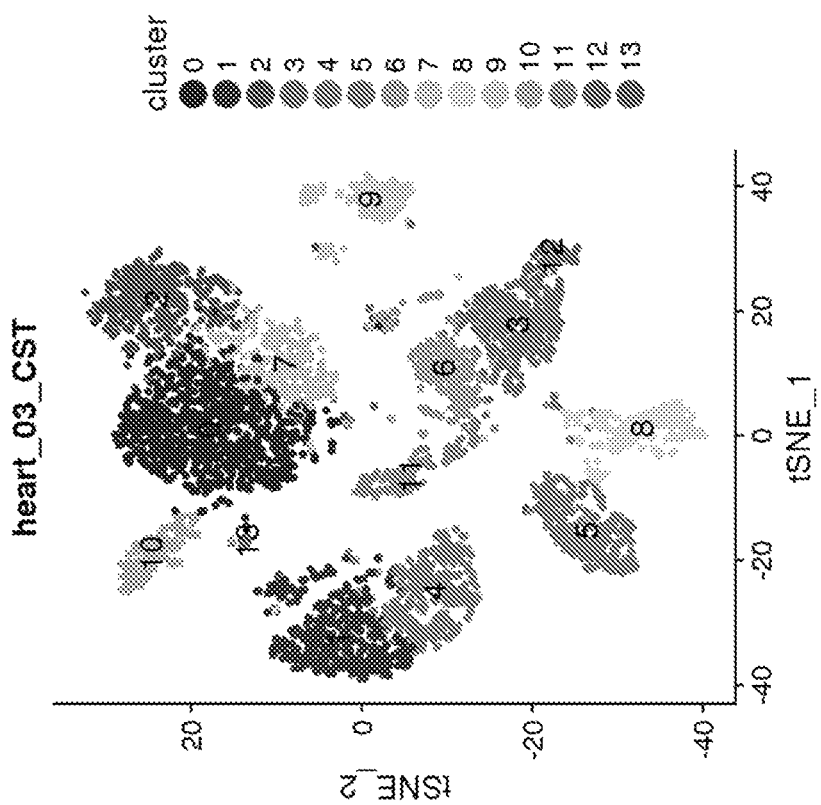
FIG. 121A
FIG. 121B

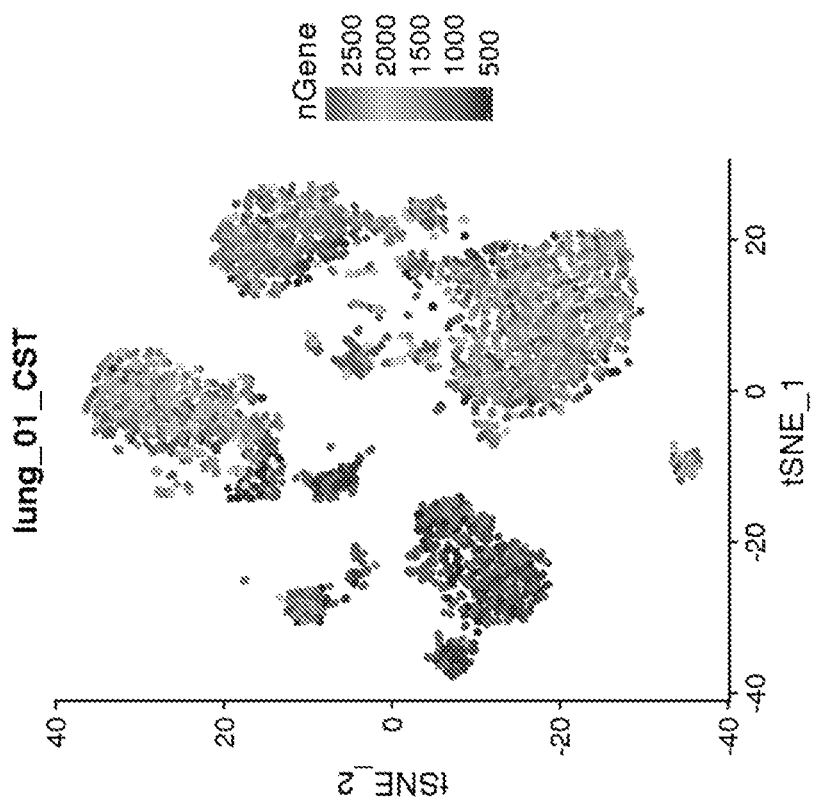
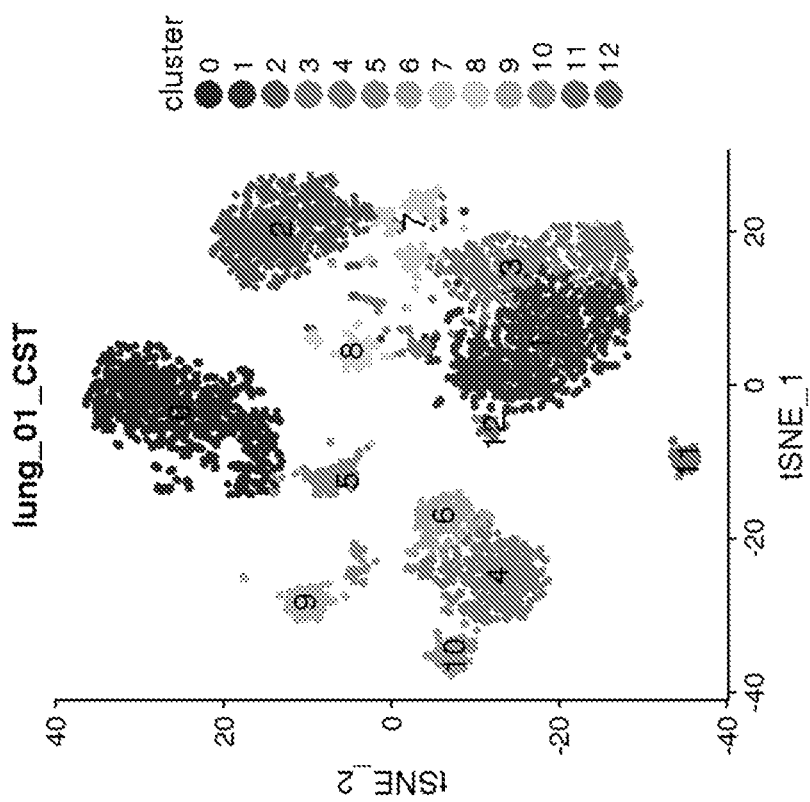
FIG. 125B
FIG. 125A

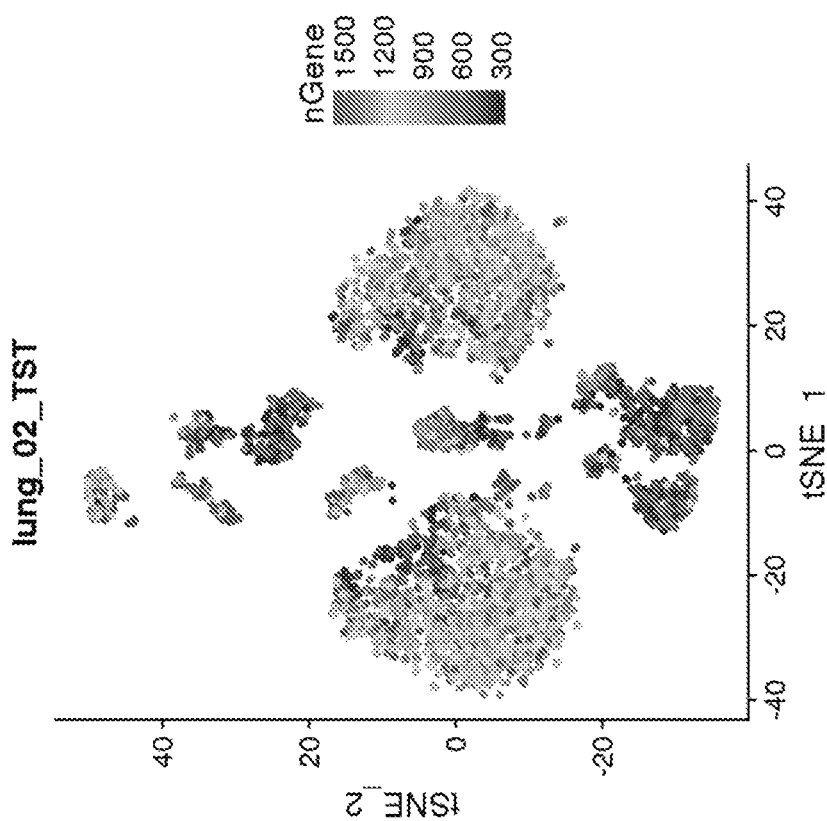
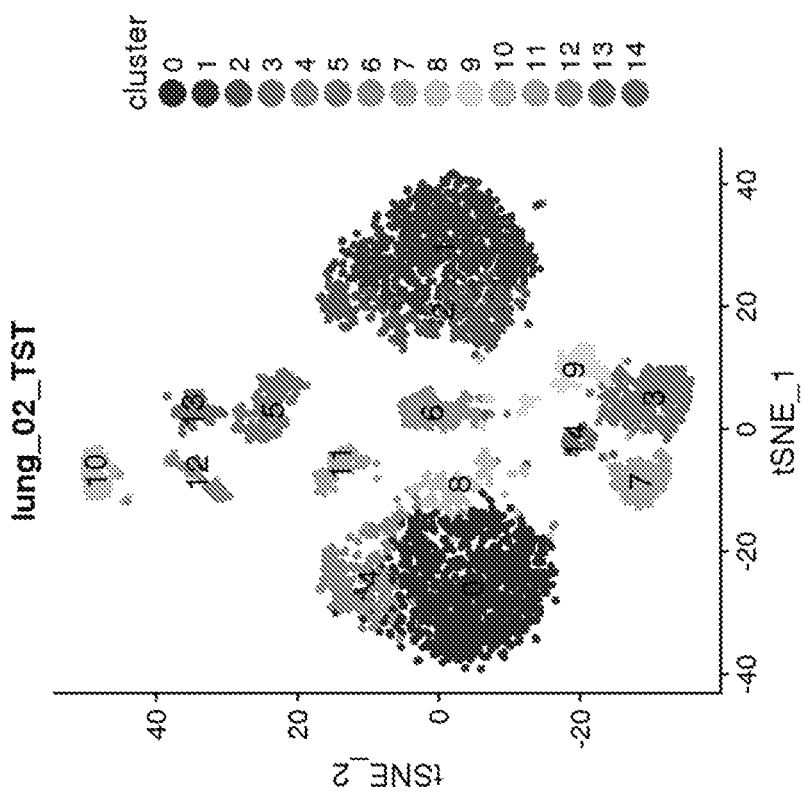
FIG. 132B
FIG. 132A

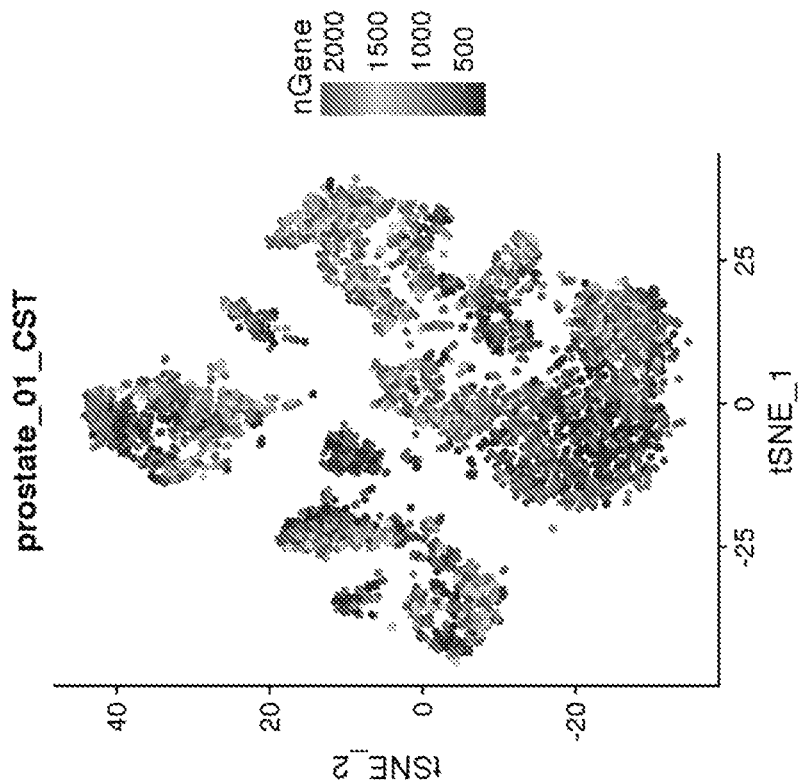
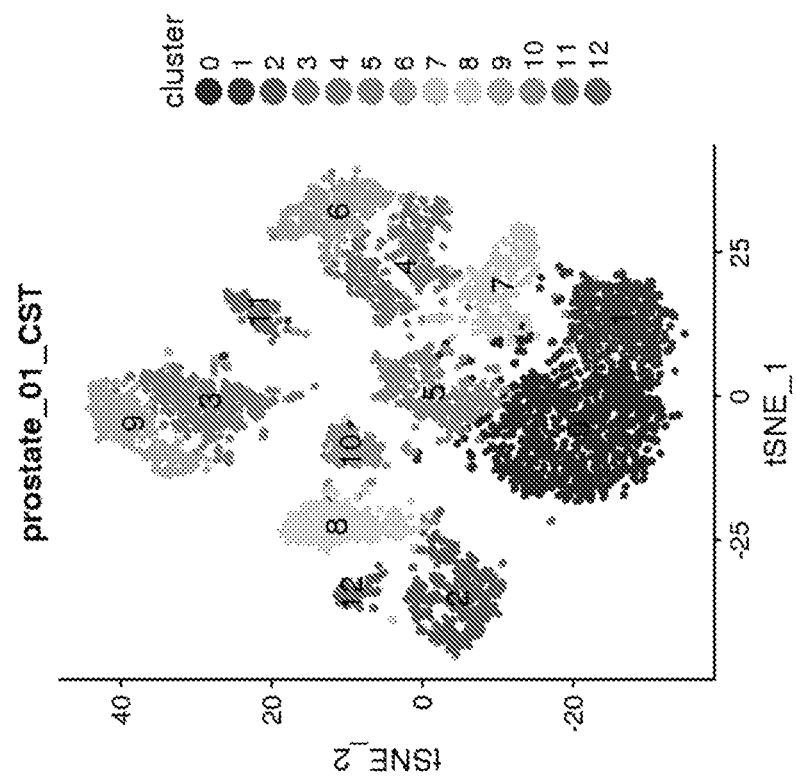
FIG. 140A
FIG. 140B

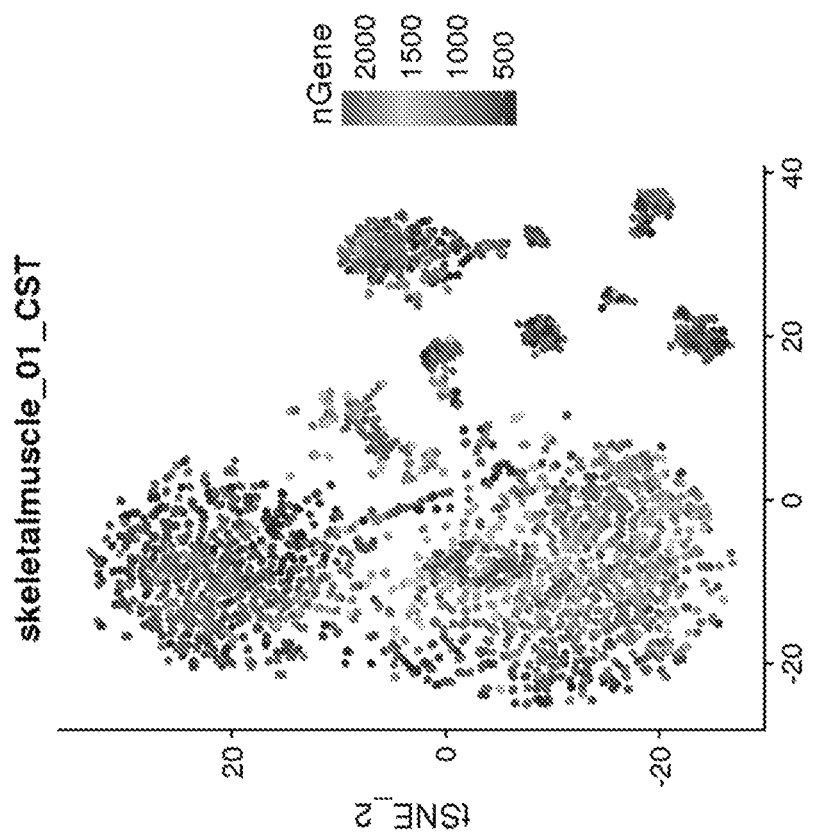
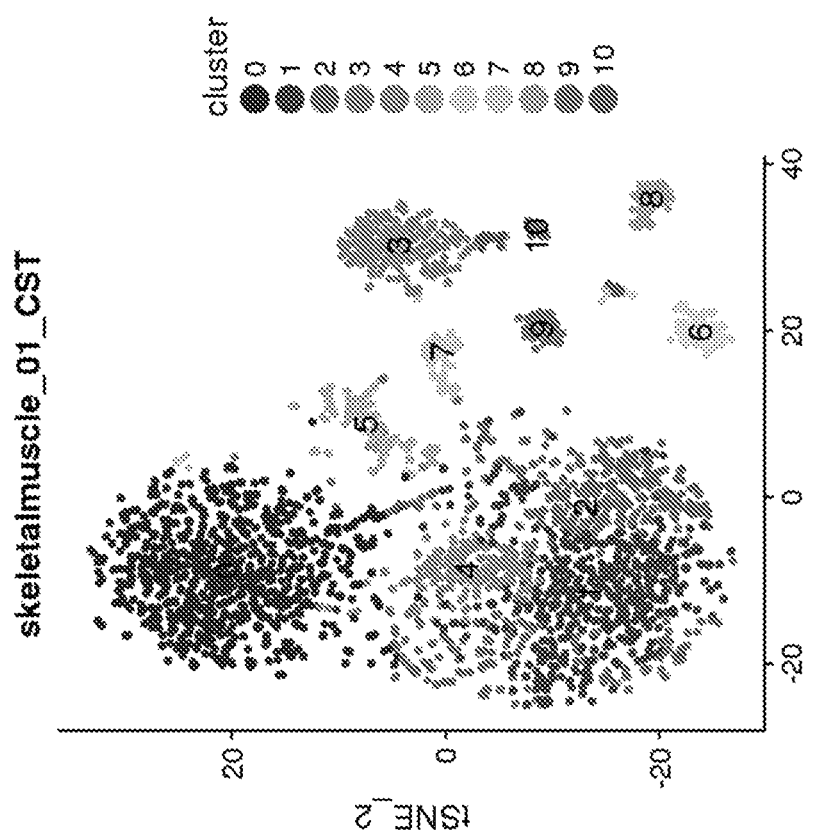
FIG. 154A
FIG. 154B

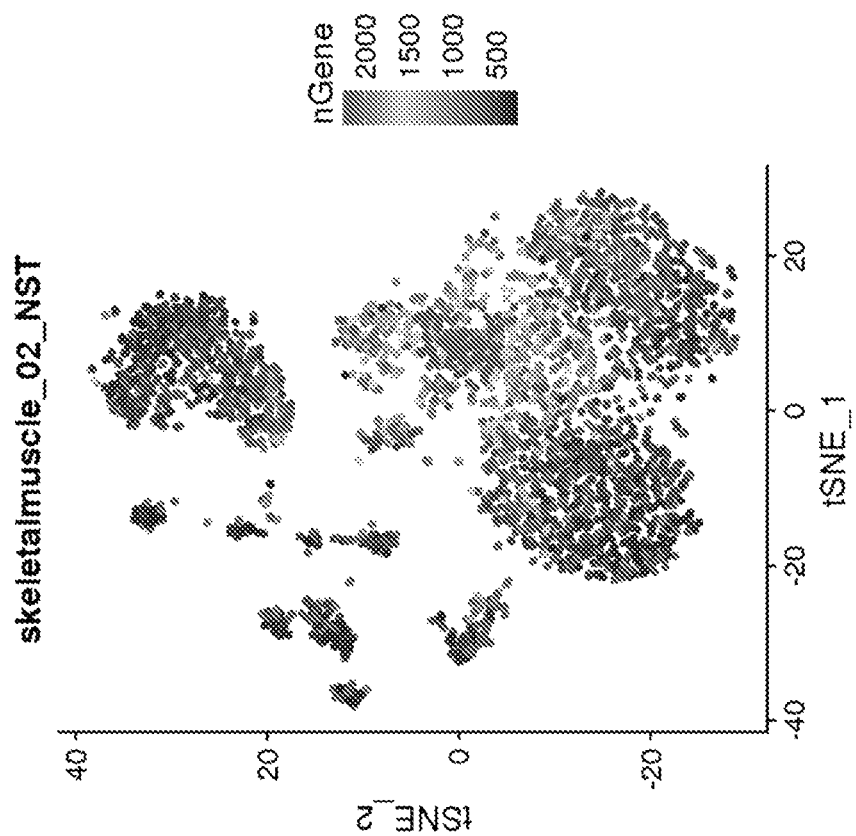
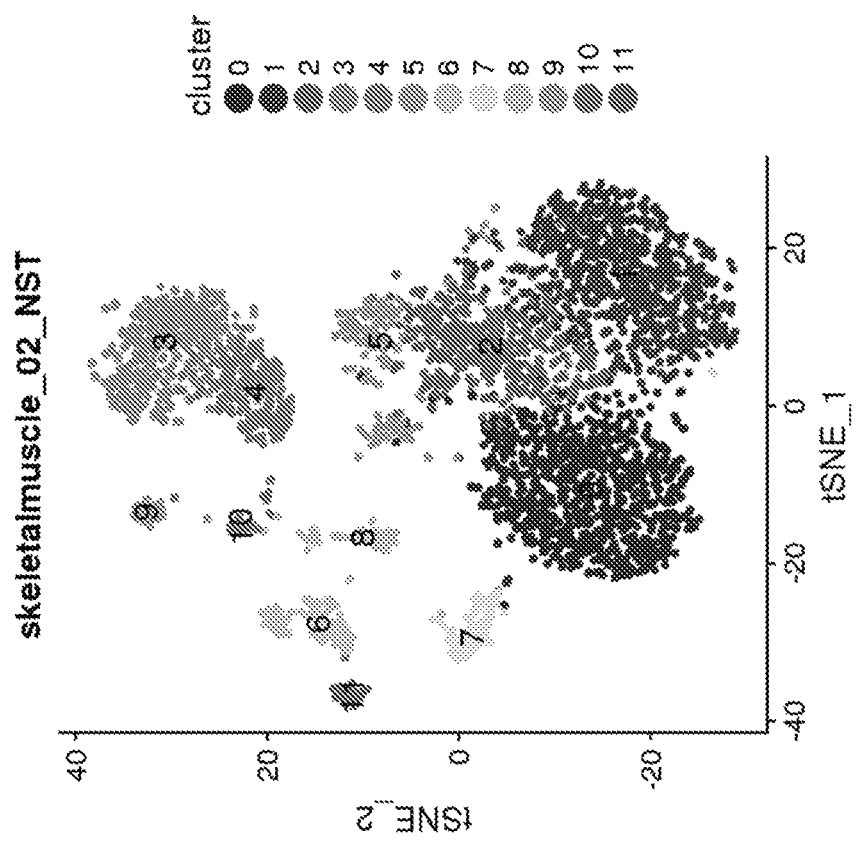
FIG. 160A
FIG. 160B

SEQUENCE LISTING

<160> NUMBER OF SEQ ID NOS: 14

<210> SEQ ID NO 1
<211> LENGTH: 8
<212> TYPE: DNA
<213> ORGANISM: Artificial Sequence

```
<220> FEATURE:
<223> OTHER INFORMATION: Synthetic Oligonucleotide

<400> SEQUENCE: 1 ttgagcct                                                              8

<210> SEQ ID NO 2
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 2 agttgctt                                                              8

<210> SEQ ID NO 3
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 3 ccagttag                                                              8

<210> SEQ ID NO 4
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 4 accaactg                                                              8

<210> SEQ ID NO 5
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 5 gtataaca                                                              8

<210> SEQ ID NO 6
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 6 caggagcc                                                              8

<210> SEQ ID NO 7
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' biotin tag
<220> FEATURE:
```

```
<221> NAME/KEY: misc_feature
<222> LOCATION: (27)..(27)
<223> OTHER INFORMATION: v = a, c, or g
<220> FEATURE:
<221> NAME/KEY: misc_feature
<222> LOCATION: (28)..(28)
<223> OTHER INFORMATION: n = a, g, c, or t

<400> SEQUENCE: 7
aagcagtggt atcaacgcag agtactvn                                           28

<210> SEQ ID NO 8
<211> LENGTH: 288
<212> TYPE: PRT
<213> ORGANISM: Artificial Sequence
<220> FEATURE:
<223> OTHER INFORMATION: Synthetic Peptide

<400> SEQUENCE: 8

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

<210> SEQ ID NO 9
<211> LENGTH: 23
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: misc_feature
<222> LOCATION: (21)..(22)
<223> OTHER INFORMATION: phosphorothioate bond
<220> FEATURE:
<221> NAME/KEY: misc_feature
<222> LOCATION: (22)..(23)
<223> OTHER INFORMATION: phosphorothioate bond

<400> SEQUENCE: 9
aagcagtggt atcaacgcag agt                                              23

<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(29)
<223> OTHER INFORMATION: RNA nucleotide

<400> SEQUENCE: 10
aagcagtggt atcaacgcag agtacatggg                                       30

<210> SEQ ID NO 11
<211> LENGTH: 183
<212> TYPE: PRT
<213> ORGANISM: Artificial Sequence
<220> FEATURE:
<223> OTHER INFORMATION: Synthetic Peptide

<400> SEQUENCE: 11

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Ala Met Thr Gln
                85                  90                  95

Phe Gly Met Ser Arg His Gly Leu Leu Gln Leu Phe Arg Arg Val Gly
                100                 105                 110

Val Thr Glu Leu Glu Ala Arg Ser Gly Thr Leu Pro Pro Ala Ser Gln
            115                 120                 125

Arg Trp Asp Arg Ile Leu Gln Ala Ser Gly Met Lys Arg Ala Lys Pro
        130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175
```

Gly Asp Gln Thr Arg Ala Ser
         180

<210> SEQ ID NO 12
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' biotin tag
<220> FEATURE:
<221> NAME/KEY: misc_feature
<222> LOCATION: (1)..(1)
<223> OTHER INFORMATION: r = g or a
<220> FEATURE:
<221> NAME/KEY: misc_feature
<222> LOCATION: (56)..(56)
<223> OTHER INFORMATION: v = a, c, or g
<220> FEATURE:
<221> NAME/KEY: misc_feature
<222> LOCATION: (57)..(57)
<223> OTHER INFORMATION: n = a, g, c, or t

<400> SEQUENCE: 12
ragcagtggt atcaacgcag agtactttt tttttttttt tttttttttt tttttvn        57

<210> SEQ ID NO 13
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (26)..(27)
<223> OTHER INFORMATION: RNA nucleotide

<400> SEQUENCE: 13
aagcagtggt atcaacgcag agtacggg                                       28

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' biotin tag
<220> FEATURE:
<221> NAME/KEY: misc_feature
<222> LOCATION: (1)..(1)
<223> OTHER INFORMATION: r = g or a
<220> FEATURE:
<221> NAME/KEY: misc_feature
<222> LOCATION: (21)..(22)
<223> OTHER INFORMATION: phosphorothioate bond
<220> FEATURE:
<221> NAME/KEY: misc_feature
<222> LOCATION: (22)..(23)

```
<223> OTHER INFORMATION: phosphorothioate bond
<220> FEATURE:
<221> NAME/KEY: misc_feature
<222> LOCATION: (23)..(24)
<223> OTHER INFORMATION: phosphorothioate bond

<400> SEQUENCE: 14
raagcagtgg tatcaacgca gagt                                         24
```

METHODS FOR DETERMINING SPATIAL AND TEMPORAL GENE EXPRESSION DYNAMICS DURING ADULT NEUROGENESIS IN SINGLE CELLS

CROSS-REFERENCE TO RELATED APPLICATIONS

This application claims the benefit of U.S. Provisional Application No. 62/585,529, filed Nov. 13, 2017; U.S. Provisional Application No. 62/723,425, filed Aug. 27, 2018; and U.S. Provisional Application No. 62/734,988, filed Sep. 21, 2018. The entire contents of the above-identified applications are hereby fully incorporated herein by reference.

REFERENCE TO AN ELECTRONIC SEQUENCE LISTING

The contents of the electronic sequence listing (BROD-3770WP.ST25.txt"; Size is 9 Kilobytes and it was created on Oct. 26, 2018) is herein incorporated by reference in its entirety.

FIELD OF THE INVENTION

The present invention generally relates to methods of determining cell type, subtype, cell state, spatial location and developmental stages of single cells obtained from a sample, preferably a tissue sample. The present invention also relates to a combination of molecular barcoding and emulsion-based microfluidics to isolate, lyse, barcode, and prepare nucleic acids from individual nuclei in a high-throughput manner.

BACKGROUND OF THE INVENTION

Single cell RNA-Seq has greatly extended our understanding of heterogeneous tissues, including the CNS (1-6), and is reshaping the concept of cell type and state. However, some key dynamic processes that occur in dense nervous tissues, such as adult neurogenesis, still remain challenging to study. Transcriptomes of individual neurons provide rich information about cell types and dynamic states. However, it is difficult to capture rare dynamic processes, because isolation from dense adult tissue is challenging. First, single cell RNA-Seq requires enzymatic tissue dissociation, which damages the integrity of neurons, compromises RNA integrity, and skews data towards easily dissociated cell types. This challenge is exacerbated as animals age, restricting this approach to fetal or young animals (1). Second, rare cells, such as adult newborn neurons found in the adult mouse hippocampus (7), are difficult to capture because they require enrichment using specific tagging and sorting for each phase of the dynamic neurogenesis process and markers for each phase are limited. Thus, there is a need for improved devices and methods to allow for understanding heterogeneous tissues and cell populations. Citation or identification of any document in the application is not an admission that such document is available as prior art to the present invention.

SUMMARY OF THE INVENTION

In one aspect, the invention provides a method of producing a temporally phased single-cell sequencing library comprising cells along a continuous trajectory of adult neurogenesis comprising (a) treating more than one population of neurogenic cells of a single cell type or subtype, or optionally a heterogeneous cell type, with a nucleoside analogue, wherein the nucleoside analogue is incorporated into replicating DNA and is configured for labeling with a detectable marker; (b) isolating a first population of neurogenic cells at one time point and isolating at least one other population of neurogenic cells at a later time point, optionally, isolating single nuclei from the isolated populations of neurogenic cells; (c) staining the nucleoside analogue incorporated into replicated DNA with the detectable marker within each population of neurogenic cells or single nuclei isolated from each population of neurogenic cells, wherein the DNA is stained with the detectable marker; (d) sorting the stained and/or unstained neurogenic cells or optionally, sorting the stained and/or unstained single nuclei into separate reaction vessels; and (e) sequencing the RNA from the sorted single neurogenic cells or optionally, sorted single nuclei, whereby single cell gene expression data is obtained for neurogenic cells at different stages of neurogenesis.

In another aspect, the invention provides a method of determining an expression profile for a neurogenic cell along a continuous trajectory of adult neurogenesis comprising (a) treating more than one population of neurogenic cells of a single cell type or subtype, or optionally a heterogeneous cell type, with a nucleoside analogue, wherein the nucleoside analogue is incorporated into replicating DNA and is configured for labeling with a detectable marker; (b) isolating a first population of neurogenic cells at one time point and isolating at least one other population of neurogenic cells at a later time point, optionally, isolating single nuclei from the isolated populations of cells; (c) staining the nucleoside analogue incorporated into replicated DNA with the detectable marker within each population of neurogenic cells or single nuclei isolated from each population of neurogenic cells, wherein the DNA is stained with the detectable marker; (d) sorting the stained and/or unstained neurogenic cells or optionally, sorting the stained and/or unstained single nuclei into separate reaction vessels; (e) sequencing the RNA from the sorted single neurogenic cells or optionally, sorted single nuclei, whereby single cell gene expression data is obtained for neurogenic lineage cells at different stages of maturation; and (f) determining an expression profile for each identified cell or cell sub-type based on the gene expression data.

In one embodiment, neurogenesis occurs in the adult brain, for example in a region of the hippocampus, for example the hippocampus dentate gyrus (DG).

In another embodiment, neurogenesis occurs in the adult spinal cord.

In another embodiment, the neurogenic cell is selected from the group consisting of: a neuronal stem cell, a neuronal precursor cell, a neuroblast, an immature neuron and a newborn neuron.

In another embodiment, the expression profile identifies the cell as a neuronal stem cell, a neuronal precursor cell, a neuroblast, an immature neuron and a newborn neuron.

In another embodiment, the expression profile identifies the cell as an adult newborn neuron or immature neuron of the spinal cord and comprises: Gad1, Gad2, Pbx3 and Meis2.

In another embodiment, the expression profile identifies the cell as an adult newborn neuron or immature neuron of the spinal cord and comprises: Gad1, Gad2, Pbx3, Meis2 and Runx1t1.

In another embodiment, the expression profile identifies the cell as a neuronal stem cell, a neuronal precursor cell, a neuroblast, an immature neuron or a newborn neuron and comprises at least one of: Fabp7, Sox9, Asc1, Insm1, Sox6, Notch1, Eomes, Tgfb2, Chd7, Sox5, Sox4, Neurod1, Neurod2, Sema3c, Igfbpl1, Sox11, Slc6a1, Dcx, Grin2b, Gad1 and Bhlhe22.

In another embodiment, the expression profile identifies the cell as a neuronal stem cell, a neuronal precursor cell, a neuroblast, an immature neuron or a newborn neuron and comprises at least one of: Sox8, Sox10, Dip2a, Ncoa3, Rorb, Id3, Sox9, Sox5, Sox6, Sox4, Eomes, Mndal, Bhlhe22, Ifi203, Sox11, Flna and Zeb1.

In another embodiment, the expression profile identifies the cell as a neuronal stem cell, a neuronal precursor cell, a neuroblast, an immature neuron or a newborn neuron and comprises at least one of: Notch1, Sox9/2, Fezf2, Pax3, Id3/4, Sox6, Chd7, Cdk2, Insm1, Eomes, Sox4, Neurod1, Neurod2, Bhlhe22, Chd5 and Hdac7.

In another embodiment, the expression profile identifies the cell as a neuronal stem cell, a neuronal precursor cell, a neuroblast, an immature neuron or a newborn neuron and comprises at least one of: Sox2, Sox9, Sox5, Sox8, Sox6, Sox4, Cdk2, Cdk2ap1, Cdk9, Cdk12, Kif11, Kif21b, Kif17, Chd7, Kdm5c, Kdm7a, Hdac8, Kdm2b, Chd5, Hdac5, Hdac7, Chd1 and Kdm3b.

In another embodiment, the expression profile identifies the cell as a neuronal stem cell, a neuronal precursor cell, a neuroblast, an immature neuron or a newborn neuron and comprises at least one of: Sox9, Rrm2, Gpr56, Draxin, Mfap4, Eomes, Sox4 and Neurod1.

In another embodiment, the expression profile identifies the cell as a neuronal stem cell, a neuronal precursor cell, a neuroblast, an immature neuron or a newborn neuron and comprises at least one of: Gfap, Mt1, Aldoc, Clu, Aqp4, Mt2, Cst3, Slc1a2, Pbxip1, Fgfr3, Slc2a1, Slpr1, Id3, Fxyd1, Notch1, Sox9, Glu1, Slc1a3, Sox2, Olig2, Aldh1 11, Prelp, Vim, Pax6, Reln, Gprl7, Tcf712, Nfib, Dbx2, Sox8, Sox5, Sox4, Emx1, Sox1, Sox6, Prox1, Dlx1, Foxg1, Neurod1, Sox11, Slit1, Gad2, Grin2b and Dcx.

In another embodiment, the expression profile identifies the cell as a neuronal stem cell, a neuronal precursor cell, a neuroblast, an immature neuron or a newborn neuron and comprises at least one of: Sox9, Notch1, Eomes and Neurod1.

In another embodiment, the expression profile identifies the cell as a neuronal stem cell, a neuronal precursor cell, a neuroblast, an immature neuron or a newborn neuron and comprises at least one of: Sox11 and Gad1.

In another embodiment, the expression profile identifies the cell as a neuronal stem cell, a neuronal precursor cell, a neuroblast, an immature neuron or a newborn neuron and comprises at least one of: Eomes, Sox4, Sox11 and Dcx.

In another embodiment, the expression profile identifies the cell as a neuronal stem cell, a neuronal stem cell, a neuronal precursor cell, a neuroblast, an immature neuron or a newborn neuron and comprises at least one of: Rrm2, Gpr56, Draxin and Mfap4.

In another embodiment, the expression profile identifies the cell as a neuronal stem cell, a neuronal precursor cell, a neuroblast, an immature neuron or a newborn neuron and comprises at least one of: Mbp, Meg3, Gad2 and Dcx.

In another embodiment, the expression profile identifies the cell as a neuronal stem cell, neuronal precursor cell, a neuroblast, an immature neuron or a newborn neuron and comprises at least one of the genes presented in Tables 18 and 19.

The invention also provides an adult newborn neuron or immature neuron derived from the spinal cord characterized by expression of Gad1 and Gad2.

The invention also provides an adult newborn neuron or immature neuron derived from the spinal cord characterized by expression of Gad1, Gad2, Pbx3 and Meis2.

The invention also provides an adult newborn neuron or immature neuron derived from the spinal cord characterized by expression of Gad1, Gad2, Pbx3, Meis2 and Runx1t1.

The invention also provides an expression profile for identifying a neuronal stem cell, a neuronal precursor cell, a neuroblast, an immature neuron or a newborn neuron derived from the brain, comprising: Sox8, Rrm2, Gpr56, Draxin, Mfap4, Eomes, Sox4 and Neurod1.

The invention also provides an expression profile for distinguishing between a neuronal stem cell, a neuronal precursor cell, a neuroblast, an immature neuron and a newborn neuron comprising one or more of the genes presented in Table 22.

The invention also provides an expression profile for distinguishing between a neuronal stem cell, a neuronal precursor cell, a neuroblast, an immature neuron and a newborn neuron comprising one or more of the genes presented in Table 23.

The invention also provides an expression profile for distinguishing between a neuronal stem cell, a neuronal precursor cell, a neuroblast, an immature neuron and a newborn neuron comprising one or more of the genes presented in Table 24.

The invention also provides an expression profile for distinguishing between a neuronal stem cell, a neuronal precursor cell, a neuroblast, an immature neuron and a newborn neuron comprising one or more of the genes presented in Table 25.

The invention also provides an expression profile for distinguishing between a neuronal stem cell, a neuronal precursor cell, a neuroblast, an immature neuron and anewborn neuron comprising one or more of the genes presented in Table 27.

The invention also provides a method of stimulating neurogenesis of a neuronal stem cell derived from the spinal cord stem by administering an agent that modulates one or more of: Gad1, Gad2, Pbx3 and Meis2 or the gene product of one or more of Gad1, Gad2, Pbx3 and Meis2.

The invention also provides a method of stimulating neurogenesis of a neuronal stem cell derived from the spinal cord stem by administering an agent that modulates one or more of: Gad1, Gad2, Pbx3, Meis2 and Runx1t1 or the gene product of one or more of: Gad1, Gad2, Pbx3, Meis2 and Runx1t1.

The invention also provides a method of stimulating neurogenesis of a neuronal stem cell derived from the spinal cord stem by administering an agent that modulates one or more of the genes presented in any one of Table 18 through Table 27; or the gene product of one or more of the genes presented in any one of Table 18 through Table 27.

The invention also provides a method of stimulating neurogenesis of a neuronal stem cell derived from the brain by administering an agent that modulates one or more of the genes presented in any one of Table 18 through Table 27 or the gene product of one or more of the genes presented in any one of Table 18 through Table 27.

The invention also provides a method of stimulating neurogenesis of a neuronal stem cell derived from the brain by administering an agent that modulates one or more of: Sox9, Rrm2, Gpr56, Draxin, Mfap4, Eomes, Sox4 and Neurod1 or the gene product of one or more of Sox9, Rrm2, Gpr56, Draxin, Mfap4, Eomes, Sox4 and Neurod1.

The invention also provides a method of modulating proliferation and/or differentiation of neuronal stem cells in the spinal cord comprising contacting the stem cells with an agent that modulates one or more of: Gad1, Gad2, Pbx3 and Meis2 or the gene product of one or more of Gad1, Gad2, Pbx3 and Meis2.

The invention also provides a method of modulating proliferation and/or differentiation of neuronal stem cells in the spinal cord comprising contacting the stem cells with an agent that modulates one or more of: Gad1, Gad2, Pbx3, Meis2 and Runx1t1 or the gene product of one or more of: Gad1, Gad2, Pbx3, Meis2 and Runx1t1.

The invention also provides a method of modulating proliferation and/or differentiation of neuronal stem cells in the spinal cord comprising contacting the stem cells with an agent that modulates one or more of: the genes presented in any one of Table 18 through Table 27 or the gene product of one or more of the genes presented in any one of Table 18 through Table 27.

The invention also provides a method of modulating proliferation and/or differentiation of neuronal stem cells in the brain comprising contacting the stem cells with an agent that modulates one or more of: the genes presented in any one of Table 18 through Table 27 or the gene product of one or more of the genes presented in any one of Table 18 through Table 27.

The invention also provides a method of modulating proliferation and/or differentiation of neuronal stem cells in the brain comprising contacting the stem cells with an agent that modulates one or more of: Sox9, Rrm2, Gpr56, Draxin, Mfap4, Eomes, Sox4 and Neurod1 or the gene product of one or more of: Sox9, Rrm2, Gpr56, Draxin, Mfap4, Eomes, Sox4 and Neurod1.

The invention also provides a method of treating a subject with a spinal cord injury, comprising administering to a subject in need thereof the gene product of one or more of Gad1, Gad2, Pbx3 and Meis2; or an agent that modulates one or more of Gad1, Gad2, Pbx3 and Meis2.

The invention also provides a method of treating a subject with a spinal cord injury, comprising administering to a subject in need thereof the gene product of one or more of Gad1, Gad2, Pbx3, Meis2 and Runx1t1; or an agent that modulates one or more of Gad1, Gad2, Pbx3, Meis2 and Runx1t1.

The invention also provides a method of treating a subject with a spinal cord injury, comprising administering to a subject in need thereof the gene product of one or more of the genes presented in any one of Table 18 through Table 27; or an agent that modulates one or more of the genes presented in any one of Table 18 through Table 27.

The invention also provides a method of treating a spinal cord injury in a subject in need thereof, comprising administering to the subject an adult newborn neuron.

The invention also provides a method for identifying a newborn neuron of the spinal cord comprising detecting the expression pattern of: Gad1 and Gad2.

The invention also provides a method for identifying a newborn neuron of the spinal cord comprising detecting the expression pattern of: Gad1, Gad2, Pbx3 and Meis2.

The invention also provides a method for identifying a newborn neuron of the spinal cord comprising detecting the expression pattern of: Gad1, Gad2, Pbx3, Meis2 and Runx1t1.

In another aspect, the invention provides for a method of single cell sequencing comprising: extracting nuclei from a population of cells under conditions that preserve: (1) a portion of the outer nuclear envelope with attached ribosomes, or (2) a portion of the outer nuclear membrane and a portion of the rough endoplasmic reticulum (RER) with ribosomes, or (3) a portion of the outer nuclear membrane, a portion of the rough endoplasmic reticulum (RER), and a portion of mitochondria; sorting single nuclei into separate reaction vessels; extracting RNA from the single nuclei; generating a cDNA library; and sequencing the library, whereby gene expression data from single cells is obtained. In some embodiments, the reaction vessels may be single cell droplets.

In one embodiment, nuclei are extracted under conditions that preserve a portion of the outer nuclear envelope and rough endoplasmic reticulum (RER), wherein the population of cells is homogenized in a lysis buffer comprising: a detergent selected from the group consisting of NP40, CHAPS and Tween-20; and an ionic strength between 100 mM and 200 mM.

In another embodiment the NP40 concentration is about 0.2%.

In another embodiment the Tween-20 concentration is about 0.03%.

In another embodiment the CHAPS concentration is about 0.49%.

In another embodiment the population of cells is treated with a reagent that stabilizes nucleic acids.

In another embodiment, the separate reaction vessels are microwells in a plate.

In another embodiment the separate reaction vessels are microfluidic droplets.

In another embodiment the population of cells is obtained from a tissue sample.

In another embodiment the tissue sample is frozen. In some embodiments, the tissue sample is frozen in a clear tube.

In another embodiment the tissue sample is obtained from the brain.

In another embodiment the tissue sample is obtained from the gastrointestinal tract, or gut.

In another embodiment the tissue sample is obtained from a subject suffering from a disease.

In another embodiment the disease is autism spectrum disorder.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

Figure 1:
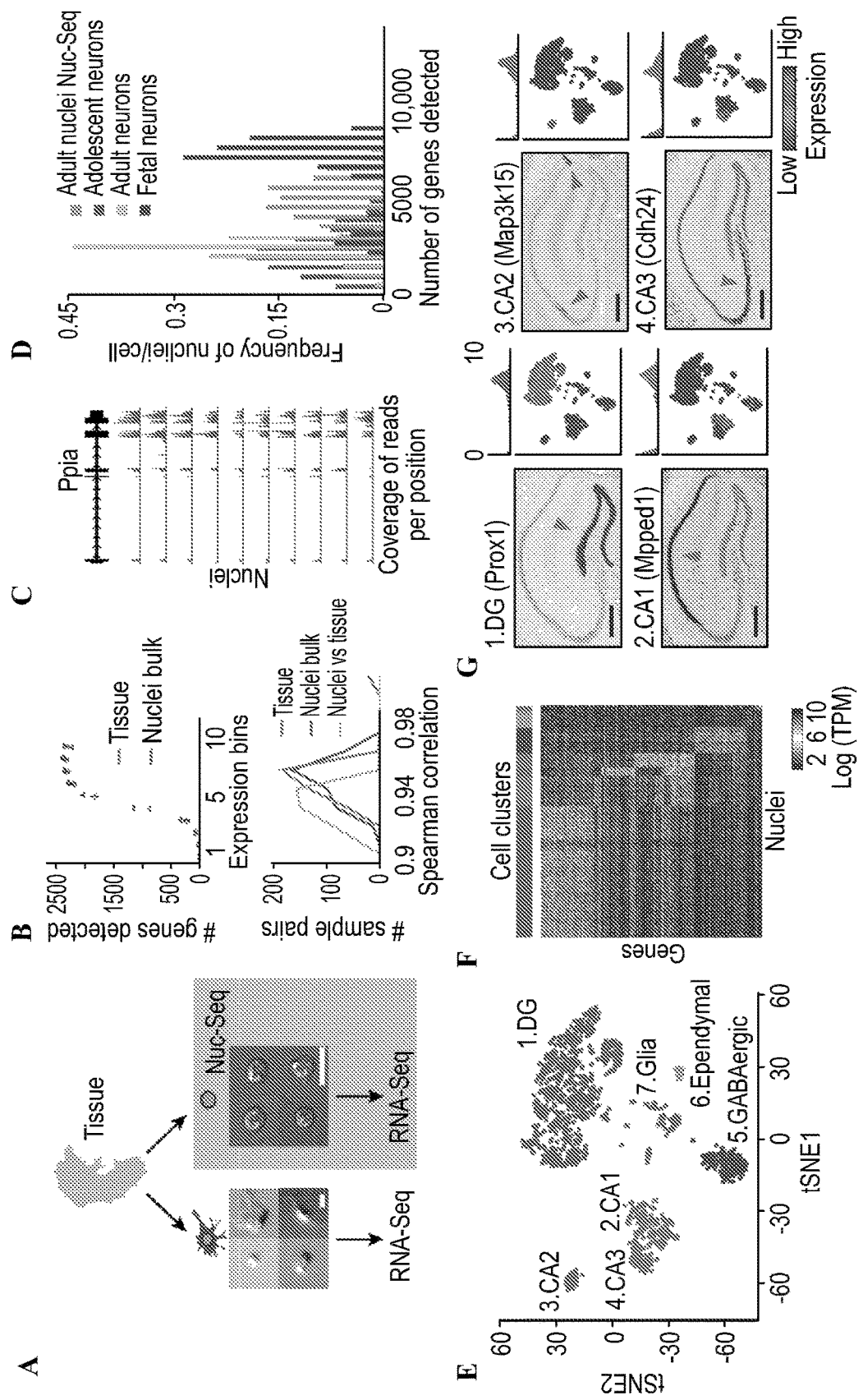
FIG. 1A-1G. Single nuclei RNA-Seq (Nuc-Seq) identifies distinct cell types. (A) Single isolated nuclei (right) are more uniform than enzymatically dissociated single neuronal cell bodies (left) from adult mouse brain tissue. Shown are images of representative examples. Scale=10 m. Overview of the Nuc-Seq method (right): Dissected tissue is fixed, nuclei are isolated and sorted using FACS, and are then processed using the Smart-Seq2 RNA-Seq protocol(34). (B) Nuc-Seq faithfully captures tissue RNA. Comparing Nuc-Seq on populations of nuclei and RNA-seq on tissue samples from the DG brain region. Shown are number of genes detected (TPM>3) per expression quantile (top) and distribution of pairwise spearman correlations across samples (bottom). (C) Nuc-Seq detects full-length, spliced transcripts in ten individual nuclei (rows). RNA-Seq read coverage at the Ppia genomic locus. (D) Nuc-Seq detects consistently higher number of genes (TPM/FPKM>3 or UMI>=1) compared to published single neuron RNA-seq in adolescent (1) or adult (4) mice, but lower number than in fetal neurons(6). (E) Major cell types identified from Nuc-Seq data reflected by 7 major cell clusters. Shown is a 2-D non-linear embedding with 7 distinct clusters of 1,188 nuclei isolated from adult hippocampus. (F) Heatmap shows the expression of marker genes specific for each of the seven clusters across single nuclei (t-test FDR<0.05, log-ratio>1, across all pairwise comparisons). Top color bar matches cluster color in E. (G) Identification of DG granule cell, CA1, CA2, and CA3 pyramidal cell clusters. For each cluster, expression of marker genes is shown as: 1, ISH image in a coronal section of the hippocampus from (13) (arrowhead indicates high expression levels of marker gene); 2, histogram quantifying expression level across all nuclei in the relevant cluster; and 3, 2-D embedding of nuclei (as in E) showing relative expression level of the marker across all clusters. Scale=400 m.

WPRE—Woodchuck Hepatitis virus posttranscriptional regulatory element, s.o.—stratum oriens, s.p.—stratum pyramidale, s.r.—stratum radiatum, g.c.l.—granule cell layer). Scale bars: 50 um (E) Nuc-Seq method overview. Dissected tissue is fixed in RNA-later for 24 hours at 4° C. (and can be subsequently stored in −80° C. or further processed); nuclei are isolated using a gradient centrifugation method [38] (samples kept at 4° C. or on ice), resuspended, and sorted using FACS to a single nucleus per well in plates. Plates are processed using the Smart-Seq2 RNA-Seq protocol [85, 41].

FIG. 6A-6H: Quality measurements of Nuc-Seq libraries. (A) Nuc-Seq detects full-length, spliced transcripts. Alignments of individual spliced reads from one single nucleus at the Ppia genomic locus. Top track: exons/introns, thick and thin lines (as in FIG. 1C). Grey bar: individual read, green line: gapped alignment. (B) Mapping rates of Nuc-Seq data. Left: Box plots showing the mapping rates to the genome, transcriptome, and rRNA. In box plots, the median (red), 75% and 25% quantile (box), error bars (dashed lines), and outliers (red dots). Right: Box plots showing the ratio of the number of reads mapped to introns and exons in Nuc-Seq libraries. (C) Nuc-Seq detects similar number of genes across animal ages, 4 weeks, 3 months and 2 years old (detected gene defined as log(TPM+1)>1.1). (D) Average of dentate gyrus (DG) and CA2/3 Nuc-Seq data correlates between replicates. Scatter plots showing comparison between average of single nuclei across technical and biological replicates. Data is shown in log(TPM+1). Spearman correlation between replicates (R), top. (E) Average of Nuc-Seq data correlates with population samples. Scatter plots showing comparison between average of single nuclei (Y axis) to populations of 100 nuclei (X axis). (F) 3' and 5' bias. Top: Mean read coverage across highly expressed genes per distance from the 3' of the gene. Showing constant coverage with a decrease around 2000 bp from the 3' end. Bottom: Mean read coverage throughout the transcripts, averaged per percentage of the transcript length (3' to 5'). (G) Distribution of number of reads mapped to the transcriptome per Nuc-Seq library. (H) Nuc-Seq libraries are enriched for long non-coding RNAs (lincRNAs). Heatmap showing differentially expressed genes between Nuc-Seq on population of nuclei (columns, pink) and tissue RNA-Seq (columns, blue). t-test FDR q-value <0.05 with log-ratio>1, mean log(TPM)>2 in at least one condition, 21 samples per condition. Left: colorbar showing the classification of genes as lincRNAs (green) and pseudogene/predicted lincRNA (orange). Names of known nuclear localized lincRNAs are marked (left).

FIG. 7A-7D: Comparison of Nuc-Seq and single cell RNA-Seq. (A) Nuc-Seq detects more genes than single cell RNA-Seq across wide expression range. Shown is the distribution of number of genes detected (Y axis, log(TPM+1) >1.1) per nucleus for Nuc-Seq and per cell for Zeisel 2015 (only CA1 neurons) [50], Tasic 2016 [86], and Thomsen 2016 [87]across expression quantiles (X axis). A different threshold (X axis, TPM>1.1) was used in the calculation of number of genes detected for Zeisel 2015, which used unique molecular identifier (UMI) counts. ScAn: Single cell sequencing of adult neuron; ScFn: Single cell sequencing of fetal neuron. Error bar: 75% and 25% quantile. (B) Nuc-Seq detects more genes than previously reported single nuclei RNA-Seq (ref) across wide expression range. (C) Transcriptinal profiles between different cell types are more distinct in Nuc-Seq than in single cell RNA-Seq [50]. Plots showing Spearman correlation coefficients (Y axis) between two subsets of averaged pyramidal neurons (Pyr) or between subsets of averaged pyramidal neurons and averaged GABAergic interneurons (Int). A subset of neurons are first randomly sampled from Nuc-Seq and single-cell RNA-Seq. Then Spearman correlation is calculated between the averages of the subsets (see Materials and Methods). (D) Nuc-Seq has significantly improved complexity compared to the previously reported single nuclei RNA-Seq [88]. Shown are rarefaction curves of previously reported two single nuclei RNA-Seq libraries and curves of Nuc-Seq libraries.

FIG. 8A-8B: Computational methods. (A) Density MA plot normalization method. MA plot showing the average log (X axis) versus the log-ratio (Y axis) of TPM expression of all genes between two single nuclei. High density region marked by a color scale. Genes within the colored density region are used to calculate the scaling factor between libraries for normalization. (B) Illustration of false negative estimation method. An expectation maximization algorithm alternates between estimation of gene expression distribution per gene (top) and the probability of detection (bottom) per cell. Top: histogram shows estimated distribution of expression of an example gene, PDF: probability density function. Bottom: each blue curve represent the probability of successfully detecting genes expressed at different levels in each cell.

FIG. 9A-9D: Validation of cell type classification based on Nuc-Seq data. (A) Identification of GABAergic, ependymal and glial clusters. For each cluster, marker gene expression is shown in two ways: 1, histogram quantifying expression level of the marker gene across all nuclei in the relevant cluster (top); and 2, 2D embedding of nuclei (as in FIG. 1E) showing relative expression level of the marker gene across all nuclei. (B) Nuc-Seq clusters agree with the anticipated cell types based on the microdissected anatomical regions. Shown are the distributions of nuclei from each microdissection source (DG, CA1, CA2 and CA3) within each of the nuclei clusters identified as DG, CA1, and CA2 and CA3 combined. (C) Computational pipeline for the validation of expression patterns using ISH. An example of comparison of the expression pattern of the Smoc2 gene across CA1, CA2, CA3, and DG Nuc-Seq clusters to its expression in the corresponding regions in ISH data. Top left: scatter plot of 2D embedding of all nuclei (as in FIG. 1E) colored by the expression of Smoc2 across all nuclei (Nuc-Seq data). Top right: the average Nuc-Seq expression levels in the CA1, CA2, CA3, and DG clusters presented in a schematics of the hippocampus (gray scale, high expression in dark grey and low expression in light grey). Bottom left: the expression pattern of Smoc2 in Allen ISH [64] image. Bottom right: the average expression levels in the CA1, CA2, CA3, and DG regions presented in a schematics of the hippocampus (gray scale). (D) Distribution of correlation coefficients of average RNA-Seq expressions and ISH [64] intensities per gene, across all differentially expressed genes between the CA1, CA2, CA3 and DG regions. Shown are all genes (blue) and lowly expressed (red) defined as averaged expression in all regions within bottom 25% quantile.

FIG. 10A-10D: Nuc-Seq identifies glial cell types. (A) Clustering of glial nuclei. Top insert: the glial cluster (blue) within all other nuclei from FIG. 1E. The glial nuclei are divided to five clusters by PCA tSNE: oligodendrocytes (ODC), astroglia (ASC), oligodendrocyte precursor cells (OPC), microglia, and a sparse cluster of diverse cells (grey). (B) Marker genes. Heatmap shows the expression of marker genes (rows, t-test FDR q-value <0.05 with log-ratio>1 across all pairwise comparisons between sub-clusters) specific for each of the five clusters in (A) (color bar, top, matches cluster color in A) across the single nuclei (columns). (C) Identification of each glial sub-cluster by marker genes. For each cluster, a marker gene expression is shown in two ways: Top: 2D embedding of nuclei (as in A) showing relative expression level of the marker gene across all nuclei. Bottom: histogram quantifying expression level of the marker gene nuclei in the relevant cluster (colored bars) and the distribution across all other nuclei (dashed red line). (D) Single nuclei transcriptional profiles match population RNA-Seq. Heat map showing the expression of top marker genes in the average of single nuclei (left) and in population RNA-Seq [74]. Bottom: Bar plot of the Pearson correlation (R) of each expression signature to the relevant population.

FIG. 11A-11E: BiSNE algorithm. (A) BiSNE algorithm. Top row, left to right: BiSNE takes as input an expression matrix of genes (rows) across nuclei (or cells, columns). It generates a 2-D plot of nuclei by dimensionality reduction using PCA followed by tSNE non-linear embedding, and then scores each gene by their expression across the 2-D plot, such that genes expressed in nuclei in proximity on the 2-D plot (dark blue points, top) are high scoring, whereas those expressed in nuclei scattered across the plot (dark blue points, bottom) are low scoring. Bottom row, right to left: Next, it takes an expression matrix of only high scoring genes (heatmap, genes (rows) across all nuclei (columns)), and repeats the dimensionality reduction. BiSNE is followed by density clustering (colored, bottom left). (B) BiSNE sub-clustering. Dendrogram of all nuclei clusters along with number of sub-clusters found by biSNE. NPC: neuronal precursor cells, ODC: oligodendrocytes, ASC: astroglia, OPC: oligodendrocyte precursor cell. (C) Expression of marker genes across 2-D embedded nuclei before and after biSNE. Shown is a panel of the same tSNE 2-D embedding of the GABAergic nuclei (from FIG. 1E), with each panel colored by the expression of a marker genes (denoted on the left). Top: using PCA-tSNE only. Bottom: using biSNE. (D) 2D embedding of cells using genes selected by generalized linear model (GLM) with different thresholds (Top). Cells are grouped in leftmost 2D embedding and denoted by group colors. GLM with less stringent thresholds selects more genes (From left to right), and results in different 2-D embedding without preserving cell grouping (from Left to Right). (E) 2-D embedding of cells using genes selected by biSNE with different thresholds (Top). biSNE with different thresholds results in similar 2-D embedding preserving cell grouping (from Left to Right).

Figure 5:
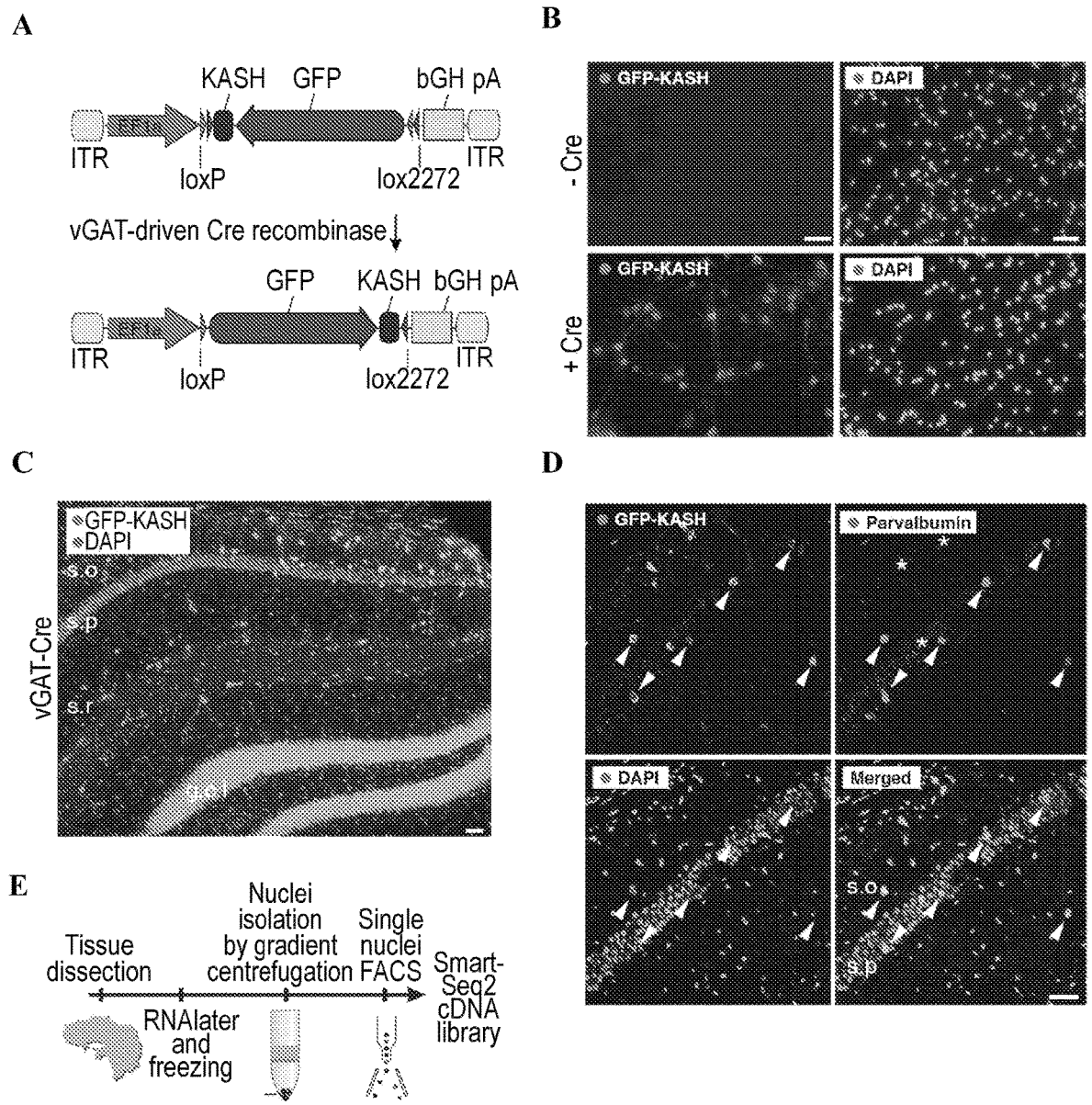
FIG. 5A-5E: Nuc-Seq is compatible with genetic labeling for enrichment of rare cells. (A) Genetic labeling of GABAergic interneurons using AAV expression vectors. Cre-mediated recombination of inverted transgenic cassette flanked by oppositely oriented loxP and lox2272 (Double-floxed Inverted Orientation, DIO) sites drives expression of GFP-KASH. Top: before recombination. Bottom: after cre driven recombination. (B) Primary cortical neurons infected with pAAV-EFla-DIO-GFP-KASH-bGHpolyA alone (top) or co-infected with pAAV-EFla-Cre-WPRE-bGH-polyA (bottom). (C) Expression of GFP-KASH in hippocampus of vGAT-Cre mice 14 d after viral delivery of pAAV-EFla-DIO-GFPKASH-bGH-polyA into CA1/CA2 stratum pyramidale (s.p.). (D) GFP-KASH labeled parvalbumin positive (arrow) and negative (arrowhead) interneurons in hippocampus of vGAT-Cre mice shown in C. (ITR—inverted terminal repeat; GFP—green fluorescent protein; KASH—Klarsicht, ANC1, Syne Homology nuclear transmembrane domain; hGH pA—human growth hormone polyadenylation signal.

FIG. 12A-12C: Transcriptional profiles of GABAergic interneurons. (A) biSNE clustering of GABAergic interneurons is independent of AAV infection or expression of transgene. Showing tSNE 2-D embedding of the GABAergic nuclei clustered with biSNE (from FIG. 2A) displaying untagged nuclei (blue) and Vgat-tagged nuclei (red) from Vgat-cre mice (FIG. 5). (B) Differentially expressed neuronal functional genes across GABAergic sub-clusters (FIG. 2A). Average centered expression of differentially expressed (t-test FDR q-value<0.05 with log-ratio>1 in at least one pairwise comparison between sub-cluster). K+channels (top left), Ca2+channels (top right), receptors (bottom right). (C) Differentially expressed neuronal functional genes shown as in (B): synaptic transmission (top left), Neuropeptides (middle left), sodium channels (bottom left), solute carriers (middle, rows), and other neuronal function (right, rows) across GABAergic sub-clusters (columns, FIG. 2A).

FIG. 13A-13E: Validation of GABAergic interneuron subtypes. (A) double fluorescent RNA in situ hybridization (dFISH) of Calb2 (green) and Vip (red). Expressions of Calb2 and Vip are largely overlapped. Scale bar: 20 um. (B) dFISH of Calb2 (green) and Htr3a (red). Expressions of Calb2 and Htr3a are partially overlapped. Scale bar: 20 um. (C) dFISH of Calb2 (green) and Pvalb (red). Expressions of Calb2 and Pvalb are not overlapped. Scale bar: 20 um. (D) Quantification of dFISH images. Bar plots showing the percent of single and double labeled cells in FISH images for each pair of genes. (E) DAPI image showing the entire view of hippocampus. Scale bar 100 um. g.c.l.—granule cell layer; m.l.—molecular layer; s.l.m.–stratum locunosum-moleculare; s.r.—stratum radiatum; p.l.—pyramidal layer; s.o.—stratum oriens.

FIG. 14A-14D: Spatial pattern of DG granule cells. (A) DG granule cells sub-clusters. Shown is a biSNE 2-D embedding of the DG granule nuclei with 3 sub-clusters denoted by colors. (B) Differential genes between clusters that have a distinct spatial pattern. 2-D embedding of nuclei (as in A), each showing the relative expression level of a gene expressed in the dorsal DG (top) or the ventral DG (bottom). (C) Schematics of hippocampal anatomy in a sagittal plane. DG marked in red. p.l.—pyramidal layer. (D) Spatial pattern of genes in the DG. ISH [64] sagittal image of the genes in (B). Top: Dorsal expression pattern. Bottom: Ventral expression. Scale bar: 400 um.

FIG. 15A-15E: Spatial assignment method (A) Spatial assignment using landmark gene expression. Nuclei sub-clusters are assigned to brain regions, by comparing a spatial map of landmark gene expression from ISH data to the expression of the landmark genes in each of the sub-clusters. An example using the landmark gene Wfs1. Left to right: creating a spatial landmark expression map from ISH data—Wfs1 Allen ISH [64] image data is quantified for its intensity in 15 bin grid (dividing the CA1 region into five grid bins along the dorsal-ventral axis and three grid bins along medial-lateral axis). (B) Left to right: Sub-cluster expression map-Wfs1 RNA-Seq expression across CA1 pyramidal nuclei (left) is fitted with regression and binarized (middle) to generate a profile (right) of the percentage of Wfs1 expressing nuclei (greyscale) in each of the CA1 pyramidal sub-clusters. (C) Hippocampus spatial anatomy in a coronal sections. Left: The mouse hippocampus 3-D structure and the coronal section (brown plane) used in this analysis. Right: Schematics of the coronal section shown on the left. CA1 (including subiculum): orange; CA3 (including the hilus): green; DG: dark grey. M: medial, L: lateral, D: dorsal, V: ventral. Sub: Subiculum. (D) Registration of CA1 pyramidal sub-clusters to CA1 sub-regions. Left: correlation of each sub-cluster to CA1 sub-regions using landmark genes. Right: sub-cluster assignments (numbered arrows and color code). (E) Registration of CA3 pyramidal sub-clusters to CA3 sub-regions. Shown as in (D). Dentate gyrus in gray is included in the schematic for spatial reference.

Figure 16:
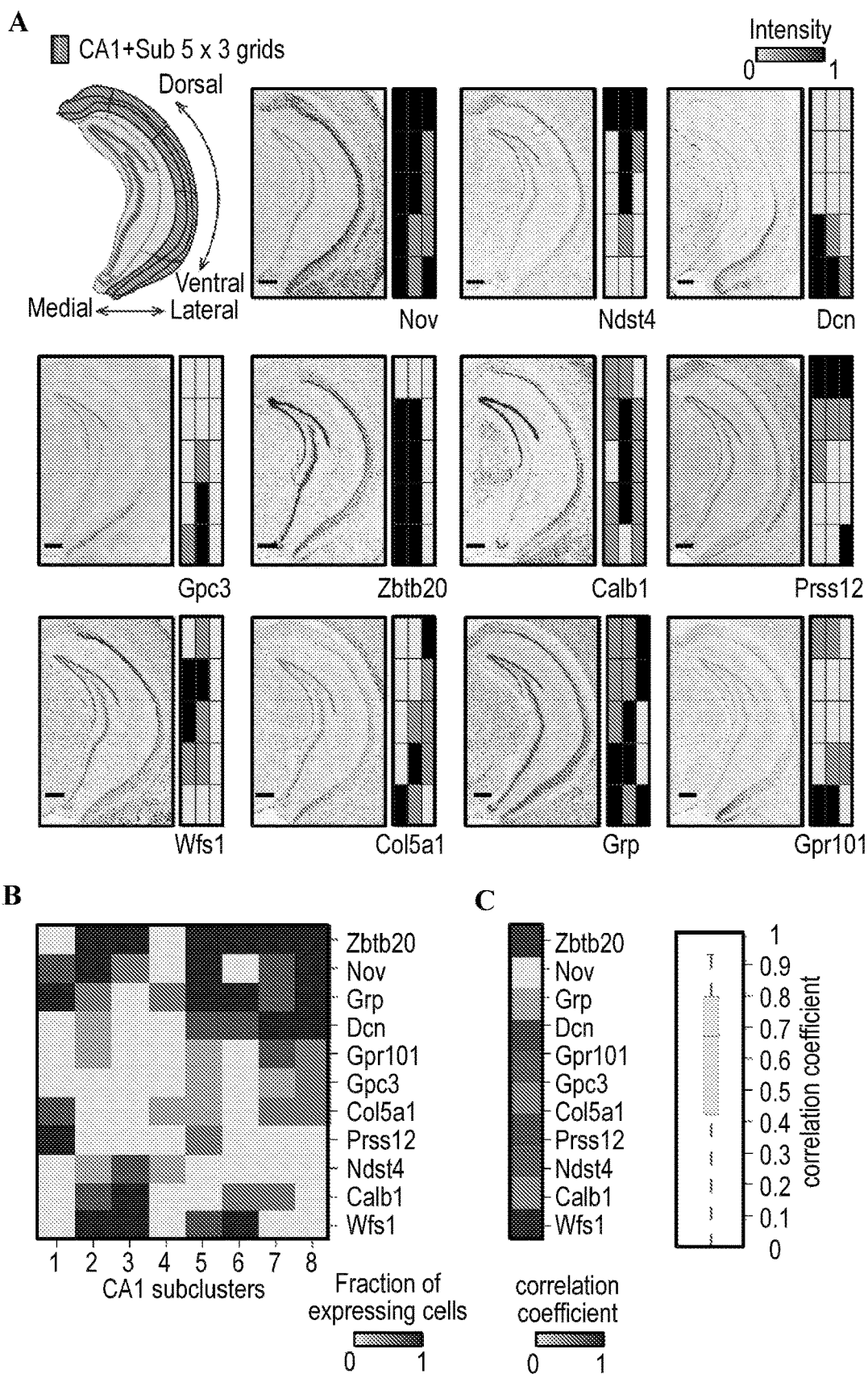

FIG. 16A-16C: Spatial landmark genes in CA1. (A) Spatial landmark genes in the CA1. Top left: Schematics of the hippocampus marking the CA1 and subiculum grid (orange). Displaying for each landmark gene an ISH [64] image showing its expression pattern in CA1 (right) and a heatmap showing the quantification of ISH intensities across the grid (left). Scale bar: 400 um. (B) Expression of landmark genes across the CA1 pyramidal sub-clusters. Heatmap showing the fractions of nuclei expressing each landmark genes in each biSNE sub-cluster. (C) Expression intensity of landmark genes in ISH [64] correlates with expression intensity predicted using Nuc-Seq data. Displayed in heat map (left) and box plot (right). In box plot, the median (red), 75% and 25% quantile (box), error bars (dashed lines).

Figure 17:
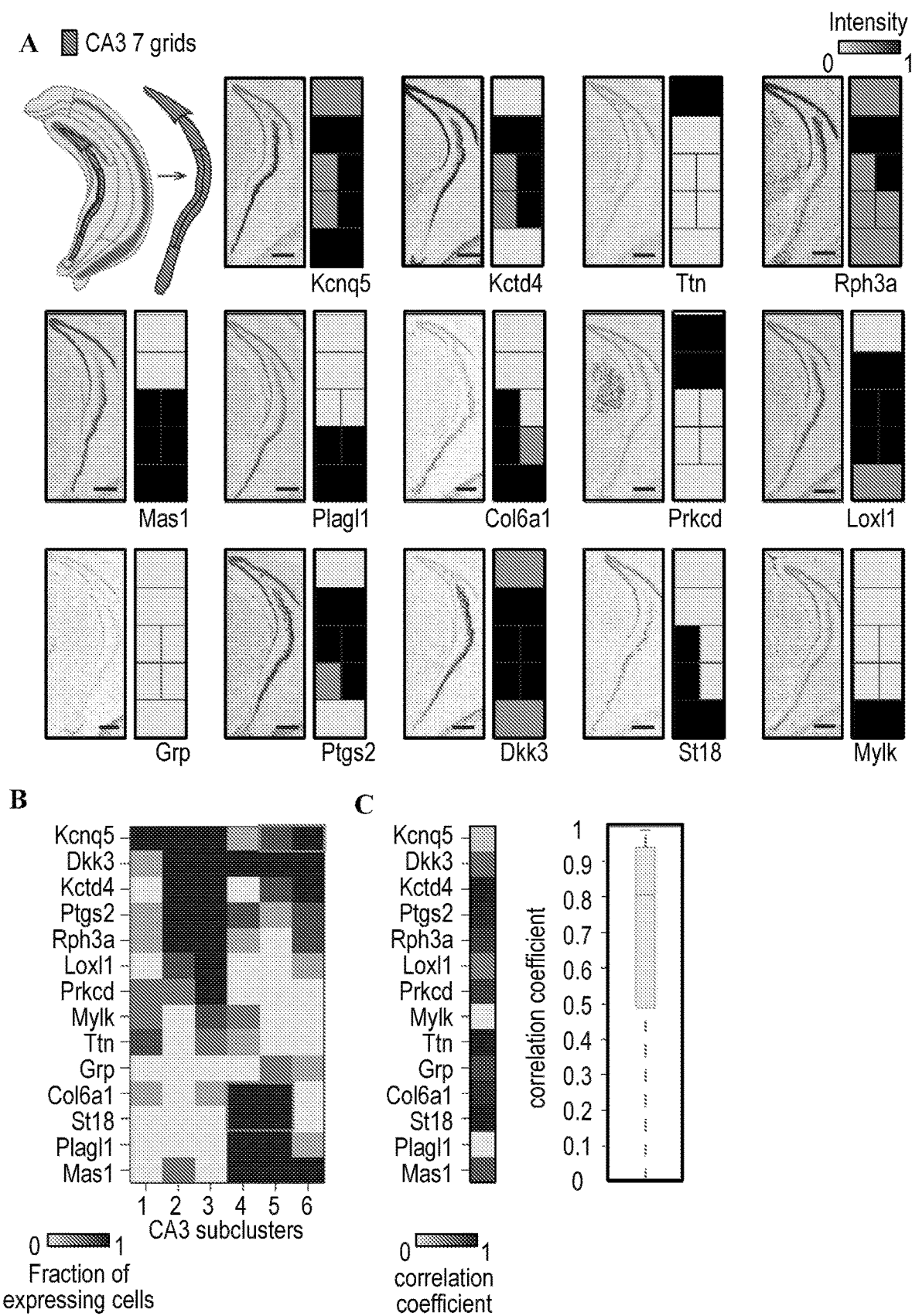

FIG. 17A-17C: Spatial landmark genes in CA3. (A) Spatial landmark genes in the CA3. Top left: Schematics of the hippocampus marking the CA3 grid (green). Displaying for each landmark gene an ISH [64] image showing its expression pattern in CA3 (right) and a heatmap showing the quantification of ISH intensities across the grid (left). Scale bar: 400 um. (B) Expression of landmark genes across the CA3 pyramidal sub-clusters. Heatmap showing the fractions of nuclei expressing each landmark genes in each biSNE sub-cluster. Marking the differentially expressed landmark genes in CA3.4, 5, 6 sub-clusters (red box). (C) Expression intensity of landmark genes in ISH [64] correlates with expression intensity predicted using Nuc-Seq data. Displayed in heat map (left) and box plot (right). In box plot, the median (red), 75% and 25% quantile (box), error bars (dashed lines).

FIG. 18A-18F: Examples of CA1 and CA3 predicted spatial expression. (A-B) Validation of spatial assignments in the CA1 pyramidal sub-clusters (denoted as CA1.1, . . . ,CA1.8). Predictions (left illustrations; dark and light boxes showing predicted differential expression regions) match well with Allen ISH [64] images (right; arrowhead: high expression; asterisk: depletion) in pairwise comparison of genes differentially expressed between two sub-clusters (genes and clusters labeled on top). (C) ISH image [64] of the example genes showing the entire view of dorsal-ventral CA1. Scale bar: 400 um. (D) ISH image [64] of the example genes showing the entire view of dorsal-ventral CA3. Scale bar: 400 um. (E) Restricted spatial expression pattern in ventral CA3 of Co16a1 and Kcnq5. Showing ISH [64] images. Top: entire view of CA3. Middle: view of region marked by the upper dashed box. Bottom: view of the region marked by the lower dashed box. (F) Validation of spatial assignments in the CA3 pyramidal sub-clusters. Shown as in (A).

Figure 19:
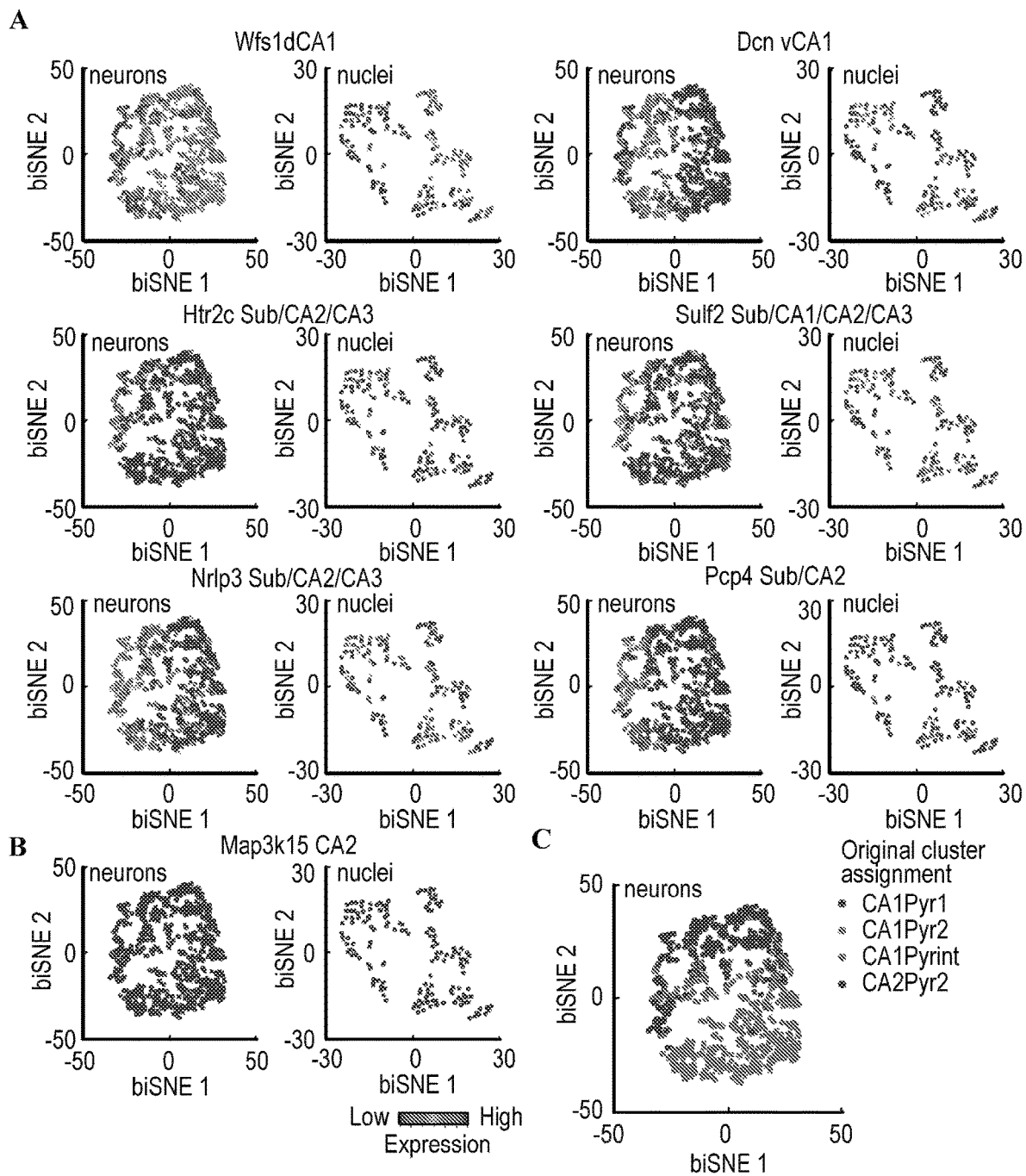

FIG. 19A-19C: Clustering of CA1 pyramidal neurons from published single cell RNA-Seq data. (A) Nuc-Seq and biSNE improve cell sub-type classification of CA1 pyramidal neurons compared to single neuron RNA-seq. Pairwise comparison of the expression levels of spatial landmark genes across 2-D biSNE embedding of of CA1 pyramidal neurons (left, data from single neurons RNA-seq [50]) and Nuc-Seq (right), showing the relative expression level of the gene (color scale). The expression of each gene is not restricted to any sub-cluster in the single neuron data [50], but is restricted to distinct subclusters in Nuc-Seq data. biSNE identified differential genes that have localized expression pattern the 2-D embedding of the single neuron RNA-Seq data. On top of each pair of plots, the anatomical region where the expression pattern of this gene is restricted to (identified in ISH [64]) is marked on the left, and the gene name on the right. dCA1: dorsal CA1; vCA1: ventral CA1; Sub: Subiculum. (B) A CA2 landmark gene Map3k15 is not selected by biSNE and does not have localized expression pattern in the 2-D embedding of the CA1 pyramidal neurons from the single cell RNA-Seq data. 2-D embedding of CA1 pyramidal neurons (Left: data from [64]) and nuclei (Right: data from Nuc-Seq) showing the relative expression level of the gene (as in A). (C) 2-D embedding of the CA1 neurons showing the original assignment to 4 sub-clusters identified in [64] and denoted by colors. CA1Pyr1: CA1 pyramidal neuron type 1; CA2Pyr2: CA1 pyramidal neuron type 2; CA1PyrInt: CA1 pyramidal intermediate; CA2Pyr2: CA2 pyramidal neuron.

FIG. 20A-20G: Expression of Penk/Cck gene signatures in the DG. (A) DG nuclei form a continuum on expressions of Penk/Cck gene signature. Top left: DG cluster (as in FIG. 1E). Bottom left: DG cells form a continuum when mapped only by the gene sets containing Penk or Cck (in B). Cells are color coded by Penk/Cck gene signature expression. (B) Gene signatures expressed across granule cells in DG, marked by Penk and Cck expression (red labels, right). Absolute log(TPM) expression values. Dashed line separates nuclei expressing Penk highly (left) or lowly (right). (C) Distribution of expression (Box plot, Y axis) of Penk (dark grey, facing up) and Cck (light grey, facing down) across each sub-clusters of GABAergic neurons and DG granule cells (X axis). Box plots show the median (red), 75% and 25% quantile (box), error bars(dashed lines), and outliers (red cross). (D) qPCR validation of two DG subpopulations differentially expressing Penk (Y axis) and Cck genes (X axis), respectively. Proportion of nuclei at each expression quadrant is marked. (E) Schematics of hippocampal anatomy in a sagittal plane. red structure represents DG, same as in FIG. 14. (F) Spatial pattern on the Penk and Co16a1 genes. ISH [64] images of two coexpressed genes Penk and Co16a1 in the sagittal plane with view of the entire DG. scale bar: 400 um. (G) Inferred transcription factors regulating the Penk/Cck gene signatures. Factors shown have known targets enriched in differentially expressed genes in the Penk/Cck gene signatures (hypergeometric p-value, Ingenuity Pathway Analysis). Edges denote transcription regulation.

FIG. 21A-21D: Continued Double FISH validates mutual exclusive expression of Penk and Oprd1. (A) From Top to Bottom: dFISH Penk/Oprd1 (green) and Htr3a/Vip/Pvalb showing expressions of Penk and Htr3a are partially overlapped. expressions of Oprd1 and Htr3a are mostly not overlapped. expressions of Penk and Vip are largely overlapped. expressions of Oprd1 and Vip are not overlapped. expressions of Penk and Pvalb are not overlapped. expressions of Oprd1 and Pvalb are largely overlapped. Scale bar: 20 um. s.r.—stratum radiatum; p.l.—pyramidal layer. (B) Quantification of dFISH images. Bar plots showing the percent of single and double labeled cells in FISH images for each pair of genes. (C) Allen ISH [64] image of Penk gene with view of the upper DG (top), and the lower DG (bottom). Shows its expression pattern in the CA1 and DG. Scale bar: 400 um. (D) Allen ISH [64] image of Oprd1 gene (as in B) shows its expression in the subiculum and its depletion in the dorsal CA1 and DG regions. Scale bar: 400 um.

FIG. 22A-22H: Nuc-seq combined with labeling of dividing cells (Div-Seq) profiles adult newborn precursors and neurons. (A) Cells expressing immature neuronal markers with EdU tagging. Left: heatmap showing 4 nuclei expressing immature neuronal marker genes: Sox4, Dcx, Sox11, and Cd24a. Right: 2-D embedding of the glial cluster of nuclei (from FIG. 1E), clustered as in FIG. 10 colored by the expression level of Sox11 gene. These nuclei are marked in the 2-D embedding of glial-like cells as in FIG. 10 (black dashed circle) (B) EdU labeled cells cluster separately from other cells. Shown is a biSNE 2-D embedding of all nuclei including the EdU labeled nuclei extracted after 2-day and 14-day post labeling. Most labeled nuclei form a distinct cluster. (C) EdU labeling tagged cells in the subgranular zone (SGZ) region. Shown are EdU staining (GFP click chemistry) and DAPI staining (blue) of tissue slice two weeks post EdU injections. (D) FACS sorting of EdU labeled nuclei. Shown is a scatter plot of log GFP intensity (X axis) and the log ruby-dye intensity (Y axis) from FACS of nuclei isolated two days after EdU injection (left) and with no EdU injections (right). Both samples were treated with click chemistry as in B. (E) Dcx immature neuronal marker gene is expressed in GABAergic neurons. Box plots showing expression levels of the Dcx gene across mature granule neurons, immature neurons (EdU labeled) and GABAergic neurons. In box plots, the median (red), 75% and 25% quantile (box), error bars (dashed lines), and outliers (red dots). (F) Most of the 14 days EdU labeled nuclei are immature neurons. Shown is the distribution of 14 days EdU labeled nuclei across cell types, assigned to by clustering (as in B) and marker gene expression: Oligodendrocyte precursor cells, OPC; granule cells, DG; Astrocytes, ASC; Oligodendrocytes, ODC. (G) Expression of known marker genes along the trajectory matches the expected dynamics. Left: Heatmap of the expression of the markers and related genes (rows), sorted by their expected pattern, along the neurogenesis trajectory (columns, running average along the trajectory). Data in log(TPM+1), color scale as in (A). Right: Heatmap of the same markers along the neurogenesis trajectory when using Div-Seq libraries at 2.5 days and 1 week post EdU injections, showing a similar dynamic expression pattern. (H) Expression level of known transcription factors across cell types, showing known regulators of each cell type. Shown are the relative average expression levels (bars) across cells.

FIG. 23A-23F: Transcriptional and epigenetic switch during adult neurogenesis and neuronal maturation. (A) Dynamically regulated TFs and chromatin regulator. Heatmap of the running average expression (log(TPM+1)) of the regulators (rows) along the trajectory (columns). Genes are sorted by the cluster they were identified in (as in FIG. 3E). Red lines mark the transition from neuronal precursor cells (NPCs) to neuroblast (NB) and from NB to immature neurons. (B) Examples of dynamic expression patterns of families of regulators. Heatmap as in A with an additional column for the expression (log(TPM+1)) of the same genes in mature granule nuclei (DG cluster). Top: Sox family genes. Middle: Cyclin (Cdk) genes. Bottom: kinesin superfamily. (C) Examples of dynamic expression patterns of families of chromatin remodelers. Presented as in B. Top: Histone deacetylases (HDACs). Middle: Chromatin dehydrogenases. Bottom: histone demethylase protein family. (D) Transcriptional switches in the BAF complex. Top: Schematics of the complex. The positions of each component within the complex are denoted by colors, and below: the heatmap of average expression of complex component genes in NPCs, NB, immature, and mature granule DG cells (log(TPM+1)). (E) Examples of families of actin/cytoskeleton and Semaphorin signaling associated genes. Presented as in B. Top: Semaphorin genes. Middle-top: Rho-associated serine/threonine kinases. Middle-bottom: serine/threonine p21-activating kinases. Bottom: Microtubule Associated Serine/Threonine Kinase 3. (F) Comparison of Div-Seq data to other datasets. Heat maps from right to left: Div-Seq data presented as in (B); RNASeq time course of in vitro derived neurons from hES cells, average of replicates per day [84]; Single cells RNA-Seq of mouse adult neuronal stem cells and progenitors in the DG across pseudotime [79]; Single cell RNA-Seq of fetal human neuronal precursor cells, hNPCs (Tirosh et al. unpublished);

FIG. 24A-24E: Transcriptional program of neuronal maturation revealed by Div-Seq. (A) Maturation signature. Shown is the expression of genes (rows) differentially expressed (t-test FDR q-value<0.01) between the mature granule cells (orange bar, top) and the immature neurons (14d labeling; grey bar, top). Key markers of immature (Dcx, Sox11, Foxg1) and mature (Calb1) neurons are marked in red. Other genes of interest are marked in black, including receptors, channels, axon guidance molecules and the GABA transporter (Gatl). (B) Differential paralog expression may lead to functional specialization of the semaphorin pathway. Shown is the semaphorin signaling pathway, highlighting genes induced in immature (red) and mature (blue) neurons. (C) Young (1-month-old) mice have a higher fraction of immature cells compared to 12 months and 2 years old animals. Shown is the distribution of maturation scores across granule cells in 2-year old mice (red), 3-months old mice (orange) and adolescent 1-month old mice (green), and immature neurons (gray). Score defined as the difference in accumulated expression levels of up-regulated and down-regulated genes between mature and immature neurons. (D) Gad1 and Gatl expression in neuronal precursor cells (NPCs), neuroblast (NB), immature and mature granule DG cells. In box plots, the median (red), 75% and 25% quantile (box), error bars (dashed lines), and outliers (red dots). (E) FISH of Gad1 (green) and Gad2 (red). Gad1 is widely expressed throughout cells in DG, whereas Gad2 is sparse. Scale bar: 100 um.

FIG. 25A-25E: (A) Workflow for microfluidic device for analyzing nuclei (Dronc-Seq.) (B) Microfluidic device design generated using AutoCAD. (C) Bright-field micrographs of droplet generation in Drop-Seq (left), and drops with barcode beads and lysed cellular material (right). (D) Bioanalyzer trace of cDNA library after whole transcriptome amplification. (E) Distribution of number of genes captured for ~500 nuclei.

Figure 26:
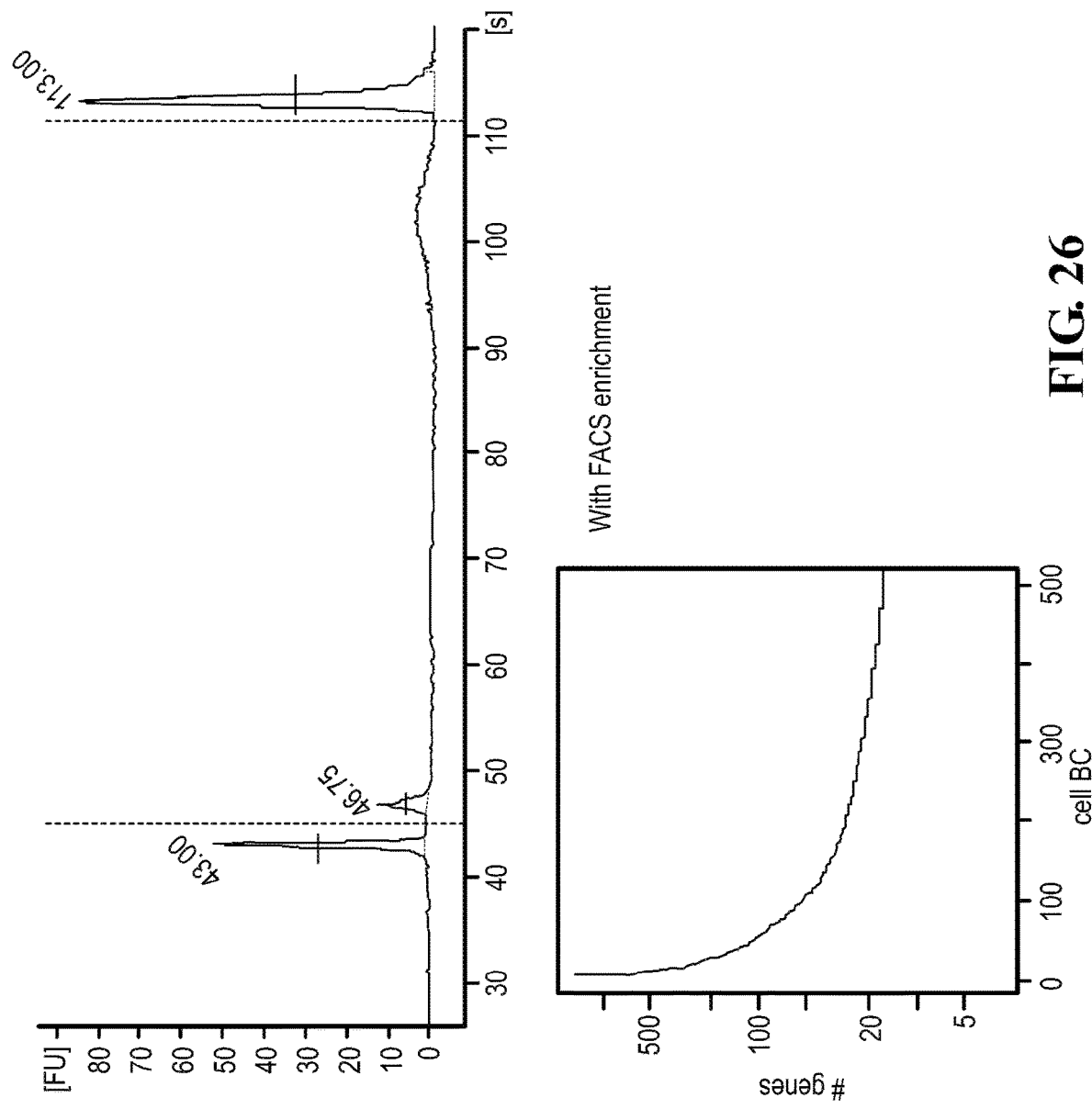

FIG. 26: Bioanalyzer trace of cDNA library after whole transcriptome amplification with FACS enrichment (top). Distribution of number of genes captured for ~500 nuclei with FACS enrichment (bottom).

Figure 27:
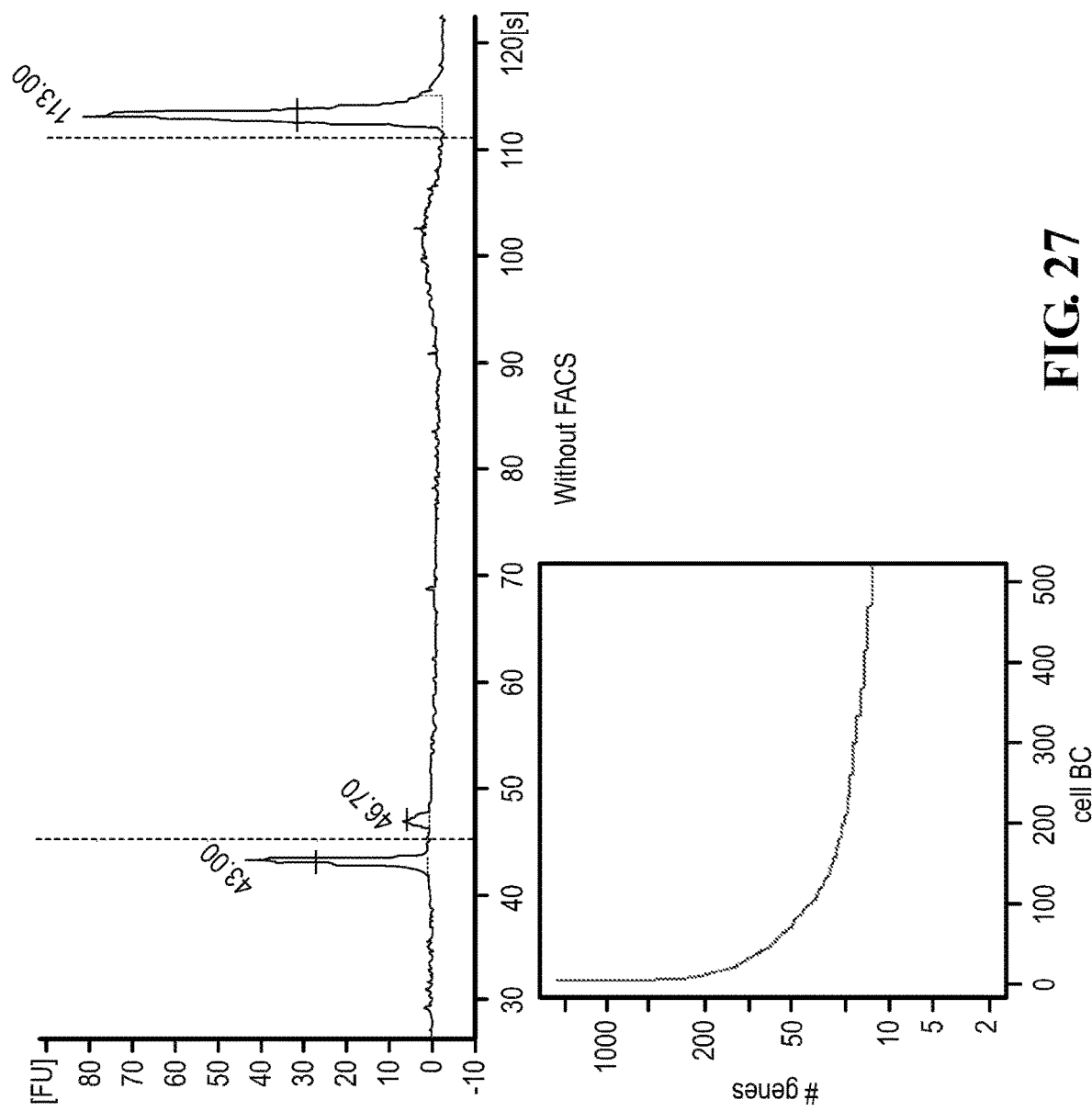

FIG. 27: Bioanalyzer trace of cDNA library after whole transcriptome amplification without FACS enrichment (top). Distribution of number of genes captured for 500 nuclei without FACS enrichment (bottom).

FIG. 28: Schematic representation of a Dronc-Seq device (left) and plates for performing Nuc-Seq (right).

Figure 29:
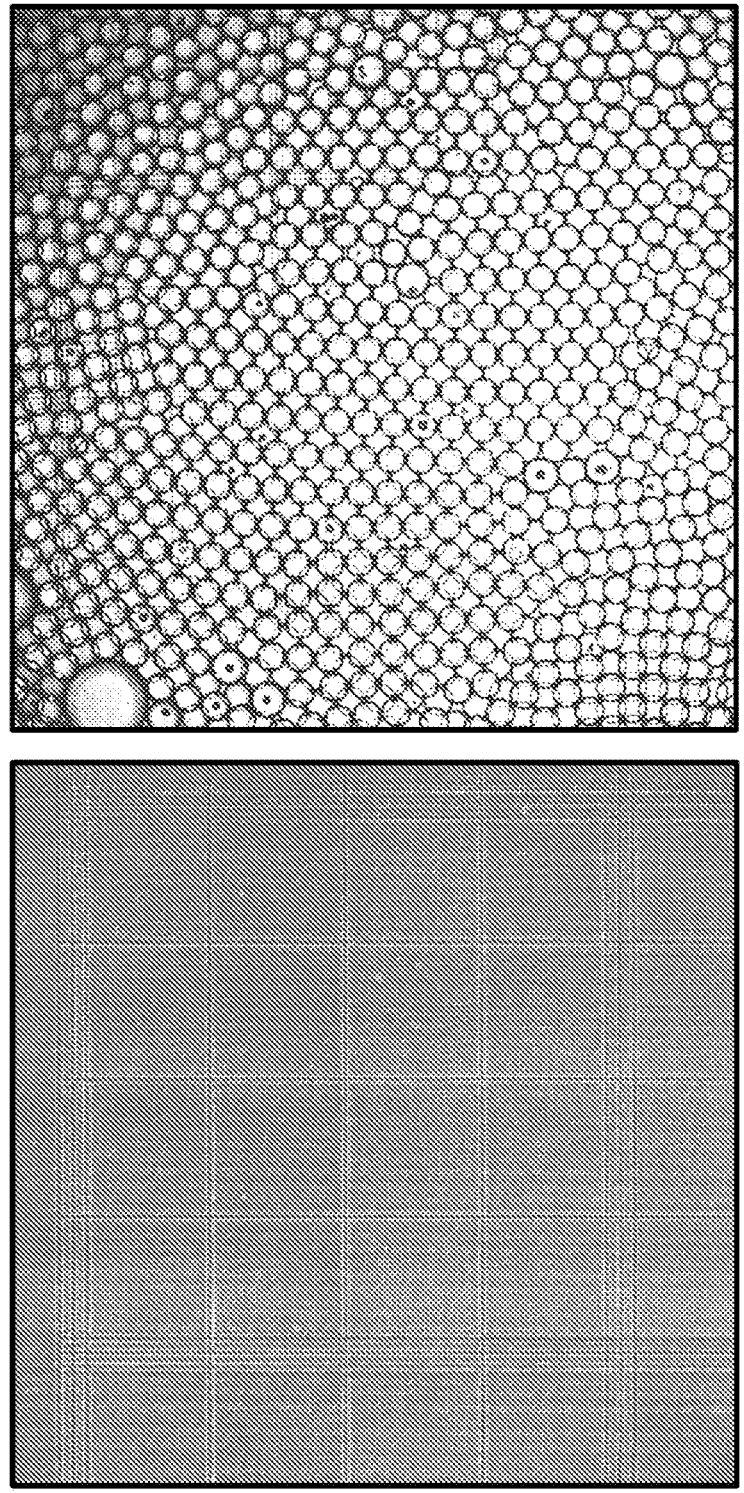

FIG. 29: Staining and photograph of droplets obtained with a Dronc-Seq device. The results were obtained using the nuclei purification protocol (Method A) as described in Example 6.

Figure 30:
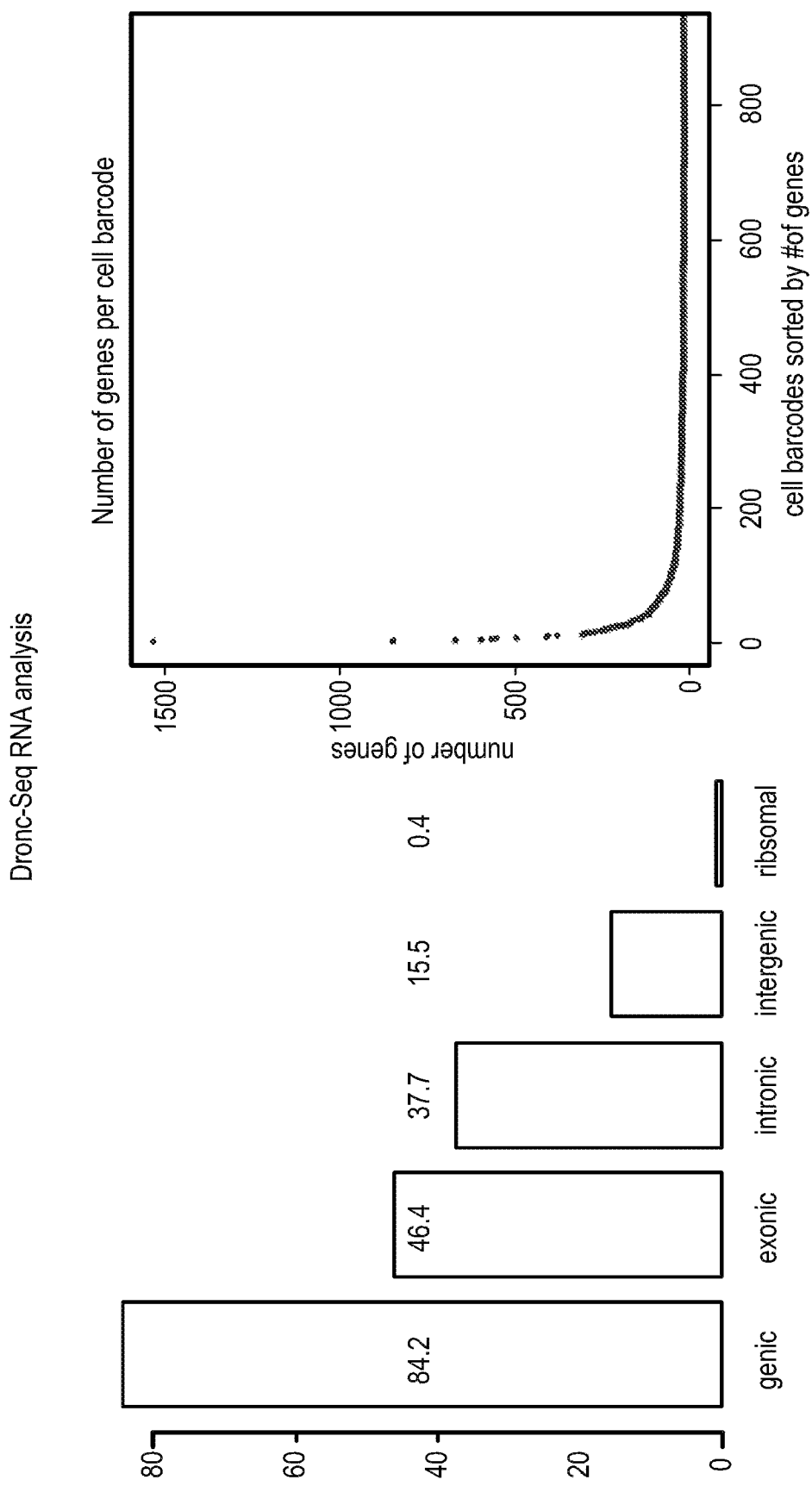

FIG. 30: RNA analysis using Dronc-Seq: single nuclei RNA profiling.

Figure 31:
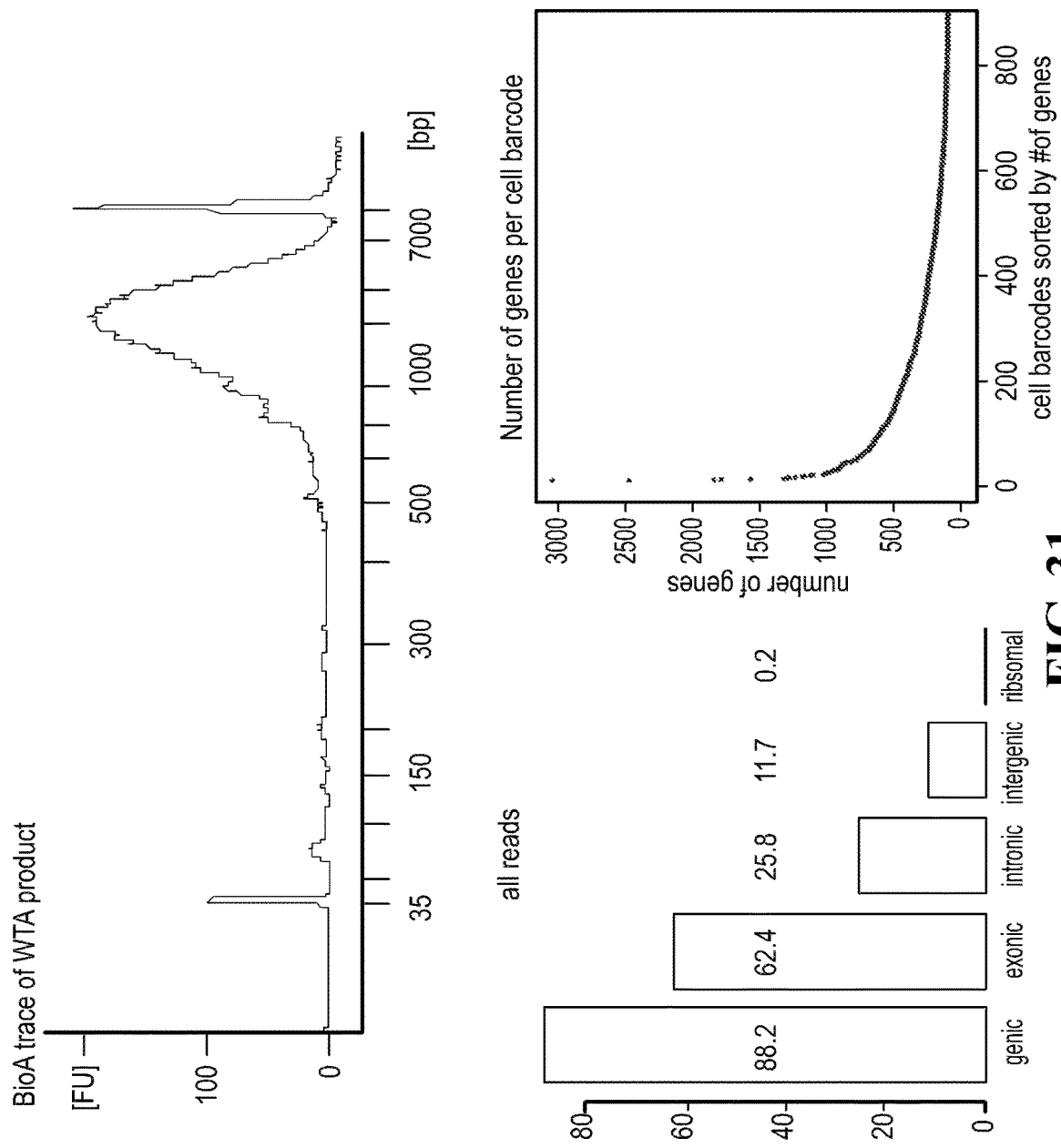

FIG. 31: RNA analysis using Dronc-Seq: single nuclei RNA profiling. WTA: Whole transcriptome analysis, showing integrity of the RNA population retrieved using Dronc-Seq.

Figure 32:
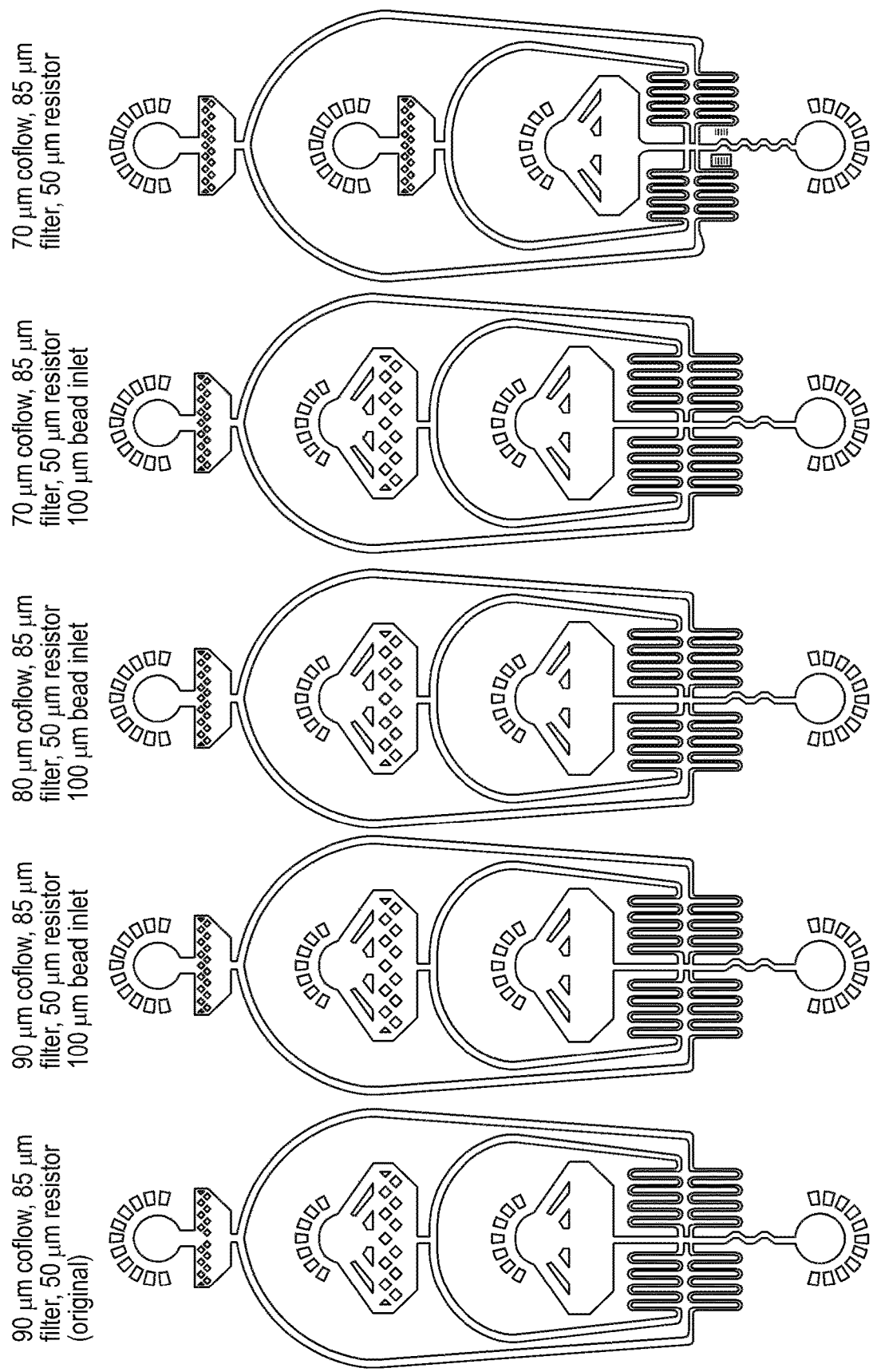

FIG. 32: Schematic representation of Dronc-Seq devices for generating droplets of various sizes. In these designs, both carrier fluid channels comprise a resistor.

Figure 33:
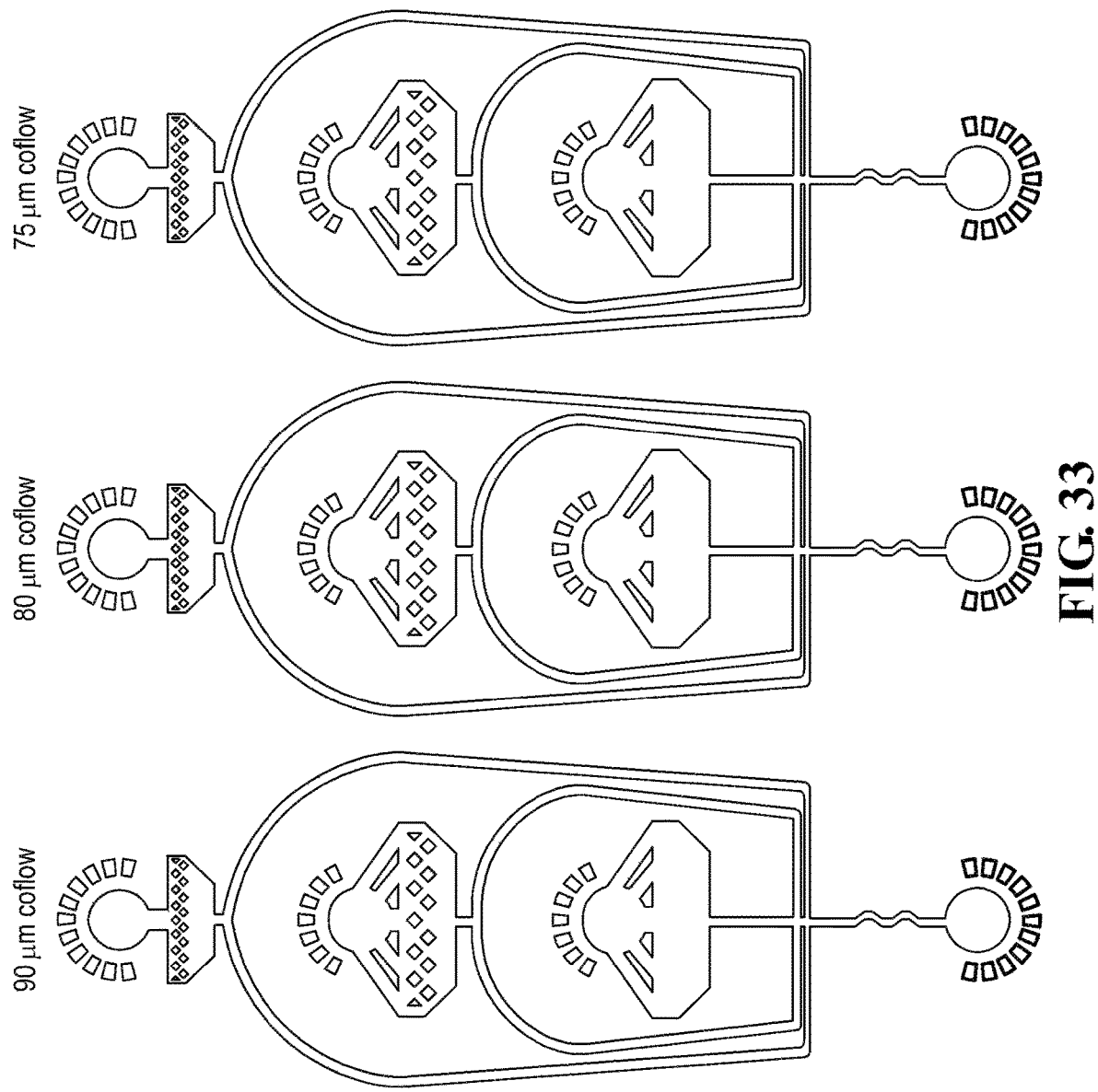

FIG. 33: Schematic representation of Dronc-Seq devices for generating 90, 80 and 75 µm droplets. In these designs, the carrier fluid channels do not comprise a resistor.

Figure 34:
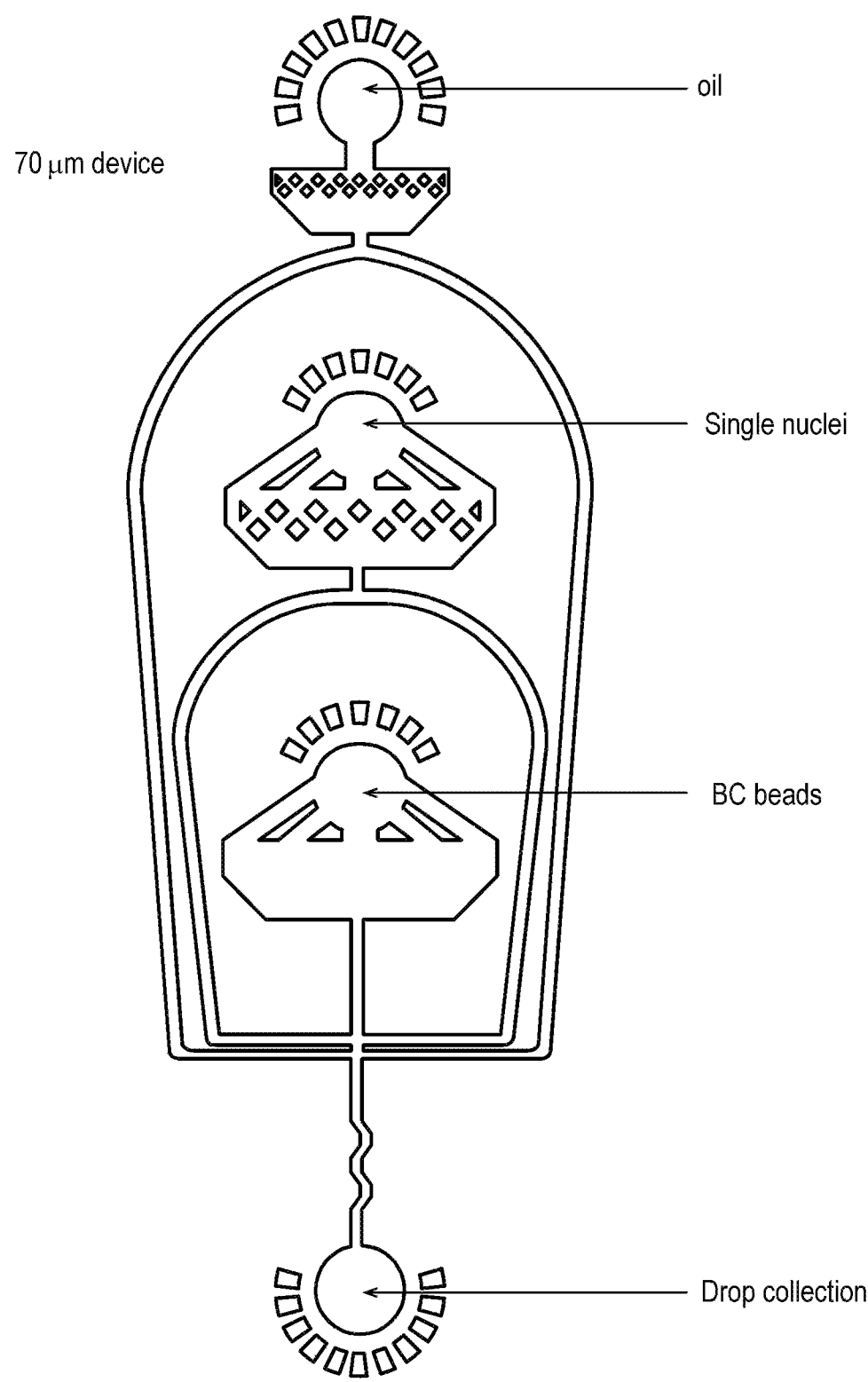

FIG. 34: Schematic representation of a Dronc-Seq device for generating 70 µm droplets.

Figure 35:
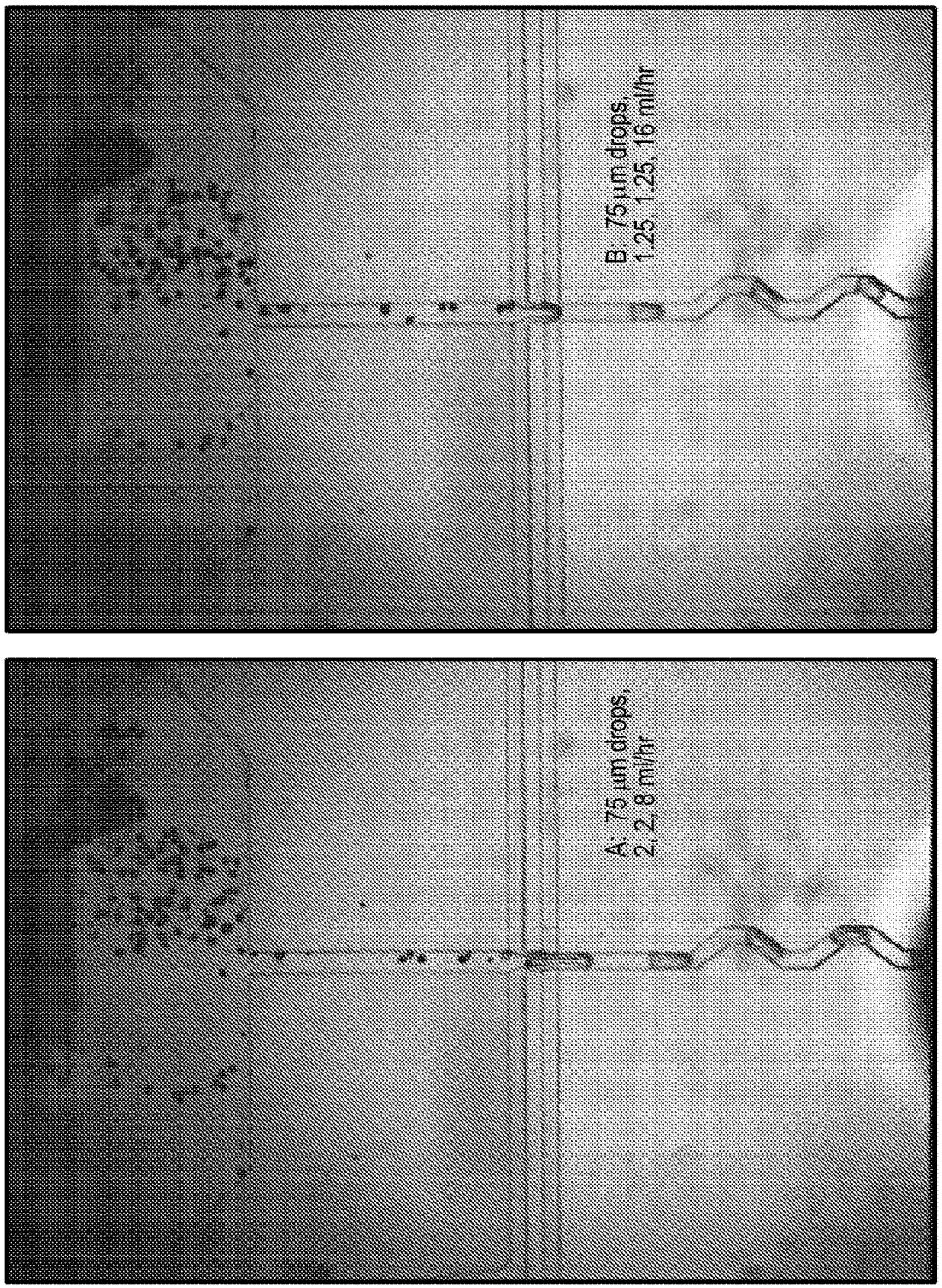

FIG. 35: Photograph of a Dronc-Seq device generating 75 µm droplets. In run A: the flow rates are 2 ml/hr for aqueous suspensions (beads, resp nuclei), and 8 ml/hr for the oilous phase. In run B: the flow rates are 1.25 ml/hr for aqueous suspensions (beads, resp nuclei), and 16 ml/hr for the oilous phase.

Figure 36:
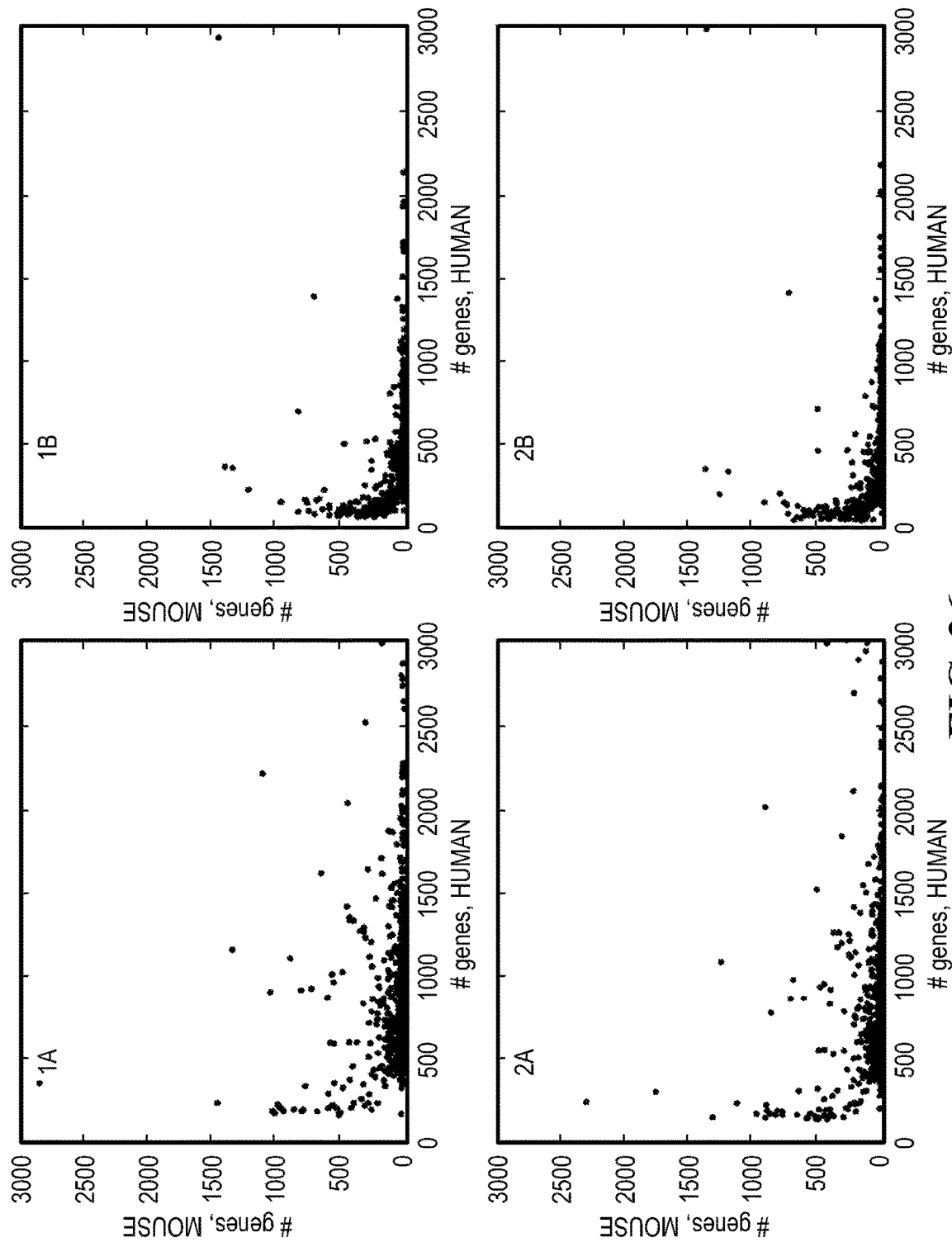

FIG. 36: Species mixing experiments: Dronc-Seq allows to accurately remember the nucleus-of-origin of the RNA. A 70 µm Dronc-Seq device was used to analyze species mixing % using Poisson loading concentrations. Beads were used at 350 k/ml and nuclei at 300k/ml with human (HEK293T cell line) and mouse (frozen brain tissue) at 1:1 number ratio.

Runs were performed in duplicate under two conditions (A and B, as depicted in FIG. 35).

Figure 37:
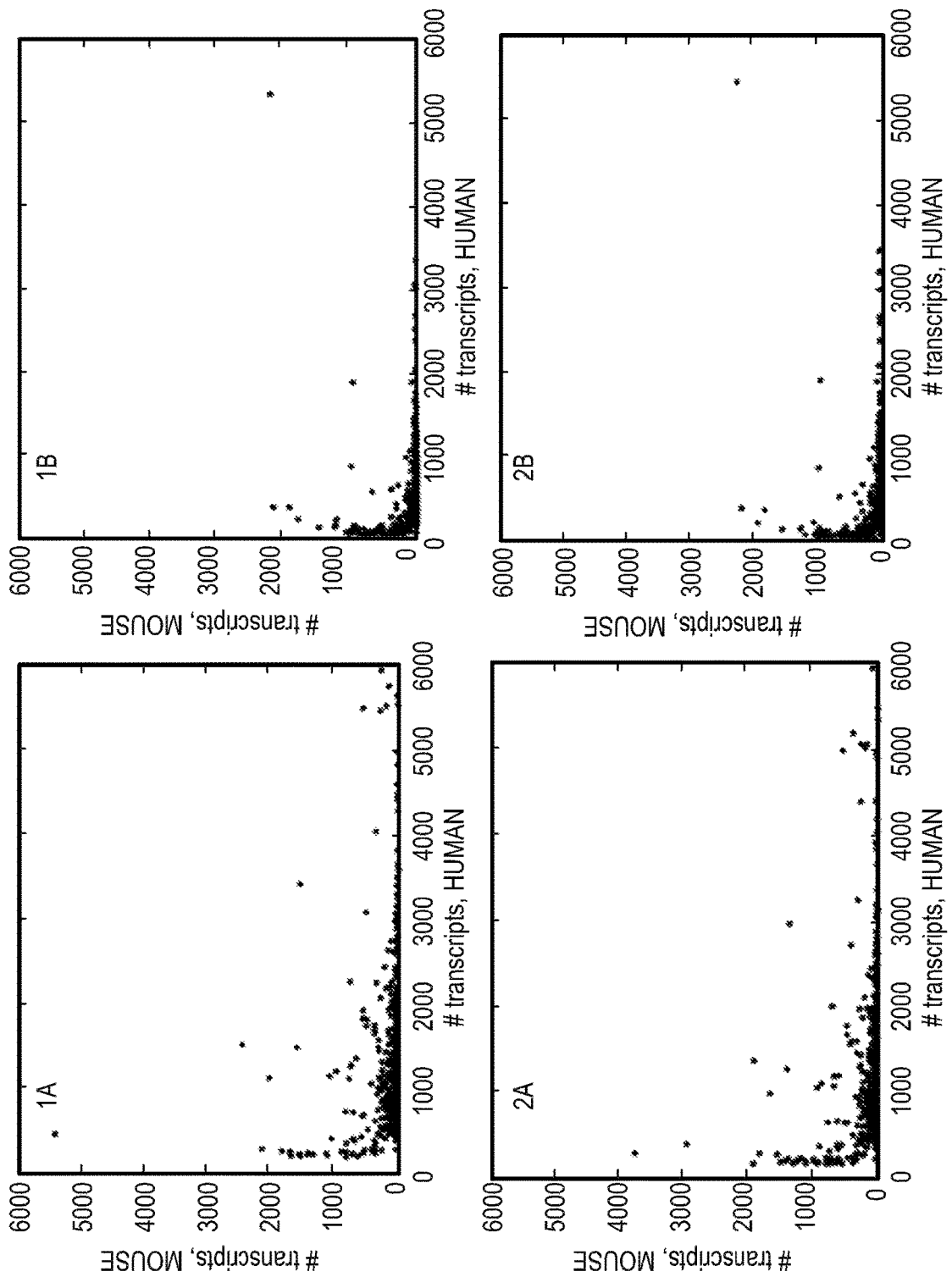

FIG. 37: Species mixing experiments: Dronc-Seq allows to accurately remember the nucleus-of-origin of the RNA. A 70 μm Dronc-Seq device was used to analyze species mixing % using Poisson loading concentrations. Beads were used at 350k/ml and nuclei at 300k/ml with human (HEK293T cell line) and mouse (frozen brain tissue) at 1:1 number ratio. Runs were performed in duplicate under two conditions (A and B, as depicted in FIG. 35).

Figure 38:
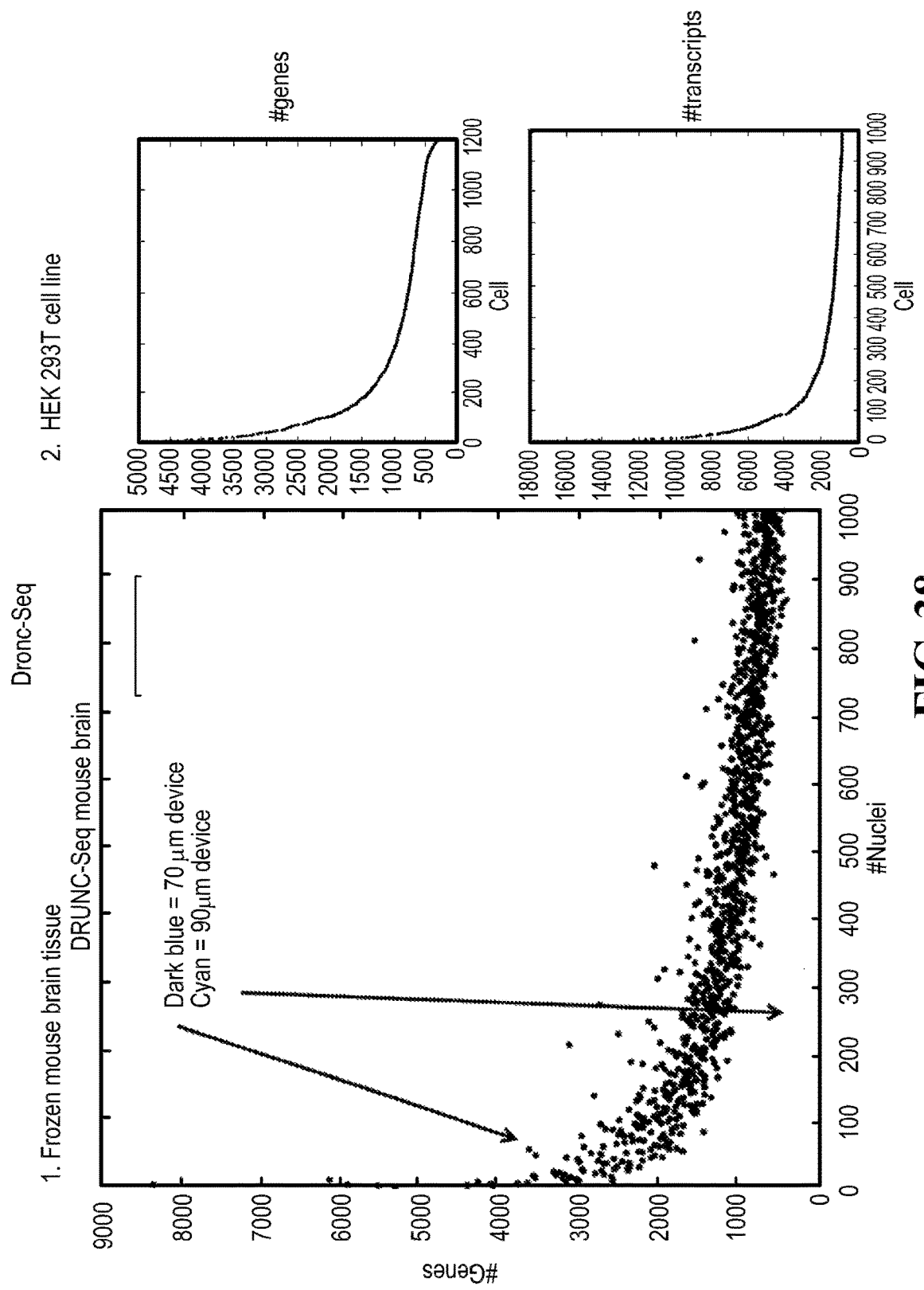

FIG. 38: Results obtained with Dronc-Seq analysis of a frozen sample (1.), and of cells of a human cell line (2.): plots of #genes or #transcripts detected per nucleus for Dronc-Seq.

Figure 39:
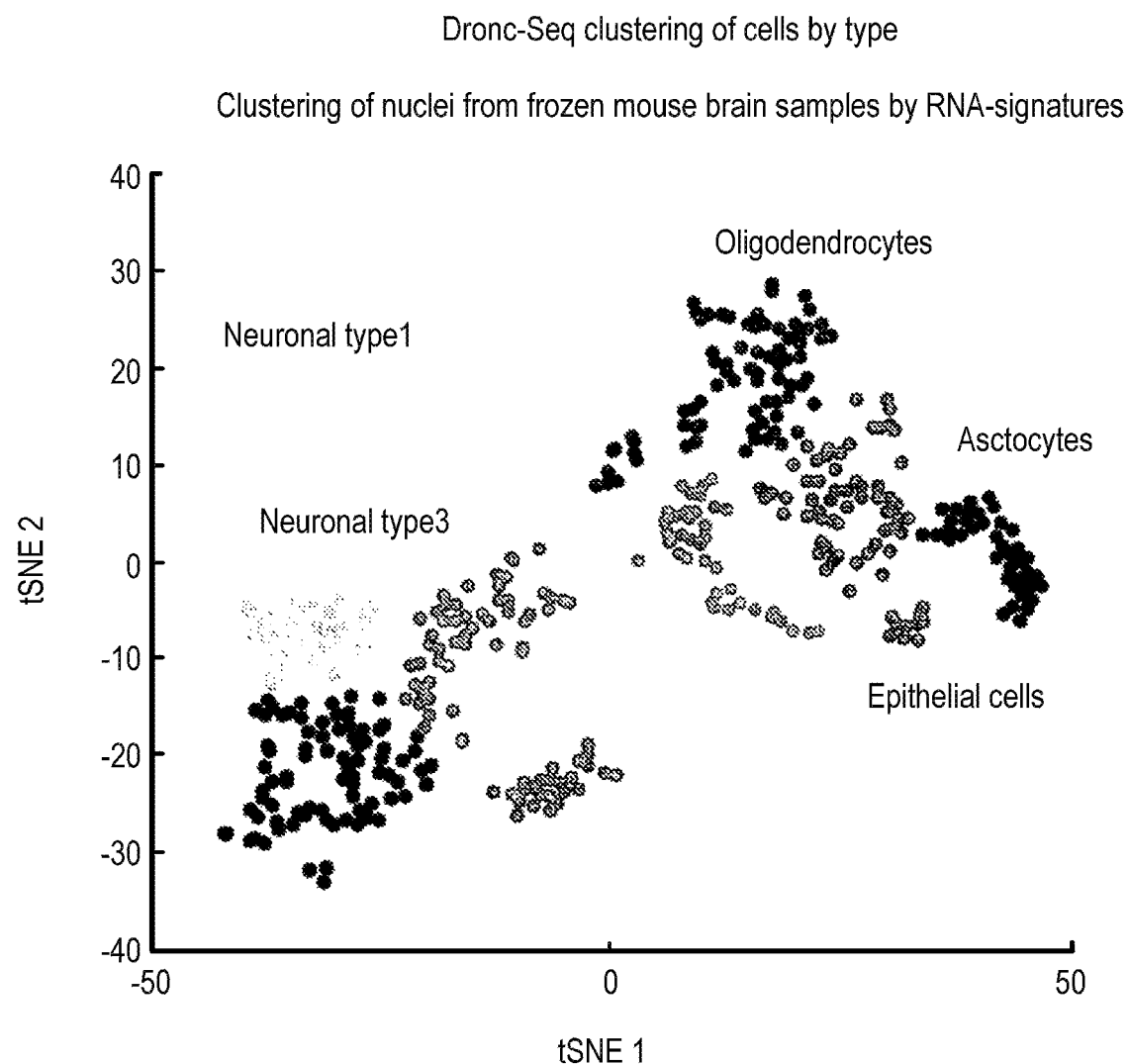

FIG. 39: Dronc-Seq analysis allows clustering of nuclei from frozen mouse brain samples by RNA-signatures.

Figure 40:
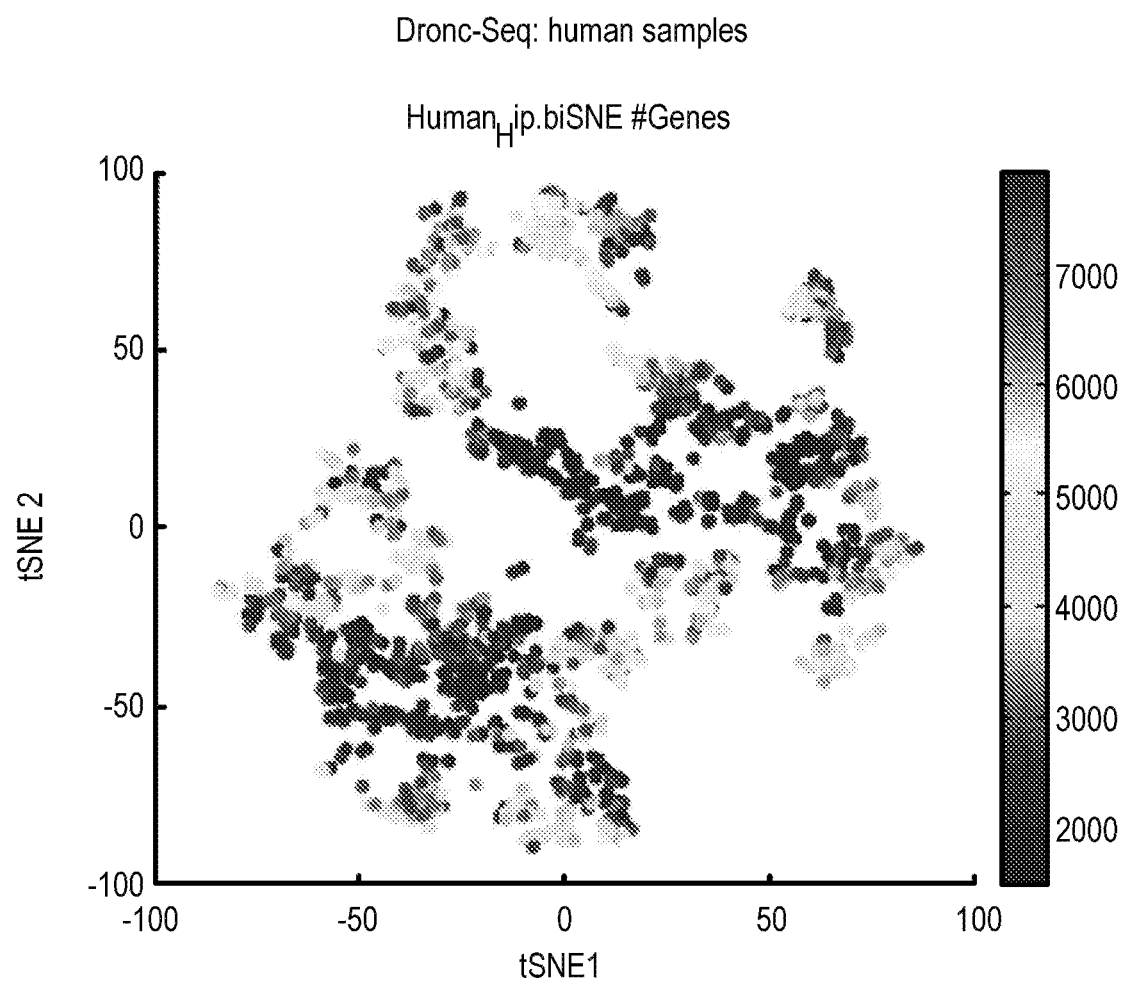

FIG. 40: Dronc-Seq results obtained on human nuclei allows cell clustering (the color indicates the number of genes detected per sample). The cells were from a postmortem human hippocampus.

FIG. 41: Transcriptional dynamics of adult neurogenesis by Div-Seq. (A) Div-Seq method: EdU is injected into adult mice and incorporates into dividing cells (5). Isolated EdU-labeled nuclei are fluorescently tagged by click-IT chemistry and captured by FACS for sNuc-Seq. (B) Adult neurogenesis in the DG (4) Tan box: timing of EdU labeling. NSC: neuronal stem cell. Bottom panel: EdU labeling and tissue dissection (gray) time course. (C) A continuous trajectory of newborn cells in the DG. biSNE 2D embedding of neuronal lineage nuclei (n-269). Arrow: direction of trajectory determined by labeling time and marker expression. Top: Colored by labeling time (1 to 14 days). Bottom: Expression of markers, shown as (i) average expression along the trajectory (left colorbar) and (ii) 2D embedding colored by the expression level (right colorbar). Markers (clockwise from top left): Sox9 (NSC). Notch1 (proliferation/differentiation). Neurod1 (immature neurons). Eomes/Tb2 (neuronal precursor). (D) Expression waves along the trajectory. Left: average expression of cluster genes along the trajectory. Middle: heat-map of average expression of each gene along the trajectory and neurogenic stages [labeled as in (B)]. Right: representative enriched biological pathways.

FIG. 42: Dynamics of adult newborn GABAergic neurons in SC. (A) Div-Seq in SC captures oligodendrocytes precursor cells (OPCs) and immature neurons. Distribution of cell types in non-EdU-labeled and 6 to 7 days EdU-labeled nuclei. (B) Div-Seq captured nuclei expressing marker genes of immature (Sox11) and GABAergic (GAdl) neurons. Box plots for immature neurons, mature neurons, and OPCs. Red: median; box: 75 and 25% quantiles. (C) Newborn cells in SC form a continuous trajectory. Two-dimensional embedding of 1 to 7 days EdU-labeled and nonlabeled nuclei (n=184 neuronal lineage nuclei), colored by labeling time. Trajectory directionality is based on EdU labeling time and marker genes. (D) Dynamically expressed genes shared in SC and DG neurogenesis (347 genes from FIG. 48B and FIG. 41D). (E) Gradual transition from a glia-like neuronal state. Neuronal trajectories in SC [as in (C)] and DG (as in FIG. 41C) colored by a glia-neuron RNA expression score. (F) Region-specific gene expression in immature neurons (6 to 7 days after EdU labeling). A total of 236 genes differentially expressed between SC and DG (t-test false discovery rate<0.05. log-ratio>1) in olfactory bulb (OB), SC, and DG. Box: average expression of example genes up-regulated in OB and SC compared to DG.

FIG. 43: Nuc-seq combined with labeling of dividing cells (Div-Seq) profiles adult newborn precursors and neurons. (A) Cells expressing immature markers with EdU tagging. Left: heatmap showing 4 nuclei expressing immature neuronal marker genes: Sox4, Dcx, Sox11, and Cd24a. Right: 2-D embedding of the glial cluster of nuclei (from FIG. 1B), clustered as in FIG. 10A colored by the expression level of Sox11 gene. These nuclei are marked in the 2-D embedding of glial like cells as in FIG. 10A (black dashed circle) (B) EdU labeled cells cluster separately from other cells. Shown is a biSNE 2-D embedding of all nuclei including the EdU labeled nuclei extracted after 2-day and 14-day post labeling. Most labeled nuclei form a distinct cluster. (C) EdU labeling tagged cells in the subgranular zone (SGZ) region. Shown are EdU staining (GFP click chemistry) and DAP1 staining (blue) of tissue slice two weeks post EdU injections. (D) FACS sorting of EdU labeled nuclei. Shown is a scatter plot of lot GFP intensity (X axis) and the log ruby-dye intensity (Y axis) from FACS of nuclei isolated two days after EdU injection (left) and with no EdU injections (right). Both samples were treated with click chemistry as in B. (E) Dcx, a commonly used marker for immature neurons, was expressed in all mature GABAergic neurons in the hippocampus, highlighting the limits of using single marker genes to identify cell types. Box plots showing expression levels of the Dcx gene across mature granule neurons, immature neurons (EdU labeled) and GABAergic neurons. In box plots, the median (red), 75% and 25% quantile (box), error bars (dashed lines), and outliers (red dots). (F) Most of the 14 days EdU labeled nuclei are immature neurons. Shown is the distribution of 14 days EdU labeled nuclei across cell types, assigned by clustering (as in B) and marker gene expression: Oligodendrocyte precursor cells, OPC, dentate gyrus granule cells, DG; Astrocytes, ASC; Oligodendrocytes, ODC. (G) Div-Seq captured cells expressing known markers of neuronal precursors, neuroblasts and immature neurons. Box plots for the 1-14 days EdU labeled nuclei (excluding nuclei classified as non-neuronal). (H) Newborn neurons cluster along a continuous trajectory independent of animal age. Data includes nuclei from 6, 8 and 11 weeks old mice. Showing 2-D embedding of 1-4 days EdU labeled nuclei colored by animal age.

FIG. 44: Transcriptional and epigenetic switch during adult neurogenesis and neuronal maturation in the DG. (A) Expression of known marker genes along the trajectory matches the expected dynamics. Left: Heatmap of the expression of the markers and related genes (rows), sorted by their expected pattern, along the neurogenesis trajectory (columns, running average along the trajectory). Data in log(TPM+1). (B) Expression level of known transcription factors (TF) across cell types, showing known regulators of each cell type. Shown are the relative average expression levels (bars) across cells. (C) Dynamically regulated TFs and chromatin regulator. Heatmap of the running average expression (log(TPM+1) of the regulators (rows) along the trajectory (columns). Genes are sorted based on their cluster identities (as in FIG. 41D). Red lines mark the transition from neuronal precursor cells (NPCs) to neuroblast (NB) and from NB to immature neurons. (D) Examples of dynamic expression patterns of families of regulators. Top: Sox family genes. Middle: Cyclin (Cdk) genes. Bottom: kinesin superfamily.

FIG. 45: Tissue validation of markers of immature neurons in hippocampus. (A) Heatmap of running average expression of genes along the DG maturation trajectory, showing known and novel stage specific gene expression. Known markers genes are marked by asterisks. (B) Coronal sections of adult mouse dentate gyrus stained with co-FISH of Draxin (green) and Eomes (red). Cell nuclei were labeled with DAPI. Insets show higher magnifications of the boxed areas indicated with asterisks. Overlaps of Draxin and Eomes are indicated with arrowheads. (C) and (D) Coronal sections of the adult mouse dentate gyrus stained with EdU labeling (green) and FISH (red) of Eomes (C) or Rrm2 (D) at 2 and 12 days after intraperitoneal (i.p.) EdU injection. Cell nuclei were labeled with DAPI. Overlaps of Eomes and Rrm2 with EdU are found at 2 days (arrows) but not at 12 days (arrowhead) post i.p. EdU injection. Scale bars: 50 m.

FIG. 46: Dynamic expression of genes during the SC adult neurogenesis. (A) Nuclei cluster primarily by cell type and maturation state and secondarily by region. Shown is biSNE 2-D embedding of cells from SC and the DG. Nuclei are colored by tissue. (B) Dynamic gene expression clusters along the SC newborn neuronal maturation trajectory. Four clusters are shown from top to bottom, presented as a heatmap of running average expression of all genes along the trajectory (n=1,239 genes). (C) Heatmap of running average expression of known cell stage and cell type marker genes along the trajectory in the SC (left) and DG (right).

Figure 47A:
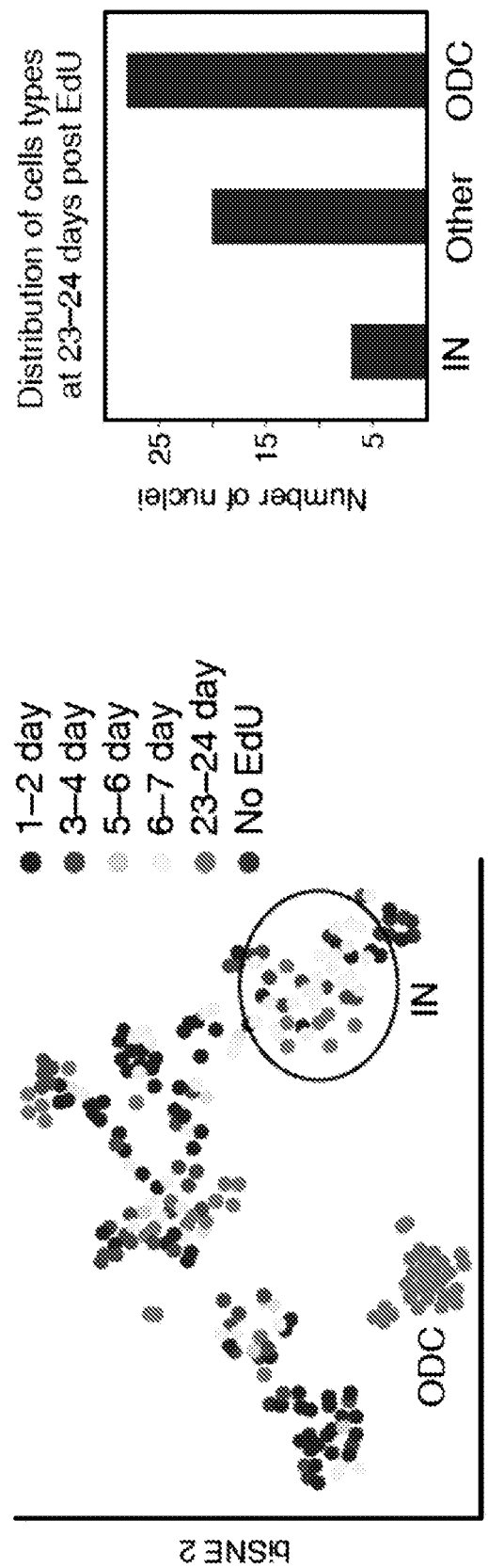
Figure 47B:
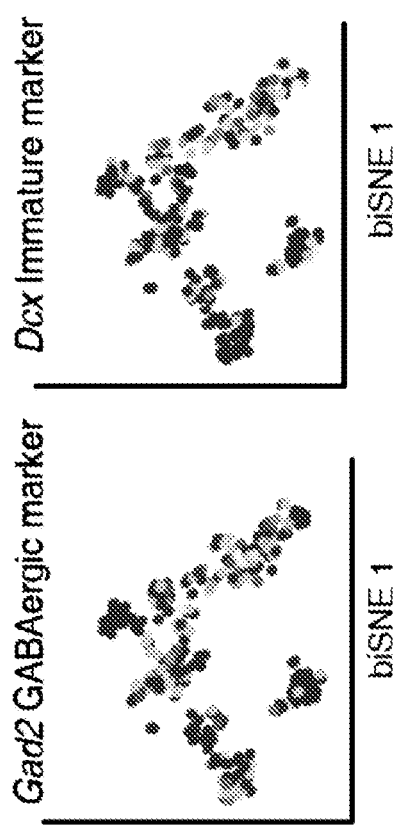
Figure 47C:
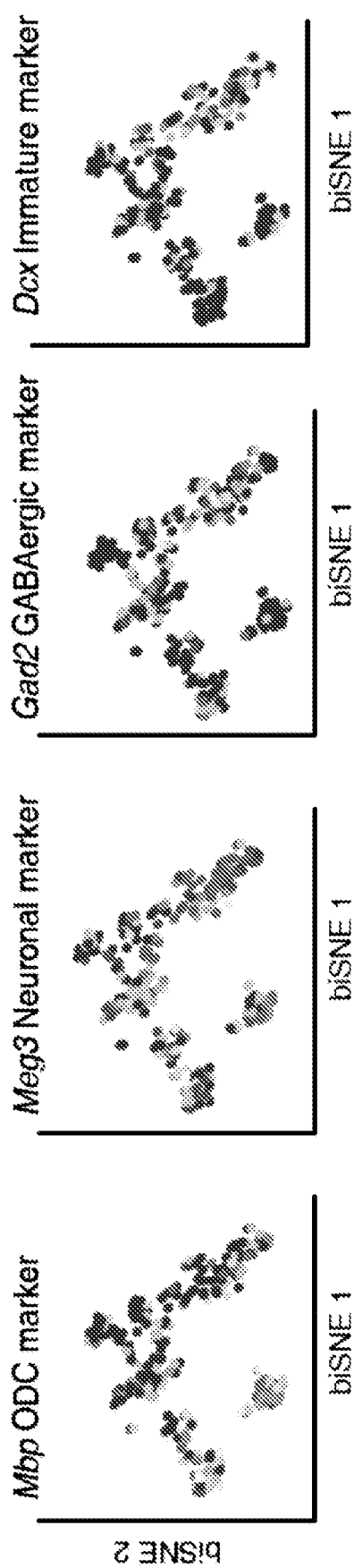

FIG. 47: Survival of newborn neurons in the SC. (A) 23-24 days post EdU nuclei embedded into the 2-D clustering of neuronal lineage genes (from FIG. 42C). Showing a set (10%) of nuclei that cluster with the immature neuronal nuclei along the trajectory. (B) Bar plot showing the number of nuclei classified as oligodendrocytes (ODC), immature/young neurons (IN) or other cell types. (C) Marker genes expressed along the combined neuronal and 23-24 days EdU labeled nuclei trajectory. From left to right: Mbp oligodendrocyte marker, Meg3 neuronal marker, Gad2 GABAergic marker, and Dcx immature neuronal marker.

Figure 48A:
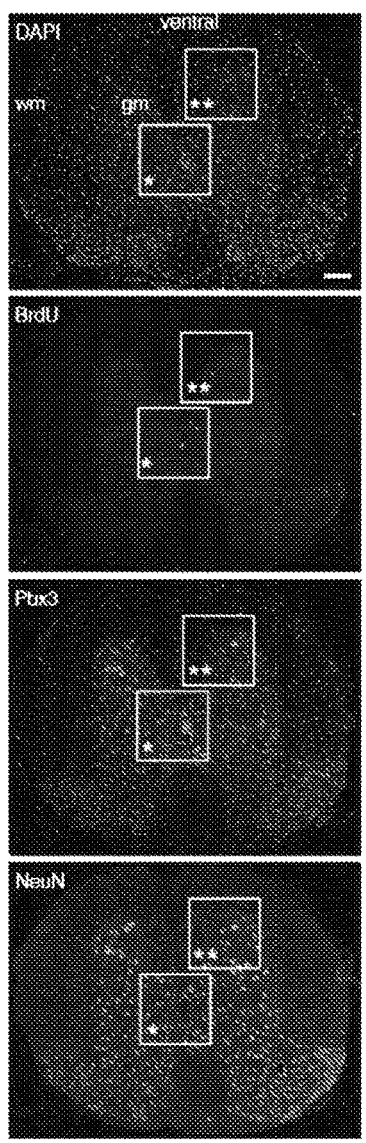
Figure 48B:
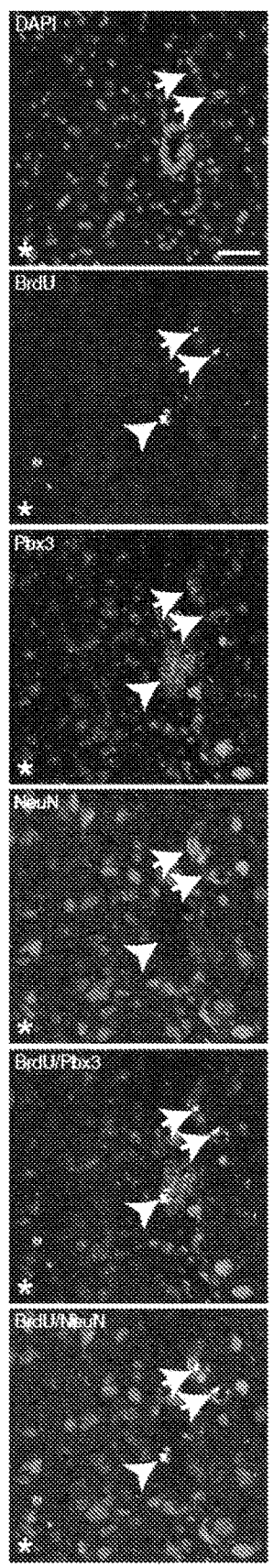
Figure 48C:
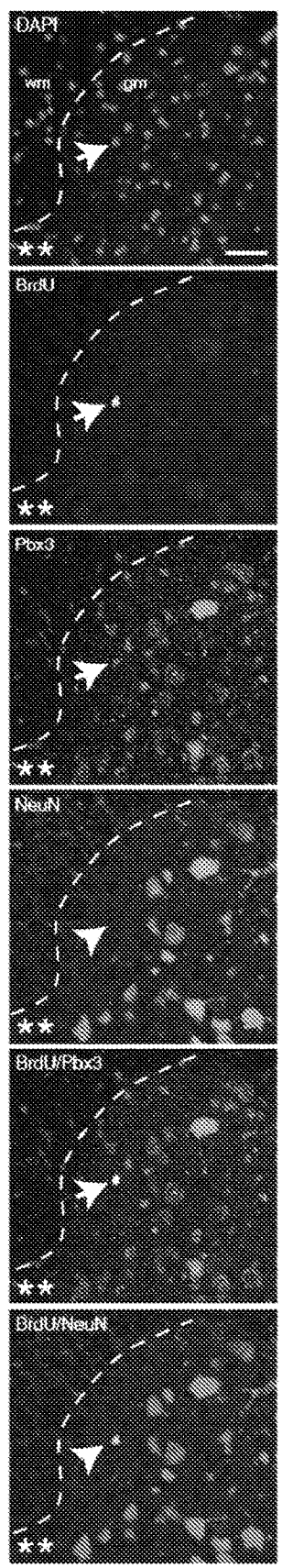

FIG. 48: Tissue validation of Pbx3 expression in newborn cells of the spinal cord. Cross section of adult mouse spinal cord 8 days after intraperitoneal BrdU injection stained with anti-BrdU (green), Pbx3 (red) and NeuN (magenta) antibodies. Cell nuclei were labeled with DAPI. (A) Overview of spinal cord shows spare BrdU labeling in grey matter (gm) and white matter (wm). (B and C) Higher magnifications of insets shown in (A) as indicated by asterisks. (B) Overlap of BrdU, Pbx3 and NeuN in newborn cells proximate to the central canal (arrows). Overlap of BrdU, Pbx3 but not NeuN in a newborn cell within the central canal ependymal cell layer (arrowhead). (C) Overlap of BrdU and Pbx3 (arrow) but not NeuN (arrowhead) in a newborn cell at the border between gm and wm (indated by dotted line). Scale bars: 50 m.

Figure 49A:
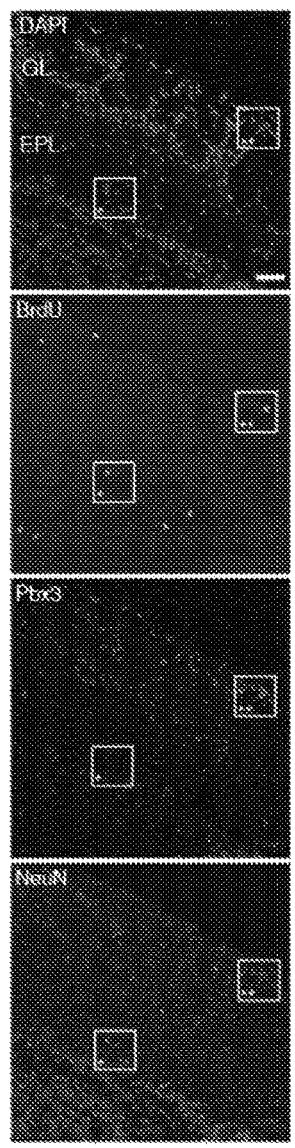
Figure 49B:
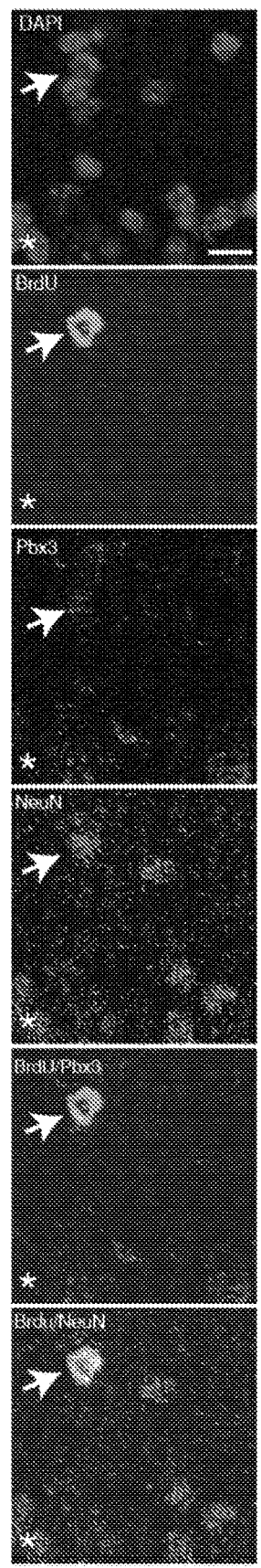
Figure 49C:
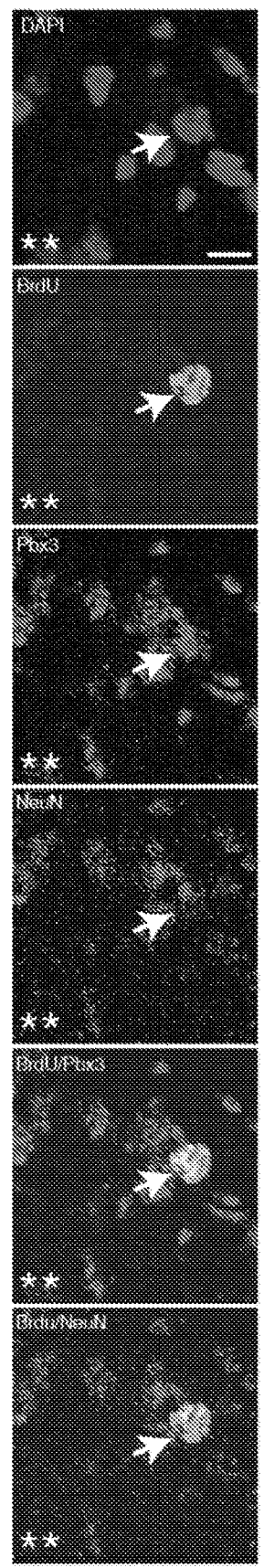

FIG. 49: Tissue validation of Pbx3 expression in newborn cells of the olfactory bulb. Sagittal section of adult mouse olfactory bulb 8 days after intraperitoneal BrdU injection stained with anti-BrdU (green), Pbx3 (red) and NeuN (magenta) antibodies. Cell nuclei were labeled with DAPI. (A) Overview of olfactory bulb shows spare BrdU labeling in the glomerular layer (GL) and external plexiform layer (EPL). (B and C) Higher magnifications of insets shown in (A) as indicated by asterisks. Overlap of BrdU, Pbx3 and NeuN in newborn cells are shown (arrows). Scale bars: 40 m (A) and 10 m (B, C).

Figure 50:
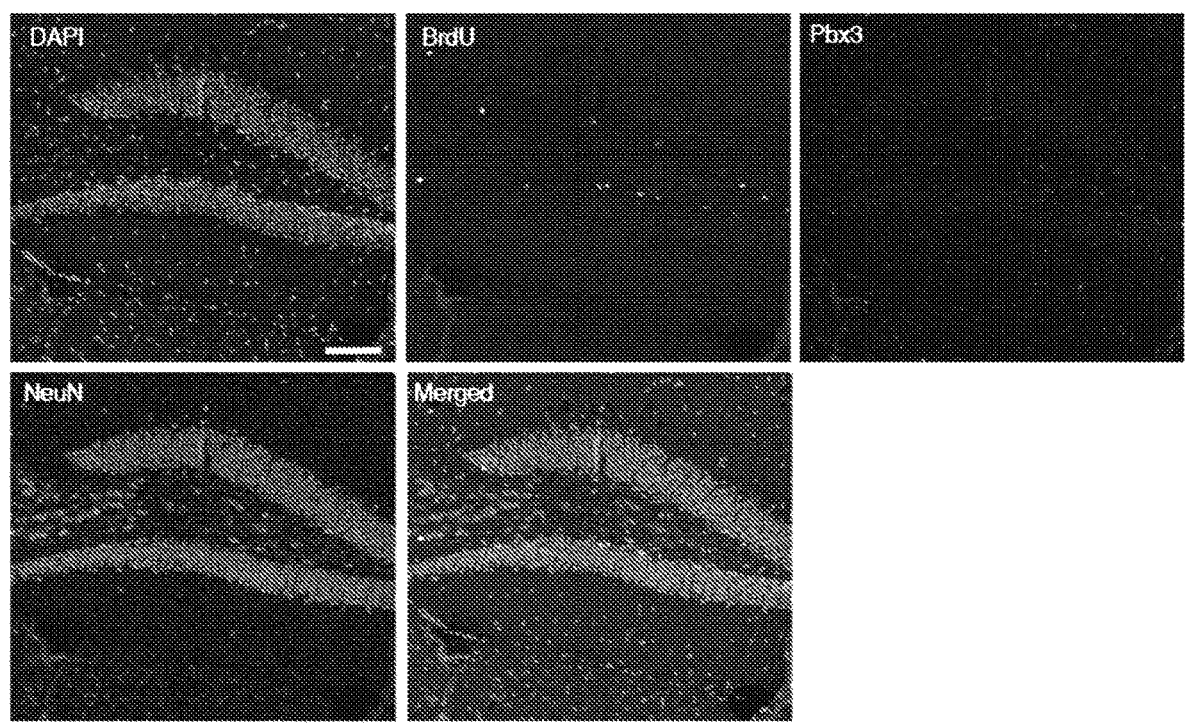

FIG. 50: Tissue validation of Pbx3 expression in newborn cells of the dentate gyrus. Sagittal section of adult mouse hippocampus 8 days after intraperitoneal BrdU injection stained with anti-BrdU (green), Pbx3 (red) and NeuN (magenta) antibodies. No detectable Pbx3 expression levels in the dentate gyrus and no overlap of Pbx3 and NeuN with newborn cells. Same confocal microscope settings have been used as in FIG. 48 and FIG. 49. Scale bar: 100 mm.

Figures 51A, 51B, 51C:
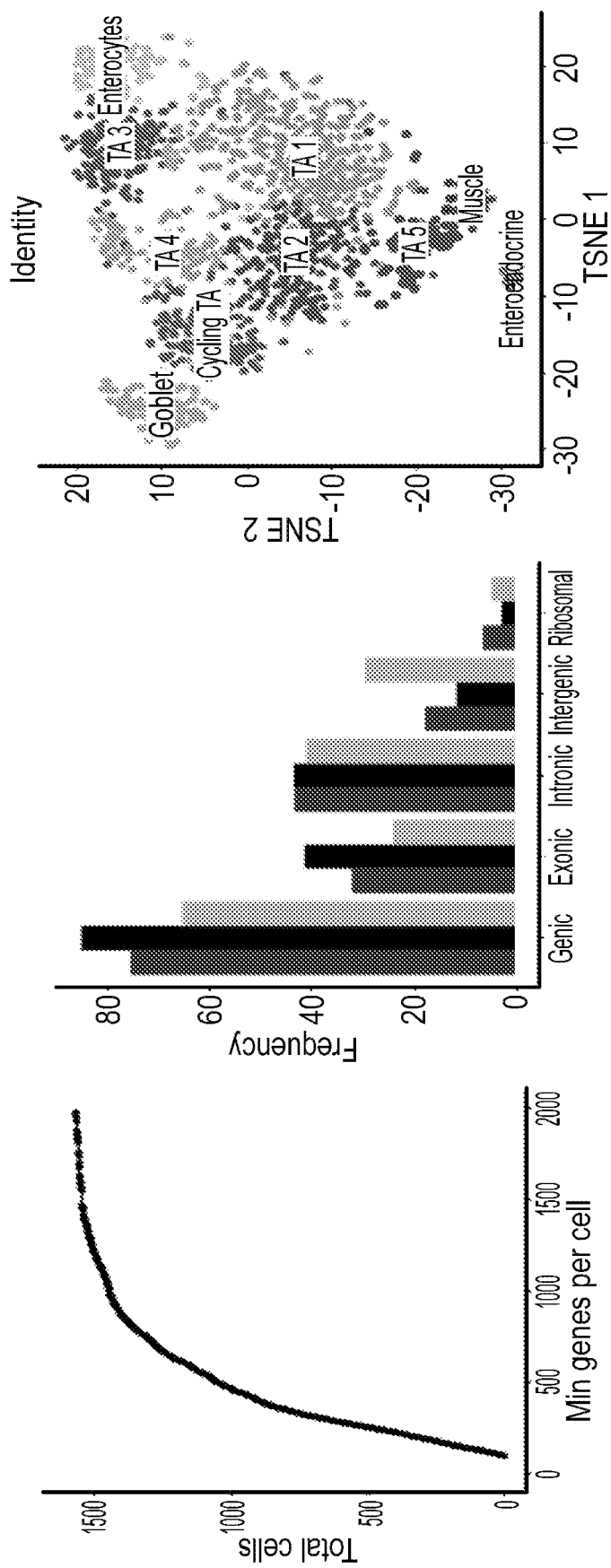
Figure 51D:
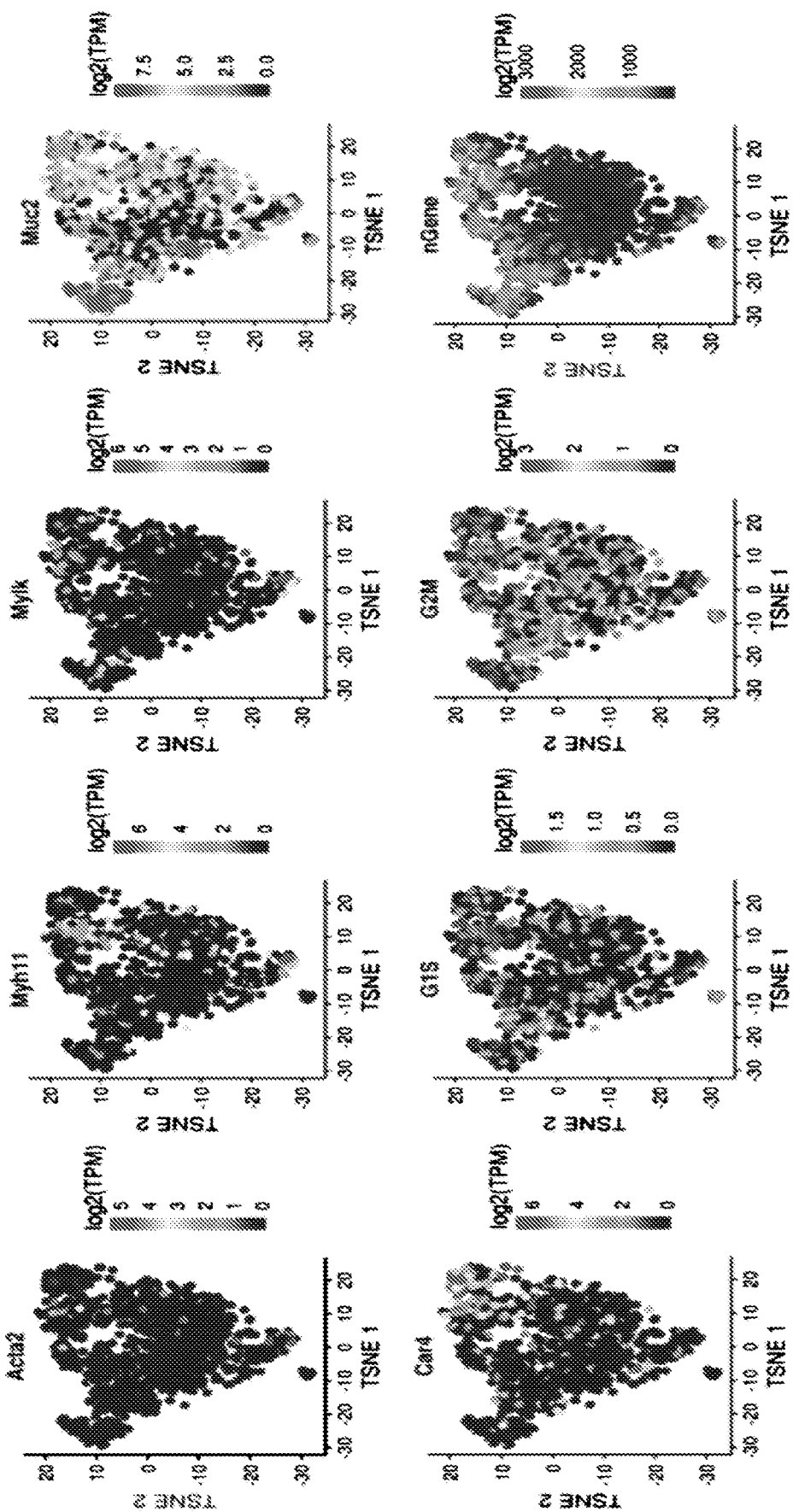
Figure 51E:
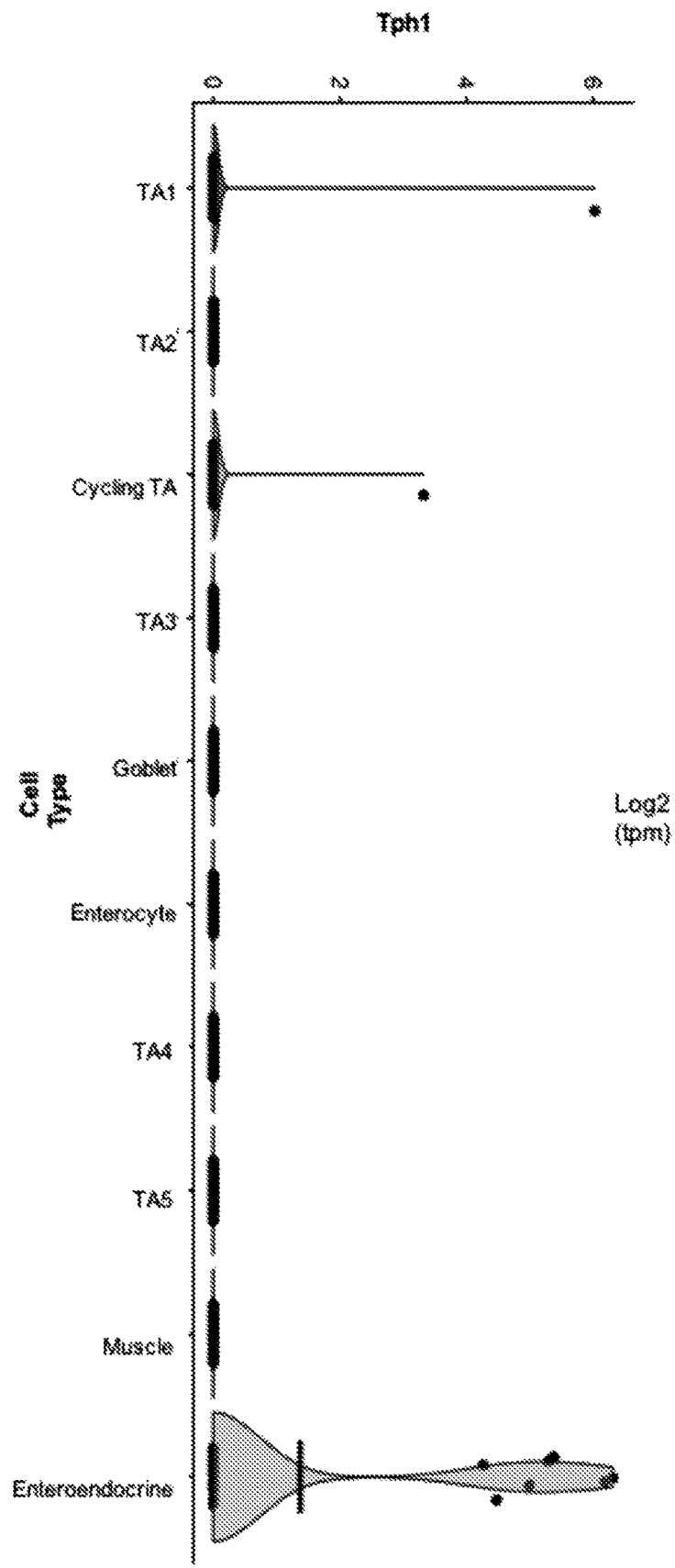

FIG. 51—Shows that DroNc-seq of nuclei from frozen mouse colon captures tissue complexity. A. Genes detected per cell; B. Reproducibility across three independent experiments; C. Clustering of X DroNc-seq single-nuclei expression-profiles into 10 classes of cells; D. Expression of example genes across classes of cells; E. Expression of tphl in enteroendocrine cells.

Figure 52A:
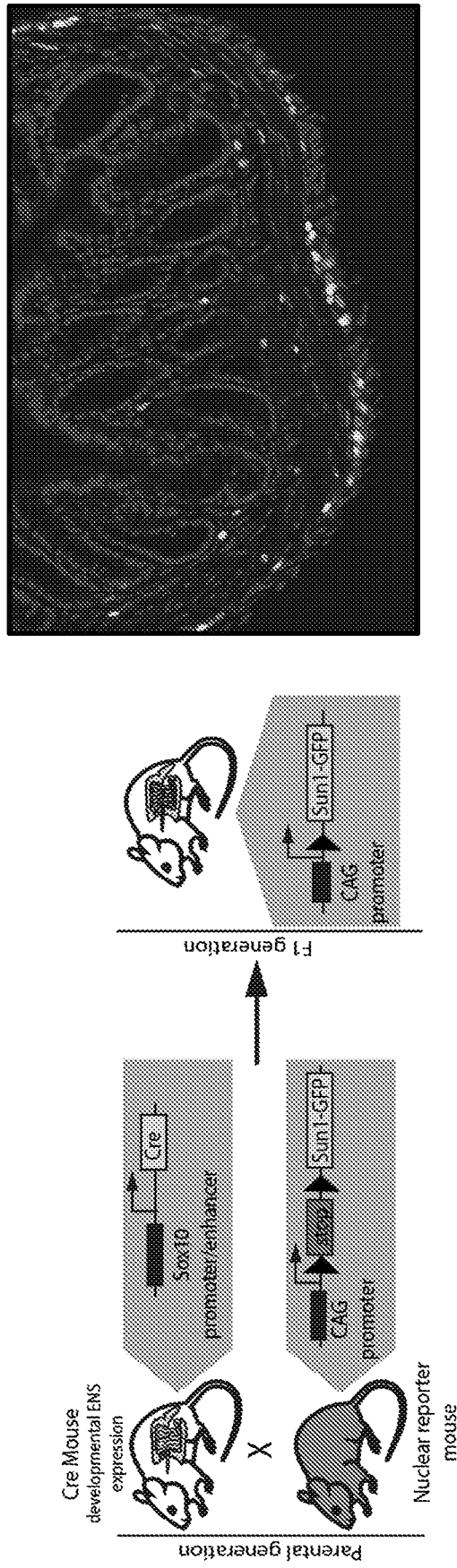
Figure 52B:
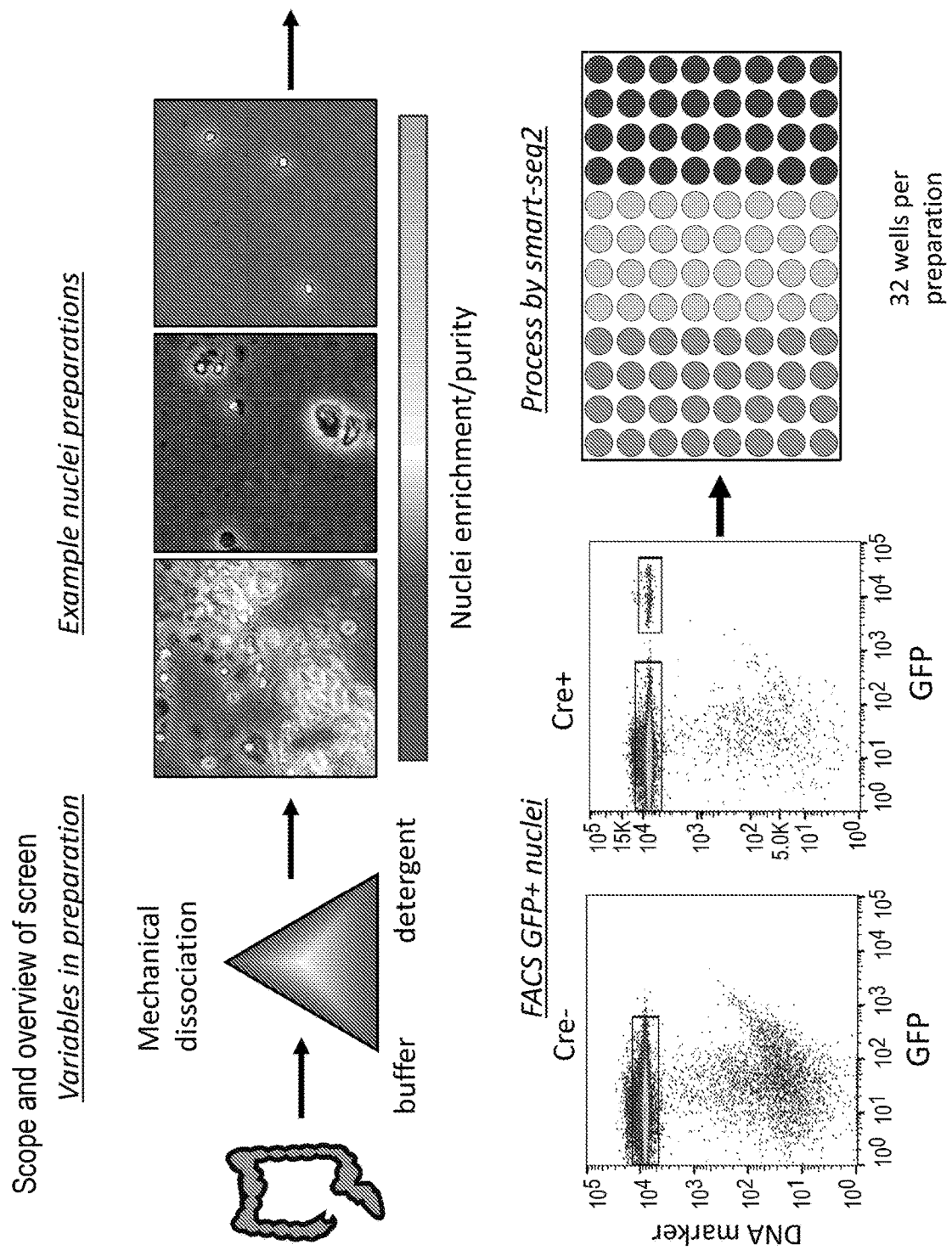

FIG. 52—A. Shows a mouse model for genetic targeting of rare cells in a complex tissue. B. Shows the scope and overview of a mouse screen to determine conditions for improved nuclei preparations. Variables tested include buffer, detergent and dissociation.

Figure 53A:
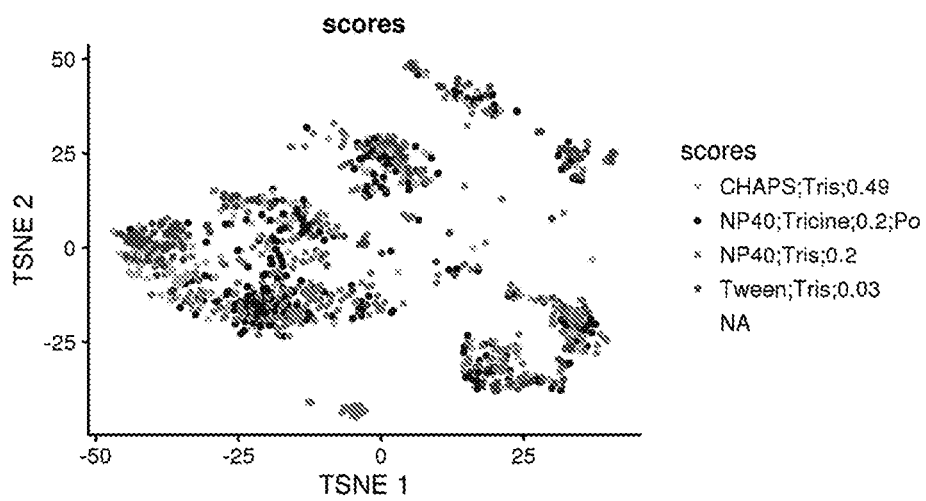
Figure 53B:
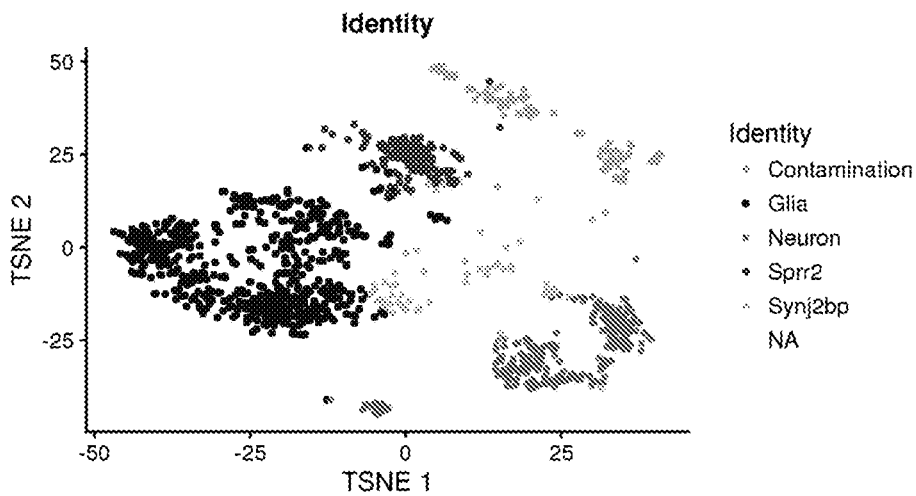
Figure 53C:
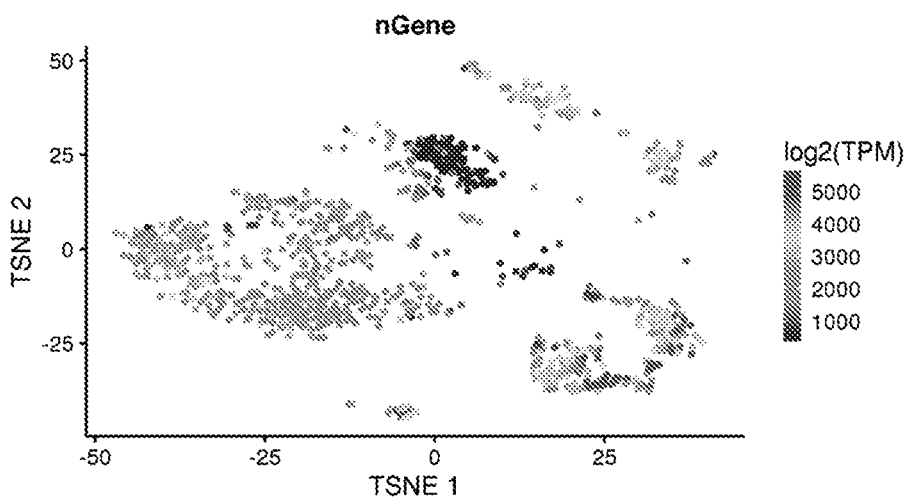

FIG. 53—A-C. shows a comparison of the top 4 buffers from screen.

Figure 54:
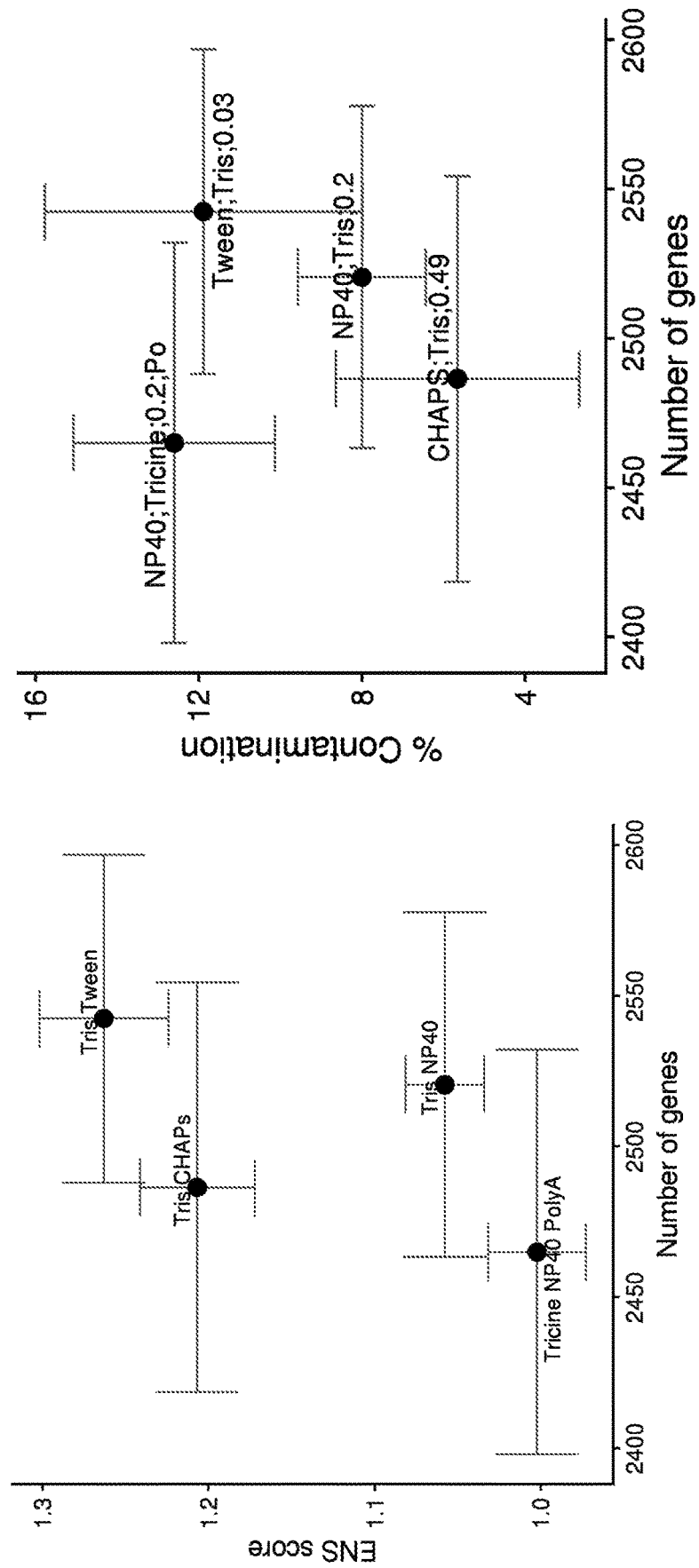

FIG. 54—Shows CST (CHAPS, Salt, Tris) and TST (Tween, Salt, Tris) have the highest ENS score (cell quality) and TST has higher contamination than CST.

Figure 55:
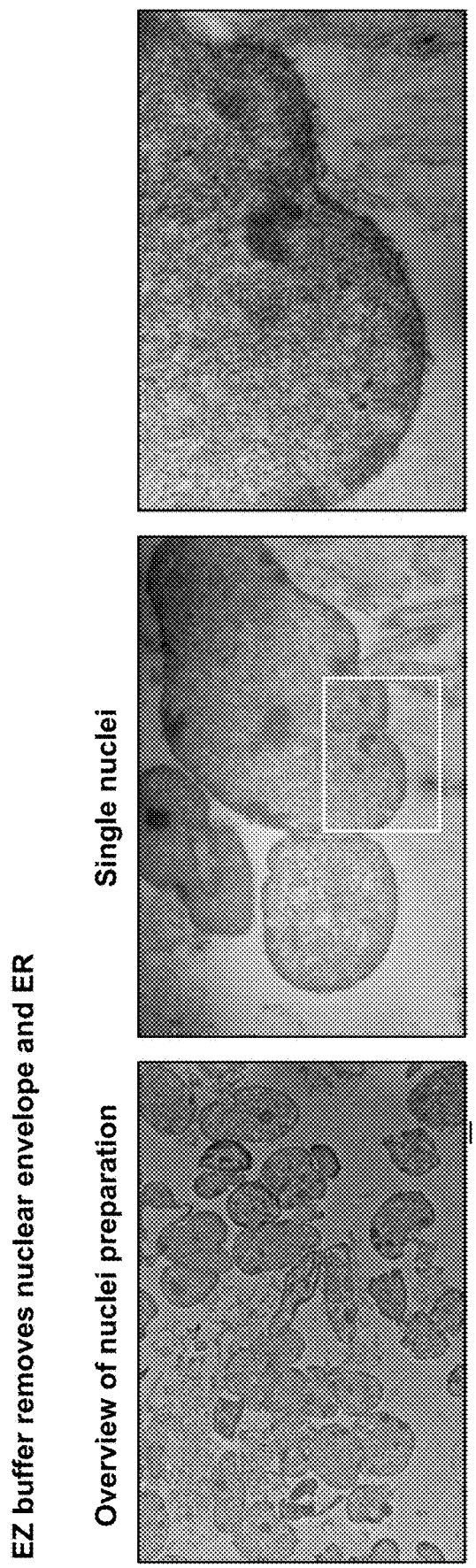

FIG. 55—Shows nuclei isolated with EZ lysis buffer.

Figure 56:
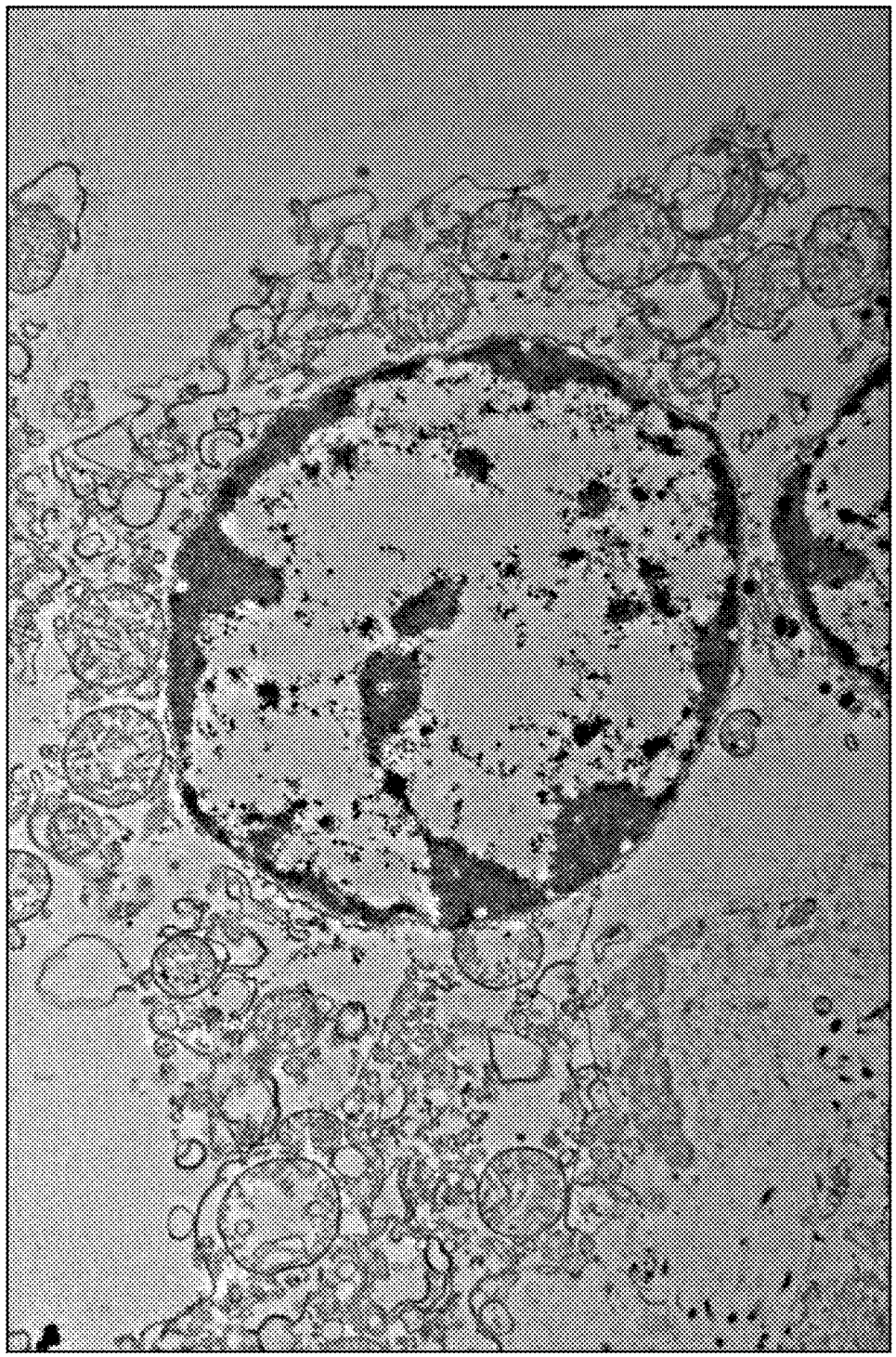

FIG. 56—Shows nuclei isolated with CST with 0.196% CHAPS.

FIG. 57—Shows nuclei isolated with CST with 0.196% CHAPS.

Figure 58:
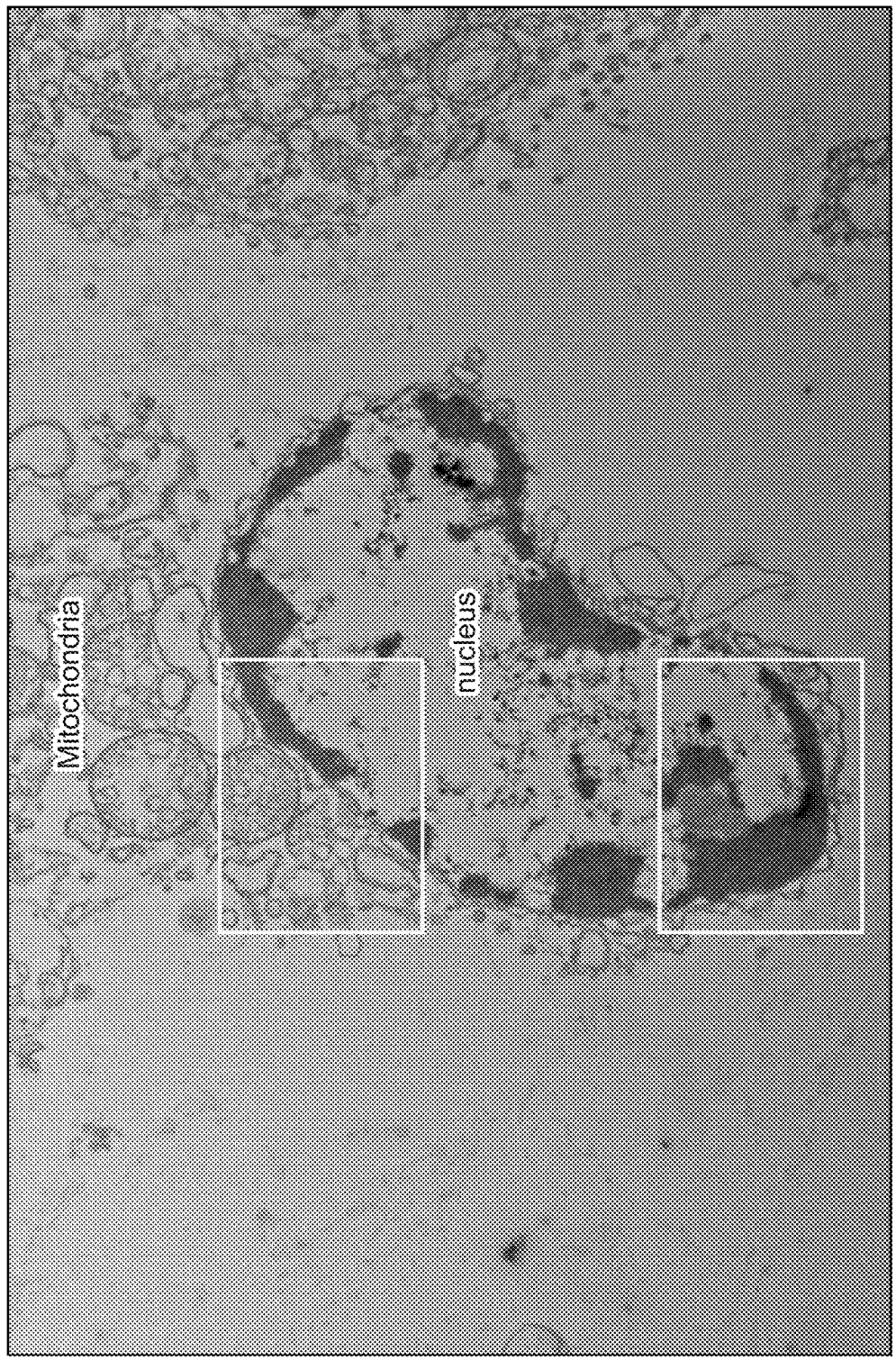

FIG. 58—Shows nuclei isolated with CST with 0.196% CHAPS.

FIG. 59—Shows nuclei isolated with CST with 0.196% CHAPS.

Figure 60:
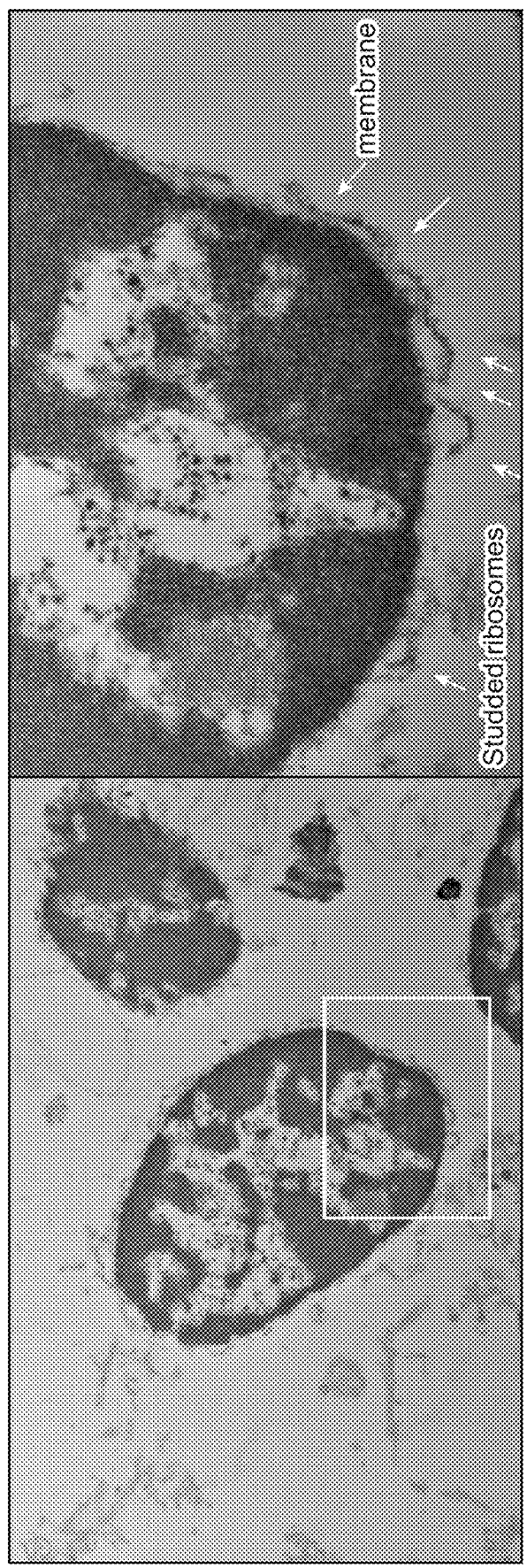

FIG. 60—Shows nuclei isolated with CST with 0.49% CHAPS.

Figure 61:
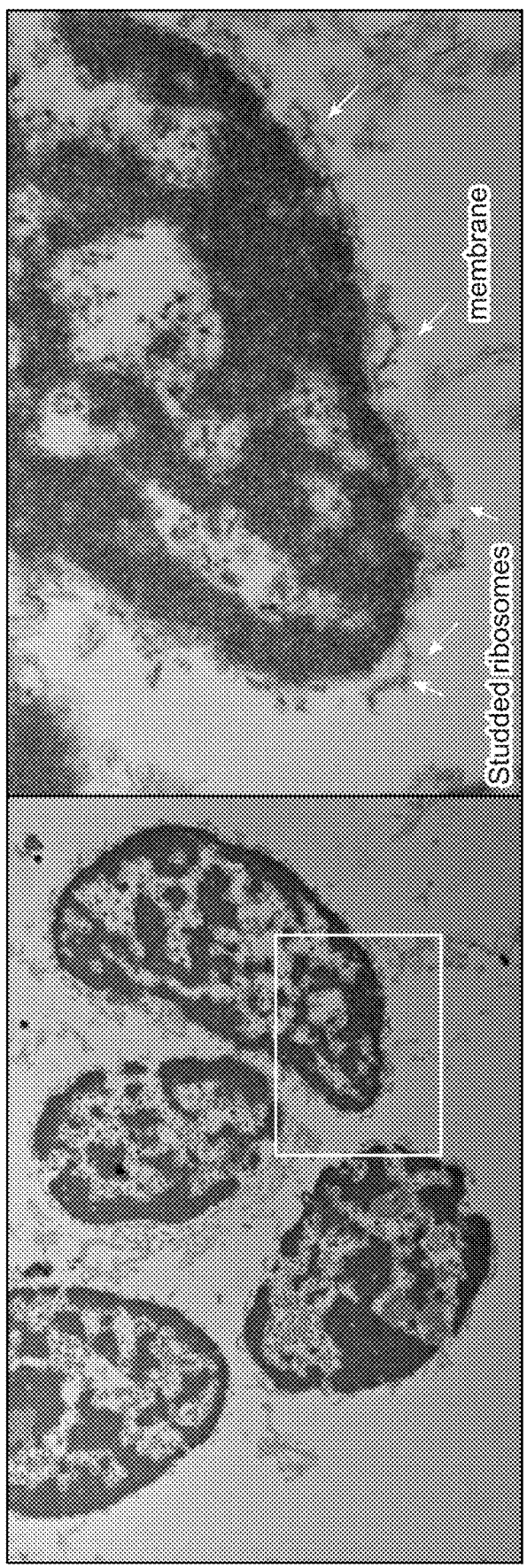

FIG. 61—Shows nuclei isolated with CST with 0.49% CHAPS.

Figure 62:
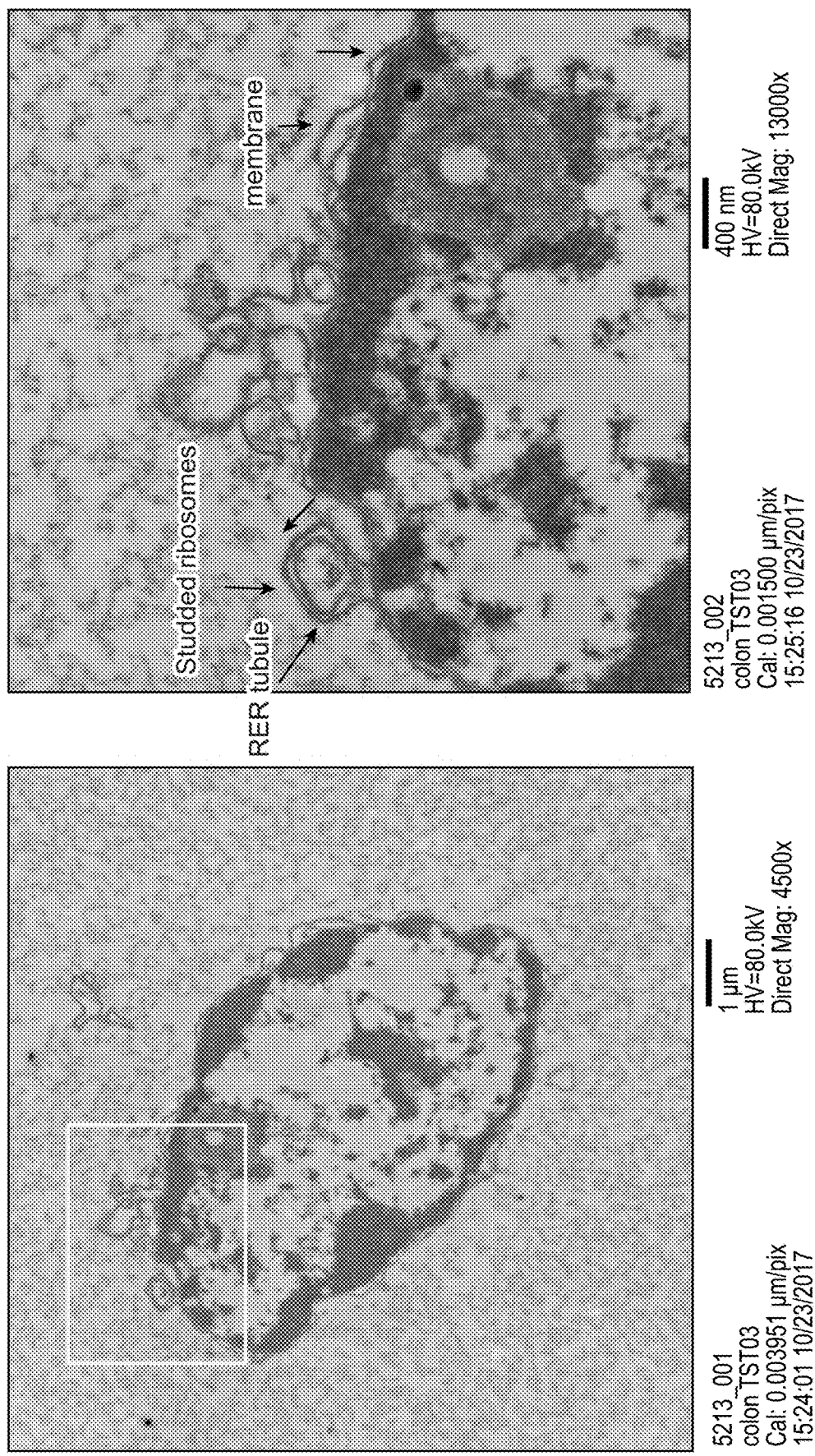

FIG. 62—Shows nuclei isolated with TST with 0.03% tween-20.

FIG. 63—Shows sNucER facilitates characterization of ENS. A. Histology of labelled cells; B. Classes of cells identified (2 glia, 3 neurons) using sNucER-seq; C. Circadian oscillation in neurons and glia of ENS.

FIG. 64—shows comparison of extraction buffers to Sigma's EZ nuclei extraction reagent. Shown are experiments with (A) EZ chop and (B) EZ frozen.

FIGS. 65A-65D—show analysis of prostate tissue by various prep methods.

FIGS. 66A-66F—shows clusters of nuclei from different classes of cells identified.

Figure 67C:
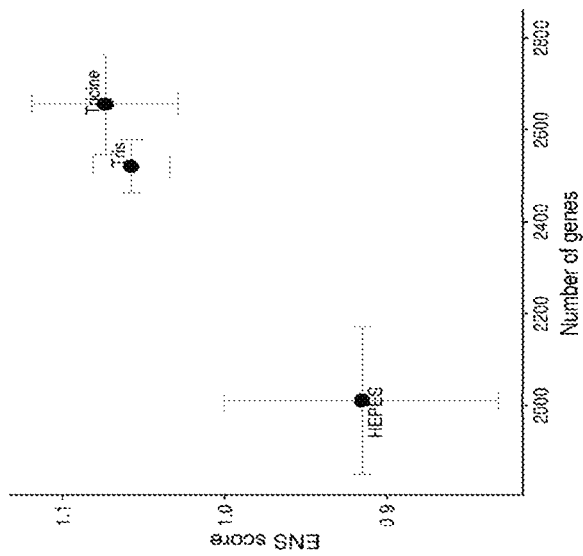
Figure 67B:
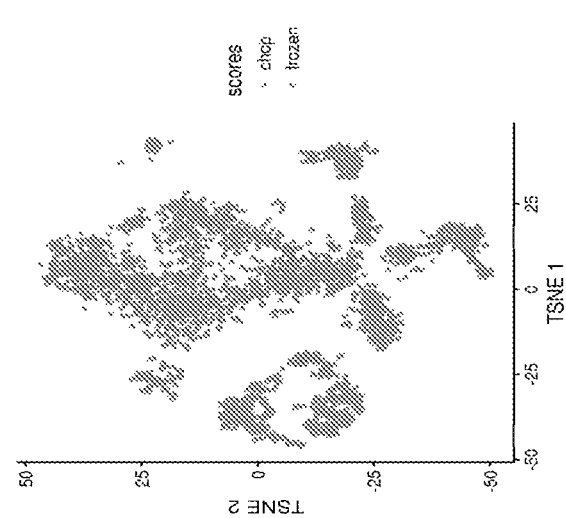
Figure 67A:
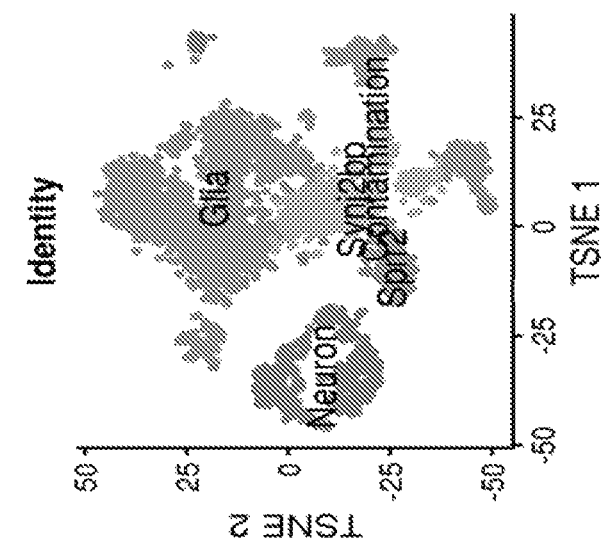

FIGS. 67A-67C—show clusters of nuclei from various sources.

Figure 68B:
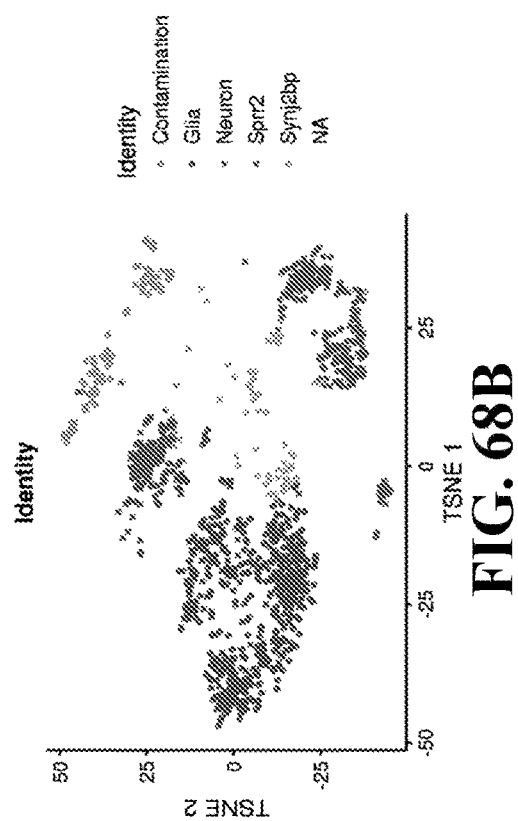
Figure 68A:
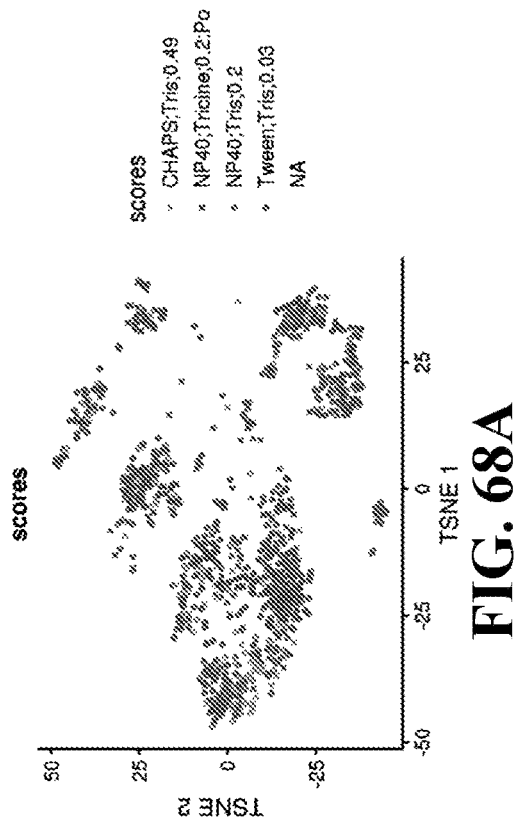
Figure 68C:
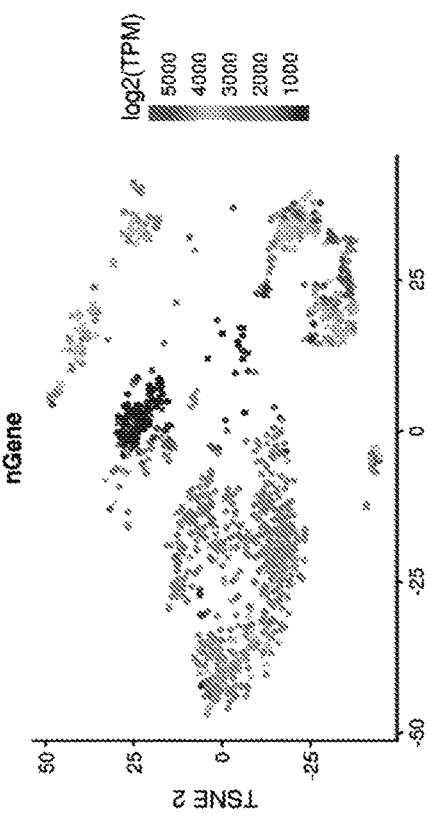

FIGS. 68A-68C—show clusters of nuclei from different cells isolated with various buffers and detergents.

FIGS. 69A-69F—shows graphs summarizing results of prep methods across tissues. Shown are one tissue per prep method. No EZ for lung tissue in this particular experiment.

Figures 70A, 70B:
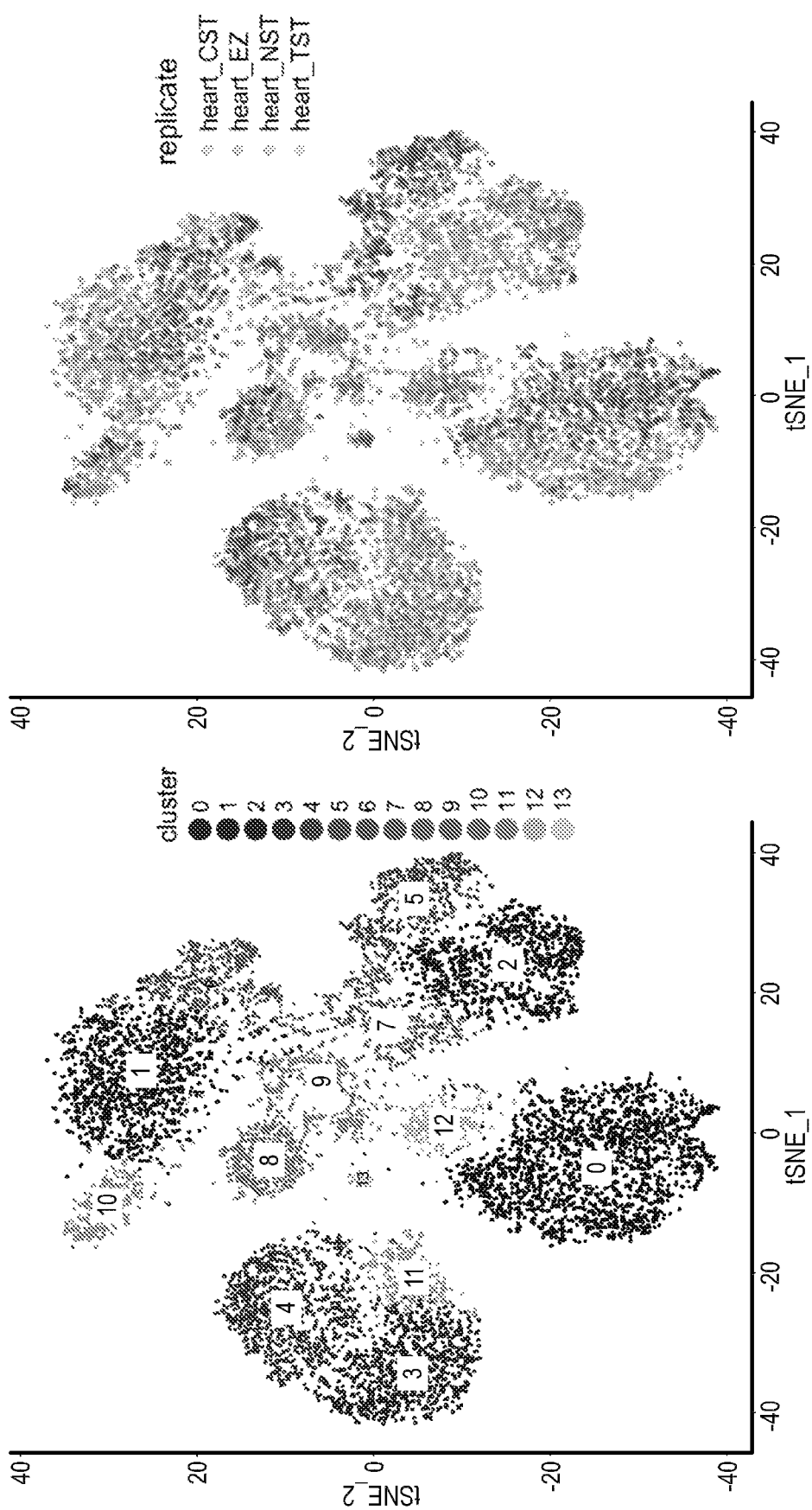
Figure 71A:
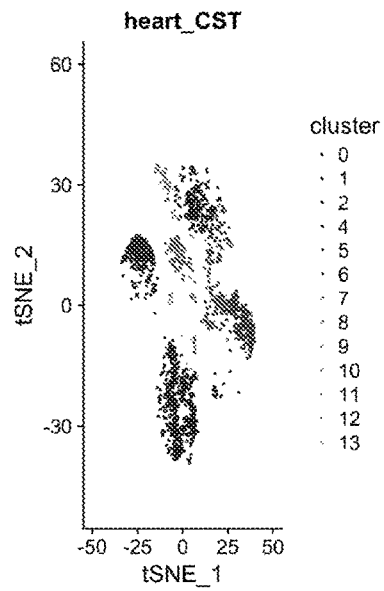
Figure 71B:
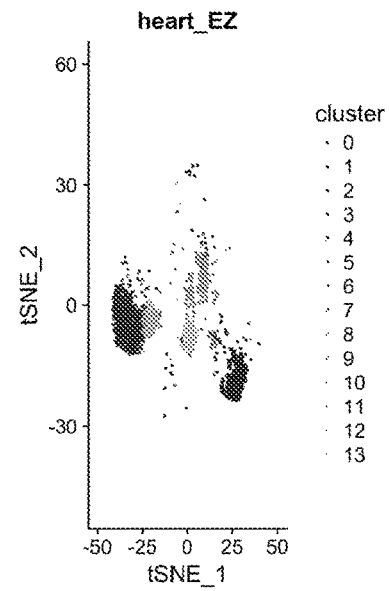
Figure 71C:
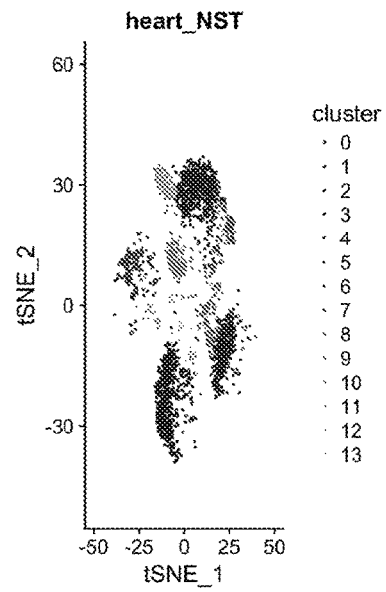
Figure 71D:
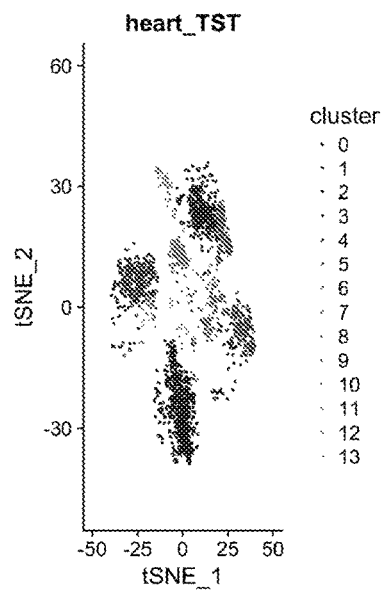
Figure 71E:
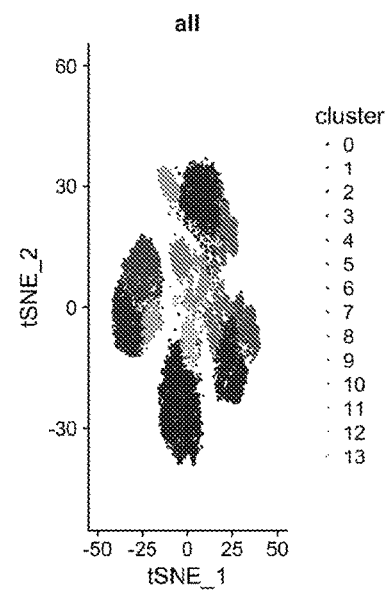

FIGS. 70A, 70B—shows clusters of nuclei from heart tissue generated by various prep methods.

FIGS. 71A-71E—shows clusters of nuclei from heart tissue generated by various prep methods.

Figure 72B:
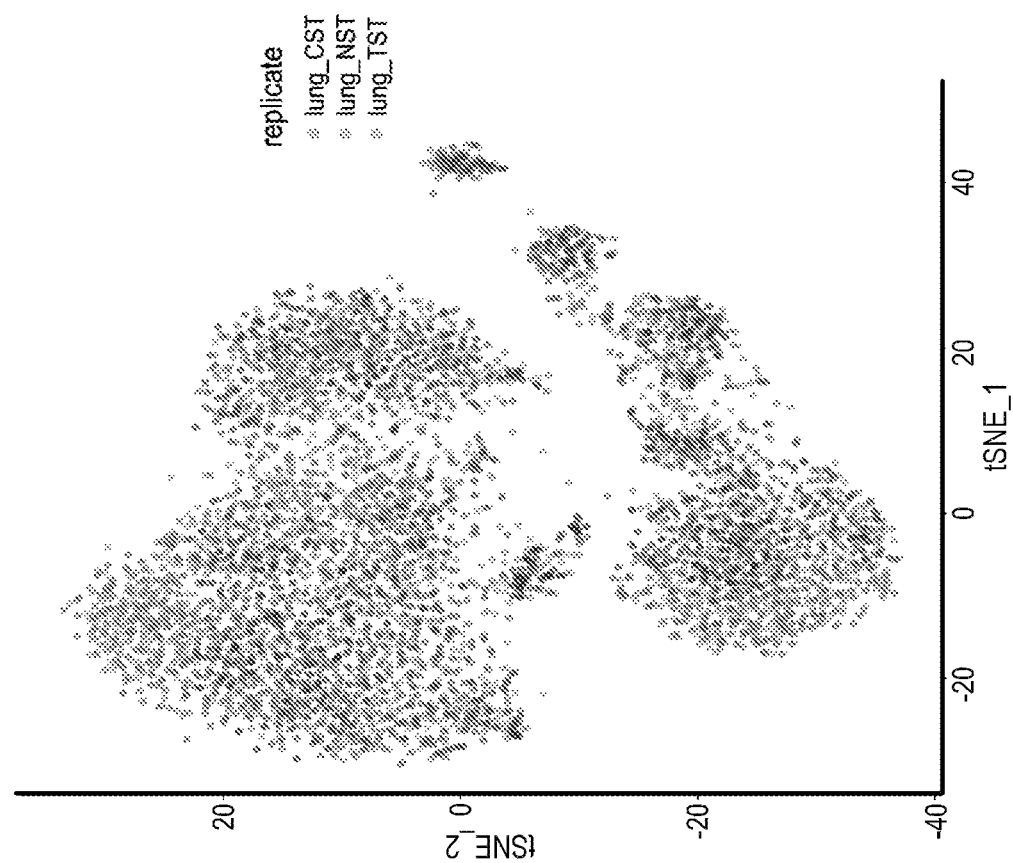
Figure 72A:
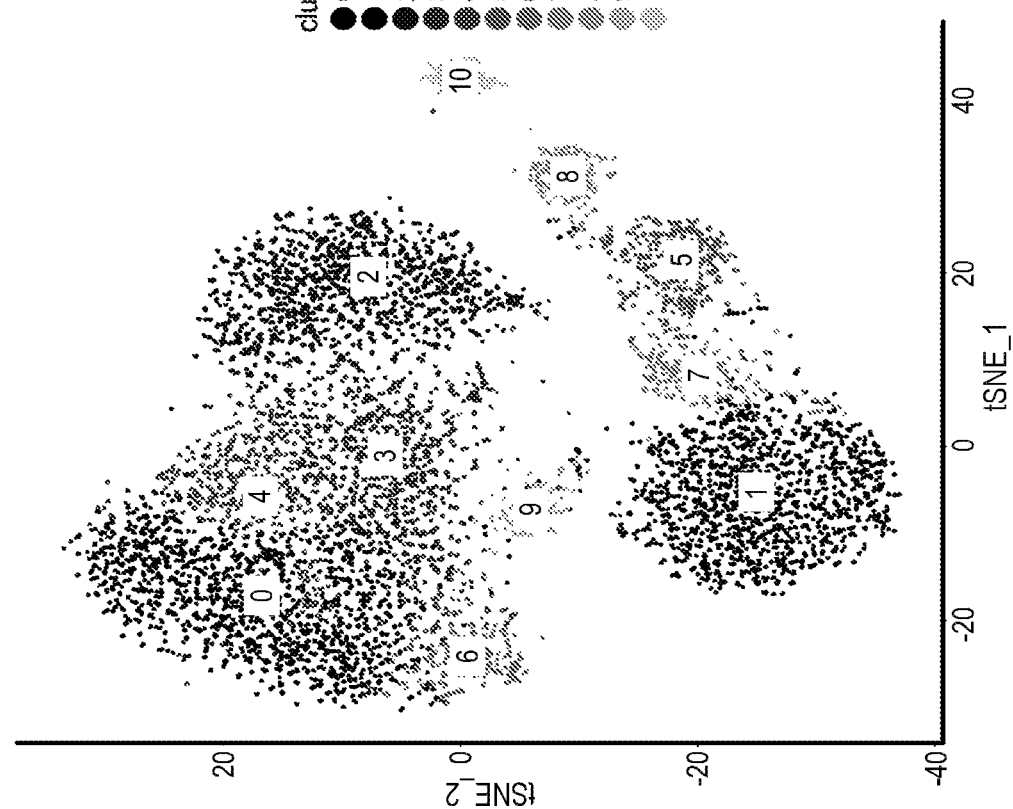
Figure 73A:
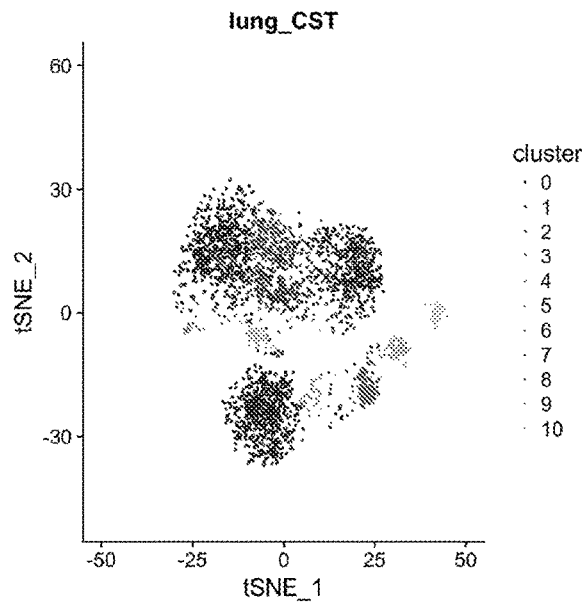
Figure 73B:
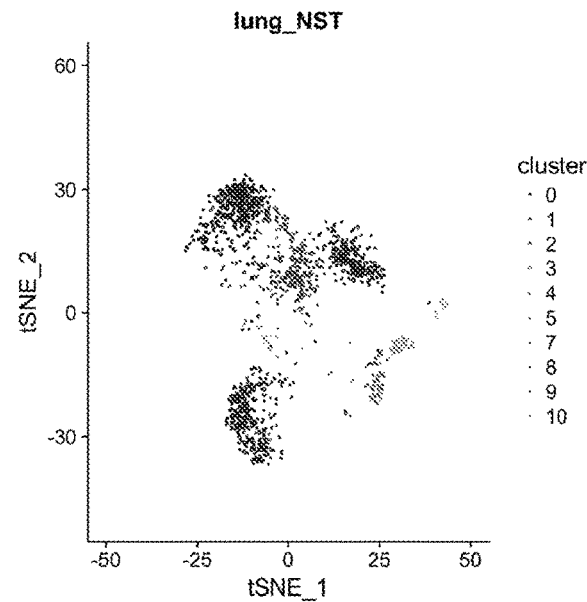
Figure 73C:
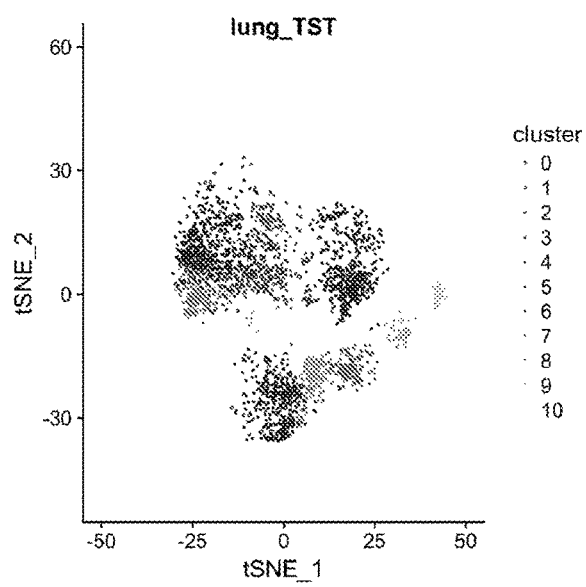
Figure 73D:
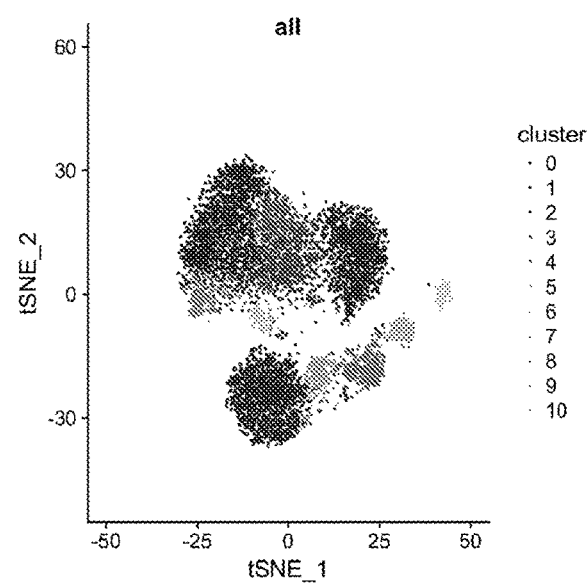

FIGS. 72A, 72B—shows clusters of nuclei from lung tissue generated by various prep methods.

FIGS. 73A-73D—shows clusters of nuclei from lung tissue generated by various prep methods.

Figures 74A, 74B:
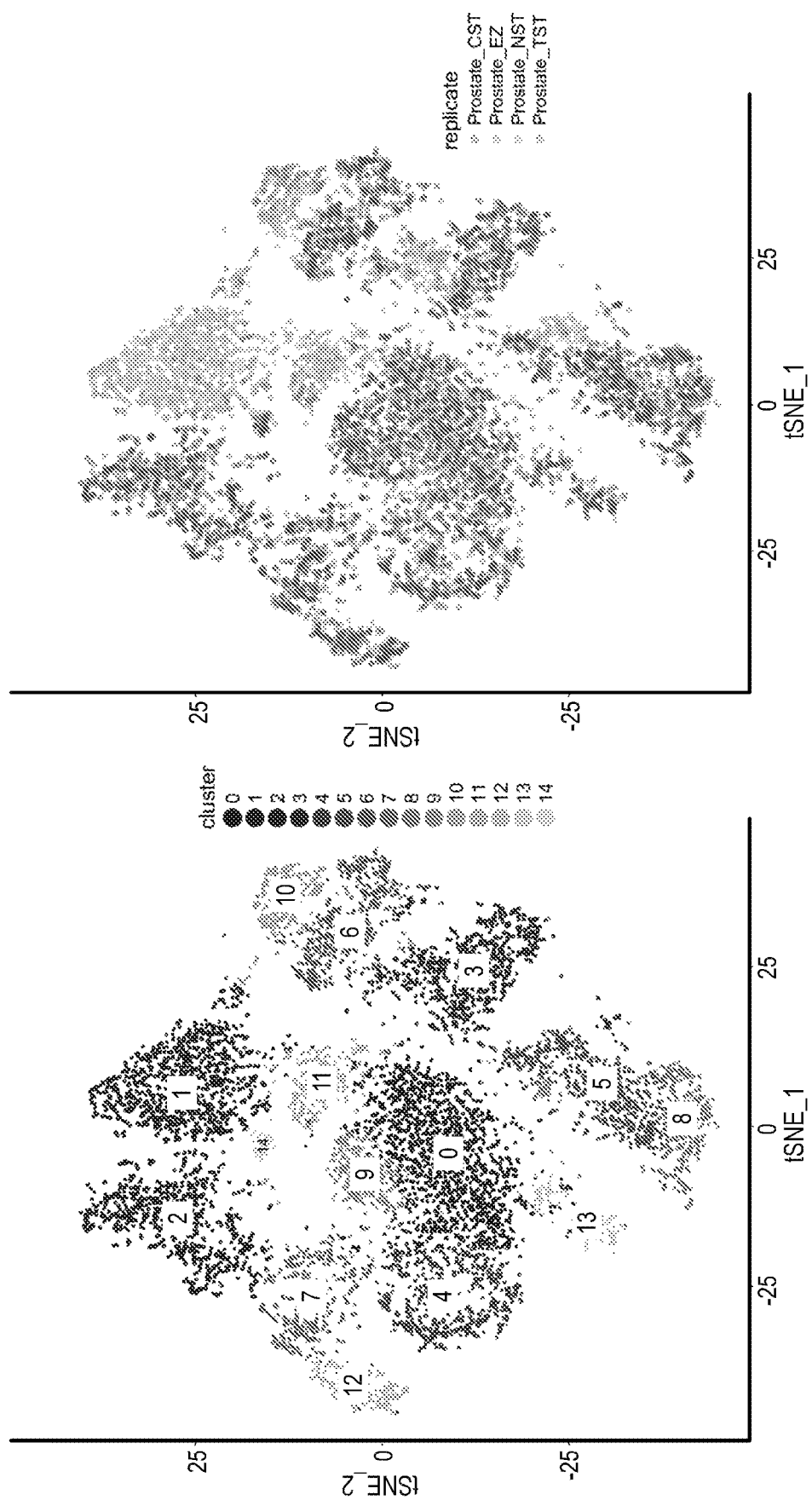
Figure 75A:
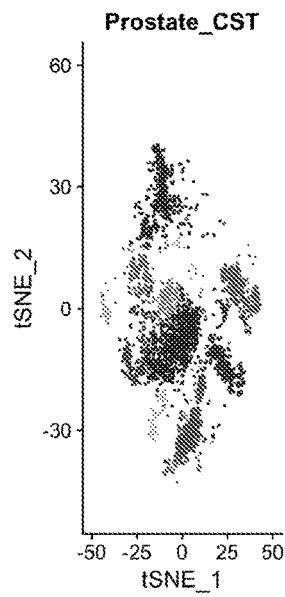
Figure 75B:
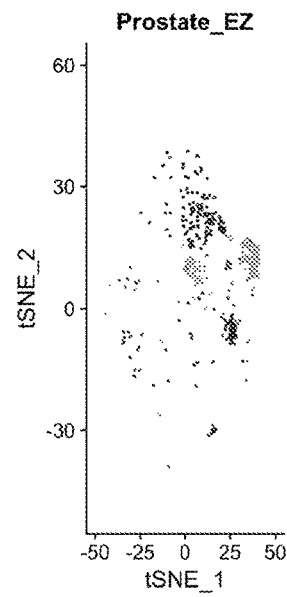
Figure 75C:
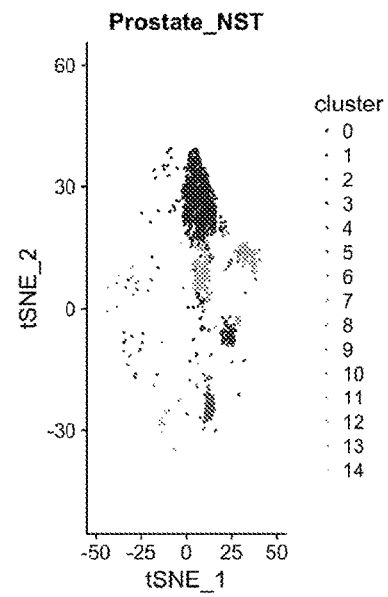
Figure 75D:
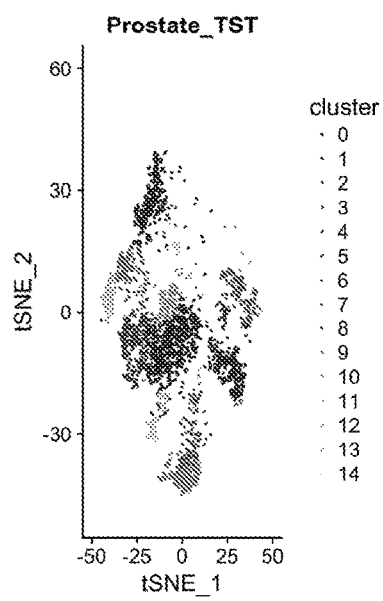
Figure 75E:
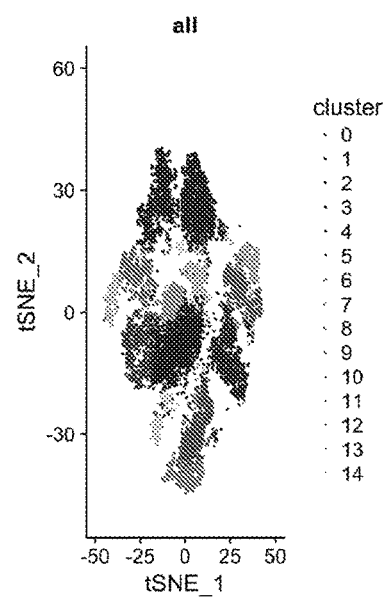

FIGS. 74A, 74B—shows clusters of nuclei from prostate tissue generated by various prep methods.

FIGS. 75A-75E—shows clusters of nuclei from prostate tissue generated by various prep methods.

Figures 76A, 76B:
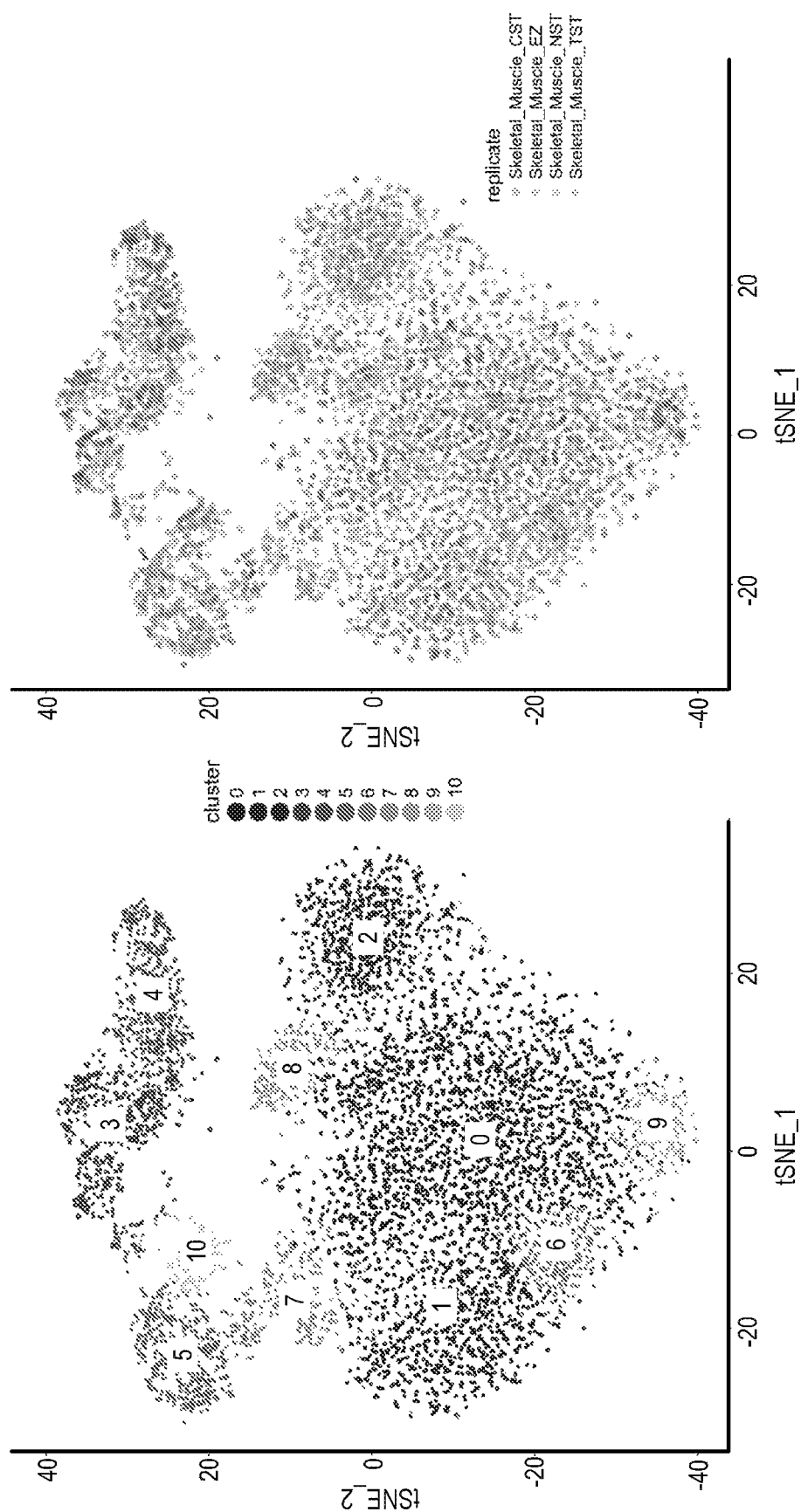

FIGS. 76A, 76B—shows clusters of nuclei from skeletal muscle tissue generated by various prep methods.

FIGS. 77A-77E—shows clusters of nuclei from skeletal muscle tissue generated by various prep methods.

Figure 78:
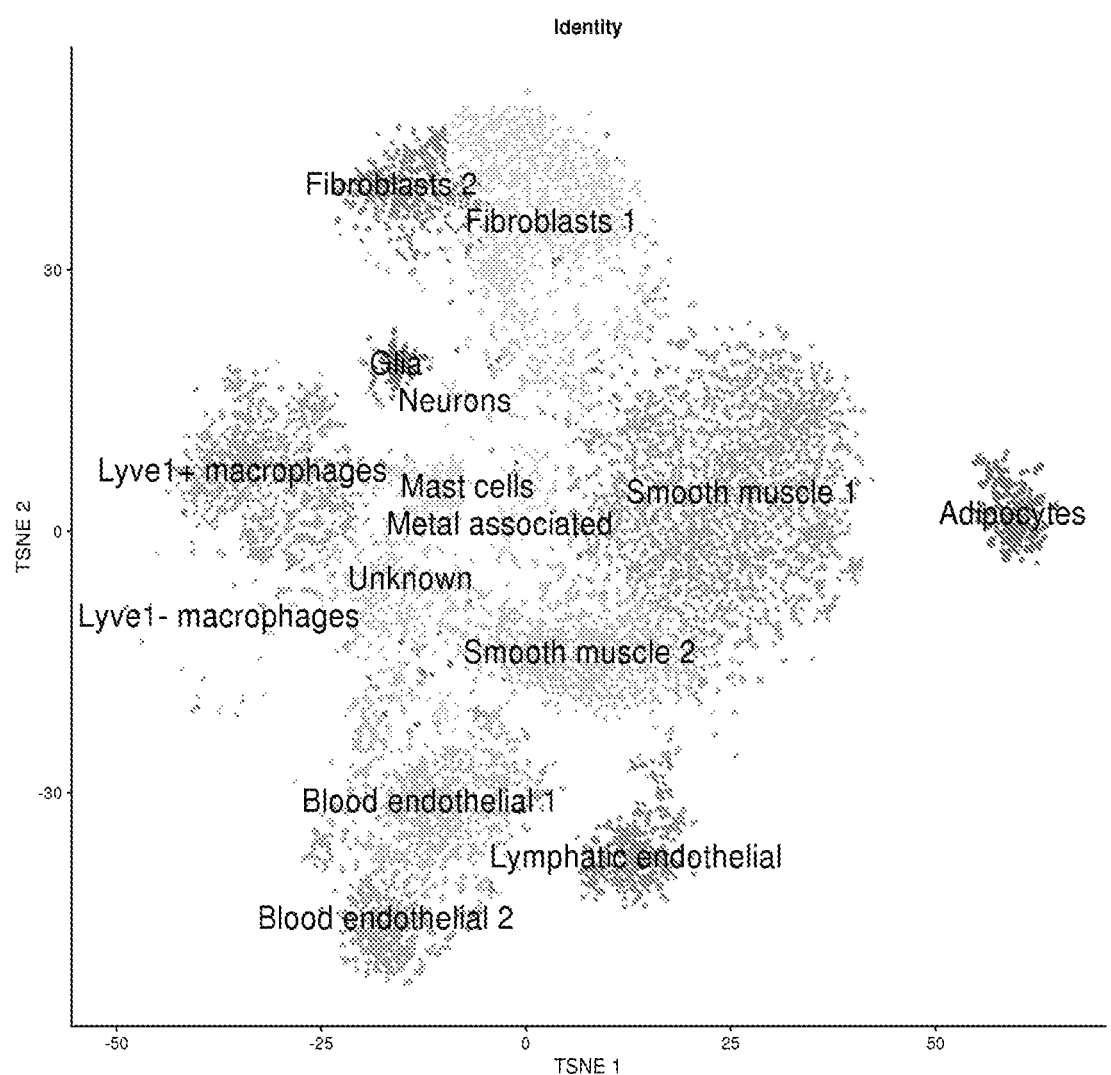

FIG. 78—Illustrates identification of major cell types in human colon muscle layer using CST prep.

Figure 79B:
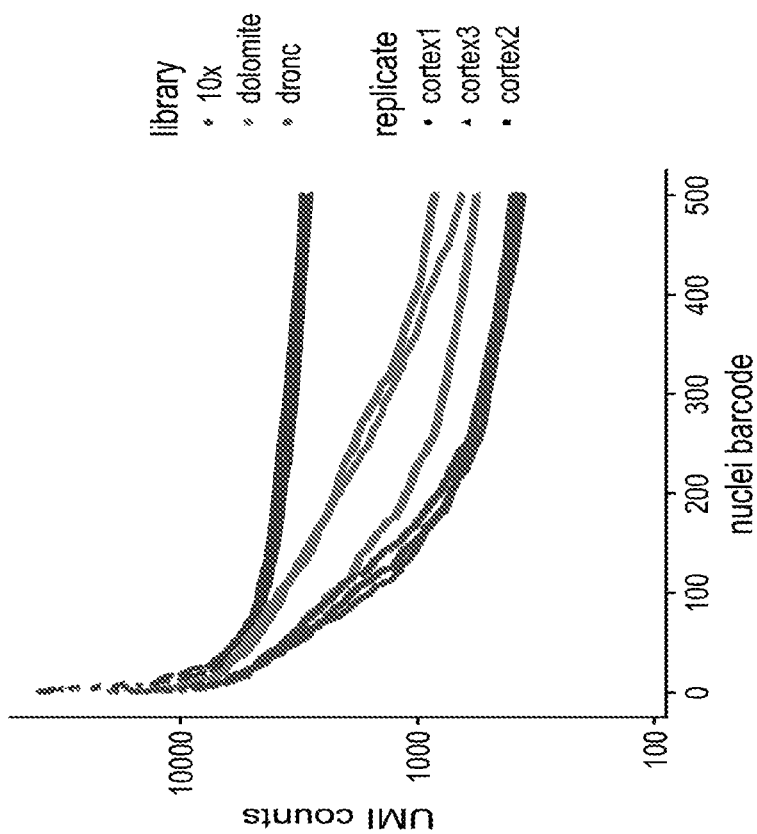
Figure 79A:
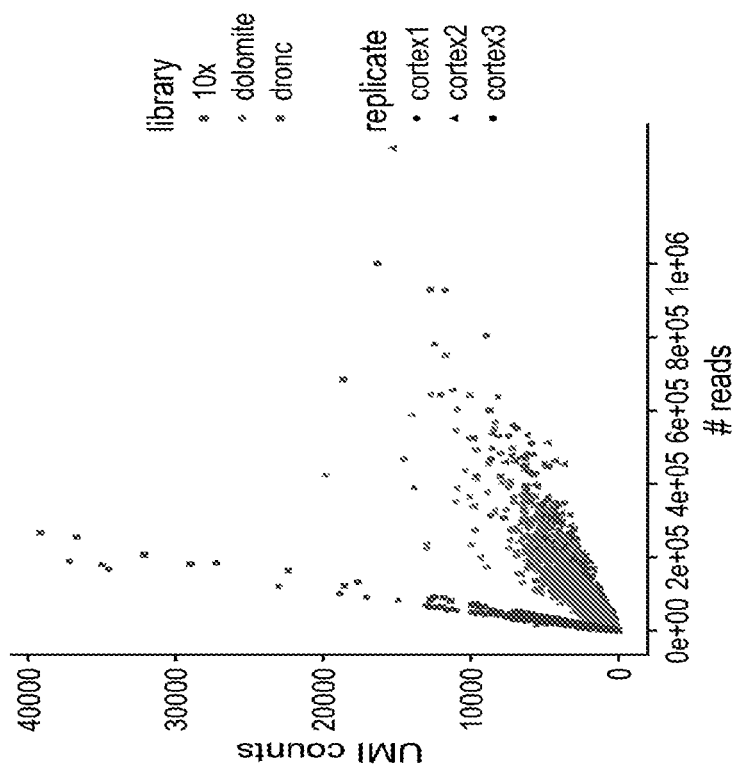

FIGS. 79A, 79B—show identification of barcodes using different microfluidics systems.

Figure 80:
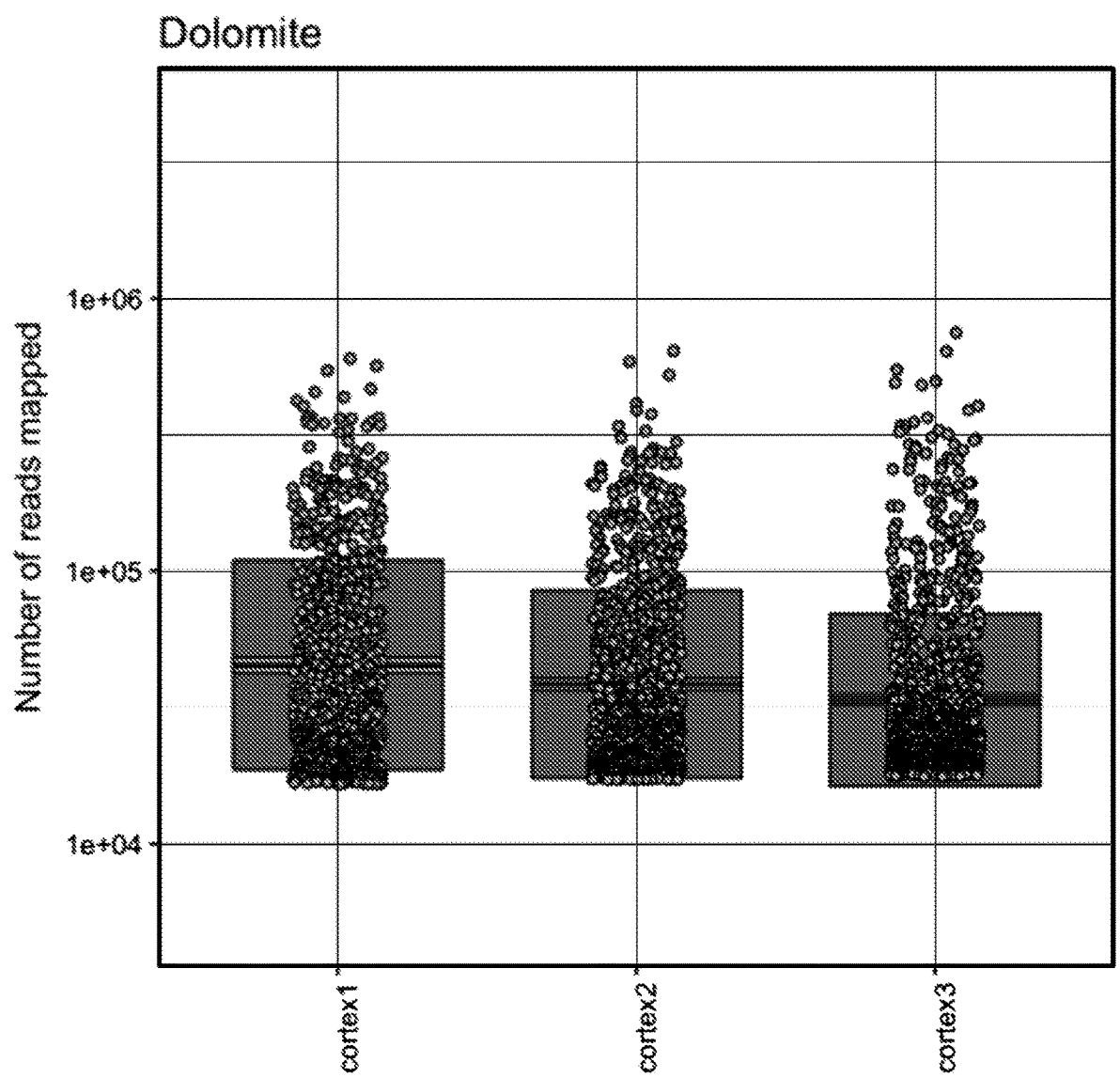
Figure 81A:
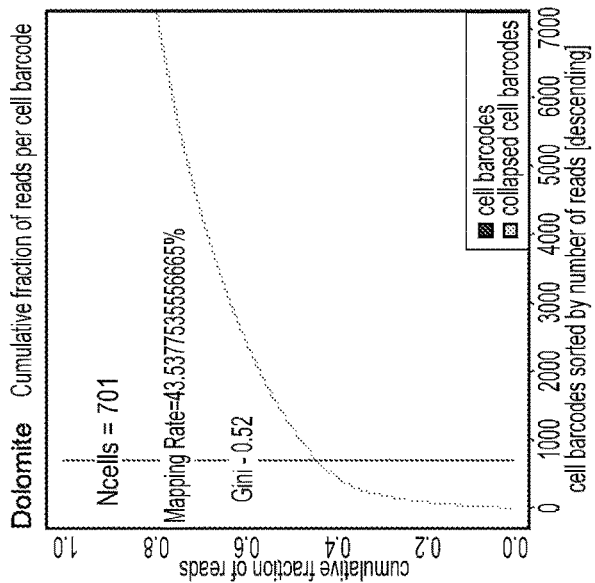
Figure 81B:
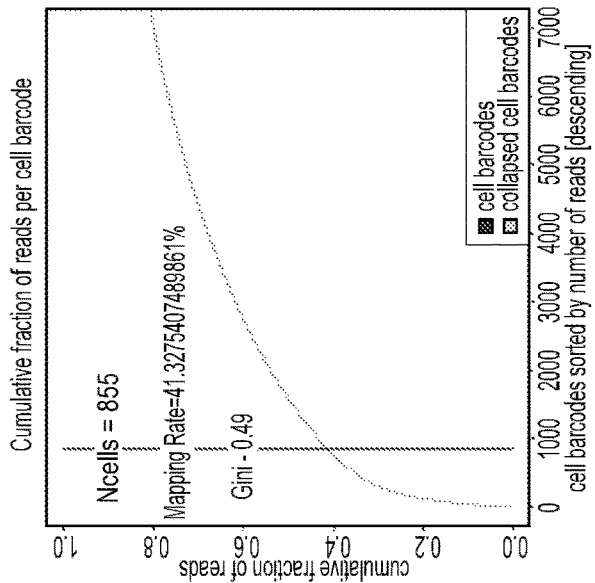
Figure 81C:
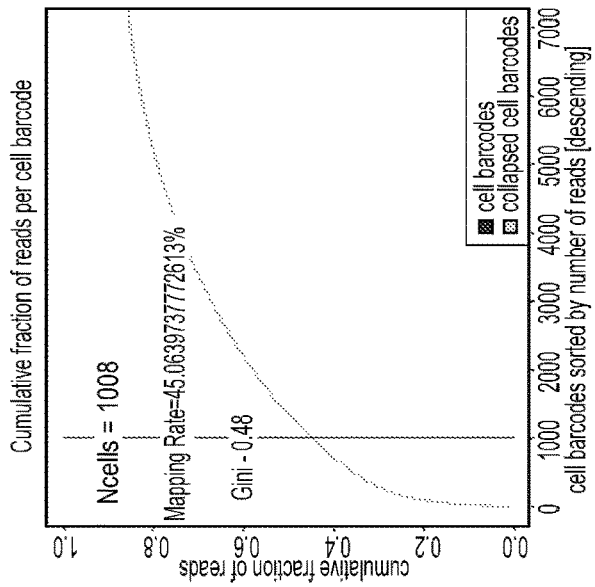
Figure 81D:
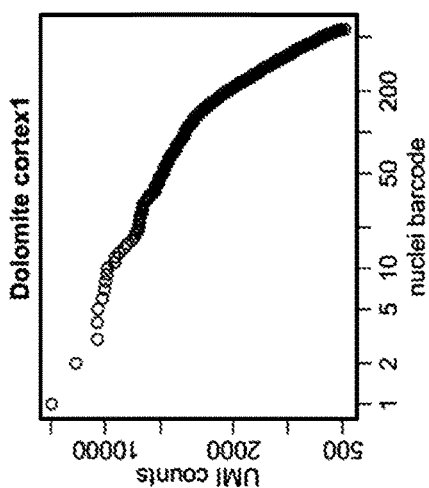
Figure 81E:
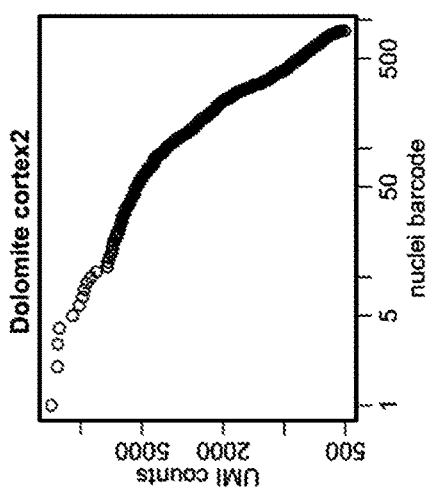
Figure 81F:
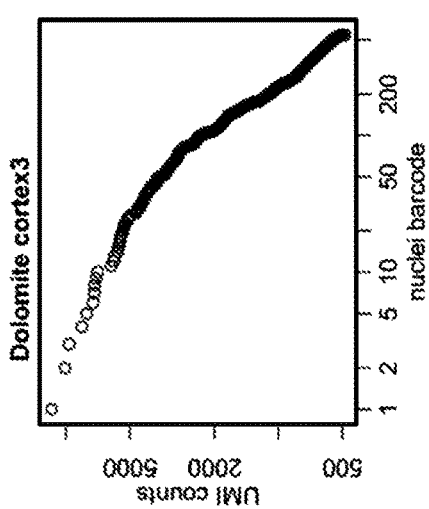

FIG. 80—shows reads mapped for each run of cortex using the Dolomite system.

FIGS. 81A-81F—shows reads and UMIs per cell barcode per run.

Figures 82A, 82B, 82C:
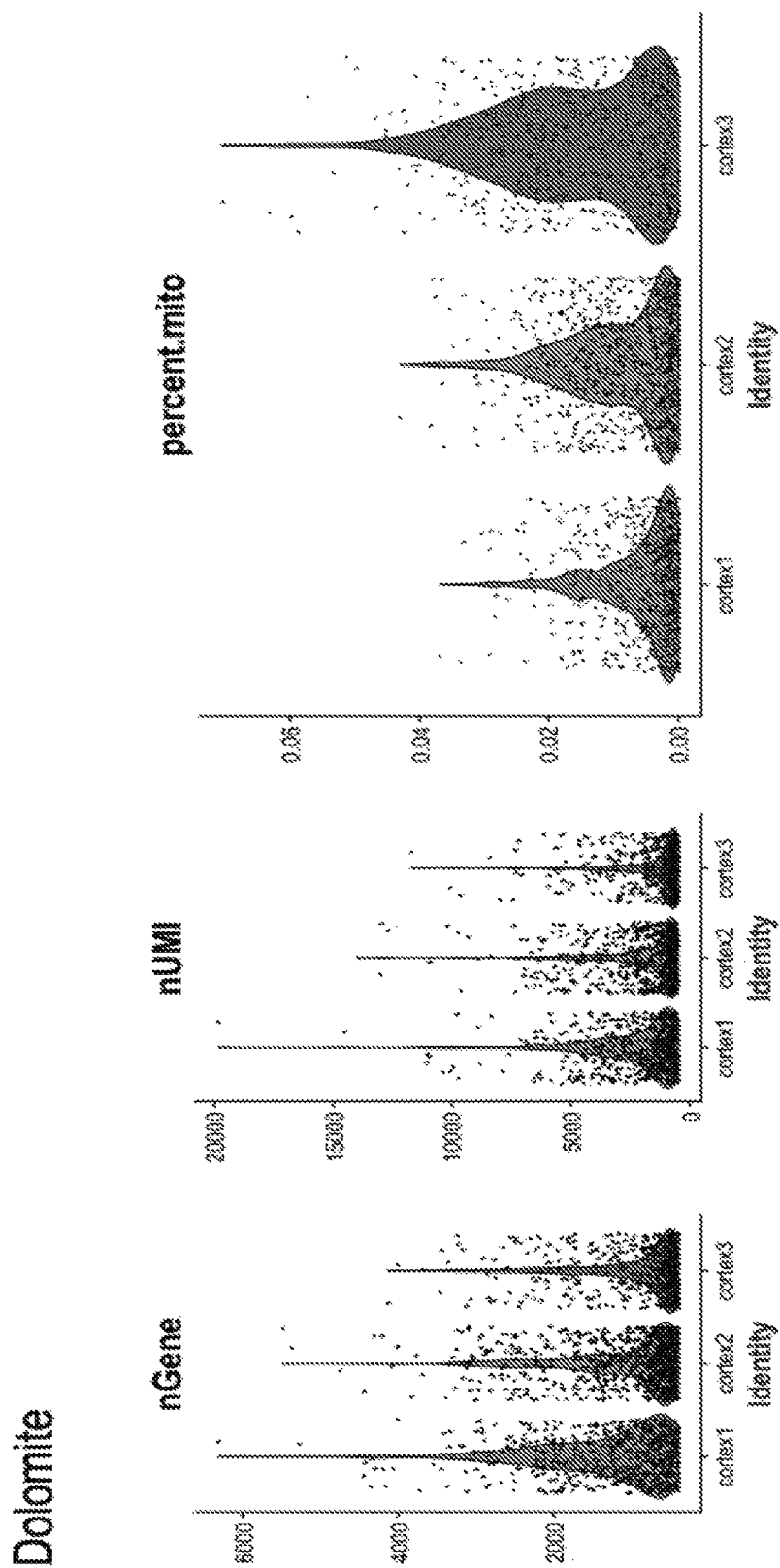
Figure 83A:
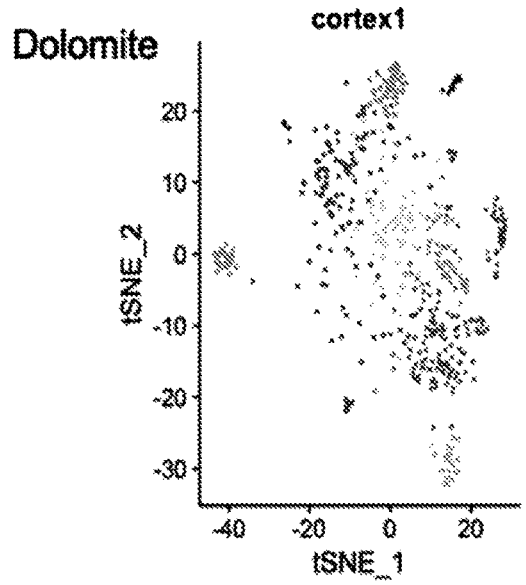
Figure 83B:
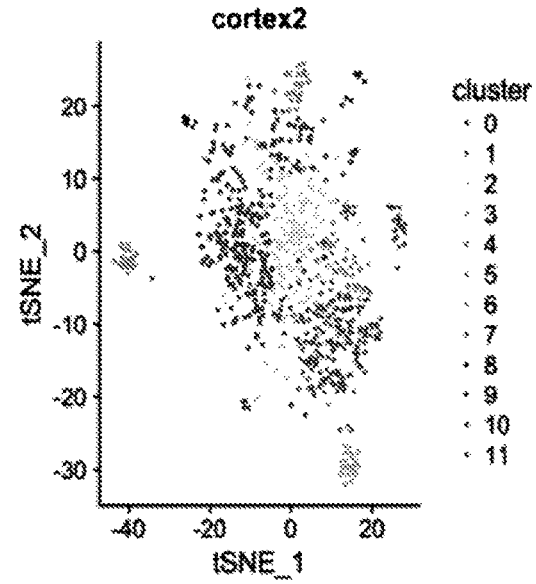
Figure 83C:
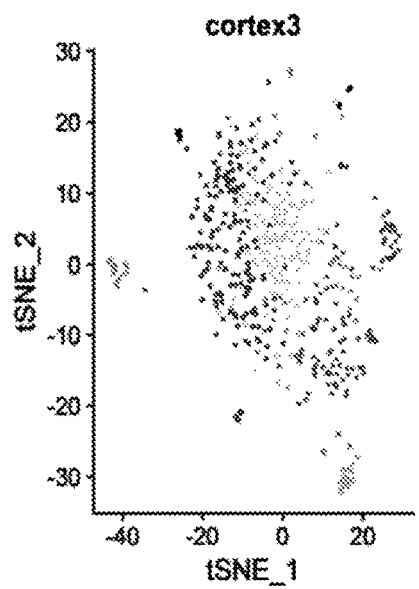
Figure 83D:
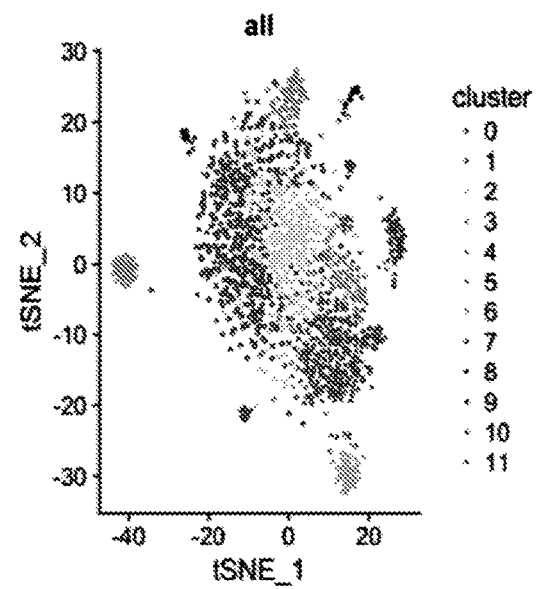

FIGS. 82A-82C—shows number of genes, UMIs, and ratio per run.

FIGS. 83A-83D—shows cell clusters obtained from different cerebral cortex samples.

Figure 84:
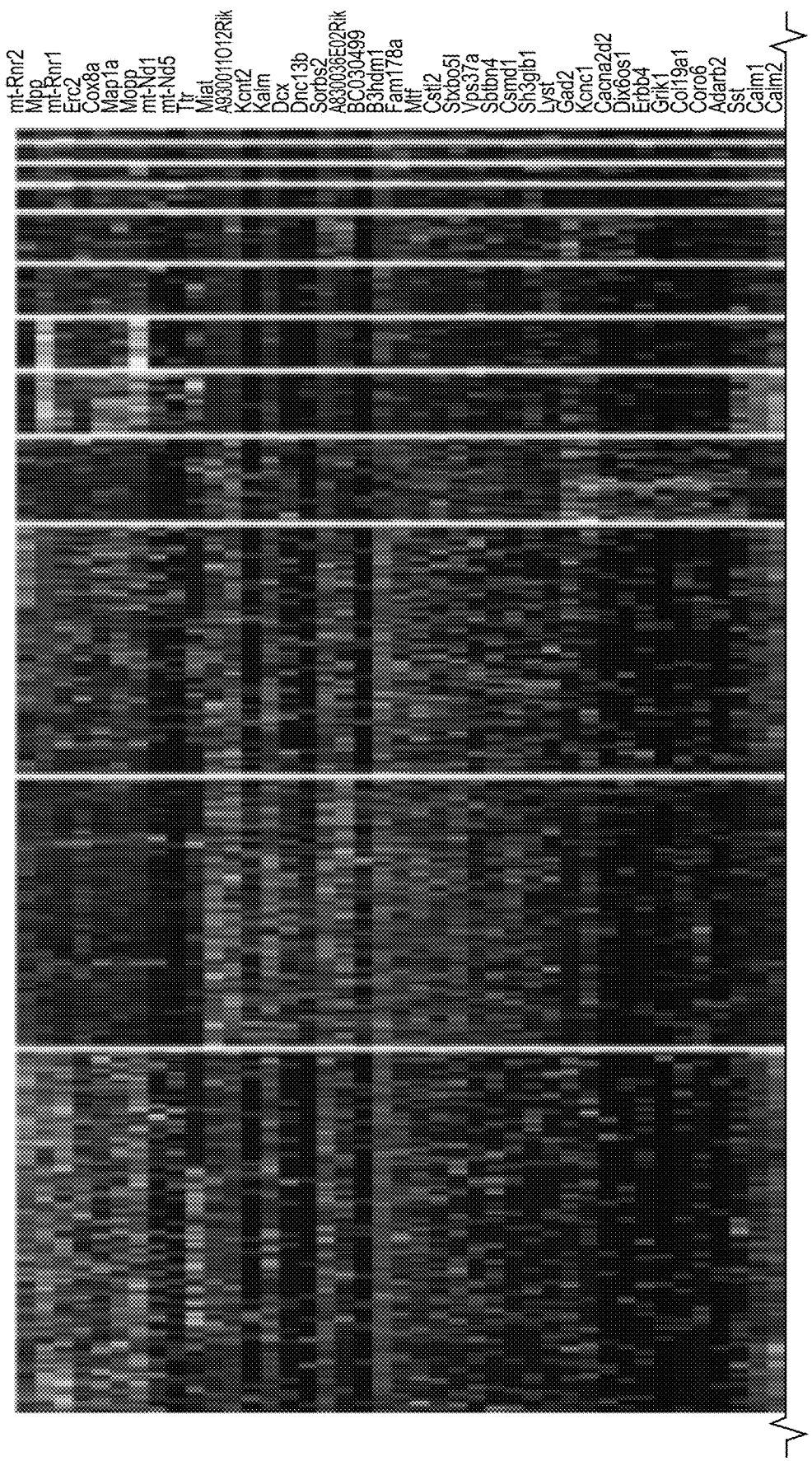

FIG. 84—shows a heatmap of the top differentially expressed genes.

Figure 85A:
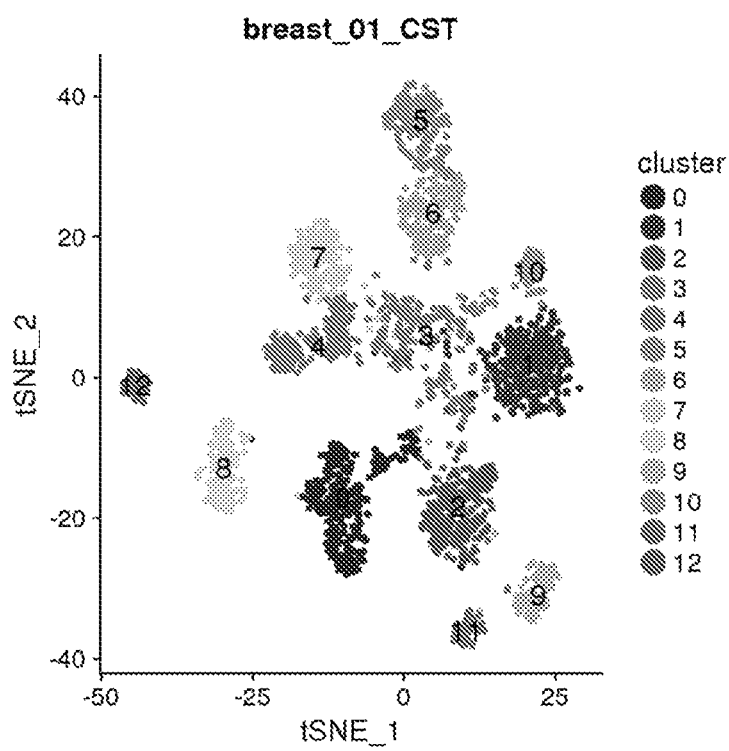
Figure 85B:
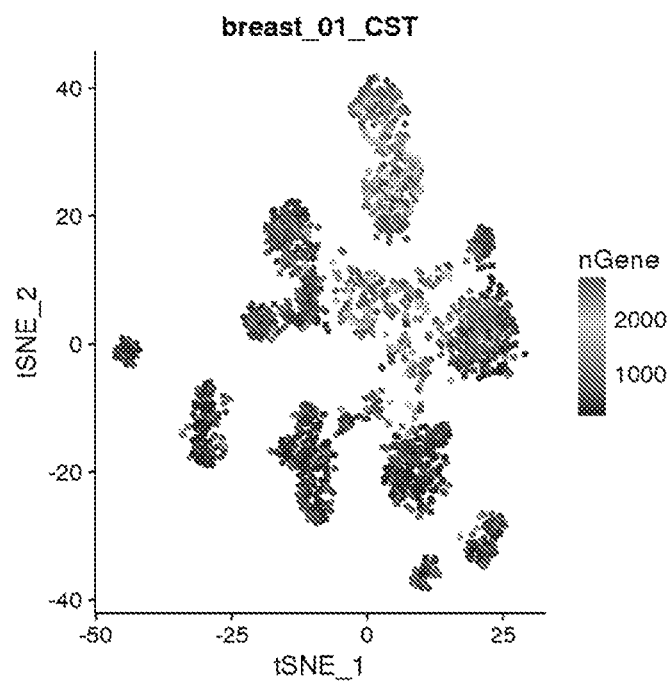

FIGS. 85A, 85B—show tSNE plots of single-nuclei RNA profiles for breast tissue samples and using the CST protocol. Shown are clusters identified by k-means clustering analysis (85A) and projection of gene expression (85B).

Figure 86B:
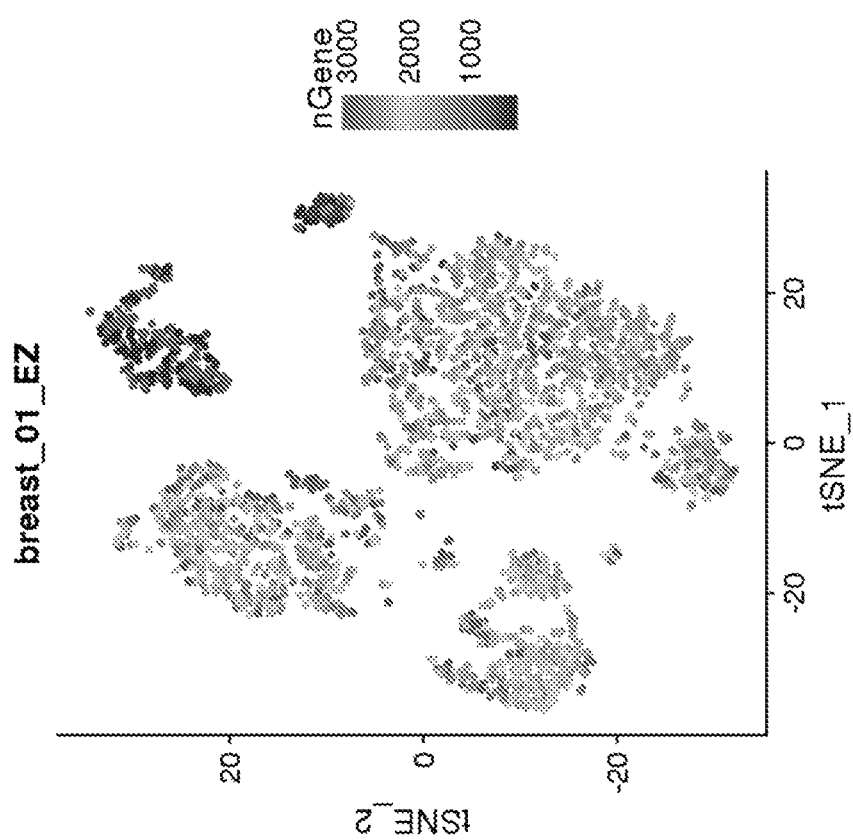
Figure 86A:
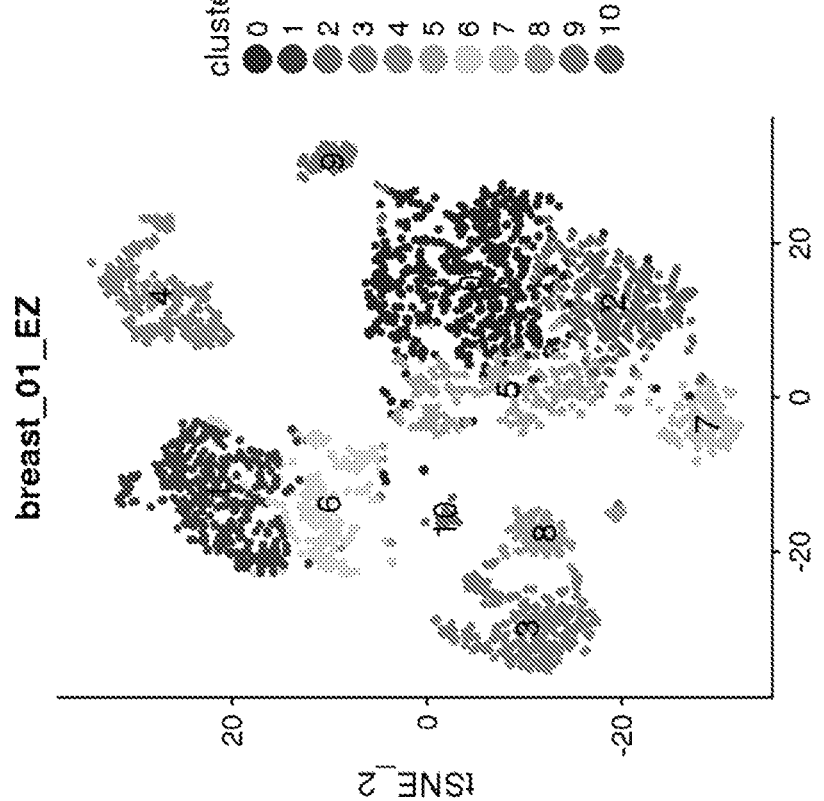

FIGS. 86A, 86B—show tSNE plots of single-nuclei RNA profiles for breast tissue samples and using the EZ protocol. Shown are clusters identified by k-means clustering analysis (86A) and projection of gene expression (86B).

Figure 87B:
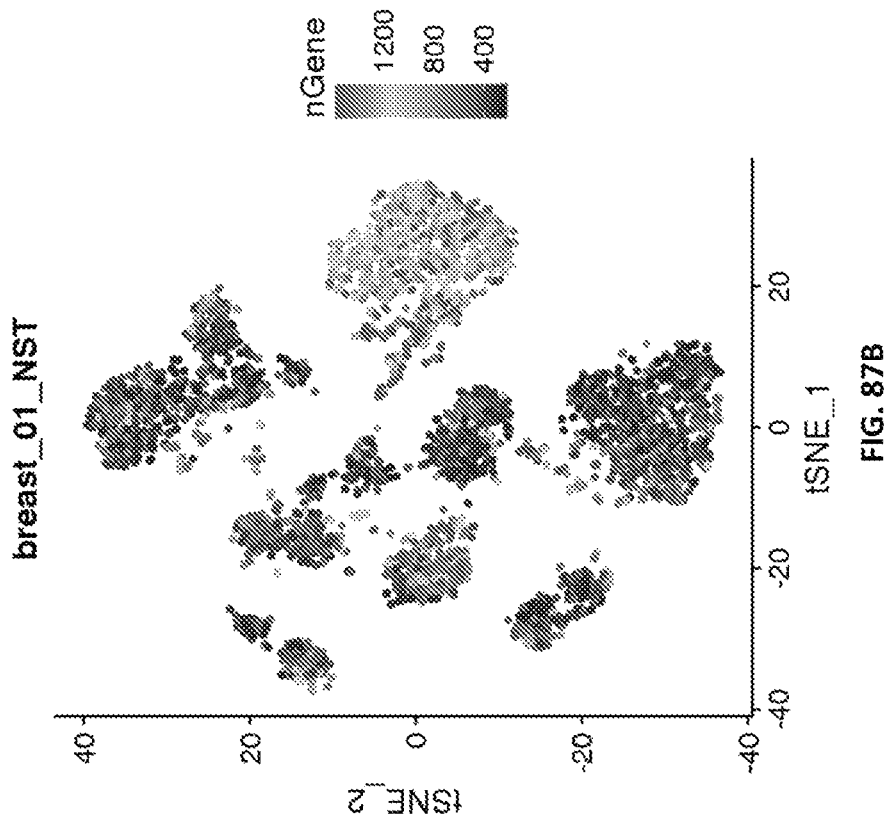
Figure 87A:
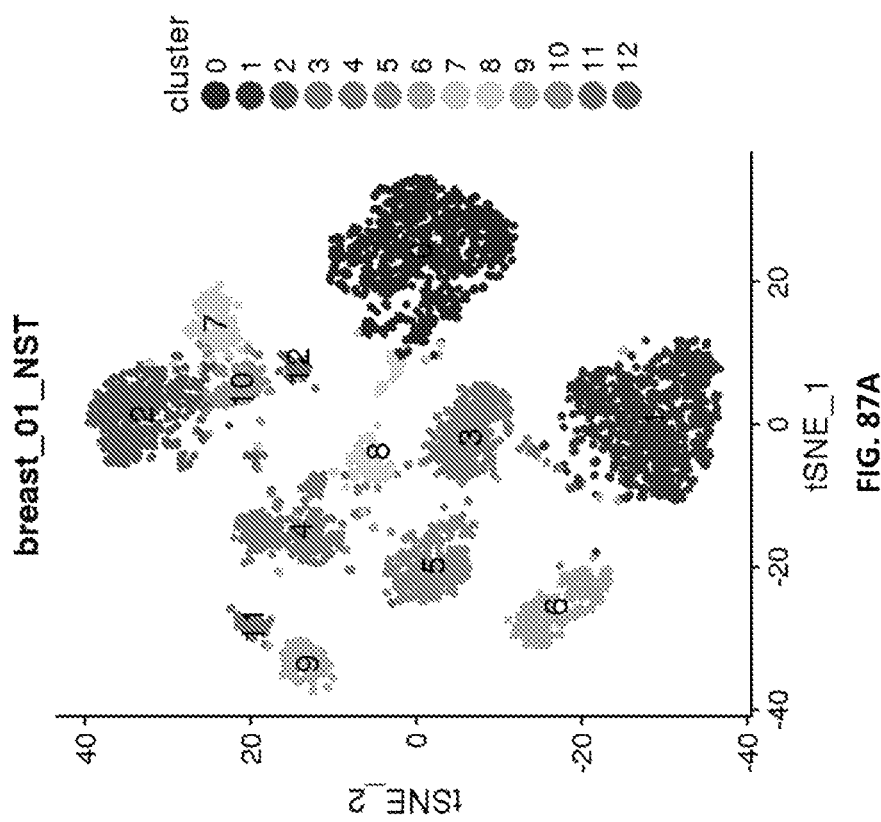

FIGS. 87A, 87B—show tSNE plots of single-nuclei RNA profiles for breast tissue samples and using the NST protocol. Shown are clusters identified by k-means clustering analysis (87A) and projection of gene expression (87B).

FIGS. 88A, 88B—show tSNE plots of single-nuclei RNA profiles for breast tissue samples and using the TST protocol. Shown are clusters identified by k-means clustering analysis (88A) and projection of gene expression (88B).

FIGS. 89A, 89B—show tSNE plots of single-nuclei RNA profiles for esophageal mucosa tissue samples and using the CST protocol. Shown are clusters identified by k-means clustering analysis (89A) and projection of gene expression (89B).

Figures 90A, 90B:
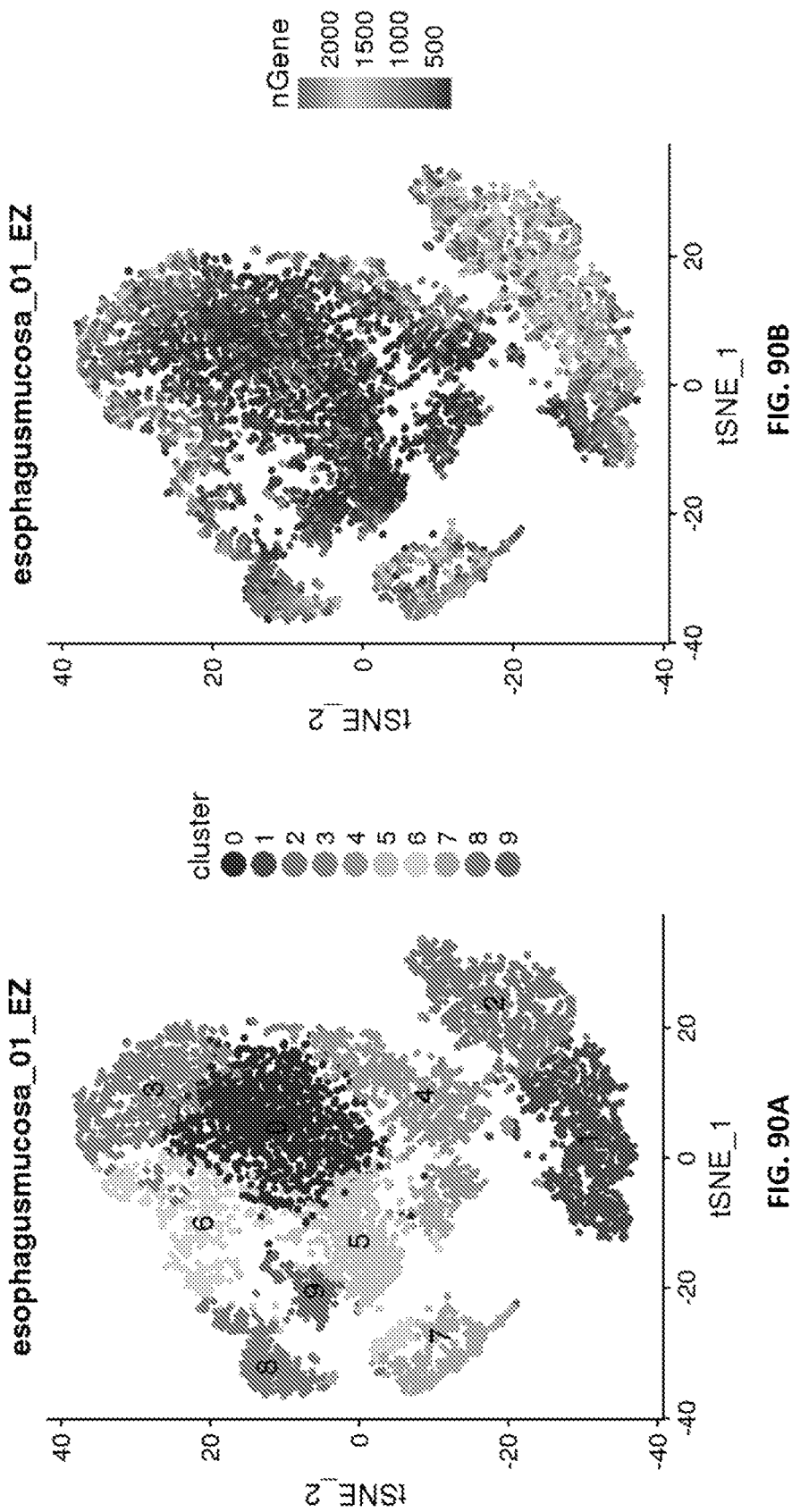

FIGS. 90A, 90B—show tSNE plots of single-nuclei RNA profiles for esophageal mucosa tissue samples and using the EZ protocol. Shown are clusters identified by k-means clustering analysis (90A) and projection of gene expression (90B).

FIGS. 91A, 91B—show tSNE plots of single-nuclei RNA profiles for esophageal mucosa tissue samples and using the NST protocol. Shown are clusters identified by k-means clustering analysis (91A) and projection of gene expression (91B).

Figures 92A, 92B:
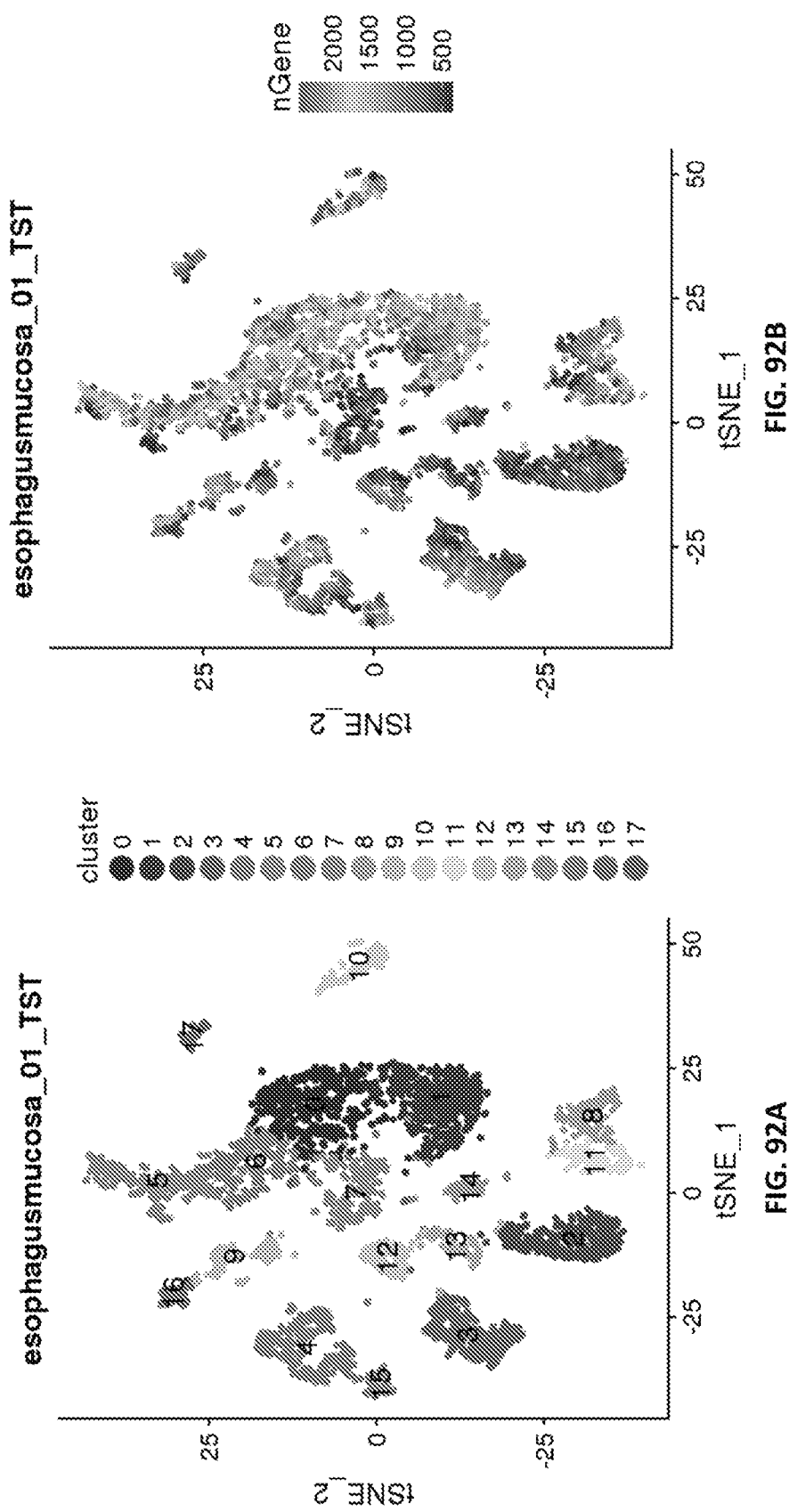

FIGS. 92A, 92B—show tSNE plots of single-nuclei RNA profiles for esophageal mucosa tissue samples and using the TST protocol. Shown are clusters identified by k-means clustering analysis (92A) and projection of gene expression (92B).

FIGS. 93A, 93B—show tSNE plots of single-nuclei RNA profiles for esophageal mucosa tissue samples and using the CST protocol. Shown are clusters identified by k-means clustering analysis (93A) and projection of gene expression (93B).

Figure 94B:
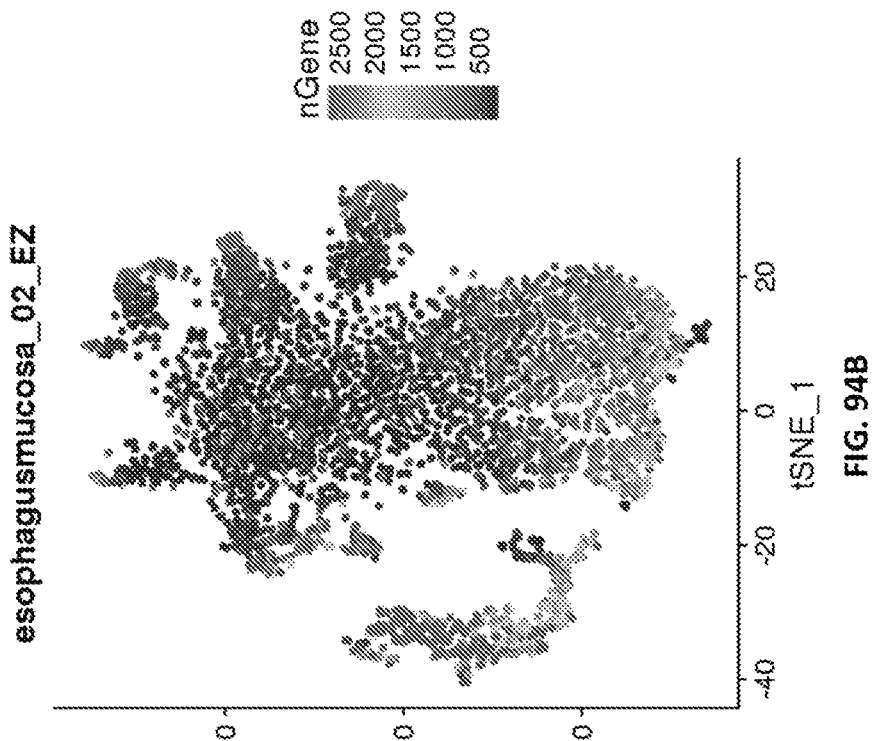
Figure 94A:
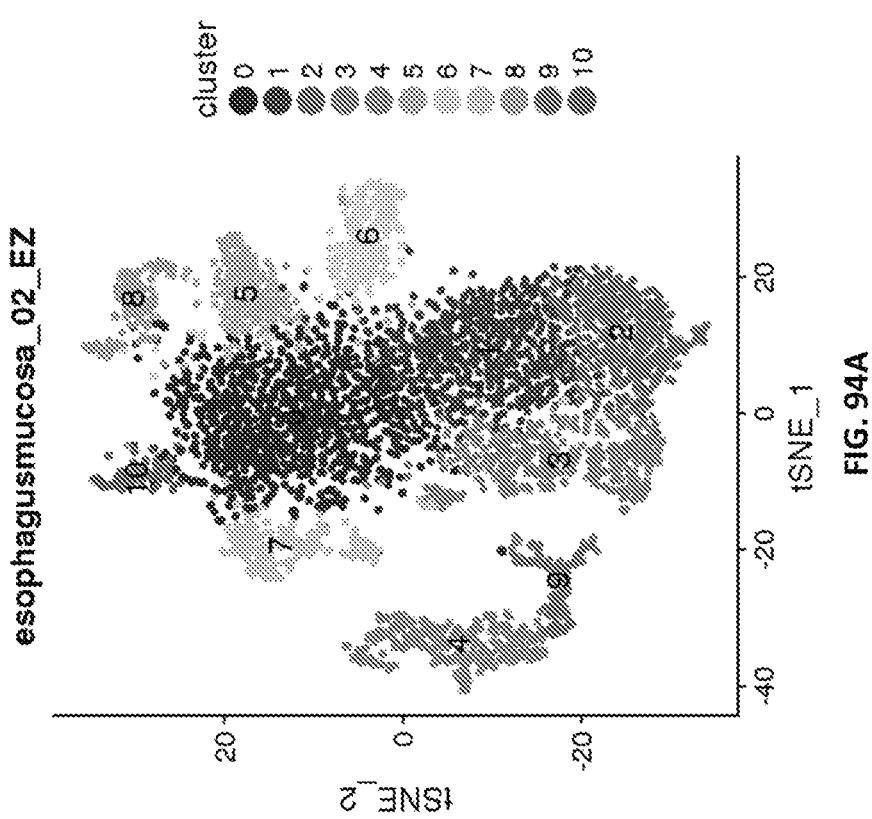

FIGS. 94A, 94B—show tSNE plots of single-nuclei RNA profiles for esophageal mucosa tissue samples and using the EZ protocol. Shown are clusters identified by k-means clustering analysis (94A) and projection of gene expression (94B).

Figures 95A, 95B:
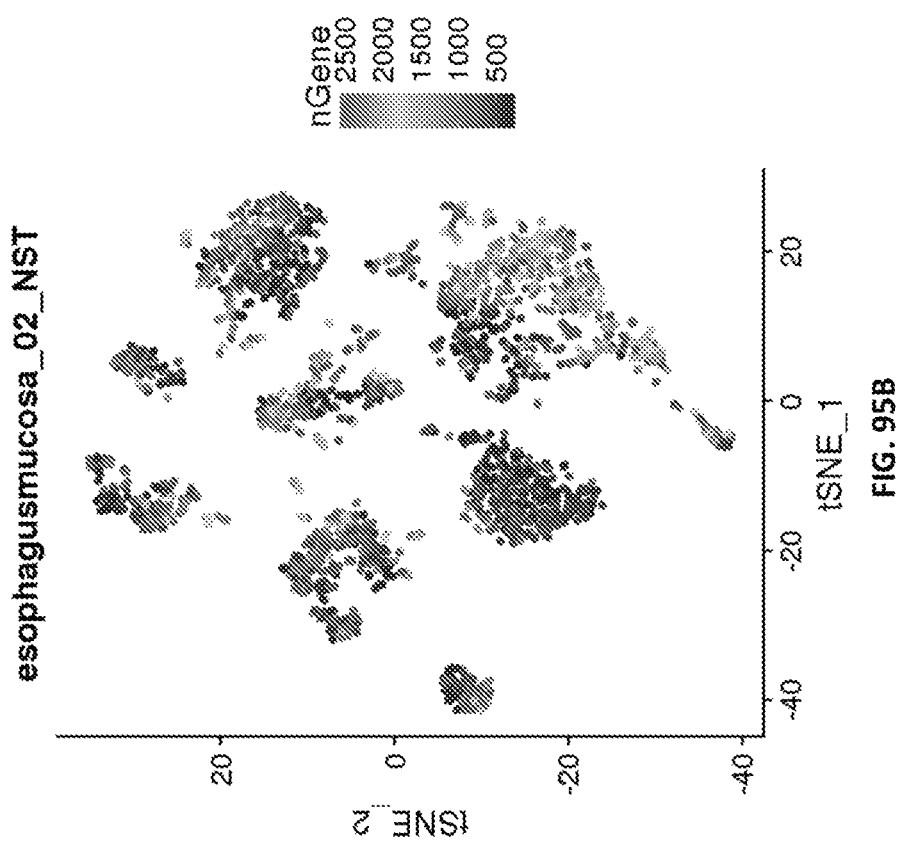

FIGS. 95A, 95B—show tSNE plots of single-nuclei RNA profiles for esophageal mucosa tissue samples and using the NST protocol. Shown are clusters identified by k-means clustering analysis (95A) and projection of gene expression (95B).

Figure 96B:
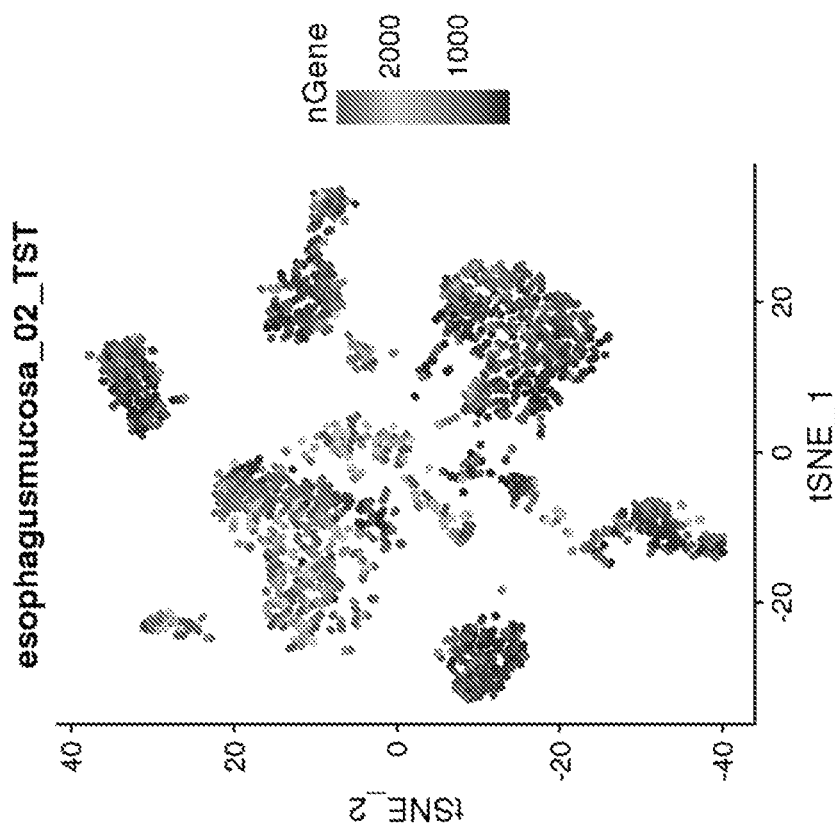
Figure 96A:
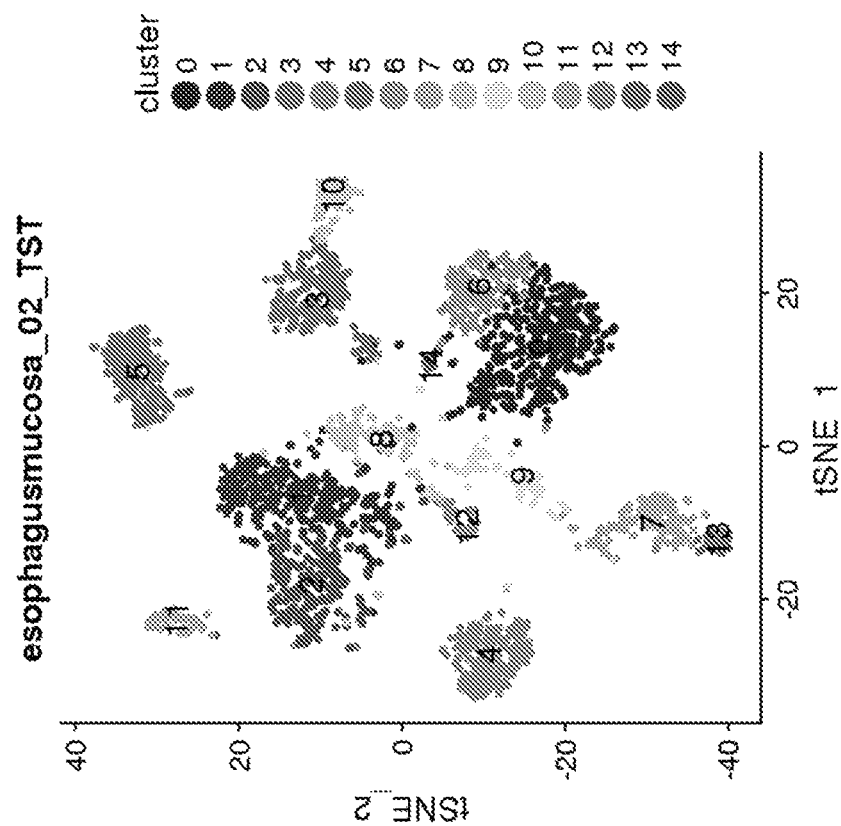

FIGS. 96A, 96B—show tSNE plots of single-nuclei RNA profiles for esophageal mucosa tissue samples and using the TST protocol. Shown are clusters identified by k-means clustering analysis (96A) and projection of gene expression (96B).

FIGS. 97A, 97B—show tSNE plots of single-nuclei RNA profiles for esophageal mucosa tissue samples and using the CST protocol. Shown are clusters identified by k-means clustering analysis (97A) and projection of gene expression (97B).

Figure 98B:
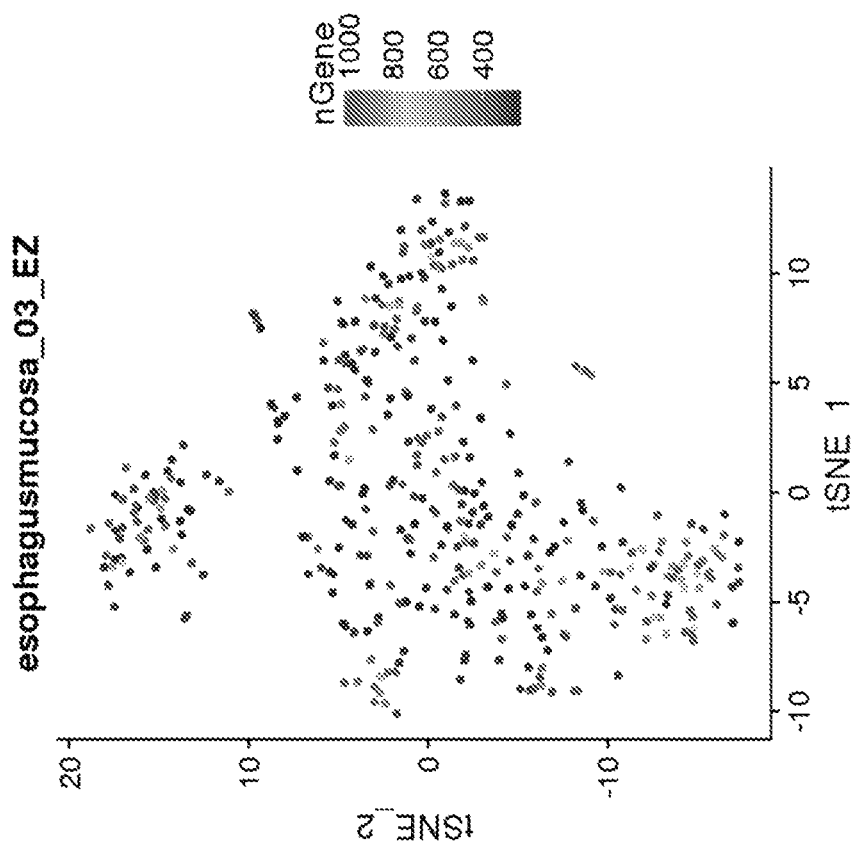
Figure 98A:
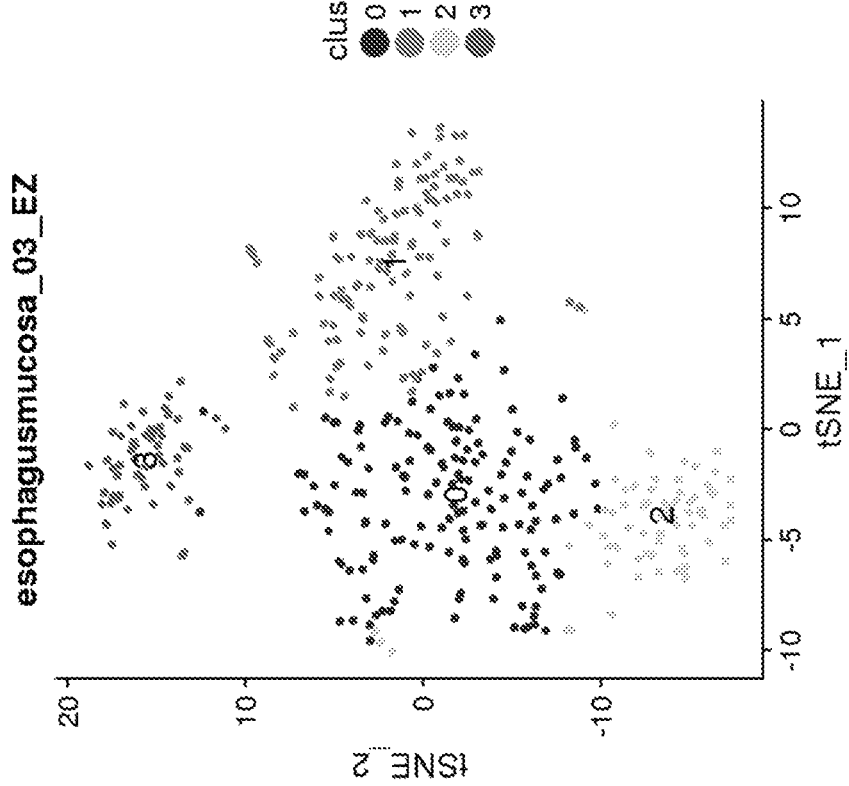

FIGS. 98A, 98B—show tSNE plots of single-nuclei RNA profiles for esophageal mucosa tissue samples and using the EZ protocol. Shown are clusters identified by k-means clustering analysis (98A) and projection of gene expression (98B).

FIGS. 99A, 99B—show tSNE plots of single-nuclei RNA profiles for esophageal mucosa tissue samples and using the NST protocol. Shown are clusters identified by k-means clustering analysis (99A) and projection of gene expression (99B).

Figures 100A, 100B:
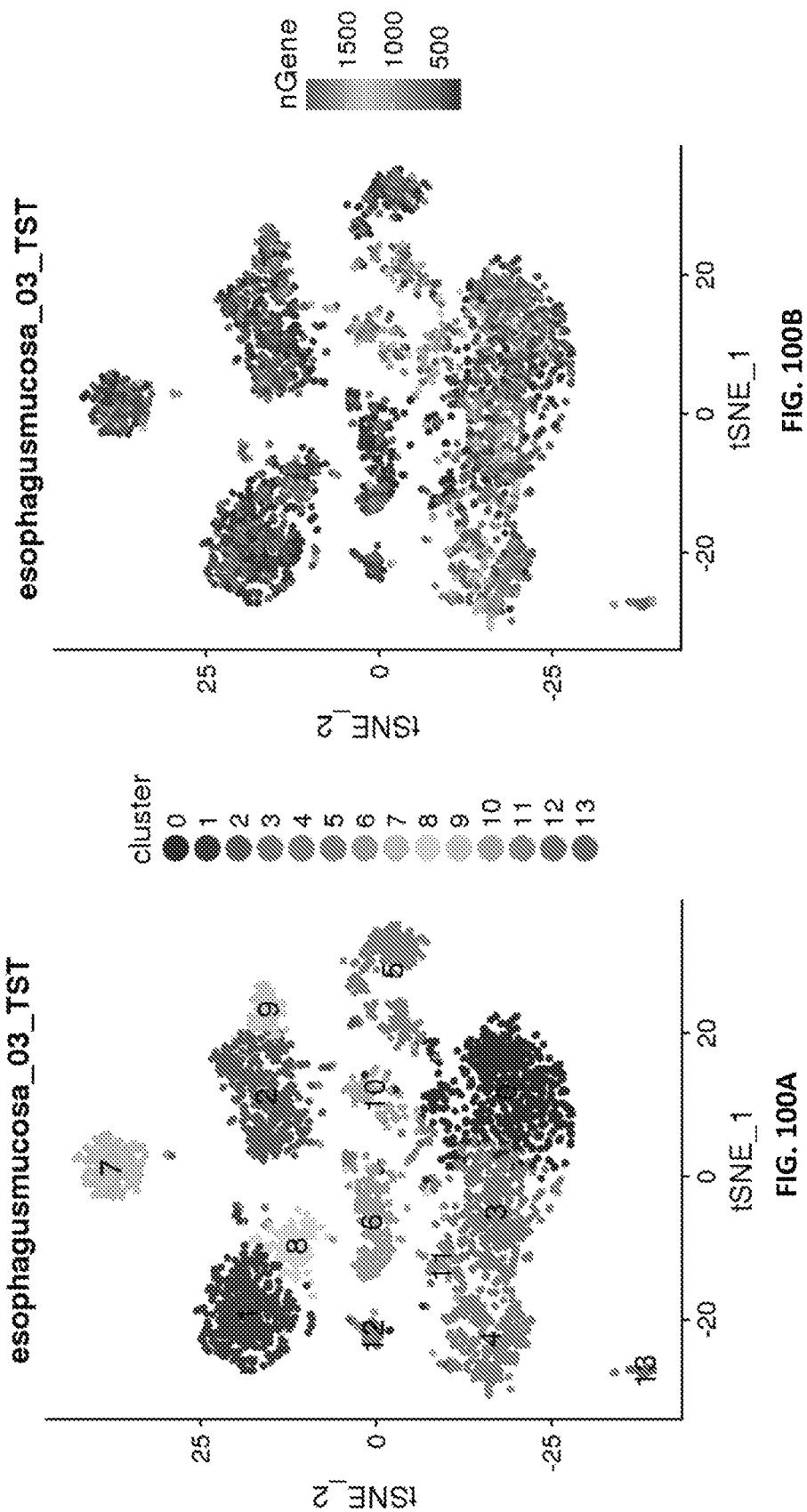

FIGS. 100A, 100B—show tSNE plots of single-nuclei RNA profiles for esophageal mucosa tissue samples and using the TST protocol. Shown are clusters identified by k-means clustering analysis (100A) and projection of gene expression (100B).

FIGS. 101A, 101B—show tSNE plots of single-nuclei RNA profiles for esophageal muscularis tissue samples and using the CST protocol. Shown are clusters identified by k-means clustering analysis (101A) and projection of gene expression (101B).

Figure 102B:
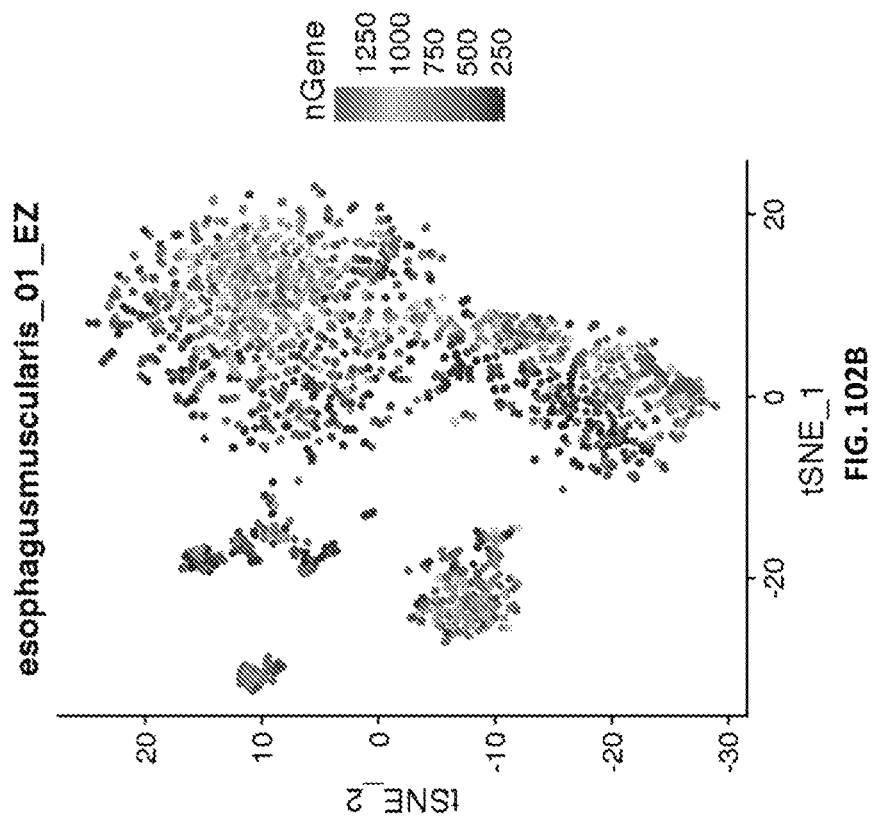
Figure 102A:
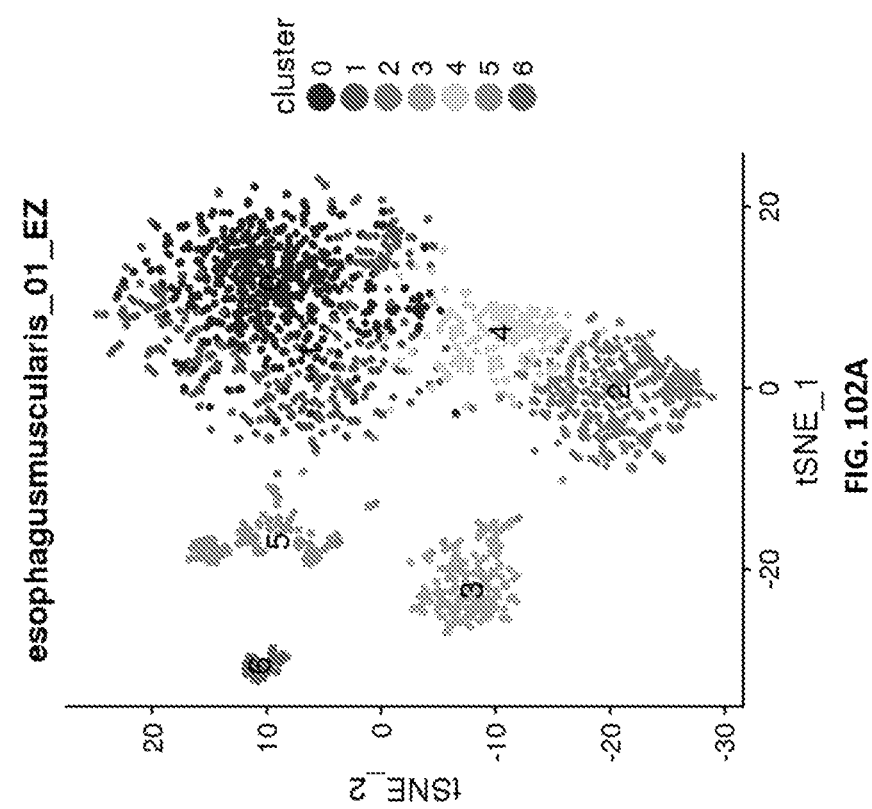

FIGS. 102A, 102B—show tSNE plots of single-nuclei RNA profiles for esophageal muscularis tissue samples and using the EZ protocol. Shown are clusters identified by k-means clustering analysis (102A) and projection of gene expression (102B).

Figure 103B:
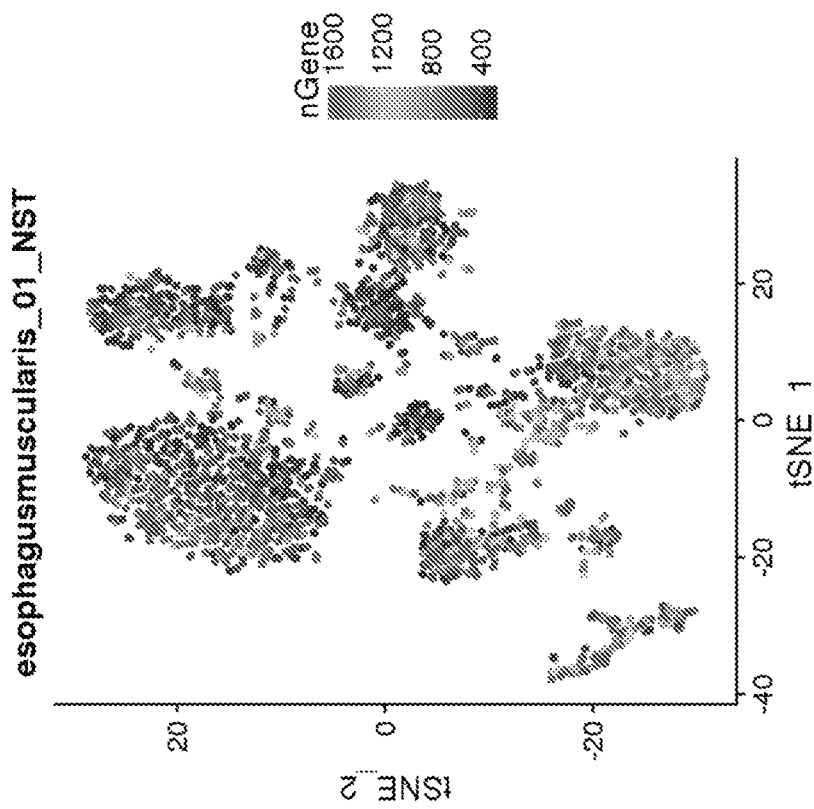
Figure 103A:
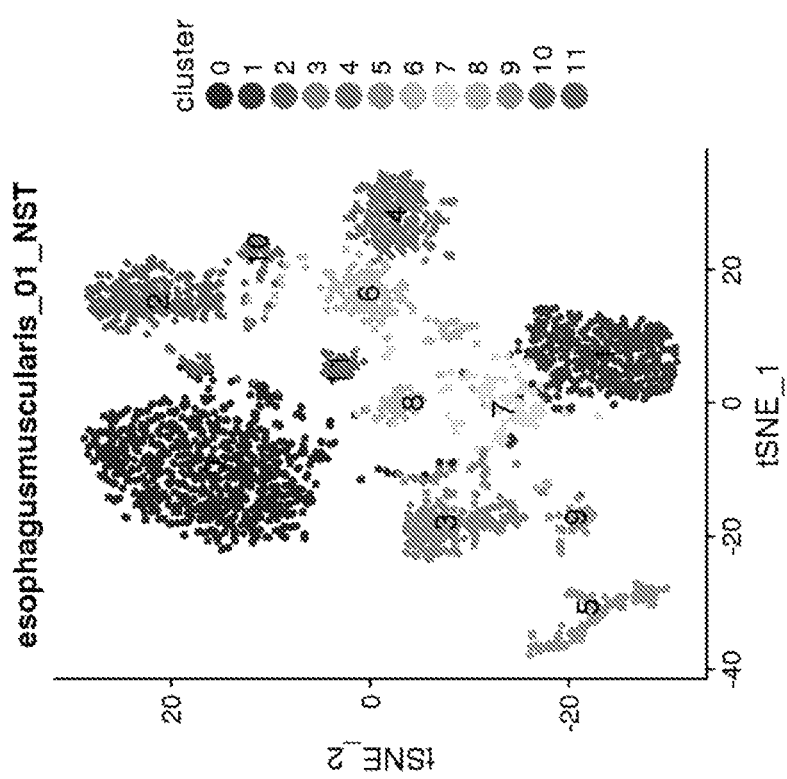

FIGS. 103A, 103B—show tSNE plots of single-nuclei RNA profiles for esophageal muscularis tissue samples and using the NST protocol. Shown are clusters identified by k-means clustering analysis (103A) and projection of gene expression (103B).

Figure 104B:
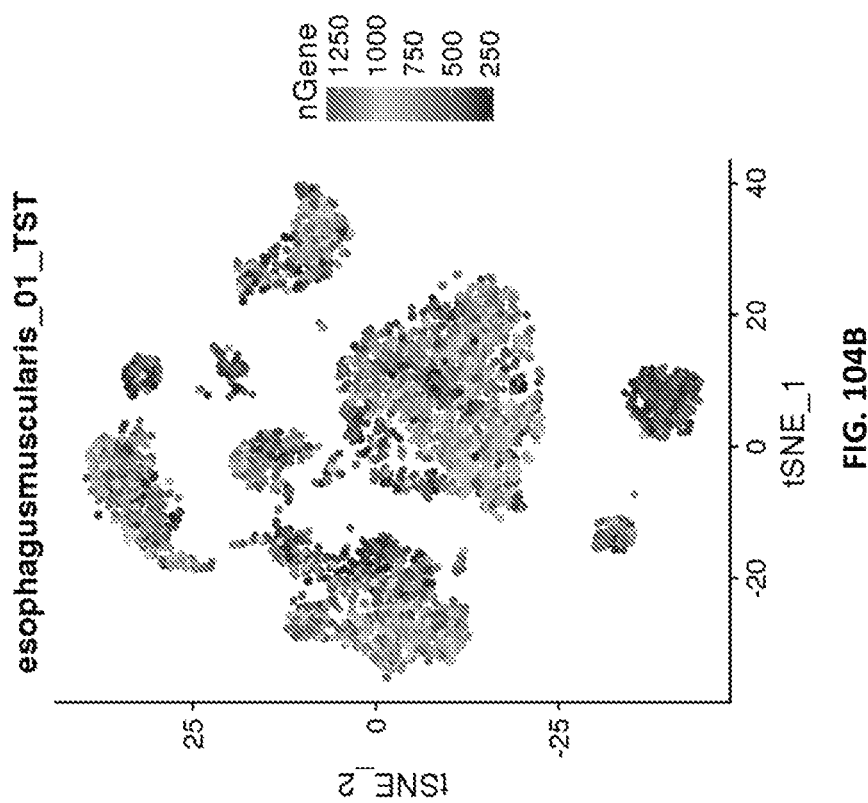
Figure 104A:
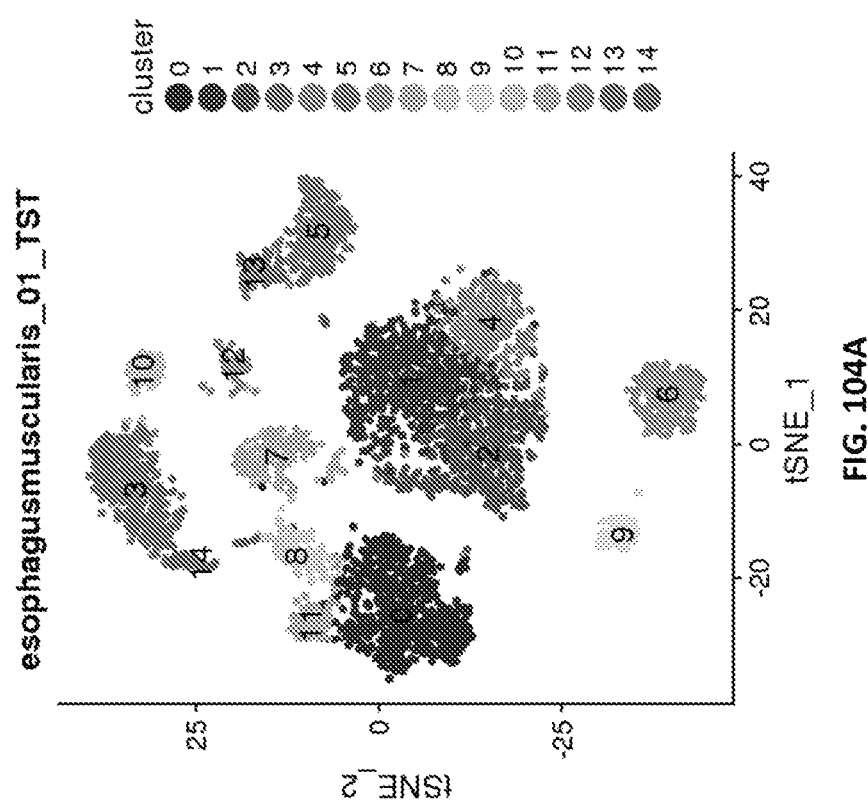

FIGS. 104A, 104B—show tSNE plots of single-nuclei RNA profiles for esophageal muscularis tissue samples and using the TST protocol. Shown are clusters identified by k-means clustering analysis (104A) and projection of gene expression (104B).

Figure 105B:
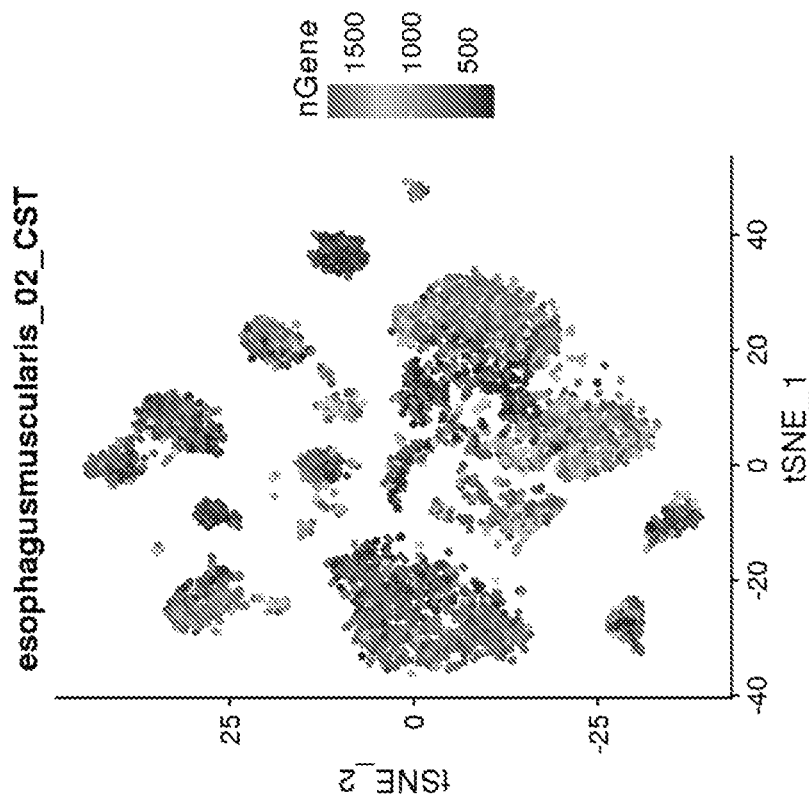
Figure 105A:
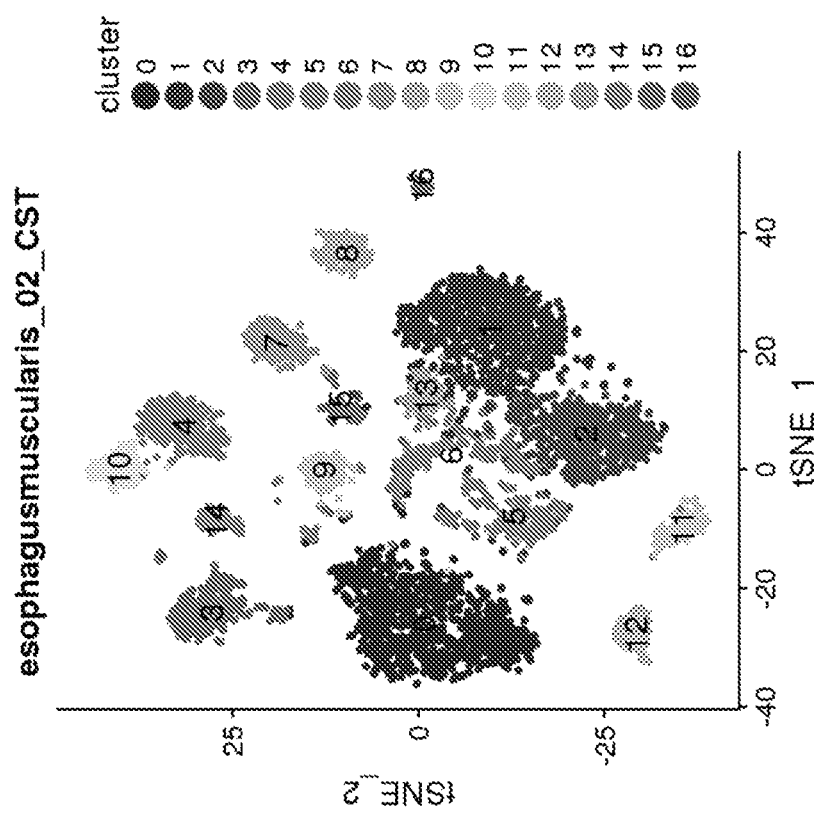

FIGS. 105A, 105B—show tSNE plots of single-nuclei RNA profiles for esophageal muscularis tissue samples and using the CST protocol. Shown are clusters identified by k-means clustering analysis (105A) and projection of gene expression (105B).

Figure 106B:
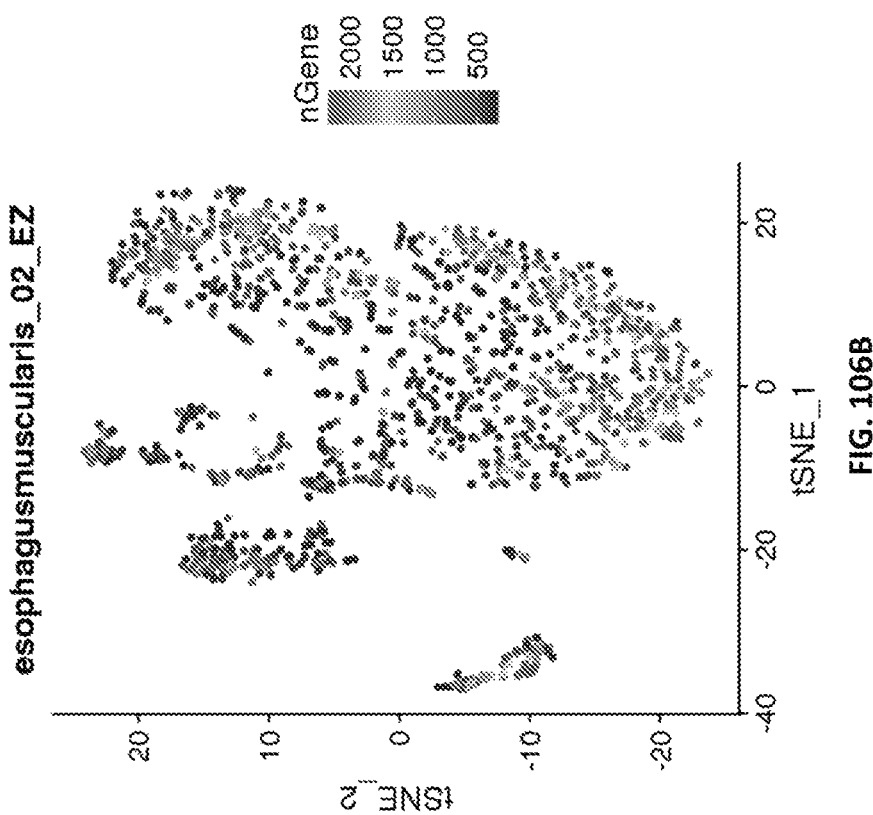
Figure 106A:
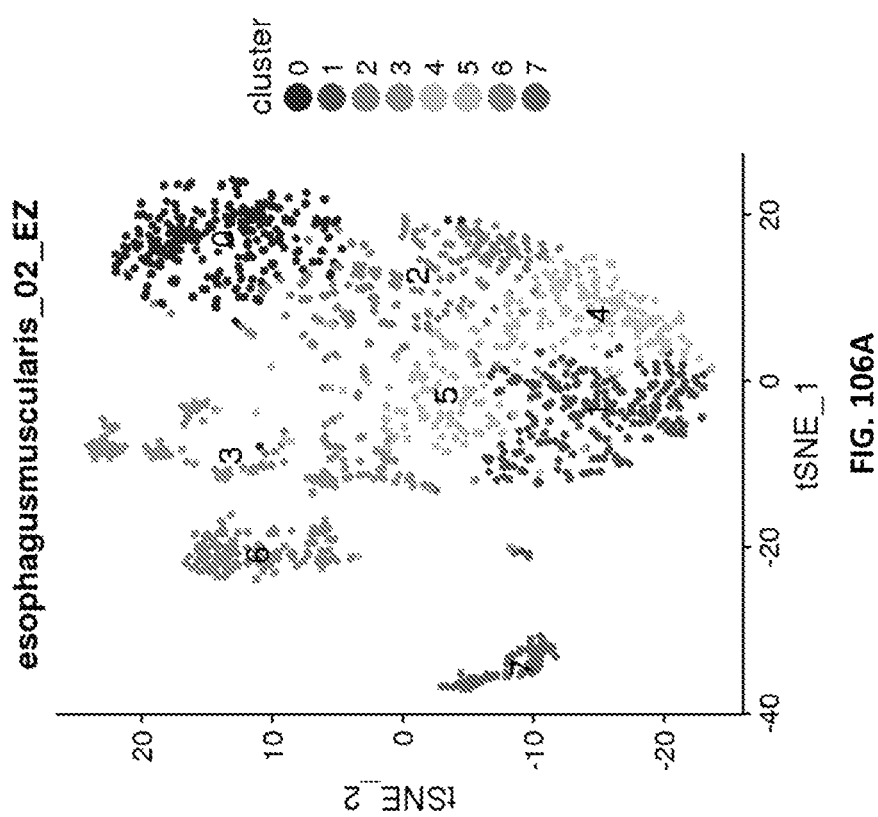

FIGS. 106A, 106B—show tSNE plots of single-nuclei RNA profiles for esophageal muscularis tissue samples and using the EZ protocol. Shown are clusters identified by k-means clustering analysis (106A) and projection of gene expression (106B).

Figure 107B:
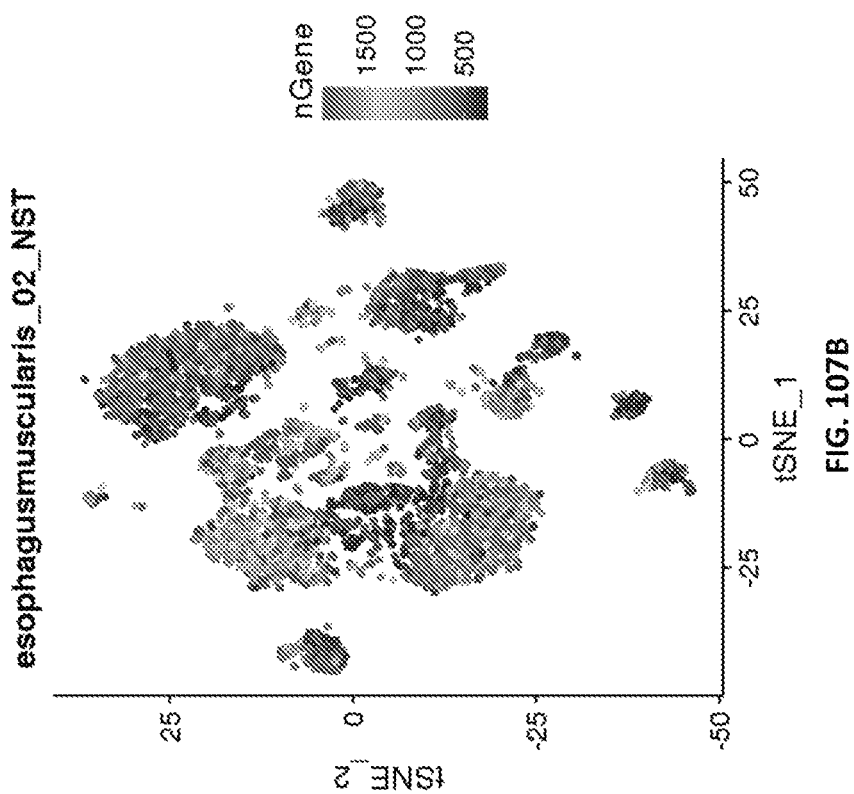
Figure 107A:
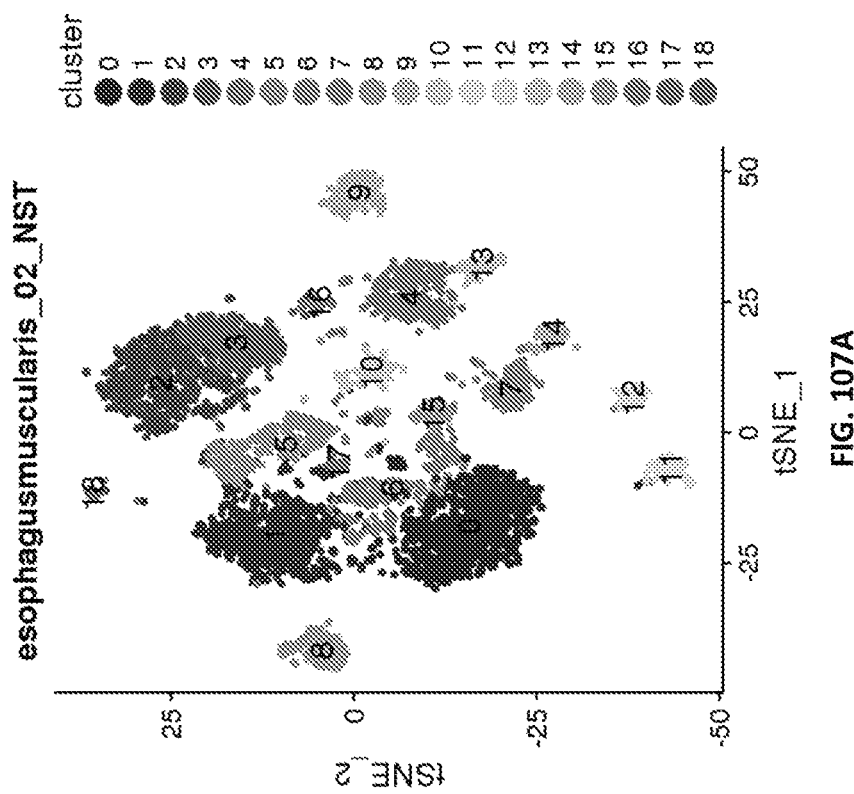

FIGS. 107A, 107B—show tSNE plots of single-nuclei RNA profiles for esophageal muscularis tissue samples and using the NST protocol. Shown are clusters identified by k-means clustering analysis (107A) and projection of gene expression (107B).

Figure 108B:
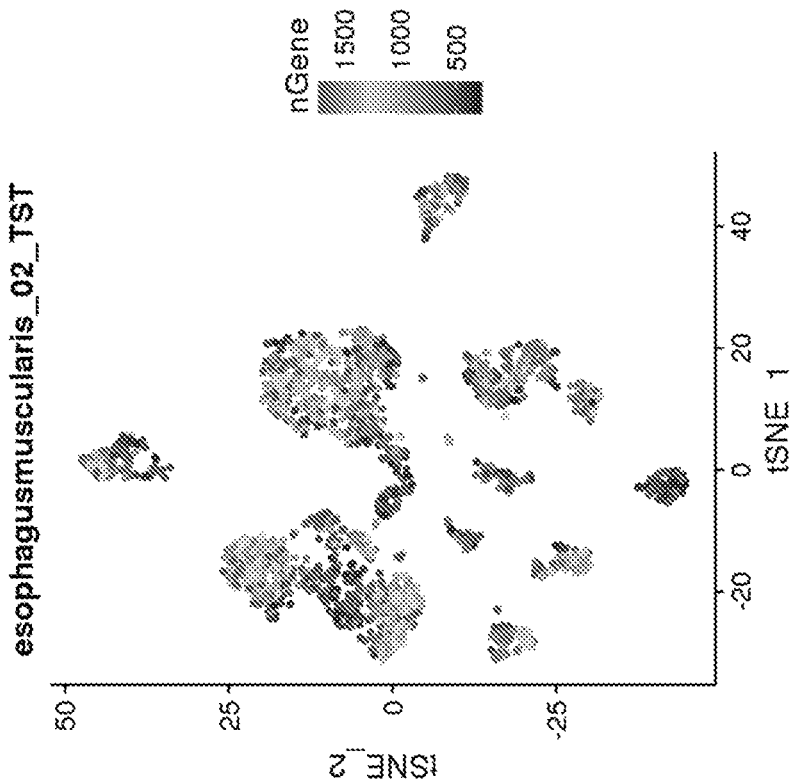
Figure 108A:
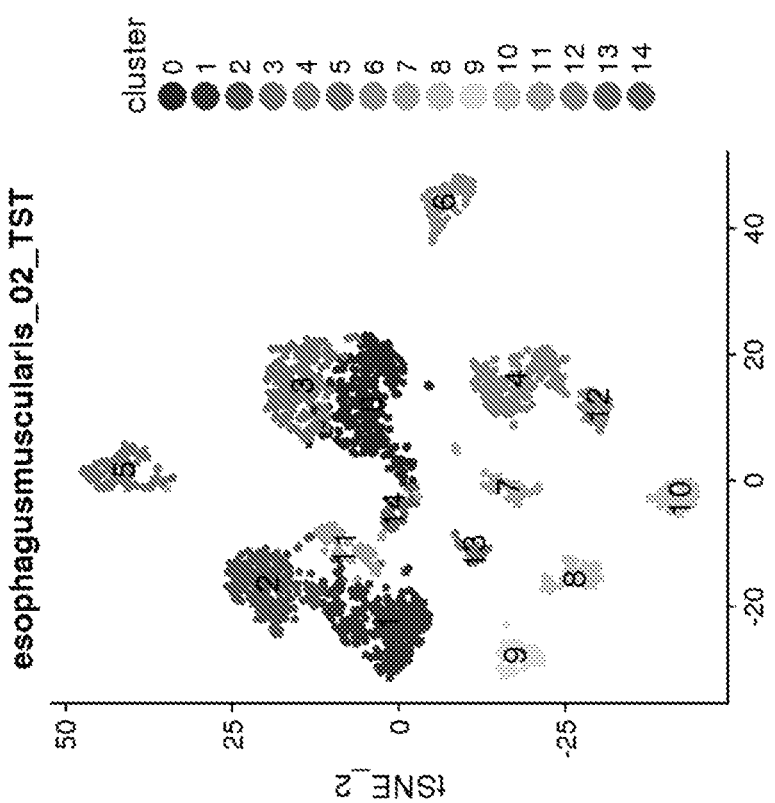

FIGS. 108, 108B—show tSNE plots of single-nuclei RNA profiles for esophageal muscularis tissue samples and using the TST protocol. Shown are clusters identified by k-means clustering analysis (108A) and projection of gene expression (108B).

FIGS. 109A, 109B—show tSNE plots of single-nuclei RNA profiles for esophageal muscularis tissue samples and using the CST protocol. Shown are clusters identified by k-means clustering analysis (109A) and projection of gene expression (109B).

Figures 110A, 110B:
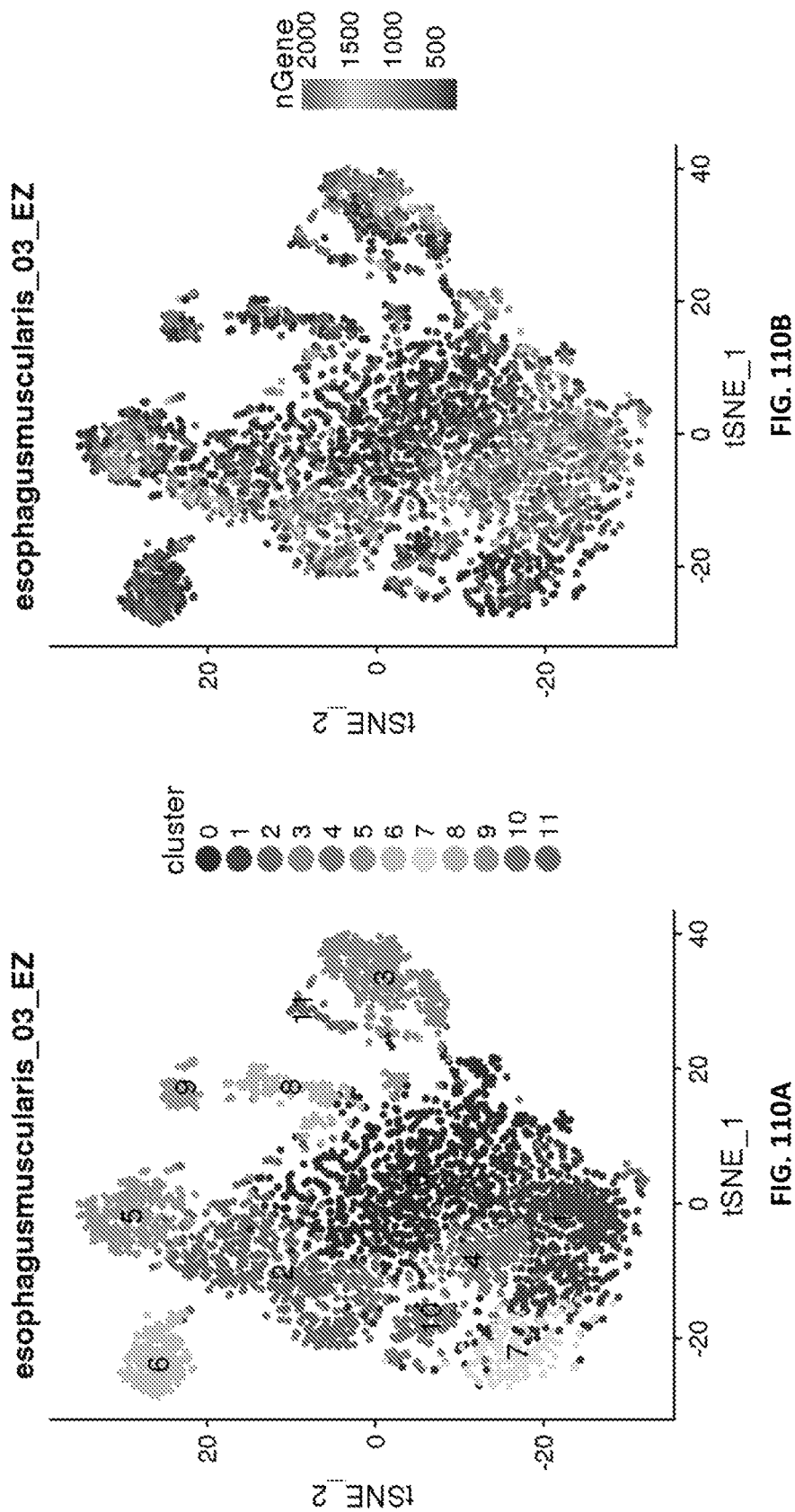

FIGS. 110A, 110B—show tSNE plots of single-nuclei RNA profiles for esophageal muscularis tissue samples and using the EZ protocol. Shown are clusters identified by k-means clustering analysis (110A) and projection of gene expression (110B).

Figure 111B:
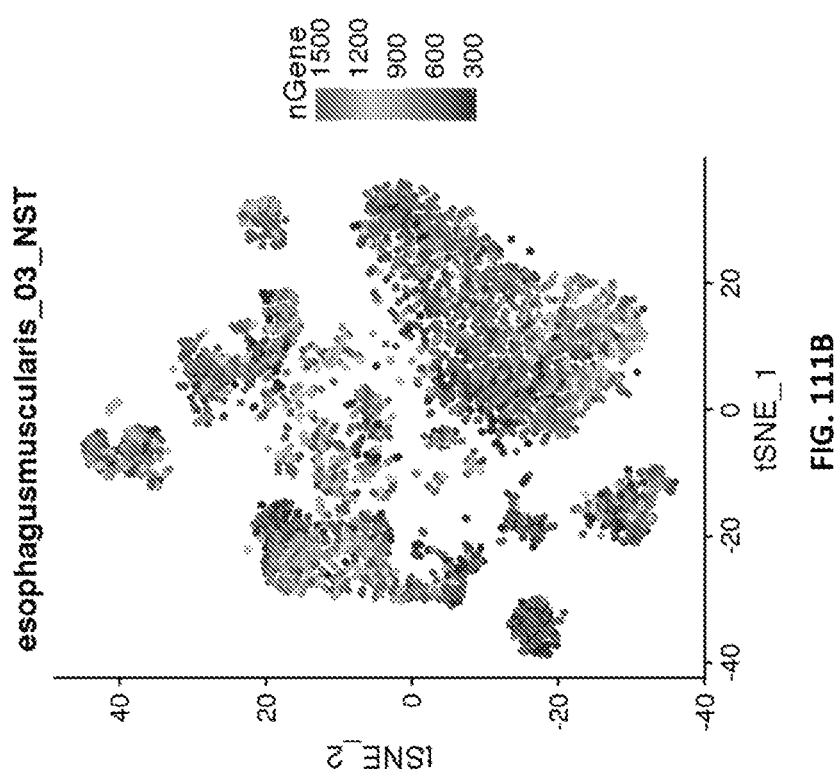
Figure 111A:
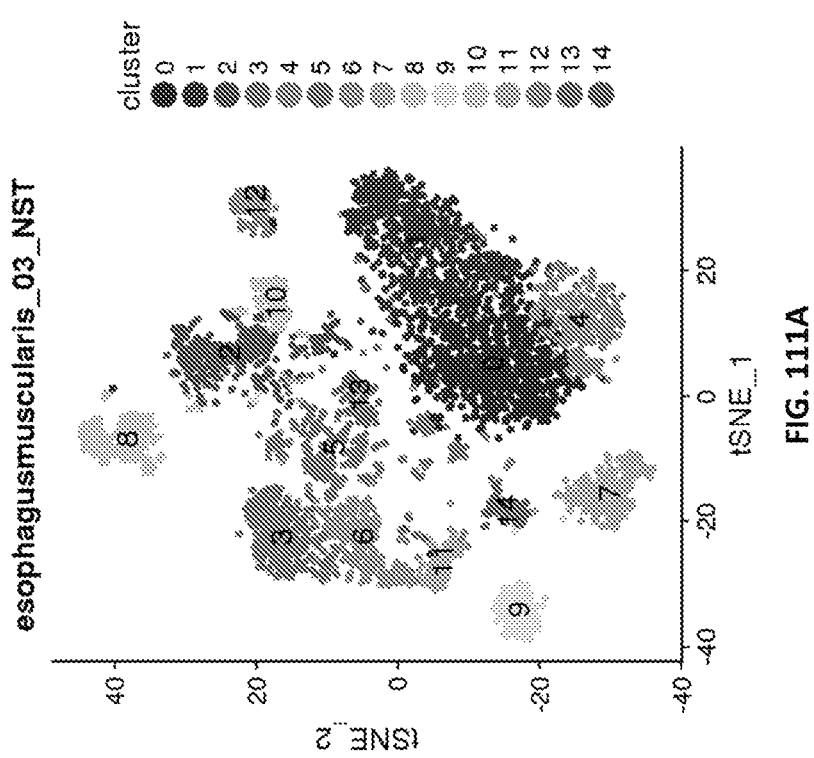

FIGS. 111A, 111B—show tSNE plots of single-nuclei RNA profiles for esophageal muscularis tissue samples and using the NST protocol. Shown are clusters identified by k-means clustering analysis (111A) and projection of gene expression (111B).

Figure 112B:
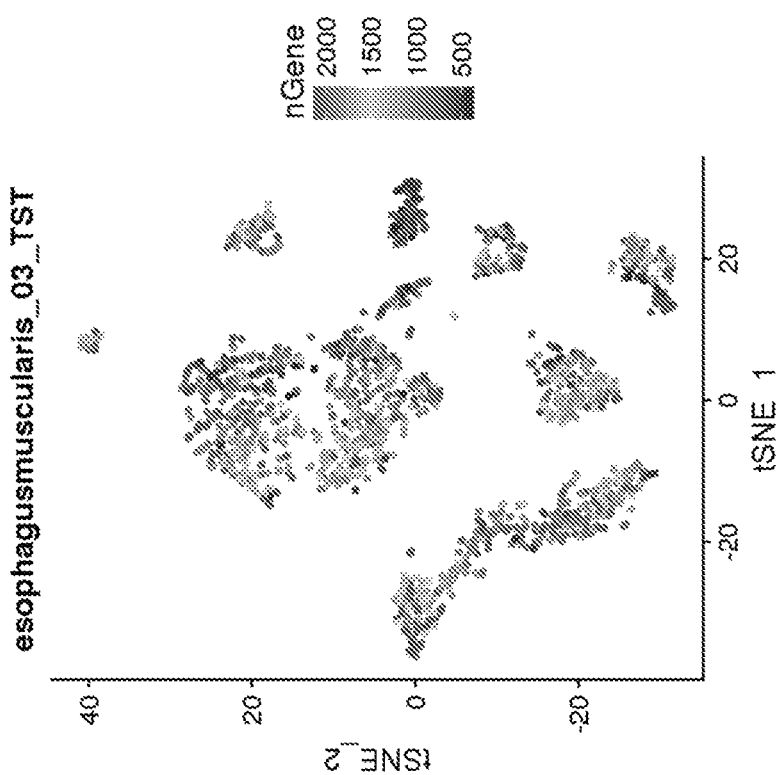
Figure 112A:
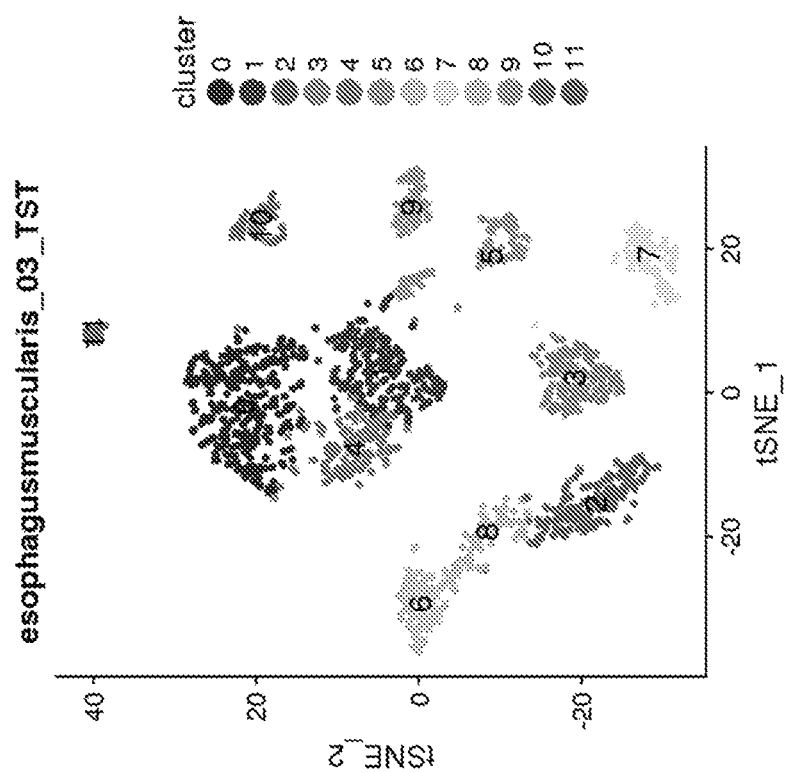

FIGS. 112A, 112B—show tSNE plots of single-nuclei RNA profiles for esophageal muscularis tissue samples and using the TST protocol. Shown are clusters identified by k-means clustering analysis (112A) and projection of gene expression (112B).

Figure 113B:
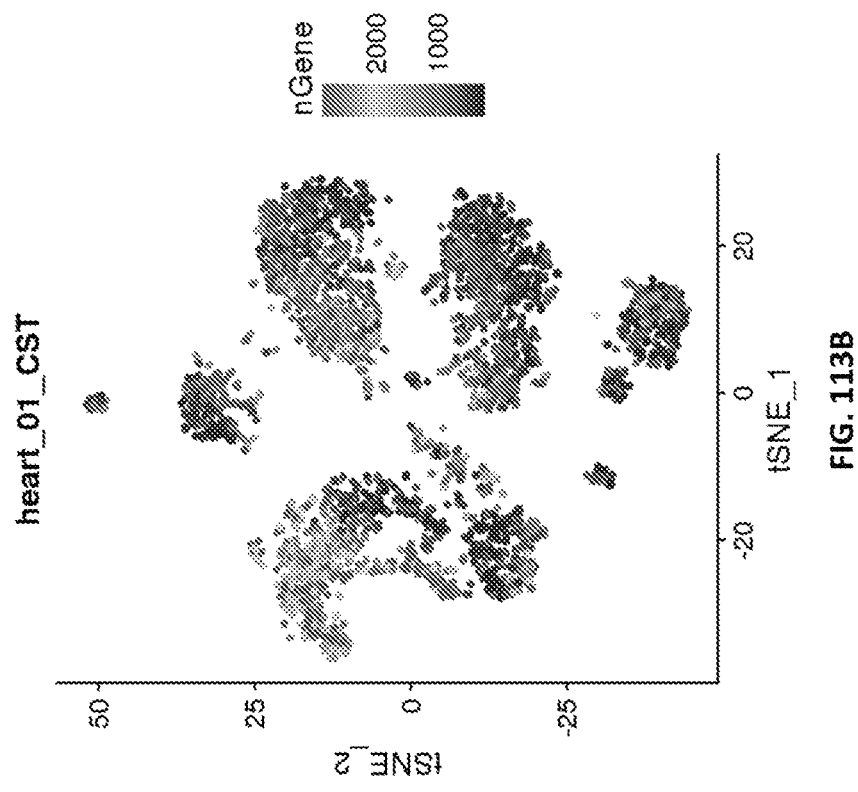
Figure 113A:
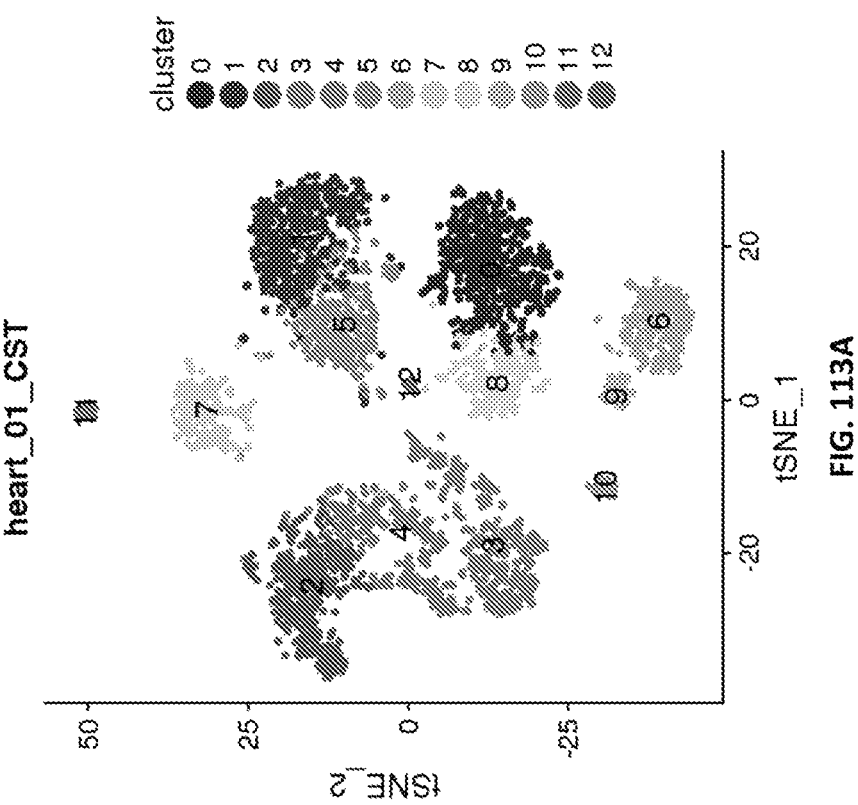

FIGS. 113A, 113B—show tSNE plots of single-nuclei RNA profiles for heart tissue samples and using the CST protocol. Shown are clusters identified by k-means clustering analysis (113A) and projection of gene expression (113B).

FIGS. 114A, 114B—show tSNE plots of single-nuclei RNA profiles for heart tissue samples and using the EZ protocol. Shown are clusters identified by k-means clustering analysis (114A) and projection of gene expression (114B).

Figure 115B:
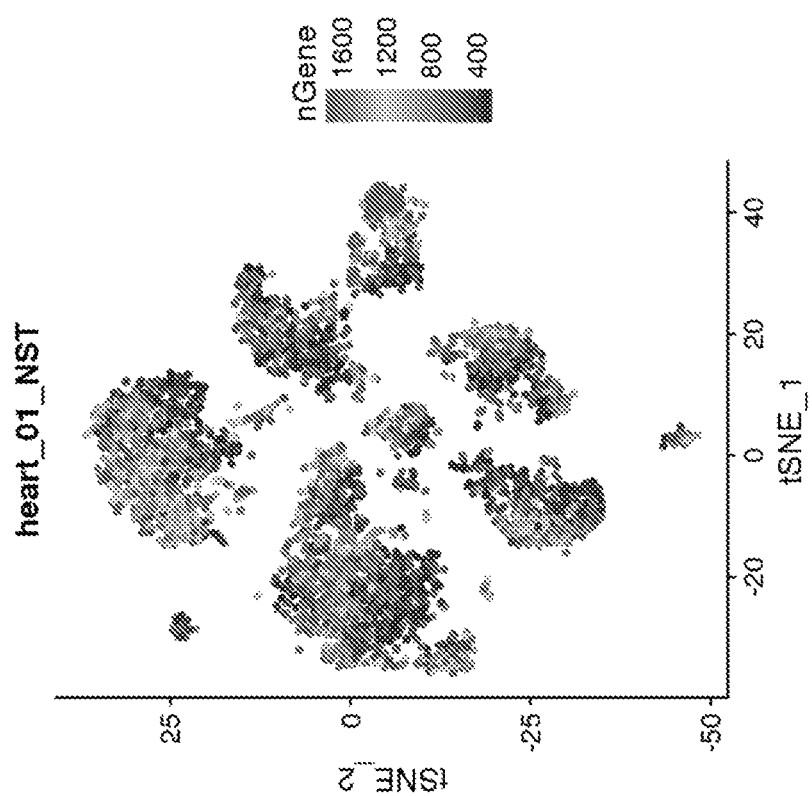
Figure 115A:
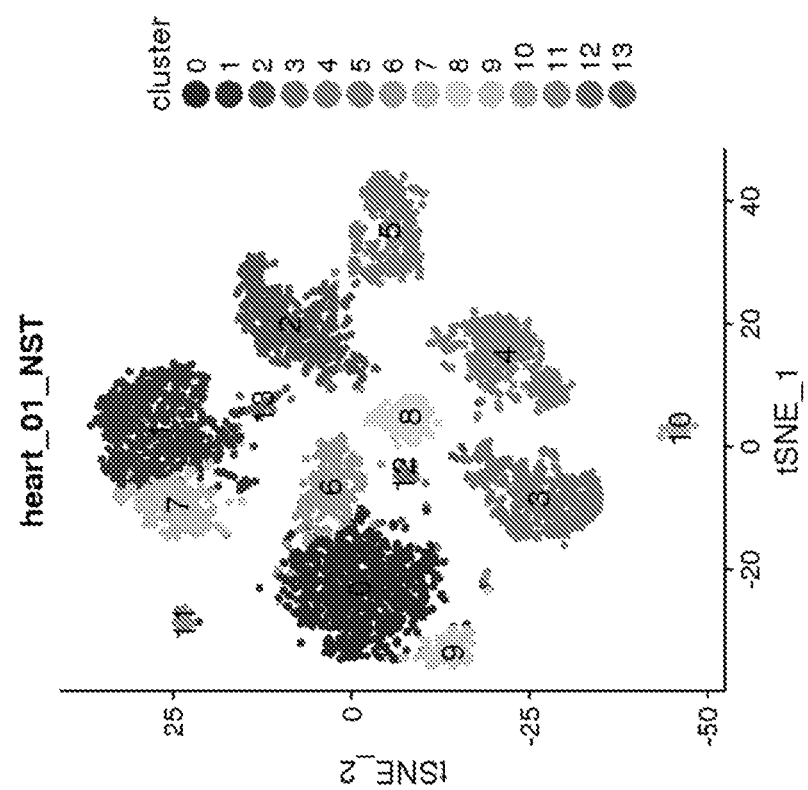

FIGS. 115A, 115B—show tSNE plots of single-nuclei RNA profiles for heart tissue samples and using the NST protocol. Shown are clusters identified by k-means clustering analysis (115A) and projection of gene expression (115B).

Figure 116B:
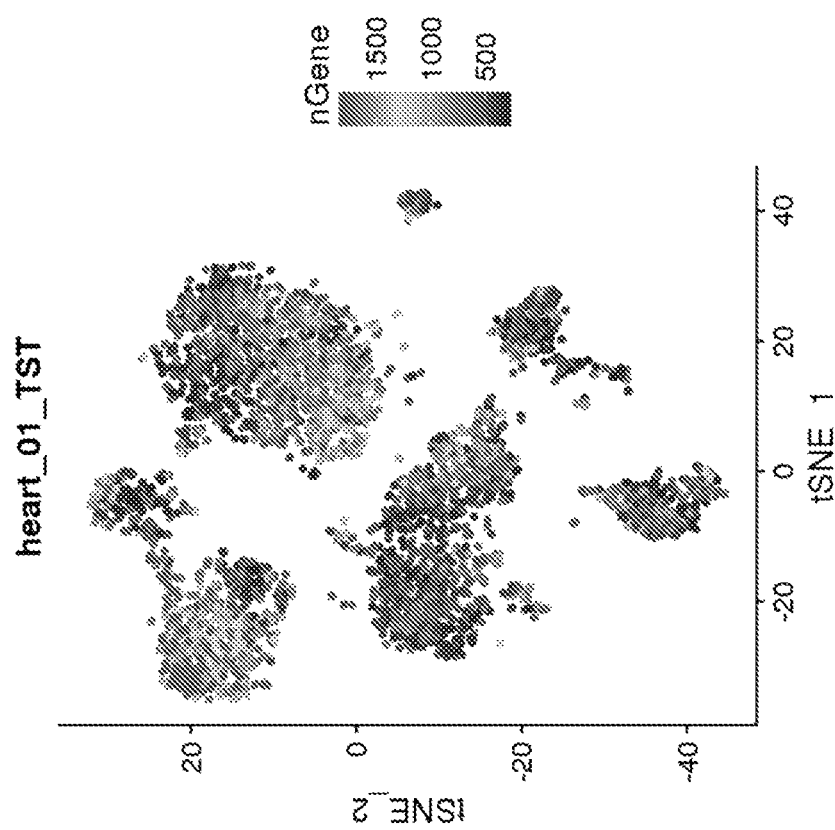
Figure 116A:
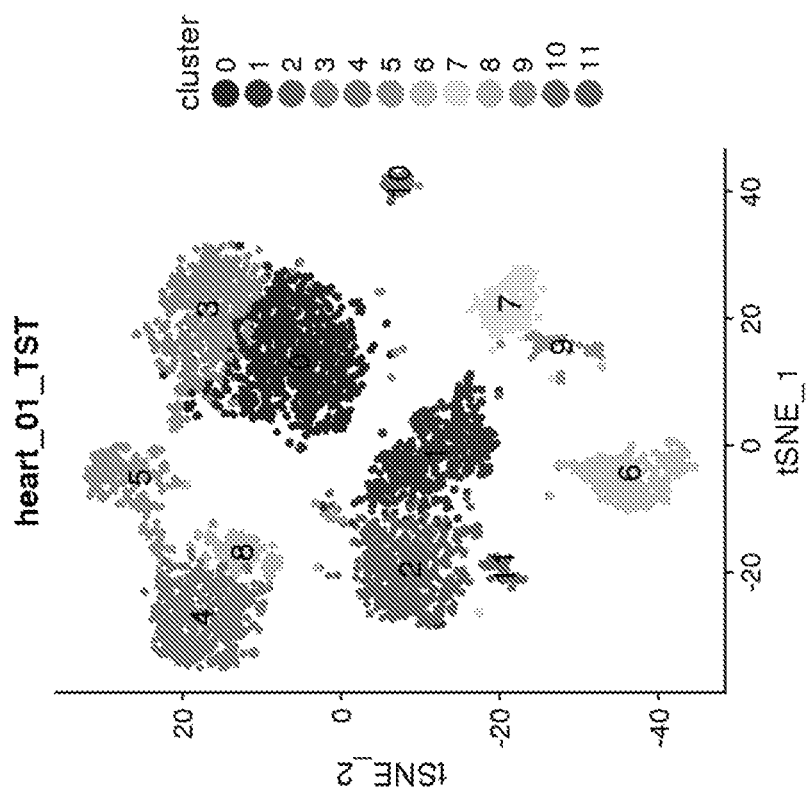

FIGS. 116A, 116B—show tSNE plots of single-nuclei RNA profiles for heart tissue samples and using the TST protocol. Shown are clusters identified by k-means clustering analysis (116A) and projection of gene expression (116B).

Figure 117B:
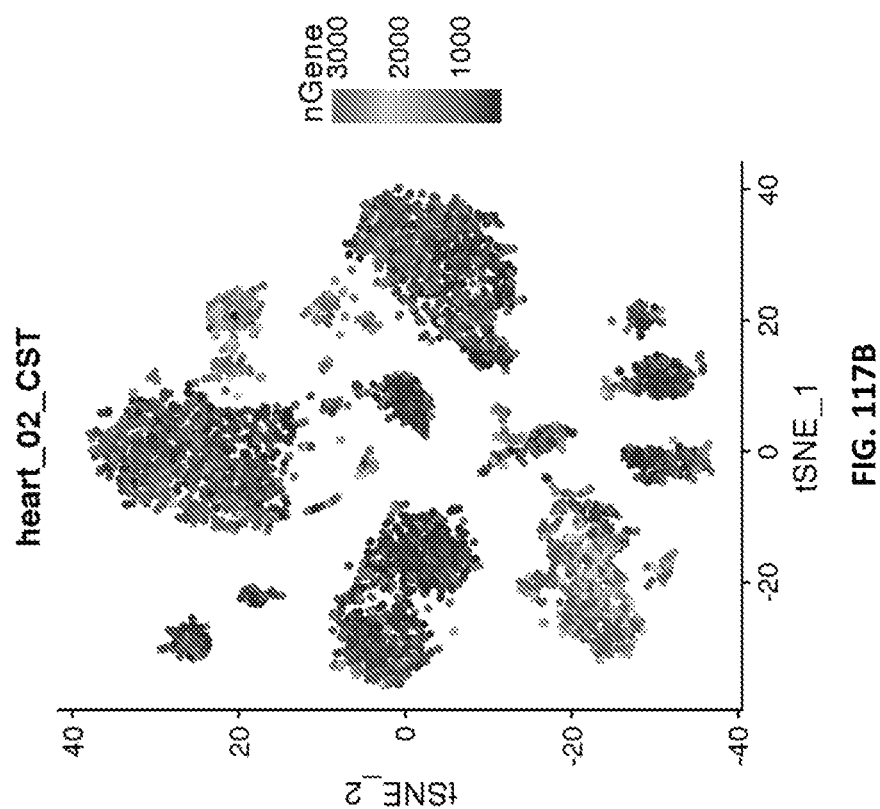
Figure 117A:
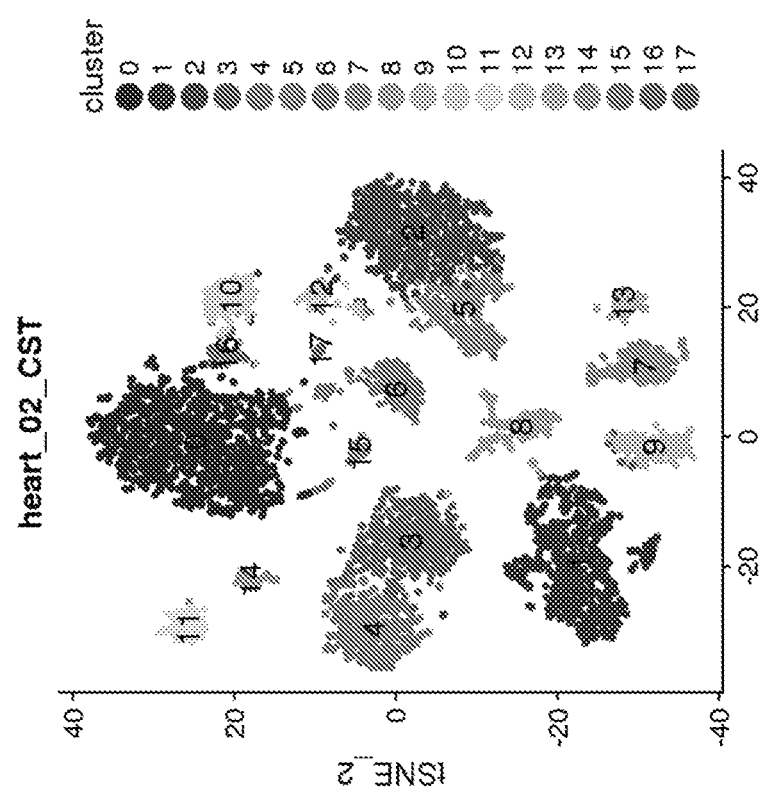

FIGS. 117A, 117B—show tSNE plots of single-nuclei RNA profiles for heart tissue samples and using the CST protocol. Shown are clusters identified by k-means clustering analysis (117A) and projection of gene expression (117B).

Figure 118B:
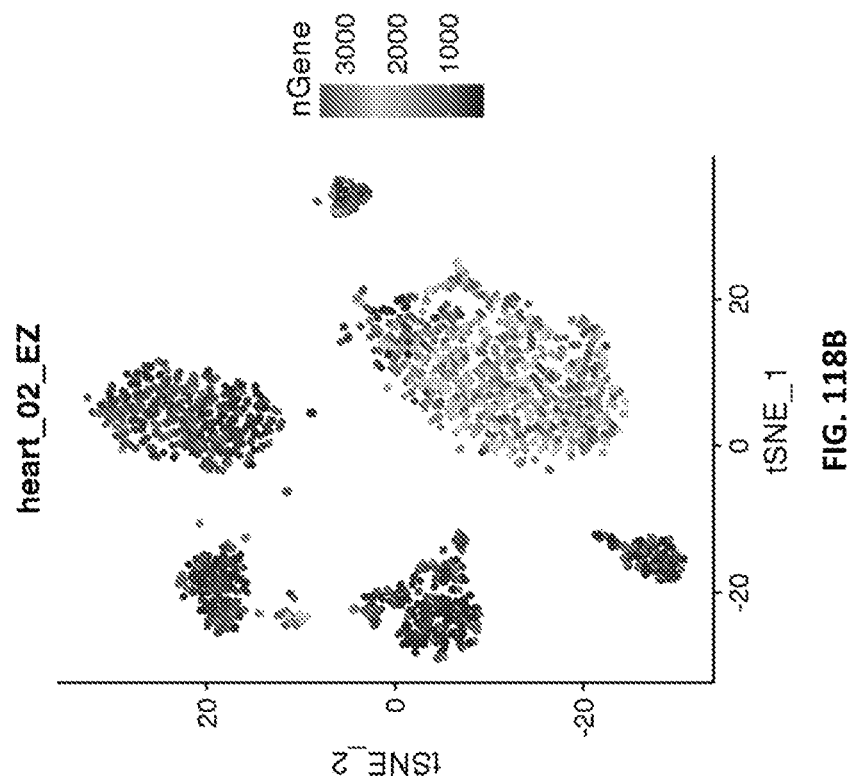
Figure 118A:
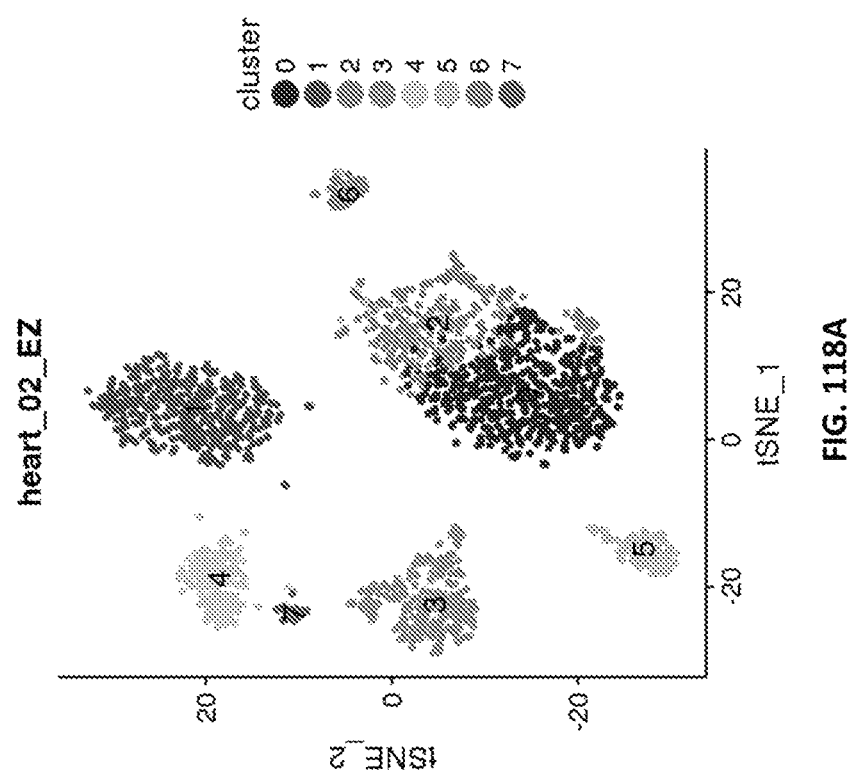

FIGS. 118A, 117B—show tSNE plots of single-nuclei RNA profiles for heart tissue samples and using the EZ protocol. Shown are clusters identified by k-means clustering analysis (118A) and projection of gene expression (118B).

Figure 119B:
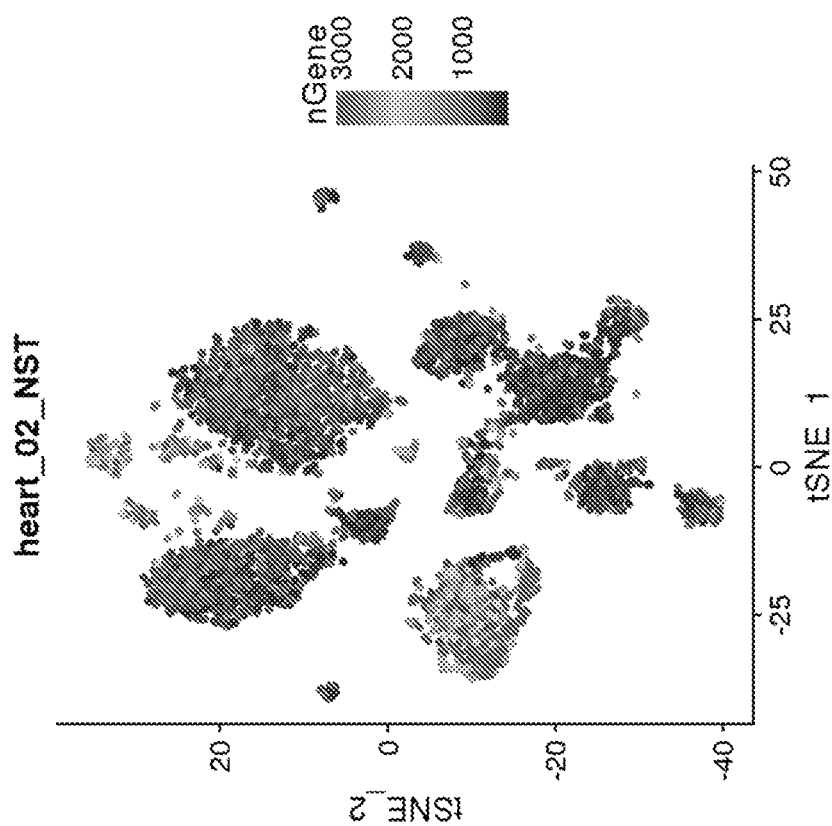
Figure 119A:
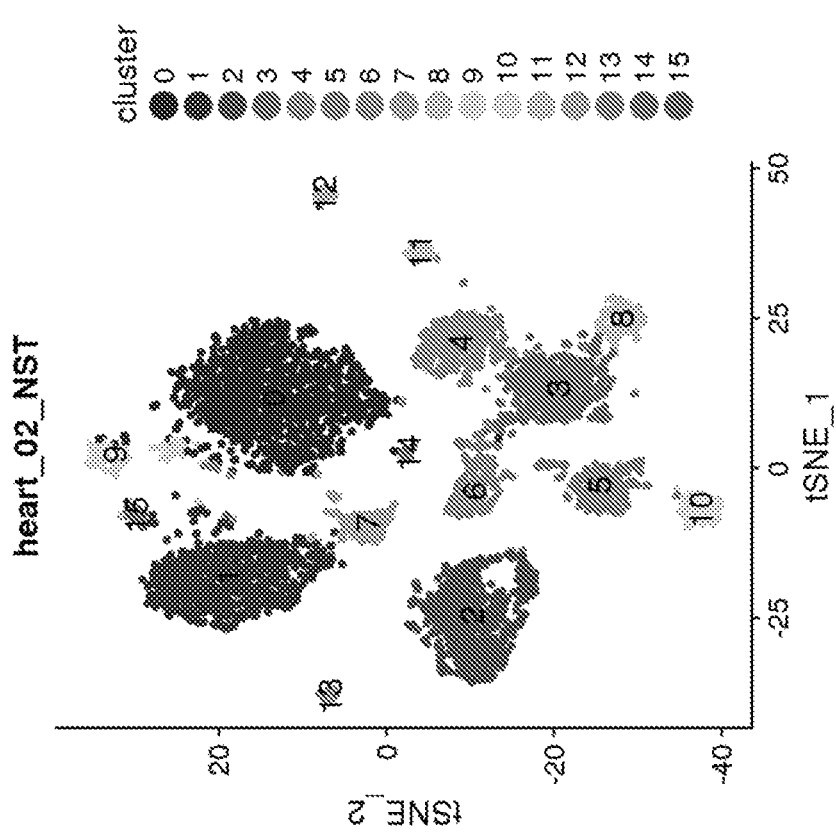

FIGS. 119A, 119B—show tSNE plots of single-nuclei RNA profiles for heart tissue samples and using the NST protocol. Shown are clusters identified by k-means clustering analysis (119A) and projection of gene expression (119B).

Figure 120B:
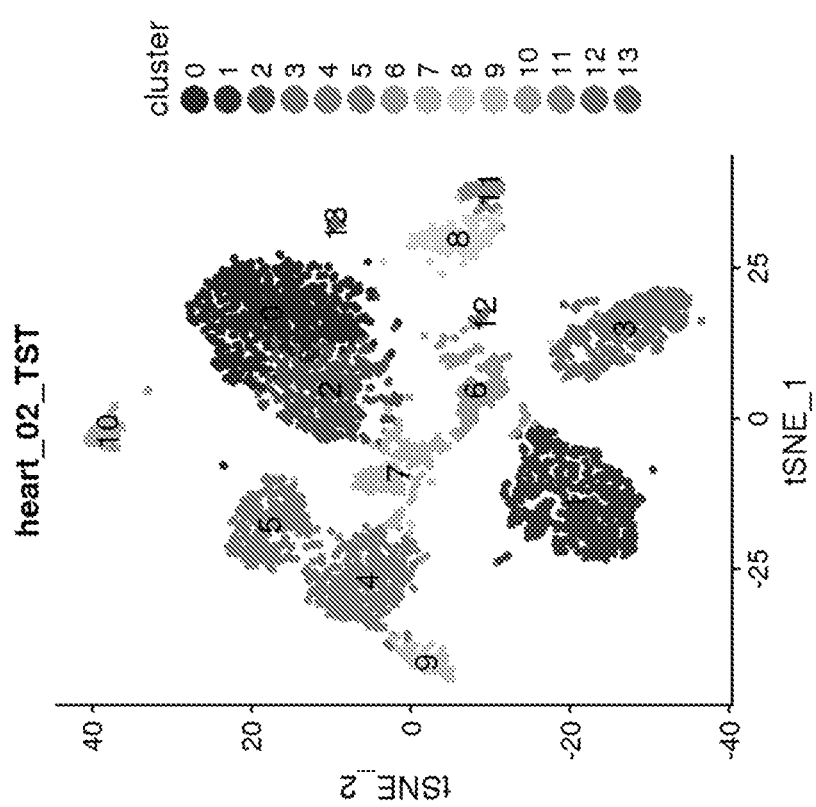
Figure 120A:
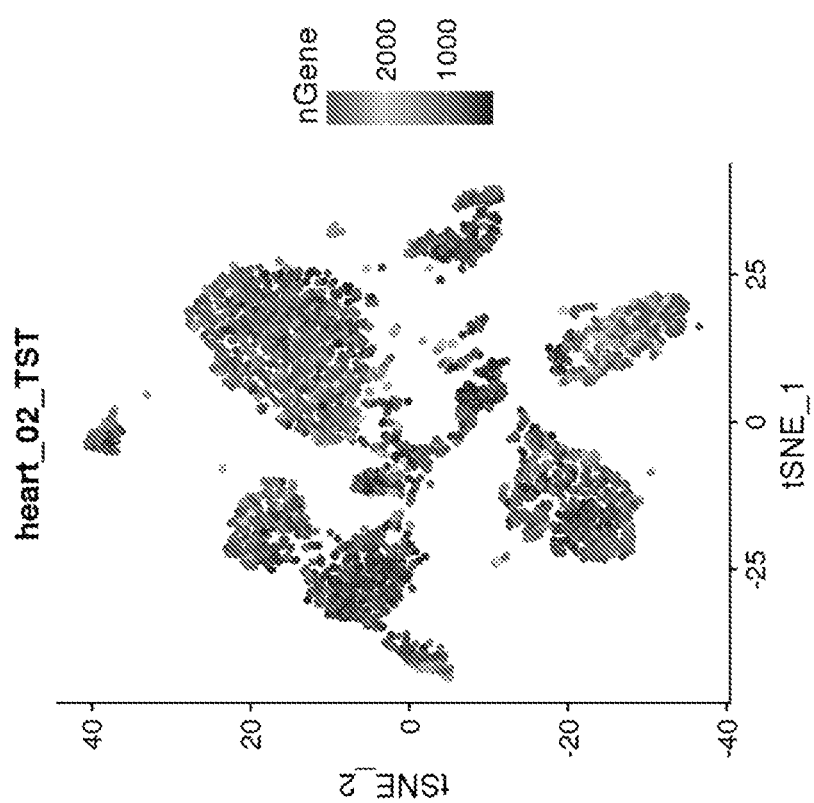

FIGS. 120A, 120B—show tSNE plots of single-nuclei RNA profiles for heart tissue samples and using the TST protocol. Shown are clusters identified by k-means clustering analysis (120A) and projection of gene expression (120B).

FIGS. 121A, 121B—show tSNE plots of single-nuclei RNA profiles for heart tissue samples and using the CST protocol. Shown are clusters identified by k-means clustering analysis (121A) and projection of gene expression (121B).

Figure 122B:
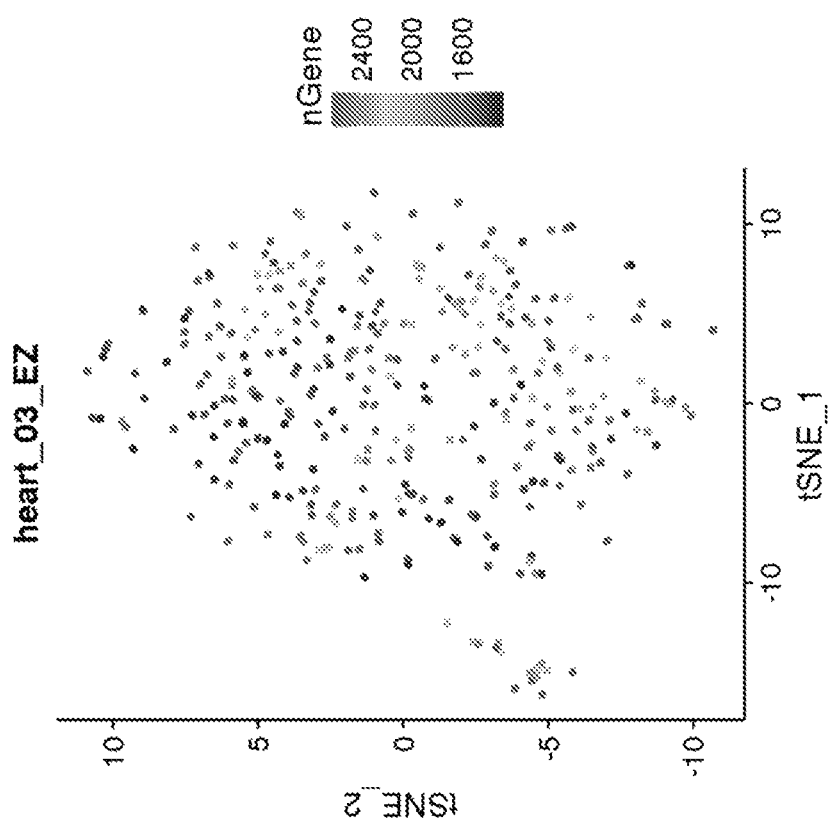
Figure 122A:
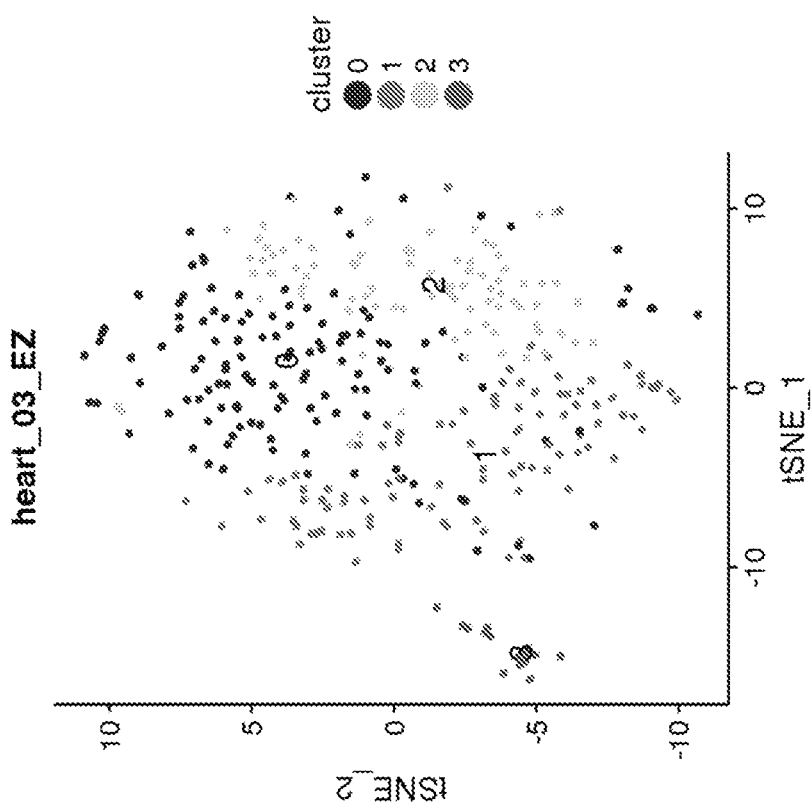

FIGS. 122A, 122B—show tSNE plots of single-nuclei RNA profiles for heart tissue samples and using the EZ protocol. Shown are clusters identified by k-means clustering analysis (122A) and projection of gene expression (122B).

Figure 123B:
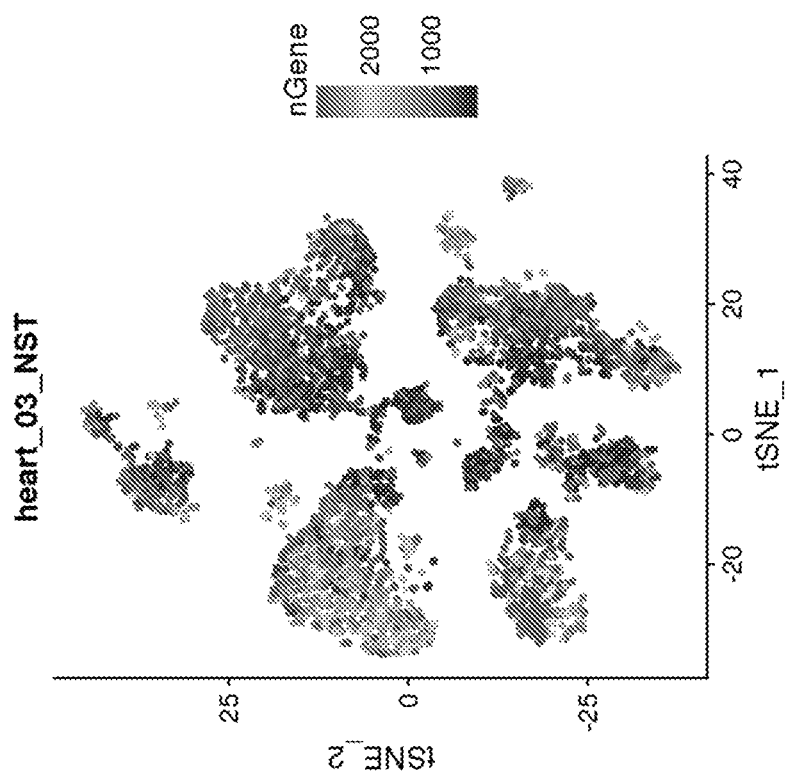
Figure 123A:
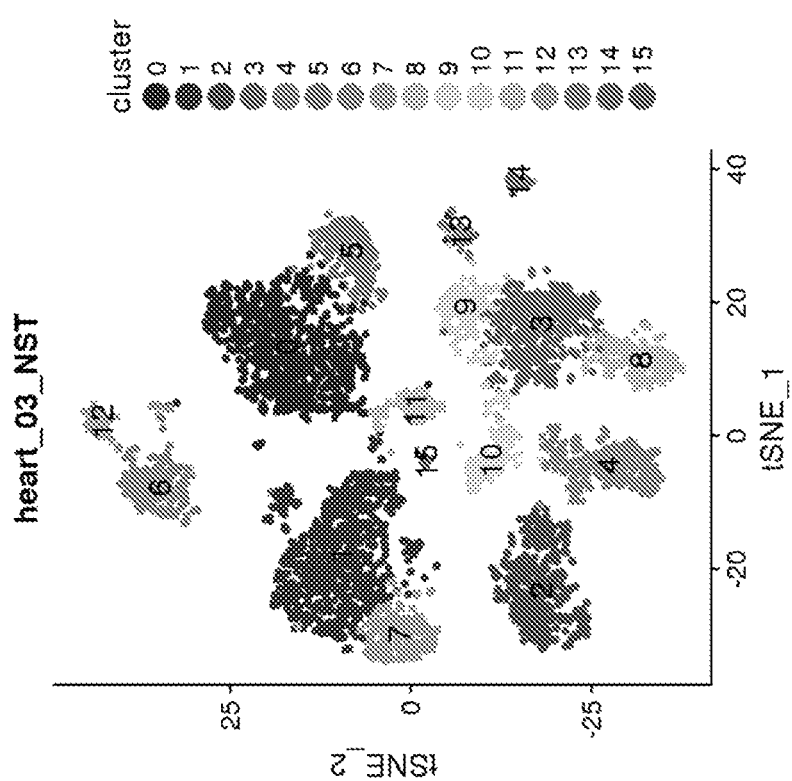

FIGS. 123A, 123B—show tSNE plots of single-nuclei RNA profiles for heart tissue samples and using the NST protocol. Shown are clusters identified by k-means clustering analysis (123A) and projection of gene expression (123B).

Figure 124B:
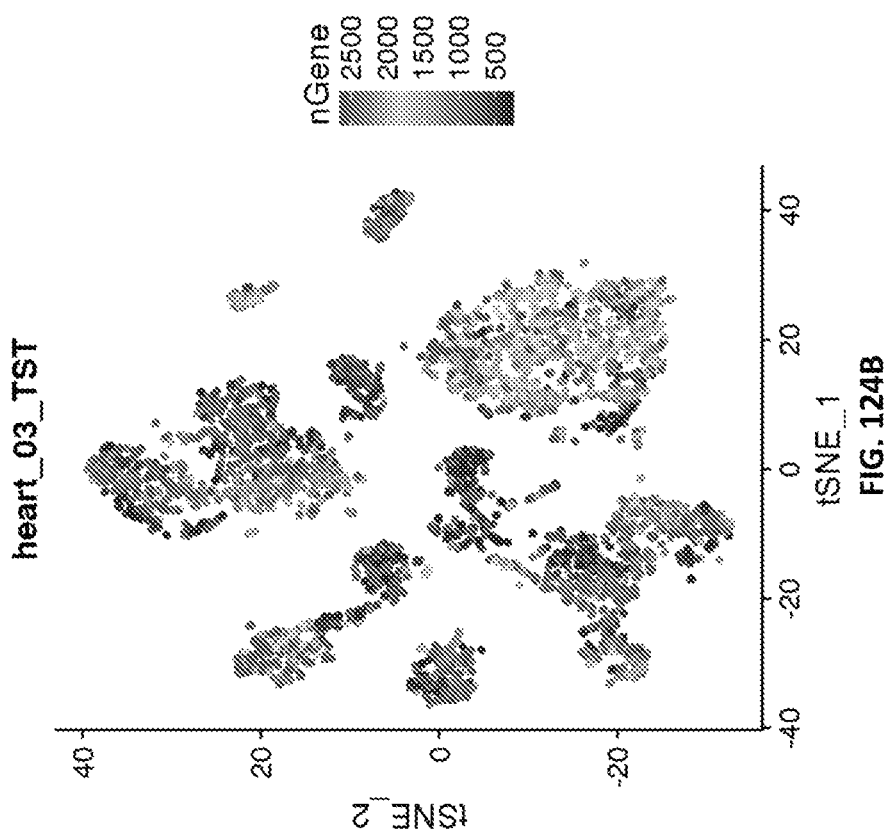
Figure 124A:
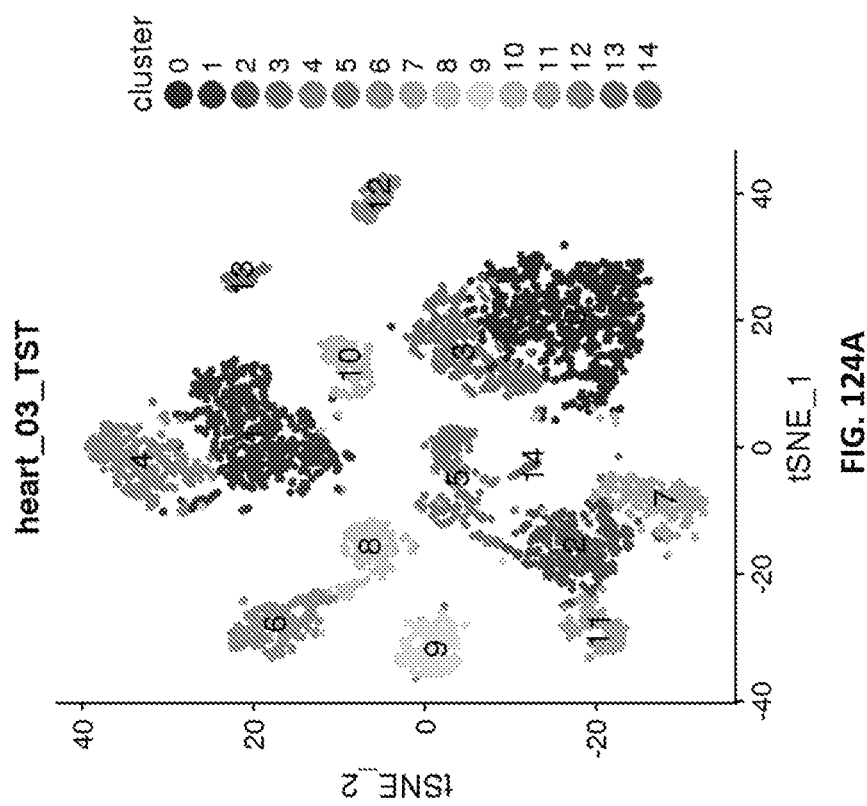

FIGS. 124A, 124B—show tSNE plots of single-nuclei RNA profiles for heart tissue samples and using the TST protocol. Shown are clusters identified by k-means clustering analysis (124A) and projection of gene expression (124B).

FIGS. 125A, 125B—show tSNE plots of single-nuclei RNA profiles for lung tissue samples and using the CST protocol. Shown are clusters identified by k-means clustering analysis (125A) and projection of gene expression (125B).

Figure 126B:
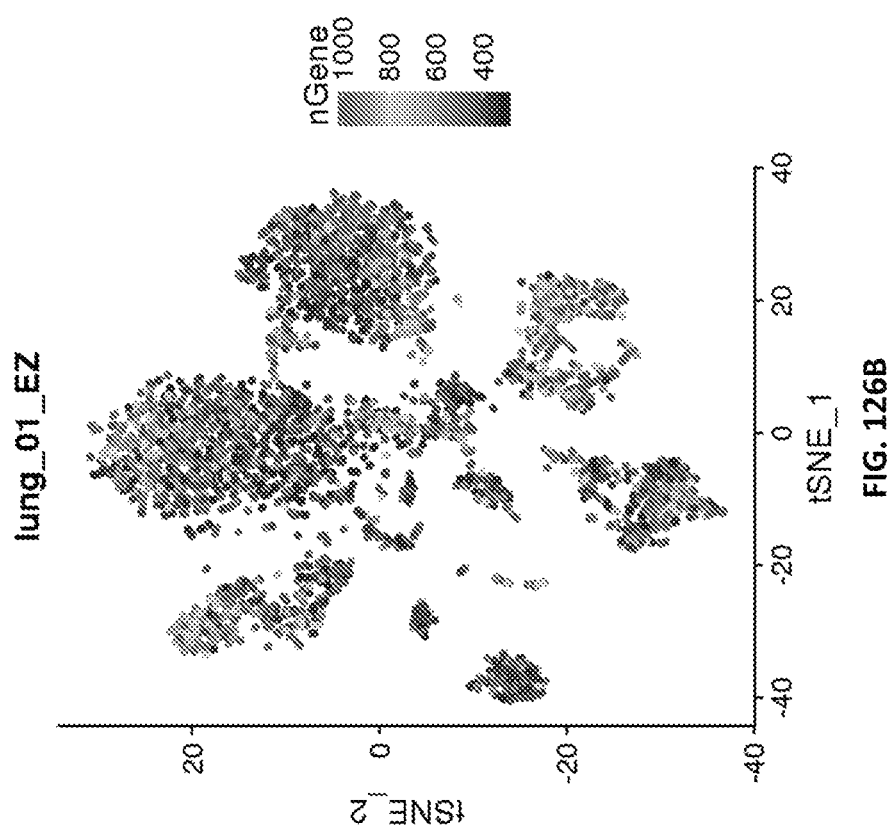
Figure 126A:
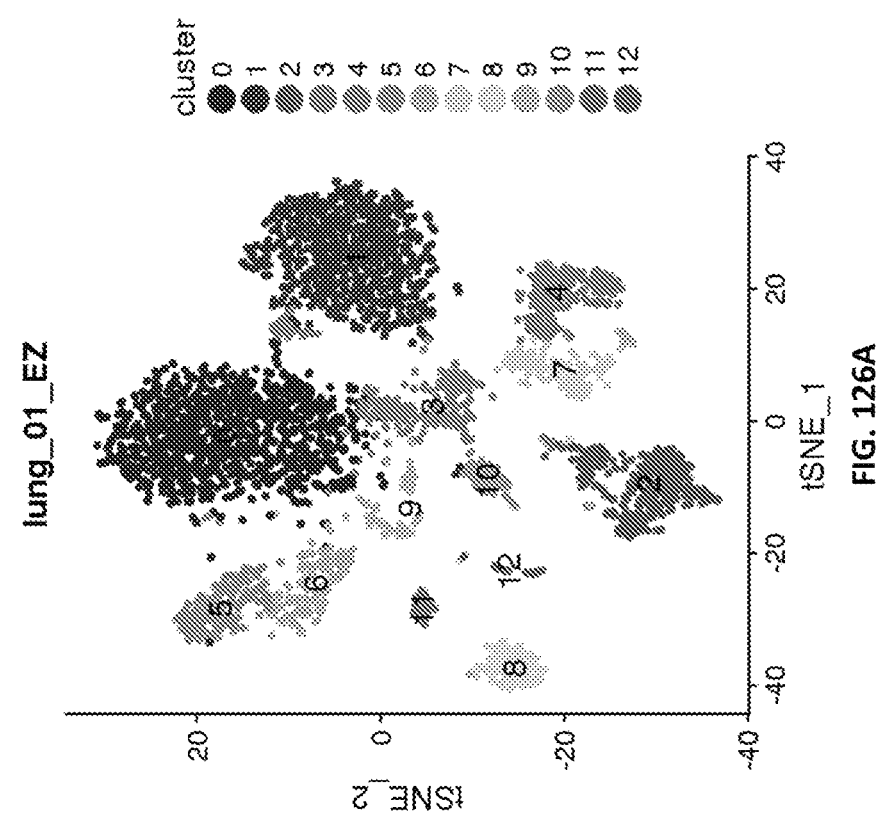

FIGS. 126A, 126B—show tSNE plots of single-nuclei RNA profiles for lung tissue samples and using the EZ protocol. Shown are clusters identified by k-means clustering analysis (126A) and projection of gene expression (126B).

Figures 127A, 127B:
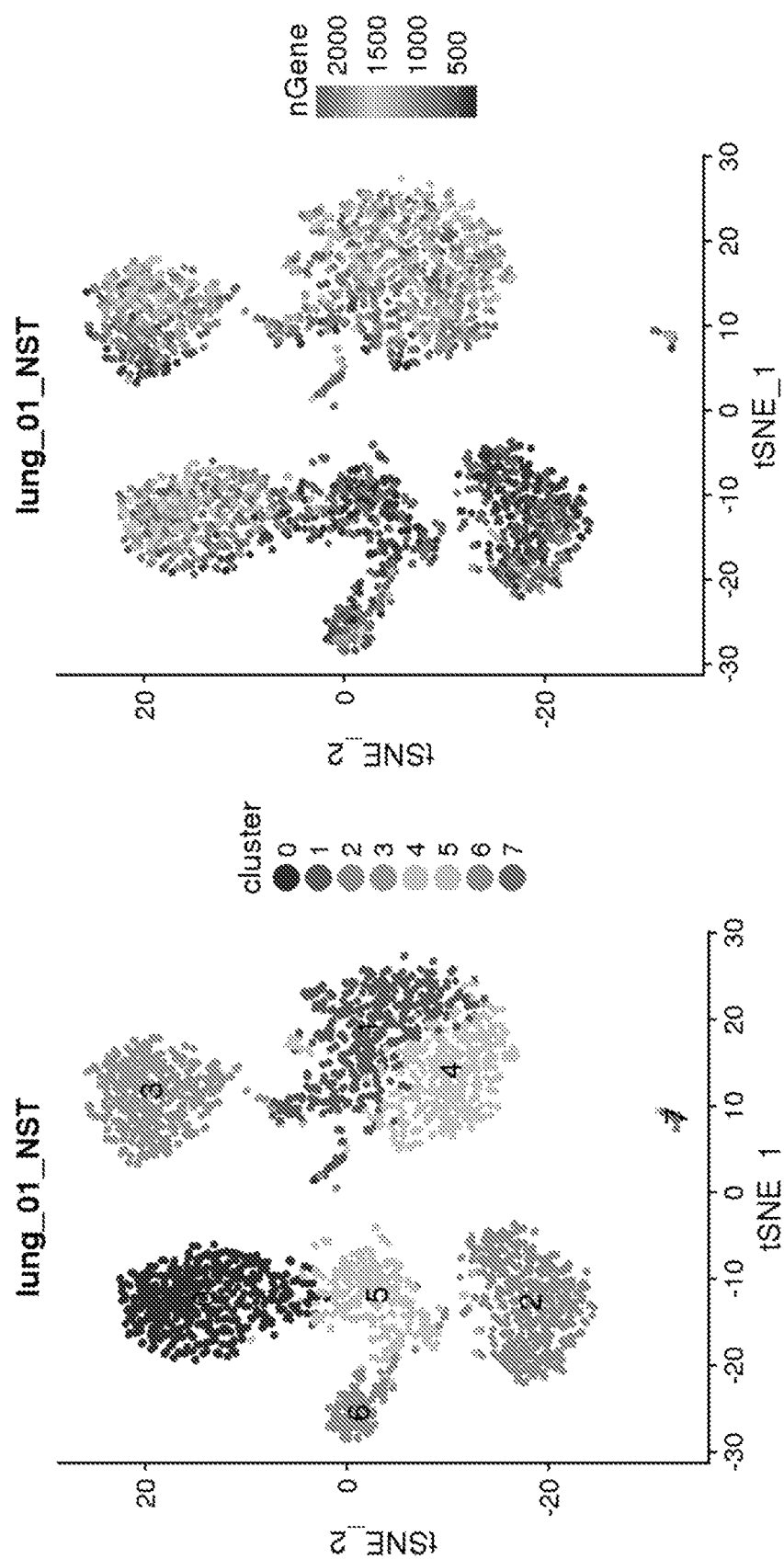

FIGS. 127A, 127B—show tSNE plots of single-nuclei RNA profiles for lung tissue samples and using the NST protocol. Shown are clusters identified by k-means clustering analysis (127A) and projection of gene expression (127B).

Figure 128B:
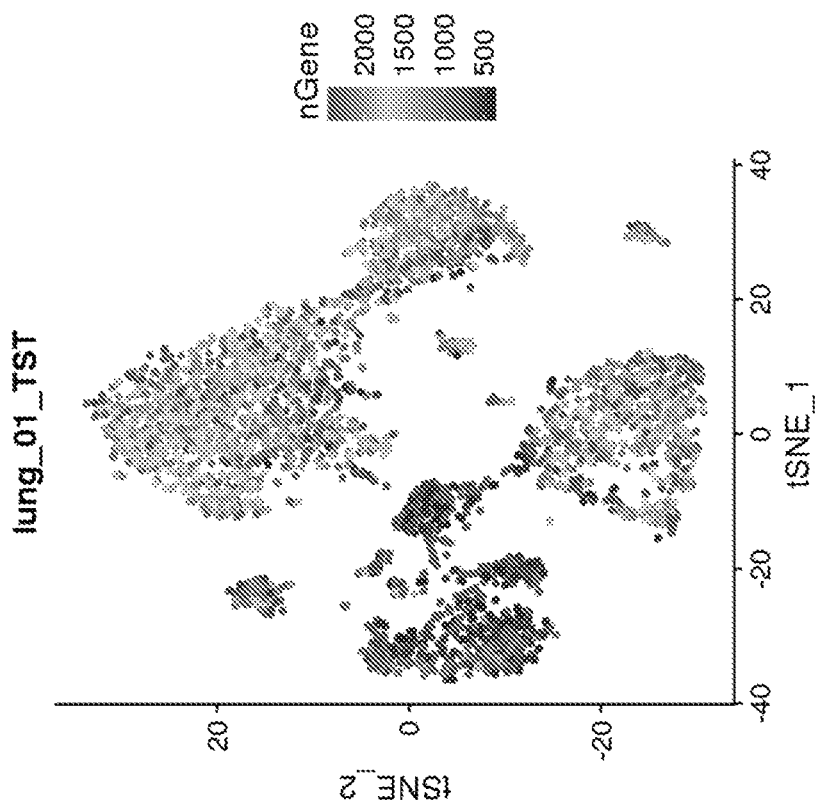
Figure 128A:
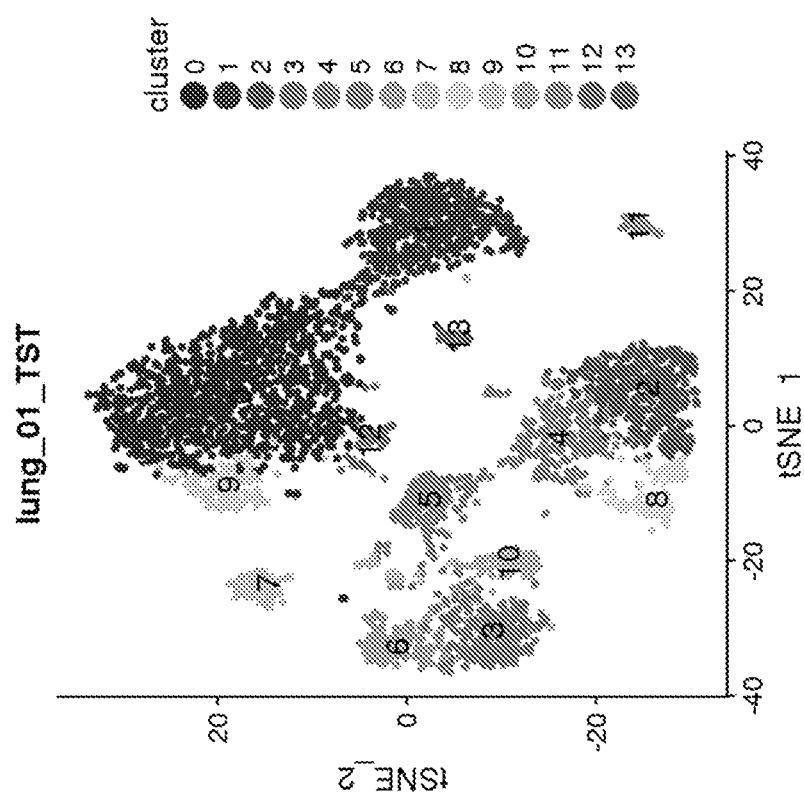

FIGS. 128A, 128B—show tSNE plots of single-nuclei RNA profiles for lung tissue samples and using the TST protocol. Shown are clusters identified by k-means clustering analysis (128A) and projection of gene expression (128B).

Figure 129B:
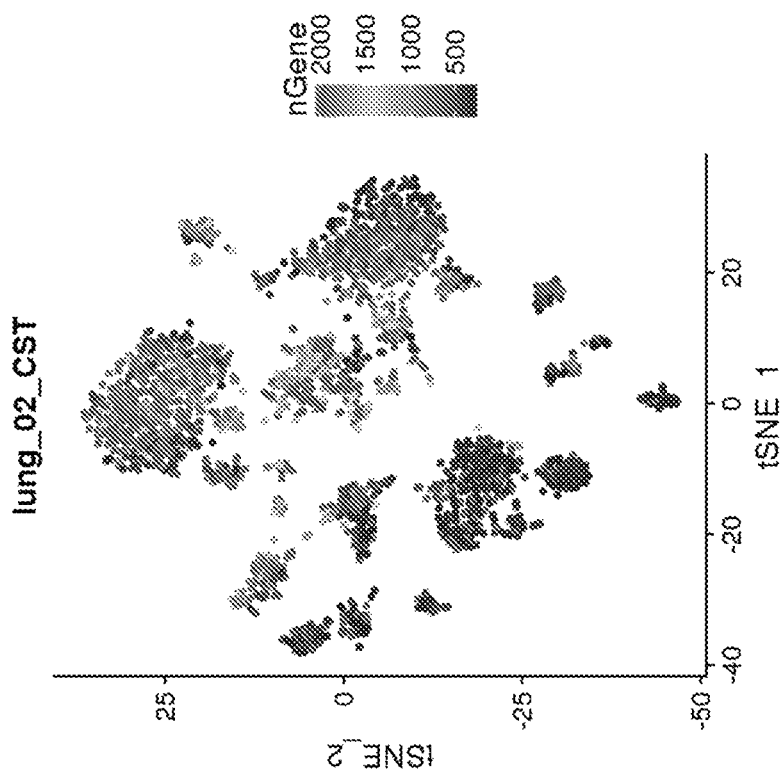
Figure 129A:
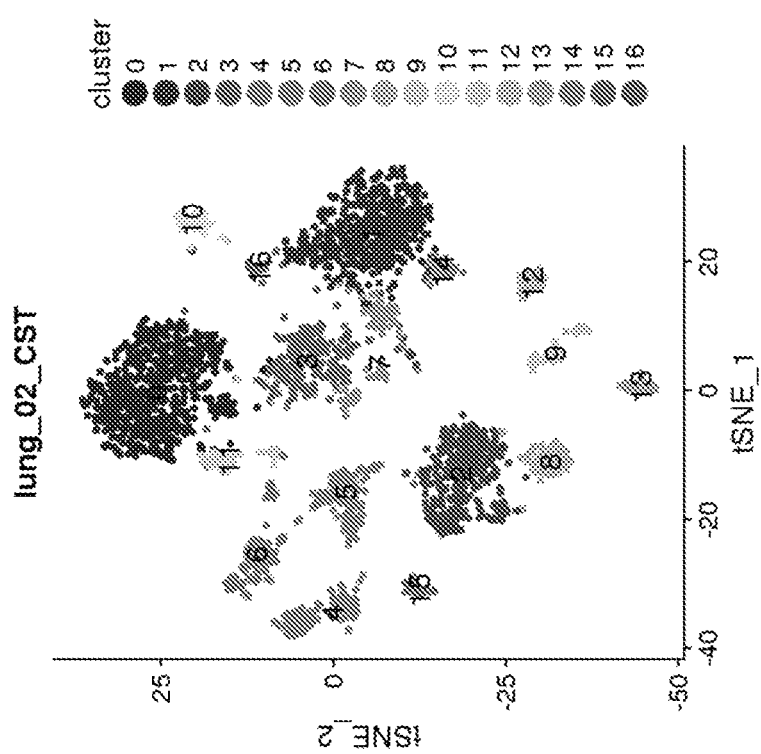

FIGS. 129A, 129B—show tSNE plots of single-nuclei RNA profiles for lung tissue samples and using the CST protocol. Shown are clusters identified by k-means clustering analysis (129A) and projection of gene expression (129B).

Figure 130B:
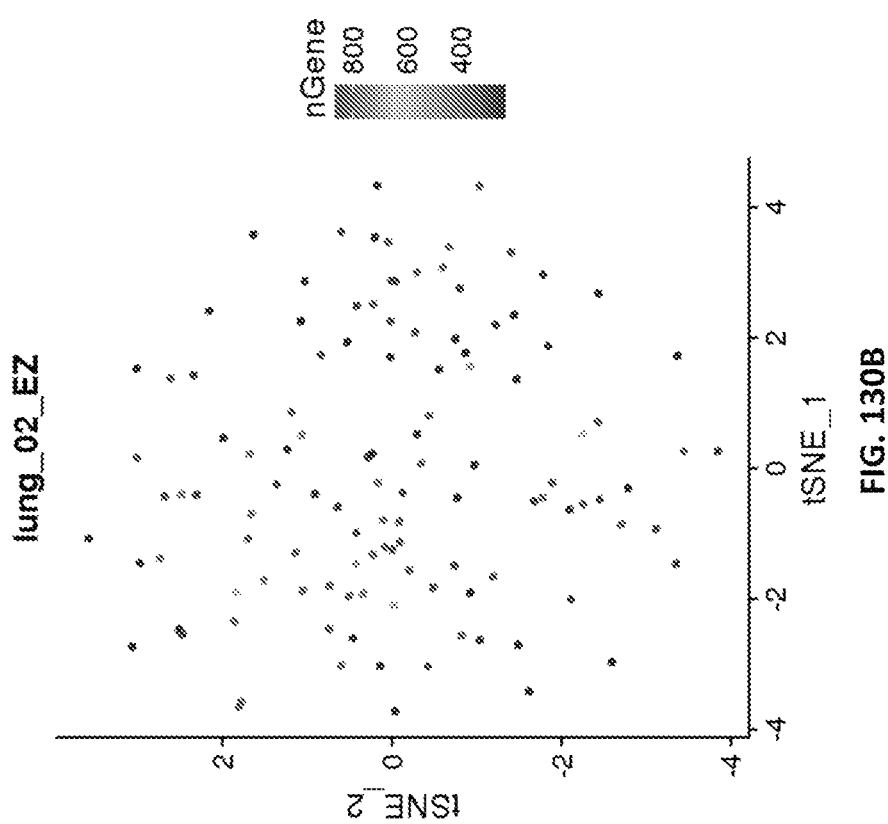
Figure 130A:
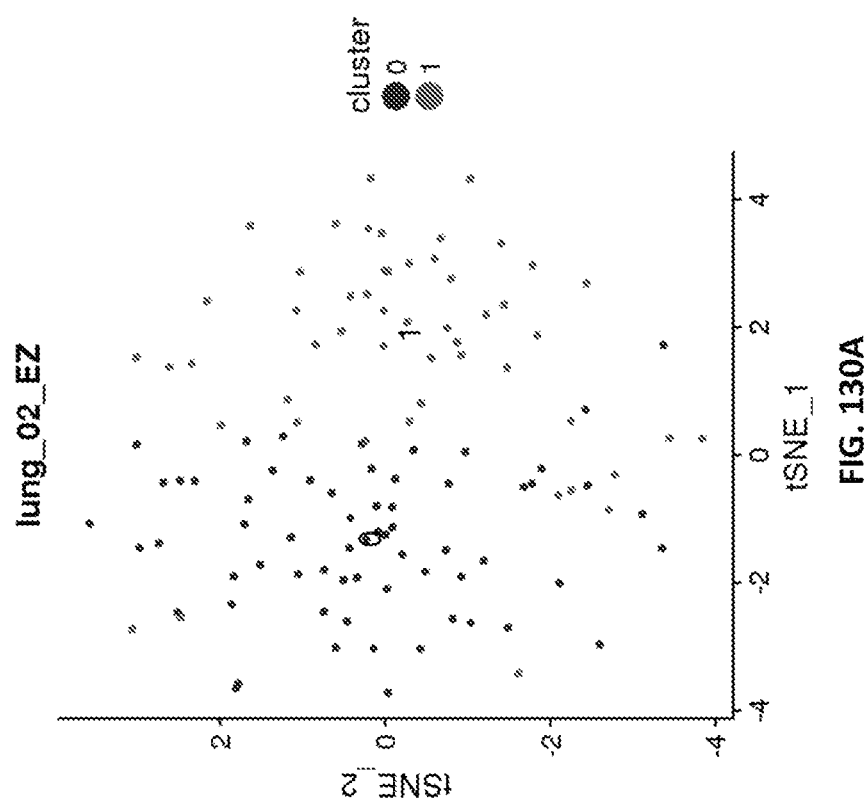

FIGS. 130A, 130B—show tSNE plots of single-nuclei RNA profiles for lung tissue samples and using the EZ protocol. Shown are clusters identified by k-means clustering analysis (130A) and projection of gene expression (130B).

Figure 131B:
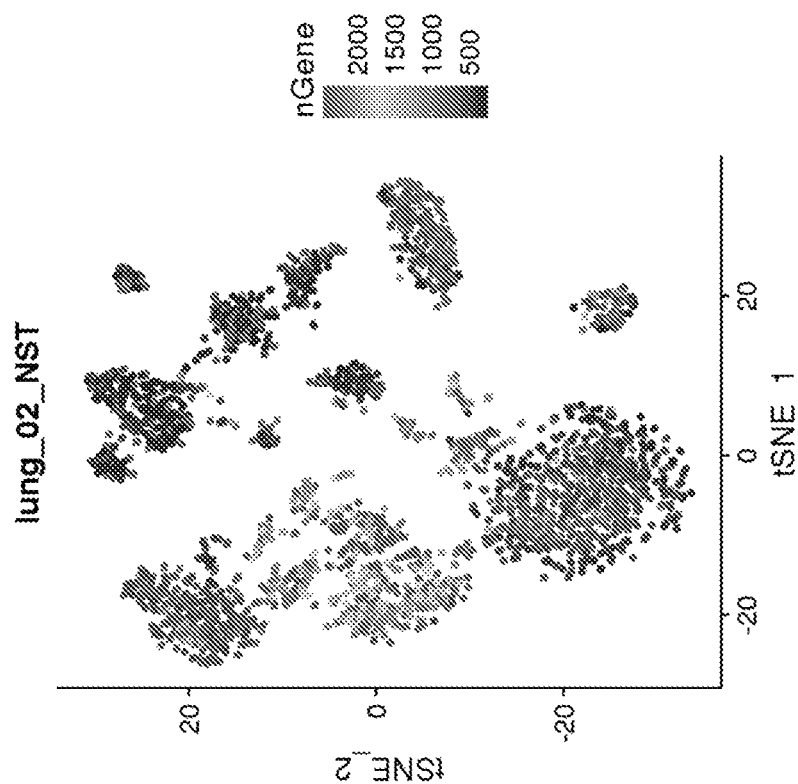
Figure 131A:
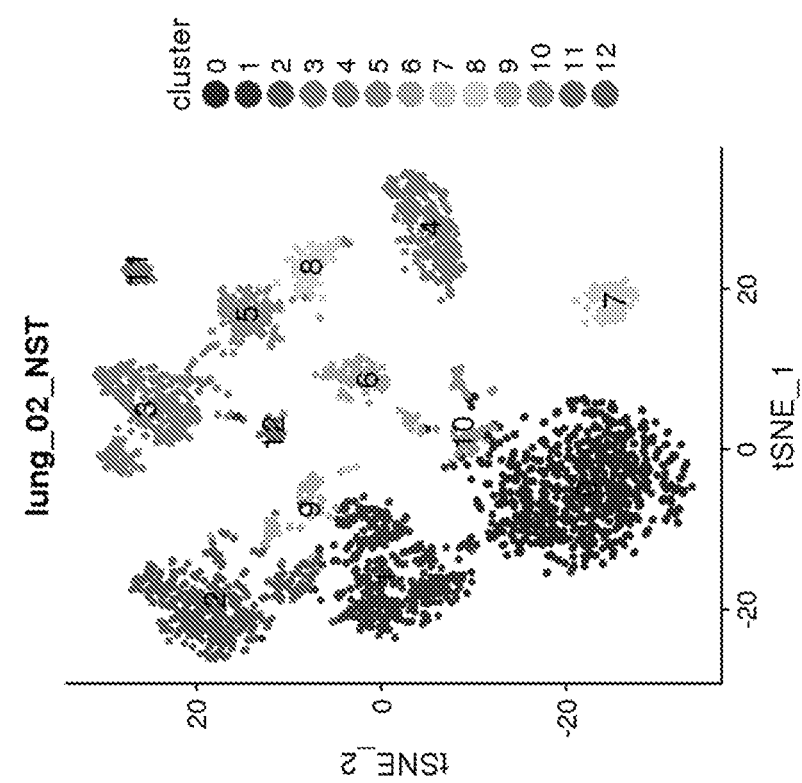

FIGS. 131A, 131B—show tSNE plots of single-nuclei RNA profiles for lung tissue samples and using the NST protocol. Shown are clusters identified by k-means clustering analysis (131A) and projection of gene expression (131B).

FIGS. 132A, 132B—show tSNE plots of single-nuclei RNA profiles for lung tissue samples and using the TST protocol. Shown are clusters identified by k-means clustering analysis (132A) and projection of gene expression (132B).

Figure 133B:
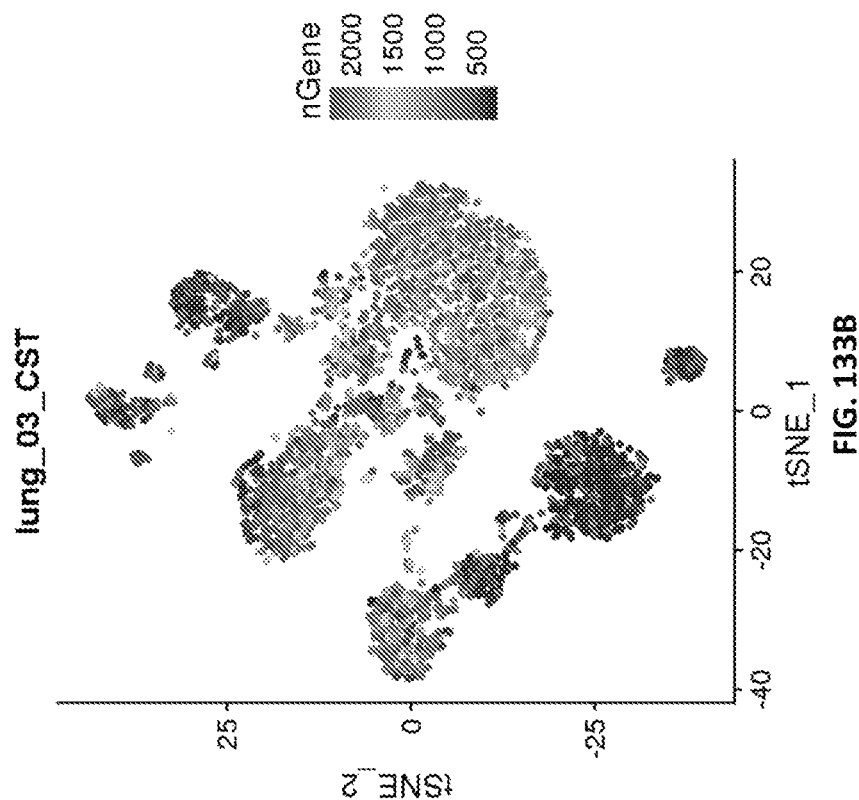
Figure 133A:
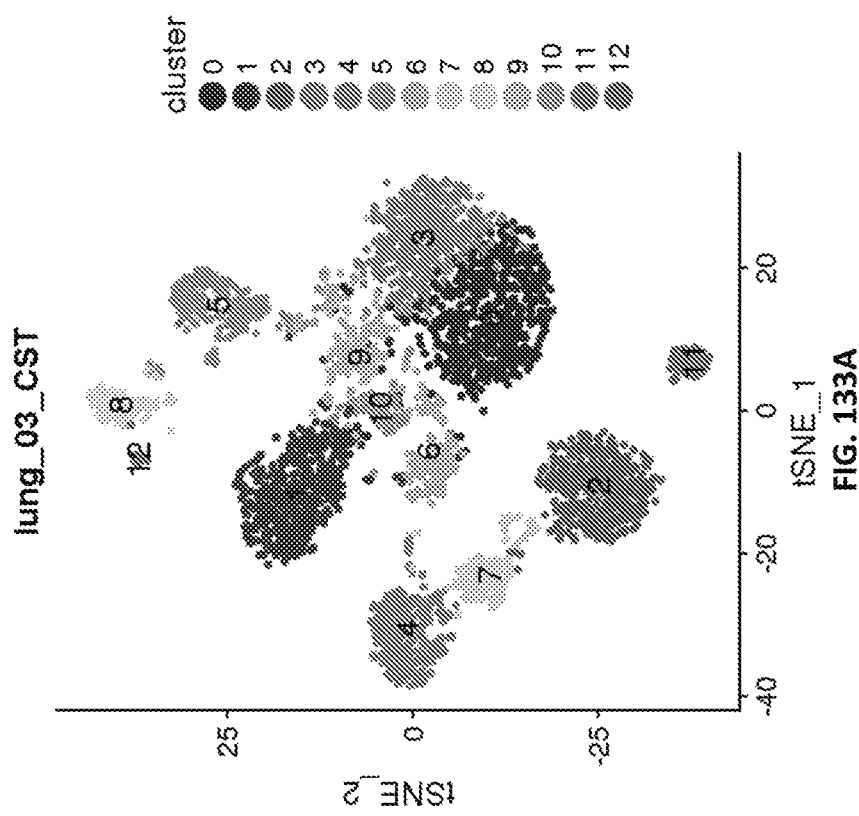

FIGS. 133A, 133B—show tSNE plots of single-nuclei RNA profiles for lung tissue samples and using the CST protocol. Shown are clusters identified by k-means clustering analysis (133A) and projection of gene expression (133B).

Figure 134B:
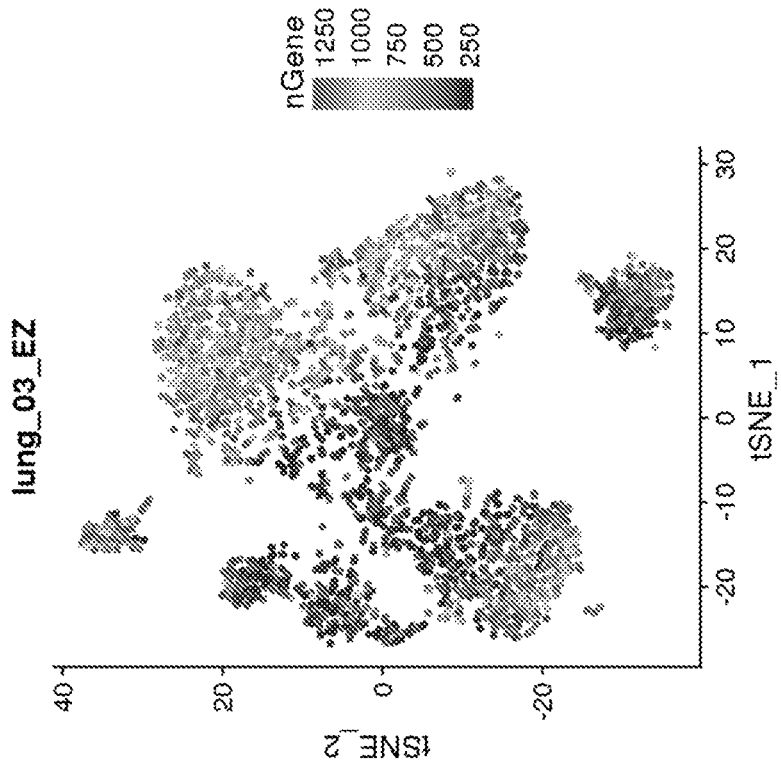
Figure 134A:
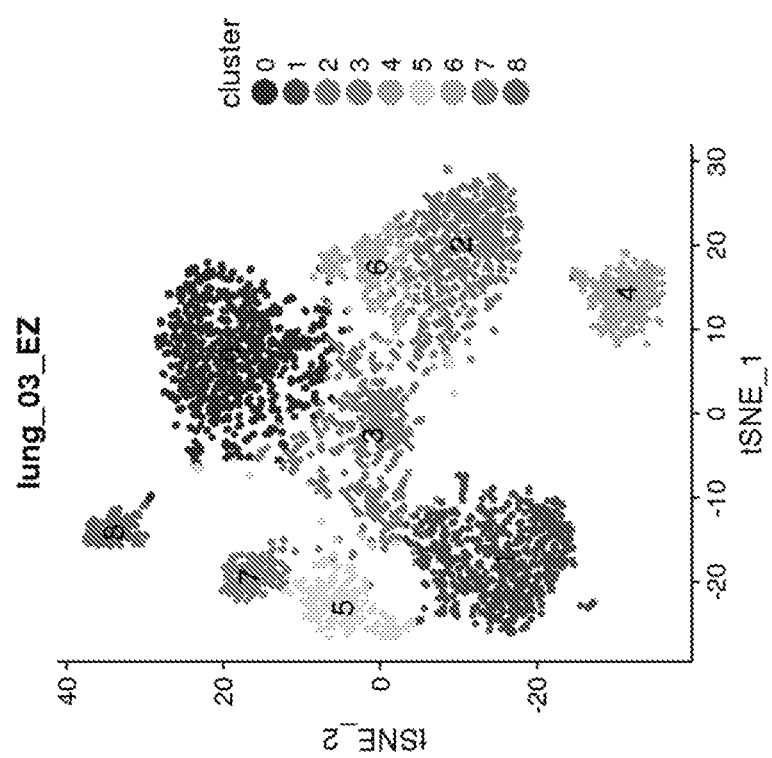

FIGS. 134A, 134B—show tSNE plots of single-nuclei RNA profiles for lung tissue samples and using the EZ protocol. Shown are clusters identified by k-means clustering analysis (134A) and projection of gene expression (134B).

Figure 135B:
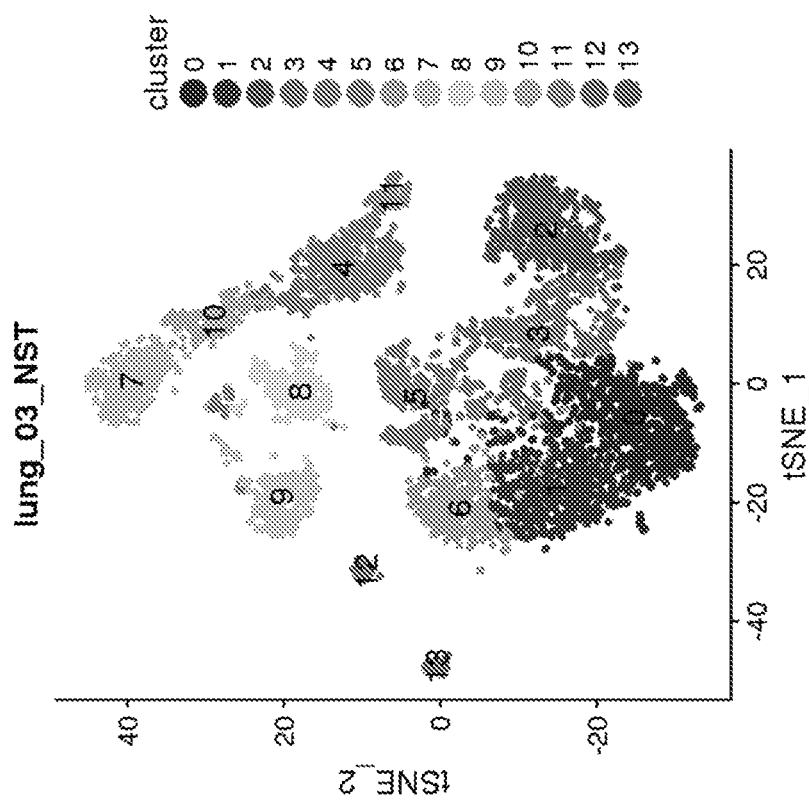
Figure 135A:
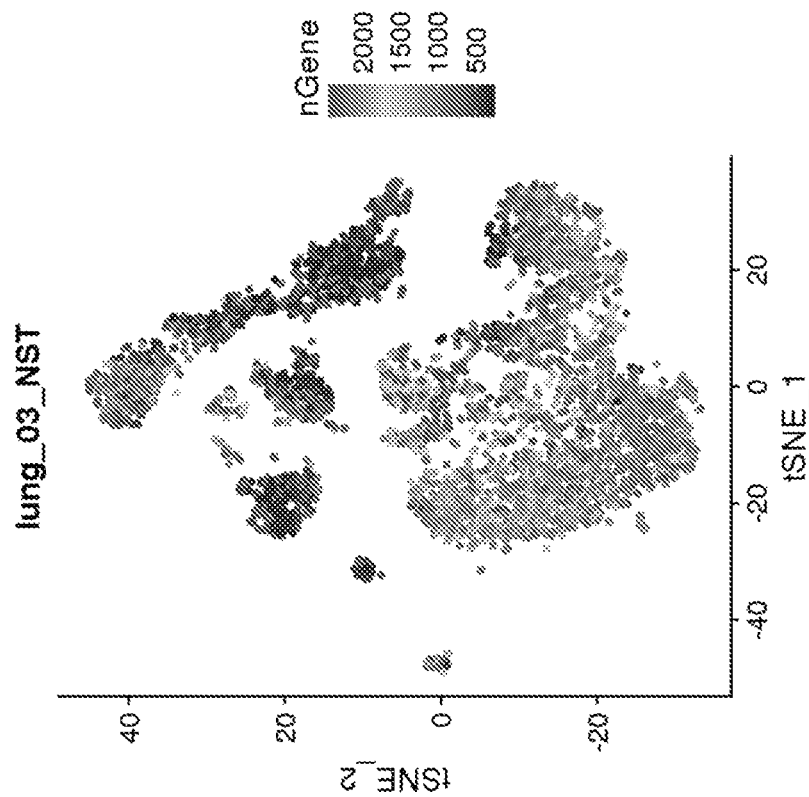

FIGS. 135A, 135B—show tSNE plots of single-nuclei RNA profiles for lung tissue samples and using the NST protocol. Shown are clusters identified by k-means clustering analysis (135A) and projection of gene expression (135B).

Figure 136B:
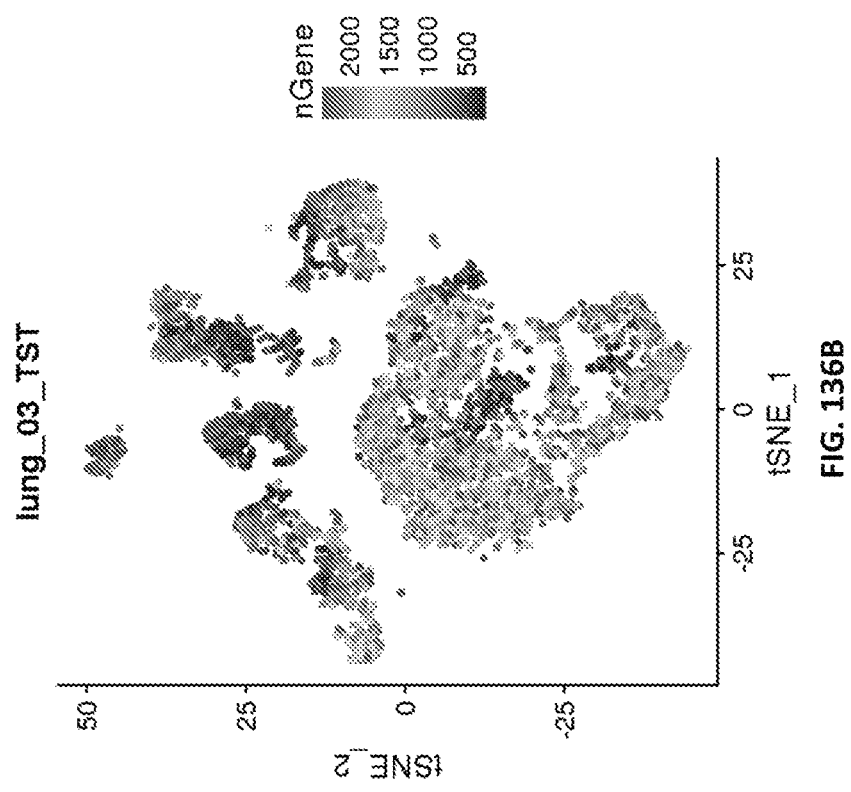
Figure 136A:
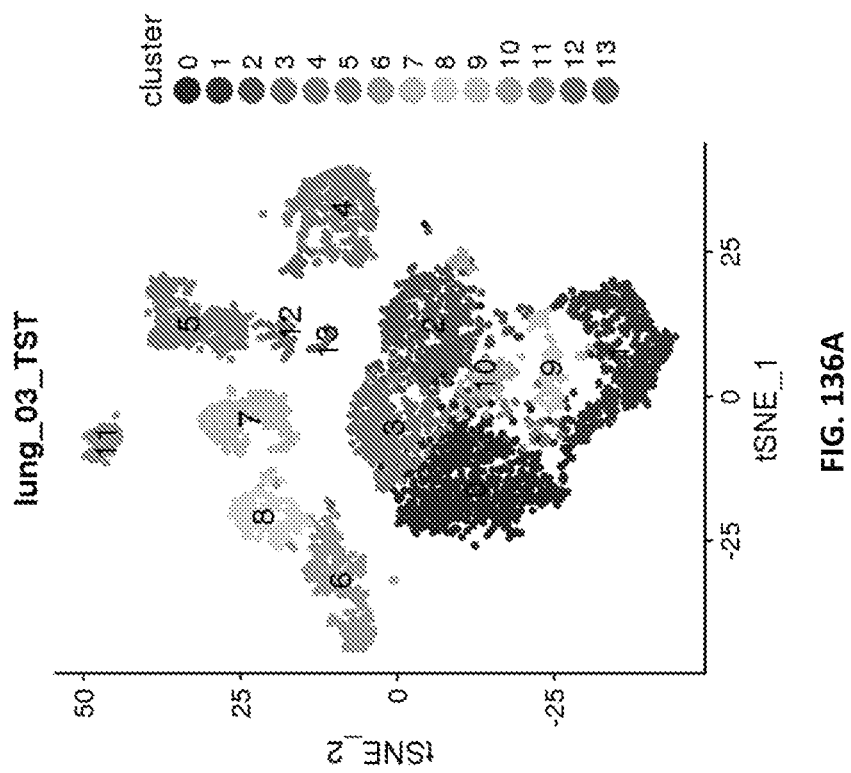

FIGS. 136A, 136B—show tSNE plots of single-nuclei RNA profiles for lung tissue samples and using the TST protocol. Shown are clusters identified by k-means clustering analysis (136A) and projection of gene expression (136B).

Figure 137B:
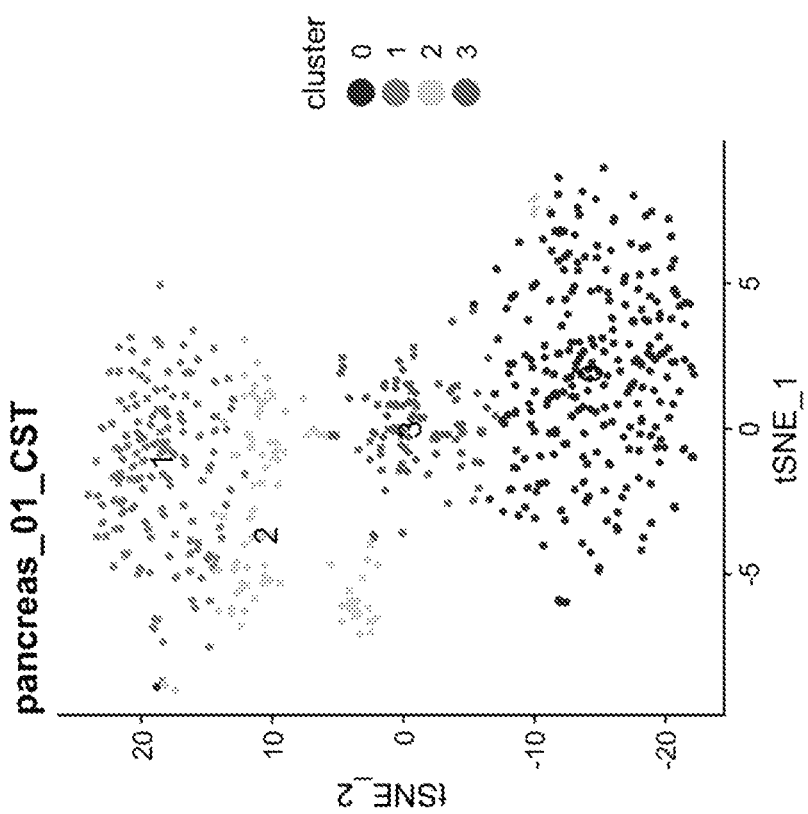
Figure 137A:
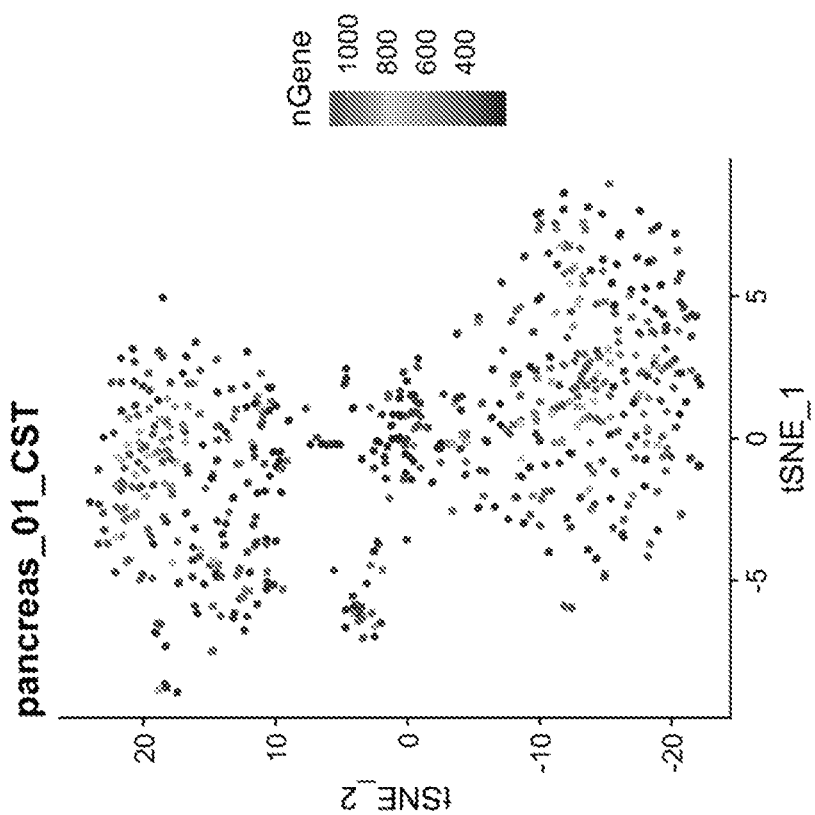

FIGS. 137A, 137B—show tSNE plots of single-nuclei RNA profiles for pancreatic tissue samples and using the CST protocol. Shown are clusters identified by k-means clustering analysis (137A) and projection of gene expression (137B).

Figure 138B:
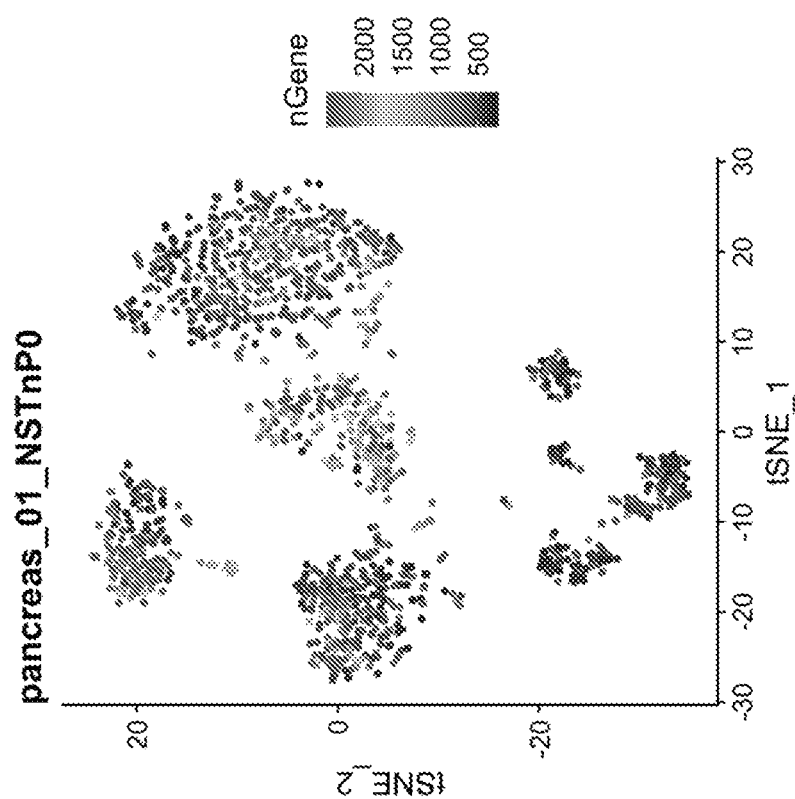
Figure 138A:
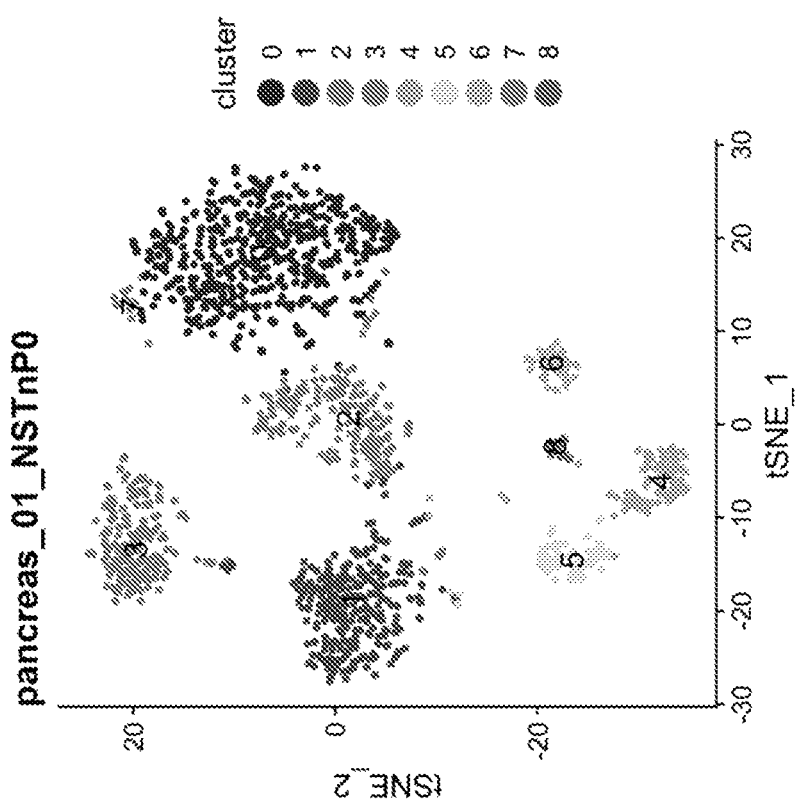

FIGS. 138A, 138B—show tSNE plots of single-nuclei RNA profiles for pancreatic tissue samples and using the NST protocol. Shown are clusters identified by k-means clustering analysis (138A) and projection of gene expression (138B).

Figure 139B:
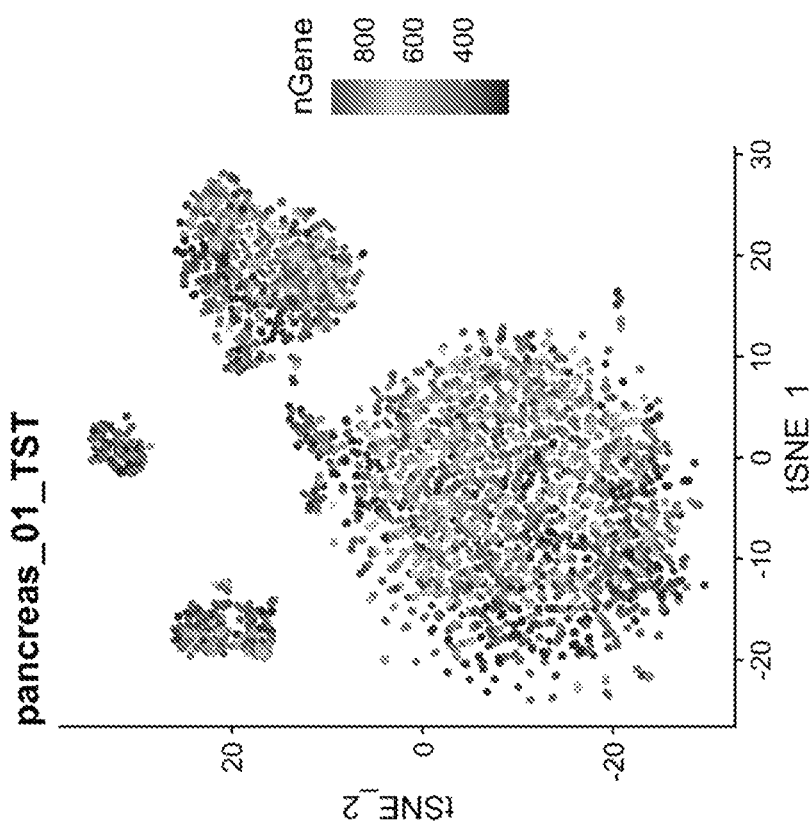
Figure 139A:
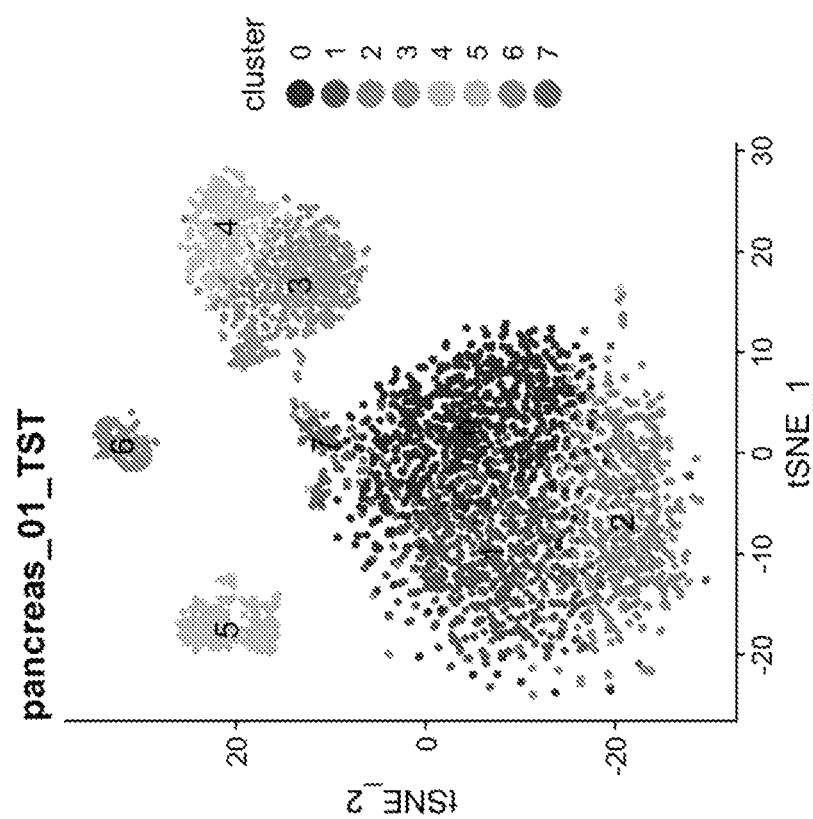

FIGS. 139A, 139B—show tSNE plots of single-nuclei RNA profiles for pancreatic tissue samples and using the TST protocol. Shown are clusters identified by k-means clustering analysis (139A) and projection of gene expression (139B).

FIGS. 140A, 140B—show tSNE plots of single-nuclei RNA profiles for prostate tissue samples and using the CST protocol. Shown are clusters identified by k-means clustering analysis (140A) and projection of gene expression (140B).

Figure 141B:
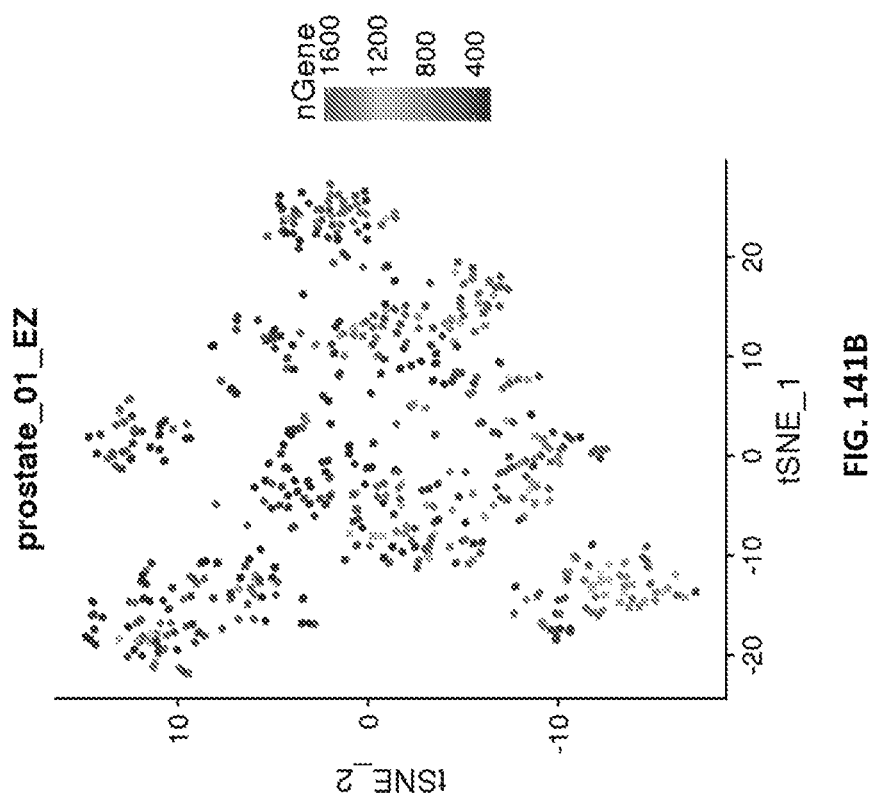
Figure 141A:
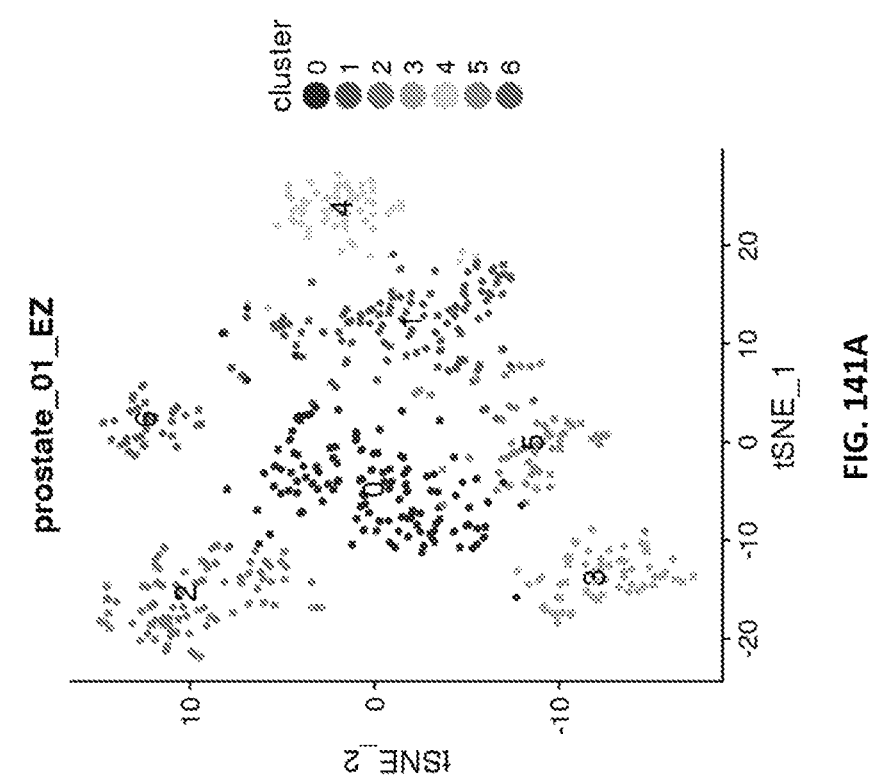

FIGS. 141A, 141B—show tSNE plots of single-nuclei RNA profiles for prostate tissue samples and using the EZ protocol. Shown are clusters identified by k-means clustering analysis (141A) and projection of gene expression (141B).

Figure 142B:
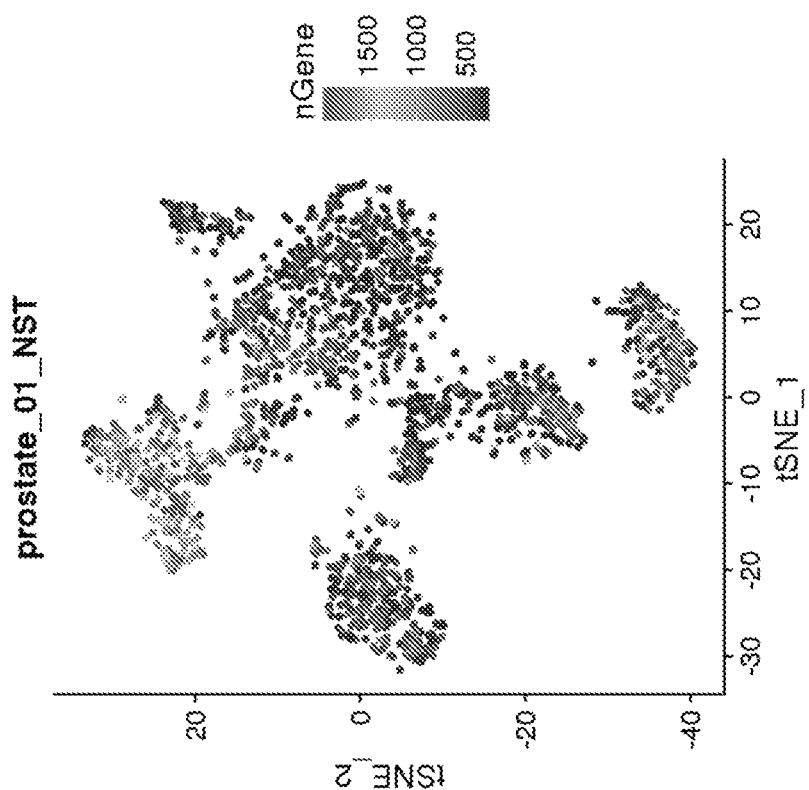
Figure 142A:
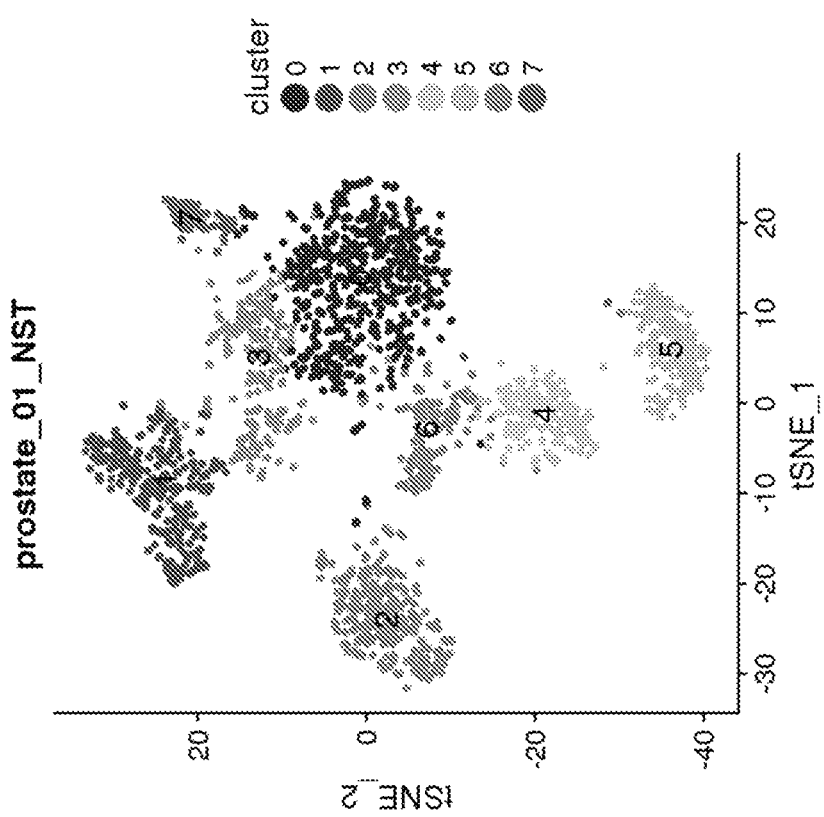

FIGS. 142A, 142B—show tSNE plots of single-nuclei RNA profiles for prostate tissue samples and using the NST protocol. Shown are clusters identified by k-means clustering analysis (142A) and projection of gene expression (142B).

Figure 143B:
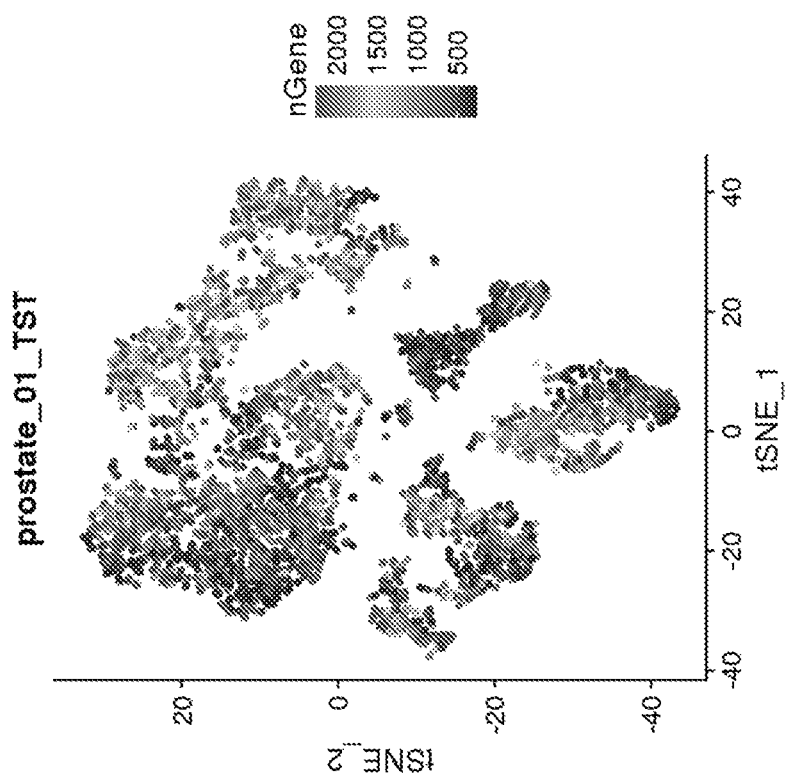
Figure 143A:
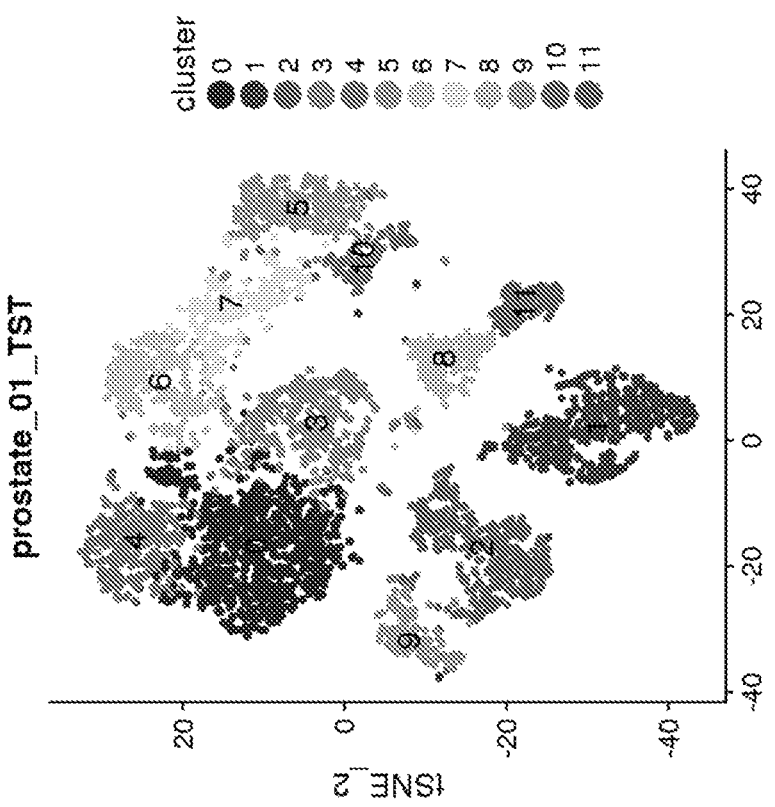

FIGS. 143A, 143B—show tSNE plots of single-nuclei RNA profiles for prostate tissue samples and using the TST protocol. Shown are clusters identified by k-means clustering analysis (143A) and projection of gene expression (143B).

Figure 144B:
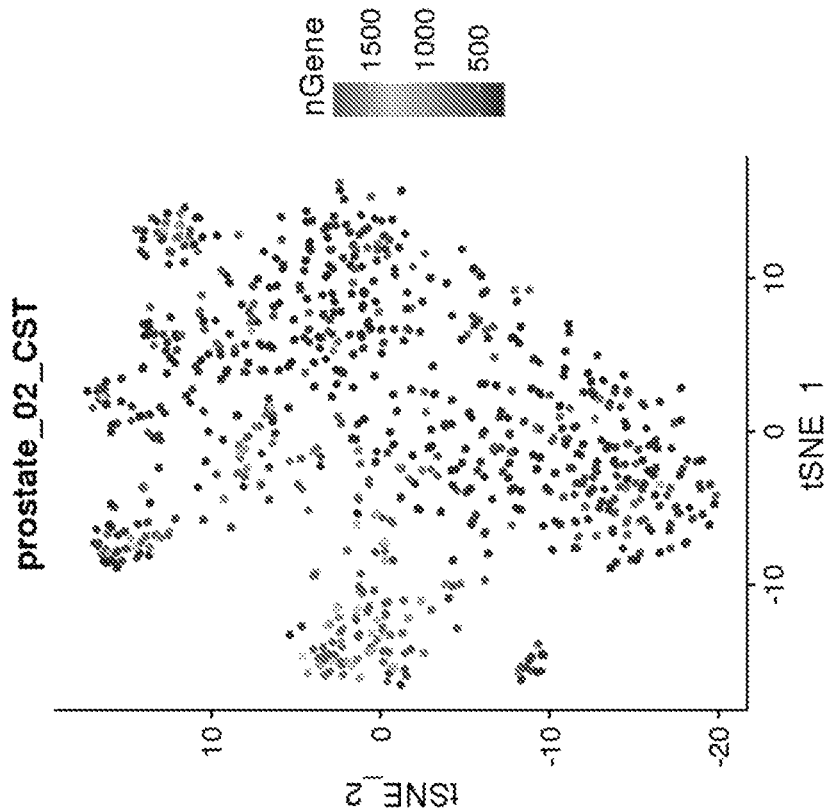
Figure 144A:
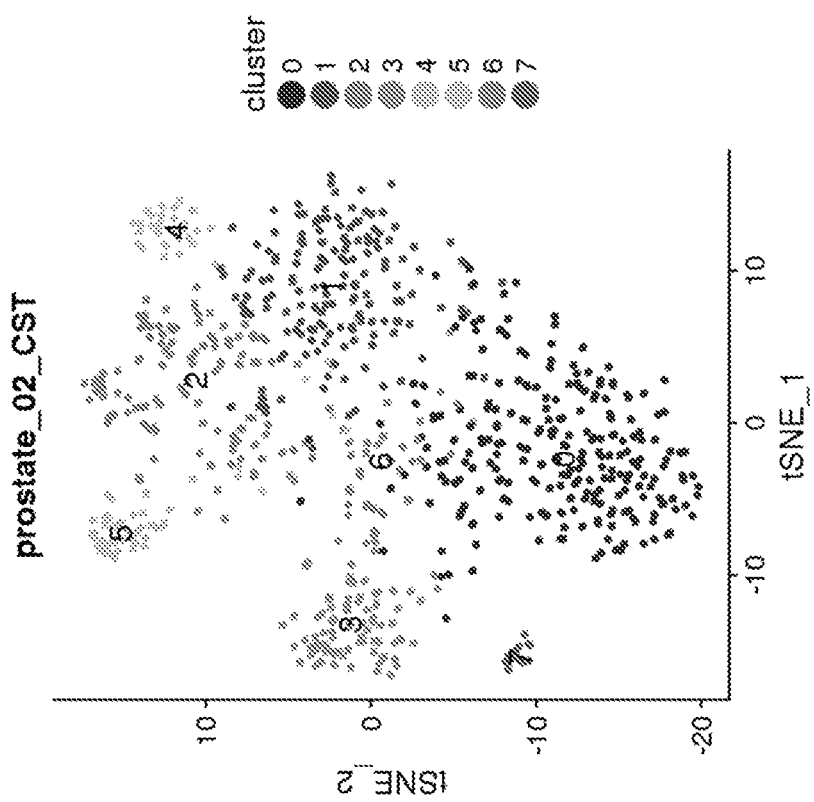

FIGS. 144A, 144B—show tSNE plots of single-nuclei RNA profiles for prostate tissue samples and using the CST protocol. Shown are clusters identified by k-means clustering analysis (144A) and projection of gene expression (144B).

Figure 145B:
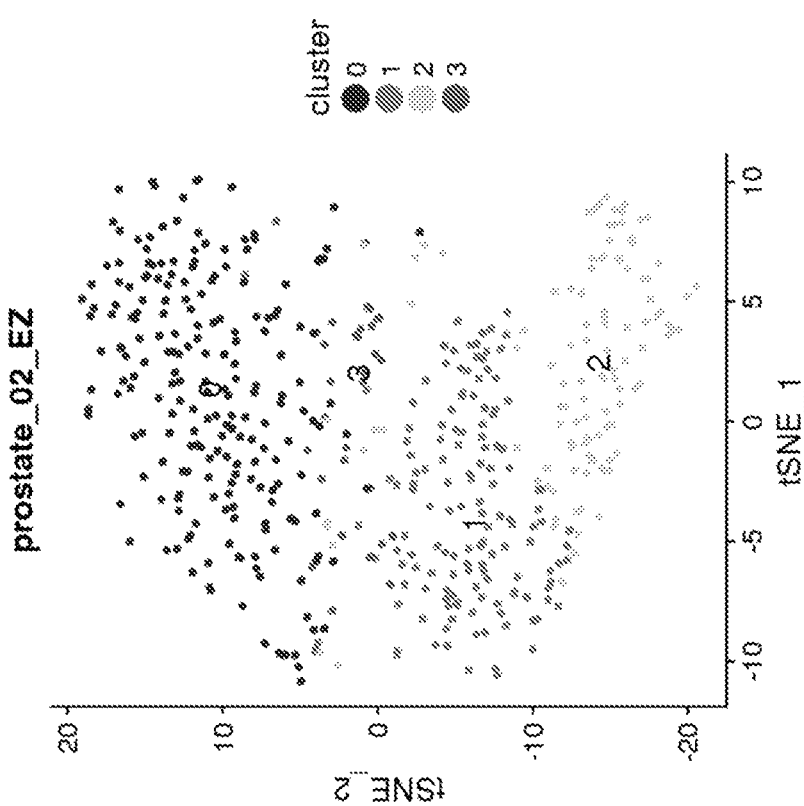
Figure 145A:
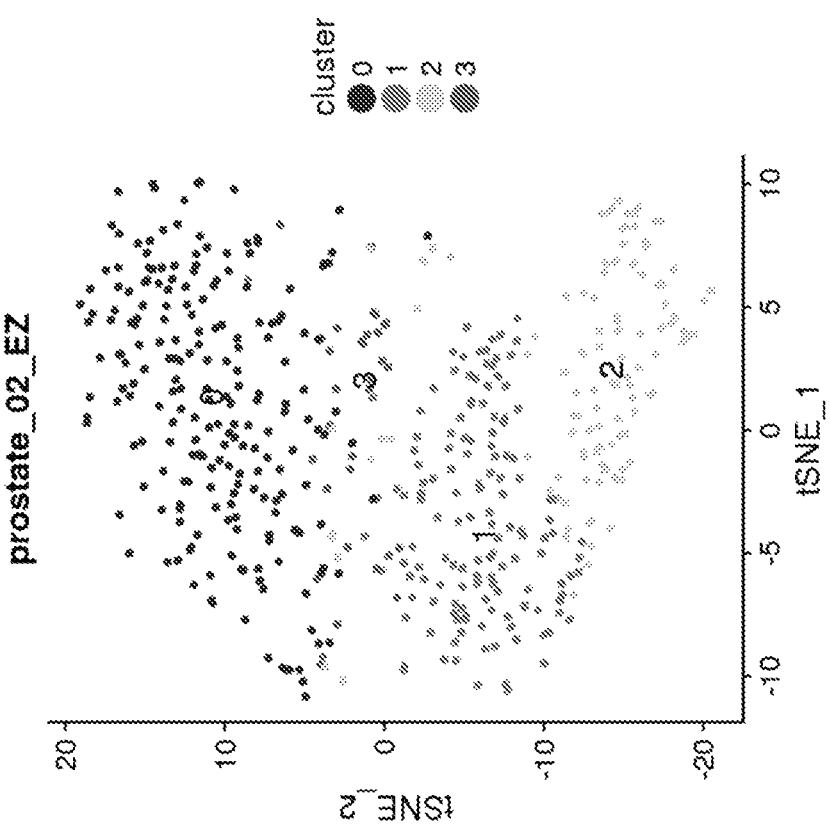

FIGS. 145A, 145B—show tSNE plots of single-nuclei RNA profiles for prostate tissue samples and using the EZ protocol. Shown are clusters identified by k-means clustering analysis (145A) and projection of gene expression (145B).

Figure 146B:
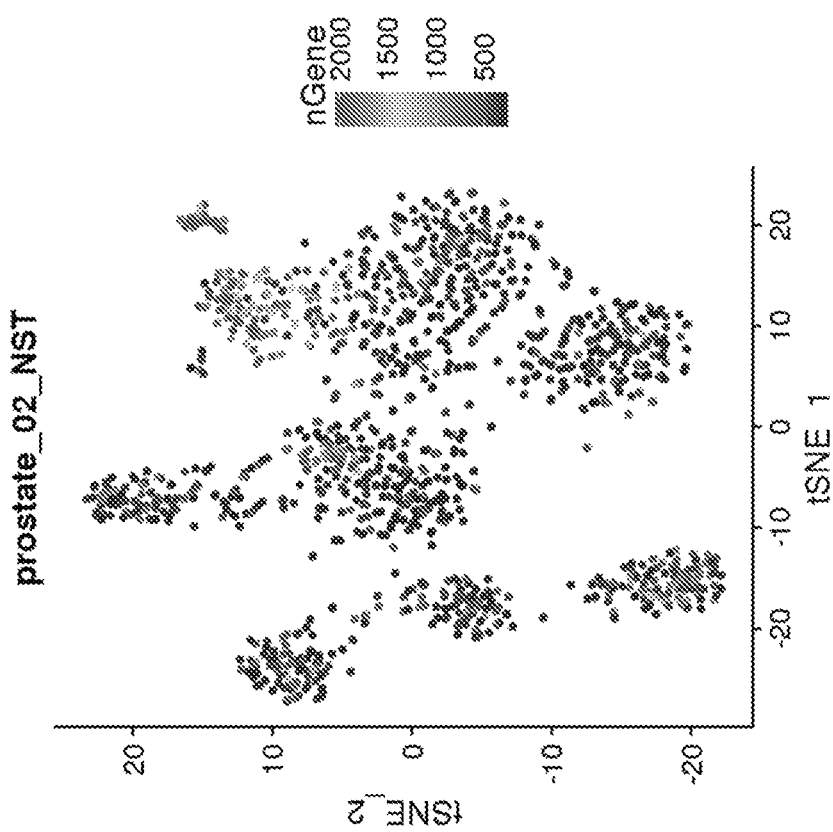
Figure 146A:
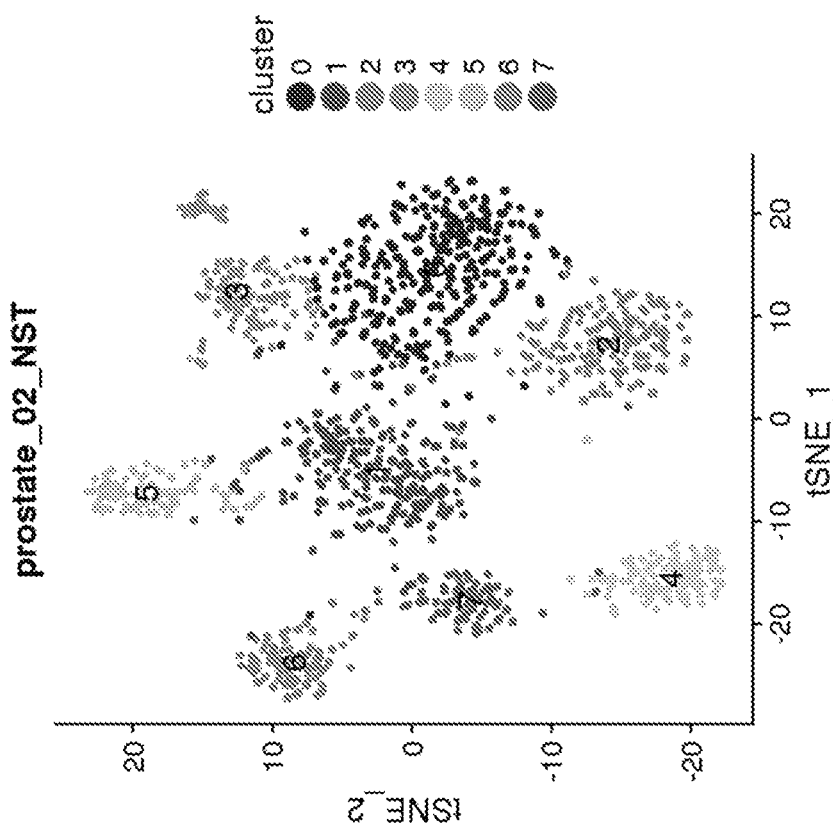

FIGS. 146A, 146B—show tSNE plots of single-nuclei RNA profiles for prostate tissue samples and using the NST protocol. Shown are clusters identified by k-means clustering analysis (146A) and projection of gene expression (146B).

Figure 147B:
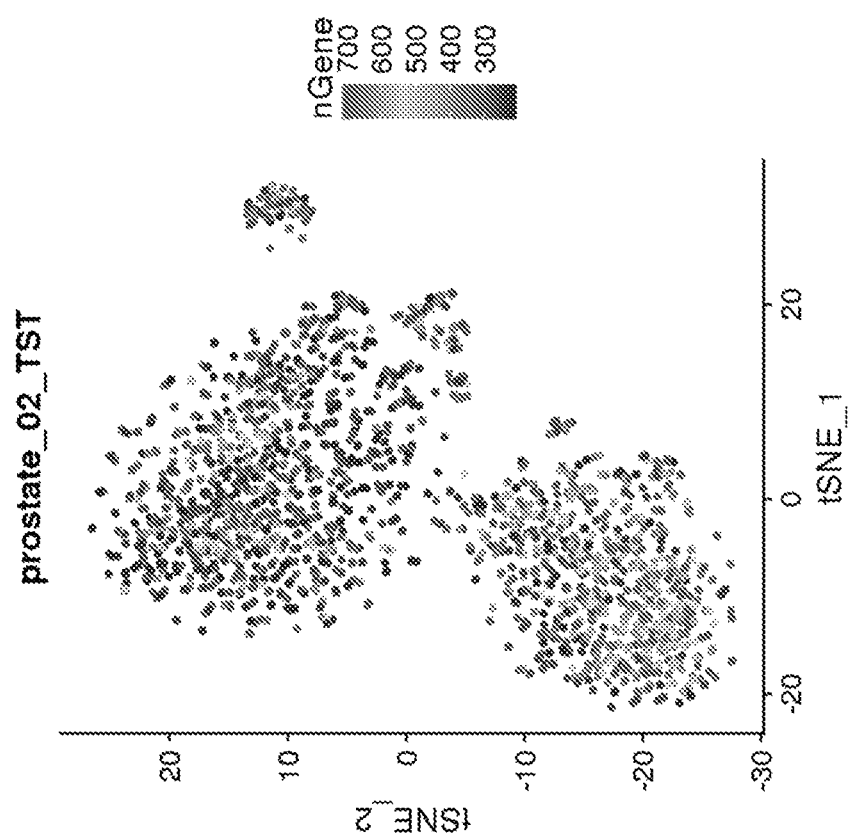
Figure 147A:
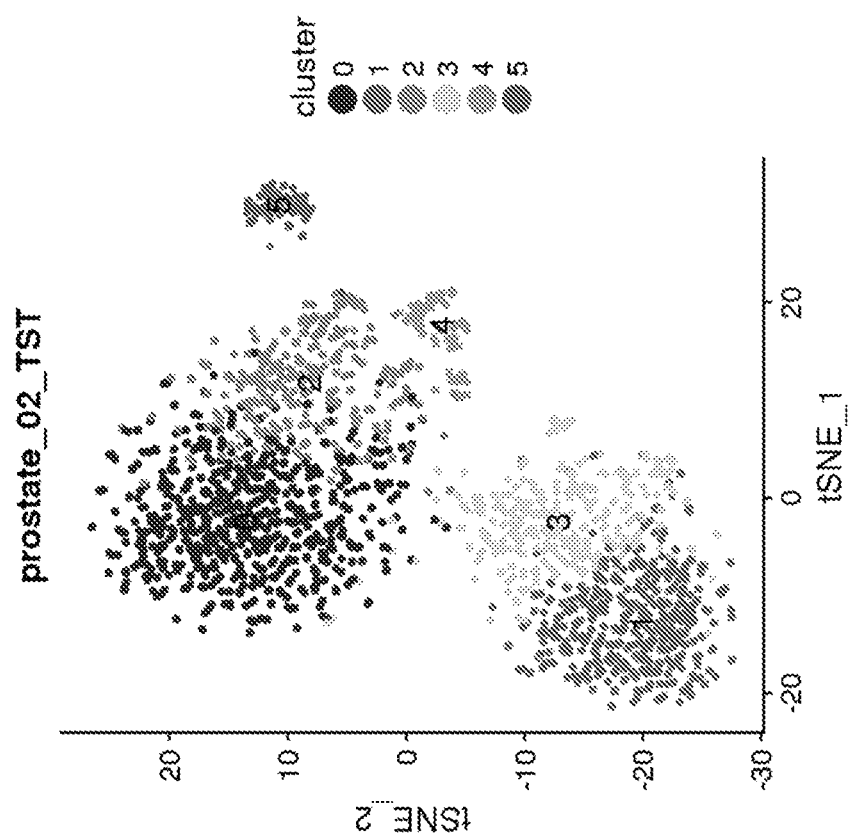

FIGS. 147A, 147B—show tSNE plots of single-nuclei RNA profiles for prostate tissue samples and using the TST protocol. Shown are clusters identified by k-means clustering analysis (147A) and projection of gene expression (147B).

Figure 148B:
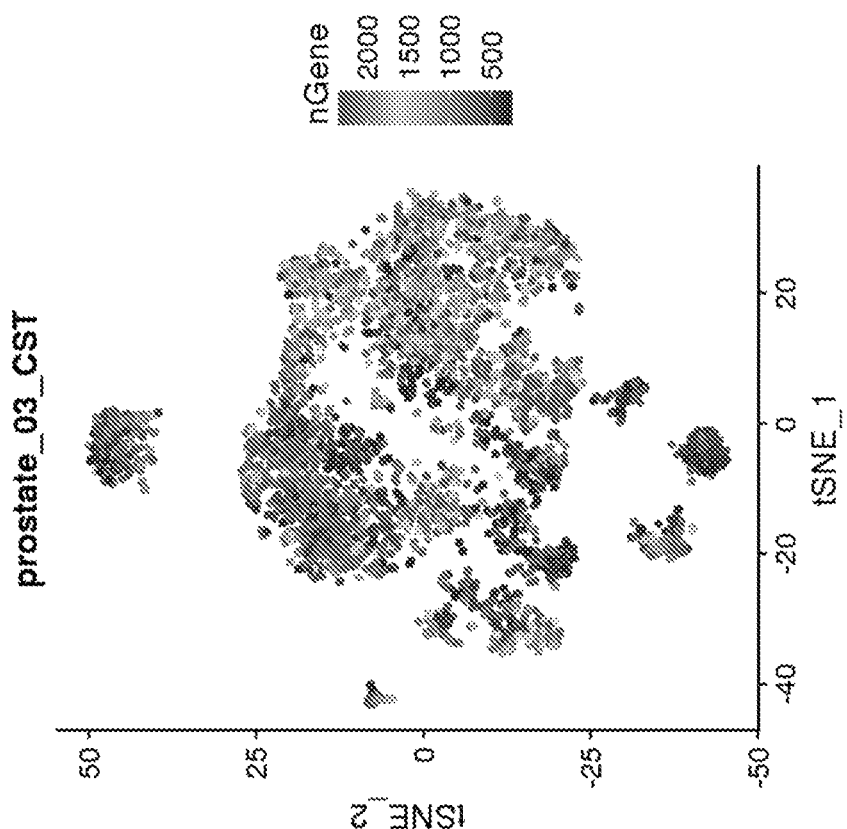
Figure 148A:
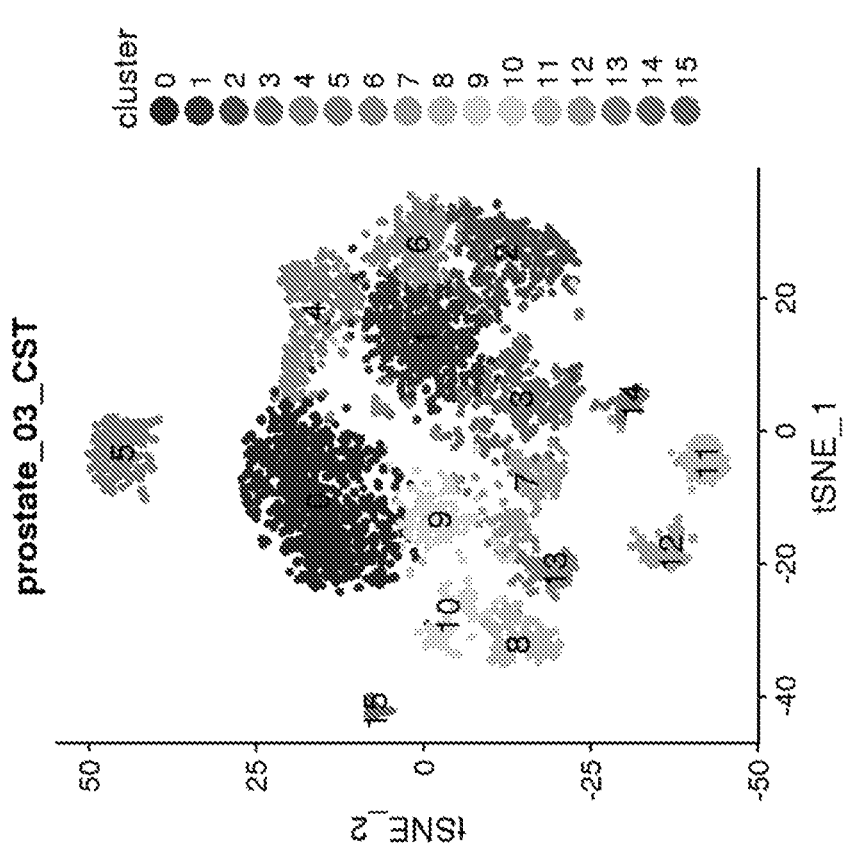

FIGS. 148A, 148B—show tSNE plots of single-nuclei RNA profiles for prostate tissue samples and using the CST protocol. Shown are clusters identified by k-means clustering analysis (148A) and projection of gene expression (148B).

Figures 149A, 149B:
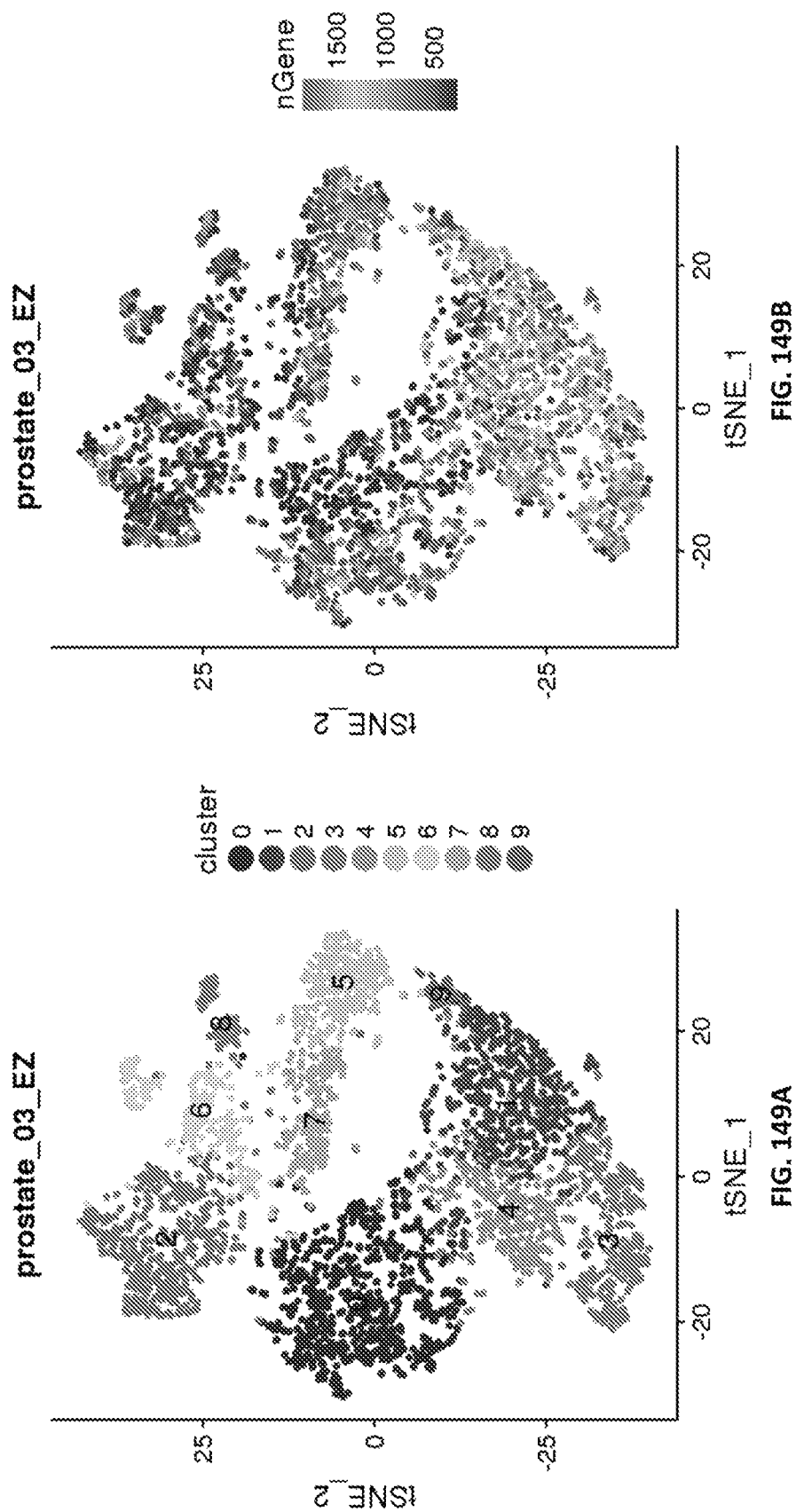

FIGS. 149A, 149B—show tSNE plots of single-nuclei RNA profiles for prostate tissue samples and using the EZ protocol. Shown are clusters identified by k-means clustering analysis (149A) and projection of gene expression (149B).

Figure 150B:
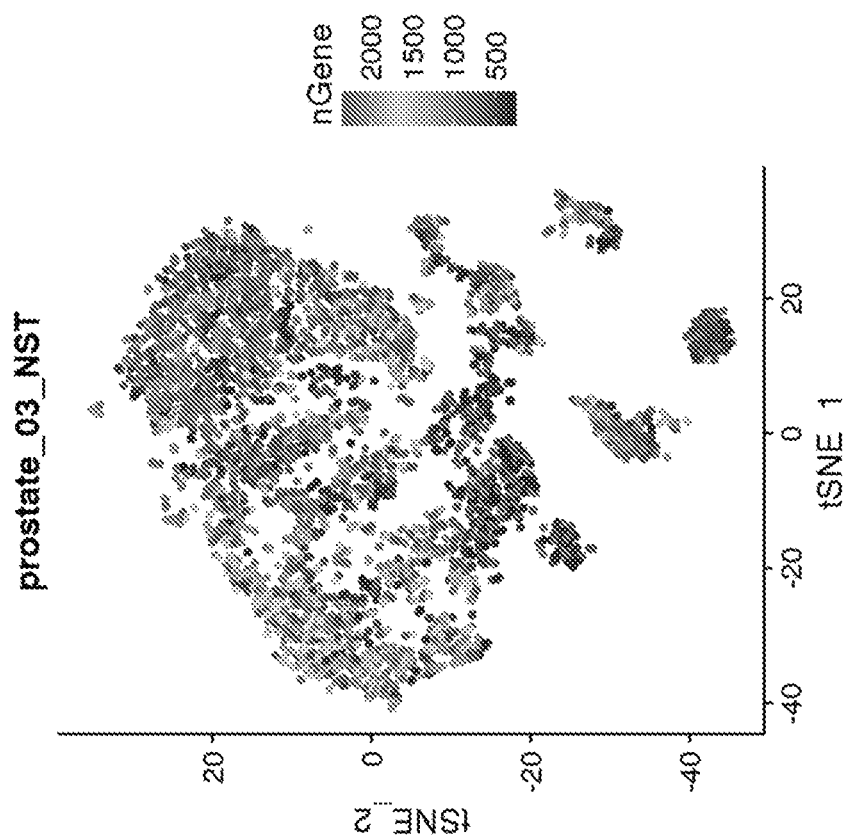
Figure 150A:
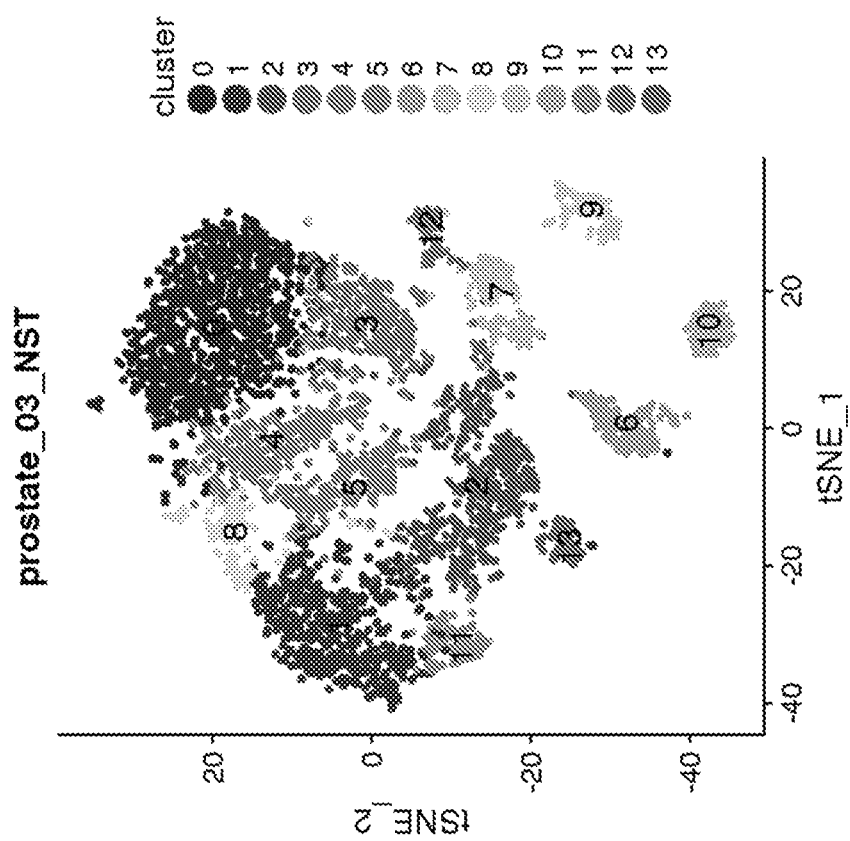

FIGS. 150A, 150B—show tSNE plots of single-nuclei RNA profiles for prostate tissue samples and using the NST protocol. Shown are clusters identified by k-means clustering analysis (150A) and projection of gene expression (150B).

Figure 151A:
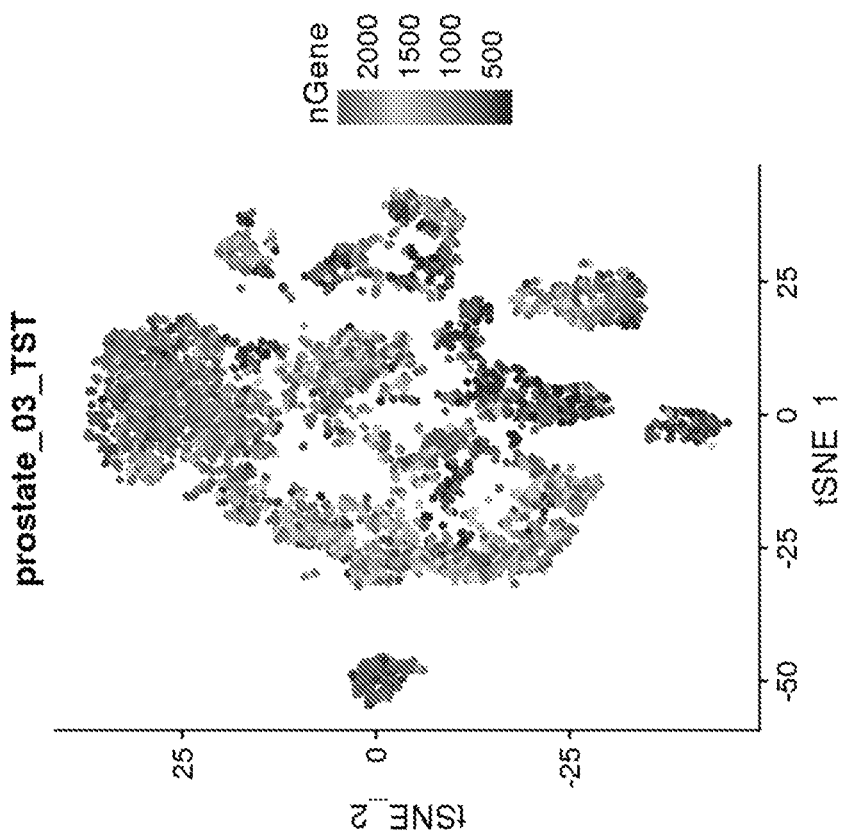
Figure 151B:
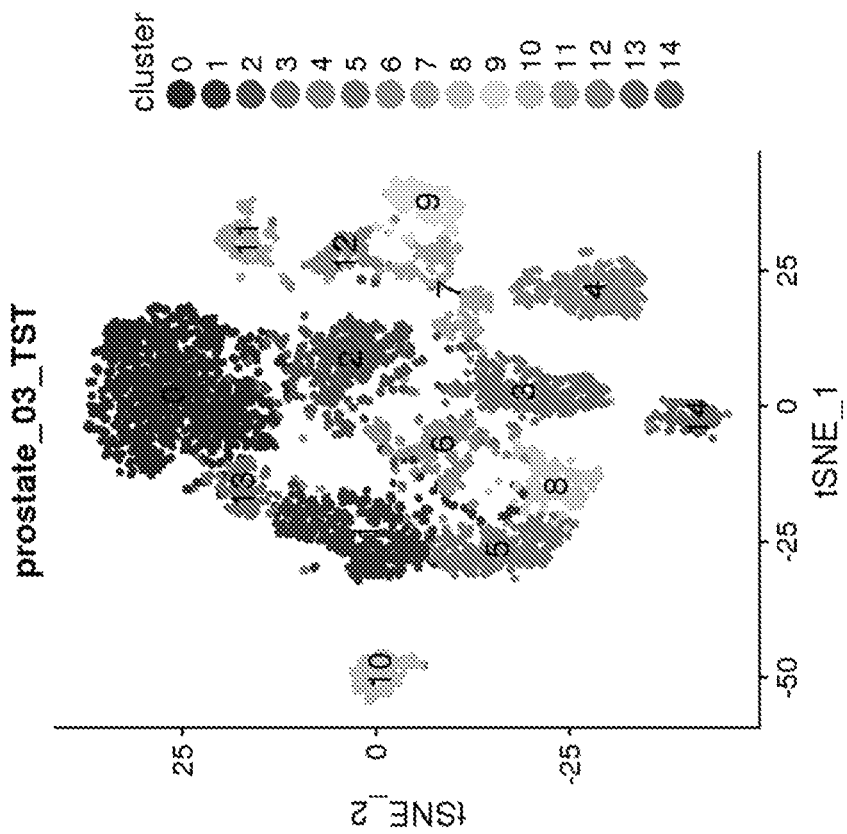

FIGS. 151A, 151B—show tSNE plots of single-nuclei RNA profiles for prostate tissue samples and using the TST protocol. Shown are clusters identified by k-means clustering analysis (151A) and projection of gene expression (151B).

Figure 152B:
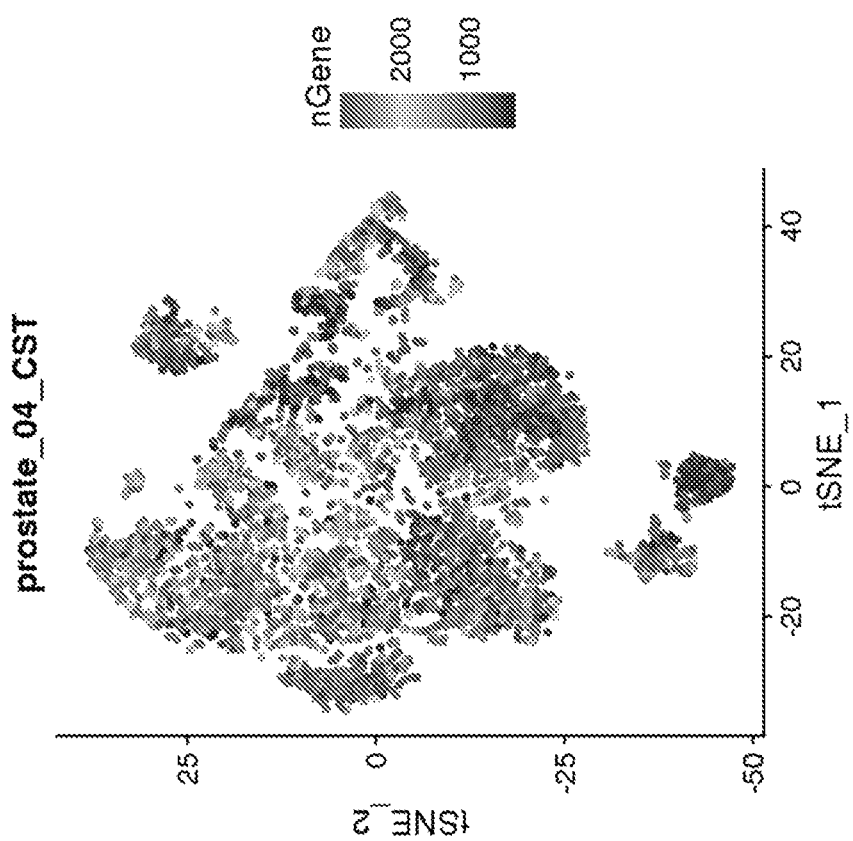
Figure 152A:
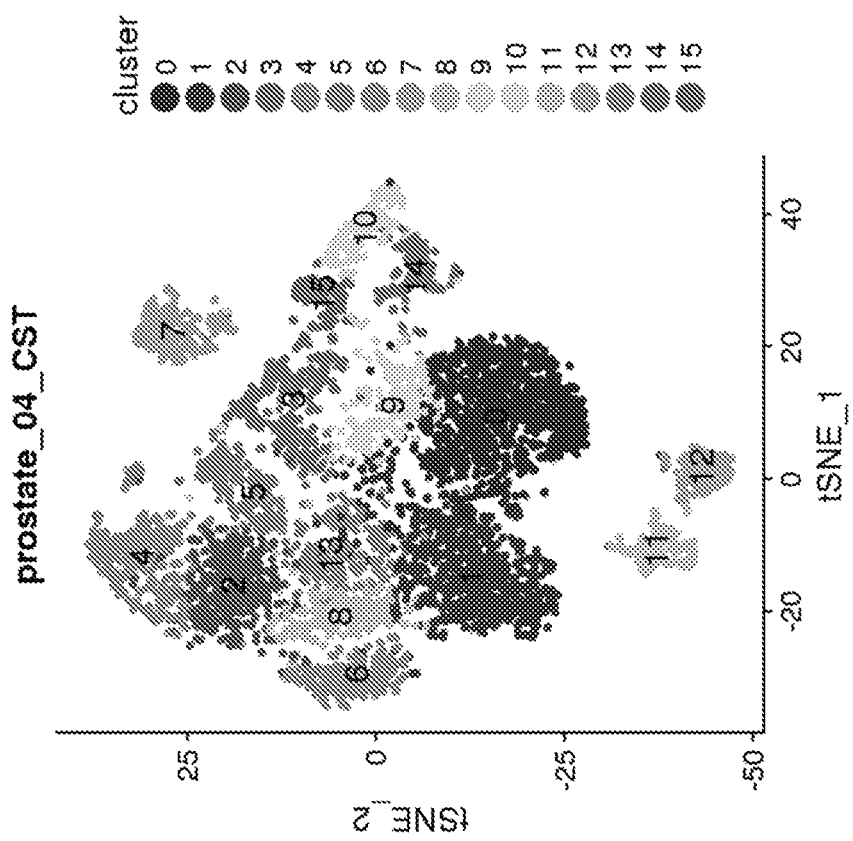

FIGS. 152A, 152B—show tSNE plots of single-nuclei RNA profiles for prostate tissue samples and using the CST protocol. Shown are clusters identified by k-means clustering analysis (152A) and projection of gene expression (152B).

Figure 153B:
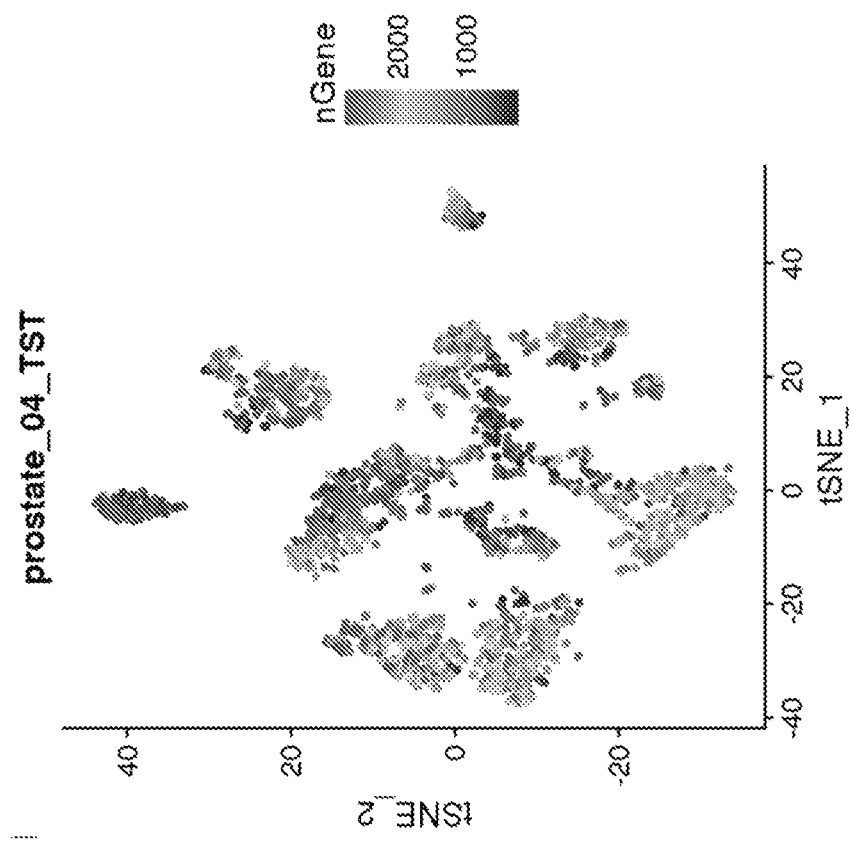
Figure 153A:
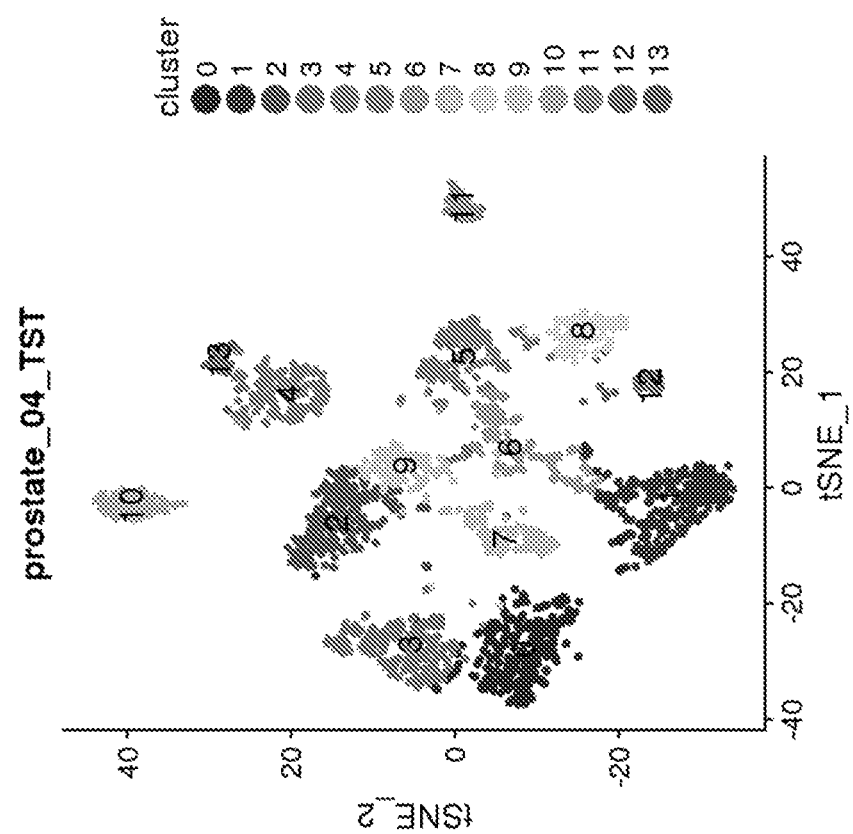

FIGS. 153A, 153B—show tSNE plots of single-nuclei RNA profiles for prostate tissue samples and using the TST protocol. Shown are clusters identified by k-means clustering analysis (153A) and projection of gene expression (153B).

FIGS. 154A, 154B—show tSNE plots of single-nuclei RNA profiles for skeletal muscle tissue samples and using the CST protocol. Shown are clusters identified by k-means clustering analysis (154A) and projection of gene expression (154B).

Figure 155B:
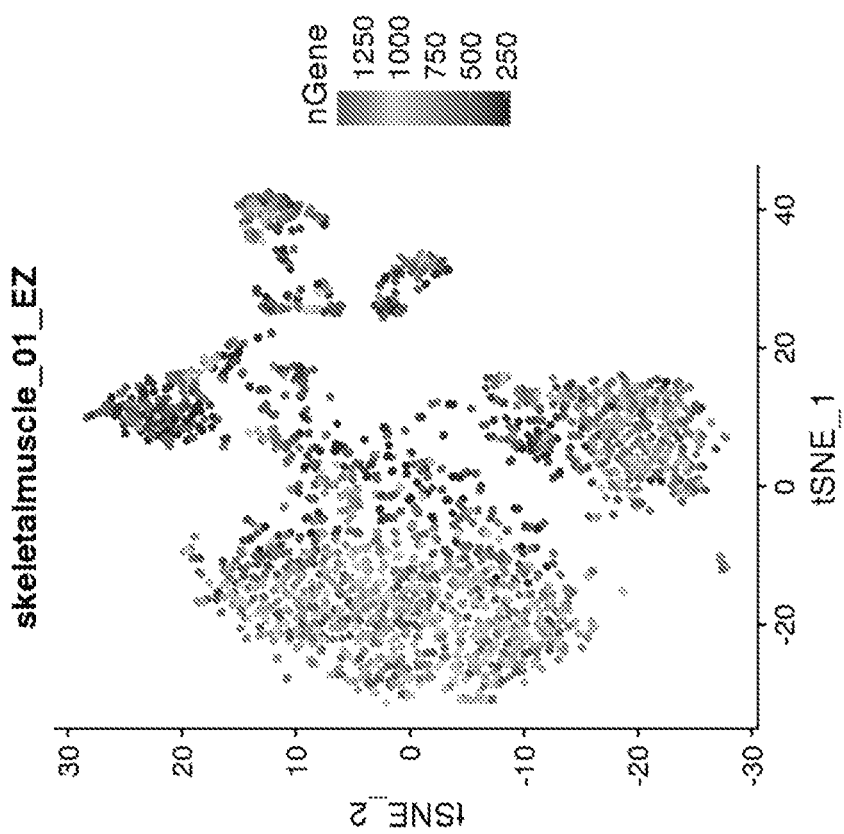
Figure 155A:
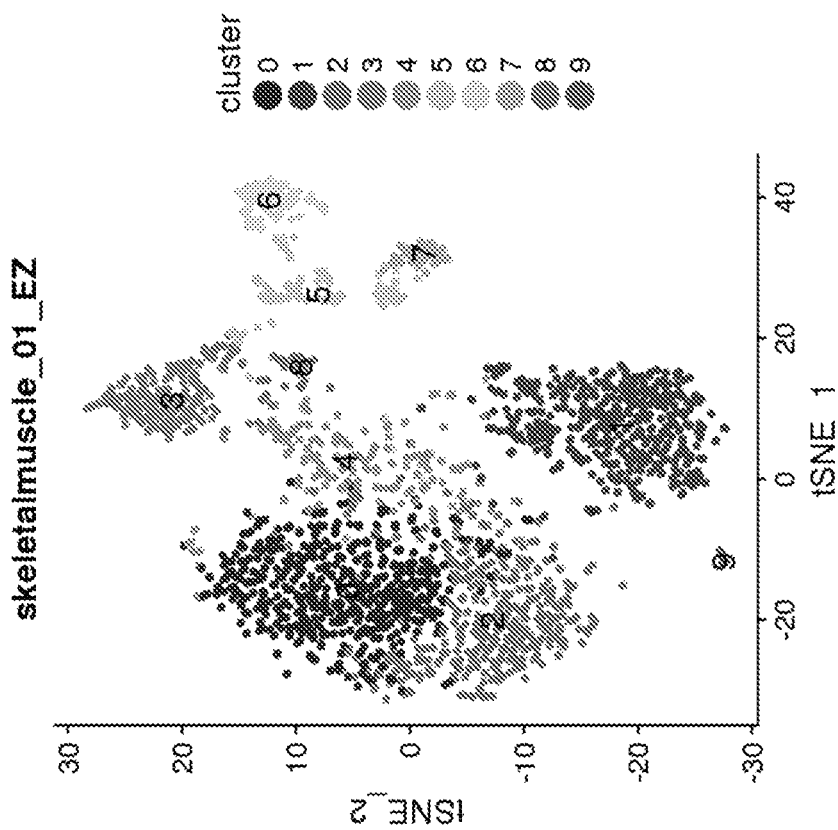

FIGS. 155A, 155B—show tSNE plots of single-nuclei RNA profiles for skeletal muscle tissue samples and using the EZ protocol. Shown are clusters identified by k-means clustering analysis (155A) and projection of gene expression (155B).

Figure 156B:
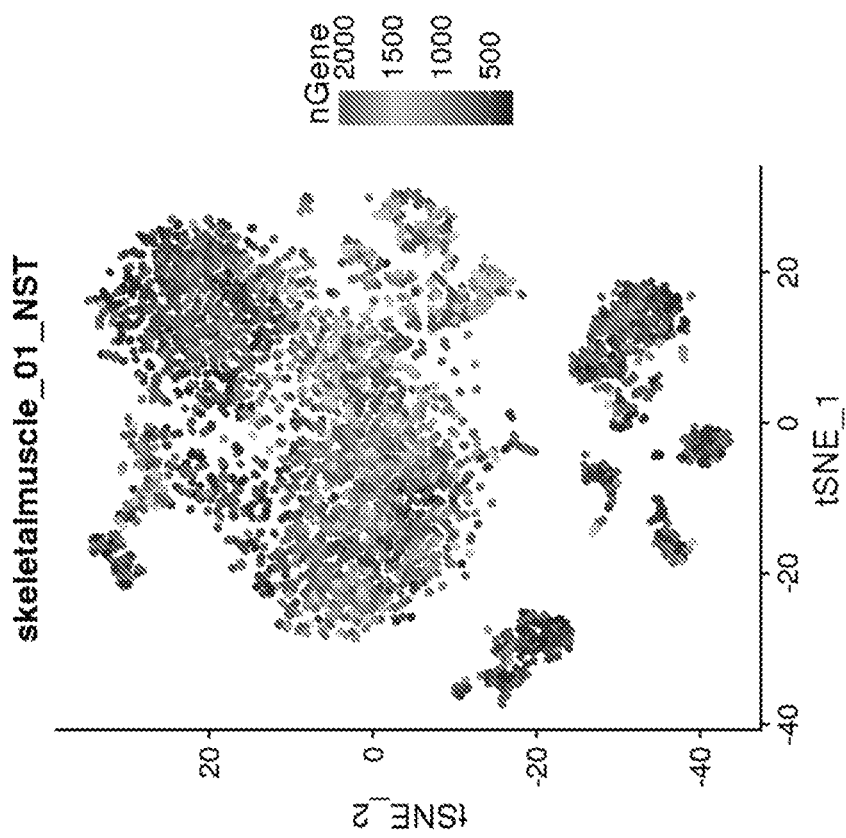
Figure 156A:
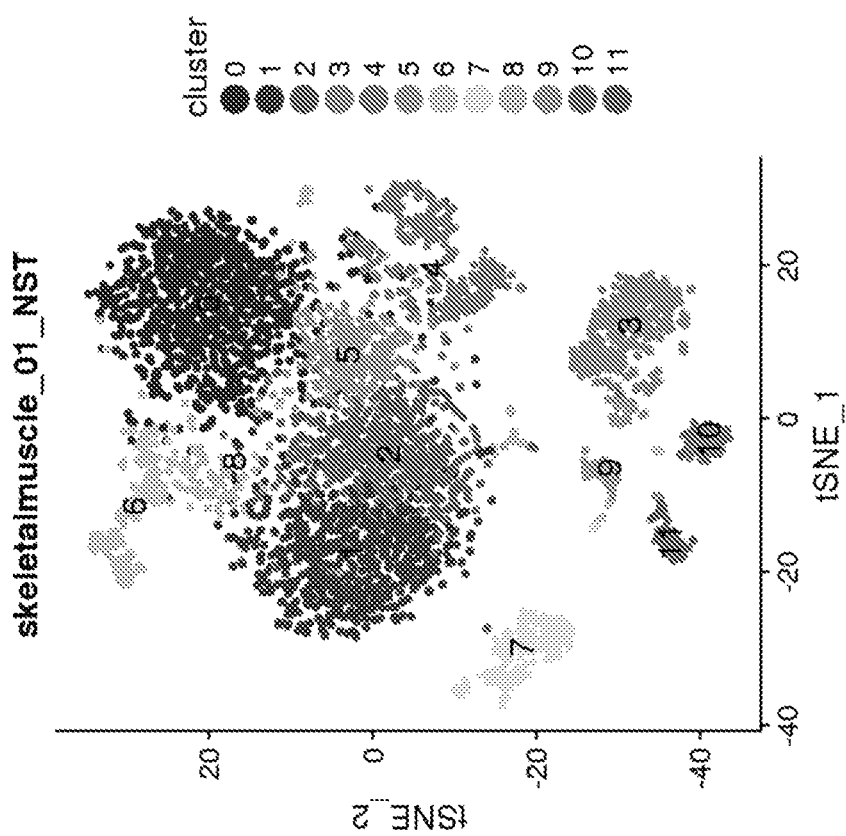

FIGS. 156A, 156B—show tSNE plots of single-nuclei RNA profiles for skeletal muscle tissue samples and using the NST protocol. Shown are clusters identified by k-means clustering analysis (156A) and projection of gene expression (156B).

Figure 157B:
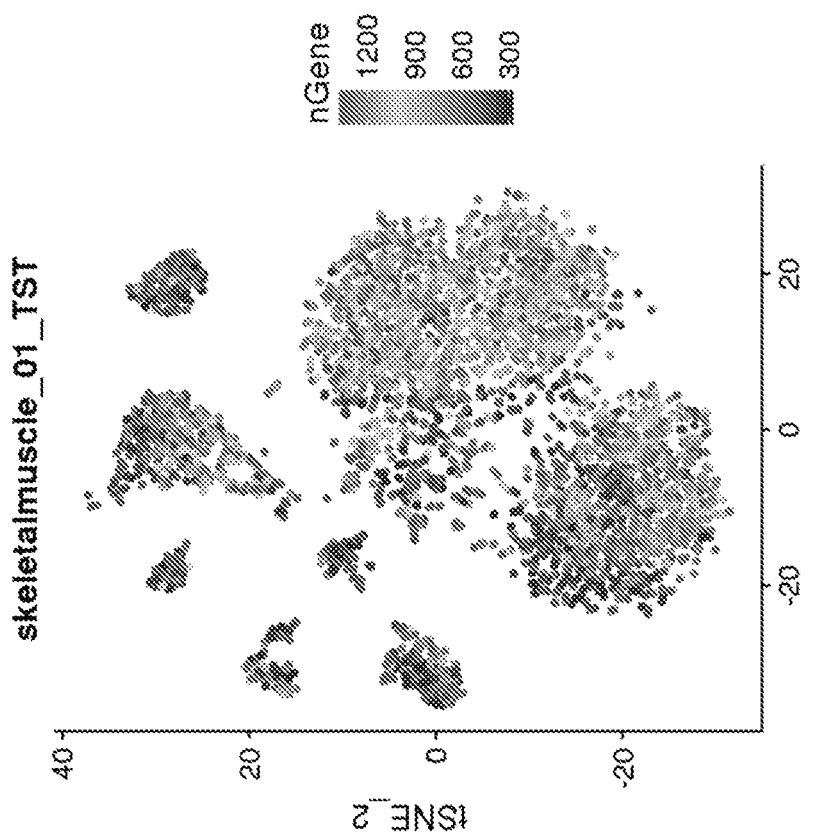
Figure 157A:
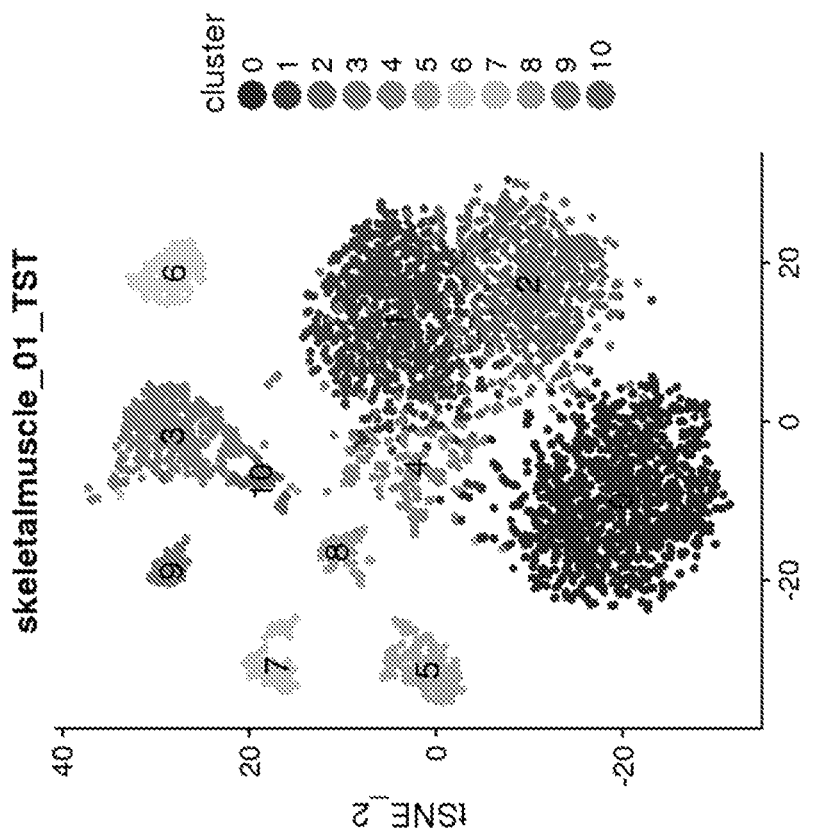

FIGS. 157A, 157B—show tSNE plots of single-nuclei RNA profiles for skeletal muscle tissue samples and using the TST protocol. Shown are clusters identified by k-means clustering analysis (157A) and projection of gene expression (157B).

Figure 158B:
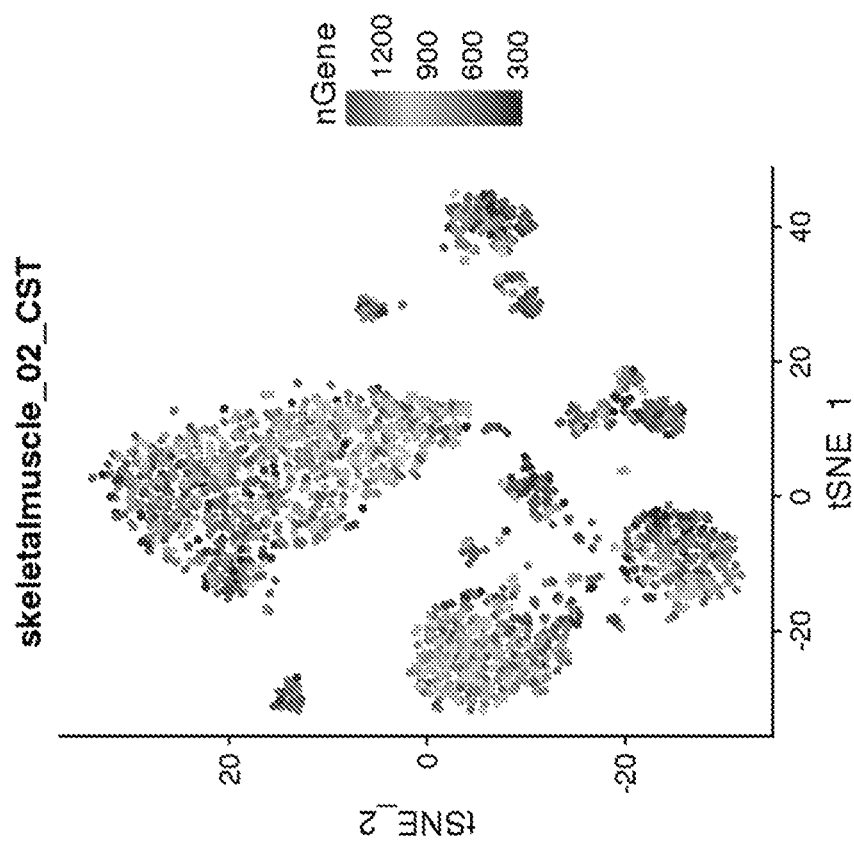
Figure 158A:
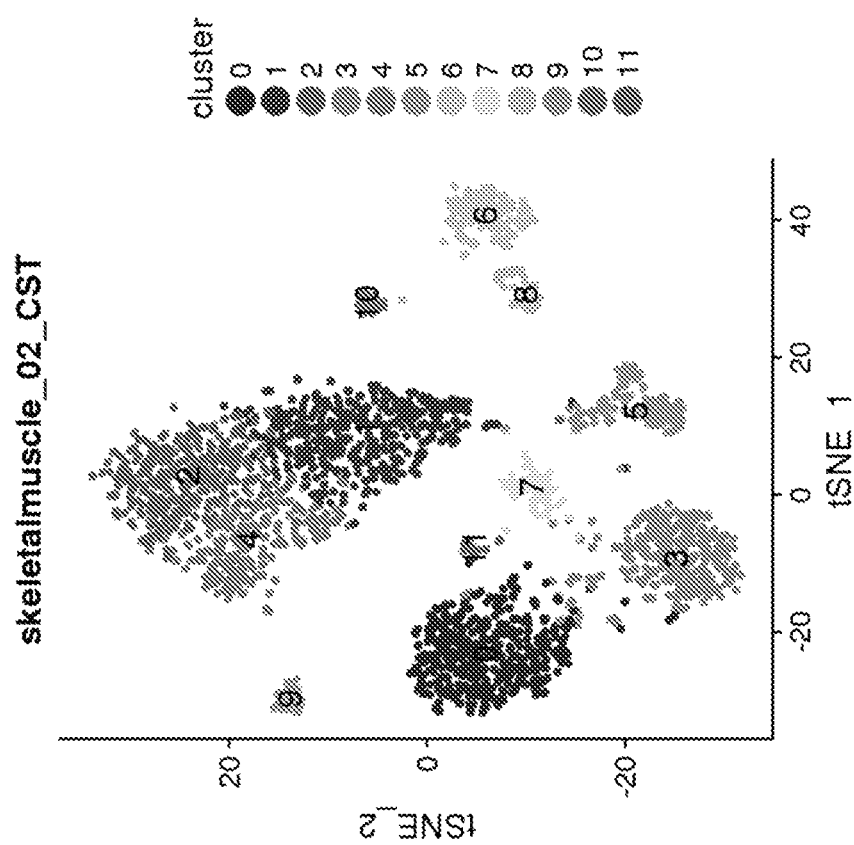

FIGS. 158A, 158B—show tSNE plots of single-nuclei RNA profiles for skeletal muscle tissue samples and using the CST protocol. Shown are clusters identified by k-means clustering analysis (158A) and projection of gene expression (158B).

Figure 159B:
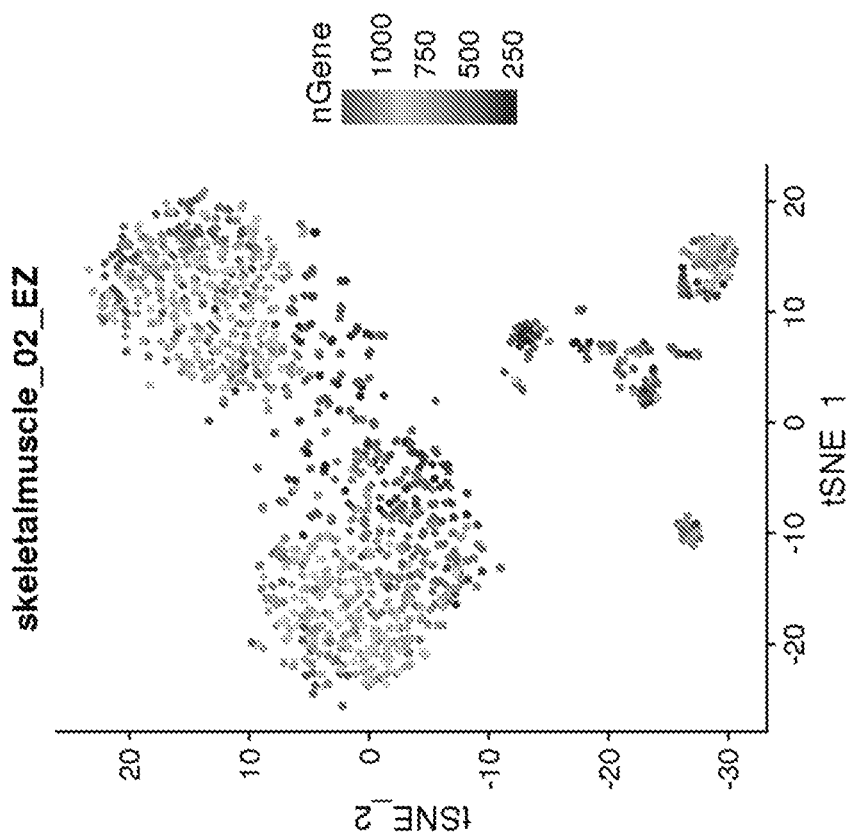
Figure 159A:
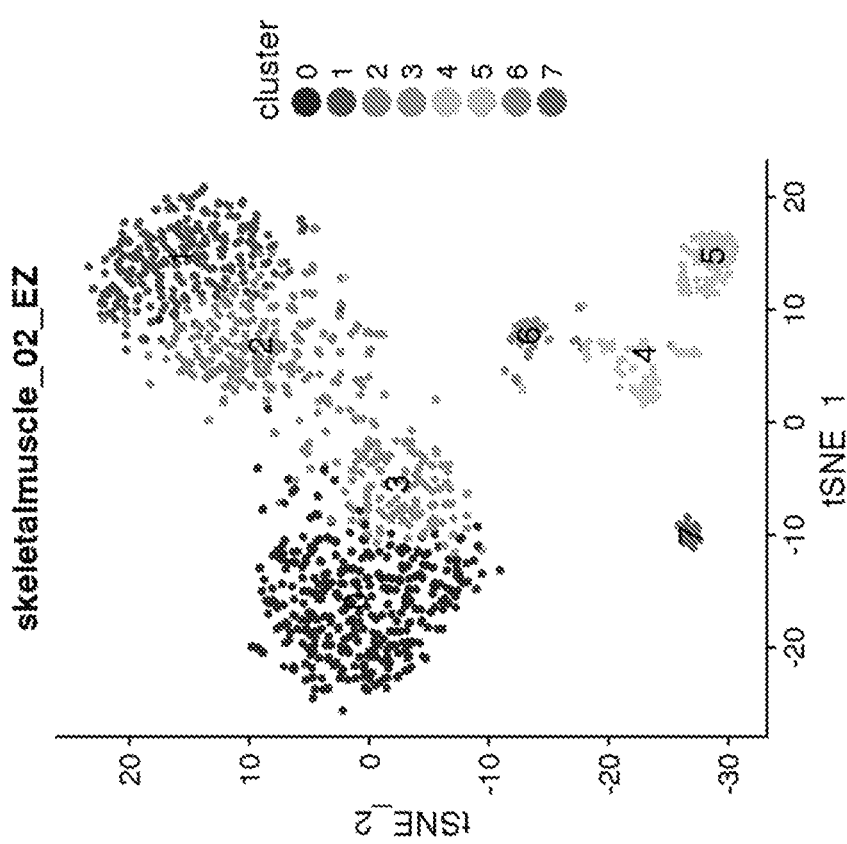

FIGS. 159A, 159B—show tSNE plots of single-nuclei RNA profiles for skeletal muscle tissue samples and using the EZ protocol. Shown are clusters identified by k-means clustering analysis (159A) and projection of gene expression (159B).

FIGS. 160A, 160B—show tSNE plots of single-nuclei RNA profiles for skeletal muscle tissue samples and using the NST protocol. Shown are clusters identified by k-means clustering analysis (160A) and projection of gene expression (160B).

Figure 161B:
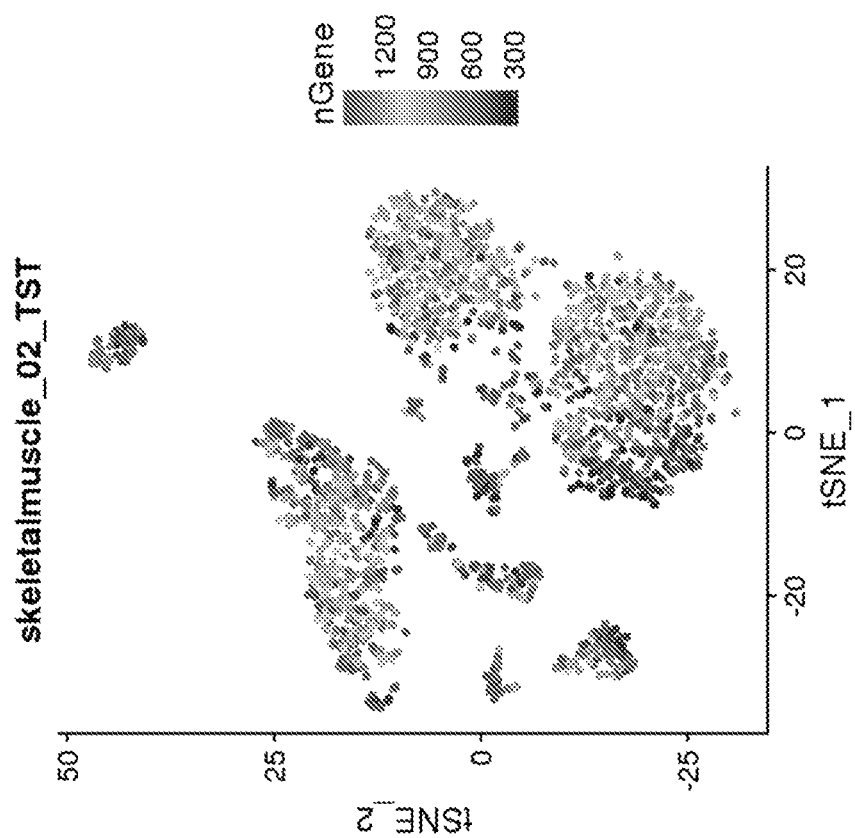
Figure 161A:
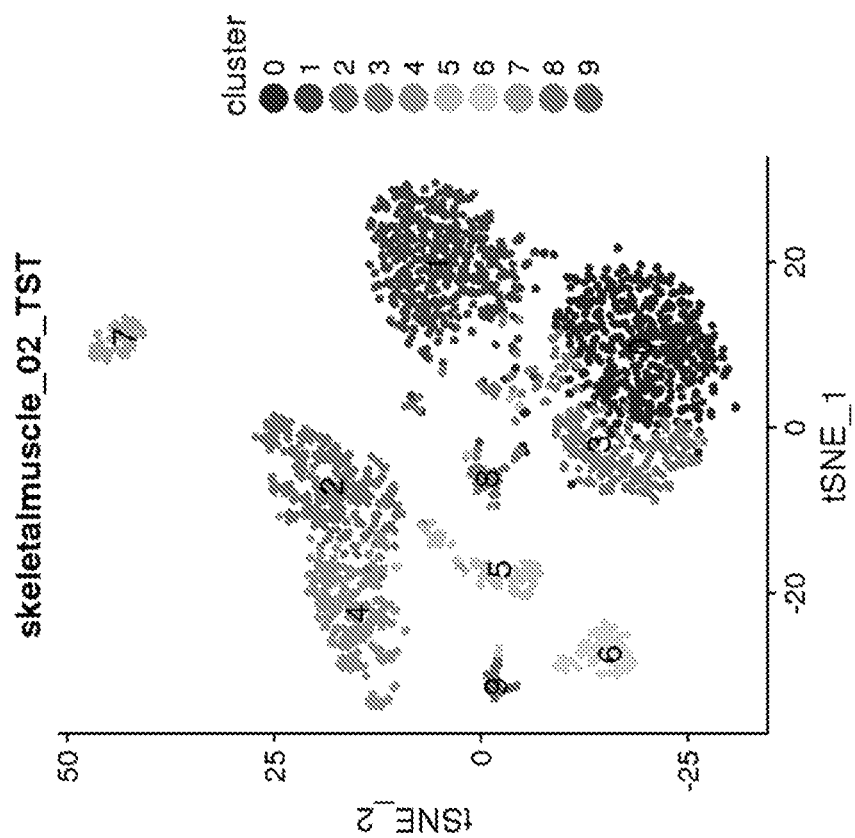

FIGS. 161A, 161B—show tSNE plots of single-nuclei RNA profiles for skeletal muscle tissue samples and using the TST protocol. Shown are clusters identified by k-means clustering analysis (161A) and projection of gene expression (161B).

Figure 162B:
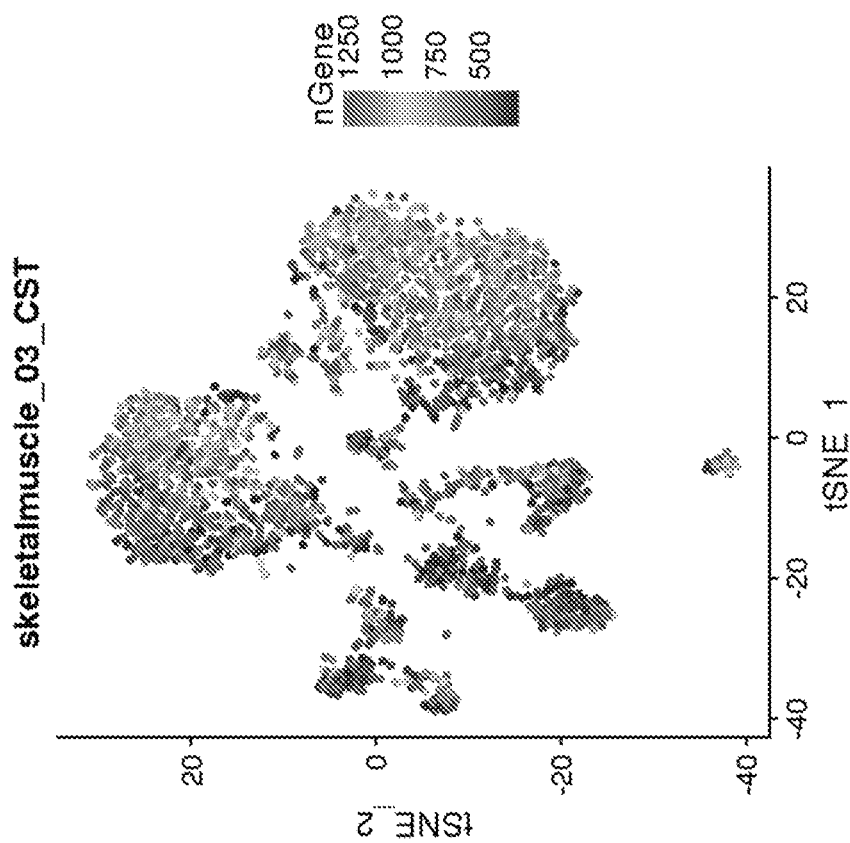
Figure 162A:
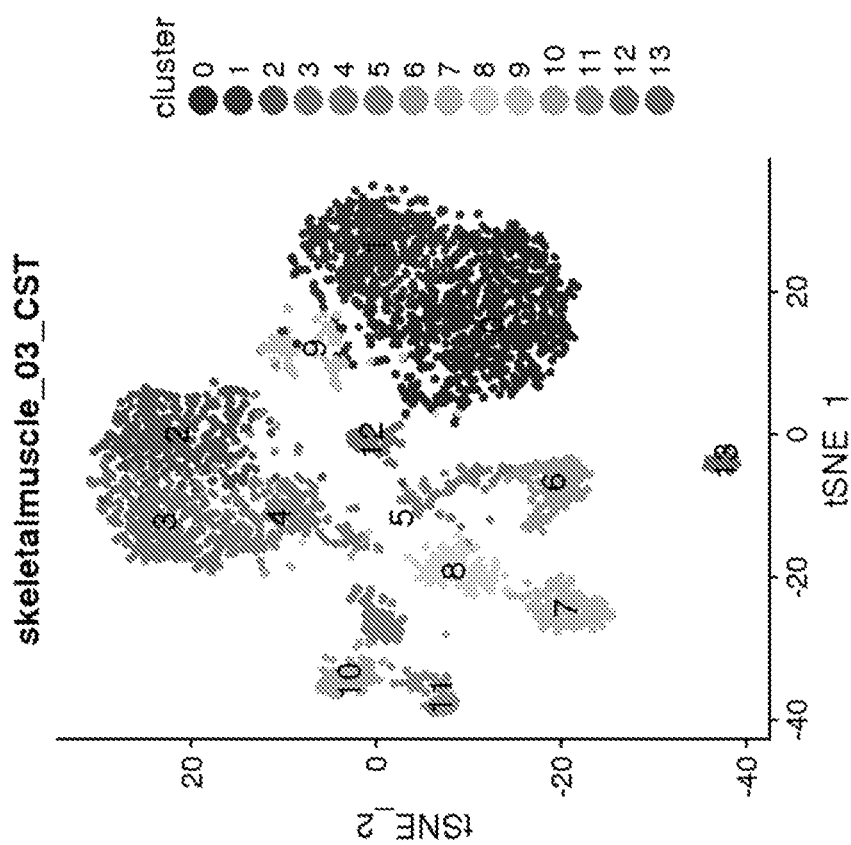

FIGS. 162A, 162B—show tSNE plots of single-nuclei RNA profiles for skeletal muscle tissue samples and using the CST protocol. Shown are clusters identified by k-means clustering analysis (162A) and projection of gene expression (162B).

Figure 163B:
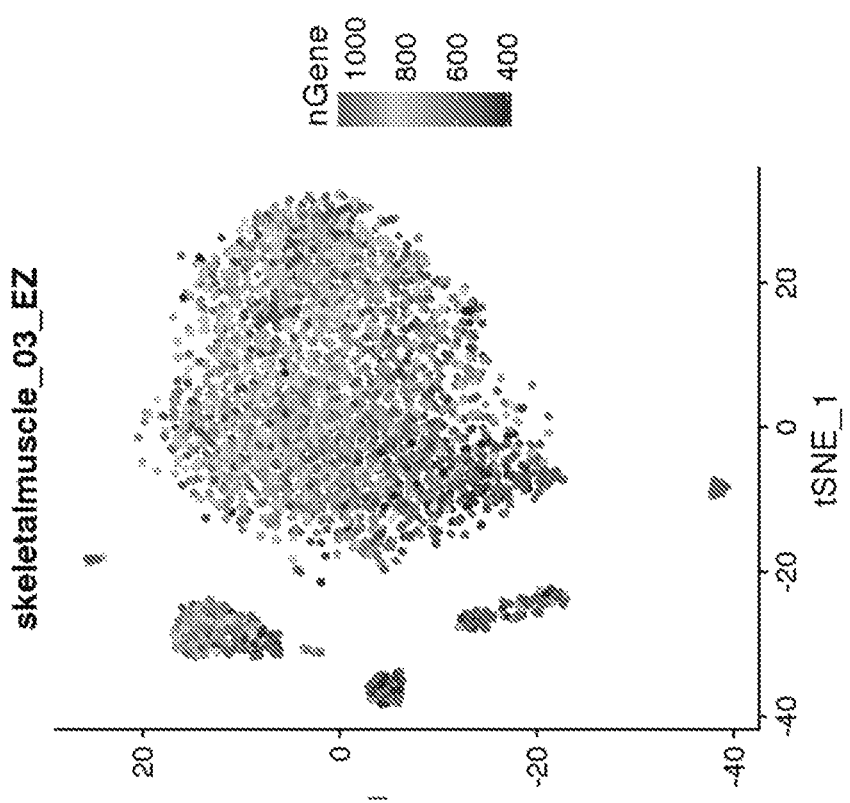
Figure 163A:
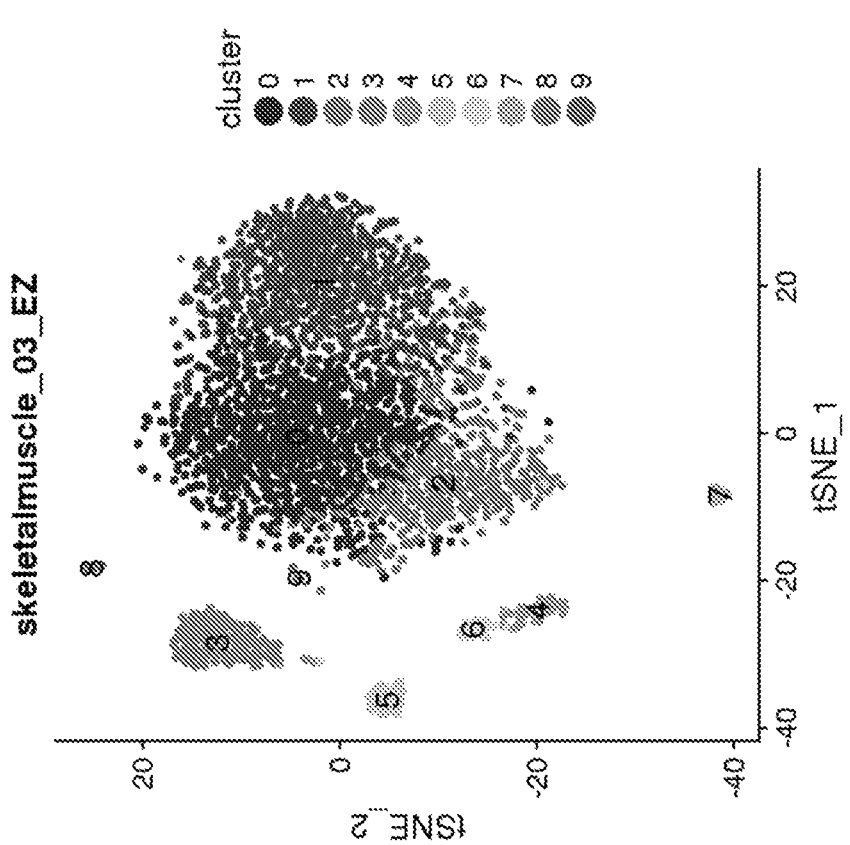

FIGS. 163A, 163B—show tSNE plots of single-nuclei RNA profiles for skeletal muscle tissue samples and using the EZ protocol. Shown are clusters identified by k-means clustering analysis (163A) and projection of gene expression (163B).

Figure 164B:
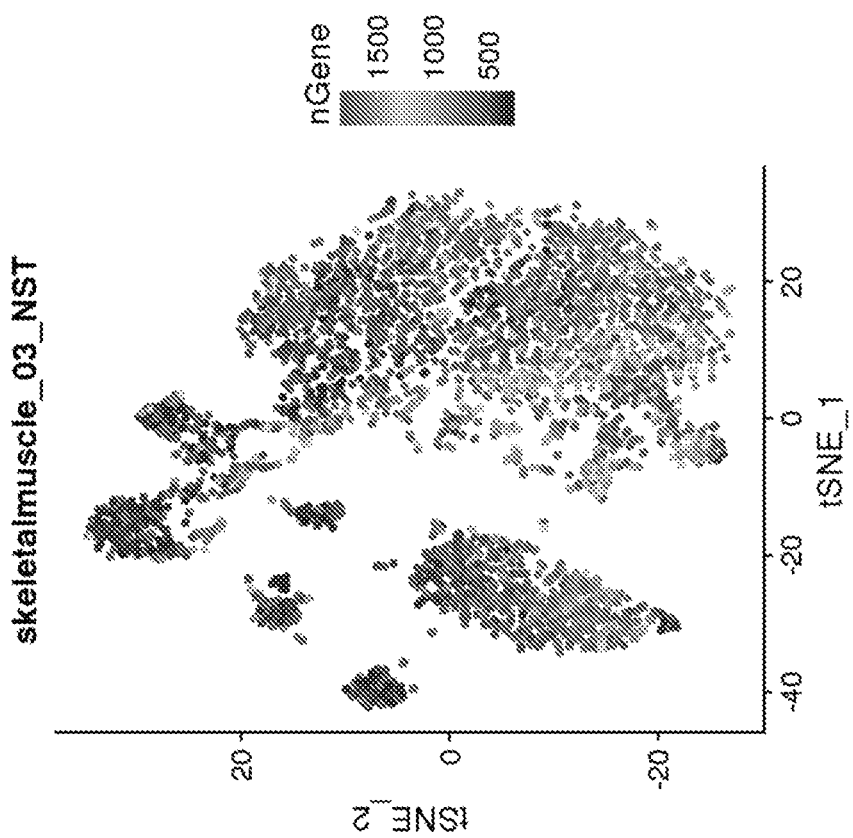
Figure 164A:
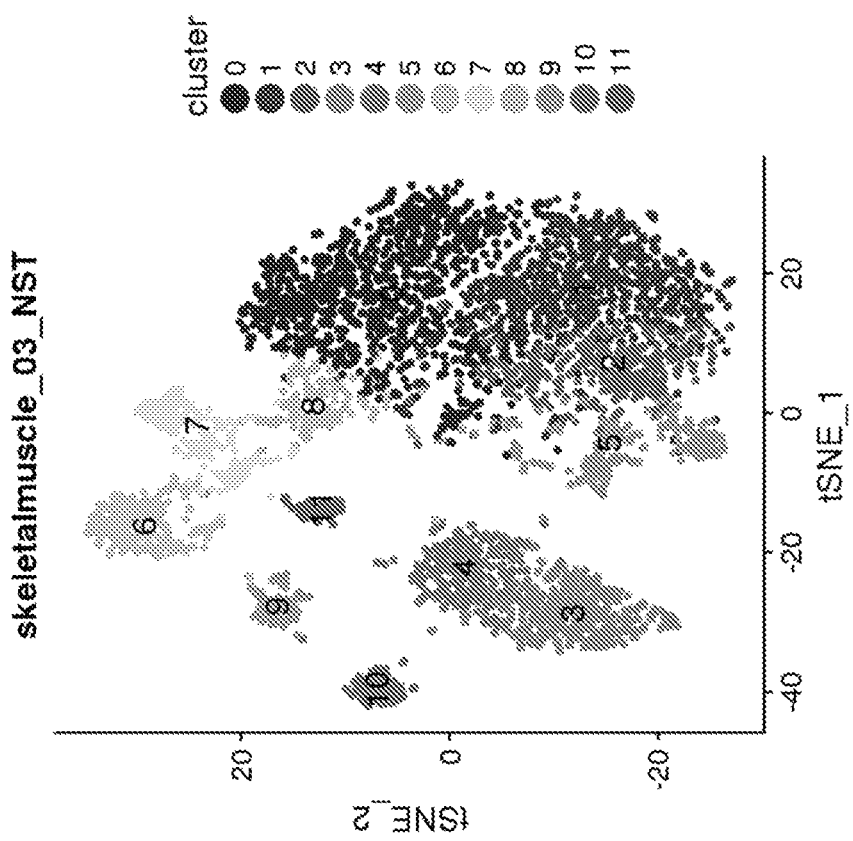

FIGS. 164A, 164B—show tSNE plots of single-nuclei RNA profiles for skeletal muscle tissue samples and using the NST protocol. Shown are clusters identified by k-means clustering analysis (164A) and projection of gene expression (164B).

Figure 165B:
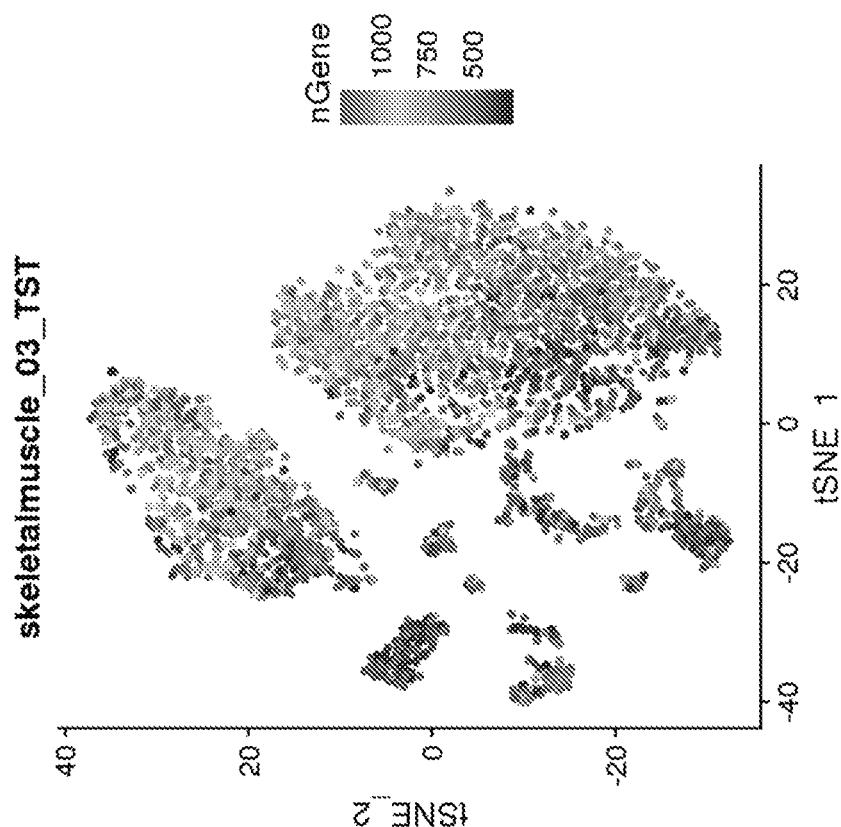
Figure 165A:
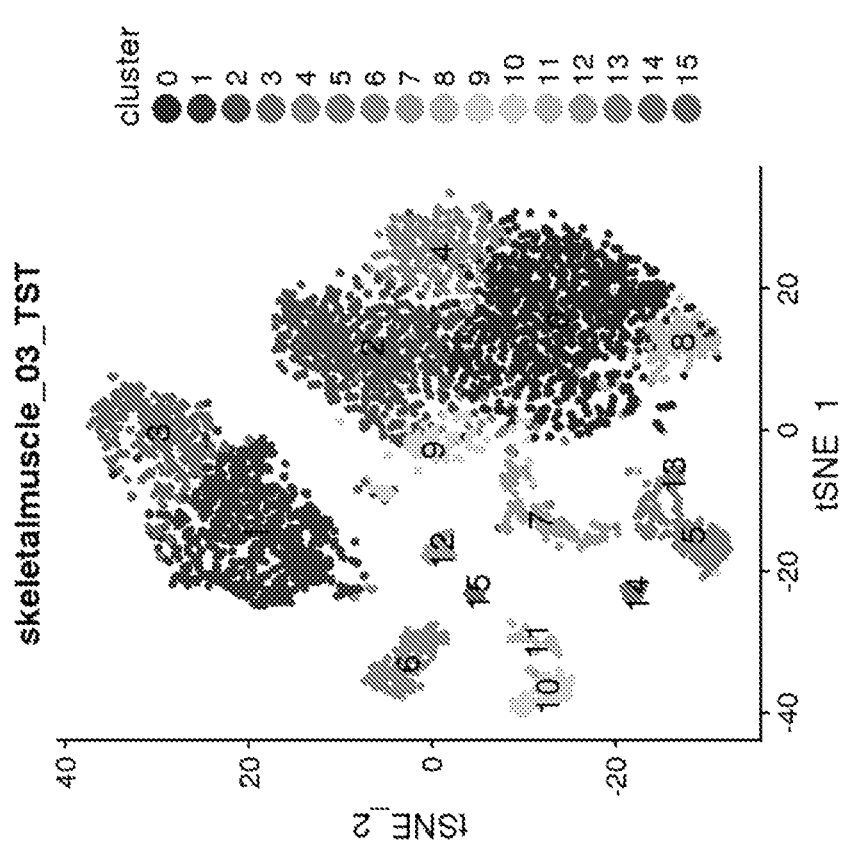

FIGS. 165A, 165B—show tSNE plots of single-nuclei RNA profiles for skeletal muscle tissue samples and using the TST protocol. Shown are clusters identified by k-means clustering analysis (165A) and projection of gene expression (165B).

Figure 166B:
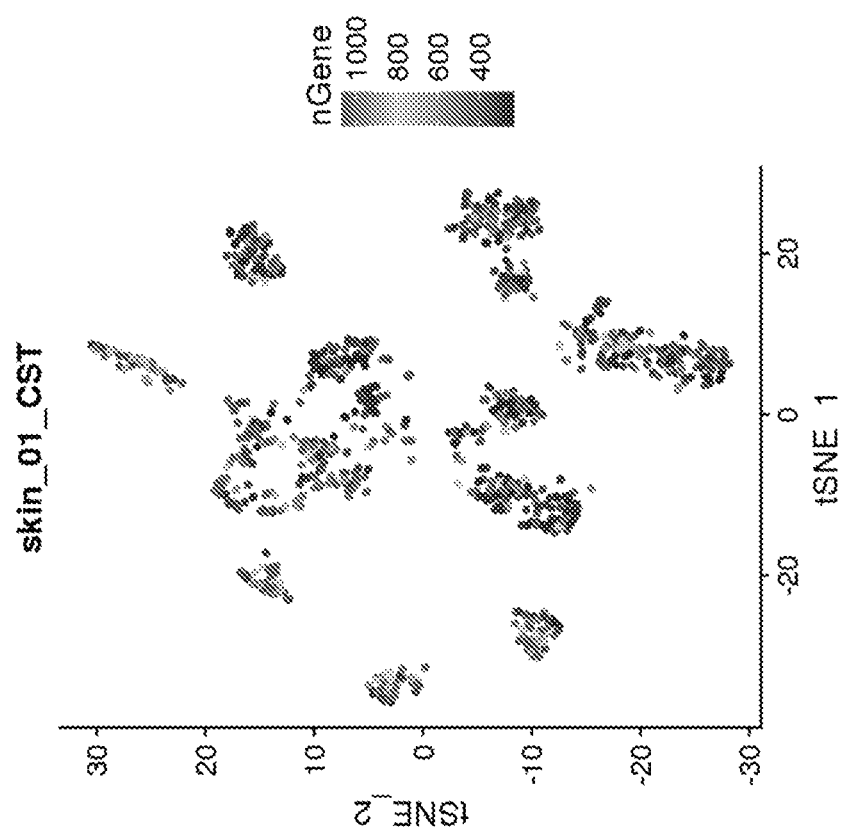
Figure 166A:
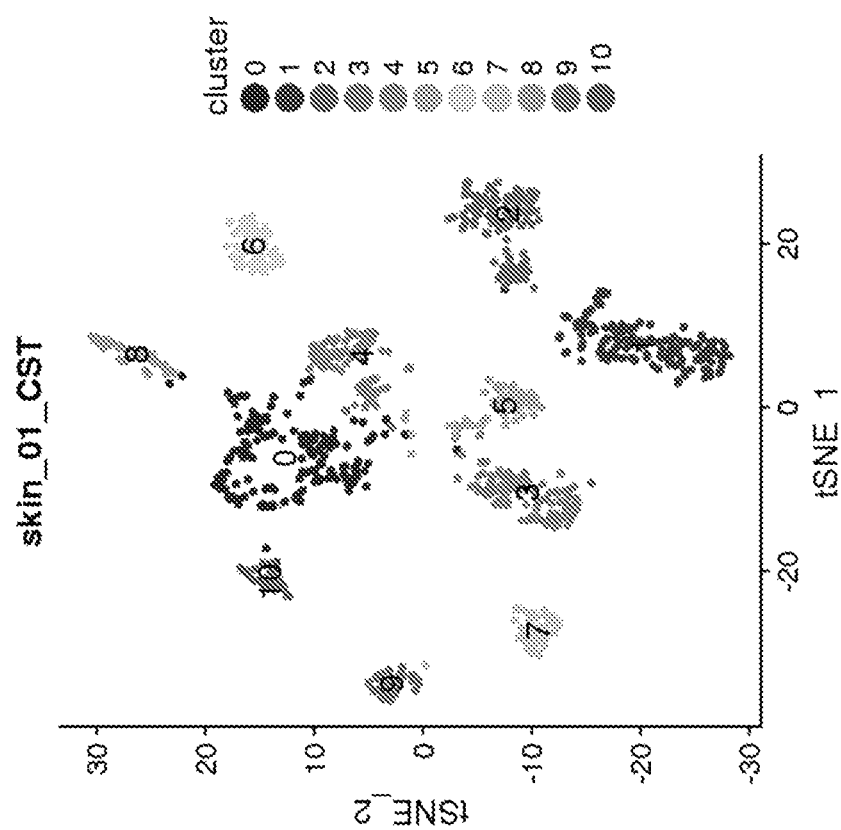

FIGS. 166A, 166B—show tSNE plots of single-nuclei RNA profiles for skin tissue samples and using the CST protocol. Shown are clusters identified by k-means clustering analysis (166A) and projection of gene expression (166B).

Figure 167B:
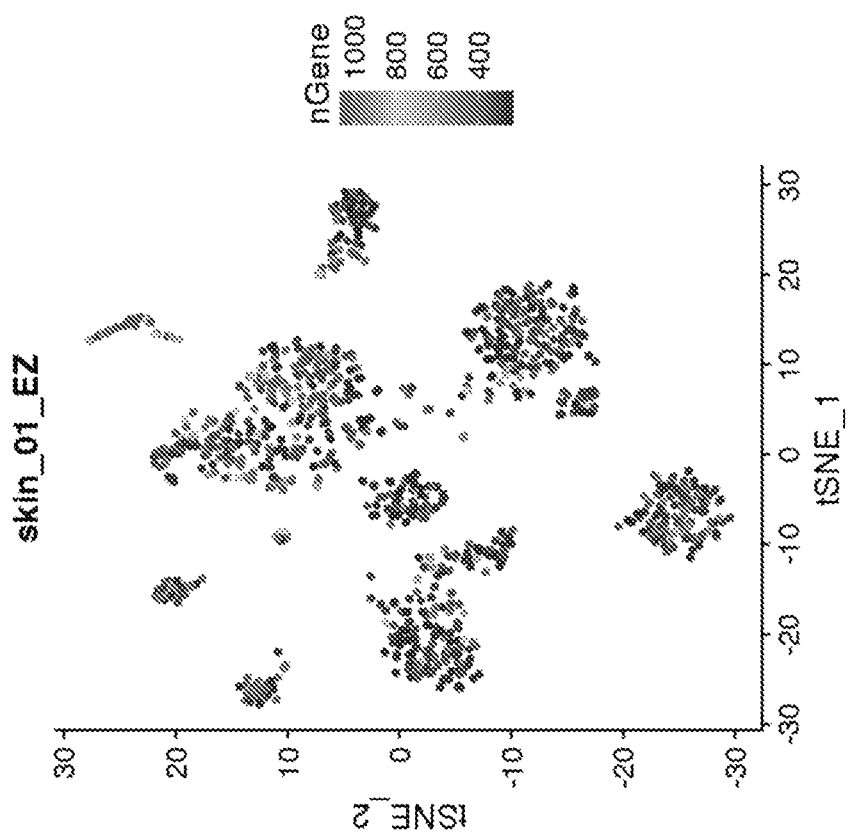
Figure 167A:
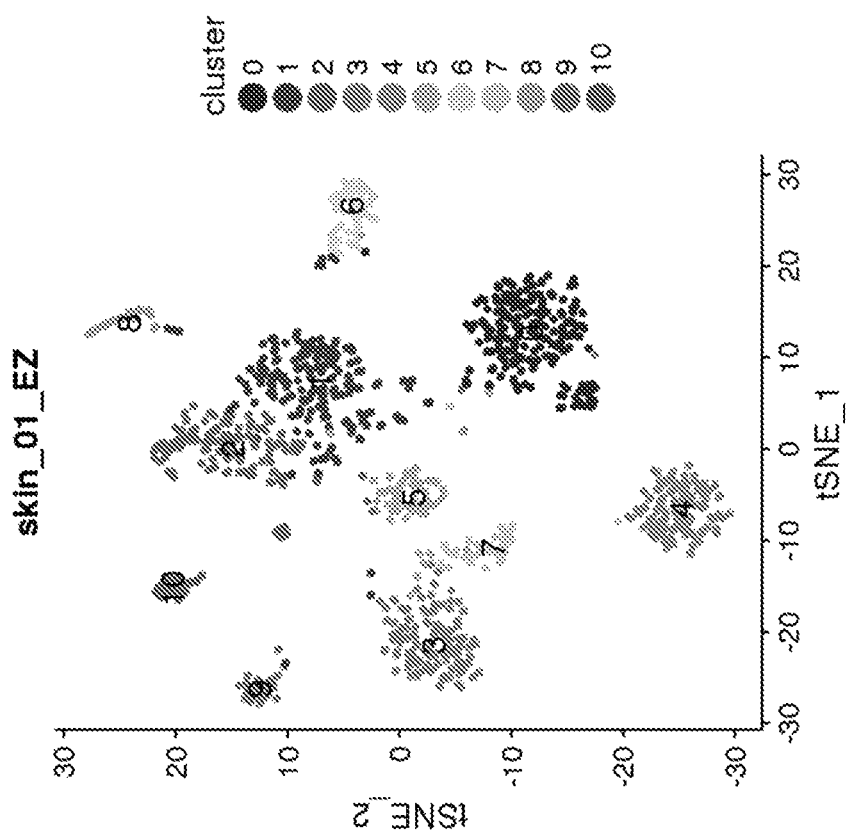

FIGS. 167A, 167B—show tSNE plots of single-nuclei RNA profiles for skin tissue samples and using the EZ protocol. Shown are clusters identified by k-means clustering analysis (167A) and projection of gene expression (167B).

Figure 168B:
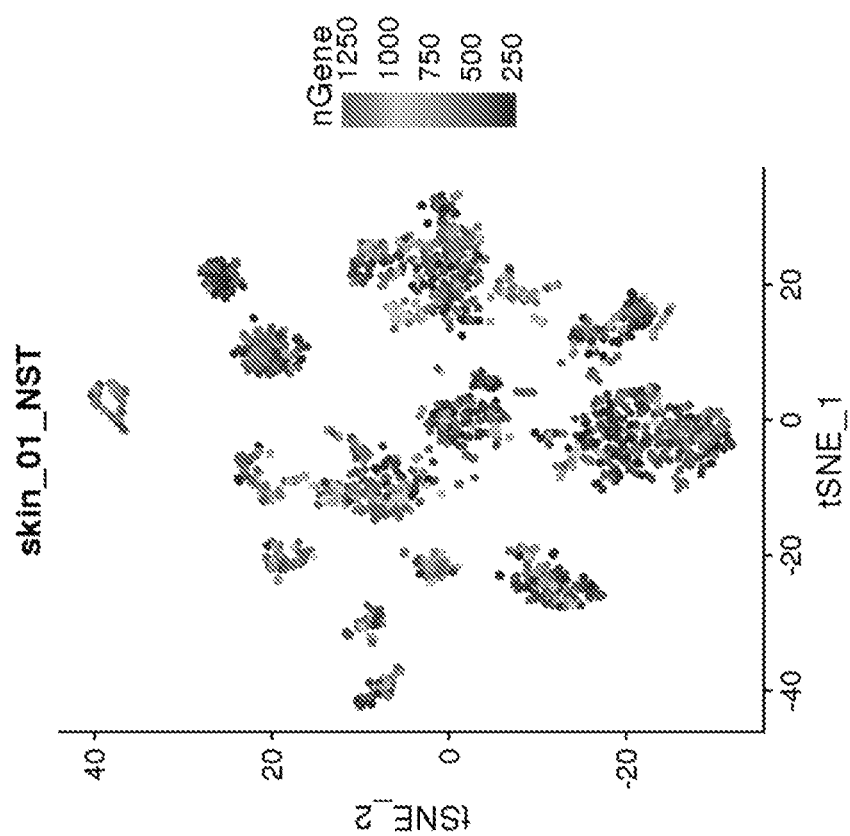
Figure 168A:
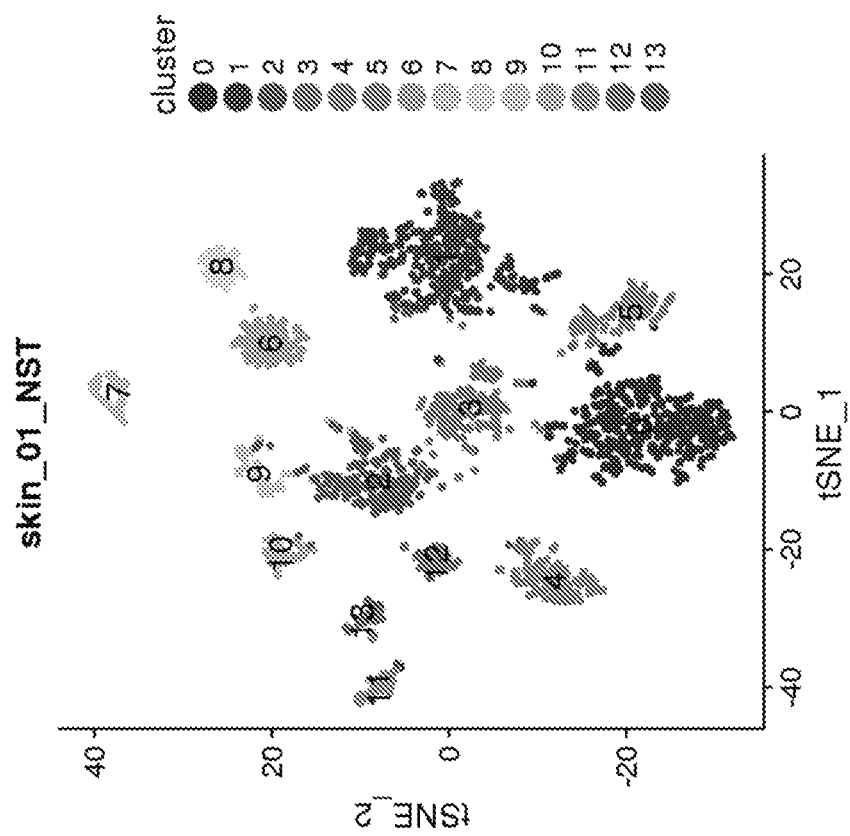

FIGS. 168A, 168B—show tSNE plots of single-nuclei RNA profiles for skin tissue samples and using the NST protocol. Shown are clusters identified by k-means clustering analysis (168A) and projection of gene expression (168B).

Figure 169A:
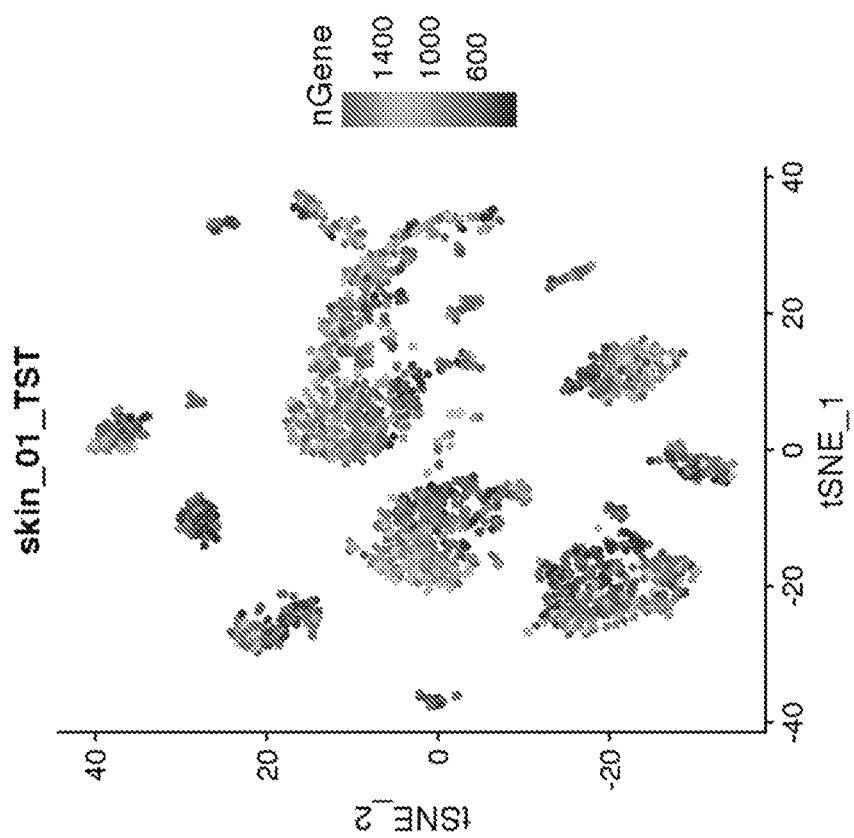
Figure 169B:
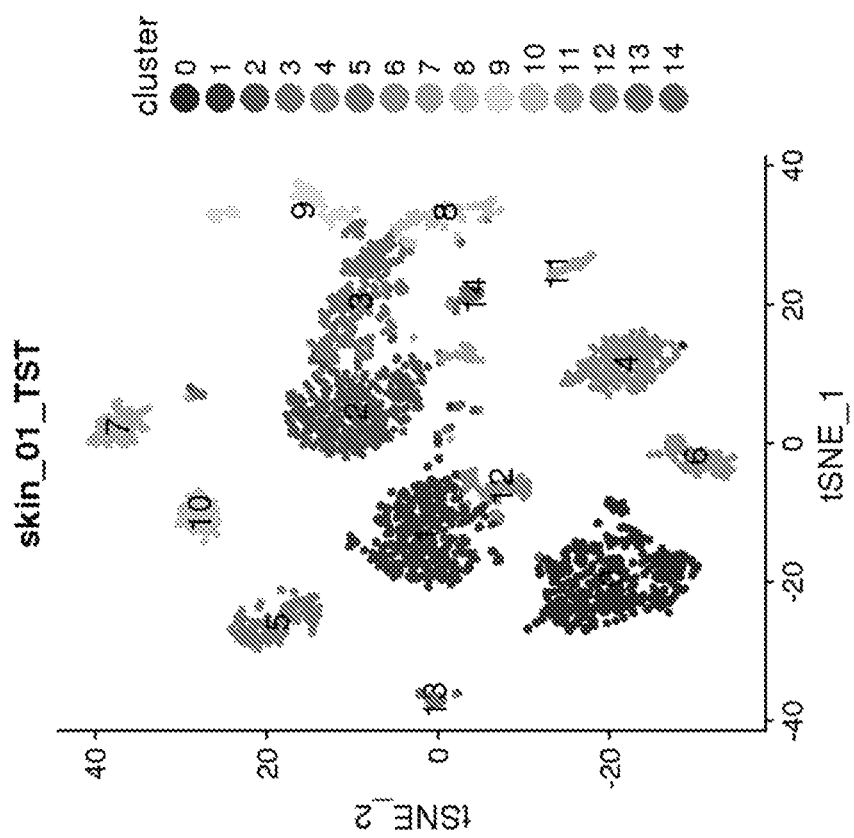

FIGS. 169A, 169B—show tSNE plots of single-nuclei RNA profiles for skin tissue samples and using the TST protocol. Shown are clusters identified by k-means clustering analysis (169A) and projection of gene expression (169B).

Figure 170:
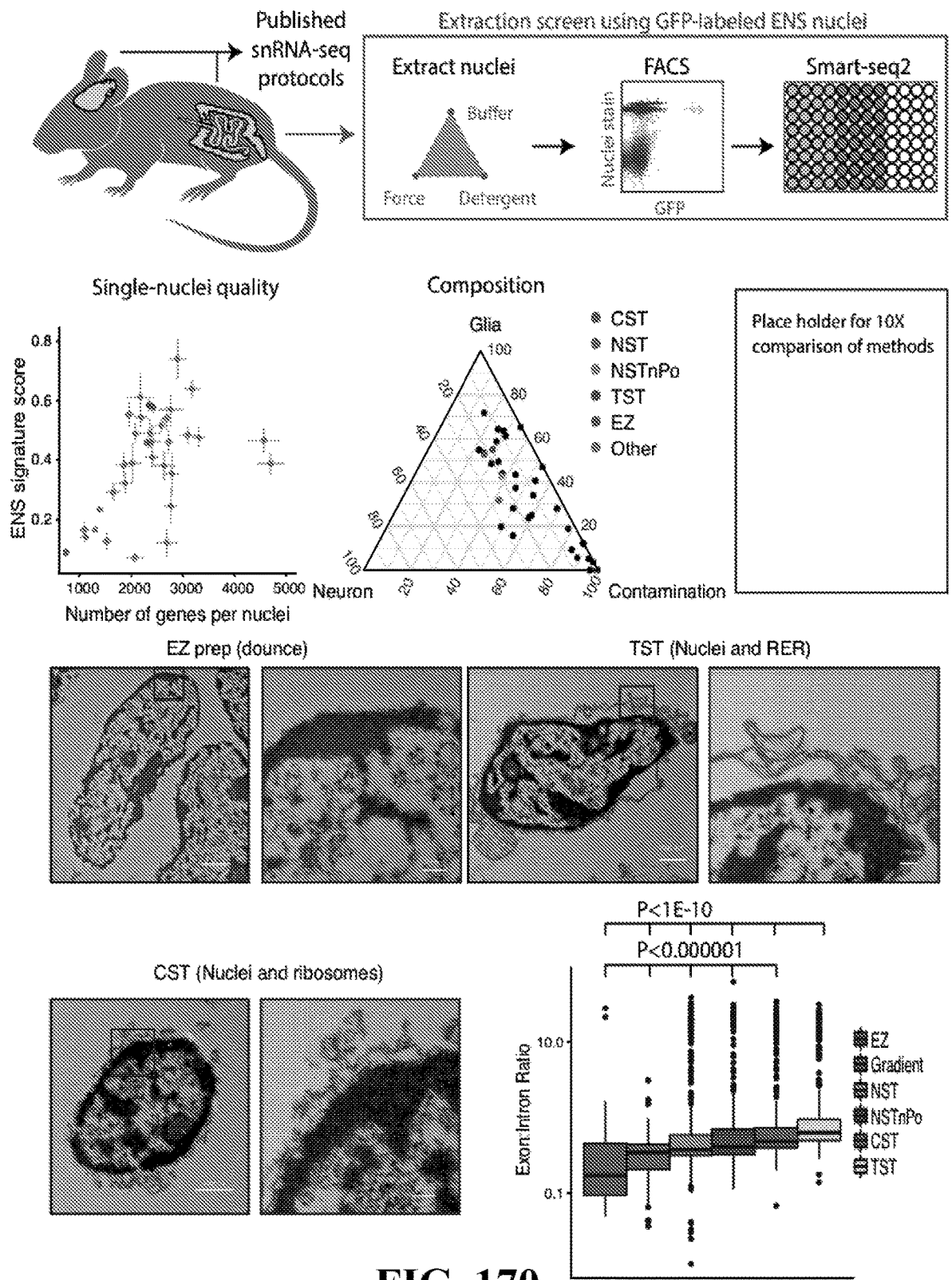

FIG. 170—shows comparison of methods for single nuclei sequencing.

DETAILED DESCRIPTION OF THE INVENTION

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F.M. Ausubel et al. eds.); the series Methods in Enzymology (Academic Press, Inc.): PCR 2: A Practical Approach (1995) (M.J. MacPherson, B.D. Hames, and G.R. Taylor eds.): Antibodies, A Laboratory Manual (1988) (Harlow and Lane, eds.): Antibodies A Laboraotry Manual, 2nd edition 2013 (E.A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "cell state" refers to a specific state of the cell, such as but not limited to an activated cell, such as activated neuron or immune cell, resting cell, such as a resting neuron or immune cell, a dividing cell, quiescent cell, or a cell during any stages of the cell cycle.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The term "developmental stage" refers to a stage of a cell that may include cell states and may include stages of development from a new born cell to a mature cell, or maturation of a progenitor undifferentiated cell, such as a stem cell, to a mature cell and all stages in between.

The terms "dimensionality reduction" or "dimension reduction" refers to the process of reducing the number of random variables under consideration, via obtaining a set "uncorrelated" principle variables.

The term "metric" refers to a mathematical function that associates a real nonnegative number analogous to distance with each pair of elements in a set such that the number is zero only if the two elements are identical, the number is the same regardless of the order in which the two elements are taken, and the number associated with one pair of elements plus that associated with one member of the pair and a third element is equal to or greater than the number associated with the other member of the pair and the third element.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

OVERVIEW

It is an object of the present invention to provide for devices and methods to allow for comprehensive analysis of gene expression in single cells obtained from heterogeneous tissues. It is another object of the present invention to identify and characterize different cell types, subtypes and cell states in a heterogeneous tissue. It is a further object of the present invention to provide methods of determining the spatial location of cell types. It is another object of the present invention to determine gene expression in cell populations based on developmental stages. The present invention advantageously provides for improved methods of determining gene expression of single cells in heterogeneous cell populations by isolating single nuclei from cells and sequencing RNA molecules. Cells may further be stained, such that cells of a single cell type and developmental stage are determined. It is further object of the present invention to provide a device or system for high throughput analysis of single nuclei. It is another object of the present invention to provide for high resolution temporal maps based on gene expression profiles.

Embodiments disclosed herein provide methods of producing a temporally phased single-cell sequencing library or determining an expression profile for a neurogenic cell comprising cells along a continuous trajectory of adult neurogenesis. To study adult neurogenesis in an unbiased manner, Applicants developed Div-Seq, a method to analyze single nuclei from recently dividing cells. Div-Seq relies on two advances. Here, Applicants developed Div-Seq, which combines Nuc-Seq, a scalable single nucleus RNA-Seq method, with EdU-mediated labeling of proliferating cells. Applicants first show that Nuc-Seq can sensitively identify closely related cell types within the adult hippocampus. Applicants apply Div-Seq to track transcriptional dynamics of newborn neurons in an adult neurogenic region in the hippocampus. Finally, Applicants find rare adult newborn GABAergic neurons in the spinal cord, a non-canonical neurogenic region. Taken together, Nuc-Seq and Div-Seq open the way for unbiased analysis of any complex tissue. Applicants apply Div-Seq to identify and profile rare newborn GABAergic neurons in the adult spinal cord, a non-canonical neurogenic region. sNuc-Seq and Div-Seq allow for unbiased analysis of diverse complex tissues.

Methods of Producing a Single-Cell Sequencing Library and Determining an Expression Profile In some embodiments, the invention provides methods of producing a temporally phased single-cell sequencing library comprising cells along a continuous trajectory of adult neurogenesis. The method may comprise treating more than one population of neurogenic cells of a single cell type or subtype, or optionally a heterogeneous cell type, with a nucleoside analogue, wherein the nucleoside analogue is incorporated into replicating DNA and is configured for labeling with a detectable marker; isolating a first population of neurogenic cells at one time point and isolating at least one other population of neurogenic cells at a later time point, optionally, isolating single nuclei from the isolated populations of neurogenic cells; staining the nucleoside analogue incorporated into replicated DNA with the detectable marker within each population of neurogenic cells or single nuclei isolated from each population of neurogenic cells, wherein the DNA is stained with the detectable marker; sorting the stained and/or unstained neurogenic cells or optionally, sorting the stained and/or unstained single nuclei into separate reaction vessels; and sequencing the RNA from the sorted single neurogenic cells or optionally, sorted single nuclei, whereby single cell gene expression data is obtained for neurogenic cells at different stages of neurogenesis.

The invention also provides a method of determining an expression profile for a neurogenic cell along a continuous trajectory of adult neurogenesis comprising: treating more than one population of neurogenic cells of a single cell type or subtype, or optionally a heterogeneous cell type, with a nucleoside analogue, wherein the nucleoside analogue is incorporated into replicating DNA and is configured for labeling with a detectable marker; isolating a first population of neurogenic cells at one time point and isolating at least one other population of neurogenic cells at a later time point, optionally, isolating single nuclei from the isolated populations of cells; staining the nucleoside analogue incorporated into replicated DNA with the detectable marker within each population of neurogenic cells or single nuclei isolated from each population of neurogenic cells, wherein the DNA is stained with the detectable marker; sorting the stained and/or unstained neurogenic cells or optionally, sorting the stained and/or unstained single nuclei into separate reaction vessels; sequencing the RNA from the sorted single neurogenic cells or optionally, sorted single nuclei, whereby single cell gene expression data is obtained for neurogenic lineage cells at different stages of maturation; and determining an expression profile for each identified cell or cell sub-type based on the gene expression data.

Single Cell Sequencing

In one embodiment, single cell or single nuclei analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment, single cell or single nuclei analysis is performed using microfluidics. Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No.WO2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353 A2; Zilionis, et al., 2017, "Single-cell barcoding and sequencing using droplet microfluidics" Nat Protoc. Jan;12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; and Rosenberg et al., 2017, "Scaling single cell transcriptomics through split pool barcoding" bioRxiv preprint first posted online Feb. 2, 2017, doi: dx.doi.org/10.1101/105163, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, both of which are herein incorporated by reference in their entirety.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single cell analysis is performed in droplets using methods according to WO2014085802. Each of these patents and publications is herein incorporated by reference in their entireties for all purposes.

Single cells or nuclei may be sorted into separate vessels by dilution of the sample and physical movement, such as micromanipulation devices or pipetting. A computer controlled machine may control pipetting and separation.

Single cells or single nuclei of the present invention may be divided into single droplets using a microfluidic device. The single cells or nuclei in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-1201 all the contents and disclosure of each of which are herein incorporated by reference in their entirety. Not being bound by a theory, the volume size of an aliquot within a droplet may be as small as 1 fL.

The present invention may include barcoding. Barcoding may be performed based on any of the compositions or methods disclosed in patent publication WO2014047561 A1, Compositions and methods for labeling of agents, incorporated herein in its entirety. Not being bound by a theory, amplified sequences from single cells or nuclei can be sequenced together and resolved based on the barcode associated with each cell or nuclei.

The term "barcode" as used herein, refers to any unique, non-naturally occurring, nucleic acid sequence that may be used to identify the originating source of a nucleic acid fragment. Such barcodes may be sequences including but not limited to, TTGAGCCT (SEQ ID NO:1), AGTTGCTT (SEQ ID NO: 2), CCAGTTAG (SEQ ID NO: 3), ACCAACTG (SEQ ID NO:4), GTATAACA (SEQ ID NO: 5) or CAGGAGCC (SEQ ID NO: 6). Although it is not necessary to understand the mechanism of an invention, it is believed that the barcode sequence provides a high-quality individual read of a barcode associated with a viral vector, labeling ligand, shRNA, sgRNA, cDNA, cell or nuclei, such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequenceable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. Feb 17;106(7): 2289-94). In one embodiment, the invention provides a method for preparing uniquely barcoded particles. Unique barcoded particles may be generated by a split pool method.

Single cells or single nuclei may be diluted into a physical multi-well plate or a plate free environment. The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. Plate free environments of the present invention utilize a single polymerizable gel containing compartmentalized cells or single nuclei. In one embodiment, extraction of single cells or single nuclei may be by a mechanical punch. Single cells or single nuclei may be visualized in the gel before a punch.

In one embodiment, to ensure proper staining of intracellular and intranuclear proteins and nucleic acids single cells or nuclei are embedded in hydrogel droplets. Not being bound by a theory, the hydrogel mesh provides a physical framework, chemically incorporates biomolecules and is permeable to macromolecules such as antibodies (Chung et al., (2013). Structural and molecular interrogation of intact biological systems. Nature 497, 332-337). In one embodiment, to further improve permeability and staining efficiency, lipids are cleared (Chung et al., 2013). Not being bound by a theory, the clearance of the lipids and the porosity of the hydrogel allow for more efficient washing. This higher accuracy of measurement is important for the high multiplex measurements and computational inference of regulatory mechanisms.

In one embodiment, the nucleic acids of single cells or nuclei are crosslinked to prevent loss of nucleic acids. Not being bound by a theory, leakage of mRNA from nuclei may be prevented by crosslinking. Nucleic acids can be reverse cross-linked after separation of cells or nuclei into separate wells or droplets. The contents of individual wells or droplets may then be sequenced. In one embodiment, crosslinking may be reversed by incubating the cross-linked sample in high salt (approximately 200 mM NaCl) at 65° C. for at least 4h.

The invention provides a nucleotide- or oligonucleotide-adorned bead wherein said bead comprises: a linker; an identical sequence for use as a sequencing priming site; a uniform or near-uniform nucleotide or oligonucleotide sequence; a Unique Molecular Identifier which differs for each priming site; optionally an oligonucleotide redundant sequence for capturing polyadenylated mRNAs and priming reverse transcription; and optionally at least one other oligonucleotide barcode which provides an additional substrate for identification.

In an embodiment of the invention, the nucleotide or oligonucleotide sequences on the surface of the bead is a molecular barcode. In a further embodiment the barcode ranges from 4 to 1000 nucleotides in length. In another embodiment, the oligonucleotide sequence for capturing polyadenylated mRNAs and priming reverse transcription is an oligo dT sequence.

In an embodiment of the invention, the linker is a non-cleavable, straight-chain polymer. In another embodiment, the linker is a chemically-cleavable, straight-chain polymer. In a further embodiment, the linker is a non-cleavable, optionally substituted hydrocarbon polymer. In another embodiment, the linker is a photolabile optionally substituted hydrocarbon polymer. In another embodiment, the linker is a polyethylene glycol. In an embodiment, the linker is a PEG-C3 to PEG-24.

The invention provides a mixture comprising a plurality of nucleotide- or oligonucleotide-adorned beads, wherein said beads comprises: a linker; an identical sequence for use as a sequencing priming site; a uniform or near-uniform nucleotide or oligonucleotide sequence; a Unique Molecular Identifier (UMI) which differs for each priming site; an oligonucleotide redundant sequence for capturing polyadenylated mRNAs and priming reverse transcription; and optionally at least one additional oligonucleotide sequences, which provide substrates for downstream molecular-biological reactions; wherein the uniform or near-uniform nucleotide or oligonucleotide sequence is the same across all the priming sites on any one bead, but varies among the oligonucleotides on an individual bead.

In an embodiment of the invention, the nucleotide or oligonucleotide sequence on the surface of the bead is a molecular barcode. In a further embodiment the barcode ranges from 4 to 1000 nucleotides in length. In another embodiment, the oligonucleotide sequence for capturing polyadenylated mRNAs and priming reverse transcription is an oligo dT sequence.

In an embodiment of the invention, the mixture comprises at least one oligonucleotide sequence, which provides for substrates for downstream molecular-biological reactions. In another embodiment, the downstream molecular biological reactions are for reverse transcription of mature mRNAs; capturing specific portions of the transcriptome, priming for DNA polymerases and/or similar enzymes; or priming throughout the transcriptome or genome. In an embodiment of the invention, the additional oligonucleotide sequence comprises a oligio-dT sequence. In another embodiment of the invention, the additional oligonucleotide sequence comprises a primer sequence. In an embodiment of the invention, the additional oligonucleotide sequence comprises a oligio-dT sequence and a primer sequence.

The invention provides an error-correcting barcode bead wherein said bead comprises: a linker; an identical sequence for use as a sequencing priming site; a uniform or near-uniform nucleotide or oligonucleotide sequence which comprises at least a nucleotide base duplicate; a Unique Molecular Identifier which differs for each priming site; and an oligonucleotide redudant for capturing polyadenylated mRNAs and priming reverse transcription.

In an embodiment of the invention, the error-correcting barcode beads fail to hybridize to the mRNA thereby failing to undergo reverse transcription.

The invention also provides a kit which comprises a mixture of oligonucleotide bound beads and self-correcting barcode beads.

The invention provides a method for creating a single-cell sequencing library comprising: merging one uniquely barcoded RNA capture microbead with a single-cell in an emulsion droplet having a diameter from 50 µm to 210 µm; lysing the cell thereby capturing the RNA on the RNA capture microbead; breaking droplets and pooling beads in solution; performing a reverse transcription reaction to convert the cells' RNA to first strand cDNA that is covalently linked to the RNA capture microbead; or conversely reverse transcribing within droplets and thereafter breaking droplets and collecting cDNA-attached beads; preparing and sequencing a single composite RNA-Seq library, containing cell barcodes that record the cell-of-origin of each RNA, and molecular barcodes that distinguish among RNAs from the same cell.

In another aspect, the present invention provides for a method for creating a composite single nuclei sequencing library comprising: merging one uniquely barcoded RNA capture microbead with a single nuclei in an emulsion droplet having a diameter from 50 µm to 210 µm, wherein the single nuclei is blocked with a nuclear pore blocking polymer; extracting mRNA onto on the RNA capture microbead; performing a reverse transcription reaction to convert the mRNA to first strand cDNA that is covalently linked to the RNA capture microbead; or conversely reverse transcribing within droplets and thereafter breaking droplets and collecting cDNA-attached beads; preparing and sequencing a single composite RNA-Seq library, containing cell barcodes that record the cell-of-origin of each RNA, and unique molecular identifiers (UMI) that distinguish among RNAs from the same cell.

In an embodiment the diameter of the emulsion droplet is between 50-210 µm. In a further embodiment, the method wherein the diameter of the mRNA capture microbeads is from 10 µm to 95 µm. In a further embodiment the diameter of the emulsion droplet is 90 µm.

The invention provides a method for preparing a plurality of beads with unique nucleic acid sequences comprising: performing polynucleotide synthesis on the surface of the plurality of beads in a pool-and-split process, such that in each cycle of synthesis the beads are split into a plurality of subsets wherein each subset is subjected to different chemical reactions; repeating the pool-and-split process from anywhere from 2 cycles to 200 cycles.

In an embodiment of the invention the polynucleotide synthesis is phosphoramidite synthesis. In another embodiment of the invention the polynucleotide synthesis is reverse direction phosphoramidite chemistry. In an embodiment of the invention, each subset is subjected to a different nucleotide. In another embodiment, each subset is subjected to a different canonical nucleotide. In an embodiment of the invention the method is repeated three, four, or twelve times.

In an embodiment the covalent bond is polyethylene glycol. In another embodiment the diameter of the mRNA capture microbeads is from 10 µm to 95 µm. In an embodiment, wherein the multiple steps is twelve steps.

In a further embodiment the method further comprises a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A); 2) repeating this process a large number of times, at least six, and optimally more than twelve, such that, in the latter, there are more than 16 million unique barcodes on the surface of each bead in the pool.

In an embodiment, the diameter of the mRNA capture microbeads is from 10 µm to 95 µm.

The invention provides a method for simultaneously preparing a plurality of nucleotide- or oligonucleotide-adorned beads wherein a uniform, near-uniform, or patterned nucleotide or oligonucleotide sequence is synthesized upon any individual bead while vast numbers of different nucleotide or oligonucleotide sequences are simultaneously synthesized on different beads, comprising: forming a mixture comprising a plurality of beads; separating the beads into subsets; extending the nucleotide or oligonucleotide sequence on the surface of the beads by adding an individual nucleotide via chemical synthesis; pooling the subsets of beads in (c) into a single common pool; repeating steps (b), (c) and (d) multiple times to produce a combinatorially a thousand or more nucleotide or oligonucleotide sequences; and collecting the nucleotide- or oligonucleotide-adorned beads.

In an embodiment of the invention, the nucleotide or oligonucleotide sequence on the surface of the bead is a molecular barcode. In a further embodiment, the pool-and-split synthesis steps occur every 2-10 cycles, rather than every cycle.

In an embodiment of the invention, the barcode contains built-in error correction. In another embodiment, the barcode ranges from 4 to 1000 nucleotides in length. In embodiment of the invention the polynucleotide synthesis is phosphoramidite synthesis. In a further embodiment, the polynucleotide synthesis is reverse direction phosphoramidite chemistry. In an embodiment of the invention each subset is subjected to a different nucleotide. In a further embodiment, one or more subsets receive a cocktail of two nucleotides. In an embodiment, each subset is subjected to a different canonical nucleotide.

The method provided by the invention contemplates a variety of embodiments wherein the bead is a microbead, a nanoparticle, or a macrobead. Similarly, the invention contemplates that the oligonucleotide sequence is a dinucleotide or trinucleotide.

The invention provides a method for simultaneously preparing a thousand or more nucleotide- or oligonucleotide-adorned beads wherein a uniform or near-uniform nucleotide or oligonucleotide sequence is synthesized upon any individual bead while a plurality of different nucleotide or oligonucleotide sequences are simultaneously synthesized on different beads, comprising: forming a mixture comprising a plurality of beads; separating the beads into subsets; extending the nucleotide or oligonucleotide sequence on the surface of the beads by adding an individual nucleotide via chemical synthesis; pooling the subsets of beads in (c) into a single common pool; repeating steps (b), (c) and (d) multiple times to produce a combinatorically large number of nucleotide or oligonucleotide sequences; and collecting the nucleotide- or oligonucleotide-adorned beads; performing polynucleotide synthesis on the surface of the plurality of beads in a pool-and-split synthesis, such that in each cycle of synthesis the beads are split into a plurality of subsets wherein each subset is subjected to different chemical reactions; repeating the pool-and-split synthesis multiple times.

In an embodiment of the invention, the nucleotide or oligonucleotide sequence on the surface of the bead is a molecular barcode. In an embodiment, the pool-and-split synthesis steps occur every 2 to 10 cycles, rather than every cycle. In an embodiment, the generated barcode contains built-in error correction. In another embodiment, the barcode ranges from 4 to 1000 nucleotides in length. In embodiment of the invention the polynucleotide synthesis is phosphoramidite synthesis. In a further embodiment, the polynucleotide synthesis is reverse direction phosphoramidite chemistry. In an embodiment of the invention each subset is subjected to a different nucleotide. In a further embodiment, one or more subsets receive a cocktail of two nucleotides. In an embodiment, each subset is subjected to a different canonical nucleotide.

The method provided by the invention contemplates a variety of embodiments wherein the bead is a microbead, a nanoparticle, or a macrobead. Similarly, the invention contemplates that the oligonucleotide sequence is a dinucleotide or trinucleotide.

The invention further provides an apparatus for creating a composite single-cell sequencing library via a microfluidic system, comprising: an oil-surfactant inlet comprising a filter and two carrier fluid channels, wherein said carrier fluid channel further comprises a resistor; an inlet for an analyte comprising a filter and two carrier fluid channels, wherein said carrier fluid channel further comprises a resistor; an inlet for mRNA capture microbeads and lysis reagent comprising a carrier fluid channel; said carrier fluid channels have a carrier fluid flowing therein at an adjustable and predetermined flow rate; wherein each said carrier fluid channels merge at a junction; and said junction being connected to a constriction for droplet pinch-off followed by a mixer, which connects to an outlet for drops.

In an embodiment of the apparatus, the analyte comprises a chemical reagent, a genetically perturbed cell, a protein, a drug, an antibody, an enzyme, a nucleic acid, an organelle like the mitochondrion or nucleus, a cell or any combination thereof. In an embodiment of the apparatus the analyte is a cell. In a further embodiment, the analyte is a mammalian cell. In another embodiment, the analyte of the apparatus is complex tissue. In a further embodiment, the cell is a brain cell. In an embodiment of the invention, the cell is a retina cell. In another embodiment the cell is a human bone marrow cell. In an embodiment, the cell is a host-pathogen cell. In an embodiment, the analyte is a nucleus from a cell.

In an embodiment of the apparatus the lysis reagent comprises an anionic surfactant such as sodium lauroyl sarcosinate, or a chaotropic salt such as guanidinium thiocyanate. In an embodiment of the apparatus the filter is consists of square PDMS posts; the filter on the cell channel consists of such posts with sides ranging between 125-135 µm with a separation of 70-100 mm between the posts. The filter on the oil-surfactant inlet comprises square posts of two sizes; one with sides ranging between 75-100 µm and a separation of 25-30 µm between them and the other with sides ranging between 40-50 µm and a separation of 10-15 µm. In an embodiment of the apparatus the resistor is serpentine having a length of 7000-9000 µm, width of 50-75 µm and depth of 100-150 mm. In an embodiment of the apparatus the channels have a length of 8000-12,000 µm for oil-surfactant inlet, 5000-7000 for analyte (cell) inlet, and 900-1200 µm for the inlet for microbead and lysis agent. All channels have a width of 125-250 mm, and depth of 100-150 mm. In another embodiment, the width of the cell channel is 125-250 µm and the depth is 100-150 µm. In an embodiment of the apparatus the mixer has a length of 7000-9000 µm, and a width of 110-140 µm with 35-45° zig-zigs every 150 µm. In an embodiment, the width of the mixer is 125 µm. In an embodiment of the apparatus the oil-surfactant is PEG Block Polymer, such as BIORAD™ QX200 Droplet Generation Oil. In an embodiment of the apparatus the carrier fluid is water-glycerol mixture.

A mixture comprising a plurality of microbeads adorned with combinations of the following elements: bead-specific oligonucleotide barcodes created by the methods provided; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

In another embodiment, a mixture comprising a plurality of microbeads, wherein said microbeads comprise the following elements: at least one bead-specific oligonucleotide barcode obtainable by the process outlined; at least one additional identifier oligonucleotide barcode sequence, which varies among the oligonucleotides on an individual bead, and thereby assisting in the identification and of the bead specific oligonucleotide molecules; optionally at least one additional oligonucleotide sequences, which provide substrates for downstream molecular-biological reactions. In another embodiment the mixture comprises at least one oligonucleotide sequences, which provide for substrates for downstream molecular-biological reactions. In a further embodiment the downstream molecular biological reactions are for reverse transcription of mature mRNAs; capturing specific portions of the transcriptome, priming for DNA polymerases and/or similar enzymes; or priming throughout the transcriptome or genome. In a further embodiment the mixture the additional oligonucleotide sequence comprising a oligio-dT sequence. In another embodiment the mixture further comprises the additional oligonucleotide sequence comprises a primer sequence. In another embodiment the mixture further comprises the additional oligonucleotide sequence comprising a oligio-dT sequence and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl) maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2', 7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.TM. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N" tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

The invention described herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organellesor single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide thousands of single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue (e.g., retinal or human bone marrow), peripheral blood mononuclear cell, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A variety of analytes may be contemplated for use with the foregoing Drop-Sequencing methods. Examples of cells which are contemplated are mammalian cells, however the invention contemplates a method for profiling host-pathogen cells. To characterize the expression of host-pathogen interactions it is important to grow the host and pathogen in the same cell without multiple opportunities of pathogen infection.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell or nuclei per droplet with only a few droplets containing more than one cell or nuclei when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, nuclei, small molecules, DNA, primers, antibodies. Smaller droplets may be in the order of femtoliter (fL) volume drops, which are especially contemplated with the droplet dispensors. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil which may comprise at least one fluorosurfactant thereby forming an emulsion library.

In specific embodiments, the method comprises treating more than one population of neurogenic cells of a single cell type or subtype, or optionally a heterogeneous cell type, with a nucleoside analogue.

Neurogenesis is the process by which nervous system cells, known as neurons, are produced by neuronal stem cells. Types of neuronal stem cells include neuroepithelial cells, radial glial cells, basal progenitors, intermediate neuronal precursors, subventricular zone astrocytes, and subgranular zone radial astrocytes, among others. Neurogenesis is most active during embryonic development, and is responsible for producing all the various types of neurons of the organism, but continues throughout adult life in a variety of organisms. Once born, neurons do not divide, and many will live the lifetime of the animal.

Compared to developmental neurogenesis, adult neurogenesis has been shown to occur at low levels, and only in two regions of the brain: the adult subventricular zone of the striatum, and the dentate gyrus of the hippocampus.

Heterogeneous cell types are cells that are of mixed, diverse, different, assorted, or varied phenotype. Such variations in cell phenotype in a single-cell-derived clone may result from asymmetric cell divisions that lead to different cell fate in a homogenous microenvironment.

The heterogeneous population of cells may be derived from a section of a tissue or a tumor from a subject. Accordingly, the term "cell population" or "population" can denote a set of cells having one or more characteristics in common, which may be, for example, source derivation. The section may be obtained by microdissection. The tissue may be nervous tissue. The nervous tissue may be isolated from the brain, spinal cord or retina. The heterogeneous population of cells may be a population of cells grown in tissue culture. The cells grown in tissue culture may be neurons. The cells grown in tissue culture may be immune cells.

In certain embodiments, nucleic acids are treated or labeled with a nucleoside analogue. The nucleoside analogue may be any nucleoside analogue known in the art or developed after the filing of the present invention that is incorporated into replicating DNA and can be detectable by a label. The label may be incorporated into the nucleoside analogue or may include a labeling step after incorporation into DNA with a detectable label. In preferred embodiments, the label is a fluorescent label. In certain embodiments, the nucleoside analogue may be EdU (5-ethynyl-2'-deoxyuridine) or BrdU (5-bromo-2'-deoxyuridine).

The treating more than one population of cells of a single cell type or subtype, or optionally a heterogeneous cell type with a nucleoside analogue may be performed in at least one subject. The subject may be a mouse. The isolating one population of cells may comprise dissection of a tissue from the subject. The tissue may be nervous tissue. The nervous tissue may be isolated from the brain, spinal cord or retina. The population of cells may be a population of cells grown in tissue culture. The cells grown in tissue culture may comprise neurons. The cells grown in tissue culture may be immune cells.

In specific embodiments, the method further comprises isolating a first population of neurogenic cells at one time point and isolating at least one other population of neurogenic cells at a later time point, optionally, isolating single nuclei from the isolated populations of neurogenic cells.

As outlined in the Examples, Applicants have unexpectedly determined that single nuclei comprising a portion of the rough endoplasmic reticulum (RER) can be isolated and the resulting nuclei provides for improved RNA recovery and single cell expression profiling. In some embodiments, the methods provide for isolation of single nuclei with partially intact outer membrane containing RER. In some embodiments, the methods allow for isolation of single nuclei with partially intact outer membrane and partially intact RER with ribosomes. In some embodiments, the methods allow for isolation of single nuclei with partially intact outer membrane, RER and mitochondria.

In specific embodiments, the method further comprises staining the nucleoside analogue incorporated into replicated DNA with the detectable marker within each population of neurogenic cells or single nuclei isolated from each population of neurogenic cells, wherein the DNA is stained with the detectable marker. Typical detectable markers may include labels or reporter molecules such as radioactive isotopes, enzyme substrates, co-factors, ligands, chemiluminescent or fluorescent agents, haptens, and enzymes.

In specific embodiments, the method further comprises sorting the stained and/or unstained neurogenic cells or optionally, sorting the stained and/or unstained single nuclei into separate reaction vessels. The single nuclei may be sorted into single wells of a plate by FACS. The sorting single nuclei into separate reaction vessels may comprise microfluidics. The single nuclei may be sorted into individual chambers on a microfluidic chip. In certain embodiments, the separate reaction vessels may be microwells in a plate. In certain embodiments, the separate reaction vessels may be microfluidic droplets.

In specific embodiments, the method further comprises sequencing the RNA from the sorted single neurogenic cells as described herein, or optionally, sorted single nuclei, whereby single cell gene expression data are obtained for neurogenic cells at different stages of neurogenesis. In certain embodiments, the invention provides single nucleus RNA sequencing, as described herein.

The invention provides for a method of single cell sequencing comprising: extracting nuclei from a population of cells under conditions that preserve: (1) a portion of the outer nuclear envelope with attached ribosomes, or (2) a portion of the outer nuclear membrane and a portion of the rough endoplasmic reticulum (RER) with ribosomes, or (3) a portion of the outer nuclear membrane, a portion of the rough endoplasmic reticulum (RER), and a portion of mitochondria; sorting single nuclei into separate reaction vessels; extracting RNA from the single nuclei; generating a cDNA library; and sequencing the library, whereby gene expression data from single cells is obtained. In some embodiments, the reaction vessels may be single cell droplets.

Methods of Producing Expression Profiles

In embodiments involving determining an expression profile for a neurogenic cell along a continuous trajectory of adult neurogenesis, the method may further comprise determining an expression profile for each identified cell or cell sub-type based on the gene expression data.

As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., neurogenic cell). In certain embodiments, the signature is dependent on epigenetic modification of the genes or regulatory elements associated with the genes (e.g., methylation, ubiquitination). Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", "transcription profile" or "expression program" may be used interchangeably. It is to be understood that also when referring to proteins (e.g. differentially expressed proteins), such may fall within the definition of "gene" signature. Levels of expression or activity may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub) population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. nervous tissue), thus allowing the discovery of novel cell subtypes or cell states that were previously invisible or unrecognized, for example, adult newborn neurons. The presence of subtypes or cell states may be determined by subtype specific or cell state specific signatures. The presence of these specific cell (sub)types or cell states may be determined by applying the signature genes to bulk sequencing data in a sample. The signatures of the present invention may be microenvironment specific, such as their expression in a particular spatio-temporal context. In certain embodiments, signatures as discussed herein are specific to a particular developmental stage or pathological context. In certain embodiments, a combination of cell subtypes having a particular signature may indicate an outcome. The signatures may be used to deconvolute the network of cells present in a particular developmental stage or pathological condition. The presence of specific cells and cell subtypes may also be indicative of a particular developmental stage, a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular stages of development or particular pathological condition, or linked to a particular outcome or progression of the disease, or linked to a particular response to treatment of the disease (e.g. resistance to therapy).

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different neurogenic cells, for example, neuronal stem cells, neuronal precursor cells, neuroblasts, immature neurons and newborn neurons, as well as comparing immune cells or immune cell (sub)populations with other immune cells or immune cell (sub)populations. It is to be understood that "differentially expressed" genes/proteins include genes/proteins which are up- or down-regulated as well as genes/proteins which are turned on or off. When referring to up-or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). Cmap can be used to screen for drugs capable of modulating an OPC-like signature in silico.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., proliferating) which can be distinguished or are uniquely identifiable and set apart from other cells of this cell type. The cell subpopulation may be phenotypically characterized, and is preferably characterized by the signature as discussed herein. A cell (sub) population as referred to herein may constitute a (sub) population of cells of a particular cell type characterized by a specific cell state.

When referring to induction, or alternatively reducing or suppression of a particular signature, preferable is meant induction or alternatively reduction or suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signatures, and/or other genetic or epigenetic signatures based on single cell analyses (e.g. single cell RNA sequencing) or alternatively based on cell population analyses, as is defined herein elsewhere.

The invention further relates to various uses of the gene signatures, protein signature, and/or other genetic or epigenetic signature as defined herein. Particular advantageous uses include methods for identifying agents capable of inducing or suppressing neurogenesis, particularly inducing or suppressing neurogenic cell(sub)populations based on the gene signatures, protein signature, and/or other genetic or epigenetic signature as defined herein. The invention further relates to agents capable of inducing or suppressing particular neurogenic cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modulate neurogenesis, and/or neurogeneic cell subpopulation composition or distribution, or functionality.

The signature genes of the present invention were discovered by analysis of expression profiles of single-cells within a population of neurogenic cells, thus allowing the discovery of novel cell subtypes that were previously invisible or rare in a population of cells within the nervous tissue. The presence of subtypes may be determined by subtype specific signature genes. The presence of these specific cell types may be determined by applying the signature genes to bulk sequencing data in a patient. Not being bound by a theory, many cells make up a microenvironment, whereby the cells communicate and affect each other in specific ways. As such, specific cell types within this microenvironment may express signature genes specific for this microenvironment. Not being bound by a theory the signature genes of the present invention may be microenvironment specific. The signature genes may indicate the presence of one particular cell type. In one embodiment, the expression may indicate the presence of proliferating cell types. Not being bound by a theory, a combination of cell subtypes in a subject may indicate an outcome.

In specific embodiments of the method described above, neurogenesis occurs in the adult brain.

In specific embodiments, neurogenesis occurs in the dorsal ganglion (DG).

In specific embodiments, neurogenesis occurs in the adult spinal cord.

In some embodiments, the neurogenic cell is selected from the group consisting of: a neuronal stem cell, a neuronal precursor cell, a neuroblast, an immature neuron and a newborn neuron.

Neuronal stem cells are self-renewing, multipotent cells that generate the neurons and glia of the nervous system of all animals during embryonic development. Some neural stem cells persist in the adult vertebrate brain and continue to produce neurons throughout life. Stem cells are characterized by their capacity to differentiate into multiple cell types. They undergo symmetric or asymmetric cell division into two daughter cells. In symmetric cell division, both daughter cells are also stem cells. In asymmetric division, a stem cell produces one stem cell and one specialized cell. Neuronal stem cells differentiate primarily into neurons, astrocytes, and oligodendrocytes.

The non-stem cell progeny of neural stem cells are referred to as neural progenitor cells. Neural progenitor cells have the capacity to proliferate and differentiate into more than one cell type. Neural progenitor cells can therefore be unipotent, bipotent or multipotent. A distinguishing feature of a neural progenitor cell is that, unlike a stem cell, it has a limited proliferative ability and does not exhibit self-renewal.

A neural or neuronal precursor cell refers to a mixed population of cells consisting of all undifferentiated progeny of neural stem cells, including both neural progenitor cells and neural stem cells. The term neural precursor cells is commonly used to collectively describe the mixed population of neural stem cells and neural progenitor cells derived from embryonic stem cells and induced pluripotent stem cells.

A neuroblast or primitive nerve cell is a postmitotic cell that does not divide further and which will develop into a neuron after a migration phase. Neuroblasts differentiate from neural stem cells and are committed to become neurons. Neuroblasts are mainly present as precursors of neurons during embryonic development. However, they can also contribute one of the cell types involved in adult neurogenesis. Adult neurogenesis is characterized by neural stem cell differentiation and integration in the mature adult mammalian brain. This process occurs in the dentate gyrus of the hippocampus and in the subventricular zones of the adult mammalian brain. Neuroblasts are formed when a neural stem cell, which can differentiate into any type of mature neural cell (i.e. neurons, oligodendrocytes, astrocytes, etc.), divides and becomes a transit amplifying cell. Transit amplifying cells are slightly more differentiated than neural stem cells and can divide asymmetrically to produce postmitotic neuroblasts and glioblasts, as well as other transit amplifying cells. A neuroblast, a daughter cell of a transit amplifying cell, is initially a neural stem cell that has reached the "point of no return". A neuroblast has differentiated such that it will mature into a neuron and not any other neural cell type.

Post-mitotic immature neurons consist of a cell body (soma) containing a nucleus and cytoplasm. Axons and dendrites will grow from each immature neuron in response to chemical signals from surrounding cells. Immature neurons must migrate in order to adopt precise final positions that allow for the formation of neural circuitries. This migration process is critical for the development of brain and spinal architecture. Neural migration may occur via one of two distinct processes—glial guidance or somal translocation. Glial cells may provide a scaffolding network along which an immature neuron can be directed to its final location. Alternatively, the neuron may form an extension at the cell's perimeter and then translocate its soma long this length.

During embryonic development, the mammalian central nervous system (brain and spinal cord) is derived from the neural tube, which contains neural stem cells that will later generate neurons. However, neurogenesis doesn't begin until a sufficient population of neural stem cells has been achieved. These early stem cells are called neuroepithelial cells, but soon take on a highly elongated radial morphology and are then known as radial glial cells. Radial glial cells are the primary stem cells of the mammalian central nervous system, and reside in the embryonic ventricular zone, which lies adjacent to the central fluid-filled cavity (ventricular system) of the neural tube. Following radial glial cell proliferation, neurogenesis involves a final cell division of the parent radial glial cell, which produces one of two possible outcomes. First, this may generate a subclass of neuronal progenitors called intermediate neuronal precursors, which will divide one or more additional times to produce neurons. Alternatively, daughter neurons may be produced directly. Neurons do not immediately form neural circuits through the growth of axons and dendrites. Instead, newborn neurons must migrate long distances to their final destinations, maturing and finally generating neural circuitry. For example, neurons born in the ventricular zone migrate radially to the cortical plate, which is where neurons accumulate to form the cerebral cortex. Thus, the generation of neurons occurs in a specific tissue compartment or 'neurogenic niche' occupied by their parent stem cells.

In another embodiment, the expression profile identifies the cell as an adult newborn neuron or immature neuron of the spinal cord and comprises: Gad1, Gad2, Pbx3 and Meis2.

In another embodiment, the expression profile identifies the cell as an adult newborn neuron or immature neuron of the spinal cord and comprises: Gad1, Gad2, Pbx3, Meis2 and Runx1t1.

In another embodiment, the expression profile identifies the cell as a neuronal stem cell, a neuronal precursor cell, a neuroblast, an immature neuron or a newborn neuron and comprises at least one of: Fabp7, Sox9, Asc1, Insm1, Sox6, Notch1, Eomes, Tgfb2, Chd7, Sox5, Sox4, Neurod1, Neurod2, Sema3c, Igfbpl1, Sox11, Slc6a1, Dcx, Grin2b, Gad1 and Bhlhe22.

In another embodiment, the expression profile identifies the cell as a neuronal stem cell, a neuronal precursor cell, a neuroblast, an immature neuron or a newborn neuron and comprises at least one of: Sox8, Sox10, Dip2a, Ncoa3, Rorb, Id3, Sox9, Sox5, Sox6, Sox4, Eomes, Mndal, Bhlhe22, Ifi203, Sox11, Flna and Zeb1.

In another embodiment, the expression profile identifies the cell as a neuronal stem cell, a neuronal precursor cell, a neuroblast, an immature neuron or a newborn neuron and comprises at least one of: Notch1, Sox9/2, Fezf2, Pax3, Id3/4, Sox6, Chd7, Cdk2, Insm1, Eomes, Sox4, Neurod1, Neurod2, Bhlhe22, Chd5 and Hdac7.

In another embodiment, the expression profile identifies the cell as a neuronal stem cell, a neuronal precursor cell, a neuroblast, an immature neuron or a newborn neuron and comprises at least one of: Sox2, Sox9, Sox5, Sox8, Sox6, Sox4, Cdk2, Cdk2ap1, Cdk9, Cdk12, Kifl1, Kif21b, Kif17, Chd7, Kdm5c, Kdm7a, Hdac8, Kdm2b, Chd5, Hdac5, Hdac7, Chd1 and Kdm3b.

In another embodiment, the expression profile identifies the cell as a neuronal stem cell, a neuronal precursor cell, a neuroblast, an immature neuron or a newborn neuron and comprises at least one of: Sox9, Rrm2, Gpr56, Draxin, Mfap4, Eomes, Sox4 and Neurod1.

In another embodiment, the expression profile identifies the cell as a neuronal stem cell, a neuronal precursor cell, a neuroblast, an immature neuron or a newborn neuron and comprises at least one of: Gfap, Mt1, Aldoc, Clu, Aqp4, Mt2, Cst3, Slc1a2, Pbxip1, Fgfr3, Slc2a1, Slpr1, Id3, Fxyd1, Notch1, Sox9, Glu1, Slc1a3, Sox2, Olig2, Aldh1 11, Pre1p, Vim, Pax6, Reln, Gprl7, Tcf712, Nfib, Dbx2, Sox8, Sox5, Sox4, Emx1, Sox1, Sox6, Prox1, Dlx1, Foxg1, Neurod1, Sox11, Slit1, Gad2, Grin2b and Dcx.

In another embodiment, the expression profile identifies the cell as a neuronal stem cell, a neuronal precursor cell, a neuroblast, an immature neuron or a newborn neuron and comprises at least one of: Sox9, Notch1, Eomes and Neurod1.

In another embodiment, the expression profile identifies the cell as a neuronal stem cell, a neuronal precursor cell, a neuroblast, an immature neuron or a newborn neuron and comprises at least one of: Sox11 and Gad1.

In another embodiment, the expression profile identifies the cell as a neuronal stem cell, a neuronal precursor cell, a neuroblast, an immature neuron or a newborn neuron and comprises at least one of: Eomes, Sox4, Sox11 and Dcx.

In another embodiment, the expression profile identifies the cell as a neuronal stem cell, a neuronal stem cell, a neuronal precursor cell, a neuroblast, an immature neuron or a newborn neuron and comprises at least one of: Rrm2, Gpr56, Draxin and Mfap4.

In another embodiment, the expression profile identifies the cell as a neuronal stem cell, a neuronal precursor cell, a neuroblast, an immature neuron or a newborn neuron and comprises at least one of: Mbp, Meg3, Gad2 and Dcx.

In another embodiment, the expression profile identifies the cell as a neuronal stem cell, neuronal precursor cell, a neuroblast, an immature neuron or a newborn neuron and comprises at least one of the genes presented in Tables 18 and 19.

Adult Newborn Neurons Derived from the Spinal Cord

In some embodiments, the invention comprises an adult newborn neuron or immature neuron derived from the spinal cord as described herein.

In some embodiments, the invention provides an adult newborn neuron or immature neuron derived from the spinal cord characterized by expression of Gad1 and Gad2. As such, the invention also provides methods for identifying a newborn neuron of the spinal cord comprising detecting the expression pattern of Gad1 and Gad2.

In some embodiments, the invention also provides an adult newborn neuron or immature neuron derived from the spinal cord characterized by expression of Gad1, Gad2, Pbx3 and Meis2. As such, the invention also provides methods for identifying a newborn neuron of the spinal cord comprising detecting the expression pattern of Gad1, Gad2, Pbx3 and Meis2.

In some embodiments, the invention also provides an adult newborn neuron or immature neuron derived from the spinal cord characterized by expression of Gad1, Gad2, Pbx3, Meis2 and Runx1t1. As such, the invention also provides methods for identifying a newborn neuron of the spinal cord comprising detecting the expression pattern of Gad1, Gad2, Pbx3, Meis2 and Runx1t1.

In some embodiments, the invention also provides an expression profile for identifying a neuronal stem cell, a neuronal precursor cell, a neuroblast, an immature neuron or a newborn neuron derived from the brain, comprising: Sox8, Rrm2, Gpr56, Draxin, Mfap4, Eomes, Sox4 and Neurod1.

Expression Profiles

Also envisioned within the scope of the invention are expression profiles for distinguishing between a neuronal stem cell, a neuronal precursor cell, a neuroblast, an immature neuron and a newborn neuron.

As described herein, an expression profile may encompass any gene or genes, protein or proteins, or epigenetic element(s) whose expression profile or whose occurrence is associated with a specific cell type, subtype, or cell state of a specific cell type or subtype within a population of cells (e.g., neurogenic cell). In certain embodiments, the signature is dependent on epigenetic modification of the genes or regulatory elements associated with the genes (e.g., methylation, ubiquitination). Thus, in certain embodiments, use of signature genes includes epigenetic modifications that may be detected or modulated. For ease of discussion, when discussing gene expression, any of gene or genes, protein or proteins, or epigenetic element(s) may be substituted. It is to be understood that also when referring to proteins (e.g. differentially expressed proteins), such may fall within the definition of "gene" signature. Levels of expression or activity may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. An expression profile may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. nervous tissue), thus allowing the discovery of novel cell subtypes or cell states that were previously invisible or unrecognized, for example, adult newborn neurons. The presence of subtypes or cell states may be determined by subtype specific or cell state specific signatures. The presence of these specific cell (sub)types or cell states may be determined by applying the signature genes to bulk sequencing data in a sample. The signatures of the present invention may be microenvironment specific, such as their expression in a particular spatio-temporal context. In certain embodiments, signatures as discussed herein are specific to a particular developmental stage or pathological context. In certain embodiments, a combination of cell subtypes having a particular signature may indicate an outcome. The signatures may be used to deconvolute the network of cells present in a particular developmental stage or pathological condition. The presence of specific cells and cell subtypes may also be indicative of a particular developmental stage, a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular stages of development or particular pathological condition, or linked to a particular outcome or progression of the disease, or linked to a particular response to treatment of the disease (e.g. resistance to therapy).

The gene expression data may be obtained from single cell sequencing. The gene expression data may be obtained from single nuclei sequencing. The single nuclei sequencing may comprise: treating the heterogeneous population of cells with a reagent that stabilizes RNA; extracting nuclei from the cells; sorting single nuclei into separate reaction vessels; extracting RNA from the single nuclei; generating a cDNA library; and sequencing the library, whereby gene expression data from single cells is obtained. The single nuclei may be sorted into single wells of a plate by FACS. The sorting single nuclei into separate reaction vessels may comprise microfluidics. The single nuclei may be sorted into individual chambers on a microfluidic chip.

In specific embodiments, the invention provides an expression profile for distinguishing between a neuronal stem cell, a neuronal precursor cell, a neuroblast, an immature neuron and a newborn neuron comprising one or more of the genes presented in Table 22.

The invention also provides an expression profile for distinguishing between a neuronal stem cell, a neuronal precursor cell, a neuroblast, an immature neuron and a newborn neuron comprising one or more of the genes presented in Table 23.

The invention also provides an expression profile for distinguishing between a neuronal stem cell, a neuronal precursor cell, a neuroblast, an immature neuron and a newborn neuron comprising one or more of the genes presented in Table 24.

The invention also provides an expression profile for distinguishing between a neuronal stem cell, a neuronal precursor cell, a neuroblast, an immature neuron and a newborn neuron comprising one or more of the genes presented in Table 25.

The invention also provides an expression profile for distinguishing between a neuronal stem cell, a neuronal precursor cell, a neuroblast, an immature neuron and a newborn neuron comprising one or more of the genes presented in Table 27.

In one aspect, the present invention provides for a method of producing at least one high resolution map for visualizing different cell subtypes or cell states in a heterogeneous population of cells comprising: performing dimensionality reduction on single cell gene expression data obtained from the heterogeneous population of cells; producing a first set of clusters of cells by a method comprising measuring the dissimilarity between sets of genes in the dimensionality reduced single cell gene expression data and applying a first metric, wherein the clusters are in a dimensionality reduced space and the clusters comprise cells with a continuous trajectory; producing a set of informative genes by a method comprising scoring genes based on their expression across the first set of clusters of cells or a continuous trajectory of cells, wherein the informative genes are uniquely expressed in cells embedded in close proximity in the dimensionality reduced space; and producing at least one second set of clusters of cells or continuous trajectory of cells by a method comprising measuring the dissimilarity between the set of informative genes and applying a second metric, whereby visualization of a map of the second set of clusters or continuous trajectory of cells indicate cell subtypes or cell states.

The method may further comprise producing at least one high resolution map for visualizing the temporal position or cell developmental stage of cells of a specific cell type, subtype or cell state during proliferation comprising: optionally, performing the method of producing at least one high resolution map for visualizing different cell subtypes or cell states in a heterogeneous population of cells as described herein, whereby heterogeneous cells are clustered by cell type, subtype, or cell state; performing dimensionality reduction on the single cell gene expression data from the stained cells of a single cell type, subtype or cell state within each population of cells or the stained single nuclei of a single cell type or subtype isolated from each population of cells; measuring the dissimilarity between sets of genes in the dimensionality reduced single cell gene expression data and applying a first metric, whereby a continuous trajectory is visualized in the dimensionality reduced space from an early time point to a later time point; producing a set of informative genes by a method comprising scoring genes based on their expression across the continuous trajectory, wherein the informative genes are uniquely expressed in cells embedded in close proximity in the dimensionality reduced space, optionally, wherein lowly expressed genes are filtered out; and producing at least one set of clusters of cells by a method comprising measuring the dissimilarity between the set of informative genes and applying a second metric, whereby visualization of the set of clusters in the dimensionality reduced space indicate the gene expression profiles of cells based on a temporal position or developmental stage. The producing the set of clusters of cells may comprise producing more than one set of clusters, wherein the first set of clusters is produced by using the highest scoring informative gene and each successive set of clusters is produced by adding the next highest scoring informative gene. The method may further comprise normalization of the single cell gene expression data, wherein gene expression of one cell is normalized to another using not highly expressed genes. The method may further comprise estimation of missed detection probability, wherein an expectation-maximization algorithm is applied. The scoring informative genes may comprise applying a Moran's I analysis and/or a Manhattan distance analysis. The dimensionality reduction may comprise PCA and/or tSNE. The nucleoside analogue may comprise EdU (5-ethynyl-2'-deoxyuridine).

The method may further comprise mapping the spatial location of the cell subtypes or cells having a cell state by performing RNA in situ hybridization (ISH) on whole tissue sections comprising said cell subtypes using probes specific for genes expressed in the cell subtypes, whereby the spatial location of cell subtypes is visualized in a biological sample. The method may further comprise mapping the spatial location of the cell subtypes or cells having a cell state by comparing gene expression data for each cell type to landmark gene expression patterns in tissue samples, whereby the spatial location of cell subtypes is visualized in a biological sample.

Producing the second set of clusters of cells may comprise producing more than one set of clusters, wherein each set of clusters is produced by using the highest scoring informative gene and each successive cluster is produced by adding the next highest scoring informative gene.

The method may further comprise normalization of the single cell gene expression data, wherein gene expression of one cell is normalized to another using not highly expressed genes. The method may further comprise estimation of missed detection probability, wherein an expectation-maximization algorithm is applied. Scoring informative genes may comprise applying a Moran's I analysis and/or a Manhattan distance analysis. The dimensionality reduction may comprise PCA and/or tSNE.

Methods of Stimulating Neurogenesis

In some embodiments, the invention provides a method of stimulating neurogenesis of a neuronal stem cell derived from the spinal cord stem by administering an agent that modulates one or more genes or gene products.

Modulating Agents

As used herein the term "altered expression" may particularly denote altered production of the recited gene products by a cell. As used herein, the term "gene product(s)" includes RNA transcribed from a gene (e.g., mRNA), or a polypeptide encoded by a gene or translated from RNA.

Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve affecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

Programmable Nucleic-Acid Modifying Agents

Programmable nucleic acid-modifying agents in the context of the present invention may be used to modify endogenous cell DNA or RNA sequences, including DNA and/or RNA sequences encoding the target genes and target gene products disclosed herein. In certain example embodiments, the programmable nucleic acid-modifying agents may be used to edit a target sequence to restore native or wild-type functionality. In certain other embodiments, the programmable nucleic-acid modifying agents may be used to insert a new gene or gene product to modify the phenotype of target cells. In certain other example embodiments, the programmable nucleic-acid modifying agents may be used to delete or otherwise silence the expression of a target gene or gene product. Programmable nucleic-acid modifying agents may used in both in vivo an ex vivo applications disclosed herein.

1. CRISPR/Cas Systems

In general, a CRISPR-Cas or CRISPR system as used herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell.

Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), CasIO, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, homologues thereof, or modified versions thereof. In certain example embodiments, the C2c2 effector protein is naturally present in a prokaryotic genome within 20kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

a) DNA Repair and NHEJ

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving by the CRISPR/Cas system can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which the CRISPR/Cas system generates a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with CRISPR/Cas system nickases induce two single strand breaks for the purpose of inducing NHEJ-mediated indels, two guide RNAs may be configured to position two single-strand breaks to provide for NHEJ repair a nucleotide of the target position.

b) dCas and Functional Effectors

Unlike CRISPR-Cas-mediated gene knockout, which permanently eliminates expression by mutating the gene at the DNA level, CRISPR-Cas knockdown allows for temporary reduction of gene expression through the use of artificial transcription factors. Mutating key residues in cleavage domains of the Cas protein results in the generation of a catalytically inactive Cas protein. A catalytically inactive Cas protein complexes with a guide RNA and localizes to the DNA sequence specified by that guide RNA's targeting domain, however, it does not cleave the target DNA. Fusion of the inactive Cas protein to an effector domain also referred to herein as a functional domain, e.g., a transcription repression domain, enables recruitment of the effector to any DNA site specified by the guide RNA.

In general, the positioning of the one or more functional domain on the inactivated CRISPR/Cas protein is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR protein.

In certain embodiments, Cas protein may be fused to a transcriptional repression domain and recruited to the promoter region of a gene. Especially for gene repression, it is contemplated herein that blocking the binding site of an endogenous transcription factor would aid in downregulating gene expression.

In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA. Idem: adapt to refer to regions with the motifs of interest In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

c) Guide Molecules

As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A.R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoide cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemicially modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (meΨ), 5-methoxyuridine(5moU), inosine, 7-methyl-guanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU (SEQ. I.D. Nos. 1-4).

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas proten (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the compelementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver BP et al. Engineered CRISPR-Cas9 nucleases with altered PAM specificities. Nature. 2015 Jul. 23; 523 (7561):481-5. doi: 10.1038/naturel4592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke BJ, Stephens AW. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green flourescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, O2 concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline<15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm2. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., http://stke.sciencemag.org/cgi/content/abstract/sigtrans;4/164/rs2), 2. FKBP-FRB based system inducible by rapamycin (or related chemicals based on rapamycin) (see, e.g., http://www.nature.com/nmeth/journal/v2/n6/full/nmeth763.html), 3. GID1-GAI based system inducible by Gibberellin (GA) (see, e.g., http://www.nature-.com/nchembio/journal/v8/n5/full/nchembio.922.html).

A chemical inducible system can be an estrogen receptor (ER) based system inducible by 4-hydroxytamoxifen (4OHT) (see, e.g., http://www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogren receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., http://www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No.8, pp. 893-900 and TranHuuHue et al in Acustica (1997) Vol. 83, No.6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes.

Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extented length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide moleucle, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F.A., Cox, D., Lin, S., Barretto, R., Habib, N., Hsu, P.D., Wu, X., Jiang, W., Marraffini, L.A., & Zhang, F. Science Feb 15;339(6121):819-23 (2013);

RNA-guided editing of bacterial genomes using CRISPR-Cas systems. Jiang W., Bikard D., Cox D., Zhang F, Marraffini LA. Nat Biotechnol Mar;31(3):233-9 (2013);

One-Step Generation of Mice Carrying Mutations in Multiple Genes by CRISPR-Cas-Mediated Genome Engineering. Wang H., Yang H., Shivalila CS., Dawlaty MM., Cheng AW., Zhang F., Jaenisch R. Cell May 9;153(4):910-8 (2013);

Optical control of mammalian endogenous transcription and epigenetic states. Konermann S, Brigham MD, Trevino AE, Hsu PD, Heidenreich M, Cong L, Platt RJ, Scott DA, Church GM, Zhang F. Nature. Aug 22;500 (7463):472-6. doi: 10.1038/Naturel2466. Epub 2013 Aug 23 (2013);

Double Nicking by RNA-Guided CRISPR Cas9 for Enhanced Genome Editing Specificity. Ran, FA., Hsu, PD., Lin, CY., Gootenberg, JS., Konermann, S., Trevino, AE., Scott, DA., Inoue, A., Matoba, S., Zhang, Y., & Zhang, F. Cell Aug 28. pii: S0092-8674 (13)01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols Nov;8(11):2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science Dec 12. (2013);

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, 0. Cell Feb 27, 156(5):935-49 (2014);

Genome-wide binding of the CRISPR endonuclease Cas9 in mammalian cells. Wu X., Scott DA., Kriz AJ., Chiu AC., Hsu PD., Dadon DB., Cheng AW., Trevino AE., Konermann S., Chen S., Jaenisch R., Zhang F., Sharp PA. Nat Biotechnol. Apr 20. doi: 10.1038/nbt.2889 (2014);

CRISPR-Cas9 Knockin Mice for Genome Editing and Cancer Modeling. Platt RJ, Chen S, Zhou Y, Yim MJ, Swiech L, Kempton HR, Dahlman JE, Parnas 0, Eisenhaure™, Jovanovic M, Graham DB, Jhunjhunwala S, Heidenreich M, Xavier RJ, Langer R, Anderson DG, Hacohen N, Regev A, Feng G, Sharp PA, Zhang F. Cell 159(2): 440-455 DOI: 10.1016/j.cell.2014.09.014 (2014);

Development and Applications of CRISPR-Cas9 for Genome Engineering, Hsu PD, Lander ES, Zhang F., Cell. Jun 5;157(6):1262-78 (2014).

Genetic screens in human cells using the CRISPR-Cas9 system, Wang T, Wei JJ, Sabatini DM, Lander ES., Science. January 3; 343(6166): 80-84. doi:10.1126/science.1246981 (2014);

Rational design of highly active sgRNAs for CRISPR-Cas9-mediated gene inactivation, Doench JG, Hartenian E, Graham DB, Tothova Z, Hegde M, Smith I, Sullender M, Ebert BL, Xavier RJ, Root DE., (published online 3 Sep. 2014) Nat Biotechnol. Dec;32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. Jan;33(1):102-6 (2015);

Genome-scale transcriptional activation by an engineered CRISPR-Cas9 complex, Konermann S, Brigham MD, Trevino AE, Joung J, Abudayyeh OO, Barcena C, Hsu PD, Habib N, Gootenberg JS, Nishimasu H, Nureki O, Zhang F., Nature. Jan 29;517(7536):583-8 (2015).

A split-Cas9 architecture for inducible genome editing and transcription modulation, Zetsche B, Volz SE, Zhang F., (published online 2 Feb. 2015) Nat Biotechnol. Feb;33(2):139-42 (2015);

Genome-wide CRISPR Screen in a Mouse Model of Tumor Growth and Metastasis, Chen S, Sanjana NE, Zheng K, Shalem O, Lee K, Shi X, Scott DA, Song J, Pan JQ, Weissleder R, Lee H, Zhang F, Sharp PA. Cell 160, 1246-1260, Mar. 12, 2015 (multiplex screen in mouse), and In vivo genome editing using *Staphylococcus aureus* Cas9, Ran FA, Cong L, Yan WX, Scott DA, Gootenberg JS, Kriz AJ, Zetsche B, Shalem O, Wu X, Makarova KS, Koonin EV, Sharp PA, Zhang F., (published online 1 Apr. 2015), Nature. Apr 9;520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan 1 351(6268): 84-88 doi: 10.1126/science.aad5227. Epub 2015 Dec 1.

Gao et al, "Engineered Cpf1 Enzymes with Altered PAM Specificities," bioRxiv 091611; doi: http://dx.doi.org/10.1101/091611 (Dec. 4, 2016). each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2cl and C2c3) contain RuvC-like endonuclease domains distantly related to Cpf1. Unlike Cpf1, C2cl depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5;353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17-Jun-15, PROTECTED GUIDE RNAS (PGRNAS); U.S. application 62/091,455, filed, 12-Dec-14, PROTECTED GUIDE RNAS (PGRNAS); U.S. application 62/096,708, 24-Dec-14, PROTECTED GUIDE RNAS (PGRNAS); U.S. applications 62/091,462, 12-Dec-14, 62/096,324, 23-Dec-14, 62/180,681, 17-Jun-2015, and 62/237,496, 5 Oct. 2015, DEAD GUIDES FOR CRISPR TRANSCRIPTION FACTORS; U.S. application 62/091,456, 12-Dec-14 and 62/180,692, 17 Jun. 2015, ESCORTED AND FUNCTIONALIZED GUIDES FOR CRISPR-CAS SYSTEMS; U.S. application 62/091,461, 12-Dec-14, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19-Dec-14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24-Dec-14, ENGINEERING OF SYSTEMS, METHODS AND OPTIMIZED ENZYME AND GUIDE SCAFFOLDS FOR SEQUENCE MANIPULATION; U.S. application 62/098,059, 30-Dec-14, 62/181,641, 18 Jun. 2015, and 62/181,667, 18 Jun. 2015, RNA-TARGETING SYSTEM; U.S. application 62/096,656, 24-Dec-14 and 62/181,151, 17 Jun. 2015, CRISPR HAVING OR ASSOCIATED WITH DESTABILIZATION DOMAINS; U.S. application 62/096,697, 24-Dec-14, CRISPR HAVING OR ASSOCIATED WITH AAV; U.S. application 62/098,158, 30-Dec-14, ENGINEERED CRISPR COMPLEX INSERTIONAL TARGETING SYSTEMS; U.S. application 62/151,052, 22-Apr-15, CELLULAR TARGETING FOR EXTRACELLULAR EXOSOMAL REPORTING; U.S. application 62/054,490, 24-Sep-14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-F EB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25-Sep-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec-14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24-Sep-14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep-14, DELIV- ERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec-14 and 62/181,690, 18 Jun. 2015, FUNCTIONAL SCREENING WITH OPTIMIZED FUNCTIONAL CRISPR-CAS SYSTEMS; U.S. application 62/055,487, 25-Sep-14, FUNCTIONAL SCREENING WITH OPTIMIZED FUNCTIONAL CRISPR-CAS SYSTEMS; U.S. application 62/087,546, 4-Dec-14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec-14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19-Aug-2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24-Sep-2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12-Feb-2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

2. TALE Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle EL. Christian M. Wang L. Zhang Y. Schmidt C, et al. Efficient design and assembly of custom TALEN and other TAL effector-based constructs for DNA targeting. Nucleic Acids Res. 2011;39:e82; Zhang F. Cong L. Lodato S. Kosuri S. Church GM. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such polypeptide monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-

1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 8)
M D P I R S R T P S P A R E L L S G P Q P D G V Q

P T A D R G V S P P A G G P L D G L P

A R R T M S R T R L P S P P A P S P A F S A D S

F S D L L R Q F D P S L F N T S L F D S L

P P F G A H H T E A A T G E W D E V Q S G L R

A A D A P P P T M R V A V T A A R P P

R A K P A P R R R A A Q P S D A S P A A Q V D L

R T L G Y S Q Q Q Q E K I K P K V R S

T V A Q H H E A L V G H G F T H A H I V A L S Q

H P A A L G T V A V K Y Q D M I A A

L P E A T H E A I V G V G K Q W S G A R A L E

A L L T V A G E L R G P P L Q L D T G Q

L L K I A K R G G V T A V E A V H A W R N A L T

G A P L N

An exemplary amino acid sequence of a C-terminal capping region is:

(SEQ ID NO: 11)
R P A L E S I V A Q L S R P D P A L A A L T N D

H L V A L A C L G G R P A L D A V K K

G L P H A P A L I K R T N R R I P E R T S H R

V A D H A Q V V R V L G F F Q C H S H P

A Q A F D D A M T Q F G M S R H G L L Q L F R

R V G V T E L E A R S G T L P P A S Q R

W D R I L Q A S G M K R A K P S P T S T Q T P

D Q A S L H A F A D S L E R D L D A P S P

M H E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID), SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

3. ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

4. Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124,369; and 8,129,134, which are specifically incorporated by reference.

5. Delivery

The programmable nucleic acid modifying agents and other modulating agents, or components thereof, or nucleic acid molecules thereof (including, for instance HDR template), or nucleic acid molecules encoding or providing components thereof, may be delivered by a delivery system herein described.

Viral Delivery

Vector delivery, e.g., plasmid, viral delivery: the chromatin 3D structure modulating agents, can be delivered using any suitable vector, e.g., plasmid or viral vectors, such as adeno associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

Compositions comprising a Cas effector module, complex or system comprising multiple guide RNAs, preferably tandemly arranged, or the polynucleotide or vector encoding or comprising said Cas effector module, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a Cas effector module CRISPR system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible Cas effector module activator allows one to induce transcription right before the screen and therefore minimizes the chance of false negative hits. Accordingly, by use of the instant invention in screening, e.g., gain of function screens, the chance of false negative results may be minimized.

In another aspect, the invention provides an engineered, non-naturally occurring vector system comprising one or more vectors comprising a first regulatory element operably linked to the multiple Cas effector module CRISPR system guide RNAs that each specifically target a DNA molecule encoding a gene product and a second regulatory element operably linked coding for a CRISPR protein. Both regulatory elements may be located on the same vector or on different vectors of the system. The multiple guide RNAs target the multiple DNA molecules encoding the multiple gene products in a cell and the CRISPR protein may cleave the multiple DNA molecules encoding the gene products (it may cleave one or both strands or have substantially no nuclease activity), whereby expression of the multiple gene products is altered; and, wherein the CRISPR protein and the multiple guide RNAs do not naturally occur together. In a preferred embodiment the CRISPR protein is a Cas effector module, optionally codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of each of the multiple gene products is altered, preferably decreased.

In one aspect, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas effector module complexed with the one or more guide sequence(s) that is hybridized to the one or more target sequence(s); and (b) a second regulatory element operably linked to an enzyme-coding sequence encoding said Cas effector module, preferably comprising at least one nuclear localization sequence and/or at least one NES; wherein components (a) and (b) are located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the CRISPR complex comprises one or more nuclear localization sequences and/or one or more NES of sufficient strength to drive accumulation of said CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the Cas effector module, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

In some embodiments, a host cell is transiently or non-transiently transfected with one or more vectors comprising the polynucleotides encoding the Cas effector module, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplidied herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the Cas effector module, system or complex for use in multiple targeting as defined herein is used to establish a new cell line comprising one or more vector-derived sequences. In some embodiments, a cell transiently transfected with the components of a Cas effector module. system or complex for use in multiple targeting as described herein (such as by transient transfection of one or more vectors, or transfection with RNA), and modified through the activity of a Cas effector module, system or complex, is used to establish a new cell line comprising cells containing the modification but lacking any other exogenous sequence. In some embodiments, cells transiently or non-transiently transfected with one or more vectors comprising the polynucleotides encoding Cas effector module, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the CRISPR complex to the respective target sequence(s) in a eukaryotic cell, wherein the CRISPR complex comprises a Cas effector module complexed with the one or more guide sequence(s) that is hybridized to the respective target sequence(s); and/or (b) a second regulatory element operably linked to an enzyme-coding sequence encoding said Cas effector module comprising preferably at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a CRISPR complex to a different target sequence in a eukaryotic cell. In some embodiments, the Cas effector module comprises one or more nuclear localization sequences and/or nuclear export sequences or NES of sufficient strength to drive accumulation of said CRISPR enzyme in a detectable amount in and/or out of the nucleus of a eukaryotic cell.

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

The guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Aspects of the invention relate to bicistronic vectors for guide RNA and (optionally modified or mutated) Cas effector modules. Bicistronic expression vectors for guide RNA and (optionally modified or mutated) CRISPR enzymes are preferred. In general and particularly in this embodiment (optionally modified or mutated) CRISPR enzymes are preferably driven by the CBh promoter. The RNA may preferably be driven by a Pol III promoter, such as a U6 promoter. Ideally the two are combined.

In some embodiments, a loop in the guide RNA is provided. This may be a stem loop or a tetra loop. The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1a promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena,* and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus,* Picrophilus, Thermoplasma, *Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium,* Azarcus, Chromobacterium, *Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga.*

Typically, in the context of an endogenous nucleic acid-targeting system, formation of a nucleic acid-targeting complex (comprising a guide RNA hybridized to a target sequence and complexed with one or more nucleic acid-targeting effector modules) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector module and a guide RNA could each be operably linked to separate regulatory elements on separate vectors. Alternatively, two or more of the elements expressed from the same or different regulatory elements, may be combined in a single vector, with one or more additional vectors providing any components of the nucleic acid-targeting system not included in the first vector. nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector module and a guide RNA embedded within one or more intron sequences (e.g. each in a different intron, two or more in at least one intron, or all in a single intron). In some embodiments, the nucleic acid-targeting effector module and guide RNA are operably linked to and expressed from the same promoter.

Ways to package inventive Cpf1 coding nucleic acid molecules, e.g., DNA, into vectors, e.g., viral vectors, to mediate genome modification in vivo may include:
  To achieve NHEJ-mediated gene knockout:
  Single virus vector:
  Vector containing two or more expression cassettes:
  Promoter-Cpf1 coding nucleic acid molecule-terminator
  Promoter-gRNA-terminator
  Promoter-gRNA2-terminator
  Promoter-gRNA(N)-terminator (up to size limit of vector)
  Double virus vector:
  Vector 1 containing one expression cassette for driving the expression of Cpf1
  Promoter-Cpf1 coding nucleic acid molecule-terminator
  Vector 2 containing one more expression cassettes for driving the expression of one or more guideRNAs
  Promoter-gRNA1-terminator
  Promoter-gRNA(N)-terminator (up to size limit of vector)
  To mediate homology-directed repair.
  In addition to the single and double virus vector approaches described above, an additional vector can be used to deliver a homology-direct repair template.
  The promoter used to drive Cpf1 coding nucleic acid molecule expression can include:
  AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cpf1.
  For ubiquitous expression, promoters that can be used include: CMV, CAG, CBh, PGK, SV40, Ferritin heavy or light chains, etc.
  For brain or other CNS expression, can use promoters: SynapsinI for all neurons, CaMKIIalpha for excitatory neurons, GAD67 or GAD65 or VGAT for GABAergic neurons, etc.
  For liver expression, can use Albumin promoter. For lung expression, can use use SP-B. For endothelial cells, can use ICAM. For hematopoietic cells can use IFNbeta or CD45. For Osteoblasts can one can use the OG-2. The promoter used to drive guide RNA can include:
  Pol III promoters such as U6 or H1
  Use of Pol II promoter and intronic cassettes to express gRNA
Adeno associated virus (AAV)
  Cpf1 and one or more guide RNA can be delivered using adeno associated virus (AAV), lentivirus, adenovirus or other plasmid or viral vector types, in particular, using formulations and doses from, for example, US Patents Nos.

8,454,972 (formulations, doses for adenovirus), 8,404,658 (formulations, doses for AAV) and 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cpf1 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:
  Low toxicity (this may be due to the purification method not requiring ultra centrifugation of cell particles that can activate the immune response) and
  Low probability of causing insertional mutagenesis because it doesn't integrate into the host genome.

AAV has a packaging limit of 4.5 or 4.75 Kb. This means that Cpf1 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cpf1 that are shorter. For example:

| Species | Cas9 Size (nt) |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Campylobacter jejuni | 2952 |
| Streptococcus thermophilus LMD-9 | 3396 | rAAV vectors are preferably produced in insect cells, e.g., Spodoptera frugiperda Sf9 insect cells, grown in serum-free suspension culture. Serum-free insect cells can be purchased from commercial vendors, e.g., Sigma Aldrich (EX-CELL 405).

These species are therefore, in general, preferred Cpf1 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 2

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids:

5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50ul of DMEM overnight at 4C. They were then aliquotted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin,Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

Use of Minimal Promoters

The present application provides a vector for delivering an effector protein and at least one CRISPR guide RNA to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4Kb. In an embodiment, the vector is an AAV vector. In another embodiment, the effector protein is a CRISPR anzyme. In a further embodiment, the CRISPR enzyme is SaCas9, Cpf1, Cas13b or C2c2.

In a related aspect, the invention provides a lentiviral vector for delivering an effector protein and at least one CRISPR guide RNA to a cell comprising a promoter operably linked to a polynucleotide sequence encoding Cpf1 and a second promoter operably linked to a polynucleotide sequence encoding at least one guide RNA, wherein the polynucleotide sequences are in reverse orientation.

In another aspect, the invention provides a method of expressing an effector protein and guide RNA in a cell comprising introducing the vector according any of the vector delivery systems disclosed herein. In an embodiment of the vector for delivering an effector protein, the minimnal promoter is the Mecp2 promoter, tRNA promoter, or U6. In a further embodiment, the minimal promoter is tissue specific.

Dosage of Vectors

In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least 1×105 particles (also referred to as particle units, pu) of adenoviral vector. In an embodiment herein, the dose preferably is at least about 1×106 particles (for example, about 1×106-1×1012 particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^{100}$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

The dosage used for the compositions provided herein include dosages for repeated administration or repeat dosing. In particular embodiments, the administration is repeated within a period of several weeks, months, or years. Suitable assays can be performed to obtain an optimal dosage regime. Repeated administration can allow the use of lower dosage, which can positively affect off-target modifications.

RNA Delivery

In particular embodiments, RNA based delivery is used. In these embodiments, mRNA of the CRISPR effector protein is delivered together with in vitro transcribed guide RNA. Liang et al. describes efficient genome editing using RNA based delivery (Protein Cell. 2015 May; 6(5): 363-372).

RNA delivery: The CRISPR enzyme, for instance a Cpf1, and/or any of the present RNAs, for instance a guide RNA, can also be delivered in the form of RNA. Cpf1 mRNA can be generated using in vitro transcription. For example, Cpf1 mRNA can be synthesized using a PCR cassette containing the following elements: T7_promoter-kozak sequence (GCCACC)-Cpf1-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

RNP

In particular embodiments, pre-complexed guide RNA and CRISPR effector protein are delived as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9;153(4): 910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Indeed, RNA delivery is a useful method of in vivo delivery. It is possible to deliver Cpf1 and gRNA (and, for instance, HR repair template) into cells using liposomes or particles. Thus delivery of the CRISPR enzyme, such as a Cpf1 and/or delivery of the RNAs of the invention may be in RNA form and via microvesicles, liposomes or particles. For example, Cpf1 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free Tocsi-BACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated.

Zou et al. ((HUMAN GENE THERAPY 22:465-475 (April 2011)) describes a method of lentiviral-mediated delivery of short-hairpin RNAs targeting PKC7 for in vivo gene silencing in the spinal cord of rats. Zou et al. administered about 10 μl of a recombinant lentivirus having a titer of 1×109 transducing units (TU)/ml by an intrathecal catheter. A similar dosage of CRISPR Cas expressed in a lentiviral vector may be contemplated for humans in the present invention, for example, about 10-50 ml of CRISPR Cas in a lentivirus having a titer of 1×109 transducing units (TU)/ml may be contemplated. A similar dosage of CRISPR Cas expressed in a lentiviral vector targeted to the brain may be contemplated for humans in the present invention, for example, about 10-50 ml of CRISPR Cas targeted to the brain in a lentivirus having a titer of 1×109 transducing units (TU)/ml may be contemplated.

Anderson et al. (US 20170079916) provides a modified dendrimer nanoparticle for the delivery of therapeutic, prophylactic and/or diagnostic agents to a subject, comprising: one or more zero to seven generation alkylated dendrimers; one or more amphiphilic polymers; and one or more therapeutic, prophylactic and/or diagnostic agents encapsulated therein. One alkylated dendrimer may be selected from the group consisting of poly(ethyleneimine), poly(polyproylenimine), diaminobutane amine polypropylenimine tetramine and poly(amido amine). The therapeutic, prophylactic and diagnostic agent may be selected from the group consisting of proteins, peptides, carbohydrates, nucleic acids, lipids, small molecules and combinations thereof.

Anderson et al. (US 20160367686) provides a compound of Formula (I):

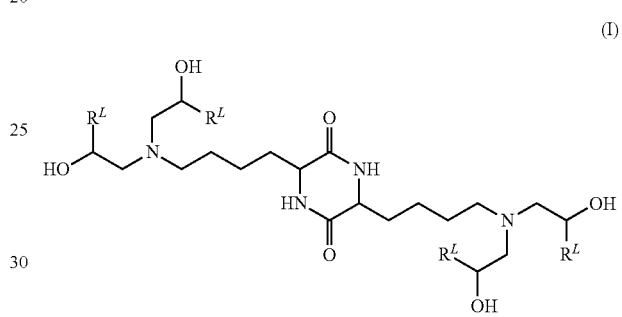

(I)

and salts thereof, wherein each instance of R L is independently optionally substituted C6-C40 alkenyl, and a composition for the delivery of an agent to a subject or cell comprising the compound, or a salt thereof, an agent; and optionally, an excipient. The agent may be an organic molecule, inorganic molecule, nucleic acid, protein, peptide, polynucleotide, targeting agent, an isotopically labeled chemical compound, vaccine, an immunological agent, or an agent useful in bioprocessing. The composition may further comprise cholesterol, a PEGylated lipid, a phospholipid, or an apolipoprotein.

Anderson et al. (US20150232883) provides a delivery particle formulations and/or systems, preferably nanoparticle delivery formulations and/or systems, comprising (a) a CRISPR-Cas system RNA polynucleotide sequence; or (b) Cas9; or (c) both a CRISPR-Cas system RNA polynucleotide sequence and Cas9; or (d) one or more vectors that contain nucleic acid molecule(s) encoding (a), (b) or (c), wherein the CRISPR-Cas system RNA polynucleotide sequence and the Cas9 do not naturally occur together. The delivery particle formulations may further comprise a surfactant, lipid or protein, wherein the surfactant may comprise a cationic lipid.

Anderson et al. (US20050123596) provides examples of microparticles that are designed to release their payload when exposed to acidic conditions, wherein the microparticles comprise at least one agent to be delivered, a pH triggering agent, and a polymer, wherein the polymer is selected from the group of polymethacrylates and polyacrylates.

Anderson et al (US 20020150626) provides lipid-protein-sugar particles for delivery of nucleic acids, wherein the polynucleotide is encapsulated in a lipid-protein-sugar matrix by contacting the polynucleotide with a lipid, a protein, and a sugar; and spray drying mixture of the polynucleotide, the lipid, the protein, and the sugar to make microparticles.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Particles

In some aspects or embodiments, a composition comprising a delivery particle formulation may be used. In some aspects or embodiments, the formulation comprises a CRISPR complex, the complex comprising a CRISPR protein and-a guide which directs sequence-specific binding of the CRISPR complex to a target sequence. In some embodiments, the delivery particle comprises a lipid-based particle, optionally a lipid nanoparticle, or cationic lipid and optionally biodegradable polymer. In some embodiments, the cationic lipid comprises 1,2-dioleoyl-3-trimethylammonium-propane (DOTAP). In some embodiments, the hydrophilic polymer comprises ethylene glycol or polyethylene glycol. In some embodiments, the delivery particle further comprises a lipoprotein, preferably cholesterol. In some embodiments, the delivery particles are less than 500 nm in diameter, optionally less than 250 nm in diameter, optionally less than 100 nm in diameter, optionally about 35 nm to about 60 nm in diameter.

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 p m. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

In terms of this invention, it is preferred to have one or more components of CRISPR complex, e.g., CRISPR enzyme or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. It will be appreciated that reference made herein to particles or nanoparticles can be interchangeable, where appropriate.

It will be understood that the size of the particle will differ depending as to whether it is measured before or after loading. Accordingly, in particular embodiments, the term "nanoparticles" may apply only to the particles pre loading.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1X PBS; and separately, DOTAP, DMPC, PEG, and cholesterol as applicable for the formulation are dissolved in alcohol, e.g., 100% ethanol; and, the two solutions are mixed together to form particles containing the complexes).

Nucleic acid-targeting effector proteins (such as a Type V protein such Cpf1) mRNA and guide RNA may be delivered simultaneously using particles or lipid envelopes. Examples of suitable particles include but are not limited to those described in U.S. Pat. No. 9,301,923.

For example, Su X, Fricke J, Kavanagh DG, Irvine DJ ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr 1) describes biodegradable core-shell structured nanoparticles with a poly(O-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

Liu et al. (US 20110212179) provides bimodal porous polymer microspheres comprising a base polymer, wherein the particle comprises macropores having a diameter ranging from about 20 to about 500 microns and micropores having a diameter ranging from about 1 to about 70 microns, and wherein the microspheres have a diameter ranging from about 50 to about 1100 microns.

Berg et al. (US20160174546) a nanolipid delivery system, in particular a nano-particle concentrate, comprising: a composition comprising a lipid, oil or solvent, the composition having a viscosity of less than 100 cP at 25.degree. C. and a Kauri Butanol solvency of greater than 25 Kb; and at least one amphipathic compound selected from the group consisting of an alkoxylated lipid, an alkoxylated fatty acid, an alkoxylated alcohol, a heteroatomic hydrophilic lipid, a heteroatomic hydrophilic fatty acid, a heteroatomic hydrophilic alcohol, a diluent, and combinations thereof, wherein the compound is derived from a starting compound having a viscosity of less than 1000 cP at 50.degree. C., wherein the concentrate is configured to provide a stable nano emulsion having a D50 and a mean average particle size distribution of less than 100 nm when diluted.

Liu et al. (US 20140301951) provides a protocell nanostructure comprising: a porous particle core comprising a plurality of pores; and at least one lipid bilayer surrounding the porous particle core to form a protocell, wherein the protocell is capable of loading one or more cargo components to the plurality of pores of the porous particle core and releasing the one or more cargo components from the porous particle core across the surrounding lipid bilayer.

Chromy et al. (US 20150105538) provides methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

Bader et al. (US 20150250725), provides a method for producing a lipid particle comprising the following: i) providing a first solution comprising denatured apolipoprotein, ii) adding the first solution to a second solution comprising at least two lipids and a detergent but no apolipoprotein, and iii) removing the detergent from the solution obtained in ii) and thereby producing a lipid particle.

Mirkin et al., (US20100129793) provides a method of preparing a composite particle comprising the steps of (a) admixing a dielectric component and a magnetic component to form a first intermediate, (b) admixing the first intermediate and gold seeds to form a second intermediate, and (c) forming a gold shell on the second intermediate by admixing the second intermediate with a gold source and a reducing agent to form said composite particle.

In one embodiment, particles/nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5 (5-6):458-68; Garrett, N. L., et al. J Raman Spect, 2012. 43(5):681-688; Ahmad, S., et al. J Royal Soc Interface 2010. 7:S423-33; Uchegbu, I.F.

Expert Opin Drug Deliv, 2006. 3(5):629-40; Qu, X.,et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles/nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

The lipid particles developed by the Qiaobing Xu's lab at Tufts University may be used/adapted to the present delivery system for cancer therapy. See Wang et al., J. Control Release, 2017 Jan 31. pii: 50168-3659(17)30038-X. doi: 10.1016/j.jconrel.2017.01.037. [Epub ahead of print]; Altmoglu et al., Biomater Sci., 4(12):1773-80, Nov. 15, 2016; Wang et al., PNAS, 113(11):2868-73 Mar. 15, 2016; Wang et al., PloS One, 10(11): e0141860. doi: 10.1371/journal.pone.0141860. eCollection 2015, Nov. 3, 2015; Takeda et al., Neural Regen Res. 10(5):689-90, May 2015; Wang et al., Adv. Healthc Mater., 3(9):1398-403, Sep. 2014; and Wang et al., Agnew Chem Int Ed Engl., 53(11):2893-8, Mar. 10, 2014.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

Zhu et al. (US20140348900) provides for a process for preparing liposomes, lipid discs, and other lipid nanoparticles using a multi-port manifold, wherein the lipid solution stream, containing an organic solvent, is mixed with two or more streams of aqueous solution (e.g., buffer). In some aspects, at least some of the streams of the lipid and aqueous solutions are not directly opposite of each other. Thus, the process does not require dilution of the organic solvent as an additional step. In some embodiments, one of the solutions may also contain an active pharmaceutical ingredient (API). This invention provides a robust process of liposome manufacturing with different lipid formulations and different payloads. Particle size, morphology, and the manufacturing scale can be controlled by altering the port size and number of the manifold ports, and by selecting the flow rate or flow velocity of the lipid and aqueous solutions.

Cullis et al. (US 20140328759) provides limit size lipid nanoparticles with a diameter from 10-100 nm, in particular comprising a lipid bilayer surrounding an aqueous core. Methods and apparatus for preparing such limit size lipid nanoparticles are also disclosed.

Manoharan et al. (US 20140308304) provides cationic lipids of formula (I)

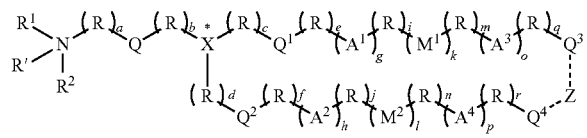

Formula (I)

or a salt thereof, wherein X is N or P; R' is absent, hydrogen, or alkyl; with respect to R1 and R2, (i) R1 and R2 are each, independently, optionally substituted alkyl, alkenyl, alkynyl, cycloalkyl, cycloalkylalkyl, heterocycle or R10; (ii) R1 and R2, together with the nitrogen atom to which they are attached, form an optionally substituted heterocyclic ring; or (iii) one of R1 and R2 is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the (R)a group adjacent to the nitrogen atom; each occurrence of R is, independently, —(CR3R4)—; each occurrence of R3 and R4 are, independently H, halogen, OH, alkyl, alkoxy, —NH.sub.2, alkylamino, or dialkylamino; or R3 and R4, together with the carbon atom to which they are directly attached, form a cycloalkyl group, wherein no more than three R groups in each chain attached to the atom X* are cycloalkyl; each occurrence of R.sup.10 is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide]and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two R10 groups; Q is absent or is —O—, —NH—, —S—, —C(O)O—, —OC(O)—, —C(O)N(R4)-, —N(R5)C(O)—, —S—S—, —OC(O)O—, —O—N.dbd.C(R5)-, —C(R5).dbd.N—O—, —OC(O)N(R5)-, —N(R5)C(O)N(R5)-, —N(R5)C(O) O—, —C(O)S—, —C(S)O— or —C(R5).dbd.N—O—C (O)—; Q1 and Q2 are each, independently, absent, —O—, —S—, —OC(O)—, —C(O)O—, —SC(O)—, —C(O)S—, —OC(S)—, —C(S)O—, —S—S—, —C(O)(NR5)-, —N(R5)C(O)—, —C(S)(NR5)-, —N(R5)C(O)—, —N(R5) C(O)N(R5)-, or —OC(O)O—; Q3 and Q4 are each, independently, H, —(CR3R4)-, aryl, or a cholesterol moiety; each occurrence of A1, A2, A3 and A4 is, independently, —(CR5R5-CR5.dbd.CR5)-; each occurrence of R5 is, independently, H or alkyl; M1 and M2 are each, independently, a biodegradable group (e.g., —OC(O)—, —C(O)O—, —SC (O)—, —C(O)S—, —OC(S)—, —C(S)O—, —S—S—, —C(R5).dbd.N—, —N.dbd.C(R5)-, —C(R5).dbd.N—O—, —O—N.dbd.C(R5)-, —C(O)(NR5)-, —N(R5)C(O)—, —C(S)(NR5)-, —N(R5)C(O)—, —N(R5)C(O)N(R5)-, —OC(O)O—, —OSi(R5).sub.20-, —C(O)(CR3R4)C(O) O—, or —OC(O)(CR3R4)C(O)—); Z is absent, alkylene or —O—P(O)(OH)—O—; each — attached to Z is an optional bond, such that when Z is absent, Q3 and Q4 are not directly covalently bound together; a is 1, 2, 3, 4, 5 or 6; b is 0, 1, 2, or 3; c, d, e, f, i, j, m, n, q and r are each, independently, 0, 1, 2, 3, 4, 5, 6, 7, 8, 9, or 10; g and h are each, independently, 0, 1 or 2; k and 1 are each, independently, 0 or 1, where at least one of k and 1 is 1; and o and p are each, independently, 0, 1 or 2, wherein Q3 and Q4 are each, independently, separated from the tertiary atom marked with an asterisk (X*) by a chain of 8 or more atoms. The cationic lipid can be used with other lipid components such as cholesterol and PEG-lipids to form lipid nanoparticles with oligonucleotides, to facilitate the cellular uptake and endosomal escape, and to knockdown target mRNA both in vitro and in vivo.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, Dec. 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3—N, N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, Dec. 2011). A dosage of 1 µg/ml of LNP or CRISPR-Cas RNA in or associated with the LNP may be contemplated, especially for a formulation containing DLinKC2-DMA.

Preparation of LNPs and CRISPR Cas encapsulation may be used/and or adapted from Rosin et al, Molecular Therapy, vol. 19, no. 12, pages 1286-2200, Dec. 2011). The cationic lipids 1,2-dilineoyl-3-dimethylammonium-propane (DLin-DAP), 1,2-dilinoleyloxy-3—N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(o-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, Dec. 2011. A lipid premix solution (20.4 mg/ml total lipid concentration) may be prepared in ethanol containing DLinKC2-DMA, DSPC, and cholesterol at 50:10: 38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Preassembled recombinant CRISPR-Cpf1 complexes comprising Cpf1 and crRNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun 6. doi: 10.1038/nbt.3596. [Epub ahead of print]

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

In some embodiments, sugar-based particles may be used, for example GalNAc, as described herein and with reference to WO2014118272 (incorporated herein by reference) and Nair, J K et al., 2014, Journal of the American Chemical Society 136 (49), 16958-16961) and the teaching herein, especially in respect of delivery applies to all particles unless otherwise apparent. This may be considered to be a sugar-based particle and further details on other particle delivery systems and/or formulations are provided herein. GalNAc can therefore be considered to be a particle in the sense of the other particles described herein, such that general uses and other considerations, for instance delivery of said particles, apply to GalNAc particles as well. A solution-phase conjugation strategy may for example be used to attach triantennary GalNAc clusters (mol. wt. ~2000) activated as PFP (pentafluorophenyl) esters onto 5'-hexylamino modified oligonucleotides (5'-HA ASOs, mol. wt. ~8000 Da; Ostergaard et al., Bioconjugate Chem., 2015, 26 (8), pp 1451-1455). Similarly, poly(acrylate) polymers have been described for in vivo nucleic acid delivery (see WO2013158141 incorporated herein by reference). In further alternative embodiments, pre-mixing CRISPR nanoparticles (or protein complexes) with naturally occurring serum proteins may be used in order to improve delivery (Akinc A et al, 2010, Molecular Therapy vol. 18 no. 7, 1357-1364).

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Aspects of the invention encompass a non-naturally occurring or engineered composition that may comprise a guide RNA (sgRNA) comprising a guide sequence capable of hybridizing to a target sequence in a genomic locus of interest in a cell and a AAV-CRISPR enzyme that may comprise at least one or more nuclear localization sequences, wherein the AAV-CRISPR enzyme comprises one or two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the AAV-CRISPR enzyme comprises one or two or more mutations in a residue selected from the group comprising, consisting essentially of, or consisting of D908, E993, or D1263 according to AsCpf1 protein; D917 or H1006 according to FnCpf1; or D832, E925, D947, or D1180 according to LbCpf1. In a further embodiment the AAV-CRISPR enzyme comprises one or two or more mutations selected from the group comprising D908A, E993A, or D1263 as to AsCpf1; D917A or H1006A as to FnCpf1; or D832A, E925A, D947A, or D1180A as to LbCpf1. In another embodiment, the functional domain comprise, consist essentially of a transcriptional activation domain, e.g., VP64. In another embodiment, the functional domain comprise, consist essentially of a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCbl2r, φCb23r, 7s, PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein. An aspect of the invention is that the above elements are comprised in a single composition or comprised in individual compositions, e.g., the AAV-CRISPR enzyme delivers the enzyme as discussed as well as the guide. These compositions may advantageously be applied to a host to elicit a functional effect on the genomic level. In general, the sgRNA are modified in a manner that provides specific binding sites (e.g., aptamers) for adapter proteins comprising one or more functional domains (e.g., via fusion protein) to bind to. The modified sgRNA are modified such that once the sgRNA forms a AAV-CRISPR complex (i.e. AAV-CRISPR enzyme binding to sgRNA and target) the adapter proteins bind and, the functional domain on the adapter protein is positioned in a spatial orientation which is advantageous for the attributed function to be effective. For example, if the functional domain comprise, consist essentially of a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target. Again, the AAV-CRISPR enzyme can deliver both the enzyme and the modified guide. The skilled person will understand that modifications to the sgRNA which allow for binding of the adapter+functional domain but not proper positioning of the adapter+functional domain (e.g., due to steric hindrance within the three dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g., aptamers) specific to the same or different adapter protein. The sgRNA may be designed to bind to the promoter region −1000–+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the AAV-CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a AAV-Cpf1 enzyme or AAV-CRISPR enzyme having advantageously about 0% of the nuclease activity of the non-mutated or wild type Cpf1 enzyme or CRISPR enzyme, or no more than about 3% or about 5% or about 10% of the nuclease activity of the non-mutated or wild type Cpf1 enzyme or CRISPR enzyme). This is possible by introducing mutations into the RuvC and HNH nuclease domains of the AsCpf1 and orthologs thereof. For example utilizing mutations in a residue selected from the group comprising, consisting essentially of, or consisting of D908, E993, or D1263 according to AsCpf1 protein; D917 or H1006 according to FnCpf1; or D832, E925, D947, or D1180 according to LbCpf1, and more preferably introducing one or more of the mutations selected from the group comprising, consisting essentially of, or consisting of D908A, E993A, or D1263 as to AsCpf1; D917A or H1006A as to FnCpf1; or D832A, E925A, D947A, or D1180A as to LbCpf1. The inactivated CRISPR enzyme may have associated (e.g., via fusion protein) one or more functional domains, e.g., at least one destabilizing domain; or, for instance like those as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different. In general, the positioning of the one or more functional domain on the inactivated AAV-CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the AAV-CRISPR enzyme. Positioning the functional domain in the Rec domain, the Rec2 domain, the HNH domain, or the PI domain of the AsCpf1 protein or any ortholog corresponding to these domains is advantageous; and again, it is mentioned that the functional domain can be a DD. Positioning of the functional domains to the Rec domain or the Rec2 domain, of the AsCpf1 protein or any ortholog corresponding to these domains, in some instances may be preferred. Fok1 functional domain may be attached at the N terminus. When more than one functional domain is included, the functional domains may be the same or different.

An adaptor protein may be any number of proteins that binds to an aptamer or recognition site introduced into the modified sgRNA and which allows proper positioning of one or more functional domains, once the sgRNA has been incorporated into the AAV-CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains. Such linkers may be used to associate the AAV (e.g., capsid or VP2) with the CRISPR enzyme or have the CRISPR enzyme comprise the AAV (or vice versa).

Thus, sgRNA, e.g., modified sgRNA, the inactivated AAV-CRISPR enzyme (with or without functional domains), and the binding protein with one or more functional domains, may each individually be comprised in a composition and administered to a host individually or collectively. Alternatively, these components may be provided in a single composition for administration to a host, e.g., the AAV-CRISPR enzyme can deliver the RNA or guide or sgRNA or modified sgRNA and/or other components of the CRISPR system. Administration to a host may be performed via viral vectors, advantageously using the AAV-CRISPR enzyme as the delivery vehicle, although other vehicles can be used to deliver components other than the enzyme of the CRISPR system, and such viral vectors can be, for example, lentiviral vector, adenoviral vector, AAV vector. Several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

In an aspect, the invention provides a particle delivery system or the delivery system or the virus particle of any one of any one of the above embodiments or the cell of any one of the above embodiments for use in medicine or in therapy; or for use in a method of modifying an organism or a non-human organism by manipulation of a target sequence in a genomic locus associated with a disease or disorder; or for use in a method of treating or inhibiting a condition caused by one or more mutations in a genetic locus associated with a disease in a eukaryotic organism or a non-human organism.; or for use in in vitro, ex vivo or in vivo gene or genome editing; or for use in in vitro, ex vivo or in vivo gene therapy.

The invention also provides a method of stimulating neurogenesis of a neuronal stem cell derived from the spinal cord stem by administering an agent that modulates one or more of: Gad1, Gad2, Pbx3 and Meis2 or the gene product of one or more of Gad1, Gad2, Pbx3 and Meis2.

The invention also provides a method of stimulating neurogenesis of a neuronal stem cell derived from the spinal cord stem by administering an agent that modulates one or more of: Gad1, Gad2, Pbx3, Meis2 and Runx1t1 or the gene product of one or more of: Gad1, Gad2, Pbx3, Meis2 and Runx1t1.

The invention also provides a method of stimulating neurogenesis of a neuronal stem cell derived from the spinal cord stem by administering an agent that modulates one or more of the genes presented in any one of Table 18 through Table 27; or the gene product of one or more of the genes presented in any one of Table 18 through Table 27.

The invention also provides a method of stimulating neurogenesis of a neuronal stem cell derived from the brain by administering an agent that modulates one or more of the genes presented in any one of Table 18 through Table 27 or the gene product of one or more of the genes presented in any one of Table 18 through Table 27.

The invention also provides a method of stimulating neurogenesis of a neuronal stem cell derived from the brain by administering an agent that modulates one or more of: Sox9, Rrm2, Gpr56, Draxin, Mfap4, Eomes, Sox4 and Neurod1 or the gene product of one or more of Sox9, Rrm2, Gpr56, Draxin, Mfap4, Eomes, Sox4 and Neurod1.

Methods of Modulating Proliferation and/or Differentiation of Neuronal Stem Cells In some embodiments, the invention provides a method of modulating proliferation and/or differentiation of neuronal stem cells in the spinal cord. Methods of modulating and modulating agents are described above. Methods of modulating proliferation and/or differentiation of neuronal stem cells in the spinal cord may comprise contacting the stem cells with an agent that modulates one or more of Gad1, Gad2, Pbx3 and Meis2 or the gene product of one or more of Gad1, Gad2, Pbx3 and Meis2.

The invention also provides a method of modulating proliferation and/or differentiation of neuronal stem cells in the spinal cord comprising contacting the stem cells with an agent that modulates one or more of: Gad1, Gad2, Pbx3, Meis2 and Runx1t1 or the gene product of one or more of: Gad1, Gad2, Pbx3, Meis2 and Runx1t1.

The invention also provides a method of modulating proliferation and/or differentiation of neuronal stem cells in the spinal cord comprising contacting the stem cells with an agent that modulates one or more of: the genes presented in any one of Table 18 through Table 27 or the gene product of one or more of the genes presented in any one of Table 18 through Table 27.

The invention also provides a method of modulating proliferation and/or differentiation of neuronal stem cells in the brain comprising contacting the stem cells with an agent that modulates one or more of: the genes presented in any one of Table 18 through Table 27 or the gene product of one or more of the genes presented in any one of Table 18 through Table 27.

The invention also provides a method of modulating proliferation and/or differentiation of neuronal stem cells in the brain comprising contacting the stem cells with an agent that modulates one or more of: Sox9, Rrm2, Gpr56, Draxin, Mfap4, Eomes, Sox4 and Neurod1 or the gene product of one or more of: Sox9, Rrm2, Gpr56, Draxin, Mfap4, Eomes, Sox4 and Neurod1.

Methods of Treatment

The invention also provides a method of treating a subject with a spinal cord injury. As used in this context, to "treat" means to cure, ameliorate, stabilize, prevent, or reduce the severity of at least one symptom or a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "in need of treatment" as used herein refers to a judgment made by a caregiver (e.g. physician, nurse, nurse practitioner, or individual in the case of humans; veterinarian in the case of animals, including non-human animals) that a subject requires or will benefit from treatment. This judgment is made based on a variety of factors that are in the realm of a caregiver's experience, but that include the knowledge that the subject is ill, or will be ill, as the result of a condition that is treatable by the compositions and therapeutic agents described herein.

The administration of compositions, agents, cells, or populations of cells, as disclosed herein may be carried out in any convenient manner including by aerosol inhalation, injection, ingestion, transfusion, implantation or transplantation. The agents described herein may be administered to a patient subcutaneously, intradermally, intratumorally, intranodally, intramedullary, intramuscularly, intrathecally, by intravenous or intralymphatic injection, or intraperitoneally.

As such, the invention also provides a method of treating a subject with a spinal cord injury, comprising administering to a subject in need thereof the gene product of one or more of Gad1, Gad2, Pbx3 and Meis2; or an agent that modulates one or more of Gad1, Gad2, Pbx3 and Meis2.

The invention also provides a method of treating a subject with a spinal cord injury, comprising administering to a subject in need thereof the gene product of one or more of Gad1, Gad2, Pbx3, Meis2 and Runx1t1; or an agent that modulates one or more of Gad1, Gad2, Pbx3, Meis2 and Runx1t1.

The invention also provides a method of treating a subject with a spinal cord injury, comprising administering to a subject in need thereof the gene product of one or more of the genes presented in any one of Table 18 through Table 27; or an agent that modulates one or more of the genes presented in any one of Table 18 through Table 27.

The invention also provides a method of treating a spinal cord injury in a subject in need thereof, comprising administering to the subject an adult newborn neuron, as described herein.

Methods of Single Cell Sequencing

Also provided within the scope of the invention is a method of single cell sequencing comprising extracting nuclei, from a population of cells under conditions that preserve a portion of the outer nuclear envelope and rough endoplasmic reticulum (RER), sorting single nuclei into separate reaction vessels, extracting RNA from the single nuclei, generating a cDNA library, and sequencing the library, whereby gene expression data from single cells is obtained.

Methods for carrying out single cell sequencing are described above. In certain embodiments, single cell expression profiling comprises single nucleus RNA sequencing. Single nucleus RNA sequencing advantageously provides for expression profiling of rare or hard to isolate cells. Additionally, single nucleus RNA sequencing may be used on fixed or frozen tissues. The ability of single nucleus sequencing to be performed on frozen tissues allows for the analysis of archived samples isolated from diseased tissues. RNA recovery from previous single nuclei sequencing methods is robust enough for measuring single cell gene expression, however, increased RNA recovery can allow increase gene reads per single cell. Applicants have unexpectedly determined that single nuclei comprising a portion of the rough endoplasmic reticulum (RER) can be isolated and the resulting nuclei provides for improved RNA recovery and single cell expression profiling. In some embodiments, the methods provide for isolation of single nuclei with partially intact outer membrane containing RER. In some embodiments, the methods allow for isolation of single nuclei with partially intact outer membrane and partially intact RER with ribosomes. In some embodiments, the methods allow for isolation of single nuclei with partially intact outer membrane, RER and mitochondria.

The single nuclei sequencing may comprise a method of high-throughput single nuclei sequencing, said method comprising: treating the heterogeneous population of cells with a reagent that stabilizes RNA; extracting nuclei; generating a suspension of isolated nuclei, wherein the suspension comprises a nuclear pore blocking polymer; optionally, enriching the nuclei suspension by FACS or magnetic-activated cell sorting (MACS); applying the nuclei suspension to a reverse emulsion microfluidic device configured for single nuclei, wherein single nuclei are individually compartmentalized with a single uniquely barcoded capture bead in an emulsion drop; extracting mRNA onto the barcoded capture beads; generating a barcoded cDNA library; and sequencing the library using paired-end sequencing, whereby gene expression data from single nuclei is obtained. The nuclei suspension may comprise 105-106 nuclei. 104-105 nuclei may be sequenced. The nuclear pore blocking polymer may be a poloxamer. The reagent that stabilizes RNA may be a reagent that comprises the properties of RNAlater.

In certain embodiments, the present invention provides for a method of single cell sequencing comprising: extracting nuclei from a population of cells under conditions that preserve a portion of the outer nuclear envelope and/or rough endoplasmic reticulum (RER); sorting single nuclei into separate reaction vessels; extracting RNA from the single nuclei; generating a cDNA library; and sequencing the library, whereby gene expression data from single cells is obtained.

In certain embodiments, extracting nuclei under conditions that preserve a portion of the outer nuclear envelope and rough endoplasmic reticulum (RER) comprises homogenizing the population of cells in a lysis buffer comprising: a detergent selected from the group consisting of NP40, CHAPS and Tween-20; and an ionic strength between 100 mM and 200 mM. The NP40 concentration may be about 0.2%. The Tween-20 concentration may be about 0.03%. The CHAPS concentration may be about 0.49%. In some embodiments, polyamines may be included.

In certain embodiments, the population of cells may be treated with a reagent that stabilizes RNA. The reagent that stabilizes RNA may be a reagent that comprises the properties of RNAlater.

In certain embodiments, the separate reaction vessels may be microwells in a plate. In certain embodiments, the separate reaction vessels may be microfluidic droplets.

In certain embodiments, the population of cells may be obtained from a tissue sample. The tissue sample may be frozen. The frozen sample may have been frozen immediately after it was removed from a subject. The frozen tissue sample may have been frozen with a cryopreservant. The frozen sample may be processed according to the present invention immediately upon thawing the frozen sample. The tissue sample may be obtained from the brain. The tissue sample may be obtained from the gut. In certain embodiments, brain and gut cells are difficult to analyze by single cell RNA sequencing due to cell morphology. In certain embodiments, single nuclei sequencing can overcome difficulty in analyzing rare cells in the gut and brain due to cell morphology. In certain embodiments, the present invention provides for genetic targeting of rare cells in a complex tissue.

In certain embodiments, the tissue sample may be obtained from the heart, lung, prostate, skeletal muscle, esophagus, skin, breast, prostate, pancreas, or colon.

In certain embodiments, the tissue sample is obtained from a subject suffering from a disease. Since samples may be frozen and analyzed by single nuclei sequencing, samples from many diseased patients may be analyzed at once. The samples do not need to be analyzed immediately after removal from a subject. Diseased samples may be compared to healthy samples and differentially genes may be detected. In certain embodiments, the disease is autism spectrum disorder. Other diseases may include, but are not limited to, cancer (e.g., brain cancer) and irritable bowel disease (IBD).

Previous methods (e.g., including commercial methods) for isolating nuclei contain lysis buffers incapable of preserving a portion of the outer nuclear envelope and ribosomes, outer nuclear envelope, rough endoplasmic reticulum (RER) with ribosomes, or outer nuclear envelope, RER, and mitochondria. Before the present invention it was not appreciated that gene expression of single cells may be improved by isolating nuclei that include a portion of the outer nuclear envelope, and/or attached ribosomes, and/or rough endoplasmic reticulum (RER). In certain embodiments, the ribosomes and/or RER is a site of RNA translation and includes fully spliced mRNA. Preserving a portion of the RER improves RNA recovery and single cell expression profiling.

In certain embodiments, single nuclei comprising ribosomes and/or RER are isolated using lysis buffers comprising detergent and salt. In certain embodiments, the ionic strength of the buffer is between 100 and 200 mM. As used herein the term "ionic strength" of a solution refers to the measure of electrolyte concentration and is calculated by:

$$p = \frac{1}{2}\sum c_i z_i^2$$

where c is the molarity of a particular ion and z is the charge on the ion.

In certain embodiments, the ionic strength of the lysis solution can be obtained with salts, such as, but not limited to NaCl, KCl, and (NH4)2SO4. For example, the buffer can comprise 100-200 mM NaCl or KCl (i.e., ionic strength 100-200 mM). In one embodiment, the salt comprises NaCl and the concentration is 146 mM.

In certain embodiments, the buffer comprises $CaCl_2$). The $CaCl_2$) may be about 1 mM. In certain embodiments, the buffer comprises MgCl2. The MgCl2 may be about 21 mM.

In certain embodiments, the buffer comprises a detergent concentration that preserves a portion of the outer nuclear envelope and/or ribosomes, and/or rough endoplasmic reticulum (RER). The detergent may be an ionic, zwitterionic or nonionic detergent. The detergent concentration may be a concentration that is sufficient to lyse cells, but not strong enough to fully dissociate the outer nuclear membrane and RER or detach ribosomes. In certain embodiments, the detergent is selected from the group consisting of NP40, CHAPS and Tween-29. Detergent concentrations may be selected based on the critical micelle concentration (CMC) for each detergent (Table 3). The concentration may be varied above and below the CMC. In certain embodiments, the detergent concentration in the lysis buffer of the present invention comprises about 0.2% NP40, about 0.49% CHAPS, or about 0.03% Tween-20. The critical micelle concentration (CMC) is defined as the concentration of surfactants above which micelles form and all additional surfactants added to the system go to micelles. Before reaching the CMC, the surface tension changes strongly with the concentration of the surfactant. After reaching the CMC, the surface tension remains relatively constant or changes with a lower slope.

The isolated nuclei comprising a preserved portion of the outer membrane and RER and/or ribosomes may be further analyzed by single nuclei sequencing, droplet single nuclei sequencing or Div-seq as described in international application number PCT/US2016/059239 published as WO/2017/164936. In certain embodiments, single nuclei are sorted into separate wells of a plate. In certain embodiments, single nuclei are sorted into individual droplets. The droplets may contain beads for barcoding the nucleic acids present in the single nuclei. The plates may include barcodes in each well. Thus, barcodes specific to the nuclei (i.e., cell) of origin may be used to determine gene expression in single cells.

TABLE 3

| | MW (Da) | CMC | gram per 1 mL | % w/v CMC |
|---|---|---|---|---|
| Nonidet P-40/IGEPAL CA-630 | ~603 | 0.08 mM (sigma); 0.05-0.3 mM (anatrace) | 0.00048 | 0.048% |
| Tween-20 | 1228 | 0.049 mM | 0.00006 | 0.006% |
| Digitonin | 70000 | <0.5 mM | 0.035 | 3.5% |
| CHAPS | 614.9 | 8 to 10 mM | 0.00492 | 0.49% |

Exemplary nuclei purification protocols may be used with a lysis buffer of the present invention (Table 4).

TABLE 4

| Composition | Buffer | Buffer concentration | Detergent | Detergent concentration (%) | Salt and concentration | Additives and concentration |
|---|---|---|---|---|---|---|
| 1 | Tris | 10 mM | NP40 | 0.2 | 146 mM NaCl, 1 mM CaCl2, 21 mM MgCl2 | |
| 2 | Tris | 10 mM | CHAPS | 0.49 | 146 mM NaCl, 1 mM CaCl2, 21 mM MgCl2 | |
| 3 | Tris | 10 mM | Tween-20 | 0.03 | 146 mM NaCl, 1 mM CaCl2, 21 mM MgCl2 | 0.15 mM spermine and |
| 4 | Tricine | 20 mM | NP40 | 0.2 | 146 mM NaCl, 1 mM CaCl2, 21 mM MgCl2 | 0.5 mM spermidine |

Nuclei Purification Protocol

Nuclei purification protocol (see., e.g., Swiech L, et al., Nat Biotechnol. 2015 Jan;33(1):102-6. doi: 10.1038/nbt.3055. Epub 2014 Oct 19). The protocol may be modified by using the lysis buffer as described above. In certain embodiments, the procedure may be used for frozen/fixed tissue. 1. Dounce homogenize tissue in 2 ml of ice-cold lysis buffer (25 times with a, 25 times with b), transfer to a 15 ml tube.

1. Rinse homogenizer with 2 ml of ice-cold lysis buffer to get final 4 ml, and collect in the same tube.
2. Mix well and set on ice for 5 minutes.

3. Collect the nuclei by centrifugation at 500×g for 5 minutes at 4° C. Carefully aspirate the clear supernatant from each tube and set the nuclei pellet on ice. Note: The supernatant contains cytoplasmic components and can be saved for later analysis or use.
4. Resuspend. Add 1 ml cold lysis buffer and mix by pipetting gently with a 1 ml tip to completely suspend nuclei pellet. Add the remaining 3 ml of lysis buffer, mix well and set on ice for 5 minutes.
5. Collect washed nuclei by centrifugation as in step 3. Carefully aspirate the clear supernatant and set the nuclei pellet on ice.
6. Optional: Wash. Resuspend in 4 ml 0.01% PBS BSA or Resuspension buffer (RB*). Collect washed nuclei by centrifugation as in step 3.
7. Resuspend with ~500 µl Resuspension buffer (RB*) or 0.01% PBS BSA+RNAse inhibitor carefully by slow vortex & pipette 10× with a 1 ml tip, then transfer to tubes (for FACS, filter through a membrane to get better purity.
8. Counterstain nuclei with Ruby Dye 1:500-1:1000 (check for clumps in the microscope before sorting).

Resuspension buffer—based on the original nuclei resuspension buffer from Swiech et al. 2015:

TABLE 5

|  | Stocks | For 10 ml |
| --- | --- | --- |
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

In certain embodiments, nuclei may be isolated by sucrose gradient centrifugation as described (Swiech L, et al. Nat Biotechnol. 2015 January;33(1):102-6).

Additional methods for extracting nuclei from a population of cells under conditions that preserve a portion of the outer nuclear envelope and RER are described in the Examples.

Methods of sequencing nucleic acids derived from single cells are described above. Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil).

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

Activation of sample fluid reservoirs to produce regent droplets is now described. The disclosed invention is based on the concept of dynamic reagent delivery (e.g., combinatorial barcoding) via an on demand capability. The on demand feature may be provided by one of a variety of technical capabilities for releasing delivery droplets to a primary droplet, as described herein.

An aspect in developing this device will be to determine the flow rates, channel lengths, and channel geometries. Once these design specifications are established, droplets containing random or specified reagent combinations can be generated on demand and merged with the "reaction chamber" droplets containing the samples/cells/substrates of interest.

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioninformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, flurophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment. In certain example embodiments, the methods disclosed herein may be used to conduct pooled CRISPR screening such as that disclosed in Datlinger et al. bioRXiv dx.doi.org/10.1101/083774.

Droplet generation and deployment is produced via a dynamic indexing strategy and in a controlled fashion in accordance with disclosed embodiments of the present invention. Disclosed embodiments of the microfluidic device described herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

A plurality of biological assays as well as biological synthesis are contemplated for the present invention.

In an advantageous embodiment, polymerase chain reactions (PCR) are contemplated (see, e.g., US Patent Publication No. 20120219947). Methods of the invention may be used for merging sample fluids for conducting any type of chemical reaction or any type of biological assay. In certain embodiments, methods of the invention are used for merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

One of skill in the art will recognize that methods and systems of the invention are not limited to any particular type of sample, and methods and systems of the invention may be used with any type of organic, inorganic, or biological molecule (see, e.g, US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA. Tissues may be freshly dissected, frozen tissue, or fixed tissue. In specific embodiments, the tissues are frozen in clear tubes.

Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules may be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-C6H4--(OCH2-CH2)xOH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer.

In another embodiment, the sample includes individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. In one embodiment of the invention protein targets are isolated from biological samples containing a variety of other components including lipids, non-template nucleic acids, and nucleic acids. In certain embodiments, protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, S-carboxymethylation, acetylation, and methylation. Protein/nucleic acid complexes include cross-linked or stable protein-nucleic acid complexes.

Extraction or isolation of individual proteins, protein complexes, proteins with translational modifications, and protein/nucleic acid complexes is performed using methods known in the art.

To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In certain embodiments, the first sample fluid will include some or all of the reagents necessary for the PCR whereas the second sample fluid will contain the balance of the reagents necessary for the PCR together with the detection probes.

Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

A droplet containing the nucleic acid is then caused to merge with the PCR reagents in the second fluid according to methods of the invention described above, producing a droplet that includes Taq polymerase, deoxynucleotides of type A, C, G and T, magnesium chloride, forward and reverse primers, detectably labeled probes, and the target nucleic acid.

Once mixed droplets have been produced, the droplets are thermal cycled, resulting in amplification of the target nucleic acid in each droplet. In certain embodiments, the droplets are flowed through a channel in a serpentine path between heating and cooling lines to amplify the nucleic acid in the droplet. The width and depth of the channel may be adjusted to set the residence time at each temperature, which may be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme.

The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets is fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

After amplification, droplets may be flowed to a detection module for detection of amplification products. The droplets may be individually analyzed and detected using any methods known in the art, such as detecting for the presence or amount of a reporter. Generally, the detection module is in communication with one or more detection apparatuses. The detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In another embodiment, examples of assays are ELISA assays (see, e.g., US Patent Publication No. 20100022414).

The present invention provides another emulsion library which may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay.

In another embodiment, single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention In other embodiments, chemical prototyping and synthetic chemical reactions are also contemplated within the methods of the invention.

In one embodiment of the invention, the method comprises obtaining at least one section from one or more tissue samples. Any suitable tissue sample can be used in the methods described herein. For example, the tissue can be epithelium, muscle, organ tissue, nerve tissue, tumor tissue, and combinations thereof. Samples of tissue can be obtained by any standard means (e.g., biopsy, core puncture, dissection, and the like, as will be appreciated by a person of skill in the art). At least one section may be labeled with a histological stain, to produce a histologically stained section. As used in the invention described herein, histological stains can be any standard stain as appreciated in the art, including but not limited to, alcian blue, Fuchsin, haematoxylin and eosin (H&E), Masson trichrome, toluidine blue, Wright's/Giemsa stain, and combinations thereof. As will be appreciated by a person of skill in the art, traditional histological stains are not fluorescent. At least one other section may be labeled with at least one fluorescently labeled reagent to produce a fluorescently labeled section. As used in the invention described herein, the panel of fluorescently labeled reagents comprises a number of reagents, such as fluorescently labeled antibodies, fluorescently labeled peptides, fluorescently labeled polypeptides, fluorescently labeled aptamers, fluorescently labeled oligonucleotides (e.g. nucleic acid probes, DNA, RNA, cDNA, PNA, and the like), fluorescently labeled chemicals and fluorescent chemicals (e.g., Hoechst 33342, propidium iodide, Draq-5, Nile Red, fluorescently labeled phalloidin), and combinations thereof. Each fluorescently labeled reagent is specific for at least one biomarker. As used herein, a "biomarker" is a molecule which provides a measure of cellular and/or tissue function. For example, and without limitation, a biomarker can be the measure of receptor expression levels, (e.g., estrogen receptor expression levels, Her2/neu expression); transcription factor activation; location or amount or activity of a protein, polynucleotide, organelle, and the like; the phosphorylation status of a protein, etc. In one embodiment, a biomarker is a nucleic acid (e.g., DNA, RNA, including micro RNAs, snRNAs, mRNA, rRNA, etc.), a receptor, a cell membrane antigen, an intracellular antigen, and extracellular antigen, a signaling molecule, a protein, and the like. In one embodiment of the invention, a panel of fluorescently labeled reagents detects at least about four different biomarkers. In another embodiment of the invention, a panel of fluorescently labeled reagents detects at least about four to about six, to about ten, to about twelve different biomarkers or more. In a further embodiment, each fluorescently labeled reagent has different fluorescent properties, which are sufficient to distinguish the different fluorescently labeled reagents in the panel.

A single biomarker can provide a read-out of more than one feature. For example, Hoechst dye detects DNA, which is an example of a biomarker. A number of features can be identified by the Hoechst dye in the tissue sample such as nucleus size, cell cycle stage, number of nuclei, presence of apoptotic nuclei, etc. In one embodiment of the invention, the imaging procedures are automated.

In one embodiment of the invention, the one or more tissue samples are isolated from one or more animals. For example, in one embodiment, the one or more animals are one or more rodents, preferably a mouse. The tissue may be isolated from a human subject. In certain embodiments tissues are isolated post mortem. In a particular embodiment, one or more tissue samples are isolated from an animal at one or more time points.

Methods of dissecting tissues from any organism are well known in the art. One method that may be utilized according to the present invention may be microdissection. Laser Capture Microdissection (LCM) enables separation of clusters of cells or even individual cells of interest from a background of millions of other cells. The collected cells can be directly visualized to verify their identity and purity. LCM is used to select small clusters of cells of interest from frozen sections of tissue by embedding them in a transfer film, e.g., a thermoplastic polymer. An example of a suitable thermoplastic polymer is ethylene vinyl acetate (EVA). The general methods of LCM are well known. See, e.g., U.S. Pat. Nos. 5,985,085; 5,859,699; and 5,843,657; as well as Suarez-Quian et al., "Laser Capture Microdissection of Single Cells from Complex Tissues," BioTechniques, Vol. 26, pages 328-335 (1999); Simone et al., "Laser-capture microdissection: opening the microscopic frontier to molecular analysis," TIG, Vol. 14, pages 272-276 (1998); and Bonner et al., "Laser Capture Microdissection: Molecular Analysis of Tissue," Science, Vol. 278, pages 1481-1483 (1997).

LCM is a process by which cells and portions of biological tissue samples are acquired directly from tissue sections mounted on glass slides or other solid surfaces. Once the cells or tissue portions of interest (tissue targets) are located in the sample, a laser is focused over the tissue targets. When the laser is fired, the thin-film located directly above the tissue targets melts, flows down and adheres to the tissue targets. The tissue targets are now stabilized and ready for molecular analysis.

The present may also be performed on tissue samples isolated from transgenic animals, such as mice. The animal may express a genome editing system such as described in "In vivo interrogation of gene function in the mammalian brain using CRISPR-Cas9" Swiech L., et al., Nat Biotechnol Oct 19. (2014). The animal may be xenograft. Xenotransplantation of tumor cells into immunocompromised mice is a research technique frequently used in pre-clinical oncology research. The tissue may express a transgene for isolating tissue specifically from a tumor. The tissue may be labeled with a nucleoside analogue in order to isolate cells of a developmental stage.

In some embodiments of the invention the population of cells may be homogenized in a lysis buffer comprising a detergent selected from the group consisting of NP40, CHAPS and Tween-20; and having an ionic strength between 100 mM and 200 mM.

In some embodiments, the NP40 concentration may be about 0.2%. In some embodiments, the Tween-20 concentration may be about 0.03%. In some embodiments, the CHAPS concentration may be about 0.49%.

In some embodiments, the population of cells is treated with a reagent that stabilizes RNA. Such reagents may include, but are not necessarily limited to, RNAlater, RNAlater-ICE, THE RNA Storage Solution, TEMPUS® Blood RNA Tubes, LeukoLock Total RNA Isolation System, Stabilyser Reagent, PAXgene Blood RNA Tube, RNA/DNA STABIL, RNASound™, or DNA/RNA SHIELD™.

In some embodiments, the separate reaction vessels in this method are microwells in a plate, as described herein. In some embodiments, the separate reaction vessels are microfluidic droplets, as described herein.

In some embodiments, the population of cells is obtained from a tissue sample, as described herein. In specific embodiments, the tissue sample may be frozen. In specific embodiments, the tissue sample may be frozen in a clear tube.

In some embodiments, the tissue sample may be obtained from the brain. In some embodiments, the tissue sample may be obtained from the gut. In some embodiments, the tissue sample may be obtained from a subject suffering from a disease. In specific embodiments, the disease is a neurological disorder, such as, but not necessarily limited to, Alzheimer's disease, amyotrophic lateral sclerosis, Asperger syndrome, autism spectrum disorder, cerebellar degeneration or hypoplasia, cerebral aneurysm, cerebral arteriosclerosis, cerebral palsy, congenital myopathy, Creutzfeld-Jakob disease, Cushing's syndrome, dementia, Lewy Body disease, diabetic neuropathy, dyslexia, epilepsy, fibromuscular dysplasia, Guillain-Barre syndrome, headache, herpes zoster infection, Huntington's disease, Kuru, Lou Gehrig's disease, Lyme disease, lupus, mitochondrial myopathies, muscular dystrophy, narcolepsy, neuronal migration disorders, prion disesases, restless leg syndrome, shingles, Sjogren's syndrome, sleep apnea, Tay-Sachs disease, Tourette syndrome, transmissible spongiform encephalopathies, or trigeminal neuralgia.

In specific embodiments, the disease may be autism spectrum disorder.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M.J. MacPherson, B.D. Hames and G.R. Taylor eds. (1995)), Harlow and Lane, eds. (1988) ANTIBODIES, A LABORATORY MANUAL, and ANIMAL CELL CULTURE (R.I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Applicants have developed methods of performing a high-throughput single-nucleus isolation and RNA-Seq method compatible with fresh, frozen, or fixed tissue (Nuc-seq). The uniform shape and fixation of the isolated nuclei (FIG. 1A) combined with nuclei labeling (FIG. 5) enables enrichment of rare cell populations by fluorescent-activated cell sorting (FACS). The method was further developed for temporal analysis of dividing cells by addition of unbiased labeling with 5-ethynyl-2'-deoxyuridine (EdU), which is incorporated into the DNA of dividing cells (8), and using Click-IT to fluorescently tag the isolated EdU labeled nuclei, which can be readily captured by FACS (FIG. 5) (Div-seq).

Figure 6:
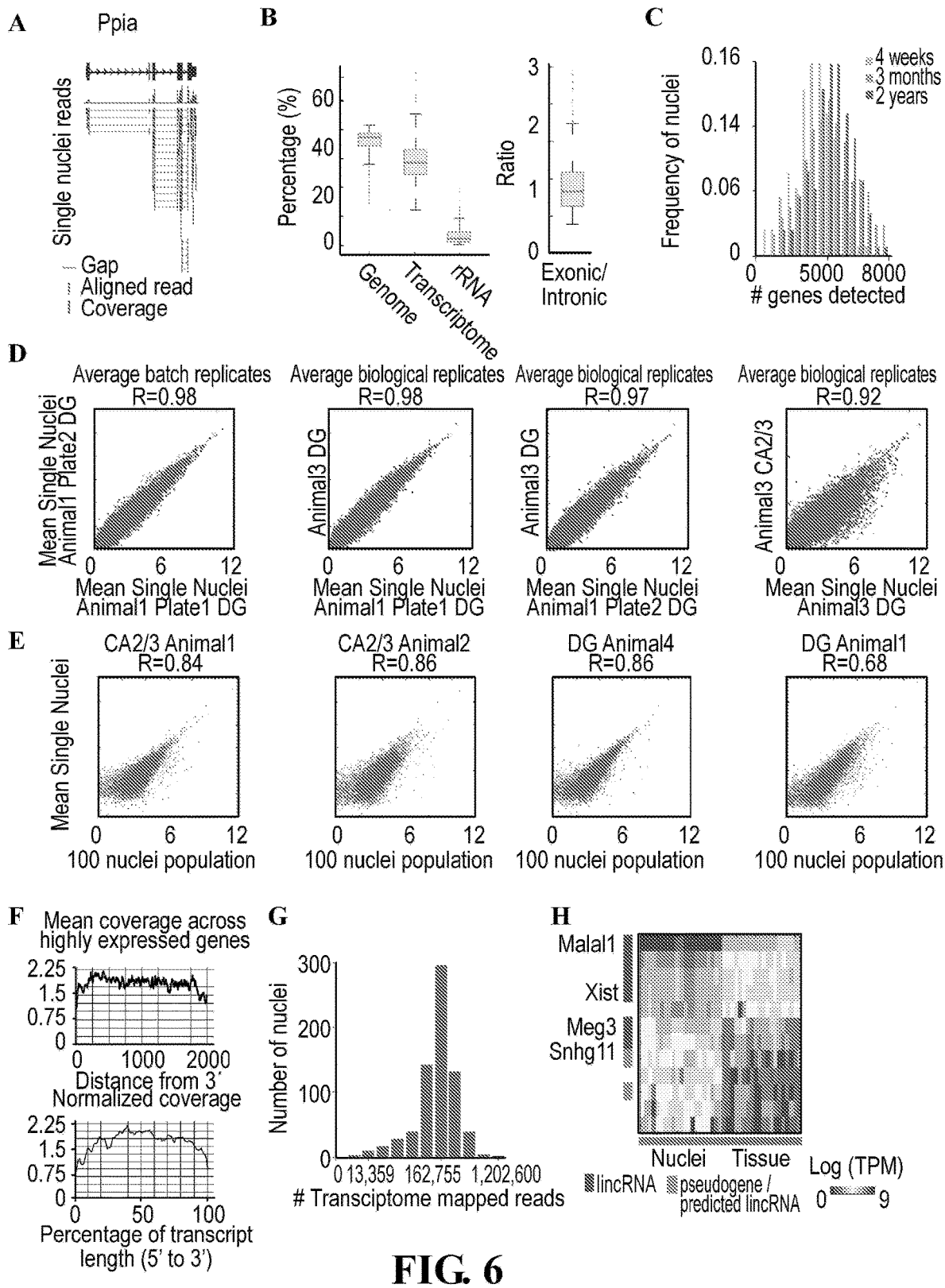

Earlier studies have shown the feasibility of single neuronal nuclei RNA-seq (9-11), however, it was previously unclear whether the type and complexity of nuclear mRNA could be effectively used for sensitive classification of cell types and states in the CNS on a large scale. Furthermore, given the relative low total amount and non-uniform distribution of RNA in neurons (nuclei, soma, axons, and dendrites), analysis of nuclei can introduce biases. Applicants thus first tested nuclei RNA-Seq (Nuc-Seq) in bulk. Comparing RNA profiles of bulk tissue and populations of nuclei from the hippocampus dentate gyrus (DG) showed remarkable agreement, with similar RNA complexity and profiles (FIG. 1B, in agreement with the previous observations (9)). Differential expression analysis shows that nuclear RNA enriches for long non-coding RNAs (FIG. 6). Thus, nuclear RNA contains as much information as tissue RNA, suggesting nuclear RNA-Seq does not introduce substantial biological biases.

Figure 7:
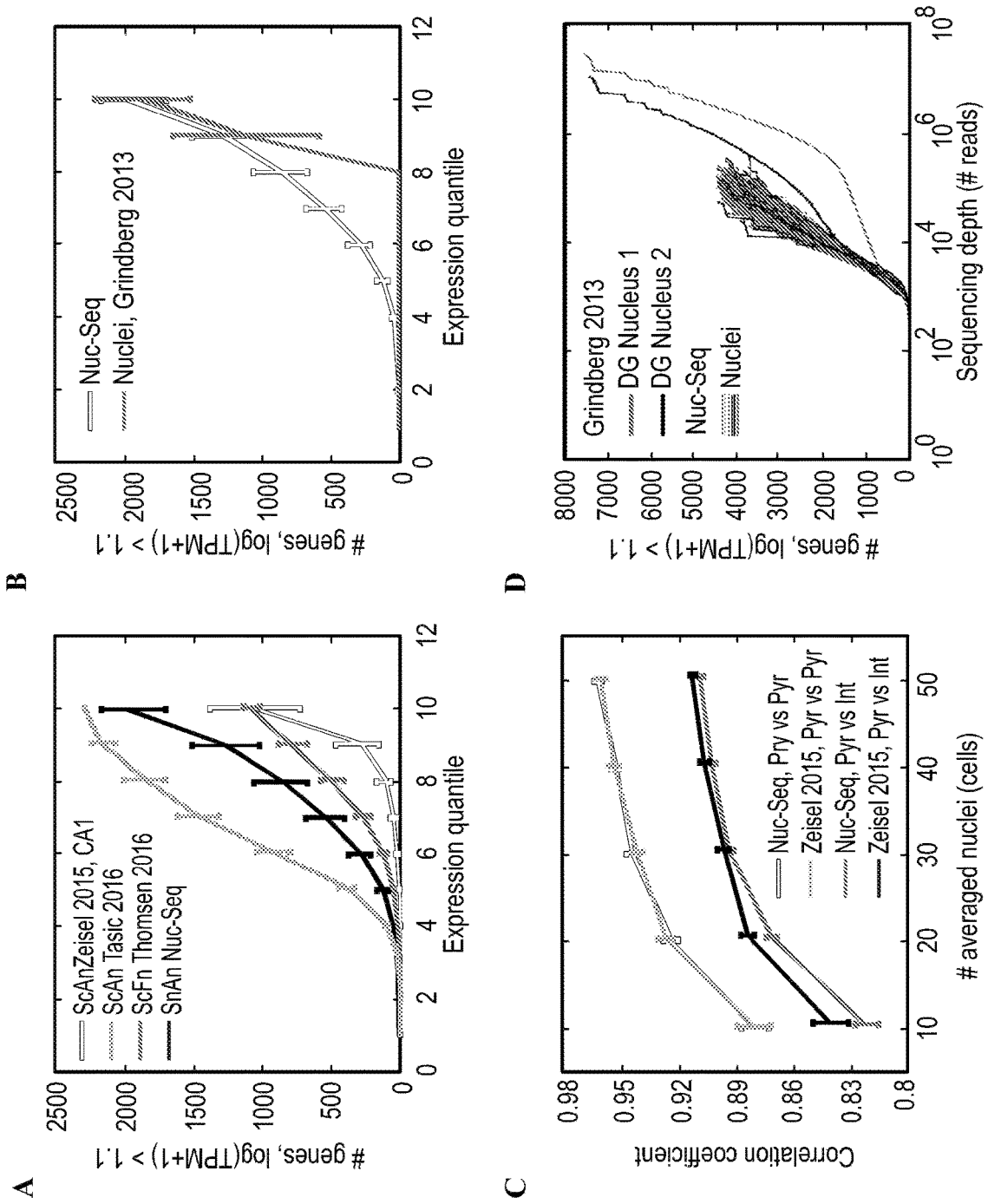

Next, Applicants analyzed 1,682 single nuclei from four hippocampal anatomical sub-regions (DG, CA1, CA2 and CA3) microdissected from adult mice, including genetically labeled and sorted GABAergic neurons nuclei that are of low abundance (~10% of total neuronal population (12), FIG. 5). Nuc-Seq detected 5,100 expressed genes per nucleus on average (FIG. 1C-D), with comparable quality metrics to single-cell (non-neuron) RNA-Seq libraries (FIG. 6) and better library complexity (1.9-fold on average) compared to published single neuron RNA-Seq data (1, 3, 4), across a wide range of expression levels (FIG. 1D, FIG. 7). The range of transcripts detected was significantly improved compared to that of previously analyzed single nuclei (9) (two nuclei, FIG. 7). Finally, the complexity of Nuc-Seq libraries were similar in young (1 month), adult (3 months), and old (2 years) mice (FIG. 6), demonstrating robustness across animal ages. Thus, Nuc-Seq generated high quality data, exceeding the sensitivity of current single neuron RNA-seq.

Example 2

Figure 10:
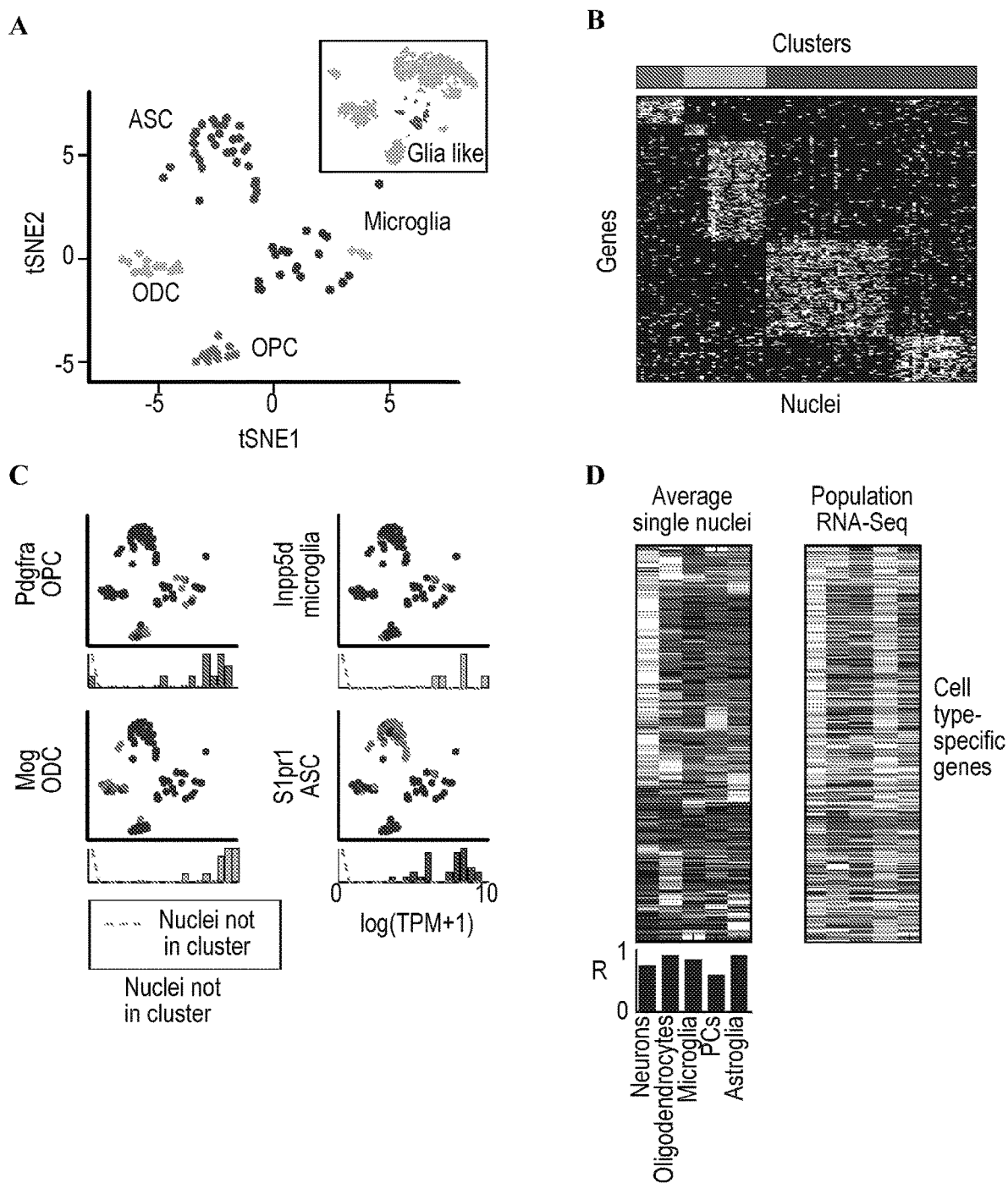

The present invention also provides for novel methods to analyze the Nuc-Seq data and generate high resolution maps (see materials and methods). Nuc-Seq analysis sensitively identified both major cell types and refined sub-types. Cluster analysis of Nuc-Seq data revealed seven major clusters of cells with distinct gene expression patterns (FIG. 1E-G, FIG. 8 and FIG. 9) that clearly correspond to known cell types and major anatomical distinctions in the hippocampus. Cluster identities were consistent with our microdissection scheme, and their gene expression patterns globally agreed with Allen Brain Atlas ISH data (Allen ISH(13), FIG. 9). Iterative re-clustering of the glia nuclei (cluster 7 in FIG. 1E. FIG. 10) recovered five known glial cell sub-types (14), and averaged expressions across each sub-cluster well-correlated with published population RNA-Seq data (14) (FIG. 10).

Figure 11:
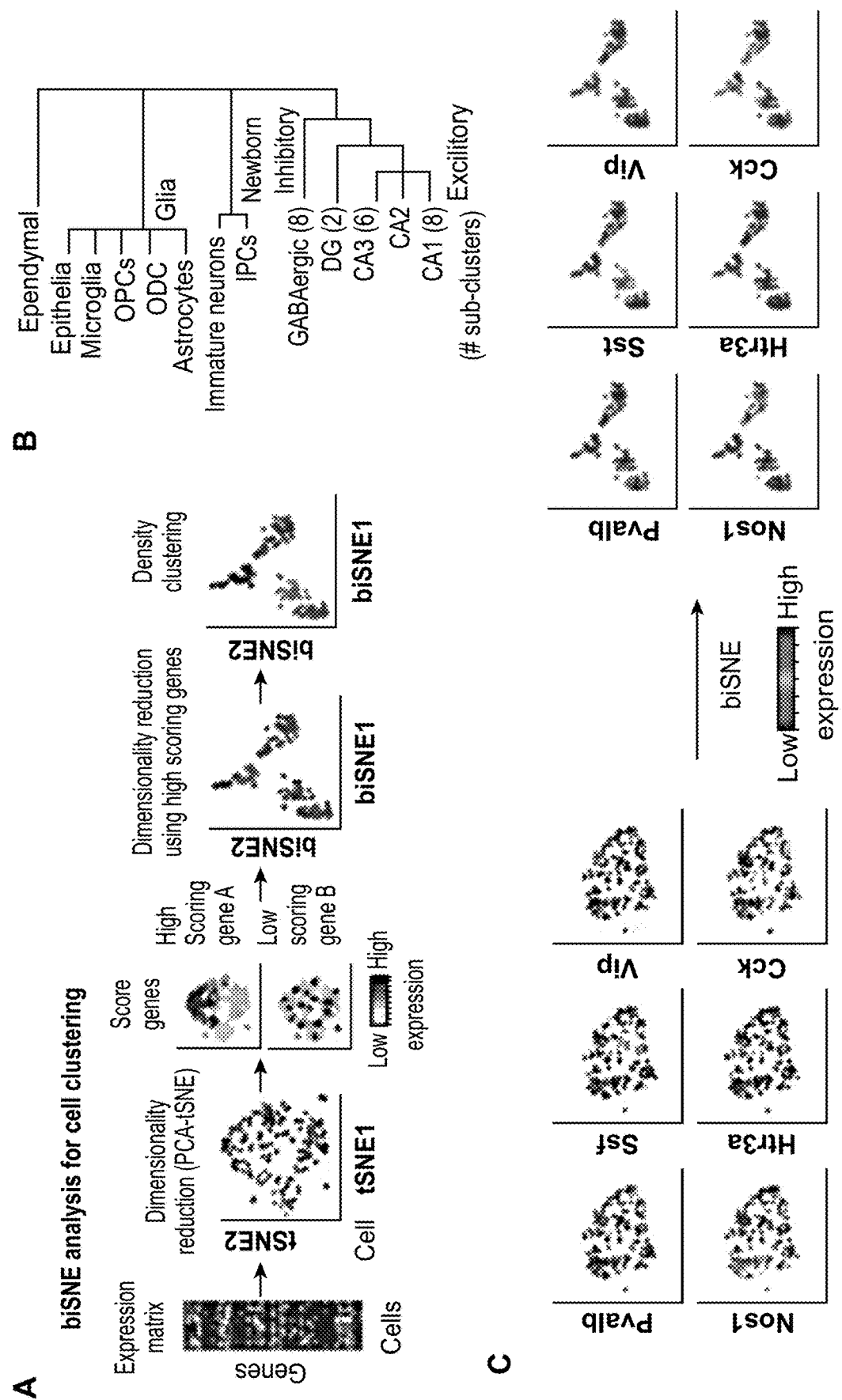
Figure 11:
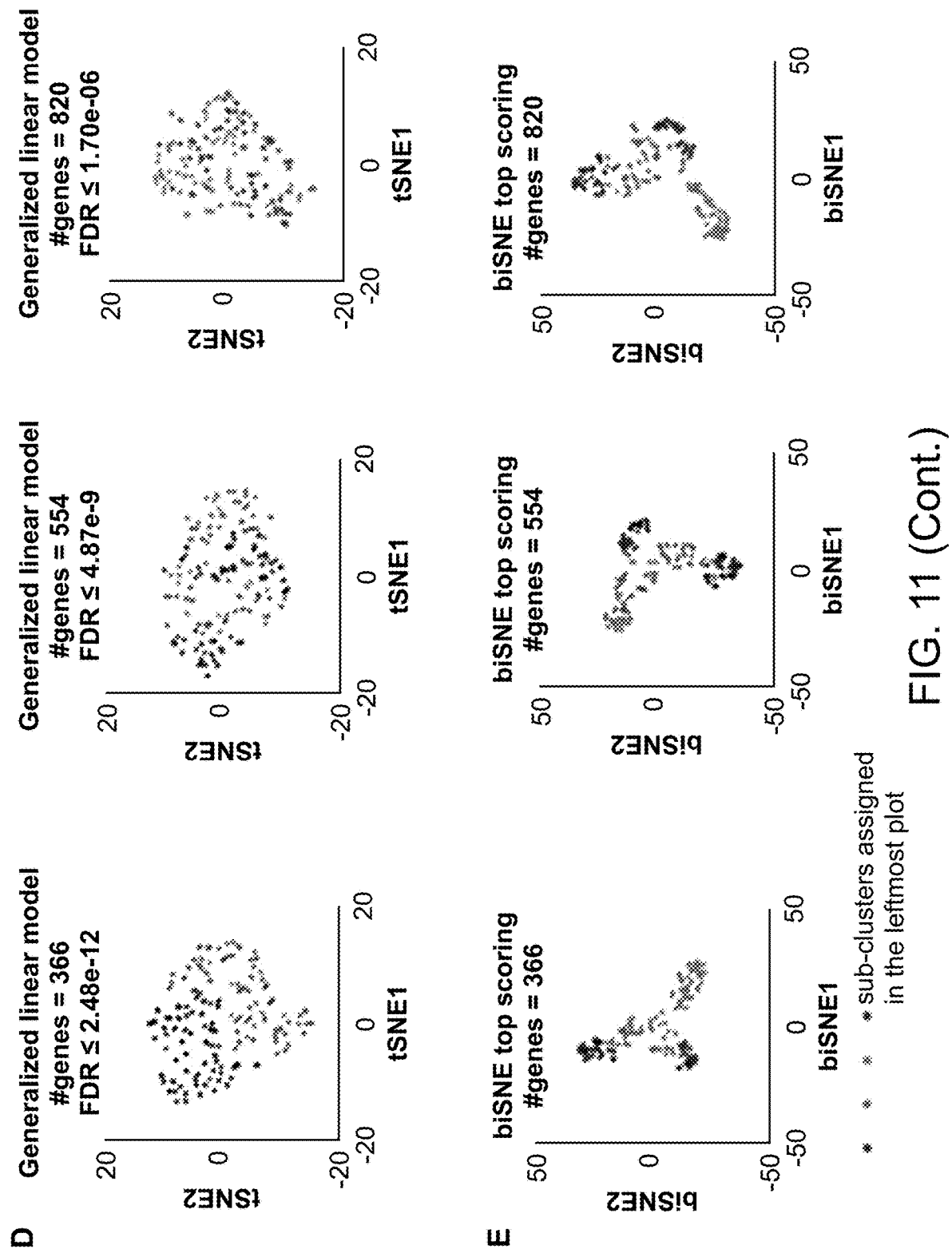
Figure 12:
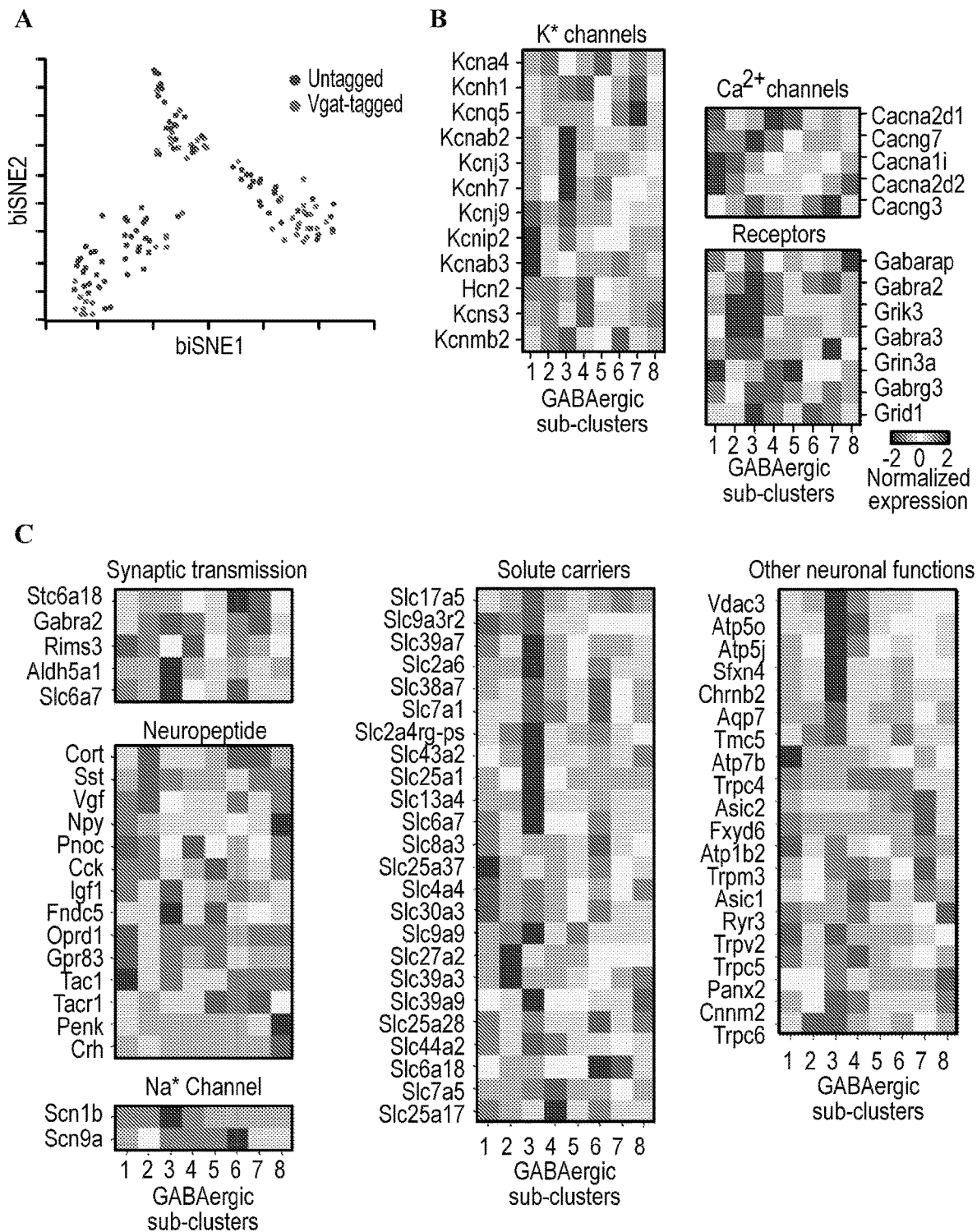
Figure 13:
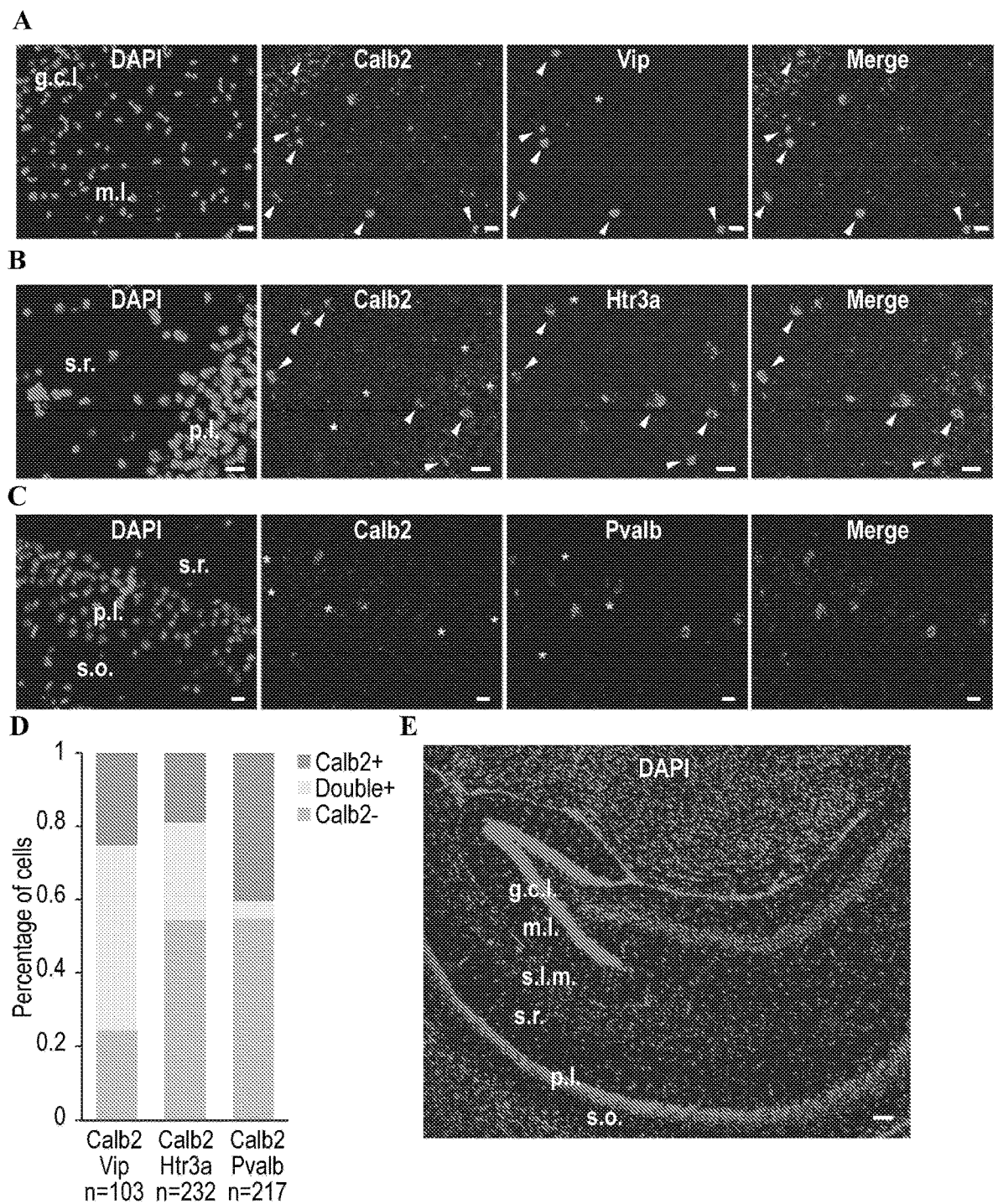

Applicants captured finer distinctions between closely related cell types using a new clustering algorithm, biSNE (biclustering on Stochastic Neighbor Embedding) (FIG. 11-12), which improved upon current methods (15) (FIG. 11). The biSNE analysis partitioned the GABAergic neurons into eight sub-clusters (FIG. 2A), each with unique expression of individual or pairs of canonical interneuron marker genes, such as Pvalb and Htr3a (FIG. 2B). Applicants validated the expression patterns of GABAergic markers by double fluorescent RNA in situ hybridization (dFISH) (FIG. 2C, FIG. 13). Applicants further characterized the sub-clusters by differential gene expression analysis, revealing for example that the calcium channel Cacnali is specifically expressed in Pvalb or Sst positive GABAergic neurons (FIG. 12).

Figure 14:
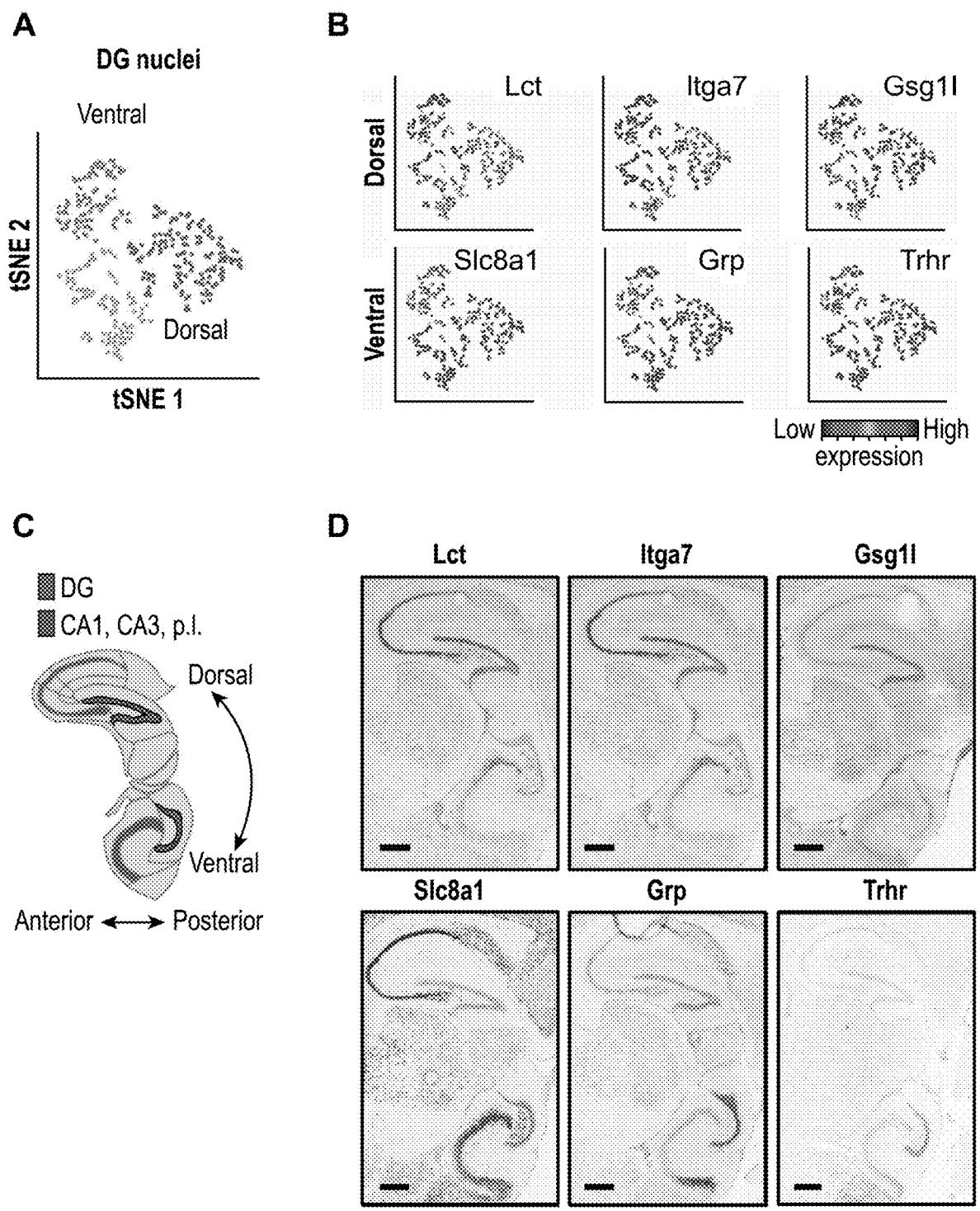
Figure 15:
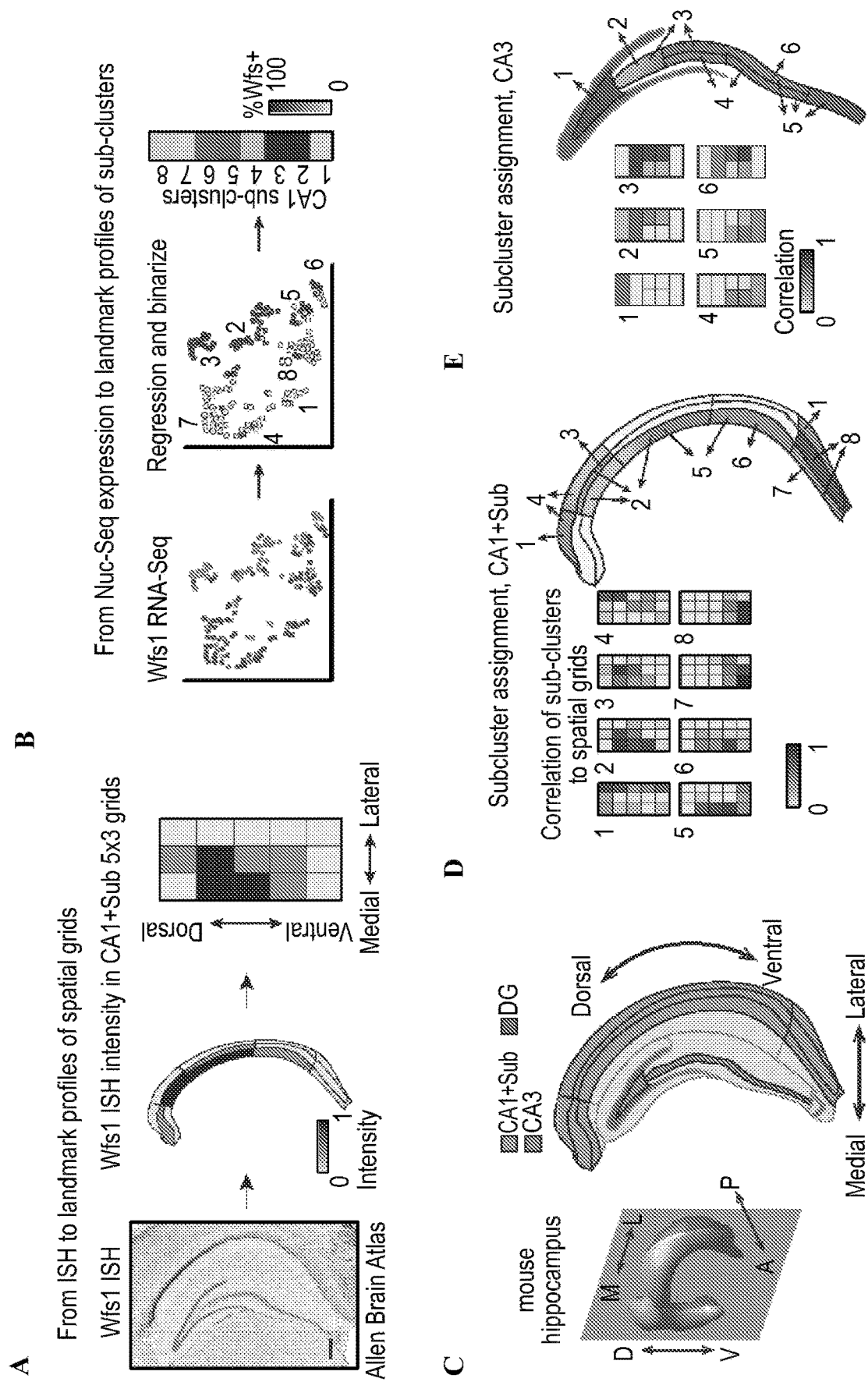
Figure 18:
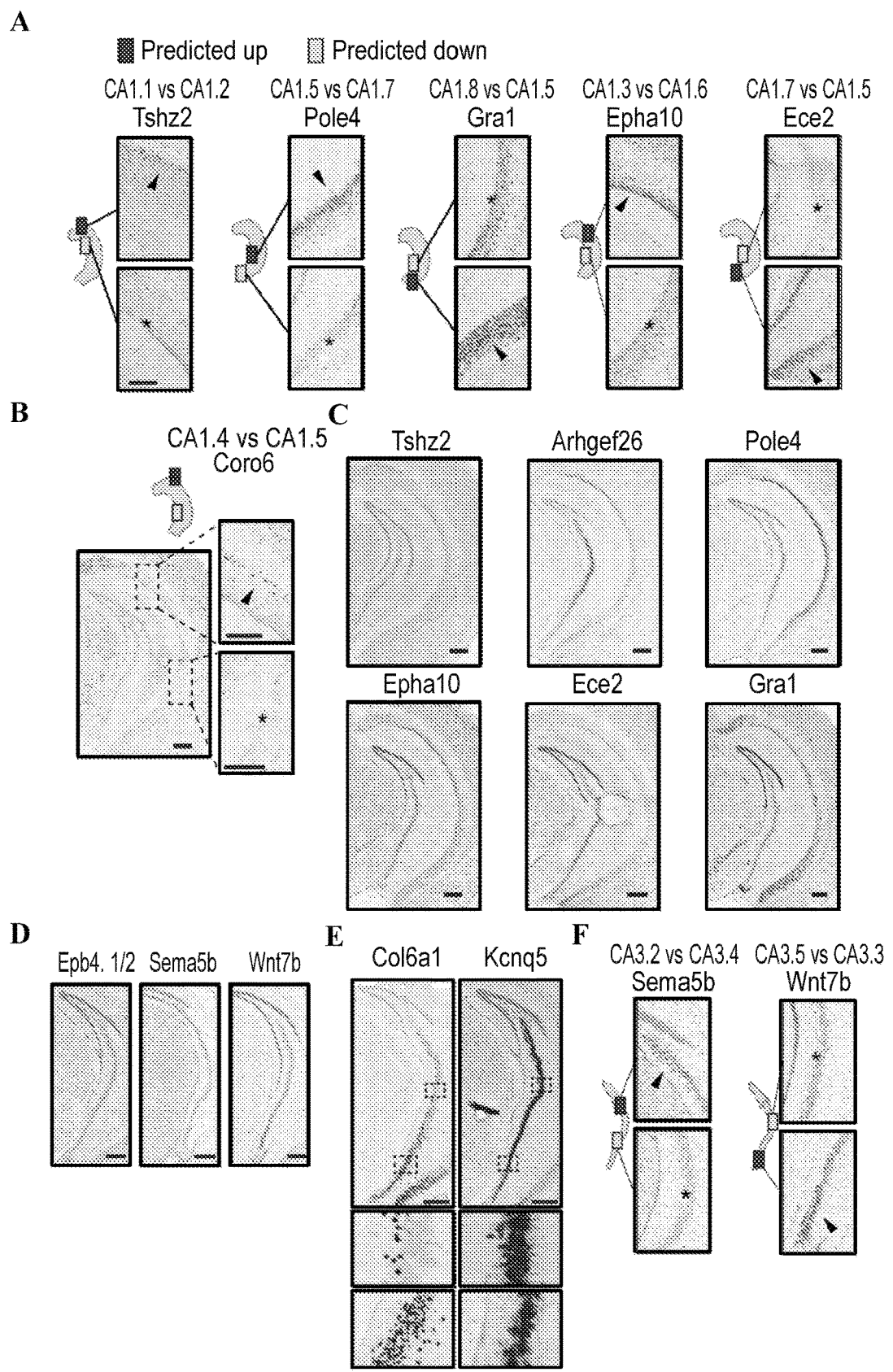

Nuc-Seq also distinguished between spatial sub-regions with divergent transcriptional profiles. biSNE analysis of NucSeq data partitioned glutamatergic cells from CA1, CA3, and DG into 8, 6, and 2 sub-clusters, respectively (FIG. 2D and FIG. 14). Analysis of sub-cluster specific gene expression highlighted several known landmark genes that exhibit spatially restricted expression patters in sub-regions of the hippocampus, indicating a correspondence between hippocampal sub-regions and sub-clusters of glutamatergic nuclei. Applicants then used the spatial expression patterns (13) of these landmark genes to map sub-clusters in CA1, CA3, and DG to distinct spatial sub-regions (FIG. 2E and FIG. 15, 16, 17). Notably, multiple sub-regions were assigned different, yet partially overlapping, sets of sub-clusters, indicating a gradual transition of transcriptional profiles between neighboring hippocampal sub-regions (FIG. 2E). Other sub-regions were assigned to a single sub-cluster; in particular, a rare set (7%) of sparse neurons in the dorsal lateral outskirts of the CA1 (FIG. 2E). To validate our mapping, Applicants selected genes that were not used in the spatial mapping, and confirmed their predicted expression patterns in sub-regions of the hippocampus using the Allen ISH dataset (FIG. 2F and FIG. 18). Previous studies using single-neuron RNA-Seq in CA1 reported two cell clusters that do not match spatial position (1) (FIG. 19), whereas our spatial mapping of Nuc-Seq data corresponds to continual transcriptional transitions within CA1 and CA3 regions, adding to the growing evidence (16, 17) that cellular diversity is not always partitioned into discrete sub-types.

Figure 20:
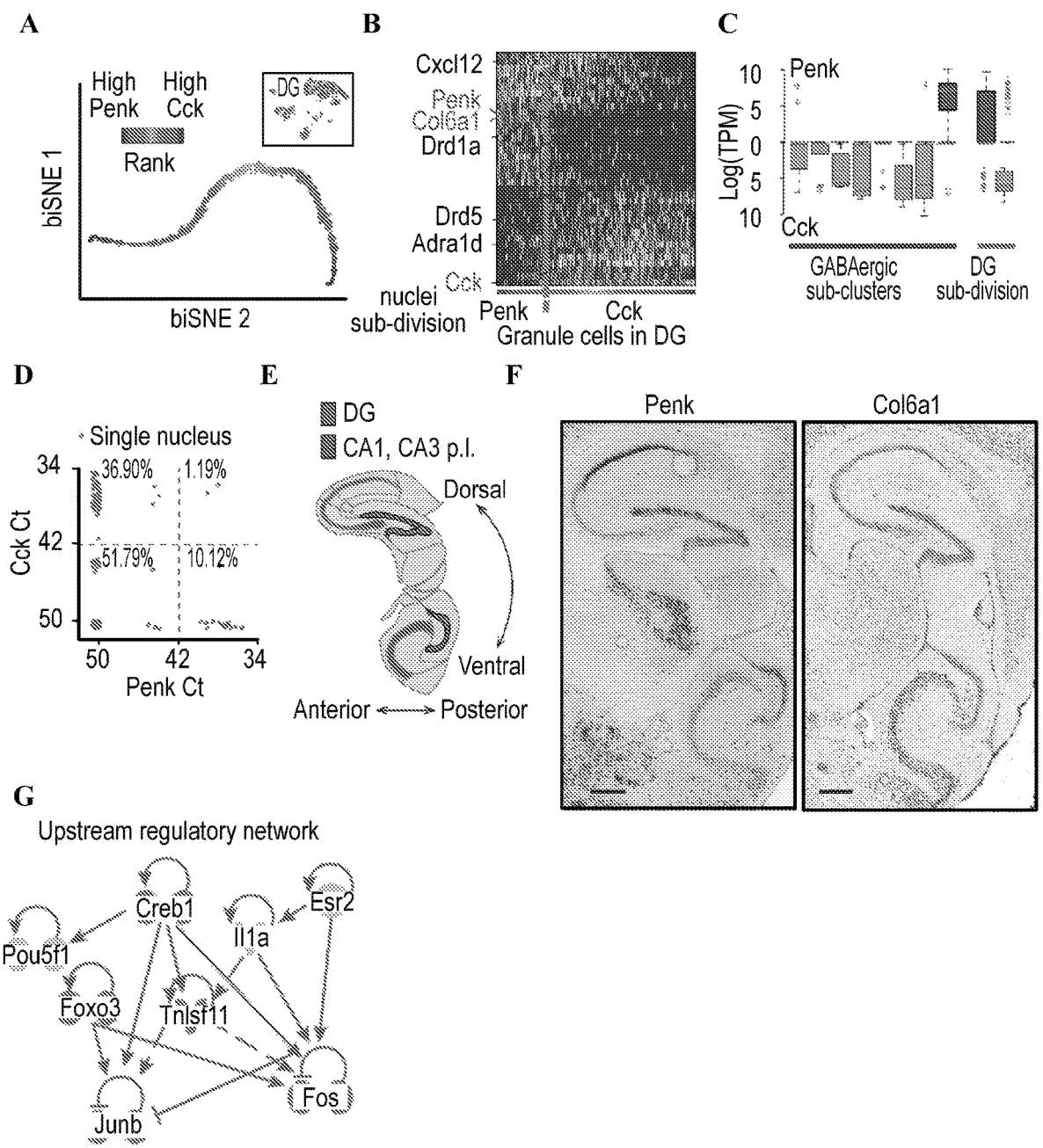
Figure 21A:
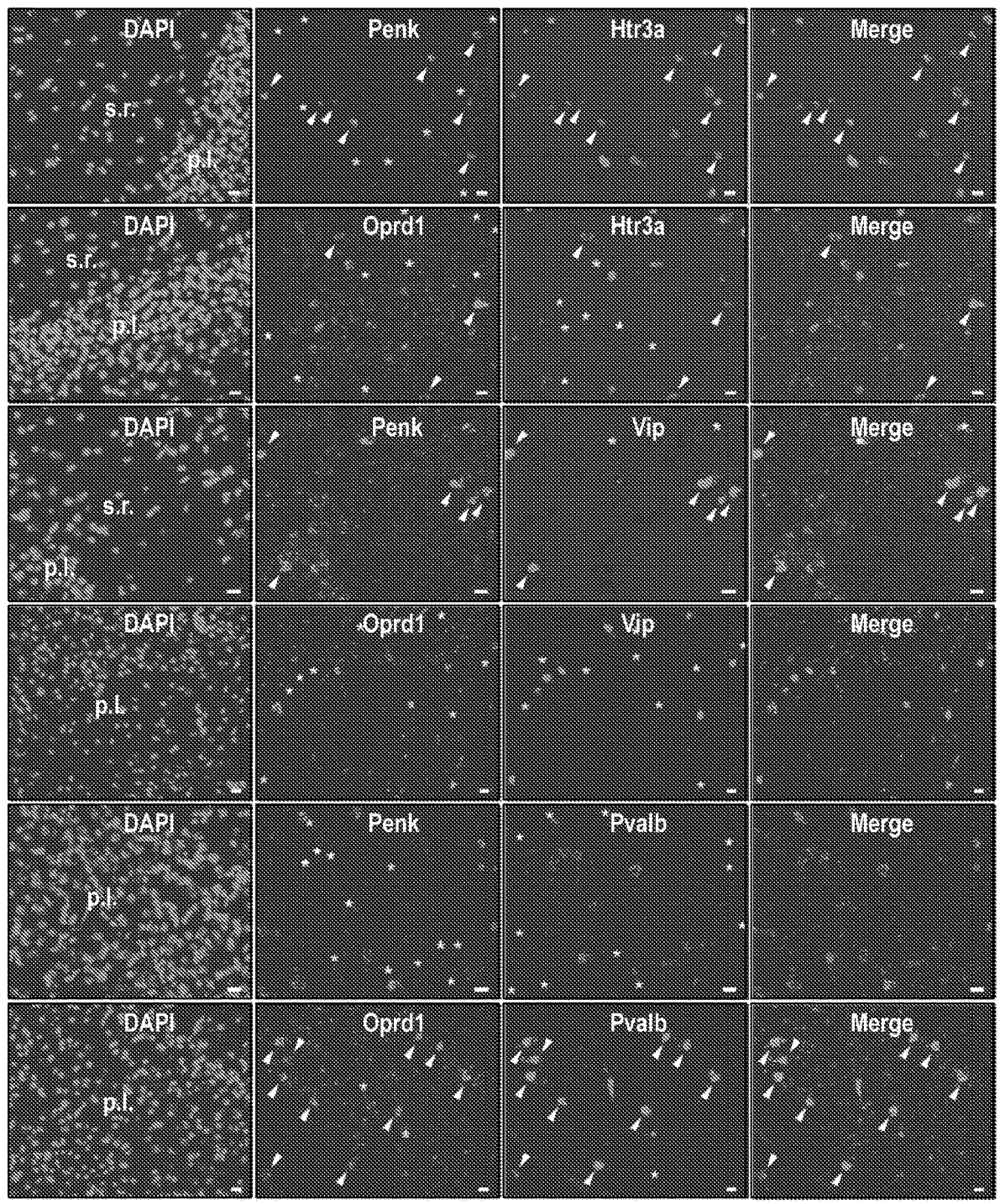

Applicants identified marker genes that are specifically associated with cell type and/or position. For example, Penk, which encodes an opioid neuropeptide (Enkephalin), and its receptor Oprd1 (18), were selectively expressed in mutually exclusive sub-clusters of cells (FIG. 2G). Applicants validated the mutually exclusive expression pattern of Penk and Oprd1 in GABAergic neurons by dFISH and their spatial expression pattern within the hippocampus by ISH (FIG. 2H, FIG. 20-21). In DG granule neurons, Applicants found mutually exclusive expression of Penk in a small subset of cells (162/674) (FIG. 20) and of Cck neuropeptide (Cholecystokinin) in all others, which Applicants validated by quantitative PCR (FIG. 20). Previous work showed that Enkephalin is secreted to the extracellular space (18), and its signaling may not require synaptic connection. Thus, the cell-type specific expression of Penk and Oprd1 points to putative cell types and spatial positions involved in the Enkephalin signaling within the hippocampal circuitry.

Example 3

Figure 22:
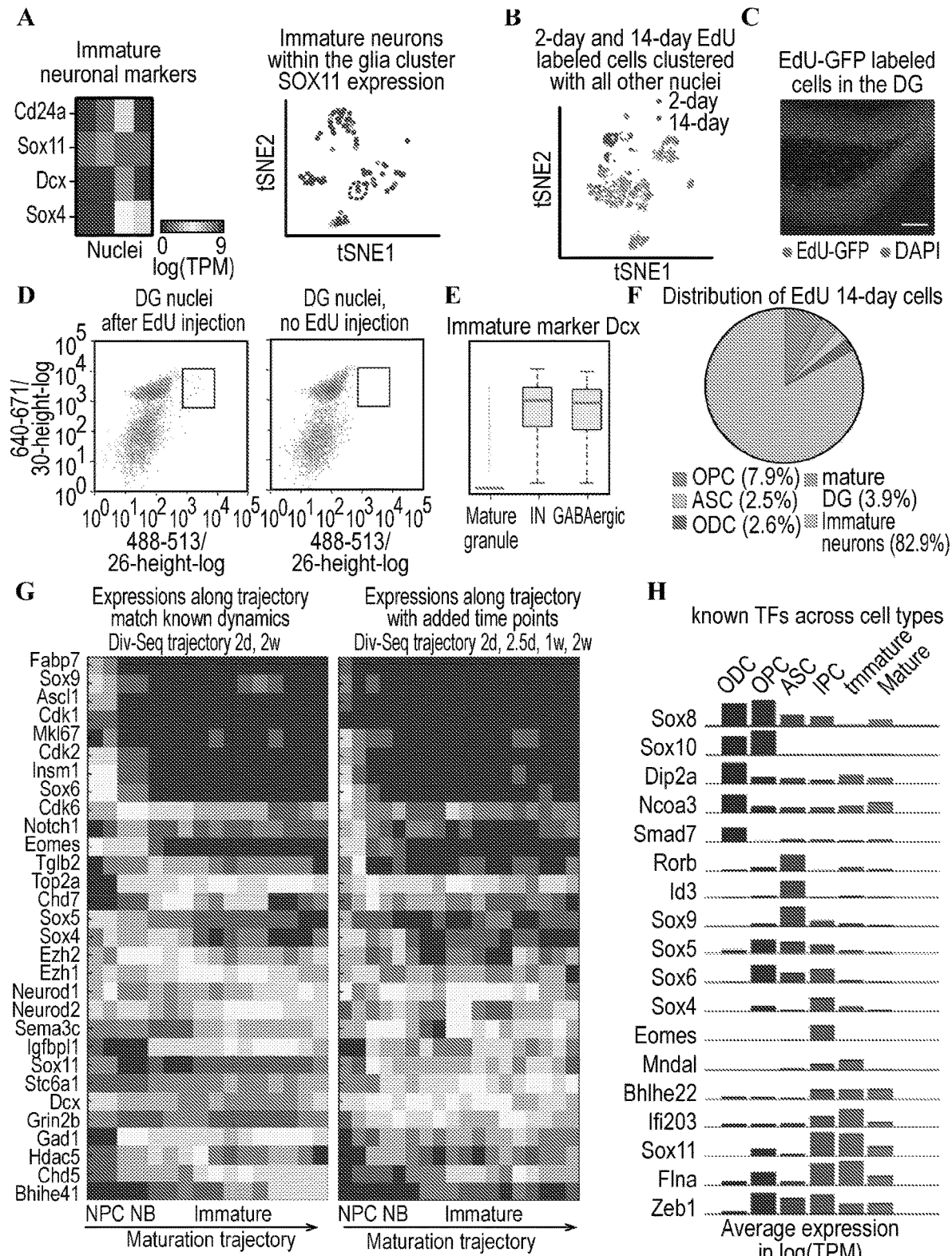

Applicants next combined Nuc-Seq with EdU labeling of dividing cells, in a method Applicants call Div-Seq (FIG. 3A). In contrast to commonly used genetic labeling techniques (3, 19, 20), which might be limited to specific cell types and requires cell types or developmental stage marker genes (3, 19, 20), EdU tags newly synthesized DNA in dividing cells at a given time window, allowing for unbiased isolation of nuclei of neural stem cells and their progeny with high temporal resolution. To study transcriptional dynamics during adult neurogenesis in the DG, one of the canonical neurogenic sites in the mammalian CNS (7), Applicants used Div-Seq to isolate nuclei at 2 and 14 days after cell division, representing neural precursor cells (NPC), neuroblasts, and immature neuronal stages of adult neurogenesis, respectively (7) (FIG. 3B, FIG. 22). Div-Seq enriched for a broad range of newborn cells (FIG. 20). Expression of stage-specific marker genes confirmed that Div-Seq captured cells at distinct stages: 2-day labeled nuclei expressed NPC (Tbr2/Eomes) and neuroblast (Sox4) markers, whereas 7-day and 14-day nuclei expressed immature neuronal markers (Sox11 and Dcx) (FIG. 3C). Of note, Dcx a commonly used marker gene for immature neurons was expressed in all mature GABAergic neurons in the hippocampus (FIG. 22), highlighting the limits of using single marker genes to identify cell types.

Clustering analysis of neuronal lineage nuclei placed the newborn neurons on a continuous trajectory. The order of nuclei along the trajectory matched the EdU labeling time, from 2-day to 14-day labeled nuclei, with partial overlap, and a few nuclei from our unbiased survey of nuclei spread throughout (FIG. 3D). Expression patterns of known neurogenesis genes along the trajectory recapitulated their known dynamics (3, 4, 21) and correctly captured the measured expression of nuclei at an intermediate time point of 7 day post EdU injection (FIG. 22), indicating that the trajectory indeed captured the maturation process.

To further characterize the transcriptional transitions of newborn neurons, Applicants used biSNE to identify genes with dynamic expression patterns along the neurogenesis trajectory (FIG. 3E), clustered genes by their expression patterns, and tested for enriched genetic pathways in each cluster. Applicants found two major coordinated transcriptional switches, involving hundreds of genes and aligning with the known transitions from NPC, through neuroblasts, to immature neurons: (i) from proliferation (cell-cycle exit)

to neuronal differentiation (consistent with previous reports (3)), and (ii) from differentiation to neuronal maturation (FIG. 3E).

Figure 23:
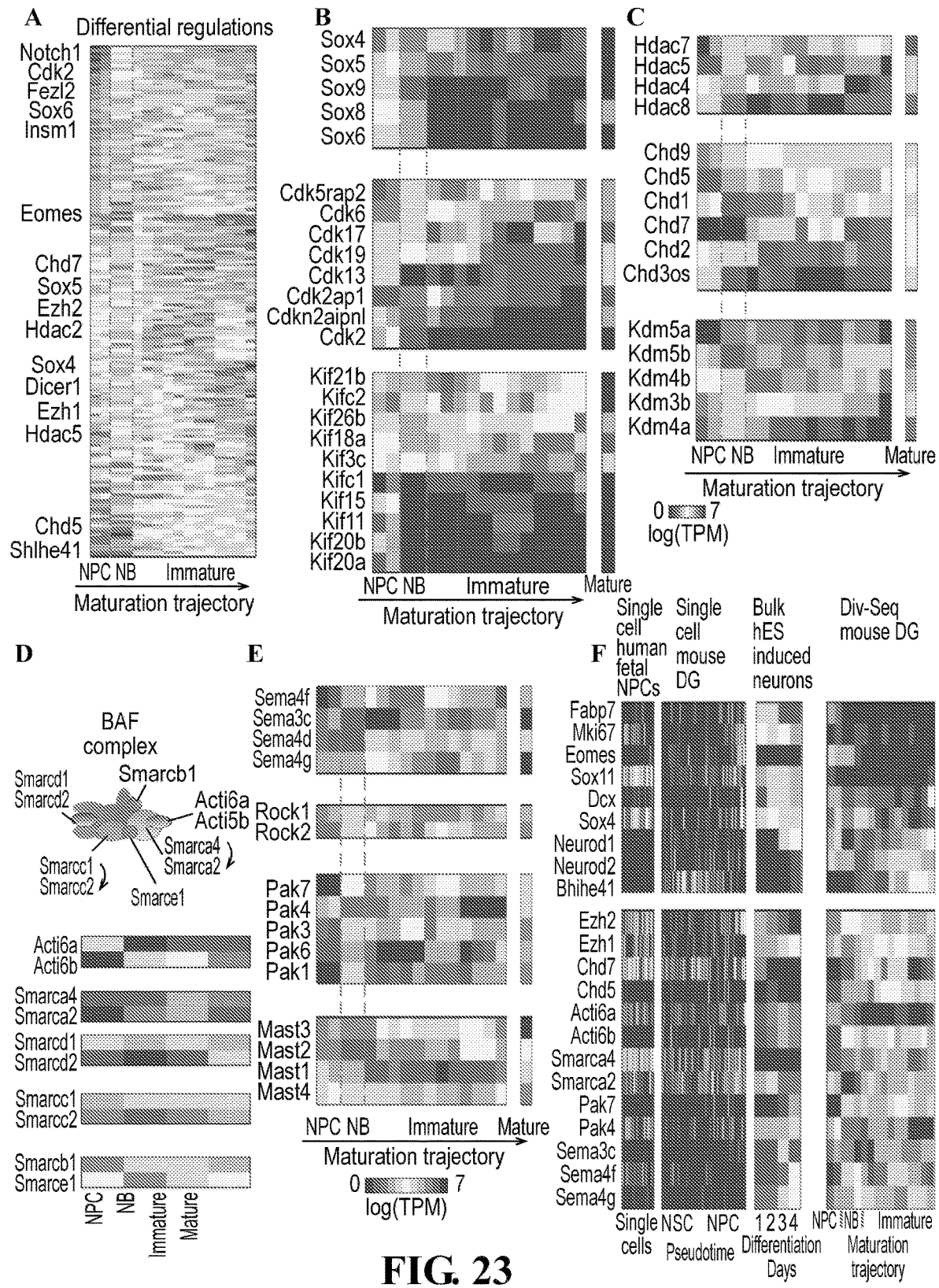

Applicants identified transcription factors (TFs) and chromatin regulators whose expression is coordinated with these two transcriptional switches (FIG. 23). For the Polycomb Complex (Prc2), Applicants observed an expression switch between Ezh2 (expressed in NPCs consistent with previous reports (22)) and its paralog Ezh1 (FIG. 3F); for the BAF (mammalian SWI/SNF) complex, Applicants observed an expression switch of Act16a/Baf53a to its paralog Act16b/Baf53b (23) and a late induction of BAF components (e.g. Smarca2/BAF190b, FIG. 3F, FIG. 23). These expression patterns are consistent with single cell RNA-Seq of mouse NPCs (3) and human NPCs (24) (FIG. 3F, FIG. 23).

Figure 24:
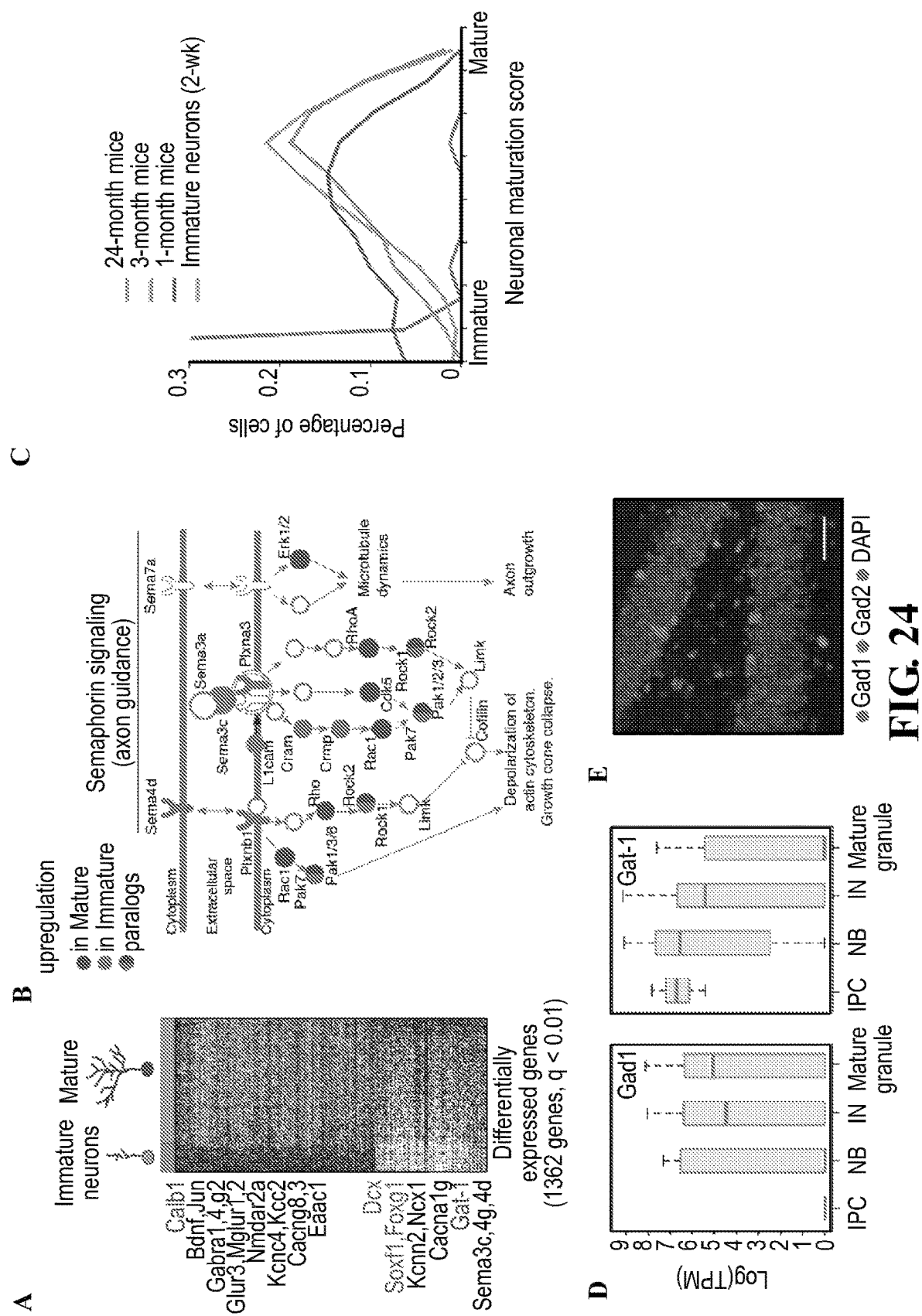

Div-Seq provides a unique opportunity to profile the transcriptional program underlying neuronal maturation. Applicants found differentially expressed genes between immature and mature DG granule neurons (t-test FDR q-value<0.01; FIG. 24, and differentially expressed splice isoforms), enriched for expected molecular pathways (q-value<0.01, FIG. 24), such as semaphorin signaling (25) (FIG. 24) and lipid metabolism (26), supporting our gene signatures. Among the differentially expressed genes Applicants found the chloride/potassium symporter Kcc2, which is pivotal for the GABA switch from excitation to inhibition during neuronal maturation (27), selectively expressed in mature neurons as previously shown (27). Interestingly, immature neurons in DG express genes for both GABA production (one of two GABA synthetase genes, Gad1, as shown (19) and transportation (Gatl, FIG. 24), despite maturing to be primarily glutamatergic neurons (7).

Figure 4:
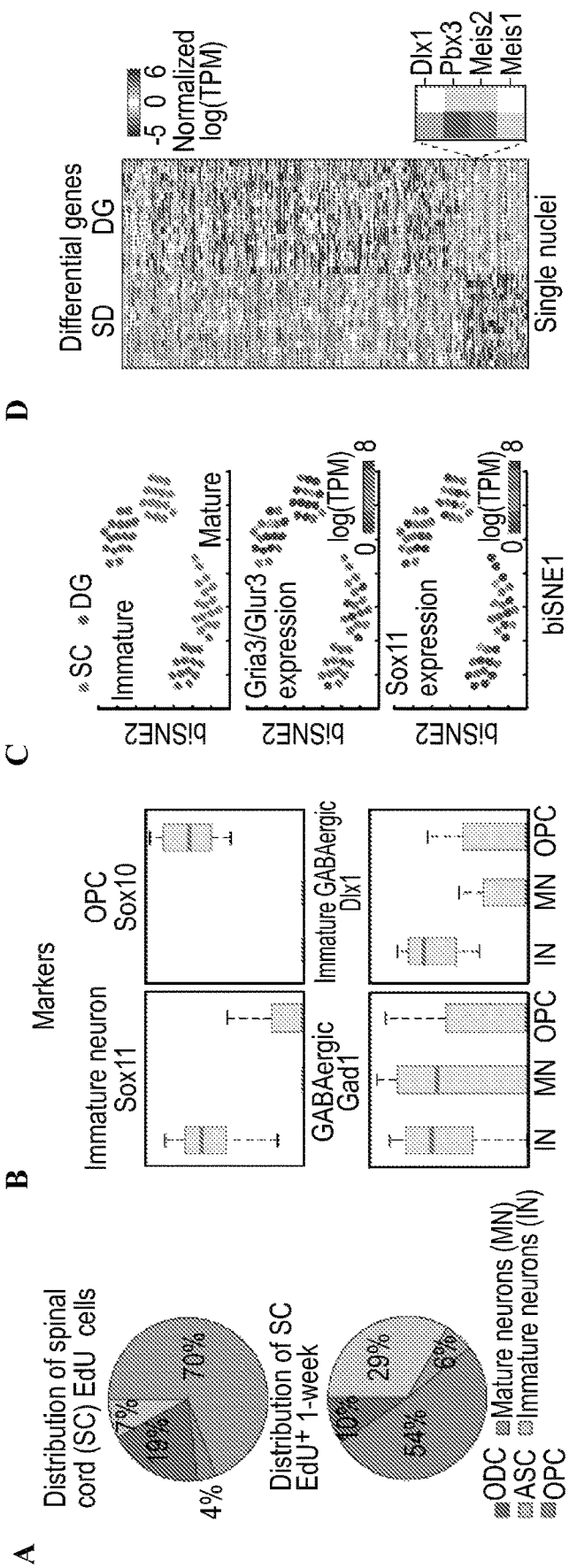
FIG. 4A-4D: Adult newborn GABAergic neurons in the spinal cord revealed by Div-Seq. (A) Div-Seq in the spinal cord (SC) captures oligodendrocyte precursor cells and immature neurons. Shown is the distribution of cell types in the SC in non-EdU-labeled (top) and 7 days EdU labeled nuclei (bottom), assigned by clustering and marker gene expression. Oligodendrocyte precursor cells, OPC; Astrocytes, ASC; Oligodendrocytes, ODC. (B) Div-Seq captured immature neurons expressing marker genes of immature neurons (Sox11), GABAergic (Gad1, Dlx1) or OPCs (Sox10) marker genes. Box plots for immature neurons (IN), mature neurons (MN) and OPCs, shown as in FIG. 2G. (C) Cells cluster primarily by maturation state and secondarily by region. All panels show biSNE 2D embedding of immature and mature neurons from both the SC and the DG. Nuclei are colored by tissue (top), by Gria3/Glur3 mature marker expression levels (middle), or by Sox11 (bottom). (D) Region specific gene expression. Heatmap shows the expression of genes specific to immature neurons in the SC (left) and DG (right), across single nuclei (t-test FDR<0.05, log-ratio>1, across all pairwise comparisons).

Evidence from diverse mammalian systems suggests that adult neurogliogenesis occurs in multiple non-canonical regions of the adult CNS (28). However, traditional methods, such as FISH, are limited in their ability to identify and fully characterize rare newborn cells. In particular, contradicting FISH evidence of a few marker genes suggests that progenitors in the adult spinal cord (SC) give rise either to only glia cells (29) or to both glia cells and neurons (30). To systematically investigate neurogliogenesis in the adult SC, Applicants applied Div-Seq and found a clear signature for dividing cells 7 days after EdU labeling (FIG. 23). Clustering analysis revealed a diverse population of newborn cells, in which the majority (54%) represented oligodendrocyte precursor cells (OPCs) (expressing Sox10), and the second largest population (29%) represented immature neurons (expressing Sox11) (FIG. 4A-B, FIG. 23). Notably, In the non-EdU labeled population Applicants found mainly mature neurons (70%) and glia (30%) with only 4% OPCs and no immature neurons, demonstrating the need for Div-Seq to capture these rare cell types. All newborn neurons Applicants detected expressed the GABA processing genes Gad1 and Gad2, suggesting that newborn neurons in the SC are GABAergic (supporting previous observations (30), FIG. 4B).

Comparison of immature and mature neurons in both the SC and the DG revealed that cells cluster primarily by maturation state and secondarily by region (FIG. 4C), demonstrating genetic similarities between immature neurons independent of their origin within the CNS. However, focusing on immature neurons Applicants identified differentially expressed genes (FIG. 4D) specific to the DG (e.g. Prox1) and the SC (e.g. Rex2), respectively. In particular, Applicants found three transcription factors, Pbx3, Meis2, and Dlx1 co-expressed specifically in the SC but not in DG immature neurons. Previous reports showed that Pbx, Meis, and Dlx super-family factors interact (31) and promote adult neurogenesis in the subventricular zone/olfactory bulb and dopaminergic fate specification (32); our data suggest that these factors may also play a regulatory role in adult neurogenesis in the SC. Taken together, the comparison of RNA signatures of newborn neurons in the SC and DG suggests that common molecular pathways cooperate with cell type-specific fate specifying factors to mediate adult neurogenesis across different brain regions.

In summary, Applicants have shown how Nuc-Seq and Div-Seq open new avenues in the study of neuronal diversity and rare dynamic processes in the adult CNS. Nuc-Seq overcomes the harsh dissociation needed for single cell RNA-Seq, yet retains rich information required to make fine distinctions between cell types and states. Combined with intra-nuclear tagging, our nuclei profiling method enables the study of rare cell populations, as done in Div-Seq to capture proliferating cells. For increased sensitivity, Nuc/Div-Seq can be integrated with other techniques, for example, integration with droplet-based microfluidics may help to increase throughput, and the use of alternative labeling approaches such as immunostaining of transcription factors (6) or a recently published fluorescent "flash" tagging of dividing cells (33) may broaden the range of cell types possible for investigation. Div-Seq's ability to clearly identify and characterize rare cells in the spinal cord shows its significantly improved sensitivity compared to traditional methods. Nuc-Seq and Div-Seq can be readily applied to diverse biological systems, and may be especially helpful for studying transcriptional dynamics, the aging brain, fixed and frozen tissue including post-mortem biopsy samples or archive samples, and time-sensitive samples such as human biopsies. Overall, our methods will help overcome broad challenges not only in neuroscience, but in many other biological systems as well.

Example 4

Method for sequencing RNA from thousands of nuclei. Drop-seq has previously been developed for generating single cell libraries. The major advantages are speed, numbers and cost: Applicants can generate libraries from around 10,000 cells per day at a total cost of $600. The cell number is at least 10× greater than was possible with previous methods, and the cost per library is about 100× lower than that of previous methods. The disadvantages include non-biological variation that arises from loss of dendrites and axons and "leakage" of cytoplasm when these processes are sheared. For Nuc-seq, advantages include increased physical stability and structural homogeneity. In addition, nuclear RNAs are enriched for recently transcribed genes, which facilitates detection of transcriptional changes following a stimulus. The current drawback is that the number of nuclei than can be profiled is limited. Applicants therefore developed a hybrid method, Dronc-seq, that combines the strengths of its two parents.

The Drop-seq method (Macosko et al., 2015) uses a microfluidic device to co-encapsulate individual cells in reverse emulsion aqueous droplets in an oil medium together with one uniquely barcoded mRNA-capture bead. The oligonucleotides on the bead are each comprised of four parts: a constant sequence (identical on all primers) for use as a priming site for PCR and sequencing; a "cell barcode" that is the same across all the primers on the surface of any one bead, but different from the cell barcodes on all other beads; a random sequence that enables reads from the same mRNA transcript to be identified computationally (UMI); and an oligo dT sequence for capturing polyadenylated mRNAs. Once the cell and bead are co-encapsulated, the cell lyses and its mRNA is captured on the bead. The emulsion is then broken, and the mRNAs are reverse-transcribed, amplified, and sequenced in a single reaction. The barcodes are used to correct for PCR amplification bias and to infer each transcript's cell of origin. Applicants used Drop-seq to profile 44,808 single cells from the mouse retina, which were clustered by an unsupervised method into 39 cell types. The clusters included all major cell classes and, for several classes, multiple cell types within several of the classes (FIG. 1, from Macasko et al., 2015). The analysis also predicted markers of new types that Applicants validated immunohistochemically. Applicants believe that classification was incomplete because 70-80% of retinal cells are rod photoreceptors, so numbers of the cells in the most heterogeneous classes (bipolar, amacrine and retinal ganglion cells) was limited —for example because ganglion cells comprise <1% of all retinal cells, less than 500 cells are expected among 44,000 analyzed cells, too few to make finer distinctions. Applicants have therefore begun purifying these classes by FACS prior to Drop-Seq. Applicants recently profiled 13,000 bipolar cells, and have been able to double the number of types in the initial dataset.

Figure 2:
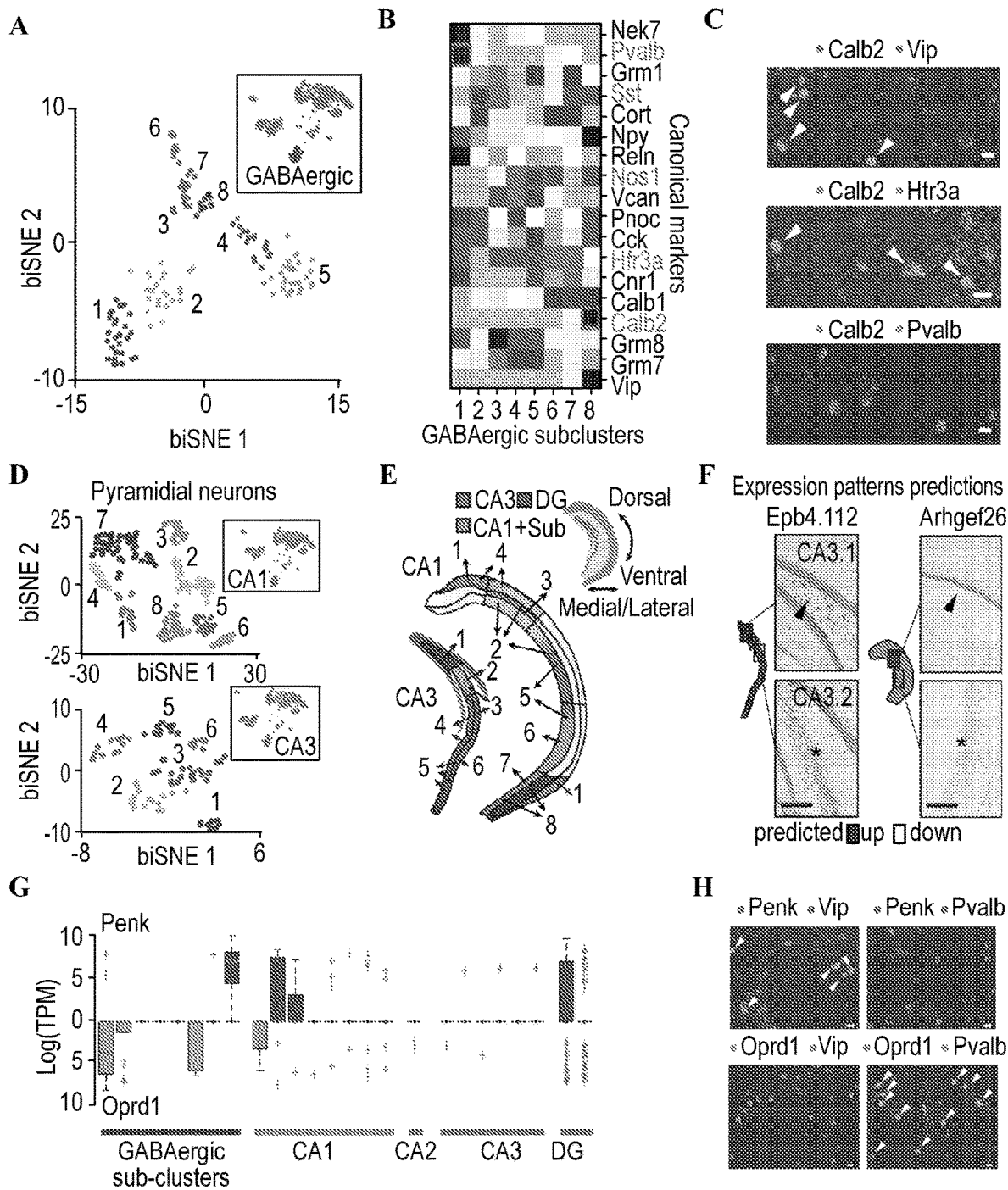
FIG. 2A-2H. Nuc-Seq and biSNE distinguish cell sub-types and transcription patterns. (A) Sub-clusters of GABAergic interneurons identified by biSNE. Shown is a biSNE 2-D embedding of GABAergic nuclei with 8 sub-clusters. Top insert: the GABAergic cluster within all other nuclei from FIG. 1E. (B) Sub-clusters are characterized by a combination of canonical marker genes. Heat map with averaged expression of canonical neuron markers (rows) across GABAergic sub-clusters (columns). (C) Double fluorescent RNA in situ hybridization (dFISH) of marker genes validating the expression pattern shown in (B). Co-expression of genes indicated by arrowheads. Scale=20 m. (D) Pyramidal CA1 and CA3 biSNE sub-clusters. Shown is a biSNE 2-D embedding of the CA1 (top) and CA3 (bottom) pyramidal nuclei with 8 and 6 sub-clusters, respectively. Top insert: the CA1 cluster (orange) within all other nuclei from FIG. 1E. (E) Spatially resolved pyramidal neuron populations in CA1 and CA3. Top: Schematics of hippocampus coronal section with CA1 (including subiculum), CA3 (including the hilus) and DG. Bottom: Registration of CA1 (right) and CA3 (left) pyramidal sub-clusters to subregions, using a map of landmark gene expression patterns from ISH data. Sub-cluster assignments are numbered and color code as in (D). Scale=200 m. (F) Example of validation of spatial assignments of CA1 and CA3 pyramidal sub-clusters. Predictions (left illustrations; boxes showing predicted differential expression regions) match with Allen ISH data (13) (right; arrowhead: high expression; asterisk: low expression) in pairwise comparison of genes differentially expressed between two sub-clusters. (G) Distribution of expression of Penk (facing up) and Oprd1 (facing down) across each neuronal sub-cluster. Box plots show the median (red), 75% and 25% quantile (box), error bars (dashed lines), and outliers (red cross). (H) dFISH of GABAergic cluster marker genes (Vip and Pvalb) with Penk or Oprd1, validating their mutual exclusive expression across GABAergic sub-clusters. Co-expression of genes indicated by arrowheads. Scale=20 m.

Recent studies demonstrated the feasibility of sequencing pre-mRNAs from isolated nuclei (Steiner et al., 2012; Henry et al., 2012). Applicants have now adapted these methods for both full-length and 3' directed single-nuclei mRNA-seq of intact nuclei. Our method robustly produces RNA libraries from single nuclei in the adult mammalian brain. The improved RNA libraries, consistently detect 4,000-7,000 genes per cell, while reducing the required sequencing depth. Applicants developed and applied Nuc-Seq to the mouse hippocampus. Applicants selectively tagged neuronal nuclei (Syn promoter) and dissected several hippocampal regions (CA1, CA2/3, Dentate Gyrus [DG]). Focusing on the DG, Applicants prepared Nuc-Seq libraries from 6 animals (~600 nuclei passing filter). Applicants developed new methods for normalization of single cells data and clustering of cell types compatible with Nuc-Seq data. Applicants showed that Nuc-Seq can classify glia vs. neurons, inhibitory vs. excitatory neurons, and neurons from different regions (FIG. 2). Some of the differentially expressed genes were confirmed by available ISH data in the Allen Brain Atlas. Most excitingly, Nuc-Seq shows that inhibitory (GABAergic) neurons in the DG have molecular profiles characteristic of "newly born neurons", consistent with the idea that GABA-related enzymes are transiently expressed during neuronal development. Applicants also found two new cell types/states among DG neurons, which were believed to be homogeneous; Applicants are now validating this with protein staining. Finally, Applicants re-assembled the transcriptome from population libraries and show that our polyA nuclear RNAs are similar to cytoplasmic RNAs in structure (largely spliced), but also reveal new splice isoforms and potential lincRNAs.

Figure 25:
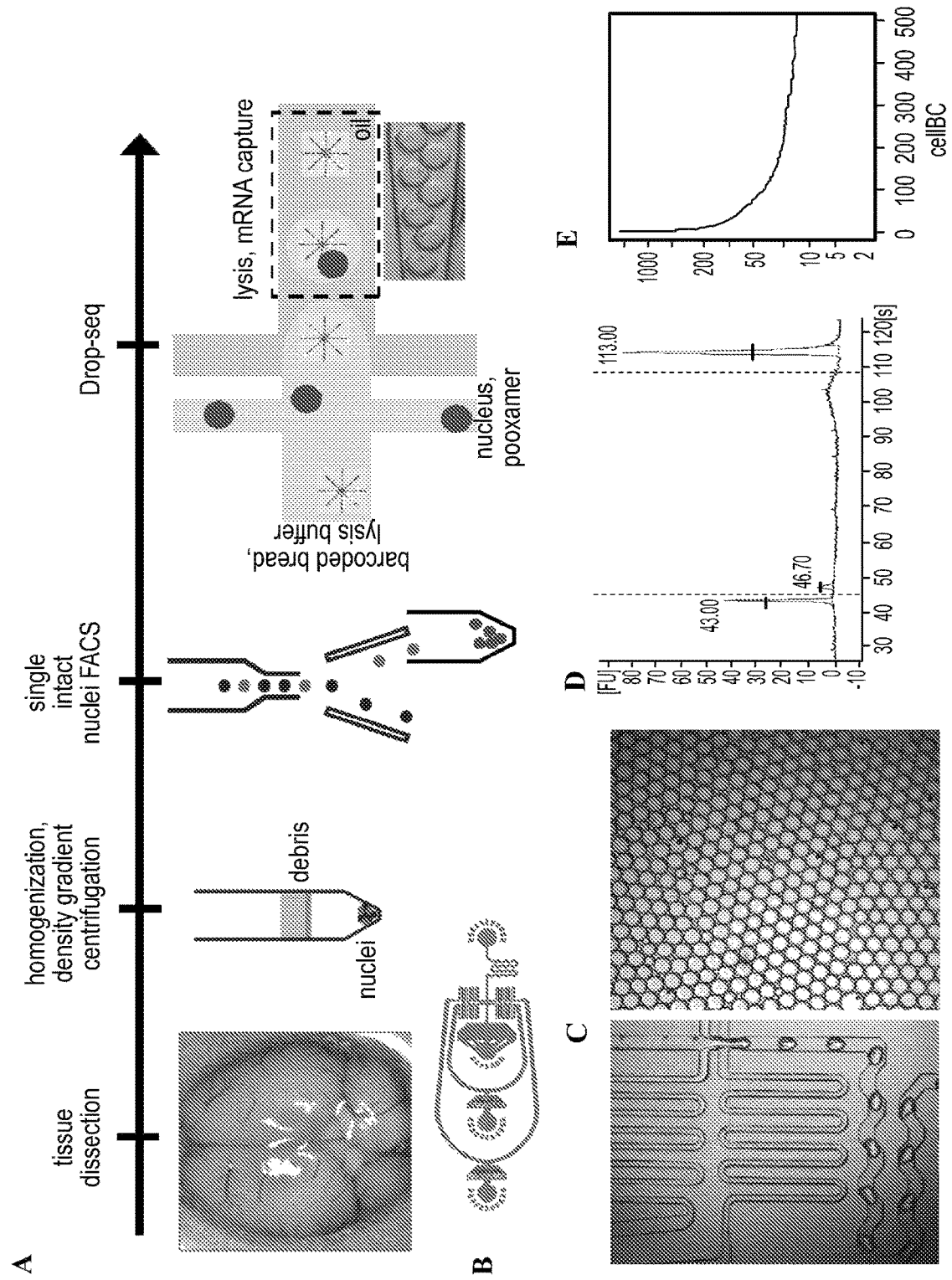

Applicants developed new microfluidic devices and protocols that allow Drop-seq analysis of thousands of isolated nuclei (Dronc-Seq) (FIG. 25, 26, 27). Furthermore, Applicants have recently made important progress with reverse emulsion devices used for other nuclei-based molecular biology applications, such as a droplet version of single-cell ATAC-Seq. To develop Dronc-Seq Applicants combined the nuclei preparation protocol of Nuc-Seq, a new device compatible with nuclei separation, and Drop-Seq reagents (barcoded beads, molecular biology protocols, lysis buffers) for the in-drop and subsequent phases of the protocol. Briefly, as in Nuc-Seq, Applicants rely on our recently published (Sweich et al., 2015) protocols for high quality generation of nuclei suspensions from mouse hippocampus. Unlike Nuc-Seq, where Applicants next sort single nuclei using FACS, in Dronc-Seq Applicants use a new microfluidics device, following on the design principles of Drop-Seq, but optimized for the size and properties of nuclei. The nuclei are lysed in drops, and their mRNA captured on the Drop-Seq beads. Notably, given the smaller quantity of mRNA in nuclei, ensuring efficient capture is key. A complementary modality (Klein et al., 2015) has higher capture but lower throughput than Drop-Seq. Finally, Applicants test for cross-contamination due to 'sticky' RNA from the lysed cytoplasms or leakage from nuclei using the cross-species controls developed for Drop-Seq (Macosko et al., 2015). Nuclei can also be sorted through FACS prior to Drop-Seq encapsulation. Applicants can also use pore-blocking polymers called poloxamers, such as F-68 and F-127 (Sengupta et al.,2015). Applicants can use Dronc-Seq in the hippocampal biological system and compare to the available of Nuc-Seq benchmarking data. Applicants can also generate Nuc-Seq and Dronc-Seq data from the retina, demonstrating its generality.

Example 5

DISCUSSION

Applicants clustered high scoring biSNE genes into coexpressed gene signatures using cross correlation while taking into account of the proximity of cells expressing these genes. Applicants found two signatures with opposing expression patterns across the DG granule cells. The DG cells span a continuous spectrum of states for the expression of these two modules (FIG. 16), with two neuropeptide genes Penk (Preproenkephalin) and Cck (Cholecystokinin) expressed in largely mutually exclusive cells (18% and 82% of DG cells, respectively). Applicants validated this expression pattern using qPCR and double-ISH. qPCR on an additional 168 single nuclei from DG microdissection shows that all but two express either Penk or Cck, but not both, at a 1:4 ratio, consistent with the Nuc-Seq result (FIG. 20). In single molecule double-ISH, two members of the Penk module (Penk and Col6a1) show overall co-expression in the same cells (FIG. 16), and their expression marks cells sparsely scattered throughout the entire DG. Finally, the genes that are differentially expressed between the Penk and Cck module expressing cells (t-test, p-value FDR q<0.01), are enriched for emotional activity related pathways and seizures (p-value<0.05, hypergeometric test). Among the inferred common upstream regulators (Methods) are several activity dependent factors (Crebl, Jun and Bdnf), consistent with the known regulators of Penk in the brain [37]. This suggests a novel state of granule cells expressing distinct signatures regulated by neuronal activity responses.

Materials And Methods

Plasmid and virus production for isolation of GABAergic neurons. EGFP-KASH construct was a generous gift of Prof Worman (Columbia University, NYC) inverted into pAAV-EFla-DIO-EYFP-WPRE-hGH-polyA (Addgene, #27056) using AscI and NcoI restriction sites, and WPRE was removed using ClaI restricition sites. pAAV-EFla-Cre-WPRE-hGH-polA was obtained from Addgene (#27056). The pAAV-hSyn-EGFP-KASH-WPRE-hGH-polyA was described [38]. Concentrated adeno-associated virus 1/2

(AAV1/2) and low titer AAV1 particles in DMEM were produced and titered as described previously [38].

Stereotactic injection of AAV1/2 into the mouse brain. Stereotactic injections were approved by the MIT Committee on Animal Care (MIT CAC). 12–16 week old male vGAT-Cre mice (Slc32altm2(cre)Lowl, The Jackson Laboratory, #016962) (Rossi J, Cell Metab 13(2):195-204) were anaesthetized by intraperitoneal (i.p.) injection of 100 mg/kg Ketamine and 10 mg/kg Xylazine and pre-emptive analgesia was given (Buprenex, 1 mg/kg, i.p.). 1 ml of high titer AAV1/2 (~4×1012 Vg/ml of pAAV-EF1a-DIO-EYFP-WPRE-hGH-polyA) was injected into dorsal and/or ventral hippocampus. The following stereotactic coordinates were used: Dorsal dentate gyrus (anterior/posterior: −1.7; mediolateral: 0.6; dorsal/ventral: −2.15), ventral dentate gyrus (anterior/posterior: −3.52; mediolateral: 2.65; dorsal/ventral: −3), dorsal CA1/2 (anterior/posterior: −1.7; mediolateral: 1.0; dorsal/ventral: −1.35) and ventral CA1/2 (anterior/posterior: −3.52; mediolateral: 3.35; dorsal/ventral: −2.75). After each injection, the pipette was held in place for 5 minutes prior to retraction to prevent leakage. Finally, the incision was sutured and postoperative analgesics (Meloxicam, 1–2 mg/kg) were administered for three days following surgery.

Animal work statement. All animal work was performed under the guidelines of Division of Comparative Medicine (DCM), with protocols (0411-040-14, 0414-024-17 0911-098-11, 0911-098-14 and 0914-091-17) approved by Massachusetts Institute of Technology Committee for Animal Care (CAC), and were consistent with the Guide for Care and Use of Laboratory Animals, National Research Council, 1996 (institutional animal welfare assurance no. A-3125-01).

Immunohistochemistry and Nissl staining. Mice were sacrificed by a lethal dose of Ketamine/Xylazine 3 weeks post viral injection, and transcardially perfused with PBS followed by 4% PFA. Sagittal sections of 30 µm were cut using vibratome (Leica, VT1000S) and sections were boiled for 2 min in sodium citrate buffer (10 mM tri-sodium citrate dehydrate, 0.05% Tween20, pH 6.0) and cooled down to room temperature (RT) for 30 min. Brain sections were blocked in 5% normal goat serum (NGS) (Cell Signaling Technology, #5425) and 5% donkey serum (DS) (Sigma, #D9663) in PBST (PBS, 0.15% Triton-X) for 1 h at RT and stained with chicken anti-GFP (Aves labs, #GFP-1020, 1:400) and mouse anti-parvalbumin (Sigma, #P3088, 1:500) in 2.5% NGS and 2.5% DS in PBST over night at 4° C. Sections were washed 3 times in PBST and stained with secondary antibodies (Alexa Fluor 488 and 568, 1:1000) at RT for 1 h. After washing with PBST 3 times, sections were mounted using VECTASHIELD HardSet Mounting Medium with DAPI (Vector Laboratories, #H-1500) and imaged using confocal microscopy (Zeiss LSM 710, Ax10 ImagerZ2, Zen 2012 Software). For Nissl staining, mice were perfused with PBS and 4% PFA. Brain samples were dehydrated and paraffin embedded and 7 µm sagittal sections were cut. Nissl staining was performed as described elsewhere [39]. Images were taken with a Zeiss microscope and AxioCam MRm camera.

Nuc-Seq.

I. Dissection of Mouse Hippocampal Subregions, Nuclei Isolation and FACS Sorting Freshly dissected mouse brain samples were placed in ice cold PBS and kept cold during microdissection. Microdissections of dentate gyrus, CA1 and CA2/3 regions were performed under a stereomicroscope as described elsewhere [40]. Dissected subregions were placed into ice-cold RNAlater (Ambion, RNAlater, #7020) and stored at 4° C. overnight. Thoracic spinal cord of EdU injected mice were dissected in icecold PBS and fixed in RNAlater at 4° C. overnight. Then samples were processed for nuclei isolation immediately or stored in −80° C. Nuclei were isolated by sucrose gradient centrifugation as described [38] with two modifications: RNAse inhibitor (Clontech, Recombinant Ribonuclease Inhibitor, #2313A, 40 units/µl) was added to the resuspension buffer (final 1U/µl), and nuclei were filtered through a 35 µm cell strainer (Falcon, #352235) before sorting. Nuclei were labeled with ruby dye (Thermo Fisher Scientific, Vybrant DyeCycle Ruby Stain, #V-10309) added to the resuspension buffer at a concentration of 1:800. Nuclei were kept on ice until sorting using Fluorescence Activated Cell Sorting (Harvard University, Bauer Core Facility, Beckman Coulter MoFlo Astrios EQ Cell Sorter) into 96 well plates containing 5 µl of TCL lysis buffer (Qiagen, #1031576) added with 10% 2-Mercaptoethanol. FACS gating was set on FSC, SSC, and on fluorescent channels to

TABLE 6

| Number of animals | Sex & strain | Brain regions | Age | Treatment |
|---|---|---|---|---|
| 4 | Male, C57BL/6 | DG, CA1, CA23 | 12-14 weeks | non |
| 9 | Male, C57BL/6 | DG | 18 weeks | non |
| 2 | Male, C57BL/6 | DG | 12-14 weeks | Sacrificed 2 weeks post pAAV-hSyn-GFP-KASH injection |
| 2 | Male, C57BL/6 | DG | 11-13 weeks | Sacrificed 2 days post EdU injection |
| 3 | Male, C57BL/6 | DG | 11-13 weeks | Sacrificed 2 weeks post EdU injection |
| 2 | Male, C57BL/6 | DG | 2 year | non |
| 2 | Male, VGAT-Cre | DG, CA123 | 12-16 weeks | Sacrificed 2 weeks post pAAV-EF1a-DIO-GFP-KASH |
| 2 | Male, C57BL/6 | DG, SC | 11-13 weeks | Sacrificed 1 week after EdU injection |
| 4 | Male, C57BL/6 | DG, SC | 11-13 weeks | Sacrificed 1 week after EdU injection |
| 4 | Female, C57BL/6 | DG | 11-13 weeks | non |
| 3 | Male, C57BL/6 | DG, SC | 8 weeks | Sacrificed 1 week after EdU injection |
| 3 | Male, C57BL/6 | DG, SC | 8 weeks | Sacrificed 2.5 days after EdU injection | include only Ruby+ or Ruby+GFP+nuclei (for nuclei tagged by GFP-KASH or EdU-GFP). Each 96 well plate included an empty well as a negative control and a population well of 50-100 nuclei as a positive control.

II. Single Nucleus RNA Library Construction and Sequencing

Single nucleus RNA was first purified using RNAClean XP beads (Beckman Coulter, Agencourt RNA-Clean XP, #A63987) at 2.2× beads to sample volume ratio. Single nucleus derived cDNA libraries were generated following a modified Smart-seq2 method [41]. Briefly, beads were eluted into 4 µl elution mix made of 1 µl RT primer (10 µm), 11 dNTP mix (10 mM each, Thermo Fisher Scientific, #R0191), 1 µl RNAse inhibitor diluted at 1:10 in water (final 1U/µl), and 1 µl H$_2$O. Eluted samples were incubated at 72° C. for 3 min and immediately placed on ice. Each sample was added with 7 µl reverse transcription (RT) mix made of 0.75p 1 H$_2$O, 0.1 µl Maxima RNase-minus RT (Thermo Fisher Scientific, Maxima Reverse Transcriptase, #EP0752), 2 µl 5× Maxima RT buffer, 2 µl Betaine (Sigma Aldrich, 5M, #B0300), 0.9 µl MgCl2 (Sigma Aldrich, 100 mM, #M1028), 1 µl TSO primer (10 µm), 0.25 µl RNase inhibitor (40U/µl). The RT reaction was incubated at 42° C. for 90 min and followed by 10 cycles of (50° C. for 2 min, 42° C. for 2 min), then heat inactivated at 70° C. for 15 min. Samples were then amplified with an addition of 14p1 polymerase chain reaction (PCR) mix made of 1 µl H$_2$O, 0.5 µl ISPCR primer (10 µm), 12.5 µl KAPA HiFi HotStart ReadyMix (KAPA Biosystems, #KK2602). The PCR reaction was performed as follows: 98° C. for 3 min, 21 cycles of (98° C. for 15 sec, 67° C. for 20 sec, 72° C. for 6 min), and final extension at 72° C. for 5 min. PCR product was purified using AMPure XP (Beckman Coulter, Agencourt AMPure XP, #A63880) twice and eluted in TE buffer (Thermo Fisher Scientific, #AM9849). Purified cDNA libraries were analyzed on Agilent 2100 Bioanalyzer (Agilent, Agilent High Sensitivity DNA Kit, #5067-4626) and quantified using picogreen (Thermo Fisher Scientific, Quant-iT PicoGreen dsDNA Assay Kit, #P11496) on a plate reader (Biotek, Synergy H4, wavelength at 485 nm, 528 nm with 20 nm bandwidth). Sequencing libraries were prepared using Nextera XT kit (Illumina, #FC-131-1024) as described previously [42]. Single nucleus cDNA libraries were sequenced on an Illumina NextSeq 500 to an average depth of 632,169 reads. Sequences of primers used in single nucleus RNA library construction are shown below (IDT: Integrated DNA Technologies). The following sequences are synthetic.

was run with default parameters on alignments created by Bowtie2 [48] (command line options -q—phred33-quals -n 2-e 99999999-1 25-I1-X 1000-a -m 200-p 4-chunkmbs 512). Estimated expression levels were multiplied by 106 to obtain transcript per million (TPM) estimates for each gene, and TPM estimates were transformed to log-space by taking log(TPM+1). Genes were considered detected if their transformed expression level equal to or above 1.1 (in log(TPM+1) scale). A library was filtered out if it had less than 2,000 detected genes or more than 8,000 detected genes (threshold set by analysis of 1, 2, 4, and populations of sorted nuclei). 3' and 5' bias was measured using the RNA-SeQC package [49].

Bulk Nuc-Seq and Tissue RNA-Seq. Fresh dorsal and ventral DG tissue was micro-dissected from 4 adult female mice (11~13 weeks) and placed in RNA-later for 24 hours. Each sample was cut in half and used as bulk tissue in RNA-Seq or bulk nuclei populations in Nuc-Seq. Nuclei isolation was done as described for Nuc-Seq protocol, except that at the last stage of the isolation, nuclei were transferred to 300 µl RLT lysis buffer (QIAGEN) instead of the resuspension buffer. Applicants proceeded immediately to extract RNA from nuclei using the RNAeasy MinElute kit (QIAGEN, #74204) according to the manufacturer's protocol. For RNA extraction from bulk tissue, the tissue was placed in 300 µl RLT lysis buffer (QIAGEN), and mechanically dissociated using tissue raptor followed by the RNAeasy MinElute protocol. For each of the 8 nuclei and 8 tissue samples, libraries were made in triplicates, using the SMARTseq2 protocol, as described for the Nuc-Seq protocol with two modifications: (1) the number of PCR cycles in the whole transcriptome amplification stage was reduced to 14 cycles; (2) 1 ul of the extracted RNA was used as the initial input to the protocol, replacing lul of water in the first RT mix. Libraries were sequenced on the NextSeq 500 to an average read depth of 3 million reads. Correlations were calculated between each pair of samples. Number of genes detected was calculated for each quantile of expression levels by counting the number of genes with expression log(TPM+1)>1.1. Differential expression was analyzed using student's t-test, with FDR<0.01, log-ratio>1, and average expression across all nuclei or tissue samples log (TPM+1)>3.

Comparison of Nuc-Seq and single neuron RNA-Seq. For comparison of correlation of averaged single neuron/nuclei of CA1 pyramidal neurons, the cells labeled as 'CA1Pyr' from the single neuron RNA-Seq dataset [50] were sub-

TABLE 7

| Primer | Sequence | SEQ ID NO. |
| --- | --- | --- |
| RT primer (IDT) | /5BiosG/AAGCAGTGGTATCAACGCAGAGTACT TTTTTTTTTTTTTTTTTTTTTTTTTTTTTVN | 12 |
| TSO primer (Exiqon) | AAGCAGTGGTATCAACGCAGAGTACrGrG+G | 13 |
| ISPCR primer (IDT) | /5BiosG/AAGCAGTGGTATCAACGCAG*A*G*T | 14 |

Single cell dissociation and cell picking. Cells were dissociated and hand picked as described [43]. Images were taken on dissociated cells.

Sequencing reads initial processing. Tophat [44] was used to align reads to mouse mm10 UCSC genome with default parameters and the mouse gene annotations (RefSeq mm10 and Ensemble GRCm38 merged using Cufflink [45]). The alignment was visualized using integrated genome brower (IGV) [46]. To estimate gene expression, RSEM v1.27 [47]

sampled to get a dataset (referred to as snRNA-Seq CA1Pyr) that has the same number of cells as the CA1 pyramidal nuclei from Nuc-Seq (referred to as Nuc-Seq CA1). To calculate correlations of averaged 10 single neuron/nuclei, snRNA-Seq CA1Pyr and Nuc-Seq CA1 were separately subsampled 20 times, each time to 10 cells with replacement, and the averaged expressions of these 10 cells were calculated. The Spearman correlation was then calculated on the 20 averaged expressions of subsampled snRNA-Seq CA1Pyr data and those of subsampled Nuc-Seq CA1 data. The same procedure was repeated for averaged 20, 30, 40, 50 single neuron/nuclei. For comparison of correlation of averaged single neuron/nuclei of CA1 pyramidal neurons and interneurons, the cells labeled as 'CA1Pyr' and 'Int' from the single neuron RNA-Seq dataset [50] were separately subsampled, each to 100 cells to get two datasets, referred to as snRNA-Seq CA1Pyr and snRNA-Seq Int respectively. The CA1 and GABAergic nuclei from Nuc-Seq were subsampled, each to 100 nuclei to get two datasets, referred to as Nuc-Seq CA1 and Nuc-Seq Int respectively. To calculate correlations of averaged 10 single neuron/nuclei, snRNA-Seq CA1Pyr, snRNA-Seq Int, Nuc-Seq CA1, and Nuc-Seq Int were separately subsampled 20 times, each time to 10 cells with replacement, and the averaged expressions of these 10 cells were calculated. The Spearman correlation was then calculated between the 20 averaged expressions of subsampled snRNA-Seq CA1Pyr and those of snRNA-Seq Int, and between 20 averaged expressions of subsampled Nuc-Seq CA1 and those of Nuc-Seq Int. The same procedure was repeated for averaged 20, 30, 40, 50 single neuron/nuclei.

Analysis of nuclei clusters. Clustering analysis partitions nuclei into groups, such that nuclei from the same group share more similarity than nuclei from different groups. The quality of the grouping can be measured using the Dunn index [51]

$$DB = \frac{\min_{1 \leq i < j \leq n} d(i, j)}{\max_{1 \leq k \leq n} d'(k)},$$

where d(i, j) represents the inter-group distance between group i and j, and d'(k) represents the intragroup distance of group k.

Applicants expect that the coherent structure in transcriptomes of cells of high similarity generates observations that lie on a low-dimensional manifold in the high-dimensional measurement space [52]. In this case, data points for cells belonging to the same group would lie on a continuous smooth low-dimensional manifold, and data points for cells from different groups would lie on different manifold structures. Applicants confine distances used in calculating the Dunn index to the low-dimensional manifold structure and define the distance d'(k) as $$\hat{\Phi}_{pq} = \underset{\Phi_{pq}}{\operatorname{argmin}} \max\{d_{mn} \mid d_{mn} \in \Phi_{pq}\}$$

$$d'(k) = \max\left\{d_{mn} \middle| d_{mn} \in \bigcup_{p,q} \hat{\Phi}_{pq}\right\},$$

where p, q, m, and n are data points belonging to the group k, dmn represents the pairwise distance of data points m and n, and _p q represents a path connecting p and q through data points belonging to the group k. Applicants define the distance d(i, j) similarly to d'(k) and confine p, q, m, and n to be data points belonging to the union of the groups i and j.

Here, Applicants describe a pipeline of techniques to obtain nuclei clusters. Applicants first normalize data, then Applicants estimate false negatives and reduce their impact on the calculation of dmn. Next, Applicants perform modified PCA and tSNE [53] to map the low-dimensional structures to a 2-D space, where dmn and _p q in the 2-D space represent their high-dimensional counterparts. The mapping transforms each of the low dimensional manifold structures to dense data clouds in the 2-D space, permitting grouping of cells by a density clustering technique [54]. This non-linear mapping is particularly useful for data sets, where the scales of d'(k) for different cell groups are very different and d'(k) are affected by large noises in the original high dimensional space. Finally, Applicants identify cell sub-clusters within each cell cluster by the biSNE algorithm. The PCA-tSNE, biSNE, and density clustering are applied hierachically to each cell clusters to obtain clusters at finer level. In each iteration, the Dunn index with the defined local distances d'(k) can be used to evaluate the quality of the clustering assignment.

Figure 8:
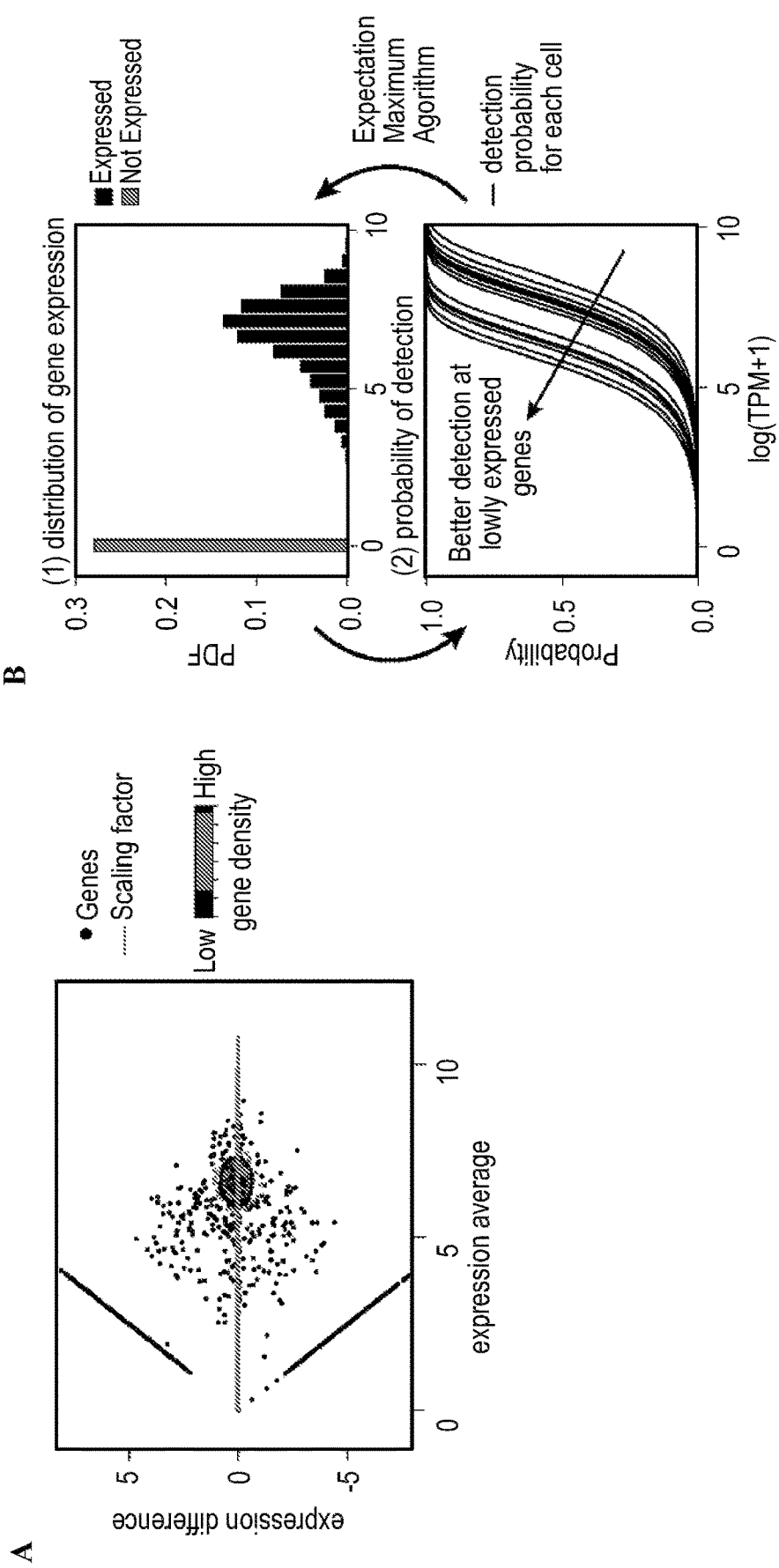
Figure 9:
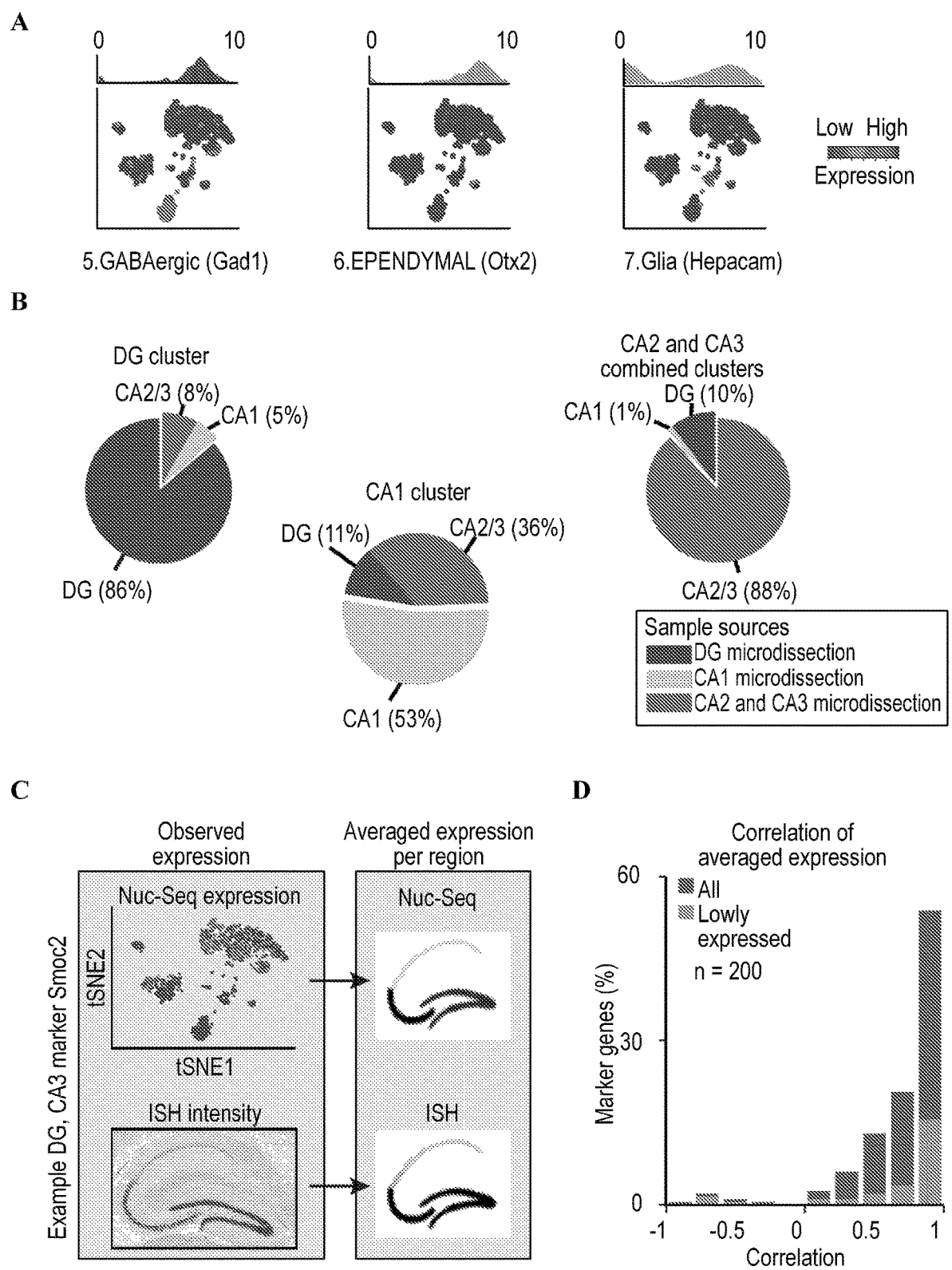

Normalization. Each library of single nuclei was prepared individually. Biases exist among libraries due to inevitable differences in lysis efficiency, priming rate at RT, amplification efficiency during the initial PCR, the equalization for tagmentation, and ratios in the final sequencing pooling [55]. Although several experimental methods have been developed to mitigate biases, including, for example, adding spike-in or using unique molecular identifiers, Applicants note that these methods would only help to reduce, at best, the amount of bias introduced after the initial PCR step, however significant amount of bias occurs before that step. Applicants assume that cells of the same type should highly express a set of genes that are tightly regulated and exhibit small "real" intercelluar variability. An example of such a gene set includes ribosomal and cytoskeleton genes in stem cells or housekeeping genes in dentritic cells that was previously used to normalize single cell sequencing data [56]. However, these is no consensus housekeeping gene set for brain cells that consist of both mature neurons, immature neurons, and glia cells. To normalized cells, Applicants developed a computational normalization procedure based on Bland-Altman (MA) plot and density estimation (FIG. 8). For a pair of cells, our procedure normalizes one cell with respect to another so that genes belonging to this gene set are not differentially expressed on average. Using only a small set of highly expressed and lowly variable genes, as opposed to using all genes [55] or genes within the middle quantile, provides robustness against noise, because measurements of highly expressed genes are resistant to sampling noise, and lowly variable measurements unlikely to have been corrupted by large noise. In addition, small intercellular variance enables simple statistical models, such as Gaussian model, to yield good estimates. Similar reasoning underlies previously described normalized methods such as TMM [57], DESeq [58]. However, these methods are designed for population RNA-Seq data, and Applicants empirically found that they not compatible with single cell data. A modified DESeq normalization which takes into account of massive false negatives common to single cell data did give comparable performance to our procedure.

Applicants first discuss the case of two cells, and later Applicants show how to generalize to a set of arbitrary size. To identify the set of genes for normalization, Applicants first calculate differences and averages of log transformed expression level of each gene between a given pair of cells, and plot the distribution of differences by averages on an MA plot. Then, gene density in this distribution is estimated [59] and genes within the most densely plotted regions are selected. Applicants calculate a scaling factor as the average of the log expression differences of selected genes. The second cell is normalized with respect to the first cell by dividing gene expressions of the second cell by the scaling factor. Specifically, the log expression difference of gene j between two cells is given by $$r_{12\_j}=\log(e_{2j})-\log(e_{1j}),$$

and the average of log expression of gene j is given by $$a_{12\_j}=[\log(e_{1j})+\log(e_{2j})]/2.$$

where $e_{ij}$ denotes the expression level of gene j in cell i. Gene j is selected into the gene set SJ, if $r_{12\_j}$ and $a_{12\_j}$, coordinates of gene j, are within the region having density above the top 70 percentile in the MA plot. The scaling factor is obtained by $$s = \sum_{j, j \in \mathbb{S}_J} r_{12\_j} / |\mathbb{S}_J|.$$

Then the second cell is normalized as $$e'_{2j}=e_{2j}/s.$$

To normalize single cells of different types, cells are first clustered into separate groups, each of which contains cells of a similar type. This step ensures that normalization complies with our assumption that cells are of the same type. Then normalization is performed for each group separately. Within each group, scaling factors are estimated for each cell with respect to multiple reference cells, which are chosen based on the number of genes detected, for example, cells having number of genes detected around the 80 percentile. Although any particular reference cell could be affected by erroneous measurements to various degrees, using multiple reference cells reduces the effect of these errors in the normalization.

Specifically, for a given group of cells $\{i|i \in C_g \text{ and } g \in G\}$, a set of cells that have number of genes detected above 80 percentile are selected as reference cells $\{r|r \in C_{gr} \text{ and } C_{gr} \subset C_g\}$. The scaling factor sir for each cell i with respect to each reference cell r is calculated. To relate sir obtained with different reference cells, Applicants solve the optimization problem $$\{\hat{a}_r \mid r \in \mathbb{C}_{gr}\} = \underset{a_r, r \in \mathbb{C}_{gr}}{\operatorname{argmax}} \sum_{i \in \mathbb{C}_g} \underset{r \in \mathbb{C}_{gr}}{\operatorname{Var}} [\log(s_{ir}) - \log(a_r)],$$

and scaling factors are estimated as $$s_i = \underset{r \in \mathbb{C}_{gr}}{\operatorname{median}}\left(\frac{s_{ir}}{\hat{a}_r}\right).$$

To normalize cells from different groups, Applicants use group scaling factors estimated for each group aggregates, which are obtained by averaging all cells within a same group. Cells from a same group are normalized using their group scaling factor. Specifically, for each group g ∈ G, the group aggregate is calculated as $$e_{gj} = \sum_{i \in \mathbb{C}_g} e'_{ij},$$

where $e_{gj}$ denotes the expression level of gene j in group g, and e' ij is the normalized expression level of gene g in cell i. Multiple reference group aggregates are selected for the estimation of group scaling factors.

Comparison of our normalization method with TMM and DESeq. Applicants consider a model for observed expression level eij given true expression level $$x_{ij}, \ e_{ij}=s_i \cdot \in_{ij} \cdot x_{ij}.$$

where si represents the scaling factor of cell i, ∈ij represents the technical noise of gene j measured in cell i, and xij represents the true expression level of gene j measured in cell i. Rewrite eij on log scale, log(eij)=log(si)+log(Eij)+log(xij). In our normalization, the normalization factor is obtained by averaging, between cell i1 and i2, the differences in the expression of selected subset of genes SJ.

$$\sum_{j \in B_J} (\log(e_{1j}) - \log(e_{2j})) / |\mathbb{S}_J| = \log(s_1) - \log(s_2) + \sum_{j \in \mathbb{S}_J} (\log(e_{1j}) - \log(e_{2j})) / |\mathbb{S}_J| + \sum_{j \in \mathbb{S}_J} (\log(r_{1j}) - \log(r_{2j})) / |\mathbb{S}_J|.$$

As Eij for j∈SJ is assumed to be log normally distributed with zero mean (modeling PCR and sampling noise), and genes within SJ are not differentially expressed on average, it follows that $$\log(s_1) - \log(s_2) = \sum_{j \in \mathbb{S}_J} (\log(e_{1j}) - \log(e_{2j})) / |\mathbb{S}_J|.$$

In TMM normalization, the SJ is replaced by $$S_Q = \{j | e_{ij} \in [e_{qa}, e_{qb}]\},$$

where $e_{qa}$ and $e_{qb}$ are $a_{th}$ and $b_{th}$ quantiles of $e_{ij}$. Applicants find the assumption that $$\Sigma_{j \in S_Q}[\log(x_{1j}) - \log(x_{2j})] = 0$$

might not hold true for single cell RNA-Seq data. In DESeq normalization, eq; is first normalized by its geometric mean across all cells, $$\log(e_{ij}) - \sum_i \log(e_{ij})/|I| = \log(s_i) - \sum_i \log(s_i)/|I| + \log(e_{ij}) - \sum_i \log(e_{ij})/|I| + \log(x_{ij}) - \sum_i \log(x_{ij})/|I|.$$

Then median is taken over all genes, $$\underset{j}{\operatorname{median}}\left(\log(e_{ij}) - \sum_i \log(e_{ij})/|I|\right) = \log(s_i) - \sum_i \log(s_i)/|I| + \underset{j}{\operatorname{median}}\left(\log(e_{ij}) - \sum_i \log(e_{ij})/|I|\right) + \underset{j}{\operatorname{median}}\left(\log(x_{ij}) - \sum_i \log(x_{ij})/|I|\right).$$

Assume that the median of Eij can be replaced by the mean of $\in_{ij}$, $$\underset{j}{\operatorname{median}}\left(\log(e_{ij}) - \sum_i \log(e_{ij})/|I|\right) = \sum_j \left(\log(e_{ij}) - \sum_i \log(e_{ij})\right) / |I||J| +$$

$$\sum_j \log(e_{ij})/|J| - \sum_i \frac{1}{|I|} \sum_j \log(e_{ij})/|J|.$$

It shows that the median of normalized eij is a good estimator for the scaling factor si only if $$\sum_j \log(e_{ij}) = 0 \text{ and } \underset{j}{\text{median}}\left(\log(x_{ij}) - \sum_i \log(x_{ij})/|I|\right) = 0.$$

However, because single cell RNA-Seq data contains substantial amount of false negative measurements, as discussed in the next section, these conditions might not hold true generally. Applicants propose a modified DESeq normalization, which gives comparable performance to our normalization method when applied to synthetic test data. In the modified DESeq normalization, the geometric mean and median are taken over only genes whose measured expression level eij>0. This leads to $$\underset{j,e_{ij}\ne 0}{\text{median}}\left(\log(e_{ij}) - \sum_i (e_{ij})/|I|\right) = \log(s_i) - \sum_i (s_i)/|I| +$$

$$\underset{j,e_{ij}\ne 0}{\text{median}}\left(\log(e_{ij}) - \sum_i \log(e_{ij})/|I|\right) + \underset{j,e_{ij}\ne 0}{\text{median}}\left(\log(x_{ij}) - \sum_i \log(x_{ij})/|I|\right).$$

In this formulation, the expression level Eij for {j|eij>0} is not subjected to false negative, and is assumed to be lognormally distributed with zero mean. Therefore, the median of Eij for {j|eij>0} is $$\underset{j,e_{ij}\ne 0}{\text{median}}\left(\log(e_{ij}) - \sum_i \log(e_{ij})/|I|\right) =$$

$$\sum_{j,e_{ij}\ne 0} \log(e_{ij})/|J| - \sum_i \frac{1}{|I|} \sum_{j,e_{ij}\ne 0} \log(e_{ij})/|J| = 0.$$

And further assume that there exist some genes that are not differentially expressed among all cells, then the median is a robust measure to find one such gene, $$\underset{j,e_{ij}>0}{\text{median}}\left(\log(x_{ij}) - \sum_i \log(x_{ij})/|I|\right) = 0.$$

Therefore, Applicants can obtain the scaling factor by $$\log(s_i) - \sum_i \log(s_i) = \underset{j,e_{ij}>0}{\text{median}}\left(\log(e_{ij}) - \sum_i \log(e_{ij})/|I|\right).$$

Estimation of missed detection probability. Single nuclei transcriptome libraries are amplified from extremely small input materials. As such, Applicants expect that some transcripts that are lowly expressed will not be detected (false negatives). The probability of such missed detection increases for lowly expressed transcripts and lower quality libraries. Such false negatives are detrimental to various analyses. For example, they invalidate the normal distribution assumption underlying typically used Student's t-test, leaving the statistical test unjustified. In addition, false negatives confound the identification of bimodally expressed genes, such as cell type specific markers. Previous studies accounted for such false negatives by combining estimation of cell quality and gene expression [55, 60]. These methods were based on parametric estimation of gene expression distribution. However, distribution of gene expression cannot be readily fitted by a single parametric function. In contrast to these methods, Applicants developed a Bayesian method to estimate the likelihood of an observed zero measurement being a missed detection. Our approach is based on a non-parametric estimation for gene expression distribution.

Our method is based on two observations: a) Detection rates depend on expression level. The higher a gene is expressed, the more likely it can be detected. b) Detection rates depend on library quality. Genes are more likely to be detected in libraries of high quality. Applicants model these two observations as prior distributions: distributions of expression levels for each gene in cells of the same type sampling probabilities: detection probabilities at different expression levels for each cell For each observed eij=0 of gene j in cell i, Applicants then estimate the posterior distribution for two mutually exclusive hypotheses that eij is a missed detection or that gene j is not expressed in cell i. Specifically, the distribution of expression level of gene j is calculated as mixture of two distributions. The first one is the probability that gene j is not expressed $$p_j(x=0) = \frac{\sum_{i \in \{e_{ij}=0\}} 1}{\sum_i 1},$$

where x denotes the true expression level. The second one is a conditional distribution of expression levels of gene j given that gene j is expressed. This distribution is estimated using a KDE based method [59] using gene expression levels et; from cells i, {i|e_{ij}>0}. Combining two parts yields $$p_j(x) = p_j(x=0) + [1 - p_j(x=0)] p_{j\_KDE}(x),$$

where x denotes the expression level. The detection probability (1—dropout probability) for a cell i is modeled using a geometric distribution parameterized by βi, as it captures the Poisson sampling process, mechanism underlying detection stochasticity $$\Lambda(x, \beta_i) = 1 - e^{-t}, t = \beta_i \begin{bmatrix} 1 \\ x \end{bmatrix} = \beta_{i0} + \beta_{i1} x$$

$$0 \le \Lambda(x, \beta_i) \le 1.$$

where x denotes expression level. Given observed data eij, the expected value of the log likelihood function is given by $$E[L] = \sum_{j \in \{e_{ij}>0\}} \log(1 \cdot \Lambda(e_{ij}, \beta_i)) + \sum_{j \in \{e_{ij}>0\}} \sum_x p_j(x) \log(p_j(x)(1 - \Lambda(x, \beta_i))).$$

In each iteration, the log likelihood function is maximized using gradient descent.

$$\hat{\beta}_i = \underset{\beta_i}{\operatorname{argmax}} E[L]$$

$$\frac{\partial E[L]}{\partial \beta_i} = \sum_{j \in \{e_{ij} > 0\}} \frac{1}{\Lambda(e_{ij}, \beta_i)} \frac{\partial \Lambda(e_{ij}, \beta_i)}{\partial \beta_i} +$$

$$\sum_{j \in \{e_{ij} > 0\}} \sum_x p_j(x) \frac{1}{1 - \Lambda(x, \beta_i)} (-1) \frac{\partial \Lambda(x, \beta_i)}{\partial \beta_i}.$$

Because $\_(x, \beta)$ is constrained to be non-negative, its derivative is modified with a rectifier so that $\_(x, \beta)$ is differentiable for any x, $$h(x) = \frac{\log(\exp(x \cdot N) + 1)}{N}, \text{ where } N \text{ is a large number}$$

$$\frac{\partial \Lambda}{\partial \beta} \approx \frac{\partial h}{\partial \Lambda} \frac{\partial \Lambda}{\partial \beta} = \frac{1}{1 + \exp(-\Lambda(x, \beta) \cdot N)} \cdot e^{-t} \begin{bmatrix} 1 \\ x \end{bmatrix}.$$

Then the distribution of expression levels are updated by $$p(e_{ij} = 0 \mid x_{ij} > 0) = \sum_x p_j(x)(1 - \Lambda(x, \hat{\beta}_i))$$

$$p(x_{ij} = 0 \mid e_{ij} = 0) = \frac{p_j(x_{ij} = 0)}{p_j(x_{ij} = 0) + p(e_{ij} = 0 \mid x_{ij} > 0)}$$

$$p_j(x = 0) = \frac{\sum_{j \in \{e_{ij}=0\}} p(x_{ij} = 0 \mid e_{ij} = 0)}{\sum_{j \in \{e_{ij}=0\}} (x_{ij} = 0 \mid e_{ij} = 0) + \sum_{j \in \{e_{ij}>0\}} 1}$$

$$p_j(x) = p_j(x = 0) + [1 - p_j(x = 0)] p_{j\_KDE}(x),$$

where $p(x_{ij}=0|e_{ij}=0)$ denotes the probability that gene j is not expressed in cell i. Applicants implemented an expectation-maximization (EM) algorithm that alternates between performing an expectation step for L, and a maximization step for searching the maximizer $\hat{\beta}_i$ of $E[L]$. The probability $p(x_{ij}=0|e_{ij}=0)$ is incorporated in calculations of summary statistics and distances to weight zero measurements. The higher the probability, the more likely that an observed zero represents an truly unexpressed gene in a cell, and the more Applicants weight the contribution of the zero. Conversely, the lower the probability, the higher the chance that it is false negative, and the lower Applicants weight its contribution in an analysis.

Specifically, Applicants weight summary statistics, Euclidean distance, Pearson correlation coefficient, and cosine similarity in the following ways.

I. the weighted gene expression mean: where $$u_j = \sum_i e_{ij} w_{ij} / \sum_i w_{ij},$$

$$w_{ij} = \begin{cases} p(x_{ij} = 0 \mid e_{ij} = 0) & \text{if } e_{ij} = 0 \\ 1 & \text{if } e_{ij} > 0 \end{cases}.$$

II. the weighted Euclidean distance between two cells x, y:

$$w_j = w_{xj} w_{yj}$$

$$d_{xy} = \frac{\sum_j (e_{xj} - e_{yj})^2 w_j}{\sum_j w_j}.$$

III. the weighted Pearson correlation coefficient between two cells x, y:

$$\hat{e}_x = e_x - u_x, \quad \hat{e}_y = e_y - u_y$$

$$S_{xy} = \sum_j \hat{e}_{xj} \hat{e}_{yj} w_j, \quad S_{xx} = \sum_j \hat{e}_{xj}^2 w_j, \quad S_{yy} = \sum_j \hat{e}_{yj}^2 w_j$$

$$\rho_{xy} = \frac{S_{xy}}{\sqrt{S_{xx} S_{yy}}}.$$

IV. the weighted cosine similarity is calculated in a similar way except no data centering.

V. the weighted Euclidean distance between two cells x, y under a linear transformation of linear combinations of genes, $Y = XA$, where X is an $i \times j$ matrix, and A is a $j \times k$ transformation matrix, is given by $$w_j = w_{xj} w_{yj}$$

$$d_{xy} = \sum_k \left( \frac{\sum_j a_{jk}(e_{xj} - e_{yj}) w_j}{\sum_j w_j} \right)^2.$$

VI. the weighted Pearson correlation coefficient between two cells x, y under a linear transformation of linear combinations of genes as above is given by $$u_x = \frac{1}{|K|} \sum_k \frac{\sum_j a_{jk} e_{xj} w_j}{\sum_j w_j},$$

$$u_y = \frac{1}{|K|} \sum_k \frac{\sum_j a_{jk} e_{yj} w_j}{\sum_j w_j}$$

$$\hat{e}_{xk} = \frac{\sum_j a_{jk} e_{xj} w_j}{\sum_j w_j} - u_x,$$

$$\hat{e}_{yk} = \frac{\sum_j a_{jk} e_{yj} w_j}{\sum_j w_j} - u_y$$

$$S_{xy} = \sum_k \hat{e}_{xk} \hat{e}_{yk},$$

$$S_{xx} = \sum_k \hat{e}_{xk}^2,$$

$$S_{yy} = \sum_k \hat{e}_{yk}^2$$

$$\rho_{xy} = \frac{S_{xy}}{\sqrt{S_{xx} S_{yy}}}.$$

VII. the weighted cosine similarity is calculated similarly as the weighted correlation coefficient except no data centering.

VIII. the weighted covariance between two genes under a linear transformation of linear combinations of genes as above is given by $$u_{xk} = \frac{\sum_i \sum_j a_{jk} \hat{e}_{ij} w_{ij}}{\sum_i \sum_j w_{ij}} = \frac{\sum_j a_{jk} \sum_i \hat{e}_{ij} w_{ij}}{\sum_i \sum_j w_{ij}} = 0,$$

$\hat{e}$ is centered along $i$ $$cov(k, k') = \frac{\sum_i \left(\sum_j a_{jk} \hat{e}_{ij} w_{ij}\right)\left(\sum_j a_{jk'} \hat{e}_{ij} w_{ij}\right)}{\sum_i (\sum_j w_{ij})^2}.$$

PCA and tSNE. To project cells to two dimensional space, Applicants first perform principal component analysis (PCA) to project original data to reduced linear dimensions, where most significant variance of the data is preserved as determined based on the largest eigenvalue gap. Applicants then calculate the cosine distance of cells on the PCA reduced dimensional space. Finally, Applicants use t-distributed Stochastic Neighbor Embedding (tSNE) [53, 61, 62] with the cosine distance to further map cells to two dimensions, where Euclidean distances of closely projected cells represent their cosine distances. The cosine distance depends the angle between two vectors defined by gene expressions in the high dimensional space. It is preferred in our analysis over Euclidean distance and correlation distance, because it is more robust to noise than Euclidean distance and it is invariant under rotational transformations, such as PCA.

I. weighted PCA. The PCA analysis is performed usually using singular value decomposition (SVD) or eigenvalue decomposition (EVD) on the covariance matrix, which scales quadratically with the number of genes. Given large number of genes, more than 25,000, in our data, it is computational costly to directly perform SVD or EVD on the large covariance matrix. In order to get principal components, or the transformation matrix A, while accounting for weights, Applicants first center the original data matrix E across genes to get t, where eij is the expression level of gene j in cell i. Next, Applicants perform SVD on centered data matrix E to get A*. Applicants calculate the weighted covariance matrix Cw on E under the linear transformation defined by the matrix A*. Applicants then perform SVD or EVD on Cw to get A.

II. tSNE with cosine distance. Applicants modified the original tSNE to allow dimensionality reduction based on a weighted cosine similarity. The original tSNE technique projects data in a non-linear way to low dimensional space, such that Euclidean distances between neighboring data points in the low dimensional space overall represent distances between these neighboring data points, or local distances, in the high dimensional space. The input to tSNE is a distance matrix, describing all pairwise distances in the high dimensional space. In order to apply tSNE, Applicants first transform the weighted cosine similarity to cosine distance by exploring relationships between the two measures on the closest data points. Specifically, given a cell and its gene expression measurements denoted by a n dimensional vector x, the measurements of its neighbor y is modeled as $$y = k(x+d),$$

where k is a scaling factor and d denotes the distance between x and y. Under the null hypothesis that x and y are measured from two cells of the same type, d is drawn from a Gaussian distribution with zero mean and variance σ. Our goal is to estimate the distance magnitude |d|, given the measured angle φ between x and y. Geometrically, the vector d lies on a hypersphere defined by radius |d|. The volume and surface area of a hypersphere of dimension n (n-sphere) has the following properties $$S_n = (n+1)V_{n+1}$$

$$dS_n = (n+1)dV_{n+1}$$

the volume element is $$dV_{n+1} = |d|^n \sin^{n-1}(\phi_1)\sin^{n-2}(\phi_2)\ldots\sin(\phi_{n-1})d|d|d\phi_1 d\phi_2\ldots d\phi_n$$
$$= \sin^{n-1}(\phi_1)d\phi_1 \cdot g(|d|, \phi_2\ldots\phi_n)$$
$$dS_n = \sin^{n-1}(\phi_1)d\phi_1 \cdot (n+1)g(|d|, \phi_2, \ldots, \phi_n).$$

The probability of drawing d in a n-sphere of radius |d| with an angle φ from x scales as $\sin n-1(\phi)$. When n is large, most of d lie perpendicular to x, thus there exists a unique mapping between |d| and φ.

$$\cos(\phi) = \frac{1}{\sqrt{(1+|d|)^2 + 1}}$$

$$|d| = \sqrt{\frac{1}{\cos^2(\phi)} - 1}$$

Differential gene expression and pathway analysis. Applicants use an adjusted Welch's t-test for identifying differentially expressed genes. Applicants applied weights in the calculation of summary statistics, such as sample mean, sample variance, and effective degrees of freedom, used in Welch's t-test. Specifically, to find the significance level of gene j between cells in group X and cells in group Y, $$n_{xj} = \sum_{i, i \in X} w_{ij}, \; n_{yi} = \sum_{i, i \in Y} w_{ij},$$

$$n_{xj} = \sum_{i, i \in X} e_{ij} w_{ij}/n_{xj}, \; n_{yj} = \sum_{i, i \in Y} e_{ij} w_{ij}/n_{yj},$$

$$S_{xj} = \sum_{i, i \in X} (e_{ij} - u_{xj})^2 w_{ij}/(n_{xj} - 1),$$

$$S_{yj} = \sum_{i, i \in Y} (e_{ij} - u_{yj})^2 w_{ij}/(n_{yj} - 1),$$

i. statistic $t_j = \dfrac{u_{xj} - u_{yj}}{\sqrt{\dfrac{S_{xj}}{n_{xj}} + \dfrac{S_{yj}}{n_{yj}}}},$ degrees of freedom $$v_j \approx \frac{(S_{xj}/n_{xj} + S_{yj}/n_{yj})^2}{S_{xj}^2/[n_{xj}^2(n_{xj}-1)] + S_{yj}^2/[n_{yj}^2(n_{yj}-1)]}.$$

The false discovery rate (FDR) is calculated for each differentially expressed gene in multiple hypothesis testing using Benjamini and Hochberg procedure [63].

Density clustering and selection of the number of clusters. Applicants used a density based clustering method [54] to partition cells embedded in the 2-D space. The method searches cluster centers that are characterized by two quantities: (1) high local density $\rho i$ and (2) large distance $\delta i$ from points of higher density, which are centers of other clusters. Applicants unify the two quantities into a single metric by taking the product of the two quantities, $si=\rho i \cdot \delta i$.

To select cluster centers, Applicants rank each data points by their si in descending order. For a given n, the number of desired clusters, Applicants select the top ranked n cluster centers, and perform the cluster assignment as described previously [54]. To evaluate the quality of the clustering, Applicants calculate the Dunn index for each n with d(i, j) and d'(k) defined as local distances. The calculation of the Dunn index can be operated in O(N3), where N is the number of total data points.

---

Algorithm: Identification of maximum
steps on shortest paths (MaxStep)

Input: pairwise distance of data points (D)
Output: the pairwise shortest link (D')
D' := D
n := # of data points
for k := 1 to n do
   |   for i := 1 to n−1 do
   |   |   for j := i+1 to n do
   |   |   |   D'(i,j) = min(D'(i,j), max(D'(i,k), D'(k,j)))
   |   |   end
   |   end
end
return D'

---

Algorithm: Calculation of the Dunn index defined on local distances (DunnnLocal)

Input: pairwise distance of data, points in the 2-D embedding (D), clustering assignment (Cl)
Output: the Dunn index ($\theta$)
cl_uiq := unique(Cl)
n := # of cl_uiq
$d'_k$ := empty array with a length of n
$d_{ij}$ := empty matrix with a size of (n, n)
for i := 1 to n do
   |   ii := index of data whose clustering assignment is cl_uiq(i)
   |   $d'_k$(i) := max(MaxStep(D(ii,ii)))
end
for i := 1 to n−1 do
   |   for j := i+1 to n do
   |   |   ii := index of data whose clustering assignment is either cl_uiq(i) or cl_uiq(j)
   |   |   $d_{ij}$(i, j) := max(MaxStep(D(ii,ii)))
   |   end
end
$\theta$ := min($d_{ij}$)/max($d'_k$)
return $\theta$

---

Large scale comparison between RNA-Seq data and ISH data. Applicants selected genes differentially expressed between any bipartition of DG, CA1, CA2, CA3 clusters in RNA-Seq data. For example, a gene is selected if it is differentially expressed between cells in a combined DE and CA2 cluster, and cells in a combined CA1 and CA3 cluster. Specifically, the differential expression was tested using the adjusted t-test between cells $\in C1$, $C1c \subset \{DG, CA1, CA2, CA3\}$ and cells $\in C2$, $C2=\{DG, CA1, CA2, CA3\}C1$. Gene$j$ is selected if
   difference in mean $m_{c_{1j}} - m_{c_{2j}} > 1$
   mean of cells $\in C_1$ $m_{c_{1j}} > 20$ TPM
   mean of cells $\in C_2$ $m_{c_{2j}} < 5$ TPM
   p values of t-test $pj < 0.01$.

The quantified ISH data [64] with 200 μm resolution was downloaded from Allen Brain Atlas (Website: 2015 Allen Institute for Brain Science. Allen Mouse Brain Atlas [Internet]. Available from: mouse.brain-map.org.) Mean expression level of ISH data was calculated as averaged energy level for each of the DG, CA1, CA2, CA3 regions. Specifically, averaged energy level eG for grids in a region G is given by $$e_G = \sum_{g, g \in G} d_g \cdot i_g / |G|,$$

where dg is the quantified expression density for grid g, and ig is the quantified expression intensity for grid g. The Indices for DG, CA1, CA2, CA3 regions are 726, 382, 423, 463. Applicants obtained two vectors $e \in R4$ comprising averaged expression levels of DG, CA1, CA2, CA3 regions for each gene, one from RNA-Seq data, and another from ISH data. Pearson correlation coefficient was calculated between these two vectors for each selected gene.

BiSNE. Cells positioned in proximity in the tSNE mapping coexpress a set of genes that are not expressed by distal cells. These set of genes could be used to distinguish different cell subpopulations. These genes are coexpressed in the cells grouped in proximity, and therefore they have localized expression patterns in the tSNE mapping.

Statistics for scoring expression patterns. Motivated by this observation, Applicants use two different statistics to identify genes with significantly localized expression patterns in the tSNE mapping and then perform PCA-tSNE using the union of these identified genes to cluster cells.

I. Moran's I. Moran's I [65] scores correlation between a measurement on a set of mapping positions and pairwise distances of these mapping positions. Given tSNE coordinates, the Moran's I for gene k is given by $$I(k) = \frac{\sum_i \sum_j Q_{ij}(e_{ik} - u_k)(e_{jk} - u_k) w_{ik} w_{jk} / \sum_i \sum_j Q_{ij} w_{ik} w_{jk}}{\sum_i (e_{ik} - u_k)^2 w_{ik} / \sum_i w_{ik}},$$

where Qij denotes the pairwise similarity transformed from dij, the Euclidean distances between cell i and j in the tSNE mapping. Applicants obtain $Q_{ij}$ from $d_{ij}$ using the Gaussian function, $$Q_{ij} = \frac{1}{\sigma\sqrt{2\pi}} \exp\left(-\frac{d_{ij}^2}{2\sigma^2}\right).$$

Applicants choose σ to set the minimal size of localized expressed pattern, as dij≈σ weights around 60% and dij2σ weights around 13.5%. The statistical significance of the pattern of gene k is tested by converting l(k) to a z score, $$E[I] = -1/(N-1), \text{ where } N \text{ is the length of } e_k$$

$$V[I] = \frac{1}{S_0^2(N^2-1)(N^2S_1 - NS_2 + 3S_0^2)} - E[I]^2$$

$$S_0 = 2\sum_i\sum_j Q_{ij}, \; S_1 = 2\sum_i\sum_j Q_{ij}^2,$$

$$S_2 = 4\sum_i\left(\sum_j Q_{ij}\right)^2$$

$$z = -\frac{I - E[I]}{\sqrt{V[I]}}.$$

Moran's I uses gene expression levels in its calculation. When identifying marker genes, only the information about whether a gene is expressed or not is necessary. Applicants use a modified Moran's I on binarized gene expression levels. Specifically, Applicants binarize gene expression level by a threshold, $$\hat{e}_{ij} = \begin{cases} 1 & \text{if } e_{ij} > 3 \text{ TPM} \\ 0 & \text{if } e_{ij} \leq 3 \text{ TPM} \end{cases}.$$

Applicants then calculate the modified Moran's I by, $$I(k) = \frac{\sum_i\sum_j Q_{ij}(\hat{e}_{ik} - \hat{u}_k)(\hat{e}_{jk} - \hat{u}_k)w_{ik}w_{jk}}{\sum_i\sum_j Q_{ij}w_{ik}w_{jk}}.$$

Moran's I is a global measure. It has biases towards genes that are widely expressed. To reduce false positives, Applicants filtered out genes expressed in more than 80% of cells.

II. Manhattan distance and order statistics. The manhattan distance is an alternative to the Euclidean distance in quantifying proximity. The advantage of using manhattan distance is that x and y coordinates can be tested independently using order statistics. Assume a given set of cells that express gene j and their positions z on a coordinate z, z is defined as the normalized z such that $$z_i = (z_i - \min(z)/(\max(z) - \min(z)), i \in \{i | e_{ij} > \text{TPM } 3\}$$

and ^z is defined as the ordered list of ⁻z, such that $\hat{z}_i < \hat{z}_{i+1}$. The range $w_z$ is defined as $w_z = \hat{z}_n - \hat{z}_1$. Assume that is a vector of i.i.d. samples from a uniform distribution, the significance level p of $w_z$ can be found using order statistics PDF of $wf_w(w) = n(n-1)\int_{-\infty}^{+\infty}[F(x+w)-F(w)]^{(n-2)}f(x)f(x+w)dx$ where $f(x)$ and $F(x)$ are PDF and CDF of z CDF of $w\, F_w(w) = n^{-1}[n-(n-1)w]$, under null hypothesis $pd=F_w(w_z)$, where PDF is the probability density function and CDF is the cumulative density function. To robustly estimate w in the presence of outliers, the distribution of z is fitted using the Gaussian distribution with robust estimators of mean and variance [66].

$$u_z = \text{median}(z)$$

$$S_x = 1.1926 \, \underset{i}{\text{median}}\left(\underset{j}{\text{median}}(|z_i - z_j|)\right)$$

$$p_i = \Phi\left(-\left|\frac{z_i - u_x}{S_z}\right|\right),$$

where Φ denotes the CDF of the standard normal distribution. Samples with pi<∈, a predefined threshold, are considered outliers and are excluded from the estimation of w. A single p value is calculated for each gene by taking the product of px and py, the p values obtained for x and y coordinates, respectively. It measures the overall significance level of each gene in both coordinates.

Selection of significant genes. For each statistic, Applicants rank genes based on their significance. Genes ranked high are likely to be informative for clustering cells, whereas genes ranked low are more likely to be noises that suppress clustering separation. Applicants use a cut off rank to select informative genes, chosen based on the statistic of eigenvalues of random matrices [67], which states that inclusion of a noisy row(gene) in a data matrix would lead to a reduction in the maximum eigenvalue gap of the matrix. Conversely, inclusion of an informative row(gene) would lead to an increase in the maximum eigenvalue gap, as the variance it introduces aligns with variances of some other genes. Therefore, the change in the maximum eigenvalue gap measures the extent a gene being informative. After genes are ranked, Applicants start with a data matrix containing the top ranked genes, and add subsequent genes with lower rank incrementally. For each addition, Applicants calculate the change in the maximum eigenvalue gap before and after adding the gene. Additionally, Applicants randomly permute measurements of this gene across cells and calculate the change in the maximum eigenvalue gap induced by adding this permuted gene. Applicants then select a cut off rank, below which there is no difference in the change of the maximum eigenvalue gap between adding a gene or its permuted counterpart. The selection cut-off can also be formally tested using minimum hypergeometric test [68]. Specifically, for a data matrix E1,j-1 and a gene j, Applicants form a new matrix $$E_{1,j} = \begin{bmatrix} E_{1,j-1} \\ e_{j,} \end{bmatrix}$$

and we obtain the eigenvalues of $E_{1,j-1}E_{j-1}^T$ using weighted SVD. The eigenvalues are normalized and sorted in order $$\lambda_1 > \lambda_2 > \ldots > \lambda_n, \text{ and } \sum_i \lambda_i = 1.$$

The distribution density (Marchenko-Pastur distribution) of higher order eigenvalues can be approximated by a linear function [67], and its cumulative distribution can be approximated by a quadratic polynomial. The sorted eigenvalues follow the inverse function of the cumulative distribution, and are fitted by $$\hat{\lambda}_i = f(i) = \alpha_0 + \alpha_1 \sqrt{\frac{i}{n}}, \alpha_0 \text{ and } \alpha_1 \in \mathbb{R}.$$

The eigenvalue gap is approximated as $$\Delta_j = \sum_{i=1}^{n} (\lambda_i - \lambda'_i).$$

For permutation comparison, expression of gene j is permuted, $$\tilde{e}_j : \tilde{e}_{ij} = e_{i'j}, i' \text{ is drawn without replacement from}[1, n]$$

$$\tilde{E}_{1,j} = \begin{bmatrix} E_{1,j-1} \\ \tilde{e}_j \end{bmatrix},$$

where i' denotes randomly permuted cell index. The eigenvalue gap~j is obtained for the permuted matrix~E 1,j. A cut off rank is chosen at k, if the change in the eigenvalue gap '~_'snot significant for genes ranked below k. To combine top genes, Applicants take the union of genes selected by different statistics. Clustering of gene signatures using cross correlation To cluster genes into gene signatures while taking into account of the similarity between cells expressing these genes, Applicants compute cross correlations between high scoring genes while taking account of the proximity of cells expressing these genes, convert the correlation coefficient to distances, and cluster these genes using t-SNE and density clustering. Specifically, spatial cross correlation between gene k and k' is given by $$I(k, k') = \frac{\Sigma_i \Sigma_j Q_{ij}(e_{ik} - u_k)(e_{jk'} - u_{k'}) w_{ik} w_{jk'} / \Sigma_i \Sigma_j Q_{ij} w_{ik} w_{jk'}}{\sqrt{(\Sigma_i(e_{ik} - u_k)^2 w_{ik} / \Sigma_i w_{ik})(\Sigma_i(e_{ik'} - u_{k'})^2 w_{ik'} / \Sigma_i w_{ik'})}}.$$

It has been noted that the range of I is not [−1, 1], unlike Pearson's correlation coefficient. Applicants empirically found that I is positively biased in the tSNE mapping. The positive bias may underestimate the strength of anti-correlation genes having complementary patterns. A scalar transformation of I that has the exact range [−1, 1] has been proposed [69].

$$\tilde{W} = (n\tilde{w})^{-1} H^T W H, \text{ where } \tilde{W} \text{ is a } (n-1) \times (n-1) \text{ matrix, and } \tilde{w} = \sum_{i,j=1}^{n} w_{ij}/n^2$$

$H = (h_1, \ldots, h_{n-1})$ is defined based on Helmert orthogonal matrix $h_i^T = (1_i^T, -i, 0_{n-i-1}^T)/\sqrt{i(i+1)}$, for $i = 1, \ldots, n-1$.

The scalar transformation of Moran's I is given by $$I_M = \begin{cases} [(n-1)I + 1]/[|(n-1)\lambda_{(1)} + 1|] & \text{if } (n-1)I + 1 < 0 \\ [(n-1)I + 1]/[(n-1)\lambda_{(n-1)} + 1] & \text{if } (n-1)I + 1 \geq 0, \end{cases}$$

where $\lambda_{(1)}$ and $\lambda(n-1)$ are the smallest and largest eigenvalues of the matrix w.

The calculation of spatial cross correlation has a computational complexity that scales quadratically with the number of gene and cells as of O(N2M2), where N is the number of cells and M is the number of genes. When the number of cells and the number of genes are large, it becomes impractical to calculate the spatial cross correlation. However, for clustering genes using tSNE [70], only the information about k nearest neighbor (knn) data points is necessary, requiring a linear complexity as of O(N2MK). The data with knn defined on a metric space can be organized using structures such as vantage point (VP) tree [71] for efficient computation. Applicants develop a conversion between spatial correlation coefficient and a metric.

Theorem For a given similarity ((k,k'), I(k,k')∈[−B,B], B∈R and B>0, define g(k,k')

$$g(k, k') = \begin{cases} 0 & \text{if } k = k' \\ \sqrt{a - I(k, k')} & \text{if } k \neq k' \end{cases}$$

with a>5/3 B, and g(I(k,k')) is a metric
Proof: For k=k', the proof is trivial, For k≠k',
1. non-negativity, $$g(k, k') = \sqrt{a - I(k, k')} > \sqrt{\frac{2}{3}B} > 0$$

2. coincidence, g(k,k')=√a−I(k,k')>0
3. symmetry, g(k,k')=√a−I(k,k')=√a−I(k',k)=g(k',k)
4. triangle inequality, g(k, k")+g(k",k')≥2√a−B> √a−(−B)>g(k,k')

Selection of principal components. Applicants choose top principal components (PCs) based on the largest Eigen value gap. Applicants used top 15 PCs for all cells, top 11 PCs for glial cells, top 13 PCs for DG granule cells, top 7 PCs and top 4 PCs before and after biSNE feature selection for GABAergic cells, top 3 PCs and top 4 PCs before and after biSNE feature selection for CA1 pyramidal cells, top 2 PCs and top 5 PCs before and after biSNE feature selection for CA3 pyramidal cells, and top 2 PCs for immature neuronal cells. For GABAergic cells, after biSNE feature selection, two rounds of PCA-tSNE were performed. The first round includes all GABAergic cells, and the second round includes cells belonging to the GABAergic sub-clusters 3, 6, 7, and 8. The same 4 PCs were used in both rounds.

Comparison of biSNE and generalized linear model. Applicants used an in-house implemented generalized linear model (GLM) [72, 73] to select highly variable genes in the GABAergic nuclei data. Three different set of genes were chosen based on three significance levels. PCA-tSNE embeddings were performed on the nuclei data using each of the chosen sets of genes. The cluster assignments were obtained on the PCA-tSNE embedding that corresponds to the most stringent significance level. Applicants used biSNE to select three sets of correlated highly variable genes in the same nuclei data. Each set contains the same number of genes as that in the corresponding set selected by GLM. PCA-tSNE embedding and the cluster assignments were performed using each of sets of genes.

Validations of glia sub-types expression signatures. Differentially expressed marker genes were found for each of the glia sub-clusters and for the neuronal clusters. Differential genes were averaged across each glia cluster and averaged across all neuronal clusters combined. Spearman correlation was calculated between these average expression patterns and cell type specific bulk RNA-Seq performed in the cerebral cortex [74]. The published dataset was log transformed.

Identification of nuclei identity based on a single marker gene. Applicants performed in silico cell sorting based on Pvalb expression, and found that the sorted cells constitute a subset of the identified Pvalb interneurons. This demonstrates that cell type identification based on the expression level of a single marker gene can suffer from false negatives, if only because of "drop outs" in single cell RNA-Seq or Nuc-Seq. Fortunately, the Pvalb expressing interneurons also share similarity in the expression of many other genes, enabling the recovery of genes commonly expressed by Pvalb interneurons, providing a robust way to determine cell type.

Localization of subclusters to anatomical regions. Localizing subclusters requires a spatial reference map of a few landmark genes [42] and the expression level of these landmark genes in each subcluster. Applicants first created a spatial reference map by dividing an anatomical region into a grid. Applicants manually scored the expression levels of known landmark genes [64] in this grid as not expressed, weakly, or highly expressed in these grids. Next, Applicants generated for each subcluster a "landmark profile" by the percentage of cells expressing each landmark in this subcluster. Applicants developed a approach similar to Seurat [42] to infer whether a given landmark gene is expressed in each cell by exploiting information from all non-landmark genes. The technique leverages the fact that many genes that are co-regulated with the landmark genes are measured in Nuc-Seq and that their expression pattern contains information about landmark genes [42]. Our anatomical alignment method is similar to Seurat in concept. Unlike Seurat, however, our method can accommodate situations when far fewer landmark genes are available (a common situation in many system unlike the heavily-studied zebrafish embryo, on which Applicants demonstrated Seurat). Applicants calcualted the percentage of inferred expressing cells in each subcluster. To relate the subclusters to the reference map, Applicants evaluted the correlation between each subcluster's landmark profile and the profile of landmark genes in each part of the reference map. Applicants positioned each of the subclusters to the highly correlated parts of the map. The accuracy of this spatial mapping is dependent on the quality of ISH images of landmark genes from the Allan brain atlas. The selected landmark genes for CA1 region are Nov, Ndst4, Dcn, Gpc3, Zbtb20, Calb1, Prss12, Wfs1, Col5a1, Grp, Gpr101. The selected landmark genes for CA3 region are Kcnq5, Kctd4, Ttn, Rph3a, Mas1, Plagl1, Col6a1, Prkcd, Loxl1, Grp, Ptgs2, Dkk3, St18, Mylk. Applicants used a supervised machine learning algorithm to fit and binarize expression of marker genes. To obtain a training data set for a given marker gene j, Applicants ranked subclusters by weighted mean expression of the marker gene, and select cells expressing the marker gene above TPM 8 in the top ranked three subclusters as positive training samples. Applicants selected cells not expressing or lowly (less than TPM 3) expressing the marker gene in the bottom ranked three subclusters as negative training samples. Specifically, Applicants use all genes except marker genes as feature data z in an L1-regularized L2-loss support vector machine $$z_{ik} = \begin{cases} 1 - p(x_{ik} = 0 \mid c_{ik} = 0) & \text{if } e_{ik} = 0 \\ 1 & \text{if } e_{ik} > 0 \end{cases}$$

$$y_{ij} = \begin{cases} 0 & \text{if } i \in \text{negative training samples} \\ 1 & \text{if } i \in \text{positive training samples} \end{cases},$$

where k∈markers, and i∈training cells. Applicants solved the unconstrained optimization problem using liblinear package [75]

$$\min_{w_j} \|w_j\|_1 + C \sum_{i=1}^{l} (\max(0, 1 - y_{ij} w_j^T z_i^T))^2$$

where C denotes the penalty parameter. Applicants performed coarse search followed by fine search using 5 fold cross validation for parameter C that yielded the best accuracy for training data. To predict whether the marker gene is expressed in cells not included in the training samples, Applicants used the decision function $$\hat{y}_{ij} = \text{sgn}(w_j^T z_j^T)$$

The fraction of cells expressing marker gene j in a subcluster C is given by $$f_{Cj} = \sum_{i,i \in C} \hat{y}_{ij} / |C|.$$

Applicants predicted expression of all marker genes in this way and calculate Pearson correlation coefficient between subclusters and subregions using fC and manually quantified expression intensity. To test whether the subclusters were driven by the selected landmark genes, Applicants excluded the landmark genes from PCA-tSNE and biSNE steps, and repeated the clustering. Applicants consistently obtained the same clustering.

Indexing cells along a trajectory on projected continuum. To obtain the ranking of cells along a given trajectory, Applicants treat the indexing as a traveling salesman problem (TSP). Cells at the start and the end points of a given trajectory are manually selected. The Euclidean distances between cells on the projected space are calculated, and normalized to integers $$d = \lfloor 10 \, d/\min(d) \rfloor$$

The distance between start and points is set to 0. The normalized distances are used in Lin-Kernighan heuristic (LKH) solver [76, 77] for TSP. The obtained ordering of cells is shifted, so that the manually selected start cell is indexed the first.

Pathway and upstream regulator analysis of DG states. The nuclei from the DG cluster (animals of all ages) were mapped to a continuum by the expression of the Penk and Cck gene signature. Applicants selected two discrete sets of nuclei to represent each state: the top 80 nuclei highly expressing the Penk and the top 100 nuclei highly expressing the Cck signature. To find differentially expressed genes between these groups, Applicants used an adjusted t-test (FDR q-value<0.01, log-ratio>1, and mean expression>20 TPM in at least one group). Up-regulated and down-regulated genes were analyzed using Ingenuity Pathway Analysis (IPA, Qiagen) to find enriched canonical pathways, disease and biological functions, (Hypergeometric p-value<0.01), and to infer upstream regulators (by enrichment of target genes, Hypergeometric p-value<0.01).

Single nucleus quantitative PCR. Single nucleus RNA was purified as described for RNA sequencing library construction. Beads were eluted into 5p1 qScript cDNA synthesis reaction (Quanta Biosciences, #95047) made of 1 µl qScript reaction mix, 0.25 µl qScript RT, 3.75 µl water. The RT reactions were performed at 22° C. for 5 min, 42° C. for 90 min, and inactivated at 85° C. for 5 min. After completion of cDNA synthesis, 4 µl samples were combined with 6 µl of quantitative PCR (qPCR) reaction mix made of 5 µl Taqman 2× Master Mix (Thermo Fisher Scientific, TaqMan Fast Advanced Master Mix 2X, #4444554), 0.5 µl of each 20×Taqman probe (Thermo Fisher Scientific, custom TaqMan VIC probe Penk Mm01212875_m1 #4448489, TaqMan FAM probe Cck Mm00446170_m1 #4331182). Each sample was split to two technical replicates, and qPCR reactions were performed in 384 well plate using LightCycler 480 II (Roche) as follows: 50° C. for 2 min, 95° C. for 20 sec, 50 cycles of 95° C. for 3 sec with temperature ramping at 4.8° C./s and 60° C. for 30 sec with temperature ramping at 2.5° C./s. The fluorescence filters were selected for FAM at wavelength 465–510 nm and for VIC at wavelength 533–580 nm.

Single molecule in situ hybridization tissue assay. For in situ hybridization (ISH) assay, mice were perfused with PBS and 4% PFA. Brain samples were dehydrated and paraffin-embedded, and 7 µm sagittal sections were cut. ISH assay was performed using QuantiGene ViewRNA ISH Tissue 2-plex Assay Kit (Affymetrix, #QVT0012) with proprietary probes designed for Penk, Col6a1, Gad1, and Gad2. The assay was optimized based on the manufacturer's protocol for FFPE samples with the following modifications: heat pretreatment for 10 min in step 5, protease digestion and fixation for 10 min in step 6, wash slides for 3 times 4 min each wash in step 17 after label probe 6-AP hybridization, in step 19 after applying fast blue substrate, and in step 22 after label probe 1-AP hybridization. For double fluorescent in situ hybridization (dFISH) assay, mice were perfused with PBS. Brain samples were immediately frozen in tissue freezing medium (O.C.T.) and kept in −80° C. overnight. Coronal sections were cut at 15 µm at −15° C. dFISH assay on O.C.T. embedded sections was performed according to Affymetrix provided protocol for O.C.T. samples, which combines QuantiGene ViewRNA ISH Tissue 2-plex Assay Kit (Affymetrix, #QVT0012) and ViewRNA ISH Cell Assay Kit (Affymetrix, #QVCM0001). Proprietary probes designed for Calb2, Htr3a, Vip, Pvalb, Penk, and Oprd1 were purchased from the vendor (Affymetrix) and used. Images were taken using fluorescent microscopy (Zeiss microscope and Hamamatsu camera C11440~22CU) and were processed in Matlab. Image background due to non-uniform illumination was removed using Matlab function strel('disk',25). The image brightness and contrast were adjusted to obtain the maximum dynamic range.

EdU labeling for staining. Labeling of proliferating cells for staining in mice was performed by intraperitoneal (i.p.) injection of EdU (5-ethynyl-2'-deoxyuridine) (Thermo Fisher Scientific, #A10044) at a dose of 200 mg/kg. Mice were sacrificed by a lethal dose of Ketamine/Xylazine 2 weeks post EdU injection, and transcardially perfused with PBS followed by 4% PFA. Brain coronal sections of 30 µm were cut using vibratome (Leica, VT1000S). Sections were washed twice in PBST with 3% BSA, permeabilized in PBS with 0.5% Triton X-100 for 20 min, and washed three times in PBST with 3% BSA. EdU staining was performed using Click-iT Edu Imaging Kit (Thermo Fisher Scientific, #C10086) according to the manufacturer's protocol. Briefly, Click-iT reaction mix was prepared as follows: 100 µl Click-iT reaction buffer, 800 µl CuSO4, 100 µl 1X Click-iT reaction buffer additive, and Alexa Fluor 488 azide. Sections were incubated with 0.5 ml reaction mix in 6 well plate for 30 min at room temperature covered in dark. Sections were washed twice in PBS 3% BSA post reaction, followed by mounting and imaging.

Div-Seq. Labeling proliferating cells in mice for Div-Seq was performed by intraperitoneal (i.p.) injection of EdU at a dose of 200 mg/kg. Mice were sacrificed 2 days and 2 weeks post EdU injection, fresh tissue was microdissected into RNA-later as described above. 24 hours after dissection nuclei were isolated as described above and resuspended in 100 µl resuspension buffer (with RNAse inhibitor), filtered and transferred to a 15 ml tube. EdU staining was performed immediately using Click-iT Edu Flow Cytometry assay Kit (Thermo Fisher Scientific, #C10086) according to the manufacturer's protocol with the following changes: 500 µl reaction buffer was added directly to the resuspention buffer (mix is made following the manufacturer's protocol), mixed well and left in RT for 30 min; 3 ml of 1% BSA PBS wash solution was added to the resuspended nuclei and mixed well, then nuclei were spun down for 10 min in 4° C., buffer was removed and nuclei were resuspended in 400 µl resuspension buffer with ruby-dye (1:800) and FACS sorted immediately.

Clustering of adult newborn cells and reconstructing pseudotime along the maturation trajectory. Applicants clustered EdU labeled nuclei together with non-EdU labeled nuclei. The PCA-tSNE followed by density clustering [54] assigned the majority of the EdU labeled nuclei together with a few non-EdU labeled nuclei to a distinct cluster. Then, Applicants performed second iteration of clustering using nuclei only from this cluster. The clustering positioned these nuclei on a trajectory. Applicants used biSNE to score and select genes differentially expressed along the trajectory (as described in Selection of significant genes) and filtered out lowly expressed genes. The intercellular Euclidean distance on the tSNE embedding reflects the intercellular transcriptional divergence. The embedding of EdU labeled cells forms a trajectory-like distribution. The Euclidean distances along the trajectory reflect transcriptional changes along the underlying biological process. Positions of each cell on that trajectory should indicate how far the cell has progressed along the process. Thus, the position of each cell along the trajectory is correlated with the pseudotime of a cell in the biological process. There is also a considerable cell distribution that makes up the width of the trajectory. The Euclidean distances orthogonal to the longitudinal axis of the trajectory reflect transcriptional divergence due to other cellular variabilities or noises. In order to find the position of each cell along the trajectory, Applicants need to distinguish the distances along the trajectory from the distances orthogonal to the trajectory. Previous methods find the cell positions using minimal spanning tree [78], or shortest possible route (travelling salesman problem) [79], neither of which take into account of the noise or other cellular variabilities. An improved method [80] uses randomization heuristics to mitigate the effect of noises. In contrast to these methods, Applicants model the noise explicitly and find a shortest spanning curve along the trajectory (Occam's razor). Applicants then project cells onto this spanning curve, and find their projected positions. Specifically, Applicants find a curve that minimizes the following objective function, $$f = \sum_i (x_i - SP(\hat{q}_i, cp))^2 + \lambda \int_0^1 \left\| \frac{\partial}{\partial t} SP(t, cp) \right\| dt,$$

where the first term reflects Gaussian noises that model the orthogonal distances, the second term is the total length of the spanning curve, and xi are the coordinates of the tSNE embedding of the cell i. The λ reflects the prior knowledge on the relative amount of noises and the transcriptional changes that align with the trajectory. The $SP(\hat{q}_i, cp)$ are the coordinates of the projected positions of cell i on the curve, and $\hat{q}_i$ is the pseudotime of the cell i along the trajectory. The $\hat{q}_i$ is given by $$\hat{q}_i = \underset{0 \leq t \leq 1}{\mathrm{argmax}}(x_i - SP(t, cp))^2.$$

The SP(x, cp) is the b-spline function [81] given by $$SP(x, cp) = \sum_i B_{i,n}(x) cp_i.$$

where cp are control points, and $B_{i,n}(x)$ is the b-spline basis function of degree n given by the following recursion formula $$B_{i,1}(x) := \begin{cases} 1 & \text{if } t_i \leq x < t_{i+1} \\ 0 & \text{otherwise} \end{cases},$$

$$B_{i,k}(x) := \frac{x - t_i}{t_{i+k-1} - t_i} B_{i,k-1}(x) + \frac{t_{i+k} - x}{t_{i+k} - t_{i+1}} B_{i+1,k-1}(x),$$

where t is a knot vector, and k is the degree of the b-spline. Applicants used a knot vector uniformly spaced between 0 and 1, and a third order b-spline. The spanning curve is found by searching for control points that minimize the objective function f, $$cp = \mathrm{argmax}\, f.$$

To initialize the curve, Applicants calculated a smoothed shortest path (using Dijkstra's algorithm) that follows the trajectory. The smoothed shortest path contains 16 points spanning from the progenitor cells to immature neurons. These points were used as the initial control points. Applicants then searched for the optimal control points using gradient descent, $$\frac{\partial f}{\partial cp_i} = 2 \sum_i (x_i - SP(\hat{q}_i, cp))(-SP(\hat{q}_i, e_i)) +$$

$$\lambda \int_0^1 \frac{1}{2} \left( \left\| \frac{\partial}{\partial t} SP(t, cp) \right\|^{-1} \left( 2 \frac{\partial}{\partial t} SP(t, cp) \frac{\partial}{\partial t} SP(t, e_i) \right) \right) dt,$$

where ei is a matrix that has the same size as cp, and entries of ei are equal to 1 at column i corresponding to the control point i and zero elsewhere. To quantify the expression of genes along the trajectory, Applicants calculated running averages of gene expressions along the smoothed shortest path that follows the trajectory. Applicants then subtracted the expression along the trajectory by the averaged expression of the first two points to obtain normalized expression pattern. Applicants clustered genes by their normalized expression pattern and chose the top consensus clusters after 5000 iterations of Kmeans clustering. The consensus clusters were found by hierarchically clustering the frequency of pairwise coassignment of genes within the same cluster across all Kmeans iterations (Hamming distance of the cluster assignments matrix).

Pathway and regulator analysis of adult newborn cells. Differentially expressed genes between immature neurons and adult neurons were found using the adjusted t-test. Enriched pathways in dynamic gene clusters and differentially expressed signatures were found (Hypergeometric p-value<0.01) using the MsigDB/GSEA resource (combining Hallmark pathways, REACTOME, KEGG, GO and BIOCARTA) [82]. Dynamically regulated TFs were defined as genes within the genes clusters that are annotated by GO category [83] to be involved in transcription regulation, DNA binding or chromatin remodeling and modification. The gene list for the semaphoring signaling pathway was taken from KEGG mouse axon guidance pathway (mmu04360) and the IPA Semaphoring signaling pathway. Applicants defined a maturation signature as the linear combination of expression levels of the set of up-regulated and down-regulated genes in mature granule cells compared to the immature granule cells in adult mice. The average relative expression of the up-regulated genes minus the average relative expression of the down-regulated genes was used to define a maturation score for each granule DG nuclei, in adult (3 months), adolescent (1 month) and old (2 year) mice.

Comparison of Div-Seq data in the DG to other datasets. Applicants compared dynamically expressed genes along the neurogenesis trajectory to other datasets, including: (1) single cells RNA-Seq of mouse adult neuronal stem cells and progenitors in the DG [79]; (2) RNASeq time course of in vitro derived neurons from hES cells [84]; (3) single cell RNA-Seq of fetal human neuronal precursor cells, hNPCs (Tirosh et al. unpublished); (4) additional Div-Seq data collected at 7 day post EdU injection; (5) Allen brain atlas ISH data. For each of the published RNA-Seq datasets Applicants log transformed the expression matrix. For the single hNPCs RNA-Seq, paired-end 75 bp reads were mapped to the UCSC human transcriptome (hgl9) by Bowtie (version 1.4.1,with parameters -n 0-e 99999999-1 25-I1-X 2000-a -m 15 iCS), and expression levels of all genes were estimated by RSEM (version 1.2.3, using the option estimate-rspd and default parameters). To compare gene expression levels between Div-Seq and these datasets Applicants used the relative intensity values per dataset across all genes and samples. For the comparison to the Allen ISH data, Applicants selected genes that have known restricted expression in the early stages of the trajectory, which is spatially restricted to the SGZ and the hillus regions of the DG. Relative expression levels across the DG subregions were manually evaluated.

Differential isoforms. Gene isoform expression levels (TPM) and percent of mapped reads (compared to other all other isoforms of the same gene) were quantified using RSEM (as described in "Sequencing reads initial processing"). Applicants restricted the analysis to highly expressed isoforms only, e.g. genes that have at least two isoforms with expression level of log(TPM)>4 in at least 10% of the analyzed nuclei. Analysis of differentially expressed isoforms between immature and mature granule neurons was done using t-test on the isoform percentage. A pair of isoforms are considered differentially expressed if both are significant in the t-test (FDR<0.01, log-ratio>1) and one is upregulated in immature neuron and the other is down regulated in the immature neuron.

Spinal cord analysis. All the 7 day EdU labeled and unlabeled cells from the spinal cord and DG were clustered by PCA tSNE and density clustering as described in "Analysis of nuclei clusters". The identities of each clusters were determined based on differentially expressed genes and known marker genes. Immature and mature neurons were clustered by biSNE (top 2 PCs, 2,522 high scoring genes with p<5.4e-5). Differentially expressed genes between immature neurons in the DG and spinal cord were calculated using student's t-test, with FDR<0.05, log(ratio)>1, and the average expression across samples in one region to be log(TPM)>2 and in the other region log(TPM)<3.

REFERENCES

1. A. Zeisel et al., Brain structure. Cell types in the mouse cortex and hippocampus revealed by single-cell RNA-seq. *Science* 347, 1138–1142 (2015).
2. S. Darmanis et al., A survey of human brain transcriptome diversity at the single cell level. *Proc Natl Acad Sci USA* 112, 7285–7290 (2015).
3. J. Shin et al., Single-Cell RNA-Seq with Waterfall Reveals Molecular Cascades underlying Adult Neurogenesis. *Cell Stem Cell* 17, 360–372 (2015).
4. B. Tasic et al., Adult mouse cortical cell taxonomy revealed by single cell transcriptomics. *Nat Neurosci* 19, 335–346 (2016).
5. D. Usoskin et al., Unbiased classification of sensory neuron types by large-scale single-cell RNA sequencing. *Nat Neurosci* 18, 145–153 (2015).
6. E. R. Thomsen et al., Fixed single-cell transcriptomic characterization of human radial glial diversity. *Nat Methods* 13, 87–93 (2016).
7. G. L. Ming, H. Song, Adult neurogenesis in the mammalian brain: significant answers and significant questions. *Neuron* 70, 687–702 (2011).
8. D. L. Moore, G. A. Pilz, M. J. Arauzo-Bravo, Y. Barral, S. Jessberger, A mechanism for the segregation of age in mammalian neural stem cells. *Science* 349, 1334–1338 (2015).
9. R. V. Grindberg et al., RNA-sequencing from single nuclei. *Proc Natl Acad Sci USA* 110, 19802–19807 (2013).
10. S. R. Krishnaswami et al., Using single nuclei for RNA-seq to capture the transcriptome of postmortem neurons. *Nat Protoc* 11, 499–524 (2016).
11. L. Swiech et al., In vivo interrogation of gene function in the mammalian brain using CRISPR-Cas9. *Nat Biotechnol* 33, 102–106 (2015).
12. H. Hu, J. Gan, P. Jonas, Interneurons. Fast-spiking, parvalbumin(+) GABAergic interneurons: from cellular design to microcircuit function. *Science* 345, 1255263 (2014).
13. E. S. Lein et al., Genome-wide atlas of gene expression in the adult mouse brain. *Nature* 445, 168–176 (2007).
14. Y. Zhang et al., An RNA-sequencing transcriptome and splicing database of glia, neurons, and vascular cells of the cerebral cortex. *J Neurosci* 34, 11929–11947 (2014).
15. S. Anders, W. Huber, Differential expression analysis for sequence count data. *Genome Biol* 11, R106 (2010).
16. M. S. Cembrowski et al., Spatial Gene-Expression Gradients Underlie Prominent Heterogeneity of CA1 Pyramidal Neurons. *Neuron*, (2016).
17. B. A. Strange, M. P. Witter, E. S. Lein, E. I. Moser, Functional organization of the hippocampal longitudinal axis. *Nat Rev Neurosci* 15, 655–669 (2014).
18. B. P. Roques, M. C. Fournie-Zaluski, M. Wurm, Inhibiting the breakdown of endogenous opioids and cannabinoids to alleviate pain. *Nat Rev Drug Discov* 11, 292–310 (2012).
19. S. Zhao et al., Fluorescent labeling of newborn dentate granule cells in GAD67-GFP transgenic mice: a genetic tool for the study of adult neurogenesis. *PLoS One* 5, (2010).
20. E. Llorens-Bobadilla et al., Single-Cell Transcriptomics Reveals a Population of Dormant Neural Stem Cells that Become Activated upon Brain Injury. *Cell Stem Cell* 17, 329–340 (2015).
21. M. Schouten, M. R. Buijink, P. J. Lucassen, C. P. Fitzsimons, New Neurons in Aging Brains: Molecular Control by Small Non-Coding RNAs. *Front Neurosci* 6, 25 (2012).
22. J. Zhang et al., Ezh2 regulates adult hippocampal neurogenesis and memory. *J Neurosci* 34, 5184–5199 (2014).
23. J. I. Wu et al., Regulation of dendritic development by neuron-specific chromatin remodeling complexes. *Neuron* 56, 94–108 (2007).
24. I. T. Andrew Venteicher, Mario Suva, Michelle Monje-Diesseroth, Aviv Regev.
25. J. A. Miller et al., Conserved molecular signatures of neurogenesis in the hippocampal subgranular zone of rodents and primates. *Development* 140, 4633–4644 (2013).
26. M. Knobloch et al., Metabolic control of adult neural stem cell activity by Fasn-dependent lipogenesis. *Nature* 493, 226–230 (2013).
27. S. Ge et al., GABA regulates synaptic integration of newly generated neurons in the adult brain. *Nature* 439, 589–593 (2006).
28. D. M. Feliciano, A. Bordey, L. Bonfanti, Noncanonical Sites of Adult Neurogenesis in the Mammalian Brain. *Cold Spring Harb Perspect Biol* 7, a018846 (2015).
29. P. J. Horner et al., Proliferation and differentiation of progenitor cells throughout the intact adult rat spinal cord. *J Neurosci* 20, 2218–2228 (2000).
30. R. Shechter, Y. Ziv, M. Schwartz, New GABAergic interneurons supported by myelin-specific T cells are formed in intact adult spinal cord. *Stem Cells* 25, 2277–2282 (2007).
31. C. A. Rottkamp, K. J. Lobur, C. L. Wladyka, A. K. Lucky, S. O'Gorman, Pbx3 is required for normal locomotion and dorsal horn development. *Dev Biol* 314, 23–39 (2008).
32. M. A. Petryniak, G. B. Potter, D. H. Rowitch, J. L. Rubenstein, Dlx1 and Dlx2 control neuronal versus oligodendroglial cell fate acquisition in the developing forebrain. *Neuron* 55, 417–433 (2007).
33. S. G. Ludovic Telley, Julien Prados, Isabelle Stevant, Serge Nef, Emmanouil Dermitzakis, Alexandre Dayer, Denis Jabaudon, Sequential transcriptional waves direct the differentiation of newborn neurons in the mouse neocortex. *Science* Online.
34. S. Picelli et al., Smart-seq2 for sensitive full-length transcriptome profiling in single cells. *Nat Methods* 10, 1096-1098 (2013).

SUPPLEMENTARY REFERENCES

37. W. Lason, B. Przewlocka, R. Przewlocki, Molecular brain research 12, 243 (1992).
38. L. Swiech, et al., Nature biotechnology 33, 102 (2015).
39. C. A. Paul, B. Beltz, J. Berger-Sweeney, Cold Spring Harbor Protocols 2008, pdb (2008).
40. H. Hideo, T. Keiko, Y. Nobuyuki, M. Tsuyoshi, Journal of Visualized Experiments (2009).
41. S. Picelli, et al., Nature methods 10, 1096 (2013).
42. R. Satija, J. A. Farrell, D. Gennert, A. F. Schier, A. Regev, Nature biotechnology 33, 495 (2015).
43. C. M. Hempel, K. Sugino, S. B. Nelson, Nature protocols 2, 2924 (2007).
44. C. Trapnell, L. Pachter, S. L. Salzberg, Bioinformatics 25, 1105 (2009).
45. C. Trapnell, et al., Nature biotechnology 28, 511 (2010).
46. J. T. Robinson, et al., Nature biotechnology 29, 24 (2011).
47. B. Li, V. Ruotti, R. M. Stewart, J. A. Thomson, C. N. Dewey, Bioinformatics 26, 493 (2010).
48. B. Langmead, S. L. Salzberg, Nature methods 9, 357 (2012).
49. D. S. DeLuca, et al., Bioinformatics 28, 1530 (2012).
50. A. Zeisel, et al., Science 347, 1138 (2015).
51. J. C. Dunn, Journal of cybernetics 4, 95 (1974).
52. S. T. Roweis, L. K. Saul, Science 290, 2323 (2000).
53. L. Van der Maaten, G. Hinton, Journal of Machine Learning Research 9, 85 (2008).
54. A. Rodriguez, A. Laio, Science 344, 1492 (2014).
55. A. K. Shalek, et al., Nature (2014).
56. A. K. Shalek, et al., Nature 498, 236 (2013).
57. M. D. Robinson, D. J. McCarthy, G. K. Smyth, Bioinformatics 26, 139 (2010).
58. M. I. Love, W. Huber, S. Anders, Genome Biol 15, 550 (2014).
59. Z. I. Botev, J. F. Grotowski, D. P. Kroese, et al., The Annals of Statistics 38, 2916 (2010).
60. P. V. Kharchenko, L. Silberstein, D. T. Scadden, Nature methods 11, 740 (2014).
61. E.-a. D. Amir, et al., Nature biotechnology 31, 545 (2013).
62. E. Z. Macosko, et al., Cell 161, 1202 (2015).
63. Y. Benjamini, Y. Hochberg, Journal of the Royal Statistical Society. Series B (Methodological) pp. 289-300 (1995).
64. E. S. Lein, et al., Nature 445, 168 (2007).
65. P. A. Moran, Biometrika pp. 17-23 (1950).
66. P. J. Rousseeuw, C. Croux, Journal of the American Statistical association 88, 1273 (1993).
67. A. Edelman, N. R. Rao, Acta Numerica 14, 233 (2005).
68. E. Eden, D. Lipson, S. Yogev, Z. Yakhini, PLoS Comput Biol 3, e39 (2007).
69. Y. Maruyama, arXiv preprint arXiv:1501.06260 (2015).
70. L. Van Der Maaten, The Journal of Machine Learning Research 15, 3221 (2014).
71. P. N. Yianilos, SODA (1993), vol. 93, pp. 311-321.
72. S. Anders, W. Huber, Genome Biology 11, R106 (2010).
73. P. Brennecke, et al., Nature methods 10, 1093 (2013).
74. Y. Zhang, et al., The Journal of Neuroscience 34, 11929 (2014).
75. R.-E. Fan, K.-W. Chang, C.-J. Hsieh, X.-R. Wang, C.-J. Lin, The Journal of Machine Learning Research 9, 1871 (2008).
76. K. Helsgaun, European Journal of Operational Research 126, 106 (2000).
77. K. Helsgaun, Mathematical Programming Computation 1, 119 (2009).
78. C. Trapnell, et al., Nature biotechnology 32, 381 (2014).
79. J. Shin, et al., Cell stem cell 17, 360 (2015).
80. S. C. Bendall, et al., Cell 157, 714 (2014).
81. C. De Boor, Mathematics of Computation (1978).
82. A. Subramanian, et al., Proceedings of the National Academy of Sciences of the United States of America 102, 15545 (2005).
83. M. Ashburner, et al., Nature genetics 25, 25 (2000).
84. V. Busskamp, et al., Molecular systems biology 10, 760 (2014).
85. J. J. Trombetta, et al., Current Protocols in Molecular Biology pp. 4-22.
86. B. Tasic, et al., Nature neuroscience (2016).
87. E. R. Thomsen, et al., Nature methods 13, 87 (2016).
88. R. V. Grindberg, et al., Proceedings of the National Academy of Sciences 110, 19802 (2013).

Example 6

Nuclei Purification Protocols
Nuclei purification protocol: method A
This method may be used for Nuc-Seq or Div-Seq.
Reference: In vivo interrogation of gene function in the mammalian brain using CRISPR-Cas9.
Swiech L, Heidenreich M, Banerjee A, Habib N, Li Y, Trombetta J, Sur M, Zhang F.
Nat Biotechnol. 2015 January;33(1):102-6. doi: 10.1038/nbt.3055. Epub 2014 Oct 19.

TABLE 8

Buffer 1:

| | Stocks | 25 ml For 2 samples (+spare) | 50 ml For 4 samples (+spare) | 75 ml For 6 samples (+spare) |
|---|---|---|---|---|
| 320 mM Sucrose | 1M | 8 ml | 16 ml | 24 ml |
| 5 mM CaCl | 1M | 125 ul | 250 ul | 375 ul |
| 3 mM Mg(Ac)2 | 1M | 75 ul | 150 ul | 225 ul |
| 10 mM Tris pH 7.8 | 1M | 250 ul | 500 ul | 750 ul |
| 0.1 mM EDTA | 0.5M | 5 ul | 10 ul | 15 ul |
| 0.1 mM PMSF | 100 mM | 25 ul | 50 ul | 75 ul |
| 0.1% NP40 | 10% | 250 ul | 500 ul | 750 ul |
| 1 mM b-mercapto | 500 mM | 50 ul | 100 ul | 150 ul |
| H20 | | 16.2 ml | 32.4 ml | 48.6 ml |

TABLE 9

Working solution (x6):

| | Stocks | 5 ml For 2 samples (+spare) | 10 ml For 4 samples (+spare) |
|---|---|---|---|
| 30 mM CaCl | 1M | 150 ul | 300 ul |
| 18 mM Mg(Ac)2 | 1M | 90 ul | 180 ul |
| 60 mM Tris | 1M | 300 ul | 600 ul |
| 0.6 mM PMSF | 100 mM | 30 ul | 60 ul |
| 6 mM b-mercapto | 500 mM | 60 ul | 120 ul |

TABLE 9-continued

Working solution (x6):

| Stocks | 5 ml For 2 samples (+spare) | 10 ml For 4 samples (+spare) |
|---|---|---|
| H2O | 4.370 ml | 8.740 ml |

TABLE 10

50% Optiprep solution:

| 1:6 | 1 sample | 2 samples - 25 ml | 4 samples - 50 ml |
|---|---|---|---|
| Working solution | 2 ml | 5 ml | 8.35 ml |
| Optiprep | 8 ml | 25 ml | 41.68 ml |

TABLE 11

29% Optiprep solution:

|  | 1 sample | 4 samples - 50 ml |
|---|---|---|
| 50% Optiprep | 5.8 ml | 29 |
| Buffer 1 | 4.2 ml | 21 |

TABLE 12

Resuspension buffer RB:

|  | Stocks | 10 ml For 4 samples |
|---|---|---|
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

Before Starting:
1. Make fresh buffers
2. All: buffers, tubes, homogenizer should be on ice at all times Protocol:
1. Dounce homogenize tissue in 2 ml Buffer 1+0.1% NP40 (25 times with a, 25 times with b), transfer to a 15 ml tube
2. Rinse homogenizer with 3 ml Buffer 1 to get final 5 ml, and collect in the same tube
3. Keep on ice 5 min
4. Add 5 ml 50% Optiprep, invert 10× (final volume 10 ml)
5. Keep on ice 5 min
6. While waiting, prepare an ultracentrifuge tube with 10 ml of 29% Optiprep.
7. Transfer the lysate to the ultracentrifuge tube carefully on top of the 10 ml 29% Optiprep solution, to form a gradient
8. Centrifuge at 7500 rpm 4c for 30 min
9. Carefully remove supernatant
10. Add ~300 µl/hp buffer RB, keep on ice 5-15 min
11. Resuspend carefully by slow vortex & pipette 10× with a 1 ml tip, then transfer to tubes (for FACS, filter through a membrane to get better purity)
12. Counterstain nuclei with Ruby Dye 1:500-1:1000 (check for clumps in the microscope before sorting)

Nuclei purification protocol: method B
This method is particularly suitable for Dronc-Seq.
EZ NUCLEI ISOLATION PROTOCOL FROM TISSUE (using EZ PREP NUC-101, Sigma)
Procedure for frozen/fixed tissue
13. Dounce homogenize tissue in 2 ml of ice-cold Nuclei EZ lysis buffer (25 times with a, 25 times with b), transfer to a 15 ml tube.
9. Rinse homogenizer with 2 ml of ice-cold Nuclei EZ lysis buffer to get final 4 ml, and collect in the same tube.
10. Mix well and set on ice for 5 minutes.
11. Collect the nuclei by centrifugation at 500×g for 5 minutes at 4° C. Carefully aspirate the clear supernatant from each tube and set the nuclei pellet on ice. Note: The supernatant contains cytoplasmic components and can be saved for later analysis or use.
12. Resuspend. Add 1 ml cold Nuclei EZ lysis buffer and mix by pipetting gently with a 1ml tip to completely suspend nuclei pellet. Add the remaining 3 ml of Nuclei EZ lysis buffer, mix well and set on ice for 5 minutes.
13. Collect washed nuclei by centrifugation as in step 3. Carefully aspirate the clear supernatant and set the nuclei pellet on ice.
14. Optional: Wash. Resuspend in 4 ml 0.01% PBS BSA or Resuspension buffer (RB*). Collect washed nuclei by centrifugation as in step 3.
15. Resuspend with ~500 µl Resuspension buffer (RB*) or 0.01% PBS BSA+RNAse inhibitor carefully by slow vortex & pipette 10× with a 1 ml tip, then transfer to tubes (for FACS, filter through a membrane to get better purity.
16. Counterstain nuclei with Ruby Dye 1:500-1:1000 (check for clumps in the microscope before sorting).

Resuspension Buffer
based on the original nuclei resuspention buffer from Swiech et al. 2015:

TABLE 13

|  | Stocks | For 10 ml |
|---|---|---|
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

Example 7

Div-Seq labelling protocol

This protocol is derived from the Click-IT EdU labeling protocol (ThermoFischer, Kit #C10424): https://www.thermofisher.com/us/en/home/references/protocols/cell-and-tissue-analysis/flow-cytometry-protocol/cell-proliferation/standard-click-it-edu-flow-cytometry-cell-proliferation-assay.html Before starting the nuclei isolation thaw reagents for Click-IT EdU labeling (in the dark, at room-temperature). Follow nuclei isolation protocol (as in Habib et al. Science. 2016), at the last elution step elute in 100 µl of resuspension buffer or PBS with 1% BSA. Follow steps for nuclei resuspension from protocol.

For each sample prepare a reaction mix (as in the Click-IT EdU labeling protocol):

TABLE 14

| Reaction mix: | Stocks |
|---|---|
| PBS, D-PBS, or TBS | 438 μL |
| CuSO4 | 10 μL |
| Fluorescent dye azide | 2.5 μL |
| Reaction Buffer Additive (10x buffer diluted to 1x with PBS) | 50 μL |
| Total reaction volume | 500 μL |

Transfer 500 μl reaction mix to a 15 ml canonical tube. Add 100 μl of the nuclei resuspension.
  Mix by inverting 10 times.
  Incubate in the dark for 20–30 minutes.
Add 3–5 ml of PBS with 1% BSA.
Spin at 500 g for 5 minutes, and carefully remove supernatant.
Resuspend with appropriate amount of Resuspension buffer (as in original nuclei isolation protocl) or 0.01% PBS BSA, add RNAse inhibitor. Resuspend carefully by slow vortex & pipette 10× with a 1ml tip, then transfer to tubes (for FACS, filter through a membrane to get better purity.
Elute in the appropriate amouse of resuspention buffer (as in the nuclei isolation protocol) orPBS+0.01% BSA.
Counterstain nuclei with Ruby Dye 1:500-1:1000 (check for clumps in the microscope before sorting).
FACS sort nuclei into 96 well plates for RNA-seq (following the sNuc-Seq SMART-Seq2 protocol).

Example 8

SMART-seq2 protocol Full-length mRNA-seq for single nuclei or small amounts of RNA samples
Tissue, Cells & Nuclei prep
  Tissue should be stored in RNA-later in 4c for 24 hours and then moved to the −80 (removing the RNA-later), or immediately frozen and stored at −80c.
  Prep cells/nuclei short time before sorting. Use RNAse free reagents.
Sorting
  Sort single cells/nuclei into 96-well plate, 5 μL TCL in each well (with bME, and optional RNAse inhibitor)
  Immediately spin for 1–2 min, 2500 RPM
  Snap freeze on dry ice, store at −80°
Prep work
  RNase-ZAP work surfaces and equipment
  30 minutes prior to purification, let RNA-SPRI beads equilibrate to room temperature
  Thaw cell plates on ice and spin down for 1 min, 2500 RPM
RNA Purification
  Add 11 μL (2.2×) RNA-SPRI beads to each well, mix
  Let at room temp for 10 minutes, place plate on magnet for 5 minutes
  Remove supernatant
  Wash in 100 μL 80% EtOH three times
  Completely remove supernatant, let dry for 8–10 minutes on magnet
  Elute in 4 μL Mix #1
  Continue immediately

TABLE 15

| | Mix #1 | | |
|---|---|---|---|
| Reagent | 1 sample (μL) | 96 samples (μL) | 96 for Bravo (μL) |
| RT primer (10 μM) | 1.0 | 115.2 | 120 |
| dNTP mix (10 mM each) | 1.0 | 115.2 | 120 |
| RDil (10% RNase-Inhib, final of 4 U/μL) | 1.0 | 115.2 | 120 |
| H₂O | 1.0 | 115.2 | 120 |
| Total | 4.0 | 460.8 | 480 |

Incubate eluted plate at 72° for 3 min, immediately place on ice

TABLE 16

| | Mix #2 | |
|---|---|---|
| Reagent | 1 sample (μL) | 96 samples (μL) |
| H₂O | 0.75 | 86.4 |
| 5x Maxima RT buffer | 2.0 | 230.4 |
| Betaine (5 M) | 2.0 | 230.4 |
| MgCl₂ (100 mM) | 0.9 | 103.68 |
| TSO (10 μM) | 1.0 | 115.2 |
| RNase Inhibitor (40 U/μL) | 0.25 | 28.8 |
| Maxima RNaseH-minus RT (200 U/μL) | 0.10 | 11.52 |
| Total | 7.0 | 806.4 |

Add 7 μl of Mix #2 (mix well & spin down)
RT PROGRAM: Incubate at 42° for 90 minutes, followed by 10 cycles of (50° for 2 min, 420 for 2 min), then heat inactivation at 70° for 15 min.

TABLE 17

| | PCR Preamplification Mix #3 | | |
|---|---|---|---|
| Reagent | 1 sample (μL) | 96 samples (μL) - x1.2 | x1.1 |
| H₂O | 1.0 | 115.2 | 105.6 |
| ISPCR Primer (10 μM) | 0.5 | 57.6 | 52.8 |
| KAPA HiFi HotStart ReadyMix | 12.5 | 1440 | 1320 |
| Total | 14 | 1612.8 | 1478.4 |

Add 14 μL of Mix #3 to each well
Cycle the PCR as follows: 98° for 3 min, 21 cycles of (98° for 15 sec, 67° for 20 sec, 72° for 6 min), final extension at 72° for 5 min.
PCR Pre-amplification Clean up
  Purify the PCR products with a 0.8×AMPure XP SPRI cleanup
    Add 20 μL AMPure XP SPRI beads, let sit for 5 min
    place plate on magnet for 6 min
    pipette off supernatant
    Wash beads by adding 100 μL fresh 70% EtOH and magnet switching
    Pipette off supernatant and repeat wash
    remove all EtOH and let dry on magnet for 10 min
  Elute material in 20 μL TE Post—PCR Pre-amplification QC
1. BioAnalze test quality
2. PICO-green in the plate reader —QC & quant Nextera-XT (modified protocol)
Make NTA:
  2.5 µl TD buffer per well
  1.25 µl sample (diluted to 0.15–0.2 ng/µl per well)
  1.25 µl ATM
Put cover, bang to mix & spin down briefly
Incubate 10 min at 55c (make NTA" program, hold at 10° C.)
Spin down
Neutralize:
  Add 1.25 NT buffer to neutralize
Spin down
Incubate on bench for 5 min
PCR:
  3.75 ul NPM
  2.5 ul of index array primers (1.25 ul of each primer)
Cover & bang to mix & spin down
PCR (NTA PCR program, following the Nextera XT protocol)
1. Perform PCR using the following program on a thermal cycler (with heated lid, program "Nextera PCR" on machine D):
  a. 72° C. for 3 minutes
  b. 95° C. for 30 seconds
  c. 12 cycles of:
    i. 95° C. for 10 seconds
    ii. 55° C. for 30 seconds
    iii. 72° C. for 30 seconds
    iv. 72° C. for 5 minutes
  d. Hold at 4° C.
Pull & cleanup:
  Pull together 2.5 ul from each well and SPRI clean twice (in each SPRI wash twice with ETOH 70%):
    1st cleanup: Add 0.9× beads (240 ul samples, 216 µl beads), elute in 50 ul TE
    2nd cleanup: Add 0.9× beads, elute in 20-25 ul
Post Nextera QC:
BioA/Tape-station and quant pool with qubit
Store at −20
Primers and oligos:
RT primer:

(SEQ ID NO: 7)
5'-bio-AAGCAGTGGTATCAACGCAGAGTACT30VN-3' where "N" is any base and "V" is either "A", "C" or "G"
Template switching oligo (TSO).

(SEQ ID NO: 10)
5' AAGCAGTGGTATCAACGCAGAGTAGATrGrG+G

IS PCR primer:

(SEQ ID NO: 9)
5'-AAGCAGTGGTATCAACGCAG*A*G*T-3'
*:phosphorothioate bond

Example 9. Transcriptional Dynamics During Adult Neurogenesis in the DG

Figures 41A, 41B, 41C, 41D:
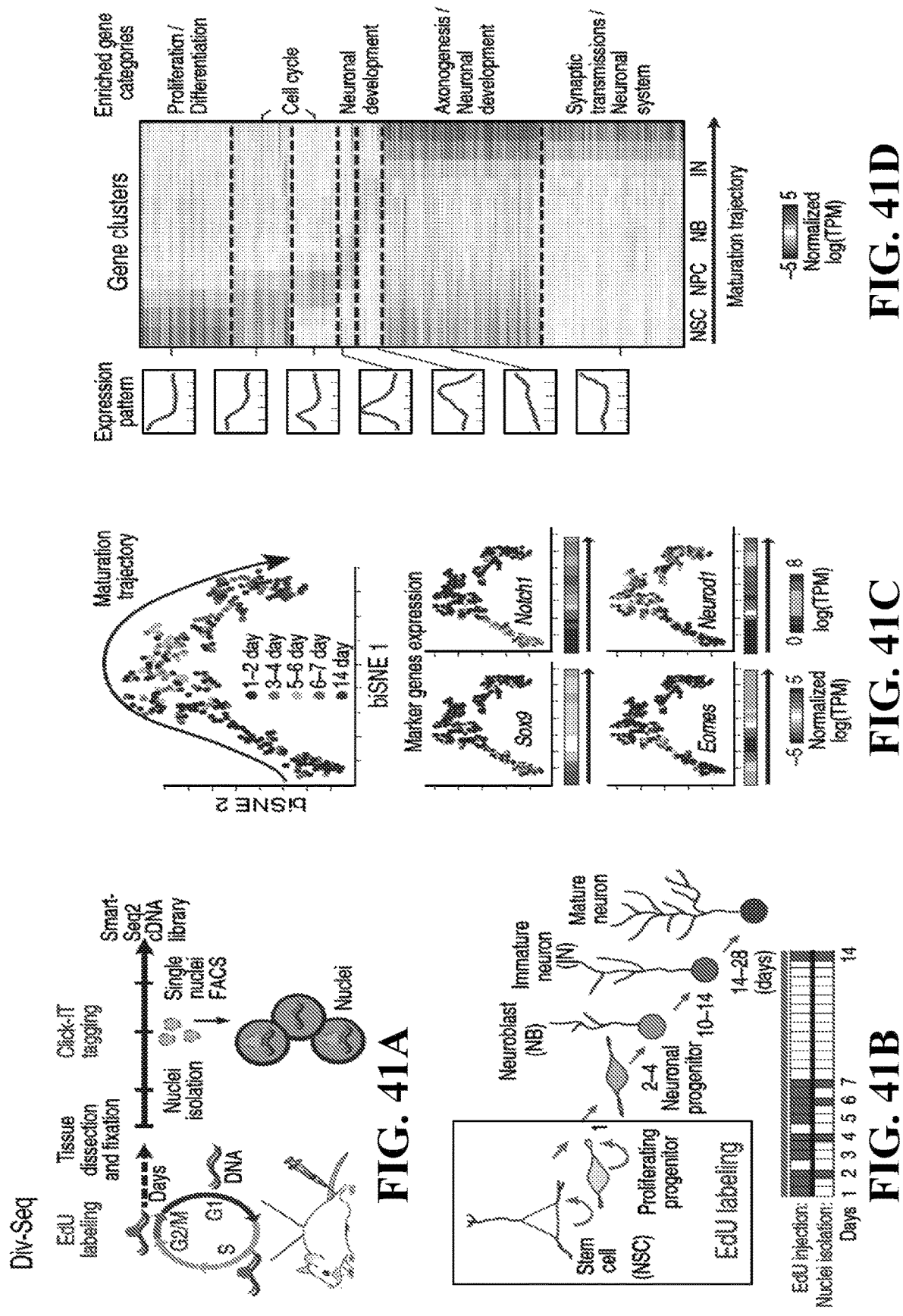
Figure 45A:
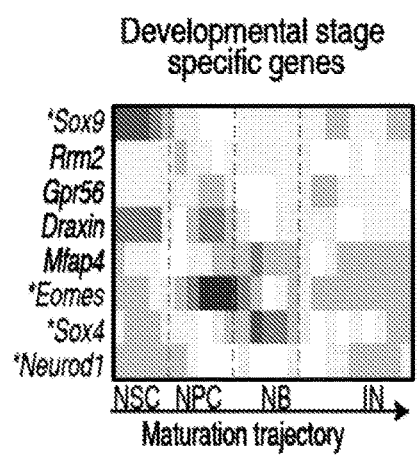
Figure 45B:
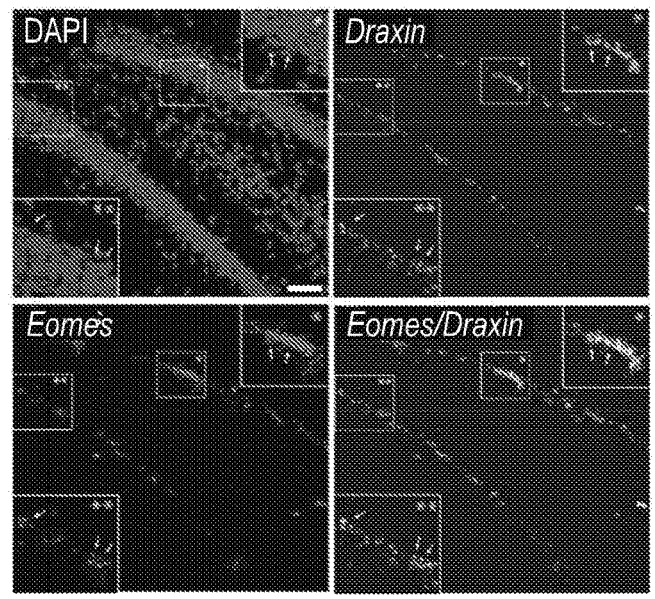
Figure 45C:
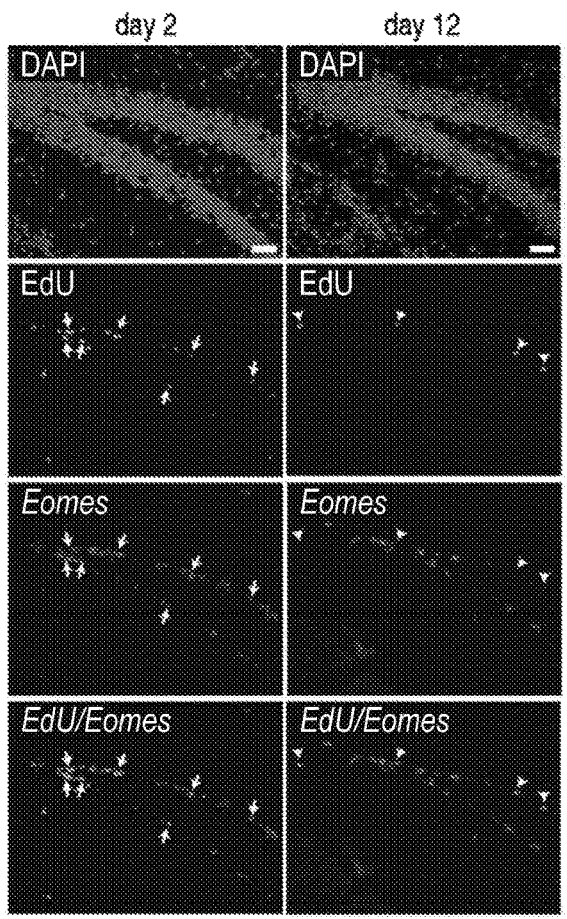
Figure 45D:
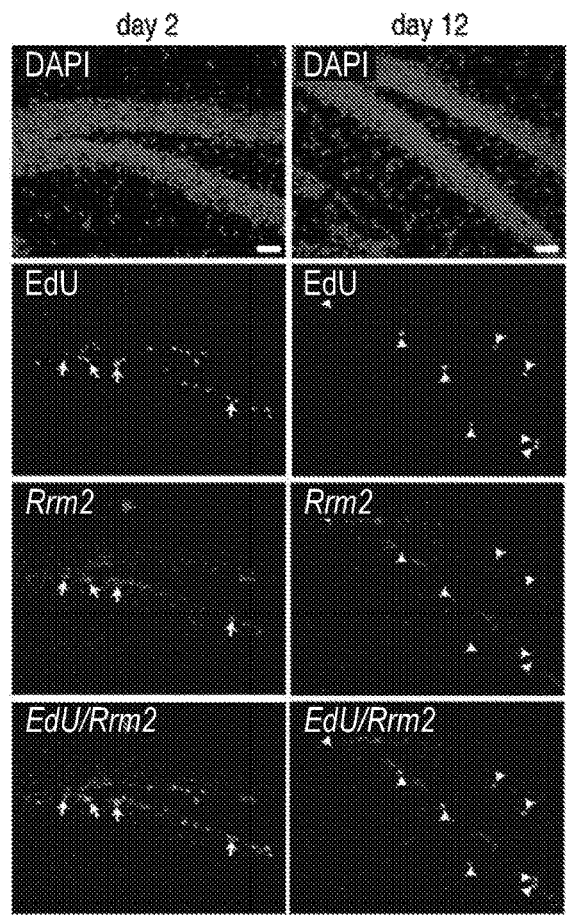

To study transcriptional dynamics during adult neurogenesis Div-Seq was used. Div-Seq combines sNuc-Seq with EdU labeleing of dividing cells (FIG. 41A). Unlike genetic labeling (2, 14), EdU tags proliferating cells at any time window, marking stem cells and their progeny with high temporal resolution. Div-Seq was applied in the DG, a canonical neurogenic niche (4), over multiple time points (1–14 days after cell division, FIG. 41B, FIG. 43, Table 20). Div-Seq enriched for diverse newborn cell types and neurogenic stages (FIG. 43F-G) from proliferating stem cells to immature neurons (4).

BiSNE analysis of neuronal lineage nuclei placed the DG newborn neurons on a continuous trajectory. The order of nuclei along the trajectory matched the EdU labeling time (FIG. 41C), was independent of animal age (FIG. 43H) and recapitulated known dynamics of neurogenesis markers (2, 3, 15) (FIG. 44A), indicating that the trajectory indeed captured the neuronal maturation process.

To characterize the transcriptional program of adult neurogenesis, genes with dynamic expression patterns along the trajectory were identified and clustered (FIG. 41D). Major coordinated transcriptional waves, involving hundreds of genes, and aligned with known transitions between neurogenic stages, with expression shifts from proliferation to neuronal differentiation (consistent with (2)), and then to neuronal integration and maturation (FIG. 41D). Genes with restricted expression in specific stages of neurogenesis (FIG. 44-45), including transcription factors and chromatin regulators were identified (FIG. 44). The early neurogenic stage-specific expression of the axon guidance molecule Draxin and the ribonucleotide reductase Rrm2 was confirmed by FISH (FIG. 45).

Example 10. Dynamics of Adult GABAaergic Neurons in Spinal Cord

Accumulating evidence suggests that adult neurogliogenesis occurs in multiple non-canonical regions (16), but traditional methods are limited for the characterization of rare newborn cells, and can lead to less definitive findings, as in the spinal cord (SC) (17)(18). Div-Seq was applied over multiple timepoints (1–7 days) in the SC (FIG. 46). SC nuclei 6–7 days post labeling (FIG. 42A-B) comprised a diverse population of newborn cells including oligodendrocyte precursor cells (OPCs, 44%) and immature neurons (19%), in contrast to 4% OPCs and no immature neurons in the non-EdU labeled population. The SC newborn neurons expressed the GABAergic markers Gad1 and Gad2, suggesting GABAergic neurogenesis (consistent with 18) (FIG. 42B). A set of immature neuronal nuclei (10%) at 23–24 days post EdU labeling was identified (FIG. 47), suggesting survival of newborn neurons in the SC.

The full set of neuronal lineage nuclei (FIG. 46A) map to a continuous trajectory (FIG. 42C), that matched labeling time and expression dynamics of known markers (FIG. 46C). Comparison of dynamically expressed genes along the SC and DG trajectories (FIG. 46B) identified 347 (28%) common neurogenesis genes (FIG. 42D, FIG. 46C), but also revealed notable distinctions in the expression dynamics and branching along the DG and SC (FIG. 42D-E (6)), which can result from differences in time scales, cell populations, or parallel gliogenesis and neurogenesis processes.

The immature neurons from SC and DG are composed of different neuronal types (GABAergic in SC, granule cells in DG). To identify candidate genes driving neuronal lineage specification, differentially expressed genes between SC and DG (t-test) were first identified, and then their expression patterns were compared to those of newborn neurons in the olfactory bulb (OB), where GABAergic neurons are born (FIG. 42F). A set of SC-specific genes was also up-regulated in the OB relative to the DG, including the transcription factors Pbx3 and Meis2. This is consistent with previous reports (19, 20), and with immunohistochemistry of Pbx3 showing expression in newborn cells both in the OB and SC but not in the GD (FIG. 48-50).

Example 11. Comparison of Adult Neurogenesis Dynamics in the SC and DG

Neuronal lineage nuclei from the full Div-Seq time course, showed a continuous trajectory in both the DG (FIG. 42C), and the SC (FIG. 42C), and broadly comparable between the two regions (FIG. 41D-E and FIG. 46C). However, there were also key distinctions between the processes in the DG and SC. First while gene expression patterns are similar at early and later stages, expression levels along intermediate time points change more sharply in the SC compared to the DG (FIG. 41D, 42D and FIG. 46B). Second, in contrast to the mostly unbranched path we observed in DG neurogenesis, the SC trajectory has several branches (FIG. 42C). Interestingly, the gene expression profiles of nuclei at side branches resemble a glia expression pattern more than a neuronal pattern (FIG. 42E).

Materials and Methods

Single molecule in situ hybridization tissue assay and EdU co-staining. Labeling of proliferating cells for staining in mice was performed by intraperitoneal (i.p.) injection of EdU (5-ethynyl-2'-deoxyuridine) (Thermo Fisher Scientific, #A10044) every 12 hr for 3 injections at a dose of 100 mg/kg. Mice were sacrificed by a lethal dose of Ketamine/ Xylazine 2-weeks post EdU injection, and transcardially perfused with PBS. Brain samples were immediately frozen in tissue freezing medium (O.C.T.) and kept at −80° C. overnight. Coronal sections were cut at 15 mm at −15° C. dFISH assay on O.C.T. embedded sections was performed according to Affymetrix provided protocol for O.C.T. samples, which combines QuantiGene ViewRNA ISH Tissue 2-plex Assay Kit (Affymetrix, #QVT0012) and ViewRNA ISH Cell Assay Kit (Affymetrix, #QVCM0001). Proprietary probes designed for Eomes, Draxin, and Rrm2 were purchased from the vendor (Affymetrix) and used. Immediately following FISH protocol, while sections were still hydrated, EdU staining was performed using Click-iT Edu Imaging Kit (Thermo Fisher Scientific, #C10340) according to the manufacturer's protocol. After the protocol was completed, sections were washed twice in 1× wash buffer from the ViewRNA ISH Cell Assay kit, followed by mounting and imaging.

Div-Seq applied to the spinal cord and olfactory bulb. The 1–7 day EdU labeled and unlabeled cells from the spinal cord and DG were clustered by PCA-tSNE and density clustering as described in "Analysis of nuclei clusters". The identities of each cluster was determined based on differentially expressed genes and known cell type marker genes. Each nucleus was assigned a cell type based on its cluster assignment. The first PC in the unbiased clustering of all the nuclei separated neuronal nuclei from glia nuclei (mainly oligodendrocytes, oligodendryocyte precursor cells, and astrocytes). The 50 highest scoring genes were defined as the "neuronal signature genes" and the 50 lowest scoring genes were defined as the "glia signature genes". These signatures were used to calculate the glia-neuron score, which was defined as the difference in the total centered expression of the neuronal signature genes and the glia signature genes. The centered expression for each gene was defined as the log(TPM+1) expression of the gene subtracted by its mean expression across all nuclei. To place the SC neurons on the maturation trajectory the neuronal lineage nuclei were clustered by biSNE similarly as done for the DG with one exception. Here, the top 670 differentiated genes and markers from the SC trajectory were used, and the top 3 PCs were used in the clustering, which embedded the nucleic on a branched trajectory.

BrdU labeling and immunohistochemistry. C57B16 adult mice (male, 6–8 weeks) were injected intraperitoneally with 200 mg/kg BrdU (Thermo Fisher Scientific, #B23151) every 12 h for 2 days. 8 days after the last injection, mice were deeply anesthetized with isoflurane, and transcardially perfused with 4% PFA. Brain and spinal cord have been dissected in ice-cold PBS and postfixed for 24 h in 4% PFA. After dehydration in a graded ethanol series, Xylene (Sigma Aldrich) incubation for 15 min, and paraffin embedding, 8 m sections were cut (Leica, Jung Multicut 2045). Sections were rehydrated in $H_2O$ and incubated in 20 mM citric acid, 60 mM disodium phosphate, and 1.50 (vol/vol) $H_2O_2$ at room temperature for 15 mi. After boiling in 40 mM Tris and 1 mM EDTA (pH 9.0), cooling to room temperature (1 h), and washing in PBS, sections were blocked with 300 Normal Goat Serum (NGS), 20% Donkey Serum (DS) in PBS and 0.1 Triton X-100 (PBST) for 1 h. Primary antibodies were added in 1.51 Normal Goat Serum (NGS), 10% Donkey Serum (DS) in PBST: rat anti-BrdU (1:50; Abcam, MA, #ab6326), rabbit anti-Pbx3 (1:q100; Abcam, #ab56239) and mouse anti-NeuN (1:200; Millipore, MA, #MAB377). After washing in PBST, the sections were incubated with Alexa Fluor 488 goat anti-rat, Alexa Fluor 555 goat anti-rabbit and Alexa Fluor 647 goat anti-mouse including (all 1:1000; Thermo Fisher Scientific). The sections were finally washed in PBST and mounted in Vectashield mounting medium with DAPI (Vector labs, #H-1500). Confocal images were taken by confocal laser-scanning microscopy (Zeiss, LSM510) and assembled using Adobe Photoshop (Adobe Systems).

TABLE 18 marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Grm2 | 6.39 | 1.96 | 0.18 | 0.30 | 0.48 | 0.64 | 0.00 |
| St3gal1 | 2.98 | 0.81 | 0.18 | 0.13 | 0.53 | 0.24 | 0.00 |
| C1ql3 | 6.66 | 2.05 | 0.00 | 0.44 | 0.22 | 0.90 | 0.16 |
| Kcnc4 | 6.14 | 3.03 | 0.39 | 0.91 | 1.59 | 0.56 | 0.15 |
| Cebpd | 3.54 | 1.11 | 0.08 | 0.65 | 0.34 | 0.68 | 0.00 |
| C1ql2 | 7.66 | 0.82 | 0.00 | 0.34 | 0.62 | 0.83 | 0.27 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Trpc6 | 5.95 | 0.53 | 0.08 | 0.13 | 2.41 | 0.37 | 0.24 |
| Pter | 5.77 | 1.18 | 0.29 | 0.48 | 0.40 | 0.77 | 0.21 |
| Kif26b | 4.88 | 1.04 | 0.12 | 1.57 | 1.22 | 0.62 | 0.00 |
| Gsg1l | 4.08 | 1.99 | 1.28 | 0.70 | 0.82 | 0.93 | 0.00 |
| Igfbp5 | 5.49 | 0.83 | 0.00 | 0.17 | 0.92 | 1.49 | 0.46 |
| Fam84a | 6.56 | 4.10 | 0.70 | 2.23 | 3.76 | 1.00 | 0.58 |
| Lrtm2 | 5.86 | 1.31 | 0.65 | 2.64 | 2.53 | 1.25 | 0.53 |
| Ehd1 | 6.24 | 2.47 | 0.99 | 3.11 | 1.78 | 1.15 | 0.67 |
| Gfra1 | 4.59 | 1.31 | 0.14 | 1.41 | 0.94 | 1.53 | 0.48 |
| Calb1 | 6.60 | 2.30 | 0.84 | 0.48 | 1.32 | 0.55 | 0.85 |
| Doc2b | 4.44 | 2.55 | 0.00 | 0.25 | 0.33 | 0.65 | 0.25 |
| Lct | 5.30 | 0.57 | 0.27 | 0.20 | 0.09 | 0.44 | 0.84 |
| Pde1b | 6.32 | 2.32 | 1.11 | 1.54 | 2.86 | 1.43 | 0.78 |
| Dock10 | 5.77 | 1.16 | 0.44 | 0.93 | 2.93 | 3.00 | 0.44 |
| Rasl10a | 6.75 | 3.76 | 0.00 | 3.52 | 0.59 | 0.92 | 0.33 |
| St18 | 5.27 | 1.44 | 0.41 | 2.04 | 0.59 | 2.35 | 1.03 |
| Jun | 6.44 | 2.88 | 0.87 | 2.42 | 0.68 | 1.16 | 1.06 |
| Dbpht2 | 6.05 | 3.07 | 2.81 | 1.09 | 1.52 | 1.58 | 1.08 |
| Pcdh8 | 5.02 | 1.39 | 1.59 | 1.79 | 2.25 | 0.85 | 0.21 |
| Slc30a3 | 7.32 | 3.41 | 2.40 | 4.06 | 2.83 | 0.97 | 0.31 |
| Mapk3 | 6.16 | 1.60 | 1.01 | 1.54 | 2.69 | 1.75 | 0.93 |
| Bhlhe22 | 3.65 | 0.98 | 0.78 | 1.49 | 0.04 | 0.66 | 0.00 |
| Sipa1l2 | 5.55 | 1.92 | 0.89 | 0.87 | 1.33 | 1.58 | 0.94 |
| Gabrd | 4.69 | 1.03 | 0.00 | 0.15 | 2.51 | 0.40 | 0.00 |
| Syt17 | 6.03 | 3.97 | 0.23 | 2.08 | 0.97 | 0.86 | 1.29 |
| Stxbp6 | 6.24 | 0.91 | 1.38 | 1.37 | 2.19 | 2.57 | 1.38 |
| Lingo2 | 6.00 | 3.91 | 0.88 | 3.35 | 4.11 | 0.71 | 0.22 |
| Pde7b | 4.38 | 0.61 | 0.00 | 0.39 | 1.12 | 2.18 | 0.21 |
| Anp32a | 5.85 | 2.74 | 2.30 | 2.71 | 2.01 | 1.81 | 0.84 |
| Gprin1 | 4.54 | 2.37 | 1.49 | 1.50 | 1.01 | 0.59 | 0.53 |
| Cacng3 | 4.98 | 3.07 | 0.80 | 2.70 | 2.39 | 0.66 | 0.16 |
| Slc39a6 | 5.89 | 2.16 | 2.51 | 1.65 | 3.26 | 0.97 | 0.67 |
| Limd2 | 6.97 | 4.14 | 3.61 | 4.51 | 1.61 | 1.78 | 1.25 |
| Plekha2 | 5.72 | 0.41 | 2.89 | 0.35 | 0.31 | 1.02 | 1.37 |
| Marcks | 5.35 | 2.06 | 0.83 | 0.78 | 1.64 | 2.99 | 0.25 |
| Rab40b | 5.06 | 2.42 | 1.86 | 2.64 | 0.79 | 0.33 | 0.64 |
| Npnt | 5.01 | 0.39 | 2.14 | 0.17 | 0.25 | 0.39 | 0.14 |
| Ppp1r1a | 6.67 | 2.99 | 3.97 | 3.25 | 1.80 | 0.69 | 0.78 |
| B4galt5 | 3.72 | 1.00 | 1.32 | 1.52 | 2.09 | 0.54 | 0.33 |
| Chst15 | 5.69 | 3.09 | 2.70 | 2.67 | 1.26 | 1.13 | 0.38 |
| Crlf1 | 4.69 | 0.74 | 0.00 | 2.58 | 0.27 | 0.31 | 0.00 |
| Dsp | 4.41 | 0.21 | 0.05 | 0.09 | 0.19 | 0.44 | 1.06 |
| Dgkh | 6.28 | 2.61 | 3.64 | 2.00 | 2.50 | 1.01 | 0.65 |
| Ntng1 | 4.72 | 3.21 | 0.46 | 0.82 | 1.00 | 0.43 | 0.55 |
| Ankrd6 | 4.21 | 2.22 | 0.00 | 1.72 | 0.89 | 0.69 | 1.11 |
| Trp53i11 | 3.74 | 1.13 | 0.61 | 1.77 | 1.55 | 0.55 | 0.31 |
| Gng7 | 5.52 | 2.32 | 2.69 | 1.10 | 2.53 | 0.70 | 0.21 |
| Hlf | 6.02 | 3.07 | 1.75 | 1.09 | 1.31 | 1.79 | 1.88 |
| Dek | 4.79 | 2.62 | 1.96 | 2.07 | 2.37 | 1.85 | 0.63 |
| Synpr | 7.40 | 1.46 | 0.64 | 3.82 | 3.73 | 1.90 | 2.29 |
| Gfod1 | 4.84 | 2.58 | 2.04 | 2.24 | 1.48 | 0.66 | 1.18 |
| Pitpnm2 | 7.41 | 5.63 | 4.70 | 5.16 | 5.85 | 5.79 | 4.73 |
| Ncdn | 8.79 | 7.73 | 6.80 | 7.62 | 6.70 | 7.33 | 6.97 |
| Gp1bb | 5.81 | 3.36 | 3.24 | 2.96 | 2.53 | 1.76 | 0.46 |
| Marcksl1 | 5.00 | 1.68 | 0.55 | 0.25 | 1.88 | 2.80 | 0.32 |
| Gpc4 | 5.94 | 1.61 | 1.86 | 0.32 | 0.69 | 0.72 | 2.07 |
| Cplx2 | 7.81 | 6.29 | 5.76 | 6.71 | 5.64 | 5.85 | 6.07 |
| Plk5 | 5.71 | 0.52 | 0.00 | 0.21 | 0.41 | 0.72 | 1.88 |
| Fam163b | 7.59 | 3.20 | 5.77 | 1.81 | 2.30 | 2.09 | 0.39 |
| Bdnf | 5.50 | 2.91 | 2.60 | 2.54 | 0.37 | 1.03 | 1.03 |
| Pcp4 | 7.08 | 1.70 | 4.09 | 2.20 | 0.57 | 1.48 | 1.53 |
| Cbfa2t3 | 4.66 | 2.99 | 1.35 | 2.85 | 0.70 | 1.28 | 0.00 |
| Ngef | 4.94 | 3.49 | 0.47 | 1.53 | 1.72 | 2.17 | 0.49 |
| Prox1 | 6.74 | 0.65 | 0.26 | 0.32 | 2.00 | 4.62 | 0.00 |
| Rilpl1 | 6.06 | 2.60 | 3.76 | 2.17 | 0.95 | 1.04 | 2.21 |
| Nkain2 | 5.18 | 3.23 | 1.68 | 3.03 | 2.07 | 1.15 | 0.38 |
| Arxes1 | 3.92 | 2.31 | 1.57 | 1.92 | 1.55 | 1.17 | 0.62 |
| Lgi3 | 6.28 | 3.84 | 1.98 | 4.53 | 2.29 | 2.74 | 0.84 |
| Atp2b4 | 4.90 | 2.86 | 0.08 | 1.00 | 0.70 | 1.25 | 2.01 |
| Gfra2 | 4.54 | 2.19 | 2.51 | 2.37 | 1.53 | 1.19 | 0.97 |
| Vav3 | 2.83 | 0.66 | 1.00 | 1.21 | 0.27 | 0.97 | 0.00 |
| Lzts3 | 5.64 | 3.35 | 1.52 | 3.32 | 2.86 | 0.94 | 1.89 |
| Fam3c | 5.51 | 2.11 | 3.02 | 1.88 | 2.20 | 1.49 | 0.19 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Zfpm2 | 3.24 | 0.85 | 0.44 | 1.83 | 0.64 | 1.12 | 0.00 |
| Amer3 | 4.57 | 2.13 | 2.21 | 2.60 | 1.42 | 0.59 | 0.81 |
| 6530402F18Rik | 3.49 | 1.91 | 0.00 | 1.98 | 0.52 | 1.24 | 0.68 |
| Rragd | 4.90 | 1.97 | 0.69 | 1.66 | 1.17 | 0.98 | 1.72 |
| Pkig | 6.87 | 2.21 | 3.35 | 1.25 | 1.86 | 1.52 | 3.08 |
| Acvr1c | 3.61 | 1.53 | 0.14 | 2.20 | 0.29 | 0.42 | 0.26 |
| Foxo1 | 5.38 | 1.49 | 0.07 | 1.57 | 0.66 | 2.08 | 2.14 |
| Napepld | 5.35 | 1.95 | 3.63 | 3.50 | 1.62 | 1.04 | 2.09 |
| Cecr2 | 4.39 | 1.24 | 1.65 | 1.86 | 1.06 | 2.50 | 1.75 |
| Pde8b | 5.88 | 3.52 | 3.05 | 4.29 | 3.02 | 2.60 | 1.16 |
| Ccdc85a | 6.08 | 2.91 | 3.95 | 2.64 | 3.33 | 1.45 | 1.07 |
| Rps23 | 6.48 | 4.69 | 2.83 | 4.16 | 3.71 | 4.04 | 2.09 |
| Dlg3 | 5.87 | 3.70 | 3.60 | 4.07 | 2.47 | 1.16 | 2.37 |
| Fnip2 | 2.91 | 0.97 | 1.43 | 1.41 | 1.65 | 0.82 | 0.40 |
| Ptchd1 | 2.80 | 1.44 | 0.28 | 0.71 | 1.69 | 0.49 | 0.00 |
| Prkd1 | 2.56 | 0.62 | 0.24 | 0.08 | 0.36 | 1.36 | 0.17 |
| Smad3 | 5.87 | 3.63 | 1.34 | 2.79 | 0.77 | 1.94 | 2.63 |
| Ncam2 | 5.14 | 2.87 | 2.78 | 2.26 | 2.09 | 2.49 | 0.80 |
| Fam19a2 | 5.61 | 1.73 | 4.00 | 2.72 | 2.58 | 0.93 | 0.81 |
| Sox11 | 4.73 | 3.02 | 1.20 | 3.35 | 2.75 | 2.31 | 0.85 |
| Dgat2 | 7.22 | 3.74 | 5.55 | 3.94 | 1.43 | 1.47 | 0.21 |
| Ptbp3 | 3.69 | 1.65 | 1.97 | 1.72 | 1.06 | 1.82 | 0.96 |
| Htr4 | 4.61 | 3.13 | 2.36 | 3.08 | 1.28 | 0.52 | 0.26 |
| Slitrk2 | 4.52 | 2.46 | 2.67 | 1.82 | 1.56 | 1.95 | 0.10 |
| Neurod1 | 4.42 | 2.29 | 1.40 | 2.90 | 0.24 | 0.59 | 0.36 |
| Thsd7a | 4.18 | 0.63 | 0.43 | 0.59 | 2.91 | 0.83 | 1.39 |
| C1qtnf4 | 5.25 | 2.36 | 3.63 | 1.04 | 1.95 | 0.77 | 0.00 |
| Lhfpl2 | 3.65 | 1.19 | 0.63 | 2.14 | 0.61 | 1.45 | 1.46 |
| Tmem98 | 4.47 | 3.34 | 2.34 | 2.33 | 2.75 | 0.57 | 0.71 |
| B3galt5 | 4.56 | 1.87 | 2.21 | 2.75 | 0.49 | 1.41 | 1.91 |
| Ncald | 7.45 | 6.02 | 5.31 | 6.22 | 6.12 | 4.69 | 4.98 |
| Rpl32 | 5.60 | 3.68 | 2.21 | 3.06 | 3.33 | 3.10 | 2.44 |
| Rmnd5a | 5.31 | 3.29 | 2.45 | 3.63 | 2.26 | 1.48 | 2.56 |
| Cdh13 | 4.56 | 2.39 | 2.62 | 2.33 | 3.21 | 2.03 | 1.14 |
| Cyp7b1 | 4.22 | 1.20 | 2.41 | 1.64 | 0.34 | 1.52 | 0.76 |
| Rplp1 | 7.41 | 5.24 | 3.15 | 5.33 | 4.67 | 4.39 | 3.71 |
| Sh3bgrl3 | 6.60 | 4.66 | 2.90 | 5.24 | 1.98 | 2.43 | 1.70 |
| Foxo3 | 5.34 | 2.71 | 0.73 | 2.22 | 2.57 | 2.78 | 2.56 |
| Diap2 | 4.62 | 2.87 | 3.10 | 2.56 | 1.74 | 1.60 | 2.15 |
| Rps15 | 7.27 | 5.39 | 2.72 | 6.07 | 5.09 | 4.43 | 4.06 |
| Sec14l2 | 3.38 | 1.69 | 0.93 | 2.21 | 0.24 | 0.73 | 0.30 |
| Spsb1 | 3.18 | 0.22 | 1.08 | 0.52 | 0.22 | 1.52 | 1.14 |
| Btg1 | 4.86 | 1.97 | 0.36 | 1.06 | 1.99 | 1.89 | 2.49 |
| Kcnip4 | 3.52 | 2.15 | 1.27 | 2.21 | 0.55 | 0.25 | 0.20 |
| Nov | 0.05 | 3.00 | 0.00 | 0.08 | 0.18 | 0.44 | 0.00 |
| Pex5l | 2.33 | 5.57 | 1.50 | 2.10 | 1.27 | 1.40 | 1.21 |
| Ldb2 | 0.07 | 3.77 | 0.18 | 1.34 | 0.49 | 0.58 | 0.72 |
| Cadps2 | 1.29 | 4.56 | 1.91 | 1.76 | 1.33 | 0.51 | 0.00 |
| Fibcd1 | 1.79 | 4.71 | 0.00 | 1.16 | 0.44 | 0.89 | 1.46 |
| Fxyd6 | 1.44 | 4.52 | 0.00 | 1.36 | 2.62 | 2.38 | 0.61 |
| Hs6st3 | 0.41 | 3.13 | 0.00 | 1.41 | 0.66 | 0.18 | 0.47 |
| Kcnk9 | 2.12 | 3.42 | 1.47 | 0.53 | 1.05 | 0.19 | 0.19 |
| Cnih3 | 6.04 | 4.59 | 0.94 | 1.80 | 1.68 | 1.30 | 0.21 |
| Ntng1 | 4.72 | 3.21 | 0.46 | 0.82 | 1.00 | 0.43 | 0.55 |
| Lypd1 | 5.79 | 4.41 | 0.99 | 1.75 | 0.84 | 1.57 | 1.30 |
| Mal2 | 4.68 | 4.96 | 0.33 | 2.64 | 2.11 | 0.96 | 1.41 |
| Ramp1 | 6.11 | 3.99 | 0.60 | 1.77 | 1.07 | 2.15 | 0.25 |
| Kcnc4 | 6.14 | 3.03 | 0.39 | 0.91 | 1.59 | 0.56 | 0.15 |
| Syt17 | 6.03 | 3.97 | 0.23 | 2.08 | 0.97 | 0.86 | 1.29 |
| Ankrd33b | 4.88 | 5.15 | 1.79 | 3.37 | 0.48 | 0.81 | 0.40 |
| A830036E02Rik | 4.82 | 2.51 | 7.89 | 2.69 | 1.00 | 0.37 | 0.44 |
| Amigo2 | 0.45 | 1.29 | 7.19 | 2.23 | 0.19 | 0.56 | 0.00 |
| Acan | 0.25 | 0.05 | 4.37 | 0.05 | 0.27 | 0.44 | 0.00 |
| Tll2 | 0.00 | 0.03 | 4.79 | 0.00 | 0.00 | 0.00 | 0.00 |
| Dock11 | 2.72 | 1.86 | 6.34 | 1.89 | 2.94 | 1.36 | 0.00 |
| Krt12 | 1.25 | 0.49 | 4.43 | 0.56 | 0.32 | 0.18 | 0.30 |
| Kcnk2 | 1.00 | 1.44 | 4.68 | 1.18 | 0.24 | 1.34 | 0.00 |
| Ptpn5 | 4.46 | 6.50 | 8.44 | 6.73 | 6.79 | 1.21 | 0.99 |
| Kalrn | 7.77 | 7.30 | 9.05 | 7.71 | 6.26 | 6.34 | 5.39 |
| Ntsr2 | 0.73 | 2.18 | 8.38 | 5.49 | 0.71 | 4.15 | 0.63 |
| A630077J23Rik | 0.01 | 0.00 | 4.34 | 0.00 | 0.00 | 0.10 | 0.00 |
| Fat3 | 4.33 | 4.57 | 6.41 | 4.56 | 2.44 | 2.08 | 0.61 |
| Rgs14 | 3.94 | 4.15 | 6.73 | 2.51 | 0.35 | 0.79 | 1.24 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Cacng5 | 0.89 | 0.19 | 4.08 | 0.25 | 0.91 | 0.53 | 0.32 |
| 9130019P16Rik | 0.72 | 0.68 | 3.09 | 0.47 | 0.24 | 0.14 | 0.00 |
| Gprl2 | 2.01 | 1.96 | 5.75 | 2.43 | 1.57 | 0.48 | 0.29 |
| Itga7 | 2.85 | 1.28 | 6.92 | 4.55 | 0.72 | 1.18 | 0.65 |
| Igfbp4 | 4.48 | 5.54 | 7.68 | 5.01 | 5.70 | 4.85 | 5.51 |
| Kcnv1 | 1.66 | 2.27 | 5.49 | 2.50 | 0.11 | 0.25 | 0.50 |
| Car7 | 1.22 | 3.12 | 5.89 | 1.95 | 0.29 | 0.09 | 0.00 |
| Gcnt4 | 0.31 | 0.29 | 3.22 | 0.35 | 0.21 | 0.51 | 0.00 |
| 5430416O09Rik | 0.18 | 0.29 | 3.48 | 0.10 | 0.14 | 0.04 | 0.34 |
| Serpina1a | 0.77 | 0.74 | 3.15 | 0.89 | 0.86 | 0.66 | 0.00 |
| Drd1a | 0.53 | 0.37 | 3.19 | 0.17 | 0.44 | 0.09 | 0.00 |
| Map3k15 | 0.10 | 0.06 | 6.48 | 0.17 | 0.07 | 0.14 | 2.65 |
| Zdhhc23 | 0.41 | 2.25 | 5.04 | 2.33 | 0.12 | 0.42 | 0.98 |
| Zfp46 | 3.34 | 2.49 | 5.49 | 2.84 | 1.40 | 0.88 | 0.32 |
| Drap1 | 2.86 | 2.28 | 6.96 | 3.54 | 1.99 | 1.47 | 2.52 |
| Aph1b | 0.86 | 2.13 | 4.79 | 1.73 | 1.06 | 0.79 | 1.45 |
| ENSMUSG00000095041 | 7.80 | 7.41 | 9.40 | 7.23 | 7.99 | 7.11 | 7.56 |
| Mchr1 | 0.15 | 2.21 | 4.97 | 2.00 | 0.29 | 0.05 | 0.21 |
| Ntf3 | 1.76 | 0.28 | 4.44 | 0.00 | 0.15 | 0.38 | 0.00 |
| Ccl21a | 2.23 | 2.35 | 5.33 | 1.32 | 1.73 | 0.54 | 0.01 |
| Atxn7l1os1 | 0.80 | 0.50 | 2.43 | 0.45 | 0.67 | 0.05 | 0.36 |
| Npas4 | 0.09 | 1.42 | 3.93 | 0.78 | 0.77 | 0.05 | 0.00 |
| Myo1b | 3.84 | 4.30 | 5.78 | 4.47 | 4.50 | 4.68 | 4.33 |
| Tac1 | 0.05 | 0.19 | 4.60 | 0.00 | 1.44 | 0.21 | 0.32 |
| Arhgap6 | 1.89 | 2.07 | 5.58 | 1.71 | 3.21 | 2.57 | 1.98 |
| 4930578G10Rik | 1.56 | 1.13 | 3.60 | 0.82 | 0.73 | 0.22 | 0.00 |
| Lingo3 | 2.90 | 2.86 | 5.42 | 2.81 | 0.33 | 0.54 | 0.00 |
| Sorcs2 | 3.83 | 4.46 | 6.55 | 4.91 | 1.91 | 2.21 | 1.08 |
| Srm | 3.08 | 3.69 | 6.00 | 3.28 | 3.33 | 1.78 | 0.93 |
| Rara | 0.16 | 0.94 | 3.09 | 0.91 | 0.35 | 0.06 | 0.75 |
| Tmem154 | 0.82 | 1.01 | 2.74 | 0.92 | 0.94 | 0.79 | 0.41 |
| Igdcc3 | 0.35 | 0.12 | 3.15 | 1.03 | 0.20 | 0.24 | 0.00 |
| Tpsg1 | 0.98 | 0.25 | 2.47 | 0.31 | 0.04 | 0.12 | 0.00 |
| Arap2 | 0.61 | 3.92 | 5.95 | 4.33 | 1.37 | 2.64 | 1.20 |
| Hunk | 0.08 | 2.47 | 4.44 | 2.28 | 1.35 | 0.81 | 0.50 |
| Slco5a1 | 0.62 | 0.47 | 2.45 | 0.57 | 0.47 | 0.26 | 0.22 |
| 1700024P16Rik | 0.05 | 0.30 | 2.99 | 0.32 | 0.08 | 0.05 | 0.71 |
| St8sia6 | 0.06 | 0.33 | 3.33 | 1.36 | 0.31 | 0.15 | 0.87 |
| BC046251 | 1.22 | 0.88 | 2.73 | 1.14 | 1.57 | 1.02 | 0.60 |
| Gm11417 | 0.52 | 0.58 | 3.10 | 0.63 | 0.45 | 0.16 | 0.83 |
| 2610042L04Rik | 1.12 | 1.78 | 4.22 | 2.06 | 1.58 | 1.64 | 1.01 |
| Grip1os3 | 0.38 | 0.31 | 2.55 | 0.20 | 0.85 | 0.86 | 0.62 |
| Kitl | 1.22 | 0.63 | 2.97 | 0.50 | 0.06 | 0.47 | 0.37 |
| Palm2 | 2.36 | 1.94 | 4.32 | 2.19 | 1.53 | 0.32 | 0.53 |
| Ptp1b | 2.28 | 3.79 | 5.76 | 3.93 | 1.54 | 2.76 | 1.88 |
| Blnk | 1.31 | 1.58 | 4.58 | 1.94 | 1.37 | 1.56 | 2.48 |
| Abcc4 | 0.81 | 0.84 | 5.36 | 2.77 | 0.29 | 0.83 | 2.78 |
| Fgf5 | 1.02 | 0.74 | 3.03 | 1.03 | 0.52 | 0.54 | 0.87 |
| Arhgef3 | 3.01 | 3.55 | 5.29 | 3.11 | 1.20 | 0.77 | 1.48 |
| Nptx2 | 0.31 | 1.14 | 2.86 | 0.71 | 0.35 | 0.40 | 0.49 |
| Cdh7 | 0.19 | 1.19 | 2.88 | 0.96 | 1.05 | 0.16 | 0.15 |
| Asic2 | 2.73 | 3.01 | 4.62 | 2.63 | 1.92 | 0.82 | 1.52 |
| Lrp12 | 2.09 | 2.61 | 5.08 | 3.12 | 0.62 | 0.57 | 0.14 |
| Cd3d | 0.77 | 0.76 | 2.28 | 0.61 | 0.61 | 0.90 | 0.27 |
| Adcy1 | 6.99 | 5.37 | 7.34 | 4.24 | 5.82 | 2.19 | 1.06 |
| Fam163b | 7.59 | 3.20 | 5.77 | 1.81 | 2.30 | 2.09 | 0.39 |
| Kcnj4 | 3.31 | 1.22 | 3.96 | 0.26 | 0.34 | 0.31 | 0.13 |
| A830036E02Rik | 4.82 | 2.51 | 7.89 | 2.69 | 1.00 | 0.37 | 0.44 |
| Tiam2 | 4.29 | 1.75 | 4.14 | 0.25 | 1.49 | 1.06 | 1.24 |
| Prdm8 | 4.53 | 1.46 | 5.20 | 3.09 | 0.08 | 0.63 | 0.84 |
| F730043M19Rik | 6.13 | 4.23 | 5.68 | 2.93 | 3.00 | 2.27 | 2.25 |
| Lphn2 | 0.13 | 3.97 | 4.85 | 0.65 | 1.07 | 0.62 | 0.25 |
| Bcl11b | 6.82 | 5.67 | 5.56 | 3.28 | 2.95 | 2.53 | 0.76 |
| Spon1 | 5.98 | 5.01 | 6.03 | 2.63 | 0.77 | 3.06 | 1.79 |
| Adamts9 | 0.49 | 0.63 | 0.50 | 4.14 | 0.36 | 0.76 | 0.37 |
| Grik4 | 5.45 | 5.30 | 5.05 | 7.11 | 2.06 | 2.10 | 1.13 |
| Car4 | 3.40 | 2.45 | 0.24 | 6.14 | 1.17 | 0.75 | 1.24 |
| Cdh24 | 0.48 | 1.60 | 0.00 | 4.92 | 0.51 | 0.32 | 0.97 |
| Gm20751 | 0.29 | 0.56 | 0.87 | 3.63 | 0.15 | 0.44 | 0.31 |
| Cpne9 | 2.46 | 3.08 | 3.51 | 5.61 | 2.10 | 2.27 | 2.60 |
| Mndal | 0.04 | 0.35 | 0.00 | 3.35 | 0.00 | 0.45 | 0.38 |
| Shisa6 | 5.18 | 5.16 | 4.64 | 6.48 | 2.63 | 1.89 | 1.72 |
| Slc22a4 | 0.52 | 0.98 | 0.00 | 3.47 | 0.61 | 1.21 | 0.00 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Galnt3 | 0.47 | 1.26 | 0.11 | 3.41 | 0.00 | 0.29 | 0.00 |
| Slco2a1 | 0.51 | 0.55 | 0.16 | 2.53 | 0.16 | 0.33 | 0.00 |
| Efr3b | 2.29 | 5.68 | 5.55 | 7.06 | 5.61 | 4.18 | 3.99 |
| Homer3 | 1.75 | 2.01 | 2.44 | 5.50 | 0.41 | 0.71 | 0.87 |
| Lnx1 | 0.28 | 2.51 | 0.00 | 6.07 | 4.34 | 0.60 | 0.80 |
| Parp8 | 0.90 | 3.37 | 0.15 | 5.25 | 1.69 | 1.73 | 1.15 |
| 3110047P20Rik | 0.88 | 1.53 | 0.72 | 3.51 | 0.35 | 0.17 | 0.87 |
| Bok | 0.85 | 2.03 | 0.84 | 5.94 | 1.10 | 0.96 | 2.04 |
| Tspan17 | 0.69 | 2.44 | 0.74 | 5.45 | 2.03 | 0.72 | 1.90 |
| Evc | 0.59 | 1.42 | 0.55 | 4.36 | 0.99 | 1.17 | 1.29 |
| Socs2 | 0.21 | 3.98 | 0.78 | 7.06 | 3.02 | 0.62 | 3.26 |
| Gm12296 | 1.31 | 1.90 | 1.59 | 4.04 | 0.82 | 0.53 | 1.21 |
| Tbata | 0.06 | 1.87 | 1.72 | 4.28 | 0.00 | 0.18 | 0.00 |
| Nkd2 | 0.07 | 1.31 | 0.41 | 3.31 | 0.26 | 0.28 | 0.49 |
| Mapk11 | 1.13 | 4.38 | 2.00 | 6.01 | 1.33 | 0.31 | 0.17 |
| Rerg | 1.15 | 1.47 | 1.24 | 3.79 | 0.78 | 0.57 | 0.59 |
| 1700017B05Rik | 1.31 | 1.15 | 1.28 | 4.08 | 0.72 | 1.19 | 1.31 |
| Kcnt2 | 2.86 | 2.39 | 1.32 | 4.18 | 2.07 | 1.05 | 0.14 |
| Scube1 | 0.09 | 3.63 | 1.36 | 5.18 | 0.77 | 0.45 | 0.46 |
| Asl | 1.14 | 2.06 | 1.16 | 4.13 | 1.94 | 1.40 | 1.31 |
| Dpf3 | 1.97 | 0.32 | 1.23 | 3.52 | 0.81 | 0.50 | 0.00 |
| Pvrl3 | 0.53 | 2.98 | 4.28 | 6.37 | 1.43 | 2.41 | 1.29 |
| Clmp | 1.73 | 0.69 | 0.14 | 3.83 | 2.19 | 0.87 | 0.00 |
| 8430431K14Rik | 1.58 | 1.55 | 1.54 | 3.84 | 0.25 | 0.40 | 0.33 |
| Adamts14 | 0.08 | 1.08 | 0.56 | 2.64 | 0.00 | 0.06 | 0.00 |
| Ptgs2 | 0.74 | 1.08 | 1.18 | 3.16 | 0.12 | 0.36 | 0.42 |
| Traf3 | 1.24 | 2.89 | 1.85 | 4.74 | 2.12 | 1.19 | 2.08 |
| P2rx7 | 0.21 | 0.89 | 0.07 | 3.14 | 0.80 | 1.51 | 0.62 |
| Stac2 | 0.08 | 2.76 | 2.37 | 4.85 | 1.31 | 0.00 | 0.00 |
| Rhebl1 | 0.32 | 1.33 | 1.22 | 3.44 | 1.49 | 0.53 | 0.49 |
| Nkain3 | 2.72 | 2.62 | 1.88 | 4.39 | 2.91 | 0.70 | 0.49 |
| Ifi203 | 2.33 | 2.48 | 2.47 | 5.74 | 2.50 | 3.54 | 2.46 |
| Hes1 | 0.19 | 1.85 | 0.20 | 3.81 | 0.25 | 0.76 | 1.41 |
| Ankrd29 | 0.15 | 1.67 | 0.48 | 3.39 | 1.53 | 0.63 | 1.23 |
| Smarcd3 | 1.18 | 2.50 | 1.94 | 4.26 | 2.68 | 1.25 | 0.66 |
| Smoc2 | 4.74 | 1.01 | 0.96 | 5.14 | 0.26 | 0.44 | 0.60 |
| Robo3 | 4.79 | 1.95 | 0.19 | 4.11 | 0.28 | 0.26 | 0.00 |
| Fstl4 | 5.86 | 2.90 | 1.43 | 4.69 | 0.58 | 0.78 | 0.88 |
| Cacna1i | 2.15 | 4.08 | 2.66 | 4.57 | 1.53 | 0.70 | 0.33 |
| Slit2 | 0.90 | 4.51 | 0.44 | 5.61 | 1.87 | 0.75 | 1.17 |
| Ak4 | 0.62 | 3.64 | 0.00 | 4.22 | 0.43 | 0.96 | 0.75 |
| Tbc1d1 | 1.38 | 4.30 | 0.77 | 4.18 | 1.40 | 0.86 | 0.20 |
| Ppp4r4 | 2.65 | 4.06 | 0.99 | 4.55 | 1.55 | 0.48 | 0.29 |
| Cpne7 | 0.68 | 8.38 | 1.62 | 8.93 | 3.64 | 1.77 | 5.08 |
| 1-Mar | 2.55 | 4.67 | 1.78 | 5.58 | 1.08 | 1.24 | 0.15 |
| Guk1 | 2.91 | 4.82 | 1.91 | 4.94 | 2.60 | 1.20 | 1.81 |
| Slc26a4 | 2.23 | 3.27 | 0.38 | 3.65 | 0.10 | 0.28 | 0.00 |
| E330009J07Rik | 1.72 | 3.13 | 0.85 | 4.05 | 1.77 | 1.81 | 0.48 |
| Sema3e | 0.58 | 4.23 | 1.59 | 5.16 | 0.83 | 1.07 | 0.59 |
| Zdhhc14 | 1.69 | 4.22 | 1.49 | 5.00 | 2.38 | 0.97 | 0.28 |
| Parp8 | 0.90 | 3.37 | 0.15 | 5.25 | 1.69 | 1.73 | 1.15 |
| Nell1 | 0.06 | 4.60 | 2.30 | 4.94 | 2.29 | 0.63 | 0.59 |
| Lingo1 | 3.84 | 6.30 | 5.29 | 6.36 | 1.22 | 1.71 | 1.41 |
| Rasl10a | 6.75 | 3.76 | 0.00 | 3.52 | 0.59 | 0.92 | 0.33 |
| Cpne6 | 8.67 | 8.67 | 6.64 | 9.52 | 7.33 | 4.94 | 3.51 |
| Wasf1 | 6.62 | 6.13 | 4.56 | 5.97 | 2.60 | 3.07 | 2.11 |
| Lmo4 | 5.59 | 6.14 | 1.90 | 6.51 | 1.12 | 2.10 | 1.51 |
| Unc5a | 6.31 | 6.15 | 4.63 | 6.07 | 3.18 | 2.00 | 0.91 |
| Zfp831 | 3.76 | 3.46 | 1.50 | 3.67 | 0.24 | 0.73 | 0.00 |
| Ywhah | 8.05 | 8.36 | 5.98 | 8.24 | 6.77 | 5.33 | 4.11 |
| 4930447C04Rik | 0.41 | 1.55 | 5.56 | 4.10 | 1.67 | 0.09 | 0.31 |
| Itga7 | 2.85 | 1.28 | 6.92 | 4.55 | 0.72 | 1.18 | 0.65 |
| Cabp7 | 2.68 | 3.38 | 6.47 | 5.51 | 0.72 | 0.89 | 0.51 |
| Il16 | 4.50 | 2.64 | 6.35 | 5.77 | 1.31 | 1.50 | 0.55 |
| Trhde | 0.75 | 1.98 | 4.39 | 5.39 | 1.51 | 0.08 | 0.47 |
| Kif1c | 2.06 | 2.26 | 4.45 | 4.03 | 1.03 | 0.71 | 1.18 |
| Arhgef26 | 0.43 | 3.54 | 5.67 | 5.55 | 1.29 | 3.09 | 2.45 |
| Tdrd5 | 0.82 | 2.07 | 4.08 | 4.49 | 0.54 | 0.27 | 0.00 |
| 4921534H16Rik | 3.78 | 3.65 | 5.75 | 6.12 | 2.44 | 0.91 | 0.69 |
| Cables2 | 1.08 | 2.35 | 4.89 | 4.24 | 1.99 | 0.70 | 0.92 |
| Il16 | 4.50 | 2.64 | 6.35 | 5.77 | 1.31 | 1.50 | 0.55 |
| Cpne4 | 5.08 | 2.97 | 6.59 | 6.50 | 1.36 | 1.04 | 1.03 |
| Prdm8 | 4.53 | 1.46 | 5.20 | 3.09 | 0.08 | 0.63 | 0.84 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Rasal1 | 2.78 | 6.17 | 6.18 | 6.70 | 0.30 | 0.80 | 0.61 |
| Rprml | 3.11 | 6.56 | 6.78 | 6.29 | 0.18 | 0.67 | 0.60 |
| Sstr4 | 1.41 | 5.95 | 5.64 | 5.20 | 0.94 | 0.25 | 0.21 |
| Rltpr | 2.11 | 4.34 | 5.09 | 5.10 | 1.75 | 0.07 | 0.38 |
| Gpr26 | 0.64 | 4.08 | 4.60 | 5.10 | 0.48 | 0.32 | 0.00 |
| Prkab2 | 2.67 | 5.34 | 5.52 | 5.80 | 2.00 | 1.41 | 0.54 |
| Lrtm1 | 1.00 | 4.05 | 5.32 | 4.95 | 1.43 | 0.44 | 0.55 |
| Ryr3 | 5.67 | 6.78 | 7.75 | 7.58 | 1.67 | 1.96 | 0.62 |
| Fam189a1 | 2.71 | 5.33 | 5.16 | 5.34 | 1.79 | 0.33 | 0.52 |
| Khdrbs3 | 0.45 | 5.89 | 5.35 | 6.35 | 1.94 | 1.57 | 1.07 |
| Hs3st4 | 0.65 | 3.50 | 4.63 | 5.07 | 0.20 | 0.74 | 0.58 |
| Ralyl | 2.30 | 5.40 | 4.77 | 5.69 | 2.01 | 0.66 | 0.97 |
| Golga7b | 2.19 | 5.42 | 4.99 | 5.13 | 1.83 | 0.59 | 0.92 |
| Specc1 | 3.69 | 5.36 | 6.75 | 5.89 | 2.78 | 1.59 | 1.28 |
| Fam5b | 0.92 | 5.64 | 6.58 | 5.97 | 3.69 | 1.27 | 1.03 |
| Frmd6 | 0.92 | 2.78 | 4.09 | 3.55 | 1.06 | 0.64 | 0.00 |
| Mdga1 | 1.85 | 4.48 | 5.13 | 5.10 | 0.26 | 0.73 | 0.96 |
| Arc | 0.29 | 3.51 | 4.29 | 4.27 | 0.26 | 0.53 | 0.61 |
| Egr1 | 1.28 | 4.31 | 3.76 | 3.77 | 1.38 | 0.99 | 0.27 |
| Pkp2 | 4.01 | 5.77 | 5.99 | 6.88 | 0.48 | 1.39 | 1.98 |
| Neurod6 | 0.16 | 6.62 | 6.48 | 7.29 | 0.20 | 1.37 | 1.91 |
| Ptpru | 0.07 | 5.56 | 5.94 | 4.99 | 1.43 | 1.09 | 1.56 |
| Fezf2 | 0.04 | 3.52 | 4.79 | 3.38 | 0.08 | 1.27 | 0.39 |
| Mgat4c | 0.99 | 3.89 | 5.52 | 6.21 | 1.61 | 1.76 | 1.03 |
| Robo1 | 0.97 | 4.10 | 5.12 | 5.31 | 2.64 | 1.34 | 0.65 |
| Ankrd27 | 2.12 | 4.13 | 4.67 | 5.31 | 2.09 | 1.00 | 0.87 |
| Cnr1 | 0.47 | 5.73 | 5.49 | 5.82 | 3.43 | 1.96 | 0.86 |
| Thsd4 | 0.70 | 4.67 | 4.96 | 5.73 | 0.47 | 1.44 | 1.78 |
| Raved | 1.10 | 5.26 | 4.42 | 6.68 | 0.58 | 0.71 | 0.57 |
| Myadm | 2.29 | 5.60 | 4.83 | 5.55 | 2.27 | 1.44 | 1.32 |
| Aff3 | 1.58 | 4.44 | 4.68 | 5.02 | 2.70 | 0.74 | 1.67 |
| Cnnm4 | 3.02 | 4.34 | 5.26 | 5.50 | 2.42 | 1.02 | 0.86 |
| Nr4a3 | 0.62 | 4.58 | 4.26 | 5.75 | 1.18 | 1.52 | 0.29 |
| Slc9a1 | 2.15 | 5.17 | 5.12 | 5.53 | 2.77 | 2.04 | 1.77 |
| Gnptab | 2.47 | 4.81 | 5.60 | 5.35 | 3.16 | 1.79 | 1.72 |
| 3110039M20Rik | 1.39 | 3.51 | 4.80 | 4.67 | 1.97 | 1.14 | 0.26 |
| Esyt2 | 2.68 | 5.17 | 4.83 | 4.99 | 2.62 | 2.17 | 1.95 |
| Mrpl3 | 3.02 | 4.87 | 5.29 | 5.33 | 3.05 | 1.47 | 1.84 |
| Rab26 | 4.12 | 6.64 | 6.03 | 7.49 | 2.71 | 1.31 | 2.33 |
| Sv2b | 0.23 | 6.63 | 6.38 | 6.71 | 0.79 | 2.18 | 2.80 |
| Gm11201 | 1.80 | 3.00 | 4.27 | 3.32 | 0.85 | 0.16 | 0.19 |
| Dkk3 | 0.95 | 6.78 | 5.61 | 6.82 | 1.03 | 3.20 | 2.23 |
| Stat2 | 2.79 | 4.64 | 4.72 | 4.65 | 2.58 | 1.50 | 0.65 |
| Pde1a | 1.63 | 6.63 | 5.78 | 6.14 | 2.04 | 2.05 | 2.40 |
| Ccdc88c | 0.23 | 4.26 | 3.82 | 3.83 | 0.44 | 1.08 | 1.13 |
| Stoml1 | 2.83 | 5.43 | 5.91 | 6.02 | 3.80 | 1.97 | 0.80 |
| Ttc8 | 3.10 | 5.43 | 5.95 | 5.81 | 3.03 | 1.66 | 2.63 |
| Actr3b | 3.52 | 5.94 | 5.80 | 5.68 | 2.55 | 1.45 | 2.49 |
| Map3k7 | 2.81 | 4.10 | 4.30 | 4.55 | 2.59 | 1.13 | 1.65 |
| Gdpd1 | 2.11 | 4.32 | 4.24 | 4.83 | 2.07 | 1.74 | 0.59 |
| Cep78 | 1.90 | 2.94 | 3.70 | 3.42 | 1.58 | 0.44 | 0.89 |
| AI115009 | 1.86 | 3.14 | 4.01 | 4.96 | 0.55 | 0.24 | 0.00 |
| Pip4k2c | 2.84 | 5.60 | 5.60 | 5.69 | 2.85 | 1.94 | 2.75 |
| Asap2 | 0.89 | 4.76 | 4.33 | 4.25 | 2.30 | 1.83 | 1.95 |
| Msra | 2.97 | 4.68 | 4.71 | 5.45 | 2.61 | 0.59 | 0.35 |
| Pfkfb3 | 1.31 | 3.26 | 3.77 | 4.85 | 1.93 | 1.92 | 0.80 |
| Kit | 0.11 | 5.86 | 4.59 | 5.92 | 1.31 | 1.13 | 1.91 |
| Dlx1 | 0.04 | 0.00 | 0.07 | 0.00 | 5.88 | 0.12 | 0.00 |
| Dlx6os1 | 0.01 | 0.04 | 0.08 | 0.12 | 7.03 | 0.06 | 0.00 |
| Grik1 | 0.05 | 0.58 | 0.00 | 0.00 | 6.96 | 0.62 | 0.00 |
| Rbms3 | 0.15 | 0.53 | 0.00 | 0.64 | 6.31 | 0.57 | 0.00 |
| Nxph1 | 0.04 | 0.27 | 0.08 | 0.18 | 6.81 | 0.80 | 0.17 |
| Dlx1as | 0.15 | 0.08 | 0.42 | 0.07 | 6.09 | 0.21 | 0.00 |
| Dpp10 | 0.15 | 0.98 | 0.00 | 0.39 | 5.20 | 0.18 | 0.00 |
| Grip2 | 0.08 | 0.45 | 0.13 | 0.39 | 5.39 | 0.21 | 0.00 |
| Cntn5 | 2.54 | 1.31 | 0.00 | 0.25 | 5.45 | 0.28 | 0.00 |
| Slc32a1 | 0.01 | 0.00 | 0.00 | 0.05 | 4.89 | 0.07 | 0.00 |
| Col19a | 0.21 | 0.65 | 0.18 | 1.71 | 7.46 | 0.11 | 0.00 |
| Alk | 0.02 | 0.30 | 0.00 | 0.11 | 4.62 | 0.06 | 0.00 |
| Lhx6 | 0.11 | 0.06 | 0.22 | 0.30 | 4.71 | 0.15 | 0.16 |
| A530058N18Rik | 0.06 | 0.42 | 0.09 | 1.06 | 6.37 | 0.13 | 0.26 |
| Reln | 0.39 | 0.66 | 0.52 | 0.34 | 5.15 | 0.64 | 0.20 |
| Kcnmb2 | 0.06 | 0.07 | 0.00 | 0.08 | 3.84 | 0.00 | 0.00 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Kcnip1 | 0.28 | 0.49 | 0.46 | 0.12 | 4.70 | 0.48 | 0.00 |
| Foxred2 | 1.67 | 1.90 | 0.00 | 0.33 | 5.37 | 1.02 | 0.00 |
| Ubash3b | 3.96 | 1.28 | 0.00 | 1.64 | 5.79 | 1.30 | 0.22 |
| Arx | 0.02 | 0.08 | 0.00 | 0.08 | 3.52 | 0.29 | 0.00 |
| Zmat4 | 3.68 | 3.46 | 0.49 | 1.21 | 6.34 | 0.48 | 0.00 |
| Gm13629 | 0.10 | 0.16 | 0.00 | 0.25 | 4.05 | 0.16 | 0.00 |
| Sema6c | 0.26 | 0.94 | 0.23 | 1.24 | 4.97 | 0.64 | 0.00 |
| Galnt16 | 0.35 | 3.70 | 0.55 | 1.86 | 6.62 | 0.81 | 0.29 |
| Pnoc | 0.05 | 0.18 | 0.15 | 0.17 | 3.28 | 0.12 | 0.00 |
| Sgcz | 0.13 | 0.71 | 0.00 | 0.07 | 3.77 | 0.23 | 0.00 |
| Unc5d | 1.59 | 2.26 | 0.94 | 1.92 | 5.32 | 0.43 | 0.35 |
| Cntnap4 | 0.05 | 0.71 | 2.08 | 0.50 | 6.33 | 0.13 | 0.13 |
| Grin2d | 0.39 | 0.52 | 0.00 | 0.12 | 2.90 | 0.18 | 0.00 |
| Tm6sf1 | 0.75 | 1.11 | 1.71 | 2.05 | 6.12 | 0.78 | 0.78 |
| Btbd11 | 0.08 | 0.21 | 0.00 | 0.04 | 5.80 | 0.26 | 0.73 |
| Arl4c | 0.17 | 0.48 | 0.74 | 0.35 | 3.82 | 0.68 | 0.35 |
| Pla2g4e | 2.09 | 0.61 | 0.39 | 0.28 | 4.61 | 0.52 | 0.00 |
| Gad2 | 0.46 | 0.75 | 0.41 | 0.64 | 7.05 | 1.17 | 1.13 |
| Usp13 | 3.38 | 2.59 | 1.27 | 0.73 | 5.01 | 0.63 | 0.46 |
| Lrrtm3 | 2.82 | 2.49 | 1.69 | 0.54 | 5.88 | 1.25 | 0.00 |
| Dner | 0.38 | 3.90 | 1.80 | 3.13 | 7.11 | 2.60 | 0.81 |
| Ank1 | 0.24 | 1.01 | 0.08 | 0.05 | 5.01 | 0.40 | 0.59 |
| Rab3b | 0.15 | 1.40 | 0.00 | 0.21 | 4.13 | 0.34 | 0.00 |
| Adra1a | 0.16 | 1.24 | 0.21 | 0.35 | 3.99 | 0.65 | 0.43 |
| Gabrg3 | 0.83 | 3.53 | 0.86 | 2.36 | 6.21 | 0.76 | 0.08 |
| Hapln1 | 0.07 | 0.14 | 0.23 | 0.07 | 3.75 | 0.42 | 0.32 |
| Hcn3 | 0.50 | 1.61 | 1.13 | 1.49 | 4.51 | 0.54 | 0.58 |
| Myo16 | 0.06 | 2.35 | 1.70 | 1.22 | 5.42 | 0.76 | 0.18 |
| Fgf9 | 1.20 | 1.34 | 1.22 | 1.54 | 4.71 | 0.31 | 0.53 |
| Dcx | 0.92 | 2.98 | 0.91 | 3.98 | 6.38 | 1.50 | 0.86 |
| Tox2 | 0.02 | 1.28 | 0.29 | 0.00 | 3.78 | 0.22 | 0.21 |
| Gm15881 | 0.04 | 3.71 | 0.00 | 2.42 | 6.46 | 0.24 | 0.00 |
| Zfp57 | 0.77 | 1.38 | 0.00 | 0.00 | 5.38 | 0.92 | 0.70 |
| Cit | 0.66 | 3.10 | 2.23 | 3.18 | 6.30 | 1.22 | 0.41 |
| Amy1 | 1.68 | 2.79 | 1.65 | 2.89 | 6.18 | 1.23 | 1.21 |
| Ptprt | 0.28 | 1.86 | 0.11 | 0.10 | 5.20 | 2.05 | 0.88 |
| Gpsm1 | 2.02 | 2.66 | 0.62 | 1.73 | 5.60 | 1.91 | 0.95 |
| Usp29 | 1.25 | 1.41 | 0.82 | 0.97 | 3.35 | 0.49 | 0.55 |
| Rcan2 | 0.29 | 0.66 | 0.04 | 0.36 | 4.72 | 2.01 | 0.24 |
| Igsf11 | 3.02 | 1.15 | 0.75 | 0.68 | 5.12 | 2.58 | 0.82 |
| Zcchc12 | 1.18 | 2.08 | 0.15 | 0.64 | 4.54 | 0.82 | 0.35 |
| Sema4g | 0.18 | 0.86 | 0.00 | 1.16 | 4.99 | 1.64 | 0.81 |
| AI504432 | 1.39 | 0.86 | 0.39 | 0.06 | 3.16 | 0.51 | 0.19 |
| Dlc1 | 0.44 | 2.89 | 2.74 | 3.77 | 5.75 | 1.70 | 0.57 |
| Ece2 | 4.29 | 2.49 | 0.32 | 3.79 | 6.52 | 1.95 | 1.34 |
| E230016M11Rik | 0.39 | 0.94 | 0.69 | 1.27 | 3.69 | 0.83 | 0.00 |
| Olfm2 | 0.44 | 1.17 | 0.29 | 0.09 | 3.64 | 1.20 | 0.29 |
| Gad1 | 5.90 | 0.92 | 0.57 | 0.83 | 8.13 | 2.26 | 2.07 |
| Tbc1d2b | 0.33 | 1.42 | 1.65 | 1.46 | 5.45 | 1.28 | 1.46 |
| Dpys15 | 1.61 | 2.63 | 1.75 | 0.19 | 5.70 | 1.30 | 0.87 |
| Spock3 | 3.67 | 1.49 | 3.09 | 2.43 | 6.05 | 1.24 | 1.07 |
| Osbpl3 | 1.16 | 1.18 | 0.33 | 0.66 | 6.01 | 0.45 | 2.06 |
| Impdh1 | 1.64 | 2.35 | 1.05 | 2.29 | 4.75 | 0.77 | 0.47 |
| A230057D06Rik | 1.04 | 2.82 | 1.67 | 3.07 | 5.39 | 0.54 | 0.30 |
| Erbb4 | 0.15 | 0.24 | 0.27 | 0.14 | 5.92 | 1.38 | 2.03 |
| Coro6 | 0.06 | 0.89 | 0.70 | 0.57 | 7.07 | 0.27 | 2.54 |
| Ptprm | 0.10 | 0.18 | 0.15 | 0.08 | 6.23 | 1.17 | 2.08 |
| Trim62 | 0.05 | 0.92 | 0.16 | 1.07 | 3.14 | 0.74 | 0.00 |
| Dlx6 | 1.68 | 1.31 | 2.12 | 1.71 | 5.34 | 1.52 | 1.80 |
| Astn2 | 0.06 | 1.12 | 0.50 | 0.05 | 2.79 | 0.52 | 0.00 |
| Plekhh2 | 1.24 | 0.74 | 1.68 | 1.30 | 3.91 | 0.40 | 0.50 |
| Plxdc2 | 1.59 | 1.30 | 0.24 | 1.10 | 5.00 | 1.71 | 1.50 |
| Dchs1 | 0.35 | 0.90 | 0.14 | 0.30 | 3.06 | 1.22 | 0.35 |
| Fam124a | 1.53 | 1.05 | 0.71 | 0.90 | 3.03 | 1.06 | 0.32 |
| Fmn1 | 0.85 | 2.03 | 1.53 | 2.03 | 4.23 | 0.63 | 0.37 |
| Frmd5 | 3.43 | 2.64 | 1.13 | 1.14 | 6.63 | 1.70 | 2.50 |
| Slc35f1 | 0.55 | 2.76 | 1.92 | 0.90 | 4.80 | 1.42 | 1.63 |
| A330076H08Rik | 2.71 | 5.46 | 5.10 | 5.49 | 7.48 | 1.79 | 0.81 |
| Rims3 | 0.08 | 0.83 | 0.06 | 0.06 | 4.05 | 0.37 | 1.23 |
| Neb | 0.11 | 0.36 | 0.06 | 0.38 | 2.73 | 0.47 | 0.58 |
| BC030500 | 0.03 | 1.69 | 0.19 | 1.48 | 3.42 | 0.06 | 0.00 |
| Fam20c | 0.64 | 1.71 | 0.63 | 1.38 | 3.51 | 0.86 | 0.00 |
| Bend6 | 1.64 | 1.94 | 1.07 | 2.07 | 4.18 | 0.75 | 0.70 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Afap1 | 1.05 | 1.51 | 1.19 | 2.24 | 6.72 | 2.87 | 2.79 |
| Nyap2 | 0.53 | 4.10 | 4.47 | 4.76 | 6.32 | 0.52 | 2.61 |
| Hook2 | 1.13 | 3.85 | 3.82 | 4.80 | 6.53 | 1.07 | 2.52 |
| Gria4 | 1.46 | 5.14 | 4.28 | 5.13 | 6.88 | 1.67 | 0.52 |
| Atp8a2 | 2.44 | 3.79 | 2.77 | 4.35 | 6.26 | 0.70 | 0.79 |
| Evl | 1.90 | 1.64 | 1.96 | 1.14 | 4.16 | 0.97 | 0.32 |
| Scn9a | 1.14 | 1.01 | 0.66 | 1.11 | 2.74 | 0.27 | 0.23 |
| Rcan3 | 0.46 | 0.19 | 0.13 | 0.08 | 3.11 | 0.66 | 0.73 |
| Dnm3os | 0.70 | 1.20 | 1.19 | 1.39 | 3.03 | 0.67 | 0.23 |
| Camk1 | 0.83 | 3.14 | 0.34 | 3.50 | 6.37 | 2.52 | 2.54 |
| Hdac9 | 1.27 | 2.74 | 3.42 | 3.33 | 5.43 | 1.17 | 0.15 |
| Slc35e3 | 1.99 | 3.53 | 2.88 | 4.04 | 5.37 | 2.17 | 0.77 |
| Pknox2 | 2.59 | 1.81 | 1.36 | 0.59 | 5.56 | 0.84 | 2.48 |
| Garnl3 | 0.87 | 3.46 | 3.66 | 1.85 | 6.12 | 1.35 | 3.05 |
| B930041F14Rik | 1.21 | 0.99 | 0.76 | 1.90 | 3.81 | 0.52 | 1.16 |
| Ptpn4 | 1.15 | 1.52 | 1.10 | 1.31 | 2.94 | 1.27 | 0.70 |
| Fnbp1l | 0.24 | 3.41 | 0.22 | 1.00 | 5.87 | 1.55 | 2.90 |
| Fchsd2 | 1.17 | 2.52 | 3.85 | 2.64 | 5.87 | 2.20 | 1.50 |
| Inha | 2.92 | 3.92 | 3.74 | 4.18 | 6.30 | 0.49 | 3.25 |
| Maf | 0.10 | 0.24 | 0.00 | 0.06 | 6.25 | 0.86 | 3.46 |
| Gm14204 | 1.07 | 1.09 | 2.01 | 1.33 | 4.46 | 1.33 | 1.92 |
| Pam | 5.35 | 5.67 | 4.75 | 5.61 | 6.93 | 2.75 | 3.38 |
| Eps8 | 0.24 | 0.74 | 1.20 | 0.26 | 3.49 | 1.39 | 1.07 |
| Scrt1 | 0.83 | 0.87 | 0.69 | 1.14 | 2.43 | 0.20 | 0.00 |
| Kcna6 | 1.59 | 2.15 | 2.01 | 2.06 | 4.07 | 2.09 | 0.21 |
| Lin7a | 2.27 | 3.08 | 2.28 | 1.84 | 4.49 | 0.74 | 0.90 |
| Capn2 | 1.07 | 2.53 | 3.69 | 2.94 | 5.79 | 1.76 | 1.56 |
| Srgap1 | 0.17 | 0.98 | 0.19 | 1.64 | 3.14 | 1.08 | 0.00 |
| Bend4 | 1.60 | 1.60 | 2.42 | 2.33 | 4.01 | 0.68 | 0.19 |
| Greb1l | 2.06 | 3.17 | 1.19 | 2.92 | 5.58 | 0.23 | 2.91 |
| Pde9a | 0.84 | 2.05 | 0.00 | 0.69 | 3.49 | 1.04 | 0.78 |
| Hdac6 | 3.65 | 3.76 | 3.67 | 4.16 | 5.55 | 1.64 | 2.38 |
| Cacna2d2 | 0.07 | 0.47 | 0.05 | 0.23 | 3.48 | 0.59 | 1.28 |
| Lama2 | 0.13 | 0.07 | 0.05 | 0.26 | 0.10 | 3.02 | 0.36 |
| Zcchc24 | 0.16 | 0.10 | 0.00 | 0.15 | 0.23 | 3.62 | 0.61 |
| Gpr56 | 0.13 | 1.80 | 0.45 | 1.99 | 0.78 | 4.14 | 0.22 |
| Htra1 | 0.50 | 1.71 | 2.52 | 2.86 | 1.69 | 5.54 | 1.20 |
| Hepacam | 0.25 | 0.34 | 0.09 | 0.41 | 0.18 | 4.74 | 1.38 |
| Gpr37l1 | 0.33 | 0.93 | 0.00 | 0.51 | 0.32 | 4.66 | 1.24 |
| Ttyh1 | 5.91 | 6.40 | 4.92 | 5.68 | 5.93 | 7.64 | 5.32 |
| Ppap2b | 0.81 | 1.56 | 2.38 | 1.43 | 0.84 | 5.09 | 1.61 |
| Kcnj10 | 0.20 | 0.38 | 0.49 | 0.31 | 0.30 | 3.58 | 1.08 |
| Slc6a11 | 0.44 | 1.42 | 1.54 | 0.96 | 0.97 | 3.28 | 0.59 |
| Hif3a | 0.30 | 0.64 | 0.61 | 0.58 | 0.58 | 2.78 | 0.77 |
| Htr2c | 0.08 | 1.71 | 0.33 | 1.81 | 0.71 | 0.18 | 9.31 |
| Wdr86 | 0.06 | 0.03 | 0.13 | 0.15 | 0.05 | 0.24 | 8.52 |
| Col9a3 | 0.12 | 0.28 | 0.13 | 0.20 | 0.33 | 2.07 | 10.55 |
| Kcnj13 | 0.27 | 0.35 | 0.27 | 0.69 | 0.79 | 0.32 | 9.43 |
| Ttr | 0.52 | 3.31 | 0.41 | 3.59 | 1.97 | 2.10 | 12.19 |
| Steap2 | 0.57 | 0.63 | 0.97 | 1.26 | 2.51 | 1.29 | 8.04 |
| Tmem72 | 0.02 | 0.07 | 0.14 | 0.19 | 0.14 | 0.23 | 7.70 |
| Prlr | 3.09 | 3.68 | 3.07 | 3.46 | 3.85 | 3.59 | 8.18 |
| Slc4a5 | 0.02 | 0.00 | 0.00 | 0.06 | 0.00 | 0.00 | 7.12 |
| Rbm47 | 0.53 | 0.42 | 1.09 | 0.65 | 0.28 | 0.97 | 7.44 |
| Trpm3 | 5.76 | 2.67 | 6.32 | 3.15 | 1.30 | 2.47 | 10.56 |
| Cab39l | 0.88 | 1.33 | 0.52 | 1.03 | 1.93 | 1.15 | 7.41 |
| Whrn | 0.04 | 1.31 | 0.00 | 0.61 | 2.59 | 1.13 | 7.06 |
| Enpp2 | 0.32 | 2.59 | 0.24 | 3.31 | 2.39 | 3.98 | 10.44 |
| Car14 | 0.07 | 0.03 | 0.00 | 0.10 | 0.18 | 0.92 | 7.60 |
| Dock6 | 0.64 | 2.15 | 0.10 | 2.47 | 0.42 | 1.62 | 7.27 |
| Lama5 | 0.42 | 0.30 | 1.08 | 0.06 | 1.24 | 0.87 | 6.83 |
| Bad | 1.25 | 1.53 | 1.23 | 1.32 | 1.18 | 0.63 | 7.72 |
| Kl | 1.40 | 1.28 | 1.22 | 1.72 | 0.23 | 0.63 | 7.47 |
| Lbp | 0.50 | 0.06 | 0.00 | 0.40 | 0.08 | 0.68 | 6.96 |
| Eps8l2 | 0.18 | 0.08 | 0.00 | 0.09 | 0.07 | 0.10 | 7.36 |
| Lrriq1 | 0.49 | 0.70 | 1.51 | 0.60 | 0.09 | 0.19 | 7.68 |
| Psd2 | 0.34 | 0.62 | 0.24 | 0.23 | 2.28 | 2.13 | 7.64 |
| Frem1 | 0.20 | 0.14 | 0.15 | 0.07 | 1.73 | 0.85 | 6.33 |
| Rdh5 | 0.16 | 0.24 | 0.45 | 0.38 | 0.29 | 0.68 | 8.82 |
| Fap | 0.14 | 0.38 | 0.34 | 0.14 | 0.24 | 0.28 | 6.87 |
| Slc6a20a | 0.07 | 0.07 | 0.00 | 0.00 | 0.18 | 0.50 | 7.95 |
| Slc2a12 | 0.38 | 0.27 | 0.37 | 0.15 | 0.25 | 0.64 | 7.14 |
| Gmnc | 0.42 | 0.00 | 0.00 | 0.05 | 0.04 | 0.09 | 6.46 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Ppp1r1b | 0.67 | 1.11 | 0.15 | 0.67 | 0.56 | 0.98 | 7.52 |
| F5 | 0.03 | 0.11 | 0.07 | 0.03 | 0.05 | 0.38 | 6.06 |
| Atp2b3 | 6.14 | 6.05 | 5.48 | 6.23 | 5.88 | 2.46 | 8.27 |
| Col4a5 | 0.01 | 0.07 | 0.00 | 0.05 | 0.05 | 0.31 | 6.35 |
| Slc7a10 | 0.29 | 0.37 | 0.49 | 0.66 | 0.23 | 3.87 | 8.72 |
| Mfrp | 0.03 | 0.06 | 0.00 | 0.06 | 0.12 | 0.00 | 6.49 |
| Car12 | 5.37 | 2.67 | 0.52 | 2.52 | 0.55 | 0.46 | 8.36 |
| Slc13a4 | 3.76 | 4.28 | 4.36 | 4.32 | 4.18 | 5.06 | 8.28 |
| Ezr | 0.14 | 0.37 | 0.00 | 0.37 | 0.37 | 1.45 | 7.12 |
| Ccdc108 | 0.37 | 2.00 | 2.38 | 1.48 | 0.19 | 0.77 | 7.70 |
| Sulf1 | 0.15 | 0.70 | 0.43 | 0.34 | 0.14 | 0.56 | 7.10 |
| Abhd2 | 5.08 | 5.01 | 4.68 | 5.09 | 5.19 | 5.31 | 7.50 |
| Stk39 | 1.79 | 2.54 | 2.15 | 2.30 | 0.91 | 0.81 | 7.84 |
| Ucp2 | 0.61 | 0.34 | 0.69 | 0.43 | 0.97 | 1.14 | 6.82 |
| Dab2 | 0.07 | 0.23 | 0.00 | 0.24 | 0.36 | 1.61 | 7.12 |
| Mitf | 0.72 | 0.89 | 1.22 | 0.52 | 1.20 | 0.97 | 5.82 |
| Slc6a20b | 0.34 | 0.75 | 0.77 | 0.67 | 0.80 | 0.64 | 5.48 |
| Col4a3 | 0.05 | 0.00 | 0.47 | 0.06 | 0.02 | 0.05 | 6.51 |
| Prdm16 | 0.29 | 0.66 | 0.00 | 0.61 | 0.35 | 2.00 | 6.16 |
| Otx2 | 0.01 | 0.07 | 0.00 | 0.00 | 0.00 | 0.00 | 7.12 |
| Trpv4 | 0.01 | 0.12 | 0.07 | 0.15 | 0.07 | 0.22 | 6.07 |
| Fras1 | 1.41 | 2.66 | 1.28 | 2.11 | 0.91 | 0.25 | 6.18 |
| Efs | 0.04 | 0.00 | 0.00 | 0.00 | 0.45 | 2.39 | 6.95 |
| Lrrc23 | 0.07 | 0.24 | 0.00 | 0.15 | 0.00 | 0.26 | 6.73 |
| 1110059M19Rik | 0.04 | 0.04 | 0.00 | 0.00 | 0.00 | 0.07 | 6.94 |
| Wdr78 | 0.78 | 1.65 | 1.85 | 1.99 | 1.22 | 0.46 | 6.73 |
| Folr1 | 0.02 | 0.08 | 0.00 | 0.00 | 0.06 | 0.21 | 6.55 |
| Ace | 0.04 | 0.25 | 0.06 | 0.15 | 0.44 | 0.28 | 5.81 |
| Fhad1 | 2.01 | 0.35 | 1.25 | 0.18 | 0.20 | 0.74 | 7.03 |
| Mpp7 | 0.68 | 0.64 | 0.78 | 0.72 | 0.67 | 0.73 | 6.21 |
| Zkscan3 | 5.53 | 5.78 | 6.14 | 5.64 | 6.10 | 5.88 | 8.09 |
| Ccdc135 | 0.01 | 0.15 | 0.00 | 0.12 | 0.00 | 0.24 | 5.91 |
| Vat1l | 0.05 | 0.45 | 0.00 | 0.00 | 1.05 | 0.18 | 6.13 |
| Sh3d19 | 1.04 | 1.41 | 3.11 | 2.40 | 0.71 | 1.23 | 6.91 |
| Spag16 | 0.80 | 0.47 | 1.22 | 0.62 | 1.18 | 0.95 | 6.28 |
| Abca4 | 0.21 | 0.18 | 0.16 | 0.59 | 0.16 | 0.28 | 5.88 |
| Arhgap42 | 0.27 | 0.98 | 0.00 | 0.50 | 0.57 | 1.30 | 5.76 |
| Cpne2 | 0.07 | 2.74 | 0.00 | 2.23 | 1.38 | 1.53 | 6.68 |
| Slc4a10 | 5.90 | 6.26 | 6.32 | 5.97 | 6.00 | 2.53 | 7.71 |
| Slc4a2 | 0.70 | 1.29 | 0.97 | 1.98 | 0.74 | 1.02 | 7.03 |
| Slc12a2 | 1.58 | 1.49 | 2.62 | 2.11 | 1.74 | 2.55 | 6.69 |
| Spata17 | 0.06 | 0.08 | 0.21 | 0.00 | 0.19 | 0.19 | 6.25 |
| Ppfibp2 | 0.06 | 0.00 | 1.15 | 0.23 | 0.02 | 1.20 | 5.67 |
| Phldb2 | 0.05 | 0.10 | 0.00 | 0.00 | 0.16 | 0.95 | 5.55 |
| Calml4 | 0.05 | 0.03 | 0.18 | 0.09 | 0.00 | 0.39 | 6.58 |
| Msx1 | 0.04 | 0.15 | 0.00 | 0.14 | 0.11 | 0.51 | 6.11 |
| Lmx1a | 0.06 | 0.05 | 0.13 | 0.00 | 0.15 | 0.00 | 4.74 |
| Dnahc6 | 0.01 | 0.10 | 0.00 | 0.03 | 0.09 | 0.25 | 5.36 |
| Myo7a | 1.06 | 0.95 | 1.52 | 1.69 | 1.40 | 1.81 | 6.20 |
| Neat1 | 0.45 | 0.65 | 0.51 | 0.96 | 0.46 | 6.07 | 9.39 |
| BC021767 | 0.00 | 0.19 | 0.36 | 0.15 | 0.65 | 0.10 | 5.85 |
| Nhsl2 | 5.32 | 4.68 | 5.46 | 4.55 | 2.37 | 1.45 | 7.81 |
| Ccdc39 | 1.82 | 3.01 | 4.05 | 3.19 | 3.87 | 1.88 | 7.21 |
| Clic6 | 0.02 | 0.12 | 0.24 | 0.26 | 0.00 | 0.17 | 6.00 |
| Mroh7 | 0.61 | 1.13 | 0.00 | 0.15 | 0.14 | 0.89 | 5.90 |
| Acad8 | 2.03 | 2.64 | 3.19 | 3.15 | 3.05 | 1.54 | 7.67 |
| Col4a4 | 0.03 | 0.00 | 0.00 | 0.05 | 0.07 | 0.00 | 4.90 |
| Ccdc114 | 4.48 | 4.60 | 4.81 | 4.73 | 4.92 | 5.18 | 7.80 |
| Oca2 | 0.02 | 0.07 | 0.00 | 0.00 | 0.31 | 0.05 | 5.65 |
| Dnah11 | 0.04 | 0.05 | 0.00 | 0.05 | 0.07 | 0.22 | 4.09 |
| Stxbp4 | 2.90 | 3.31 | 3.16 | 3.39 | 2.99 | 2.19 | 7.27 |
| Vwa3a | 4.26 | 0.36 | 0.88 | 0.88 | 0.27 | 0.73 | 6.70 |
| Arsg | 0.30 | 0.54 | 0.72 | 0.96 | 0.58 | 1.48 | 6.11 |
| Pbxip1 | 0.25 | 0.44 | 0.27 | 0.40 | 0.17 | 2.84 | 6.74 |
| Mycbpap | 0.05 | 0.18 | 0.00 | 0.00 | 0.33 | 0.22 | 5.74 |
| 4932438H23Rik | 0.07 | 0.06 | 0.12 | 0.53 | 0.04 | 0.06 | 5.22 |
| St6galnac2 | 0.42 | 0.27 | 0.27 | 0.72 | 1.00 | 0.31 | 5.79 |
| Best3 | 1.12 | 0.21 | 0.00 | 0.55 | 0.14 | 0.05 | 5.72 |
| Ifi27 | 0.07 | 1.98 | 0.17 | 1.51 | 1.81 | 0.99 | 6.42 |
| Gm216 | 0.02 | 0.54 | 0.13 | 0.21 | 0.12 | 0.53 | 5.45 |
| 5930403L14Rik | 0.30 | 0.26 | 1.14 | 0.34 | 0.24 | 0.96 | 5.51 |
| 4632427E13Rik | 5.73 | 5.79 | 5.72 | 6.01 | 6.07 | 6.42 | 7.90 |
| Cgnl1 | 0.04 | 0.03 | 0.00 | 0.05 | 0.09 | 0.08 | 5.06 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Sostdc1 | 0.19 | 0.31 | 0.30 | 0.29 | 0.11 | 0.29 | 5.68 |
| Zfp185 | 0.31 | 0.42 | 0.00 | 0.60 | 0.00 | 0.04 | 5.51 |
| Lef1 | 0.59 | 0.33 | 1.43 | 0.79 | 0.58 | 0.91 | 4.98 |
| 1500015O10Rik | 0.07 | 0.31 | 0.12 | 0.16 | 0.14 | 0.52 | 6.28 |
| Slco1a4 | 0.02 | 0.00 | 0.00 | 0.12 | 0.00 | 0.10 | 5.03 |
| Sned1 | 0.49 | 0.24 | 0.27 | 0.70 | 0.49 | 2.08 | 6.05 |
| Pltp | 0.04 | 0.30 | 0.18 | 0.00 | 0.27 | 0.98 | 5.51 |
| Arl6ip1 | 7.08 | 7.32 | 6.26 | 6.81 | 6.00 | 6.37 | 8.79 |
| Synm | 0.76 | 1.35 | 1.31 | 1.24 | 0.73 | 0.91 | 5.13 |
| Fam161a | 0.39 | 0.55 | 0.00 | 0.57 | 0.22 | 1.02 | 5.48 |
| Igf2 | 0.04 | 0.11 | 0.13 | 0.06 | 0.05 | 0.47 | 4.70 |
| Sytl2 | 0.16 | 1.81 | 0.00 | 0.80 | 2.01 | 0.82 | 5.57 |
| Six3os1 | 1.03 | 0.62 | 1.69 | 0.71 | 0.73 | 1.46 | 5.02 |
| Nwd1 | 0.74 | 0.78 | 0.89 | 1.02 | 1.38 | 4.46 | 7.51 |
| Slc16a8 | 0.01 | 0.02 | 0.00 | 0.00 | 0.00 | 0.00 | 5.05 |
| Ifi27l1 | 0.30 | 3.43 | 0.20 | 2.64 | 2.16 | 1.78 | 7.04 |
| Pcolce2 | 0.50 | 1.17 | 0.97 | 1.21 | 0.69 | 0.56 | 5.27 |
| Ccdc141 | 4.95 | 4.90 | 5.64 | 5.36 | 5.32 | 5.78 | 7.69 |
| Kcne2 | 0.04 | 0.10 | 0.00 | 0.17 | 0.12 | 0.16 | 5.74 |
| Dnahc2 | 0.39 | 0.39 | 0.15 | 0.31 | 0.24 | 0.56 | 4.13 |
| Slc38a3 | 0.16 | 0.27 | 0.00 | 0.09 | 0.29 | 3.67 | 7.28 |
| L3mbtl3 | 0.54 | 0.61 | 0.31 | 0.75 | 1.10 | 0.45 | 4.96 |
| Cldn2 | 0.01 | 0.05 | 0.00 | 0.17 | 0.14 | 0.07 | 4.96 |
| Aar2 | 2.49 | 2.78 | 1.17 | 2.15 | 1.65 | 1.28 | 6.33 |
| Dnahc7b | 0.17 | 0.43 | 0.00 | 0.69 | 1.21 | 1.74 | 5.11 |
| Baiap2l1 | 0.30 | 0.48 | 1.44 | 0.96 | 0.49 | 0.10 | 5.44 |
| Gm26648 | 1.05 | 1.49 | 1.77 | 1.97 | 2.33 | 0.86 | 5.75 |
| Acacb | 0.06 | 0.08 | 0.00 | 0.06 | 0.14 | 0.71 | 4.73 |
| Gt(ROSA)26Sor | 2.21 | 3.56 | 3.33 | 5.30 | 2.80 | 0.63 | 8.15 |
| Sgk1 | 2.28 | 3.85 | 4.40 | 5.38 | 3.60 | 3.74 | 7.96 |
| Ttc21a | 0.01 | 0.04 | 0.00 | 0.00 | 0.00 | 0.16 | 4.20 |
| Tuft1 | 0.05 | 0.33 | 0.83 | 0.07 | 0.38 | 0.26 | 5.07 |
| Otx2os1 | 0.00 | 0.00 | 0.00 | 0.08 | 0.00 | 0.00 | 4.55 |
| Rfx2 | 0.26 | 0.13 | 0.00 | 0.22 | 0.06 | 0.30 | 4.75 |
| Efcab1 | 1.14 | 1.42 | 0.47 | 0.83 | 0.62 | 0.60 | 5.36 |
| Frrs1 | 0.20 | 0.16 | 0.00 | 0.21 | 0.09 | 0.15 | 4.66 |
| Crb2 | 0.27 | 0.29 | 0.39 | 0.10 | 0.06 | 0.52 | 4.46 |
| Epn3 | 0.02 | 0.11 | 0.00 | 0.11 | 0.04 | 0.15 | 4.88 |
| Mospd1 | 0.52 | 0.97 | 0.24 | 1.08 | 1.10 | 0.25 | 5.39 |
| Acaa2 | 0.59 | 0.45 | 0.45 | 0.50 | 0.61 | 0.59 | 5.25 |
| Ctnnal1 | 1.08 | 1.79 | 3.80 | 1.77 | 3.59 | 1.63 | 7.01 |
| Id3 | 0.13 | 0.16 | 0.00 | 0.24 | 0.82 | 2.06 | 6.61 |
| Sema3b | 0.09 | 0.32 | 0.00 | 0.16 | 0.18 | 0.42 | 4.50 |
| Tmem237 | 1.09 | 1.41 | 1.82 | 1.81 | 1.10 | 1.03 | 5.78 |
| Elovl7 | 0.56 | 0.82 | 2.71 | 1.02 | 0.76 | 1.43 | 5.77 |
| Pcp4l1 | 0.04 | 0.59 | 0.70 | 0.45 | 2.04 | 0.53 | 5.87 |
| Esrrb | 0.06 | 0.03 | 0.00 | 0.08 | 0.11 | 0.09 | 3.75 |
| Mapk4 | 2.54 | 2.16 | 0.21 | 0.94 | 1.43 | 2.19 | 5.74 |
| Zfp280d | 6.02 | 6.10 | 5.91 | 6.20 | 6.22 | 6.31 | 7.53 |
| Cfap44 | 1.26 | 1.70 | 0.94 | 1.34 | 0.20 | 0.41 | 5.41 |
| Wdr52 | 0.74 | 1.16 | 0.41 | 0.86 | 0.10 | 0.30 | 4.83 |
| Gadd45g | 1.90 | 1.84 | 2.27 | 2.39 | 0.96 | 1.98 | 6.49 |
| Cldn1 | 0.06 | 0.36 | 0.00 | 0.00 | 0.25 | 0.13 | 4.12 |
| Sgms1 | 3.30 | 5.55 | 5.78 | 5.66 | 5.81 | 2.12 | 7.39 |
| Msx1as | 0.01 | 0.00 | 0.00 | 0.06 | 0.09 | 0.07 | 4.68 |
| Spag6 | 1.16 | 1.18 | 1.45 | 0.98 | 0.42 | 0.52 | 5.32 |
| Lhb | 0.02 | 0.00 | 0.00 | 0.07 | 0.09 | 0.09 | 4.47 |
| Rilp | 0.15 | 0.08 | 0.16 | 0.08 | 0.04 | 0.00 | 4.45 |
| Ccdc24 | 0.25 | 0.73 | 0.59 | 0.43 | 0.81 | 0.60 | 5.08 |
| Ifi35 | 0.02 | 0.03 | 0.24 | 0.59 | 0.06 | 0.17 | 4.75 |
| 6720401G13Rik | 5.34 | 5.44 | 6.25 | 5.96 | 6.15 | 4.76 | 7.36 |
| Amer1 | 0.99 | 1.44 | 1.86 | 1.06 | 1.39 | 1.04 | 5.54 |
| Zfp119a | 0.94 | 1.18 | 1.05 | 1.25 | 0.72 | 0.83 | 4.82 |
| Crhr2 | 0.30 | 0.18 | 0.00 | 0.00 | 0.05 | 0.18 | 4.35 |
| Gm17200 | 0.24 | 0.04 | 0.24 | 0.15 | 0.33 | 0.16 | 4.21 |
| Csrp2 | 0.15 | 0.21 | 0.00 | 0.31 | 0.37 | 0.24 | 4.74 |
| Dmpk | 1.48 | 1.88 | 1.95 | 2.94 | 1.57 | 2.24 | 5.89 |
| Gm7173 | 0.18 | 0.43 | 0.00 | 0.20 | 0.29 | 0.24 | 5.08 |
| Cnst | 2.19 | 2.11 | 1.97 | 2.26 | 1.57 | 0.93 | 5.77 |
| Ctnna1 | 0.66 | 0.59 | 0.26 | 0.64 | 1.06 | 2.17 | 5.73 |
| Lepr | 0.80 | 1.06 | 1.17 | 1.61 | 1.09 | 1.09 | 4.37 |
| Intu | 4.09 | 4.82 | 4.57 | 4.58 | 4.66 | 4.73 | 6.24 |
| Antxr1 | 0.06 | 0.30 | 0.19 | 0.68 | 0.45 | 0.88 | 4.48 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Atp10d | 1.14 | 0.80 | 2.16 | 1.55 | 0.81 | 1.15 | 5.76 |
| E530011L22Rik | 1.08 | 0.87 | 1.01 | 1.12 | 1.55 | 0.81 | 4.54 |
| Slc39a13 | 1.56 | 2.17 | 2.52 | 2.23 | 2.77 | 1.50 | 6.20 |
| Ccnd3 | 1.06 | 1.77 | 1.46 | 1.32 | 0.92 | 1.99 | 5.82 |
| Spata13 | 3.05 | 0.35 | 0.09 | 0.00 | 0.36 | 1.40 | 5.50 |
| Igfbp2 | 0.09 | 0.35 | 0.00 | 0.28 | 0.26 | 1.25 | 5.75 |
| Top3b | 5.60 | 6.09 | 5.93 | 6.40 | 6.39 | 3.85 | 8.08 |
| Ephx1 | 0.30 | 0.73 | 0.84 | 1.87 | 0.34 | 0.78 | 5.32 |
| Cish | 0.09 | 0.26 | 0.00 | 0.45 | 0.43 | 0.32 | 4.24 |
| Vcam1 | 0.06 | 0.10 | 0.00 | 0.23 | 0.19 | 0.75 | 4.43 |
| Tns1 | 0.06 | 0.44 | 0.28 | 0.24 | 0.24 | 1.67 | 4.79 |
| Setd5 | 5.94 | 6.17 | 5.98 | 6.45 | 6.23 | 6.35 | 7.81 |
| Tubb4b | 4.96 | 6.60 | 3.93 | 6.49 | 5.33 | 4.79 | 8.04 |
| 2010015L04Rik | 3.29 | 2.40 | 2.97 | 2.28 | 2.66 | 2.50 | 6.06 |
| Igfn1 | 0.03 | 0.08 | 0.16 | 0.07 | 0.00 | 0.00 | 3.64 |
| Krt18 | 0.02 | 0.00 | 0.00 | 0.00 | 0.16 | 0.20 | 4.60 |
| Slco1c1 | 0.09 | 0.12 | 0.00 | 0.18 | 0.23 | 1.78 | 5.61 |
| Myo5c | 0.18 | 0.37 | 0.29 | 0.18 | 0.69 | 0.15 | 3.33 |
| Ap1s2 | 3.38 | 1.38 | 0.34 | 0.66 | 3.56 | 2.27 | 6.55 |
| Arhgap28 | 0.01 | 0.08 | 0.00 | 0.17 | 0.06 | 0.07 | 3.48 |
| Frmd4b | 5.65 | 2.23 | 1.72 | 1.85 | 2.74 | 4.68 | 6.96 |
| Efcab12 | 0.65 | 1.81 | 1.30 | 1.02 | 0.74 | 0.32 | 4.97 |
| Dhrs11 | 0.10 | 0.28 | 0.00 | 0.89 | 0.57 | 0.44 | 4.12 |
| Tjp3 | 0.01 | 0.06 | 0.09 | 0.58 | 0.04 | 0.39 | 4.34 |
| Spef2 | 0.09 | 0.07 | 0.31 | 0.13 | 0.05 | 0.42 | 4.13 |
| Tinagl1 | 0.02 | 0.00 | 0.00 | 0.07 | 0.03 | 0.16 | 4.36 |
| Ttll5 | 3.40 | 5.03 | 5.20 | 5.66 | 5.67 | 3.80 | 7.23 |
| Sgms2 | 0.28 | 0.48 | 0.92 | 0.55 | 0.69 | 0.46 | 4.35 |
| Cflar | 4.16 | 4.43 | 4.13 | 4.72 | 4.13 | 4.79 | 6.61 |
| Stard13 | 2.86 | 0.87 | 3.87 | 1.78 | 1.02 | 2.91 | 6.33 |
| Id1 | 0.03 | 0.08 | 0.00 | 0.00 | 0.11 | 0.72 | 5.05 |
| 4930556M19Rik | 0.51 | 0.29 | 0.97 | 0.41 | 0.64 | 0.96 | 4.75 |
| Ssfa2 | 1.52 | 2.33 | 3.29 | 4.50 | 2.18 | 3.10 | 6.47 |
| Iqub | 0.26 | 0.35 | 0.00 | 0.64 | 0.08 | 0.39 | 3.82 |
| Slc5a3 | 3.36 | 5.43 | 4.76 | 5.55 | 5.27 | 2.93 | 6.94 |
| Plekhg3 | 0.68 | 0.11 | 0.14 | 0.10 | 0.12 | 1.28 | 4.58 |
| Klhdc7a | 0.03 | 0.06 | 0.00 | 0.12 | 0.04 | 0.59 | 3.70 |
| Flcn | 5.44 | 5.49 | 5.33 | 5.30 | 5.68 | 5.40 | 7.32 |
| Fam86 | 0.95 | 0.72 | 1.37 | 0.84 | 1.13 | 1.41 | 5.07 |
| 10-Sep | 0.16 | 0.21 | 0.31 | 0.36 | 0.39 | 0.42 | 4.07 |
| Bcl2l1 | 5.40 | 5.01 | 3.24 | 5.03 | 4.25 | 4.61 | 7.46 |
| Spag8 | 0.14 | 0.45 | 0.15 | 0.17 | 0.25 | 0.16 | 4.03 |
| Parp4 | 0.11 | 0.12 | 0.68 | 0.19 | 0.18 | 0.78 | 4.29 |
| Arid5b | 1.92 | 2.10 | 1.40 | 0.38 | 2.47 | 1.52 | 5.11 |
| Tc2n | 4.06 | 4.20 | 3.88 | 4.27 | 4.54 | 4.82 | 6.09 |
| Suv420h2 | 2.06 | 2.15 | 2.57 | 2.76 | 2.30 | 2.23 | 5.78 |
| Kif9 | 0.41 | 1.35 | 1.93 | 1.10 | 0.43 | 0.51 | 4.90 |
| Gpr98 | 4.47 | 4.49 | 4.52 | 4.66 | 4.75 | 5.40 | 6.60 |
| C1qtnf5 | 0.08 | 0.08 | 0.00 | 0.00 | 0.13 | 0.19 | 3.95 |
| Foxj1 | 0.07 | 0.11 | 0.00 | 0.12 | 0.07 | 0.18 | 3.26 |
| Zic5 | 0.08 | 0.13 | 0.07 | 0.04 | 0.36 | 0.72 | 3.88 |
| Sgk3 | 1.34 | 1.45 | 1.72 | 1.41 | 1.14 | 1.98 | 4.96 |
| Cobll1 | 1.08 | 1.00 | 1.86 | 0.92 | 0.85 | 2.50 | 5.28 |
| Phactr2 | 0.36 | 1.60 | 0.90 | 2.98 | 1.17 | 1.73 | 5.47 |
| Sorbs3 | 0.06 | 0.19 | 0.00 | 0.13 | 0.19 | 3.37 | 6.24 |
| Steap1 | 0.03 | 0.12 | 0.09 | 0.10 | 0.05 | 0.00 | 3.70 |
| Hyal1 | 0.79 | 1.05 | 1.43 | 1.43 | 1.79 | 1.50 | 5.17 |
| Armc2 | 1.47 | 2.07 | 2.48 | 2.49 | 2.59 | 1.24 | 5.16 |
| Spint2 | 2.44 | 1.52 | 0.47 | 1.02 | 0.31 | 0.32 | 5.47 |
| Aox1 | 0.54 | 0.57 | 1.05 | 1.31 | 0.63 | 2.57 | 5.69 |
| Serhl | 1.72 | 2.19 | 1.94 | 2.38 | 2.03 | 2.32 | 5.64 |
| Tsix | 0.11 | 0.21 | 0.00 | 0.48 | 0.04 | 0.28 | 3.40 |
| Tekt1 | 0.08 | 0.31 | 0.92 | 0.09 | 0.04 | 0.28 | 4.06 |
| 1810022K09Rik | 2.29 | 2.88 | 2.26 | 2.61 | 2.16 | 1.77 | 5.75 |
| C030017K20Rik | 1.09 | 0.91 | 0.92 | 0.69 | 0.61 | 0.75 | 4.30 |
| Slc12a4 | 0.29 | 0.13 | 0.00 | 0.11 | 0.10 | 2.69 | 5.68 |
| Cfap69 | 0.76 | 3.62 | 4.45 | 3.41 | 1.91 | 0.57 | 6.83 |
| Rai14 | 0.06 | 0.44 | 0.13 | 0.13 | 0.08 | 0.36 | 3.55 |
| Slc31a1 | 0.76 | 0.83 | 0.66 | 1.18 | 0.68 | 0.61 | 4.43 |
| Nek5 | 0.03 | 0.04 | 0.00 | 0.06 | 0.00 | 0.19 | 3.85 |
| Dnah2 | 0.65 | 0.44 | 0.26 | 0.41 | 0.29 | 0.59 | 3.84 |
| Nqo1 | 0.12 | 0.07 | 0.00 | 0.09 | 0.13 | 0.17 | 3.63 |
| Col8a1 | 0.04 | 0.08 | 0.00 | 0.13 | 0.05 | 0.15 | 3.39 |

TABLE 18-continued marker genes for the major cell types in the adult hippocampus
Average expression over all nuclei in each sub-cluster, log TPM value

| Gene names | Granule cells DG | Pyramidal neurons CA1 | Pyramidal neurons CA2 | Pyramidal neurons CA3 | GABAergic interneurons | Glia-like cells | Ependymal cells |
|---|---|---|---|---|---|---|---|
| Tes | 0.03 | 0.07 | 0.00 | 0.22 | 0.06 | 0.87 | 3.72 |
| Scarf1 | 0.13 | 0.16 | 0.08 | 0.06 | 0.17 | 0.09 | 3.25 |
| Pcbp3 | 3.30 | 4.28 | 3.00 | 4.50 | 2.81 | 1.09 | 6.43 |
| Cd59a | 0.19 | 0.18 | 0.11 | 0.15 | 0.56 | 0.34 | 3.63 |
| Ccp110 | 1.97 | 3.51 | 1.56 | 3.63 | 3.20 | 3.03 | 5.98 |
| Syne2 | 2.75 | 2.95 | 5.19 | 3.79 | 3.65 | 2.82 | 6.76 |
| Pid1 | 0.91 | 3.22 | 3.18 | 3.64 | 3.01 | 3.43 | 6.31 |
| 9530091C08Rik | 4.51 | 4.39 | 3.60 | 4.68 | 4.78 | 5.26 | 6.53 |
| Ptgds | 0.85 | 2.85 | 0.95 | 2.28 | 2.07 | 5.30 | 8.41 |
| D630024D03Rik | 0.03 | 0.04 | 0.00 | 0.00 | 0.00 | 0.27 | 3.63 |
| Prob1 | 0.23 | 0.12 | 0.12 | 0.26 | 0.47 | 0.25 | 3.15 |
| Hist1h2br | 0.30 | 0.08 | 0.44 | 0.12 | 0.15 | 0.51 | 3.71 |
| Hist1h2bq | 0.30 | 0.08 | 0.44 | 0.12 | 0.15 | 0.51 | 3.71 |
| Slc16a6 | 0.40 | 1.09 | 0.48 | 0.81 | 0.47 | 0.43 | 3.96 |
| Slcl16a2 | 4.72 | 3.39 | 1.89 | 2.99 | 1.31 | 2.41 | 6.17 |
| Slc23a2 | 5.81 | 6.07 | 6.08 | 5.80 | 6.15 | 4.83 | 7.46 |
| Strip2 | 0.96 | 2.80 | 6.72 | 4.10 | 2.16 | 1.36 | 7.92 |
| Fam53b | 4.73 | 2.97 | 2.17 | 3.11 | 1.97 | 3.06 | 6.85 |
| Esrrg | 0.58 | 0.81 | 1.21 | 0.63 | 1.91 | 0.33 | 4.78 |
| Heg1 | 1.35 | 0.25 | 0.38 | 1.07 | 1.30 | 1.59 | 4.81 |
| Pikfyve | 3.80 | 4.26 | 3.38 | 4.28 | 4.06 | 4.04 | 5.75 |
| Lamb2 | 0.06 | 0.00 | 0.00 | 0.31 | 0.13 | 1.13 | 3.92 |
| Sowahc | 0.21 | 0.46 | 0.19 | 0.06 | 0.94 | 0.60 | 3.62 |
| Pex11a | 0.74 | 0.53 | 0.59 | 0.53 | 0.45 | 0.47 | 3.76 |
| Gm13139 | 1.11 | 1.25 | 1.38 | 0.56 | 1.07 | 2.11 | 5.05 |
| Trip10 | 0.21 | 0.29 | 0.08 | 0.60 | 0.13 | 0.56 | 3.36 |
| Slc19a1 | 1.07 | 2.16 | 0.97 | 2.02 | 1.32 | 0.74 | 4.78 |
| Brwd3 | 1.42 | 1.43 | 1.92 | 1.69 | 0.99 | 0.44 | 4.53 |
| Mast4 | 5.60 | 5.57 | 5.59 | 5.89 | 5.36 | 5.63 | 7.31 |
| Mapk6 | 0.53 | 1.09 | 0.92 | 1.56 | 1.55 | 1.06 | 4.08 |
| Tspan32os | 0.02 | 0.00 | 0.11 | 0.07 | 0.04 | 0.52 | 3.70 |
| Cgn | 0.50 | 2.60 | 2.11 | 1.47 | 4.09 | 0.79 | 5.93 |
| Tbc1d9 | 1.04 | 2.34 | 0.80 | 2.09 | 5.28 | 1.01 | 6.48 |
| Cpq | 0.05 | 0.13 | 0.00 | 0.00 | 0.28 | 0.76 | 3.94 |
| Heatr8 | 0.16 | 0.22 | 0.00 | 0.06 | 0.06 | 0.35 | 2.49 |
| Msi1 | 0.32 | 0.55 | 0.84 | 0.52 | 1.28 | 1.67 | 4.09 |
| Agtrap | 0.25 | 0.26 | 0.80 | 0.48 | 0.15 | 0.77 | 3.44 |
| Rfwd3 | 1.46 | 1.82 | 1.99 | 2.07 | 1.35 | 0.74 | 4.42 |
| 9830147E19Rik | 3.96 | 4.12 | 3.98 | 3.95 | 4.04 | 4.26 | 5.91 |
| Shroom3 | 0.04 | 0.13 | 0.00 | 0.20 | 0.17 | 0.58 | 3.09 |
| Slc39a12 | 0.09 | 0.16 | 0.00 | 0.27 | 0.24 | 2.37 | 5.41 |
| Msi2 | 2.96 | 4.70 | 4.35 | 4.65 | 5.47 | 5.38 | 6.98 |
| Col27a1 | 0.20 | 0.36 | 0.26 | 0.24 | 0.28 | 2.12 | 5.01 |
| Mok | 1.02 | 2.21 | 1.79 | 1.58 | 1.02 | 0.72 | 4.55 |
| Rbbp8 | 0.07 | 0.47 | 0.59 | 0.71 | 0.50 | 0.57 | 3.41 |
| Nckap5 | 3.21 | 4.31 | 3.33 | 4.21 | 3.52 | 4.91 | 6.19 |
| 4930522L14Rik | 0.39 | 0.57 | 0.74 | 0.25 | 0.58 | 0.62 | 3.31 |

TABLE 19

| Gene names | Oligo progenitor cells | Microglia cells | Oligodendrocytes | Astrocytes | Epthelial cells | Non-glia cells |
|---|---|---|---|---|---|---|
| Gpr17 | 8.832719052 | 0 | 0 | 0 | 0 | 0.518609052 |
| Sox10 | 7.523606185 | 0 | 5.219070604 | 0 | 0 | 0 |
| Cspg4 | 7.603306528 | 0 | 0.88557816 | 0.169305204 | 0 | 0.407777078 |
| Tnr | 6.854621364 | 0.973066037 | 0.775973973 | 0.261387192 | 6.652558815 | 3.164594105 |
| Pcdh15 | 7.24970093 | 0 | 1.160614479 | 0.351375984 | 3.143928178 | 2.794881365 |
| Matn4 | 8.160856553 | 0 | 1.003881506 | 0 | 0 | 0.237888999 |
| Vcan | 7.492374522 | 0 | 0 | 1.341934215 | 1.626833684 | 1.463013583 |
| Pdgfra | 7.555046748 | 0 | 0 | 0.234576539 | 1.311409033 | 1.413492744 |
| Dscam | 5.966799141 | 0 | 0.842215575 | 0.232478338 | 1.937709259 | 1.576047705 |
| Olig1 | 8.201075516 | 0 | 5.909690321 | 1.682938891 | 0 | 0 |
| Hip1r | 6.572227926 | 1.802258804 | 0.603892194 | 3.007310684 | 0 | 0.531805493 |
| Ppfibp1 | 5.835644264 | 0 | 0.342049407 | 0.275194949 | 1.300749392 | 0.857995945 |
| Grin3a | 5.822854732 | 1.373837144 | 0.287514217 | 1.298601256 | 0.526719306 | 0.518269973 |
| Neu4 | 6.867573295 | 0 | 0 | 0.232877335 | 0 | 0.796380065 |
| Itga9 | 4.001226145 | 0.963036217 | 0.377436409 | 0 | 0 | 0 |
| 3110035E14Rik | 6.30435214 | 0.940684585 | 2.128266042 | 0.688911983 | 1.620018333 | 0.970606772 |
| Slc35f1 | 5.332169771 | 0 | 0 | 0.416231471 | 1.592528646 | 1.714743767 |
| Slc1a1 | 6.347134086 | 0 | 2.058097882 | 0.693918118 | 3.4134583 | 1.573675939 |

TABLE 19-continued

| Gene names | Oligo progenitor cells | Microglia cells | Oligodendrocytes | Astrocytes | Epthelial cells | Non-glia cells |
|---|---|---|---|---|---|---|
| Cacng4 | 6.001560107 | 0.791415606 | 0.79636208 | 0.949700725 | 0.417353891 | 0.641203213 |
| Olig2 | 6.4531754 | 0 | 3.837137316 | 1.019747272 | 0 | 0.483046104 |
| Pllp | 6.787601133 | 0 | 6.32043075 | 0.652864236 | 0 | 0 |
| Cercam | 5.086968028 | 1.267836738 | 3.419105885 | 0.691206183 | 1.269595202 | 1.011713749 |
| Rgcc | 6.190493187 | 0 | 0.626598353 | 1.358150269 | 0 | 0 |
| Traf4 | 5.051557826 | 0 | 0 | 0.430332093 | 0 | 0 |
| Ugdh | 6.293718001 | 1.835536691 | 1.047423688 | 0.669026589 | 1.379579264 | 1.878438659 |
| Elfn2 | 5.017846829 | 0 | 1.430548839 | 0.850771857 | 0.981638143 | 1.650642983 |
| Cask | 5.122124232 | 0.71726827 | 2.151428959 | 1.686531898 | 2.267289729 | 1.713712469 |
| Cobl | 4.733038577 | 0 | 0.798682823 | 0.465933377 | 1.913923714 | 0.872732516 |
| Xylt1 | 5.359092668 | 0 | 0 | 1.892381327 | 1.024502685 | 1.192144571 |
| Cdh13 | 5.925549332 | 0 | 1.033790852 | 0.797920805 | 3.339795946 | 2.516277804 |
| C1ql1 | 4.780276669 | 0 | 0 | 0 | 0 | 0 |
| Cyth4 | 0 | 8.522163877 | 0.289144464 | 0.182689037 | 0 | 0.228577806 |
| Hmha1 | 0 | 7.782350336 | 0 | 0.153708317 | 0 | 0 |
| Inpp5d | 0.503965892 | 8.143425389 | 0 | 0.133352258 | 0 | 0.387640662 |
| Laptm5 | 0 | 7.922814682 | 0 | 0 | 0 | 0 |
| Cd33 | 0 | 7.649899053 | 0 | 0 | 0 | 0.658840294 |
| Csf1r | 0 | 8.610179786 | 0.414684276 | 0 | 0 | 0 |
| Mpeg1 | 0 | 6.600558218 | 0 | 0 | 0 | 0.193057447 |
| Abca9 | 0 | 6.102785094 | 0 | 0 | 0.428411732 | 0.470191931 |
| Pag1 | 2.131607677 | 7.35349373 | 0.57284443 | 2.232393348 | 1.979222955 | 1.00610005 |
| Cldn11 | 1.50547059 | 0 | 10.04359368 | 0.590051283 | 0 | 0.6994067 |
| Mobp | 0.594379969 | 0 | 9.360633203 | 1.338094778 | 1.40827271 | 0 |
| Mag | 0.790980182 | 0 | 9.617560606 | 0.65745809 | 0 | 0 |
| Mal | 1.086222235 | 0 | 9.535746592 | 0.986574825 | 0 | 0.207662186 |
| Mog | 0.748812119 | 0 | 9.332085936 | 1.027605258 | 0 | 0 |
| Qdpr | 3.081943897 | 0 | 9.016425689 | 1.682399213 | 2.934288187 | 1.619216226 |
| Csrp1 | 0.626319153 | 0 | 8.209099917 | 3.258647896 | 0 | 0 |
| Efnb3 | 3.128397993 | 0.85841784 | 7.628213375 | 0.554997545 | 0 | 2.404113268 |
| Ttyh2 | 1.023326828 | 0.837112173 | 8.091802622 | 2.699204586 | 1.021771182 | 0.954861496 |
| Epb4.1l3 | 2.001901858 | 0 | 7.532861048 | 1.559838859 | 0 | 2.505532211 |
| Apod | 0.860037375 | 1.499429634 | 8.74859057 | 1.072360103 | 0 | 1.582417314 |
| Slc44a1 | 1.416094051 | 0 | 6.932329936 | 0.652363163 | 1.516491153 | 1.413753624 |
| Kndc1 | 0 | 0 | 8.101647026 | 1.395772473 | 4.009812097 | 2.748140161 |
| Gpr37 | 0 | 1.152589831 | 7.714810926 | 1.513404159 | 0 | 0.51169748 |
| Tmem151a | 0 | 1.68638452 | 7.419077535 | 1.084685093 | 0 | 1.462979645 |
| Cntn2 | 0.484479448 | 0.596540989 | 7.333549195 | 1.327258933 | 0 | 1.545096092 |
| 4-Sep | 0.7876138 | 0 | 9.241903655 | 2.035633134 | 0 | 1.925500297 |
| Itpk1 | 2.13883406 | 0 | 7.18145095 | 1.804875204 | 0 | 0.873064089 |
| Car2 | 0.750909557 | 0 | 8.408628855 | 2.148650441 | 0 | 1.280156244 |
| Cryab | 0.709910743 | 0 | 7.921326208 | 0.849547012 | 0 | 0.892571504 |
| Tspan2 | 2.030450942 | 0 | 7.857294956 | 0.474532324 | 0 | 1.273241131 |
| Tnfaip6 | 0.400631923 | 0.836728809 | 7.499439995 | 0.439287369 | 0 | 0.227996559 |
| Gm10471 | 1.652638834 | 0 | 6.751051944 | 0.662592988 | 3.076202849 | 2.691949991 |
| Plekhh1 | 0 | 0 | 6.668970008 | 0.436963996 | 1.23557593 | 0.816374788 |
| Gm7347 | 0.628801896 | 0 | 6.298340442 | 0.502138106 | 1.627194346 | 1.970740946 |
| Hapln2 | 0.571026117 | 0 | 7.753534893 | 0.577303069 | 0 | 0.222081773 |
| Arhgap23 | 1.892393303 | 0.815607287 | 6.380662693 | 2.435175414 | 0 | 1.817233201 |
| Myrf | 1.561804488 | 0 | 6.174053299 | 0.194854304 | 0 | 0.187197769 |
| Lgi3 | 1.446460097 | 1.613802835 | 7.543534628 | 1.724423598 | 3.449110306 | 0.942533415 |
| Arhgef10 | 1.865156669 | 0 | 6.81219218 | 1.823640684 | 1.693522201 | 1.556141358 |
| Ugt8a | 4.159336352 | 0 | 7.027870792 | 0.293020457 | 1.407441702 | 0.785936136 |
| Dip2a | 1.628419765 | 0 | 6.056393283 | 2.043507644 | 0 | 2.172453899 |
| Ccp110 | 3.096337663 | 0 | 6.824314002 | 1.621859672 | 0 | 2.775206976 |
| Asphd1 | 0 | 0.804332452 | 6.711030237 | 0.796274223 | 0 | 1.880122304 |
| 5031410I06Rik | 0.550997241 | 0 | 6.539823104 | 0.78067073 | 4.170396216 | 1.951021455 |
| Fa2h | 4.092903919 | 0 | 6.899354806 | 0.544266327 | 0 | 0 |
| Ndrg1 | 0 | 0.710851796 | 6.636788803 | 0.222218669 | 0 | 1.820444583 |
| Stmn4 | 3.095719177 | 0 | 6.847160282 | 1.363201669 | 0 | 2.434076882 |
| Jam3 | 3.013538493 | 0.936817689 | 7.192842885 | 1.210154719 | 0 | 1.329829244 |
| Unc5b | 0 | 0 | 5.247379007 | 0.770890629 | 0 | 0.755302055 |
| Taldo1 | 2.613655489 | 3.463744106 | 7.24132304 | 1.651320963 | 4.001148065 | 0.600511923 |
| Erbb2ip | 0 | 1.35179665 | 5.620504405 | 1.936805634 | 0 | 2.512968187 |
| Tmem63a | 0 | 0 | 6.648636551 | 0.517967683 | 0 | 0 |
| Ypel2 | 0.701392954 | 0.921994723 | 5.678161604 | 0.910252341 | 0.937553785 | 1.931690061 |
| Wdr54 | 2.47805419 | 0 | 5.408236165 | 1.201325018 | 2.328825539 | 1.323572752 |
| Tpm | 0.730583815 | 2.004623322 | 5.888063691 | 0.2585393 | 0 | 0.859194958 |
| Gm21847 | 0.641764352 | 0 | 6.287652829 | 0.898663482 | 3.88421368 | 1.75393034 |
| Ado | 2.093498585 | 1.460047784 | 6.246967368 | 0.710237516 | 0 | 0.190301166 |
| Kctd13 | 0.744369403 | 0 | 6.859223678 | 1.893367804 | 1.829531473 | 0.898731673 |
| Serinc5 | 5.174930147 | 0 | 6.045701954 | 0.354973149 | 2.737554552 | 2.00737141 |
| Speer7-ps1 | 1.860588524 | 0 | 6.687969308 | 1.01283213 | 5.153546693 | 2.004311921 |
| Adamts4 | 0.371338024 | 2.383848404 | 5.50271938 | 0.169319605 | 0 | 0.702255822 |
| Slc12a2 | 2.177575532 | 1.984788326 | 6.306342451 | 1.24992104 | 3.234629708 | 0.812438427 |
| Tppp3 | 0 | 0 | 6.732527931 | 0.866733679 | 0 | 2.509307643 |
| Gm10220 | 0.454889324 | 0 | 6.004574041 | 0.600004503 | 2.570204285 | 2.223566521 |
| Pik3c2b | 1.919879781 | 0.890498622 | 5.493361305 | 0.301367192 | 0 | 2.185714132 |

TABLE 19-continued

| Gene names | Oligo progenitor cells | Microglia cells | Oligodendrocytes | Astrocytes | Epthelial cells | Non-glia cells |
|---|---|---|---|---|---|---|
| Speer4a | 0.492864714 | 0 | 5.718727532 | 0.666094784 | 2.14946956 | 2.173332309 |
| Pex5l | 0.375687313 | 0 | 5.301371662 | 0.66778623 | 0 | 0.5683071 |
| Rcbtb1 | 0.61291222 | 3.783328968 | 6.436295715 | 1.128644025 | 1.463741814 | 2.057305755 |
| Desi1 | 1.368798102 | 0 | 6.588247258 | 2.740335275 | 0 | 0.802252809 |
| Slain1 | 0 | 0 | 5.359826334 | 0.406628197 | 0 | 0.282883714 |
| Pacs2 | 1.395354811 | 0.824434267 | 5.816109014 | 2.17130709 | 0 | 1.535126527 |
| Pllp | 6.787601133 | 0 | 6.32043075 | 0.652864236 | 0 | 0 |
| Pigz | 0 | 0 | 5.347369562 | 0.487836678 | 0 | 0.442153046 |
| Opalin | 1.207633041 | 0 | 6.067192404 | 0.523767139 | 0 | 0 |
| Grb14 | 3.369545029 | 0 | 6.472739275 | 0.494959573 | 4.63935243 | 2.385608329 |
| Endod1 | 0 | 0 | 5.732877827 | 0.888475391 | 0.905177577 | 0.872120751 |
| Scd1 | 0 | 0 | 5.073705786 | 1.196435682 | 0 | 0.249898941 |
| Smad7 | 0 | 1.167505665 | 4.368701337 | 0.51521095 | 0 | 0 |
| Litaf | 0.669809888 | 2.538841423 | 5.465292582 | 0.519630084 | 0 | 0.237969484 |
| Pip4k2a | 0.667025733 | 1.678241123 | 4.986891421 | 0.147802947 | 0 | 0 |
| Rtkn | 4.808162575 | 0 | 6.581994916 | 1.198065983 | 3.609465215 | 0.904418566 |
| Nkain1 | 0.502224813 | 0 | 5.09302832 | 0.650985455 | 0 | 0.88174543 |
| Agpat4 | 2.297006252 | 1.404802308 | 5.970847957 | 0.885437494 | 1.141505826 | 3.336229294 |
| Dusp26 | 2.586479855 | 0 | 6.2957577 | 0.164792059 | 0 | 1.398540491 |
| Gjb1 | 0 | 0 | 5.23833384 | 0 | 0 | 0 |
| Kctd3 | 2.982969604 | 0 | 5.572413052 | 1.430034054 | 1.070650493 | 1.163136821 |
| Arrdc3 | 0.707705127 | 1.00890997 | 5.642130545 | 1.613681471 | 0.802574229 | 0.829539485 |
| Dnajb2 | 0 | 0 | 6.07652155 | 2.638149482 | 0 | 0.814306079 |
| Speer8-ps1 | 0 | 1.300146194 | 4.630751361 | 0 | 1.711670845 | 1.468891342 |
| Evi2a | 1.38900034 | 4.005811066 | 5.894572643 | 0.769292146 | 0 | 0.733455649 |
| Speer4d | 0 | 0 | 4.810331954 | 0.260261395 | 2.611323495 | 1.251260388 |
| Plekhg3 | 0 | 1.311435173 | 4.59717432 | 0.444448547 | 0 | 0.883412502 |
| Arsg | 1.586622145 | 1.021031074 | 5.247779225 | 0.6723159 | 0 | 0 |
| Slc6a9 | 0.993679899 | 0 | 5.590510287 | 1.476210427 | 1.374525236 | 1.311616441 |
| Hid1 | 0.535548105 | 0 | 4.680332382 | 0.51034834 | 4.239992247 | 2.645360706 |
| Rhob | 1.904103296 | 0 | 5.483012904 | 2.022505518 | 1.8632957 | 1.743759122 |
| Galnt6 | 0 | 0 | 4.051318347 | 0 | 0 | 0 |
| Gjc2 | 0 | 0 | 4.783566198 | 0.255738356 | 0 | 0 |
| Il33 | 0 | 0 | 4.545627336 | 0 | 0 | 0.229920952 |
| Gnai1 | 1.313530217 | 0 | 5.205016234 | 0.882593706 | 0 | 0.457691155 |
| Mcam | 0.534699396 | 0 | 4.649885824 | 0 | 0 | 0 |
| 1700047M11Rik | 2.051609752 | 0 | 4.634245642 | 0.893451285 | 0 | 0.397418819 |
| 8-Mar | 1.759260724 | 0 | 4.477850137 | 0.547545283 | 0 | 0.365843997 |
| Sox10 | 7.523606185 | 0 | 5.219070604 | 0 | 0 | 0 |
| Plin4 | 0 | 0 | 4.935770195 | 1.251239846 | 1.821561408 | 1.094956585 |
| Speer4b | 1.205715713 | 0 | 4.411210908 | 0.727733629 | 1.181627689 | 1.872697151 |
| Lpar1 | 0 | 0 | 4.372270557 | 0.3551402 | 0 | 0.355655391 |
| Arrdc2 | 0.695390378 | 0 | 4.755554146 | 1.826114546 | 0 | 0 |
| 5031439G07Rik | 1.776317917 | 2.839685509 | 4.415639698 | 1.093536932 | 1.454649078 | 0.814423888 |
| Dixdc1 | 2.664623881 | 0.960231624 | 5.35223974 | 0.998126364 | 2.349879346 | 3.105222834 |
| Ephb1 | 0 | 0 | 4.726460221 | 1.431524284 | 1.417811025 | 1.312634773 |
| Ubxn1 | 1.432249659 | 5.660358732 | 5.454891409 | 1.773861333 | 0 | 1.08718276 |
| Pgm2l1 | 1.145590525 | 0 | 5.572216037 | 1.915870002 | 4.058010114 | 2.076956351 |
| Cpm | 0.685515907 | 0.780849651 | 4.715840447 | 0.612759376 | 1.234248723 | 0.52947271 |
| Dmpk | 2.155052629 | 0 | 5.158324295 | 1.679592228 | 0 | 1.697151304 |
| Chn2 | 1.68911894 | 1.661924662 | 4.860610962 | 0.508733539 | 1.146323566 | 0 |
| Gpt | 0.59870809 | 0 | 4.90235297 | 1.850700269 | 0 | 1.287204953 |
| Rcan2 | 2.317961936 | 0 | 5.060746263 | 1.580295089 | 0.954734275 | 0.904592061 |
| Usp30 | 1.30496883 | 0 | 4.285525591 | 0.404296133 | 1.264997904 | 0.604983377 |
| 4933400F21Rik | 1.673580304 | 0 | 3.969910444 | 0 | 0 | 1.294540972 |
| Trim59 | 1.398966838 | 0 | 3.963389572 | 0.140034917 | 1.091716273 | 0.893698951 |
| Bcas1 | 6.099920153 | 0 | 5.021471538 | 0.920679787 | 0 | 0.697517286 |
| Pak7 | 1.552865177 | 0 | 4.467077147 | 0.377656245 | 2.07246233 | 1.350239613 |
| Adipor2 | 1.07182796 | 1.313536953 | 4.71162928 | 0.43406177 | 1.250487875 | 1.186012442 |
| Gstm7 | 0.640711798 | 0 | 4.368740133 | 0.510880733 | 0 | 1.307048959 |
| St18 | 0.391508014 | 1.641510472 | 4.614217561 | 1.368863266 | 3.89937908 | 2.659960484 |
| Elovl7 | 0.630726581 | 1.535917309 | 4.198220774 | 0.932292837 | 0 | 0.483675 |
| Inpp5j | 0.7436784 | 0 | 3.989032036 | 0.608670548 | 1.469122161 | 0.763713964 |
| Micall1 | 0.92785325 | 1.502498032 | 4.369233871 | 1.273211355 | 1.237491495 | 1.815470293 |
| Sec14l5 | 0 | 0 | 3.626725128 | 0.337287581 | 0 | 0 |
| Tm7sf3 | 2.267294984 | 0 | 5.320526283 | 2.408222331 | 1.682244456 | 1.585905474 |
| Spock1 | 1.222282459 | 0 | 4.674059335 | 1.319184352 | 0 | 1.914609429 |
| Tyro3 | 1.37246003 | 0.725952604 | 4.207388041 | 0.220746206 | 0 | 0 |
| Nrsn1 | 1.252975409 | 0 | 5.073595916 | 0.882159246 | 1.918991191 | 1.31936469 |
| Plcl1 | 0.581356053 | 1.477438235 | 3.885070352 | 0.83275498 | 1.247120423 | 0.104373379 |
| Ankrd13a | 1.107321882 | 2.148974434 | 4.057884659 | 0.42881637 | 1.910542397 | 0.419817837 |
| Pls1 | 0.395523228 | 0 | 3.589984686 | 0.524685446 | 0 | 0 |
| Ablim2 | 1.398323686 | 1.837827915 | 5.331027336 | 1.203473165 | 1.982189167 | 3.383596362 |
| Thumpd1 | 0 | 0.990311155 | 3.915811158 | 0.524833936 | 0 | 0 |
| Mpp2 | 1.63540089 | 0 | 4.757882249 | 0.877006666 | 2.448933161 | 1.629322127 |
| S1pr1 | 0.505973575 | 0 | 0.637710246 | 7.333001643 | 0 | 0.894255238 |
| Gja1 | 0.748092342 | 0 | 0.634962395 | 8.843996326 | 0 | 1.966000203 |
| Ntsr2 | 2.804169427 | 0.98615935 | 0.545074664 | 8.97023452 | 0 | 1.112810355 |

TABLE 19-continued

| Gene names | Oligo progenitor cells | Microglia cells | Oligodendrocytes | Astrocytes | Epthelial cells | Non-glia cells |
|---|---|---|---|---|---|---|
| Sdc4 | 0.794704183 | 1.837527649 | 0 | 7.362343128 | 0.859988585 | 1.813473606 |
| Farp1 | 2.081729072 | 0.777042825 | 0 | 6.950264596 | 0 | 1.767775082 |
| Slc7a10 | 5.60292212 | 0 | 0 | 7.673977079 | 0 | 0.247924151 |
| Nwd1 | 3.442278133 | 1.124513913 | 1.039124534 | 7.757788898 | 2.011087276 | 1.895534128 |
| Fgfr3 | 1.852153761 | 0 | 0.451343831 | 8.134068542 | 1.341033038 | 2.778813781 |
| Mlc1 | 0 | 0 | 0.380586275 | 7.164953511 | 0.976466291 | 2.092521554 |
| Pla2g7 | 0.741899165 | 0 | 1.753141827 | 7.607985549 | 1.430373301 | 1.604597307 |
| Slc6a11 | 1.433139872 | 0 | 0.780242937 | 6.399012805 | 0.636511663 | 1.656722131 |
| Adrbk2 | 2.334136219 | 1.83757803 | 0.936643405 | 6.942446056 | 0 | 2.439785187 |
| Fam107a | 0 | 3.638964044 | 3.178706089 | 7.029777841 | 0 | 1.602480058 |
| Gjb6 | 1.322665087 | 0 | 0 | 7.058196095 | 0 | 2.116670484 |
| Mfge8 | 3.231252822 | 1.196261724 | 0 | 7.832976167 | 1.038955311 | 2.05988604 |
| Cyp2d22 | 0.514530007 | 0 | 0 | 6.086126071 | 0 | 1.638191149 |
| Sox9 | 0 | 0 | 0 | 5.791730371 | 0 | 2.579925142 |
| Prex2 | 0 | 0 | 0.48164374 | 5.199432608 | 1.663325881 | 1.778709626 |
| Pnpla7 | 0 | 5.272179828 | 3.095957323 | 6.932466794 | 0 | 0.713243212 |
| Lama2 | 0 | 0 | 2.299190207 | 5.674436263 | 1.381992893 | 1.568191955 |
| Vcl | 1.410988602 | 0 | 0.295818974 | 5.636133658 | 0 | 1.494875718 |
| Cbs | 0 | 0 | 0 | 5.71995663 | 0 | 0.858579737 |
| Ednrb | 3.990073621 | 0 | 0.314975659 | 6.214615414 | 0.738566834 | 1.388191804 |
| C4b | 0.652066637 | 0 | 0.752211597 | 6.216316306 | 0 | 0.896073997 |
| Scara3 | 0 | 0 | 0 | 5.994306206 | 0 | 1.060963003 |
| Mertk | 2.384602713 | 6.391602763 | 0 | 6.413416912 | 1.841389656 | 0.726413321 |
| Lcat | 2.882921588 | 0 | 0.343503263 | 6.216494966 | 0 | 0.772020464 |
| Rorb | 0.932117566 | 0 | 0 | 4.921340884 | 1.596997836 | 0.501940375 |
| Prodh | 0.958533486 | 0.845327689 | 0 | 5.994505402 | 1.948649801 | 1.422445413 |
| Igdcc4 | 1.578016876 | 0 | 0 | 5.170404246 | 0 | 1.688909359 |
| Tril | 5.247615886 | 0.929672283 | 0 | 5.993471239 | 0 | 0.499748238 |
| Mt2 | 0.608061158 | 0 | 0.993629445 | 6.202580381 | 0 | 2.070808258 |
| Slc39a12 | 0 | 1.009494581 | 0 | 5.305813273 | 1.048047852 | 1.161157322 |
| Arhgef26 | 1.370342471 | 0 | 1.428663897 | 5.562742086 | 1.397008421 | 1.937115774 |
| Fam20a | 0.687752845 | 1.44551448 | 0 | 5.054562508 | 0 | 0 |
| Gfap | 1.226650688 | 0 | 1.755387197 | 6.558419521 | 0.999585163 | 1.478063727 |
| Acsbg1 | 0 | 0 | 1.069734352 | 5.642274674 | 3.237710145 | 0 |
| Pbxip1 | 0 | 3.890156524 | 0 | 5.558431976 | 0 | 1.790695055 |
| Atp13a4 | 1.273608059 | 0 | 0 | 5.051032675 | 1.338611732 | 0 |
| Paqr8 | 0 | 0 | 1.403069141 | 5.125551394 | 1.242974914 | 0.491233969 |
| Slco1c1 | 0 | 0 | 0 | 4.731030474 | 0 | 0 |
| F3 | 2.608151865 | 0 | 0 | 6.232754598 | 1.562320856 | 2.19644716 |
| Cldn10 | 1.34115996 | 0 | 0.554702114 | 5.676930799 | 0 | 0.980164543 |
| Entpd2 | 0 | 0 | 0 | 4.906576563 | 0 | 0 |
| Fam213a | 0.773005644 | 0 | 0.69528722 | 5.769246269 | 0 | 2.512996588 |
| Pdgfrb | 0.441663599 | 0 | 0 | 4.047084894 | 0 | 0.98068142 |
| Slc15a2 | 0.682739959 | 1.613216865 | 1.957649583 | 5.122609486 | 0 | 0.945011706 |
| Fgd6 | 0 | 0.708728688 | 0.856927112 | 4.025870204 | 1.023079681 | 1.03106854 |
| Grin2c | 0 | 0 | 0 | 4.591312138 | 0 | 0.282638672 |
| Cxcl14 | 1.18700291 | 0 | 0 | 4.638711827 | 0 | 1.209173926 |
| Acss1 | 2.491584755 | 0 | 0.645875715 | 5.032059762 | 1.555054222 | 0.978422483 |
| Tmem47 | 0.972961059 | 0 | 0.513590903 | 5.921609631 | 2.137168746 | 4.053924843 |
| Gm13872 | 0 | 0 | 0 | 4.358374794 | 0 | 0.3412992 |
| Rmst | 0 | 0 | 0.406291255 | 4.390438735 | 0 | 1.390600511 |
| Gpc5 | 4.844686606 | 0 | 1.403675445 | 5.850620307 | 1.239981296 | 1.039125978 |
| Ptplb | 0.491584255 | 0 | 1.307217725 | 4.794688434 | 0 | 2.789712454 |
| Psd2 | 0.456734201 | 0.986621364 | 0 | 4.421348195 | 0.674966694 | 0.946022609 |
| Grm3 | 0.742605566 | 0 | 5.184635717 | 5.40781243 | 0 | 0 |
| Agt | 0.784700911 | 0 | 0 | 4.60286853 | 1.335361883 | 0 |
| Cyp2j9 | 4.020927549 | 0 | 0.466626855 | 5.085613409 | 0 | 1.252523295 |
| Phka1 | 2.13802323 | 0.902176091 | 1.15410382 | 5.546097631 | 1.48089929 | 1.847897682 |
| Lrig1 | 1.23424866 | 0 | 0.396244315 | 3.795282868 | 0 | 0.591703454 |
| Thrsp | 0 | 0 | 0.5277011 | 5.133160457 | 0 | 2.409229172 |
| Cyp4f15 | 0.381377434 | 0 | 0.408078316 | 4.334321324 | 0.960038214 | 0.395108841 |
| Phkg1 | 0 | 0 | 0 | 3.532188263 | 0 | 0.505105014 |
| Gramd3 | 0.368017523 | 0 | 0.837448089 | 3.797948929 | 0 | 0.709133693 |
| Lgi4 | 0.296800996 | 0 | 0 | 3.605531697 | 0 | 0.797281806 |
| Sema4b | 0.96746538 | 1.151381294 | 0 | 5.326948533 | 1.551206831 | 3.719952202 |
| Dio2 | 0.544448722 | 0 | 0.444568403 | 3.614380677 | 1.376572646 | 0 |
| Acot11 | 0 | 0 | 0.46792946 | 4.355151417 | 1.984608965 | 1.982610669 |
| Tenm3 | 2.096431638 | 0 | 1.855719789 | 5.183532035 | 0 | 2.219161815 |
| Utp14b | 1.559488565 | 1.515906514 | 0.445859201 | 4.192795029 | 0 | 0 |
| Aifm3 | 0 | 0.958619262 | 0.41296235 | 5.161643071 | 3.398012827 | 2.165883357 |
| Aldh1l1 | 0 | 0 | 0 | 3.592529062 | 0 | 0.639630067 |
| Acat3 | 0.568531813 | 1.176334752 | 0 | 3.507808126 | 0 | 0 |
| Bmpr1b | 0 | 0 | 0 | 3.050792442 | 0 | 0 |
| Slc1a4 | 0.619413508 | 0.695012194 | 0 | 4.35575166 | 0.632162385 | 1.449399498 |
| Arhgef19 | 0 | 0 | 0.322664238 | 4.030003865 | 0 | 1.405731663 |
| Myo10 | 1.786857198 | 0 | 0.484047114 | 4.716599187 | 0 | 1.565721076 |
| Daam2 | 0 | 0 | 4.875165808 | 5.341537216 | 1.242580604 | 0.832269576 |
| Gpam | 0.577339963 | 0 | 0.235655539 | 3.45430138 | 0 | 0.398743513 |

TABLE 19-continued

| Gene names | Oligo progenitor cells | Microglia cells | Oligodendrocytes | Astrocytes | Epthelial cells | Non-glia cells |
|---|---|---|---|---|---|---|
| Id3 | 0 | 0 | 0 | 4.730525995 | 0 | 1.696902122 |
| Prkd1 | 0 | 0 | 0.369226038 | 3.089374979 | 0 | 0.698908101 |
| Dbx2 | 1.899607725 | 0 | 0 | 3.657590117 | 0 | 0.330575039 |
| Etnppl | 0 | 0.975572626 | 0 | 4.188944178 | 0 | 0.506823462 |
| Gli2 | 0 | 0 | 0.911936697 | 3.270680241 | 0 | 0.486852014 |
| Paqr6 | 0 | 0 | 0.581951509 | 4.144484282 | 0 | 1.043107669 |
| Lfng | 0.388083454 | 0.761799727 | 0 | 3.234053852 | 0 | 0 |
| Mapk4 | 0 | 0 | 1.031203705 | 4.046364936 | 1.924364174 | 0.883201399 |
| 4930480K15Rik | 3.185265917 | 0 | 0 | 4.44583328 | 0 | 1.627541645 |
| Hif3a | 1.869161439 | 0 | 2.717824457 | 4.497590179 | 1.591561024 | 1.317663424 |
| Oplah | 1.380986568 | 0 | 1.53702199 | 5.014703622 | 0 | 2.687984896 |
| Spry2 | 3.485100682 | 0 | 3.008689359 | 4.998707746 | 0 | 0.368982112 |
| Paqr7 | 0.699024765 | 0 | 1.613287897 | 4.403464301 | 3.18233617 | 0.776662514 |
| Chst2 | 2.395469083 | 0.798037781 | 2.707245514 | 5.135732779 | 1.997551486 | 1.26175777 |
| Prdm16 | 0 | 1.435797032 | 0.543041361 | 3.888555448 | 0 | 1.526762989 |
| Ngef | 0.597831203 | 0 | 0 | 4.337685722 | 4.794853864 | 1.048023143 |
| Aldh7a1 | 2.276220302 | 0 | 1.100852285 | 4.096925335 | 1.180597347 | 0.272285815 |
| Rfx4 | 1.956836998 | 0 | 0 | 4.01913406 | 1.095761994 | 1.062211559 |
| Aqp4 | 1.956707094 | 0.628315212 | 0 | 4.281466545 | 0 | 0.984955794 |
| Csgalnact1 | 2.385473809 | 0 | 0 | 4.084324161 | 0.884369184 | 0.683873623 |
| Il18 | 2.587502739 | 2.840108251 | 1.444846211 | 5.288808603 | 0 | 1.70670264 |
| Slc13a3 | 0 | 1.491418461 | 0 | 3.514775332 | 1.020515107 | 1.072113645 |
| Fxyd1 | 0 | 1.481552456 | 0 | 3.851163928 | 0 | 1.591635201 |
| Drp2 | 0.836422045 | 0 | 0.313455951 | 3.629855941 | 1.366731887 | 0.9186862 |
| Cml3 | 2.100476373 | 0 | 0.751572197 | 4.032550961 | 2.822860375 | 0.847193877 |
| Msi1 | 0 | 0 | 0.777158206 | 3.243688682 | 0 | 1.381382232 |
| Mras | 1.518258084 | 1.328125443 | 0.479800127 | 4.181243822 | 3.738218989 | 0.716282476 |
| Arap2 | 0 | 0.820261365 | 3.841490712 | 4.499066258 | 0 | 1.062275769 |
| Slitrk2 | 2.318528934 | 0.599623329 | 0.604128507 | 3.461929913 | 0.983149952 | 0.190161057 |
| Pcdh10 | 1.560354562 | 0 | 1.214548446 | 3.56988803 | 0 | 0.797118868 |
| Klf15 | 2.64548752 | 0 | 3.160996344 | 4.610566041 | 0 | 0 |
| Anks1 | 0 | 1.068604587 | 1.024742783 | 3.696445035 | 0 | 1.988844133 |
| Zic2 | 0 | 0 | 0 | 2.71719845 | 0 | 1.281053835 |
| Ctso | 0.530463738 | 0 | 1.708813296 | 3.741461333 | 0 | 0.503492736 |
| Rgma | 0.455923159 | 0 | 1.624538669 | 2.910446068 | 0 | 0.217090617 |
| Rftn2 | 3.010579824 | 0.931044809 | 2.058190997 | 4.577570231 | 0 | 1.349640847 |
| Asrgl1 | 2.344316035 | 0.834354629 | 2.106518247 | 4.579352529 | 1.481077568 | 1.586950265 |
| Fndc4 | 2.090077002 | 0 | 2.038197376 | 4.83805305 | 0 | 2.069918765 |
| Snta1 | 0 | 1.414382052 | 0.605758577 | 3.564831794 | 2.095025842 | 0.622367479 |
| Ppargc1a | 0.70620437 | 1.088003672 | 0.306241026 | 3.628222634 | 0 | 2.145356368 |
| Slc41a1 | 0 | 0 | 1.294184091 | 4.221943585 | 0 | 2.836491993 |
| Axl | 3.22791351 | 3.883956018 | 0 | 4.089205861 | 0 | 0.343428396 |
| 2610203C20Rik | 1.02637386 | 0.954617187 | 1.895822011 | 4.739967359 | 1.787204833 | 2.78895229 |
| Atl2 | 0.49965267 | 0 | 0.528392141 | 3.366167334 | 2.459077577 | 1.192057805 |
| Glis3 | 0 | 0.991547781 | 0.745019817 | 3.599034636 | 3.600992013 | 0.95059004 |
| Nt5c2 | 2.28420115 | 0 | 1.811419829 | 4.454819238 | 0 | 2.573972264 |
| Rnf31 | 0 | 0 | 0.405359888 | 3.165212054 | 0 | 1.709249439 |
| Npas3 | 2.558123834 | 0 | 0.989745546 | 3.665883203 | 1.068195817 | 1.376656501 |
| Gna13 | 1.351272246 | 1.139498674 | 1.303144776 | 3.899724537 | 0 | 1.554532449 |
| 2310022B05Rik | 0 | 0 | 2.598849732 | 3.607359501 | 1.167976436 | 0.853101396 |
| Utrn | 1.806077372 | 0.828247546 | 0 | 3.706275183 | 1.213363878 | 2.159714176 |
| Trpm3 | 1.476250013 | 1.474369682 | 1.837386145 | 4.081586563 | 2.475547782 | 0.667580563 |
| Abhd3 | 1.977634968 | 2.571574378 | 1.634593827 | 4.512472275 | 0 | 1.732613859 |
| Fbxo2 | 1.158707514 | 0 | 2.002982083 | 3.765762345 | 0 | 0.889990938 |
| Hivep1 | 1.362571109 | 1.008438987 | 0.728217698 | 3.876443543 | 2.80536677 | 1.688314387 |
| Stk116 | 1.002253233 | 0 | 1.4036645 | 5.017220212 | 3.843126886 | 3.139967383 |
| Dclk2 | 3.458740787 | 0 | 0.452722962 | 4.242186669 | 0 | 1.276010502 |
| Lgr4 | 1.066140257 | 0 | 0.55675094 | 3.582105441 | 1.012428064 | 2.070731491 |
| Kank1 | 5.874930105 | 0 | 1.065172909 | 4.690879092 | 0 | 0.590192723 |
| B3galt2 | 0.699273462 | 0 | 1.250283327 | 3.344956454 | 1.237171021 | 1.047435878 |
| Zfp219 | 3.26503965 | 1.826204584 | 0 | 4.235901228 | 0 | 2.184581504 |
| Dbp | 2.369746302 | 0 | 0.404989896 | 3.713475333 | 0 | 2.018858882 |
| Hdac8 | 0.652428972 | 1.22212964 | 1.65525172 | 3.658084942 | 1.61374431 | 0.511439525 |
| Ap3m1 | 1.354793272 | 1.553089763 | 2.346171932 | 3.953015249 | 2.159653082 | 0.604173098 |
| Col11a2 | 4.761884307 | 0 | 1.45733758 | 4.212578757 | 0 | 0.28537135 |
| Aox1 | 0.870742887 | 1.564543094 | 0.715717678 | 3.773980048 | 1.167418255 | 3.185160266 |
| Trp53bp2 | 0 | 1.046940629 | 3.368846327 | 3.747258234 | 0 | 1.353925054 |
| Fbxo44 | 0.700146971 | 0 | 3.920174649 | 4.917470563 | 2.13894739 | 1.47981695 |
| Kcnt1 | 3.299737309 | 1.12348094 | 0.382401927 | 4.479071814 | 0 | 2.262458572 |
| Tmem164 | 1.409560004 | 0.914558423 | 0 | 3.844235401 | 3.553694158 | 2.111893162 |
| Vegfa | 3.631453696 | 0.991097274 | 0 | 3.659158235 | 0 | 1.464940309 |
| Efs | 4.368191732 | 0.888814566 | 0.375902143 | 3.853619538 | 0 | 0.821811978 |
| Tead1 | 1.132860038 | 1.458044565 | 0.791421259 | 4.28733079 | 1.023187786 | 3.523058862 |
| Aldh2 | 1.358754648 | 2.015868036 | 1.157432738 | 3.8335715 | 0 | 1.667178451 |
| Tmem44 | 1.618757118 | 2.702047131 | 0.291410871 | 3.799401325 | 0.549957903 | 1.736015688 |
| Igsf11 | 0.449794731 | 0 | 2.856577787 | 3.970834456 | 3.444609372 | 1.760374506 |
| Ptprt | 4.210559855 | 0 | 0.73813017 | 3.433335564 | 0 | 0.256923343 |
| Mro | 4.451138574 | 1.233573415 | 0 | 3.981421667 | 1.335369495 | 1.618933215 |

TABLE 19-continued

| Gene names | Oligo progenitor cells | Microglia cells | Oligodendrocytes | Astrocytes | Epthelial cells | Non-glia cells |
|---|---|---|---|---|---|---|
| Acadvl | 2.163731702 | 1.011606884 | 1.553977482 | 4.497384849 | 1.578206258 | 2.380339877 |
| Tspan9 | 0.750726726 | 0 | 1.21153368 | 3.218755463 | 0 | 1.73485947 |
| Eya1 | 2.22120397 | 0 | 0 | 3.10972308 | 2.380864959 | 1.252918464 |
| Rb1 | 1.895194885 | 0 | 2.006792866 | 3.824846403 | 0 | 1.818483794 |
| Lix1 | 1.187769965 | 1.998453403 | 0.534477233 | 3.489450475 | 1.371195217 | 1.365007463 |
| Prrx1 | 2.580894844 | 1.665290472 | 0.449833028 | 3.193233418 | 0.491086005 | 0.996737728 |
| Fam163b | 0.46944717 | 0 | 1.712611185 | 1.20860583 | 8.249903854 | 2.70042016 |
| Gm16223 | 1.246082948 | 1.245352896 | 0.480240579 | 0.669769287 | 4.440472326 | 2.377683208 |
| 2010300C02Rik | 1.439274099 | 0 | 1.736695587 | 1.613425439 | 7.192814718 | 1.888605325 |
| Airn | 1.217836679 | 1.26614811 | 1.56907863 | 2.010914452 | 4.528943804 | 2.310088939 |
| Lrrtm4 | 2.114479255 | 0 | 0.624543318 | 0.514298262 | 6.048625689 | 2.340793344 |
| Gm10364 | 1.116029682 | 2.116093999 | 1.16229709 | 0.407377421 | 4.767642122 | 2.809164095 |
| Gm10662 | 0 | 0 | 0.600627387 | 0.182959221 | 5.420684274 | 0.256498844 |

TABLE 20

Animal Information

Figure 3:
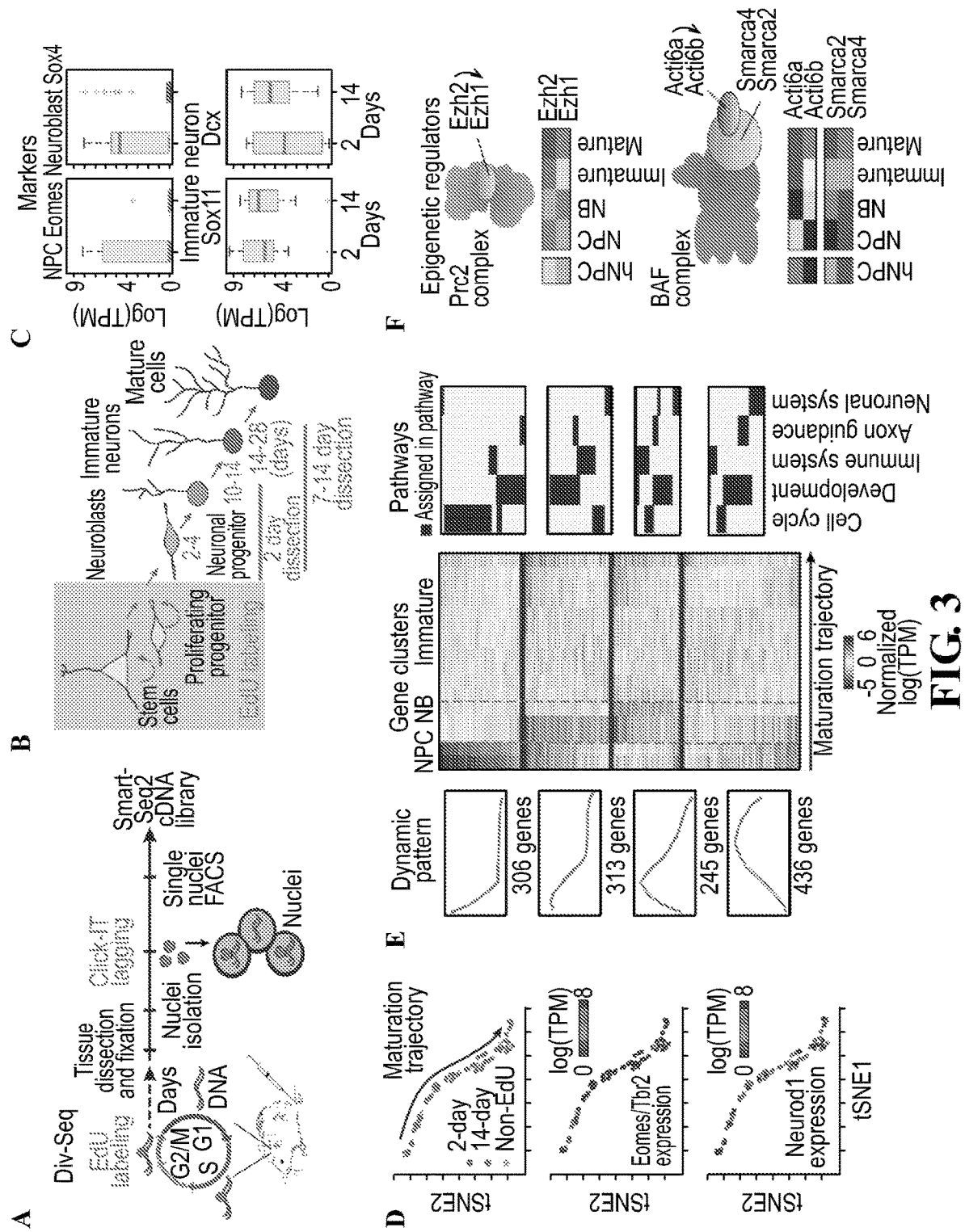
FIG. 3A-3F: Transcriptional dynamics of adult neurogenesis revealed by Div-Seq. (A) Schematics of Div-Seq method. EdU is injected to mice and incorporates into the DNA of dividing cells (8). After isolation, EdU labeled nuclei are fluorescently tagged and captured by FACS for single nuclei RNA-Seq. (B) Schematics of adult neurogenesis in the dentate gyrus(7). Timing of EdU labeling (tan box) and nuclei isolation are marked. (C) Div-Seq captured cells expressing known markers of neuronal precursors, neuroblasts and immature neurons. Box plots for the 2 days (2d) and 14 days (14d) EdU labeled nuclei (excluding nuclei classified as non-neuronal). Boxplots shown as in FIG. 2G. (D) Newborn cells form a continuous trajectory. All panels show 2-D embedding of 2d labeled nuclei, 14d labeled nuclei and nuclei from unbiased survey. Nuclei are colored by source (top), by Eomes/Tbr2 marker gene expression (middle), or by Neurod1 marker expression (bottom). Trajectory directionality is chosen by the position of the 2d labeled neurons and known marker genes. (E) Dynamic gene expression clusters. Four clusters are shown from top to bottom. Left: Running average expression level of the genes in each cluster over the nuclei ordered along the trajectory (as in D). Middle: a heatmap of running average expression of all genes along the trajectory. Red lines mark the transcriptional switches from neuronal precursor cell (NPC) to neuroblast (NB), and from NB to immature neuron. Right: proportions of genes assigned to five major biological pathways (F) Changes in the composition of the Polycomb Complex (Prc2, top) and the BAF (SWI/SNF) complex (bottom). For each complex, schematics of the complex is shown, and the heatmap of average expression of genes in NPC(NP), NB, immature neurons and mature granule DG cells, and compared to human NPCs (hNPC, absolute log (TPM)).

| Number of animals | Sex & strain | Brain regions | Age | Treatment | FIGS. | Assay |
|---|---|---|---|---|---|---|
| 4 | Male, C57BL/6 | DG, CA1, CA23 | 12-14 weeks | non | FIG. 1, 2 | RNA-seq |
| 2 | Male, C57BL/6 | DG | 12-14 weeks | Sacrificed 2 weeks post pAAV-hSyn-GFP-KASH injection | FIG. 1, 2 | RNA-seq |
| 2 | Male, VGAT-Cre | DG, CA123 | 12-16 weeks | Sacrificed 2 weeks post pAAV-EF1a-DIO-EYFP-WPRE-hGH-polyA | FIG. 1, 2 | RNA-seq |
| 2 | Male, C57BL/6 | DG, SC | 11 weeks | Sacrificed 1 week post EdU injection | FIG. 3, 4 | RNA-seq |
| 2 | Male, C57BL/6 | DG | 18 weeks | non | FIG. 1, 2 | RNA-seq |
| 2 | Male, C57BL/6 | DG | 4 weeks | non | Supplement | RNA-seq |
| 2 | Male, C57BL/6 | DG | 2 year | non | Supplement | RNA-seq |
| 4 | Male, C57BL/6 | DG, SC | 11 weeks | Sacrificed 1 week post EdU injection | FIG. 3, 4 | RNA-seq, FISH |
| 2 | Male, C57BL/6 | DG | 6 weeks | Sacrificed 2 days post EDU injection | FIG. 3 | RNA-seq |
| 2 | Male, C57BL/6 | DG | 6 weeks | Sacrificed 2 weeks post EDU injection | FIG. 3 | RNA-seq |
| 3 | Male, C57BL/6 | DG, SC | 8 weeks | Sacrificed 1 week post EdU injection | FIG. 3, 4 | RNA-seq |
| 3 | Male, C57BL/6 | DG, SC | 8 weeks | Sacrificed 2.5 days post EdU injection | FIG. 3, 4 | RNA-seq |
| 7 | Male, C57BL/6 | DG, SC, OB | 8 weeks | Sacrificed 6-7 days post EdU injection, injected 3 times with 12 hours intervals | FIG. 3,4 | RNA-seq, IHC |
| 5 | Male, C57BL/6 | DG, SC | 8 weeks | Sacrificed 5-6 days post EdU injection, injected 3 times with 12 hours intervals | FIG. 3, 4 | RNA-seq |
| 5 | Male, C57BL/6 | DG, SC | 8 weeks | Sacrificed 3-4 days post EdU injection, injected 3 times with 12 hours intervals | FIG. 3, 4 | RNA-seq |
| 9 | Male, C57BL/6 | DG, SC | 8 weeks | Sacrificed 1-2 days post EdU injection, injected 3 times with 12 hours intervals | FIG. 3, 4 | RNA-seq, IHC, FISH |
| 3 | Male, C57BL/6 | DG, SC | 11 weeks | Sacrificed 3-4 days post EdU injection, injected 3 times with 12 hours intervals | FIG. 3, 4 | RNA-seq |
| 2 | Male, C57BL/6 | DG | 8 weeks | Sacrificed 11-12 days post EdU injection, injected 3 times with 12 hours intervals | Supplement | FISH |

TABLE 21

| Mean-TPM-Immature | Mean-TPM-Mature | Mean-Percent-Immature | Mean-Percent-Mature | FDR-q-value |
|---|---|---|---|---|
| 3.63 | 4.04 | 23.19 | 11.99 | 6.05E−03 |
| 3.15 | 1.76 | 30.44 | 9.6 | 3.19E−05 |
| 3.44 | 6.69 | 35.62 | 76.01 | 2.65E−09 |
| 0.67 | 0.95 | 3.86 | 2.11 | 2.21E−01 |
| 5.92 | 4.02 | 87.3 | 44.04 | 1.07E−18 |
| 0.2 | 1.6 | 1.04 | 13.93 | 3.04E−13 |
| 0.25 | 0.94 | 1.56 | 6.3 | 1.61E−03 |
| 0.17 | 1.1 | 1.07 | 8.09 | 9.35E−07 |
| 0.04 | 0.6 | 0.02 | 3.45 | 7.21E−08 |
| 0.78 | 1.94 | 5.83 | 18.92 | 2.08E−05 |
| 0.38 | 0.43 | 1.46 | 2.93 | 1.55E−01 |
| 0.06 | 0.23 | 0.26 | 3.9 | 8.83E−04 |
| 0.46 | 0.81 | 6.83 | 11.52 | 1.47E−01 |
| 0.72 | 0.49 | 11.18 | 8.02 | 2.24E−01 |
| 1.02 | 2.03 | 18.72 | 36.32 | 4.39E−03 |
| 0.13 | 0.09 | 0.45 | 1.05 | 2.09E−01 |
| 2.27 | 1.21 | 41.03 | 17.51 | 8.31E−04 |
| 0.11 | 0.28 | 1.08 | 4.72 | 2.58E−02 |
| 0.09 | 0.03 | 1.49 | 0.57 | 2.66E−01 |
| 3.86 | 2.7 | 72.77 | 25.82 | 2.35E−12 |
| 1.08 | 3.58 | 13.93 | 58.85 | 4.93E−16 |
| 0.67 | 0.45 | 6.82 | 6.65 | 3.78E−01 |
| 0.09 | 0.47 | 1.31 | 6.34 | 9.94E−03 |
| 0.13 | 0.57 | 3.11 | 3.83 | 3.21E−01 |
| 1.24 | 0.72 | 18.36 | 7.92 | 1.76E−02 |
| 3.1 | 1.7 | 65.4 | 22 | 6.47E−10 |
| 0.44 | 2.88 | 3.98 | 27.86 | 2.43E−20 |
| 0.44 | 2.88 | 3.98 | 27.86 | 2.38E−20 |
| 5.03 | 3.36 | 59.6 | 32.75 | 2.28E−05 |
| 1.28 | 4.1 | 9.24 | 44.61 | 2.60E−17 |
| 0.16 | 0.22 | 0.57 | 3 | 2.06E−02 |
| 1.85 | 1.67 | 16.79 | 13.5 | 2.23E−01 |
| 3.76 | 2.58 | 85.9 | 51.37 | 2.89E−09 |
| 0.63 | 2.19 | 7.2 | 35.47 | 2.88E−11 |
| 0.08 | 0.14 | 0.87 | 1.85 | 2.02E−01 |
| 0.87 | 0.68 | 13.74 | 9.49 | 2.19E−01 |
| 0.32 | 0.45 | 4.71 | 5.6 | 3.20E−01 |
| 1.99 | 0.81 | 42.69 | 13.32 | 3.55E−05 |
| 0.29 | 0.18 | 3.06 | 3.56 | 3.40E−01 |
| 0.27 | 0.67 | 4.28 | 7.5 | 1.80E−01 |
| 1.02 | 2.19 | 15.13 | 39.38 | 2.21E−06 |
| 1.03 | 2.3 | 5.62 | 21.69 | 5.80E−08 |
| 6.4 | 4.89 | 91.34 | 65.08 | 7.62E−14 |
| 0.98 | 1.15 | 2.57 | 5.61 | 4.27E−02 |
| 0.08 | 0.09 | 0.46 | 0.31 | 3.30E−01 |
| 1.26 | 1.53 | 12.1 | 15.66 | 2.03E−01 |
| 0 | 0.06 | 0 | 0.44 | 7.24E−02 |
| 1.24 | 2.54 | 10.78 | 29.23 | 2.40E−05 |
| 0.65 | 0.5 | 5.54 | 5.23 | 3.69E−01 |
| 3.55 | 2.19 | 53.14 | 29.3 | 1.11E−03 |
| 0.49 | 0.63 | 4.64 | 4.93 | 3.66E−01 |
| 0.7 | 2.74 | 4.88 | 28.72 | 1.88E−11 |
| 0.08 | 0.05 | 0.07 | 0.44 | 1.67E−01 |
| 0.58 | 0.99 | 6.42 | 7.78 | 2.99E−01 |
| 0.52 | 0.31 | 7.62 | 2.74 | 1.43E−01 |
| 1.56 | 0.53 | 24.41 | 4.87 | 2.86E−03 |
| 1.35 | 3.19 | 22.12 | 41.72 | 3.11E−03 |
| 1.07 | 0.48 | 8 | 2.52 | 6.44E−02 |
| 1 | 0.21 | 7.27 | 0.71 | 4.00E−02 |
| 1.8 | 0.48 | 11.78 | 2.07 | 3.59E−03 |
| 1.17 | 0.25 | 7.83 | 1.4 | 2.64E−02 |
| 0.93 | 0.28 | 6.96 | 2.46 | 1.02E−01 |
| 1.27 | 0.49 | 7.53 | 2.53 | 6.39E−02 |
| 2.63 | 3.4 | 23.25 | 27.23 | 2.13E−01 |
| 3.07 | 4.41 | 27.36 | 57.29 | 1.42E−07 |
| 1.09 | 2.51 | 16.53 | 52.23 | 7.36E−09 |
| 3.24 | 1.46 | 73.13 | 29.06 | 2.94E−09 |
| 0.7 | 2.18 | 2.61 | 16.49 | 2.04E−12 |
| 7.21 | 5.72 | 97.39 | 83.51 | 2.05E−12 |
| 2.08 | 0.94 | 51.68 | 20.77 | 1.16E−05 |
| 0.39 | 0.35 | 4.35 | 5.84 | 2.70E−01 |
| 1.74 | 1.03 | 33.58 | 22.35 | 5.61E−02 |
| 0.55 | 1.54 | 6.95 | 27.65 | 1.31E−06 |
| 2.4 | 2.41 | 21.33 | 21.39 | 3.88E−01 |
| 3.38 | 2.2 | 51.9 | 31.89 | 5.63E−03 |
| 2.49 | 3.55 | 23.32 | 46.42 | 3.26E−05 |
| 0.21 | 2.31 | 0.59 | 17.71 | 3.81E−25 |
| 0.33 | 2.05 | 3.06 | 15.23 | 1.06E−07 |
| 4.14 | 2.79 | 84.28 | 23.4 | 4.06E−20 |
| 0.6 | 2.18 | 6.61 | 21.66 | 3.08E−05 |
| 0.16 | 2.1 | 0.29 | 20.53 | 7.15E−27 |
| 0.78 | 2.36 | 11.69 | 40.74 | 2.16E−07 |
| 0.14 | 0.11 | 3.21 | 1.76 | 2.63E−01 |
| 0.18 | 0.15 | 2.52 | 1.97 | 3.33E−01 |
| 0 | 0.05 | 0 | 0.49 | 1.26E−01 |
| 2.16 | 0.92 | 40.28 | 13.96 | 5.70E−04 |
| 0.06 | 0.15 | 0.92 | 1.9 | 2.15E−01 |
| 4.19 | 2.76 | 86.78 | 50.88 | 1.81E−13 |
| 1.01 | 2.27 | 12.54 | 38.51 | 2.07E−08 |
| 0 | 0.02 | 0 | 0.29 | 1.68E−01 |
| 0.1 | 0.16 | 0.68 | 2.14 | 9.95E−02 |

TABLE 22

Fabp7
Sox9
Ascl1
Insm1
Sox6
Notch1
Eomes
Tgfb2
Chd7
Sox5
Sox4
Neurod1
Neurod2
Sema3c
Igfbpl1
Sox11
Slc6a1
Dcx
Grin2b
Gad1
Bhlhe22

TABLE 23

Sox8
Sox10
Dip2a
Ncoa3
Smad7
Rorb
Id3
Sox9
Sox5
Sox6
Sox4
Eomes
Mndal
Bhlhe22
Ifi203
Sox11
Flna
Zeb1

TABLE 24

Notch1
Sox9/2

TABLE 24-continued

Fezf2
Pax3
Id3/4
Sox6
Chd7
Cdk2
Insm1
Eomes
Sox4
Neurod1
Neurod2
Bhlhe22
Chd5
Hdac7

TABLE 25

Sox2
Sox9
Sox5
Sox8
Sox6
Sox4
Cdk2
Cdk2ap1
Cdk9
Cdk12
Kif11
Kif21b
Kif17
Chd7
Kdm5c
Kdm7a
Hdac8
Kdm2b
Chd5
Hdac5
Hdac7
Chd1
Kdm3b

TABLE 26

Developmental Stage Specific Genes

Sox9
Rrm2
Gpr56
Draxin
Mfap4
Eomes
Sox4
Neurod1

TABLE 27

Gfap
Mt1
Aldoc
Clu
Aqp4
Mt2
Cst3
Slc1a2
Pbxip1
Fgfr3
Slc2a1
S1pr1
Id3
Fxyd1
Notch1
Sox9
Glul

TABLE 27-continued

Slc1a3
Sox2
Olig2
Aldh1l1
Prelp
Vim
Pax6
Reln
Gpr17
Tcf7l2
Nfib
Dbx2
Sox8
Sox5
Sox4
Emx1
Sox1
Sox6
Prox1
Dlx1
Foxg
Neurod1
Sox11
Slit1
Gad2
Grin2b
Dcx

REFERENCES AND NOTES

1. A. Zeisel et al., Science 347, 1138–1142 (2015).
2. J. Shin et al., Cell Stem Cell 17, 360–372 (2015).
3. B. Tasic et al., Nat. Neurosci. 19, 335–346 (2016).
4. G. L. Ming, H. Song, Neuron 70, 687–702 (2011).
5. D. L. Moore, G. A. Pilz, M. J. Aranzo-Bravo, Y. Barral, S. Jessberger, Science 349, 1334–1338 (2015).
6. Materials and methods are available as supplementary materials on Science Online.
7. B. Lacar et al., Nat. Commun. 7, 11022 (2016).
8. L. Swiech et al., Nat. Biotechnol. 33, 102–106 (2015).
9. H. Hu, J. Gan, P. Jonas, Science 345, 1255263 (2014).
10. E. S. Lein et al., Nature 445, 168–176 (2007).
11. Y. Zhang et al., J. Neurosci. 34, 11929–11947 (2014).
12. M. S. Cembrowski et al., Neuron 89, 351–368 (2016).
13. B. P. Roques, M. C. Fournie-Zaluski, M. Wurm, Nat. Rev. Drug Discov. 11, 292–310 (2012).
14. E. Llorens-Bobadilla et al., Cell Stem Cell 17, 329–340 (2015).
15. M. Schouten, M. R. Buijink, P. J. Lucassen, C. P. Fitzsimons, Front. Neurosci. 6, 25 (2012).
16. D. M. Feliciano, A. Bordey, L. Bonfanti, Cold Spring Harb. Perspect. Biol. 7, a018846 (2015).
17. P. J. Homer et al., J. Neurosci. 20, 2218–2228 (2000).
18. R. Shechter, Y. Ziv, M. Schwartz, Stem Cells 25, 2277–2282 (2007).
19. Z. Agoston et al., Development 141, 28–38 (2014).
20. C. A. Rottkamp, K. J. Lobur, C. L. Wladyka, A. K. Lucky, S. O'Gorman, Dev. Biol. 314, 23–39 (2008).
21. S. Picelli et al., Nat. Methods 10, 1096–1098 (2013).

Example 12

DroNc-seq to Understand Autism

Autism Spectrum Disorder (ASD) is a profound developmental disorder, which has risen dramatically in reported incidence (to ~2% in the US), presenting a compelling urgency for elucidating its underlying disease biology. ASD has been viewed primarily as a neurodevelopmental disorder, caused by a combination of genetic and environmental factors. Although a high rate of gastrointestinal (GI) perturbations is concomitant with ASD, it is only recently that the role of the GI tract has emerged as a modifier of behavior and brain physiology. For example, mimicking maternal viral infection in a rodent model, termed maternal immune activation, causes offspring to exhibit ASD-like behaviors and GI perturbations. Alteration of the microbiome in these offspring leads to an amelioration of abnormal behavior (Hsiao, E. Y. et al. Cell 155, 1451–1463 (2013)). The interactions by which GI physiology regulates brain function, known as the gut-brain axis (GBA), has yet to be elucidated.

Applicants aim to utilize single-cell genomics to gain an unbiased, high-throughput analysis of the myriad of cells comprising the colon and their perturbation in disease. Applicants developed single-nucleus sequencing (sNuc-Seq), a technology that allows for the characterization of single cells even within tissues that cannot be readily dissociated. sNuc-Seq can be applied to fresh and frozen tissues, including small clinical samples. More recently, Applicants modified Drop-Seq to accommodate nuclei, termed DroNc-seq, allowing for the rapid profiling of RNA content from thousands of nuclei (Habib, N. et al. Nature Methods 14, 955–958 (2017)). Here Applicants apply DroNc-seq to nuclei extracted from the mouse colon. Evaluation of the data reveals the major cell-types, including. secretory, absorptive and muscle. Applicants are now applying this technology to both healthy and diseased mouse and human tissue.

Results include the following: DroNc-seq allows for the rapid profiling of single cells from frozen mouse colon, DroNc-seq provides reproducible results across experiments and DroNc-seq identifies major colon cell types. FIG. 51 shows that DroNc-seq of nuclei from frozen mouse colon captures tissue complexity. The cells cluster by cell type and can be identified by expression of cell type specific markers.

The application of DroNc-seq to banked clinical samples is truly exciting in its potential to elucidate complex systems-wide diseases. Applicants are in the process of applying DroNc-seq to multiple clinical tissues and diseases. The goal is to understand which cell types are perturbed (e.g., differential gene expression, differential epigenetic marks) within individual tissues, and their systems-wide effects on disease progression. In particular, Applicants have a keen interest in ASD due to emerging evidence that the gut-brain axis is involved in the disease phenotype.

Example 13 sNucER-seq

Previously, Applicants developed single nucleus RNA sequencing (sNuc-seq) as a method to profile the expression of single cells. The outer membrane of the nucleus is continuous with the rough endoplasmic reticulum (RER). The RER is a site of RNA translation. Preserving a portion of it with the nucleus would improve RNA recovery and single cell expression profiling. Applicants conducted a screen to improve sNuc-seq (FIG. 52). The compositions of nuclei isolation solutions that worked best preserve a portion of the nuclear outer membrane/RER along with ribosomes as determined by electron microscopy. This method is referred to as single nucleus and rough endoplasmic reticulum (sNucER)-seq.

Screen summary: Applicants focused on the enteric nervous system, which represents a rare cell population in a complex tissue. Applicants used a double transgenic mouse which labels enteric nervous system nuclei with GFP and allows for FACS following nuclei isolation. Selected nuclei were processed using smart-seq2 and sequenced (FIG. 53 to 54).

Detergents: Applicants conducted a screen to optimize single nucleus RNA profiling of cells from tissues. Applicants tested a range of detergents that have previously been reported for nuclei extraction (Tween-20, Nonidet P-40/IGEPAL CA-630, Digitonin), and not reported (CHAPS). Applicants also compared a commercial nuclei extraction reagent (Nuclei EZ lysis buffer, SIGMA).

Based on the published literature it was not clear which concentrations of detergents would be optimal for nuclei extraction for sNuc-seq. Additionally, there was no data on CHAPS. Applicants chose to include CHAPS to increase detergent diversity. Tween-20, and Nonidet P-40/IGEPAL CA-630 are both non-ionic detergents. CHAPS is a zwitterionic detergent; as a note, CHAPS performed the best, and it is likely other zwitterionic detergents could do equally well.

Applicants chose the detergent concentrations based on the critical micelle concentration (CMC) for each detergent. Applicants then varied it either above or below the CMC.

Buffers: As part of the screen, Applicants also tested different buffers that have been used in the literature (Tris, Tricine, and HEPES). Although Tris performed the best, it is likely that the buffer choice is less critical than the detergents.

Salts: Applicants chose fixed salts concertation for the tests, although Applicants did try hypotonic solutions. The salts concentration was based on cellular concentrations of salts and what has been previously reported. Applicants used 146 mM NaCl, 1 mM $CaCl_2$), and 21 mM MgCl2. The NaCl concertation can likely be varied up to 300 mM, or completely eliminated, and replaced with another salt such as KCl (as has been done in various biochemistry preparations as needed). Similar, $CaCl_2$) can likely be replaced with other calcium containing salts and concentrations can be increased to 20 mM or more. The same is true for varying MgCl2 or adding in other salts.

Results: From the screen Applicants identified four compositions that worked the best for isolating enteric nervous system nuclei (appropriate cell types detected, high gene representation of expected cell types, most genes per cell, least background).

Applicants performed a further comparison among these four and compositions 2 and 3 (Table 4) performed the best. Applicants examined these nuclei preparations with electron microscopy and found that they preserved a portion of the outer nuclear envelope/RER with the nuclei. As a comparison, Applicants tested the commercial Nuclei EZ lysis buffer from Sigma, which did not preserve the nuclear envelope. Applicants are in the process of performing EM on preparations from the other 2 buffers. (see, FIGS. 55-62).

FIG. 55 shows that EZ lysis reagent does not preserve the outer nuclear envelope and RER.

CST with 0.49% CHAPS was the top extraction solution with the highest ENS score and lowest contamination. The nuclei have a nuclear membrane (not double membrane in all places), the membrane contiguous with RER and has ribosomes, and mitochondrial contamination was reduced.

Applicants found that the CST buffer has a lower intron/exon ratio compared to nuclei-only preps with EZ lysis reagent supporting more spliced RNA. The Intron/Exon ratio for each were as follows: CST=1.27904; EZ frozen=1.642955; and EZ chop=2.081659.

Additionally, Applicants confirmed that droplet based, DroNcER-seq works and that the isolated nuclei are compatible with the Chromium 10x single cell system. Additionally, Applicants are testing whether sNucER-seq works with other cell types and tissues. Preliminary data suggest the method is compatible with epithelial cells, brain cells, most cell types tested (immune, epithelial, vasculature, lyphatics, muscle, adipose, neuron, glia, muscle) and the 10x system.

Example 14. sNucER Facilitates Characterization of ENS

Figure 63A:
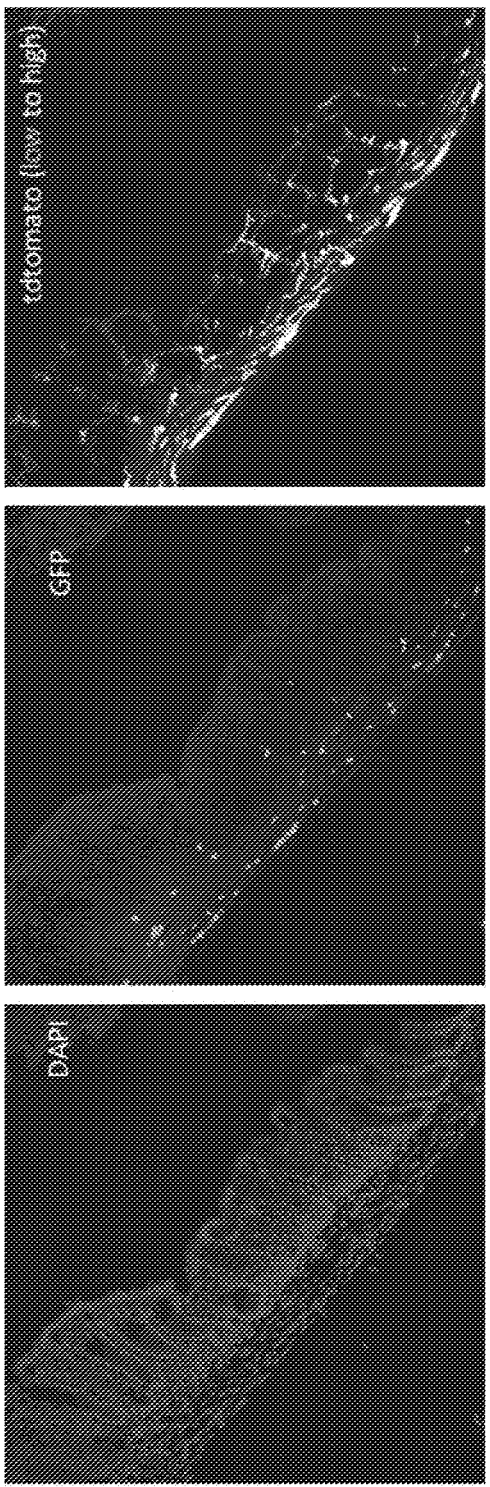
Figure 63B:
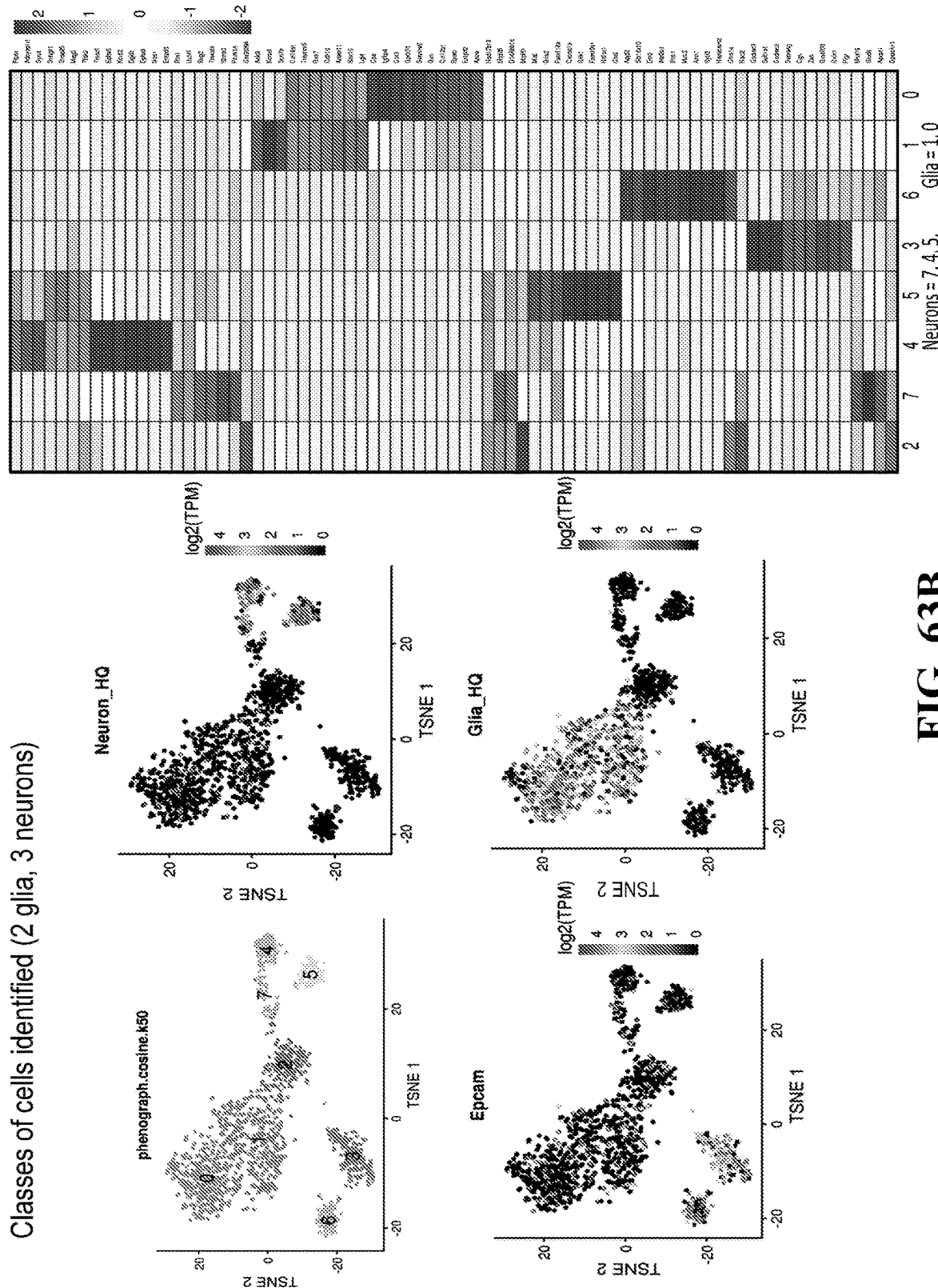

FIG. 63a shows histology of labelled cells. Triple transgenic mice were used only for histology (Sox10::Cre, Conditional Sun1-GFP, Conditional tdtomato). For sorting nuclei only a double-transgenic mouse is used. FIG. 63b shows classes of cells identified (2 glia, 3 neurons). FIG. 63c shows circadian oscillation in neurons and glia of ENS.

Example 15

Isolation of nuclei

All buffers were used to extract nuclei by chopping tissue with scissors for 10 minutes in the respective buffer. Subsequently, extracted nuclei were filtered through a 40 micron filter, and washed once. The compositions of the four buffers used are shown in Table 28. Reagents used to make buffers were procured from VWR, Sigma, and other vendors.

TABLE 28

Compositions of Buffers

| Buffer | Buffer Concentration | Detergent | Detergent Concentration (%) | Salt and Concentration | Additives and Concentration |
|---|---|---|---|---|---|
| Tris | 10 mM | NP40 | 0.2 | 146 mM NaCl, 1 mM CaCl$_2$, 21 mM MgCl$_2$ | |
| Tris | 10 mM | CHAPS | 0.49 | 146 mM NaCl, 1 mM CaCl$_2$, 21 mM MgCl$_2$ | |
| Tris | 10 mM | Tween-20 | 0.03 | 146 mM NaCl, 1 mM CaCl$_2$, 21 mM MgCl$_2$ | |
| Tricine | 20 mM | NP40 | 0.2 | 146 mM NaCl, 1 mM CaCl$_2$, 21 mM MgCl$_2$ | 0.15 mM spermine and 0.5 mM spermidine |

Figure 64B:
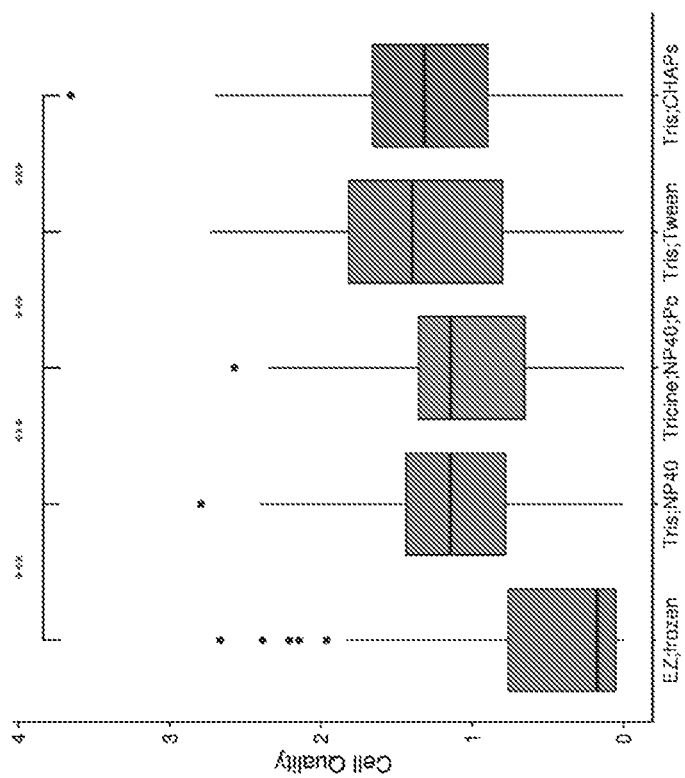
Figure 64A:
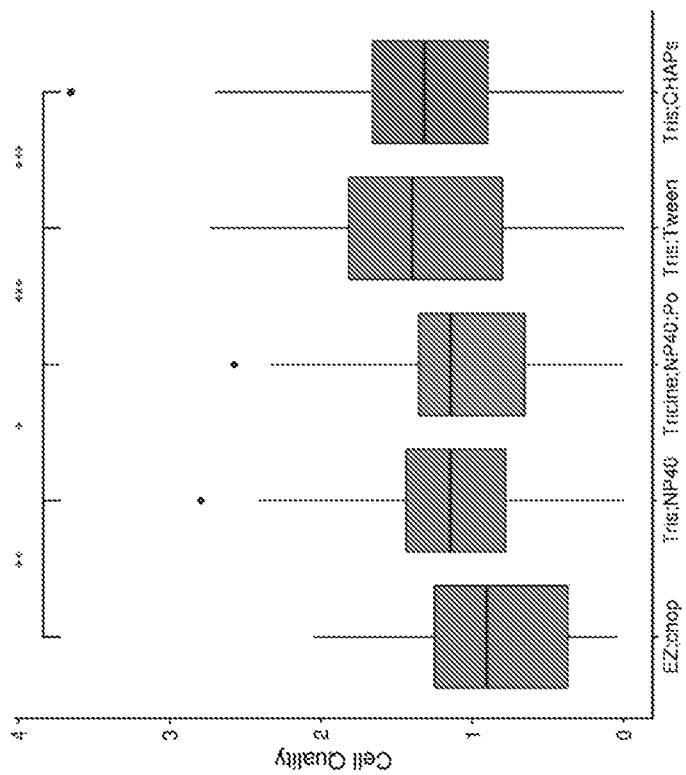

The buffers were compared to two different preparations of Sigma's EZ nuclei extraction reagent (FIGS. 64A and 64B). One preparation was EZ chop, which was generated by chopping tissue with scissors in accordance with the previously described protocol. The other, EZ frozen, entailed first fracturing the tissue in liquid nitrogen and then using a dounce. The cell quality score is defined by the average score of 'quality' expressed genes that were expected. Since all of the nuclei were sorted from the enteric nervous system, we used genes that are expected to be expressed in the neurons and glia of the enteric nervous system.

Experiments similar to those described above have been carried out in human samples.

Example 16. Freezing of Samples

Pieces of tissue should be small; ~100-200 mg, about 1 cm3, or half an almond. If tissue is limited, one can go as low as 25 mg. More than this is not needed for one preparation and smaller pieces are generally better because it is hard to cut larger pieces without freeze thawing and ruining the remainder of the tissue.

For a pilot experiment, 4 pieces are needed for 4 nuclei preparations.

Tissue should not be allowed to freeze in liquid. It is recommended to take tissue pieces from the petri dish/solution/etc and wiping it on the side of the container. It should then be placed on the side of a cryotube. If it sticks on the side of the tube then the tube can be closed and buried in dry ice. If it does not stick, but rather slides to the bottom, then it will likely end up in a pool of liquid and damage the tissue upon freezing. If it slides down, then the tissue should be removed and placed on the side of new cryotube. Also, tissue should not be patted dry as this may damage it.

Clear tubes should be used rather than colored tubes, so the tissue can be seen prior to processing.

Once the tissue is in a closed tube, the tube should be buried fully in dry ice and moved to −80° C. when possible for longer term storage.

Example 17. Protocol for Isolation of Nuclei from Tissues

All steps are performed on ice or at 4° C. Pre-cool all plates/tubes. Alternative buffer componant concentrations that deviate from the buffers below may be used. In certain embodiments, tricine may improve small molecule diffusion. Regarding buffering agents (e.g., Tris, Tricine, HEPES, PIPES) if a tissue is neutral pH then the buffer concentration may be close to zero (e.g. 1 mM). Regarding detergents, Applicants tested down to 0.0012 for tween-20. In certain embodiments, the concentration for detergents is between 0.001 or 0.0005%. In certain embodiments, detergent concentration is up to$_1$–2%. Regarding salts, the buffer may be adjusted down to 10 mM for NaCl, 0.1 mM for CaCl$_2$), and 1 mM for MgCl2. Regarding polyamines, the buffer may be adjusted down to 0.1 mM for both spermidine and spermine.

1. Place tissue (25 mg-300 mg) into 1 mL of either CST, NST, NSTnPo, or TST. Applicants use 1 well of a 6-well dish.
2. Manually disaggregate with sharp dissection scissors for 10 min.
3. Filter into 50 mL tube through 40 micron nylon cell strainer (Falcon 352340).
4. Wash well with 1 mL of CST, NST, NSTnPo, or TST and put through cell strainer.
5. Add 3 mL of ST to cell strainer.
6. Transfer 5 mL of nuclei extract to 15 mL tube.
7. Spin down at 500× g for 5 minutes.
8. Remove ALL supernatant.
9. Re-suspend in ST (50 uL-200 uL).
10. Filter into polystyrene tube with 35 uM nylon strainer cap (Falcon 352235).
11. Count nuclei and dilute as needed for 10x or FACS.

TABLE 29

Compositions of Buffers.

| Composition | Buffer | Buffer conc. | Detergent | Detergent concentration (%) | Salt conc. | Additives concentration |
|---|---|---|---|---|---|---|
| ST | Tris | 10 mM | | | 146 mM NaCl, 1 mM CaCl2, 21 mM MgCl2 | |
| CST | Tris | 10 mM | CHAPS | 0.49 | 146 mM NaCl, 1 mM CaCl2, 21 mM MgCl2 | 0.01% BSA |
| TST | Tris | 10 mM | Tween-20 | 0.03 | 146 mM NaCl, 1 mM CaCl2, 21 mM MgCl2 | 0.01% BSA |
| NSTnPo | Tricine | 20 mM | NP40 | 0.2 | 146 mM NaCl, 1 mM CaCl2, 21 mM MgCl2 | 0.15 mM spermine 0.5 mM spermidine 0.01% BSA |
| NST | Tris | 10 mM | NP40 | 0.2 | 146 mM NaCl, 1 mM CaCl2, 21 mM MgCl2 | 0.01% BSA |

Example 18

Quality Control for Samples analyzed. Table 30 shows the data for the human tissues analyzed in FIGS. 85-170. Shown are the tissue, subject buffer used, number of cells, mean reads per cell, median genes per cell and the number of clusters identified.

TABLE 30

| tissue | individual | buffer | Estimated Number of Cells | Mean Reads per Cell | Median Genes per Cell | Number of Clusters |
|---|---|---|---|---|---|---|
| breast | 1 | CST | 2747 | 18833 | 617 | 13 |
| breast | 1 | EZ | 2836 | 6801 | 1766 | 11 |
| breast | 1 | NST | 3947 | 16295 | 509 | 13 |
| breast | 1 | TST | 2666 | 18674 | 457 | 10 |
| esophagus_mucosa | 1 | CST | 4644 | 13669 | 878 | 17 |
| esophagus_mucosa | 2 | CST | 4342 | 13974 | 1007 | 16 |
| esophagus_mucosa | 3 | CST | 3991 | 14376 | 432 | 13 |
| esophagus_mucosa | 1 | EZ | 6171 | 8339 | 652 | 10 |
| esophagus_mucosa | 2 | EZ | 4471 | 7895 | 534 | 11 |
| esophagus_mucosa | 3 | EZ | 397 | 9157 | 286 | 4 |
| esophagus_mucosa | 1 | NST | 5172 | 9112 | 556 | 15 |
| esophagus_mucosa | 2 | NST | 2380 | 20428 | 764 | 13 |
| esophagus_mucosa | 3 | NST | 2303 | 17292 | 396 | 11 |
| esophagus_mucosa | 1 | TST | 3920 | 15982 | 1217 | 18 |
| esophagus_mucosa | 2 | TST | 2521 | 19685 | 728 | 15 |
| esophagus_mucosa | 3 | TST | 3349 | 16638 | 514 | 14 |
| esophagus_muscularis | 1 | CST | 4309 | 7440 | 649 | 14 |
| esophagus_muscularis | 2 | CST | 5234 | 6544 | 678 | 17 |
| esophagus_muscularis | 3 | CST | 9910 | 2758 | 588 | 19 |
| esophagus_muscularis | 1 | EZ | 1829 | 14215 | 568 | 7 |
| esophagus_muscularis | 2 | EZ | 1333 | 22095 | 539 | 8 |
| esophagus_muscularis | 3 | EZ | 4104 | 11775 | 529 | 12 |
| esophagus_muscularis | 1 | NST | 2862 | 15075 | 583 | 12 |
| esophagus_muscularis | 2 | NST | 5368 | 8297 | 702 | 19 |
| esophagus_muscularis | 3 | NST | 4887 | 6274 | 653 | 15 |
| esophagus_muscularis | 1 | TST | 4577 | 7424 | 659 | 15 |
| esophagus_muscularis | 2 | TST | 2411 | 20144 | 897 | 15 |
| esophagus_muscularis | 3 | TST | 1721 | 23880 | 1063 | 12 |
| heart | 1 | CST | 3425 | 11381 | 742 | 13 |
| heart | 2 | CST | 5075 | 7319 | 717 | 18 |

TABLE 30-continued

| tissue | individual | buffer | Estimated Number of Cells | Mean Reads per Cell | Median Genes per Cell | Number of Clusters |
|---|---|---|---|---|---|---|
| heart | 3 | CST | 4591 | 8724 | 809 | 14 |
| heart | 1 | EZ | 3436 | 20,315 | 647 | 11 |
| heart | 2 | EZ | 1974 | 16,648 | 853 | 8 |
| heart | 3 | EZ | 345 | 16,639 | 1654 | 4 |
| heart | 1 | NST | 4963 | 9586 | 617 | 14 |
| heart | 2 | NST | 4976 | 7140 | 681 | 16 |
| heart | 3 | NST | 4972 | 8314 | 855 | 16 |
| heart | 1 | TST | 4432 | 8203 | 628 | 12 |
| heart | 2 | TST | 4224 | 9670 | 809 | 14 |
| heart | 3 | TST | 3731 | 10115 | 987 | 15 |
| lung | 1 | CST | 4026 | 16613 | 1376 | 13 |
| lung | 2 | CST | 3169 | 11825 | 610 | 17 |
| lung | 3 | CST | 3936 | 11615 | 860 | 13 |
| lung | 1 | EZ | 4159 | 4718 | 467 | 13 |
| lung | 2 | EZ | 116 | 4046 | 279 | 2 |
| lung | 3 | EZ | 3195 | 9447 | 592 | 9 |
| lung | 1 | NST | 2659 | 23323 | 1045 | 8 |
| lung | 2 | NST | 2738 | 13540 | 625 | 13 |
| lung | 3 | NST | 4807 | 10073 | 944 | 14 |
| lung | 1 | TST | 3950 | 15517 | 1321 | 14 |
| lung | 2 | TST | 4704 | 8424 | 931 | 15 |
| lung | 3 | TST | 5023 | 9171 | 1196 | 14 |
| pancreas | 1 | CST | 613 | 6776 | 315 | 4 |
| pancreas | 1 | NSTnP0 | 1524 | 44509 | 692 | 9 |
| pancreas | 1 | TST | 3273 | 13515 | 454 | 8 |
| prostate | 1 | CST | 5015 | 8006 | 687 | 13 |
| prostate | 2 | CST | 763 | 13187 | 313 | 8 |
| prostate | 3 | CST | 4642 | 8154 | 823 | 16 |
| prostate | 4 | CST | 6082 | 8322 | 1007 | 16 |
| prostate | 1 | EZ | 568 | 12224 | 425 | 7 |
| prostate | 2 | EZ | 493 | 6083 | 322 | 4 |
| prostate | 3 | EZ | 3590 | 12504 | 678 | 10 |
| prostate | 1 | NST | 1908 | 20309 | 458 | 8 |
| prostate | 2 | NST | 1240 | 9417 | 345 | 8 |
| prostate | 3 | NST | 4660 | 7096 | 810 | 14 |
| prostate | 1 | TST | 4747 | 11773 | 786 | 12 |
| prostate | 2 | TST | 1844 | 7851 | 317 | 6 |
| prostate | 3 | TST | 4757 | 8472 | 927 | 15 |
| prostate | 4 | TST | 2298 | 17985 | 1275 | 14 |
| skeletal_muscle | 1 | CST | 3006 | 10493 | 802 | 11 |
| skeletal_muscle | 2 | CST | 2444 | 14182 | 749 | 12 |
| skeletal_muscle | 3 | CST | 3733 | 8152 | 599 | 14 |
| skeletal_muscle | 1 | EZ | 2207 | 16394 | 697 | 10 |
| skeletal_muscle | 2 | EZ | 1215 | 24851 | 703 | 8 |
| skeletal_muscle | 3 | EZ | 4011 | 4168 | 714 | 10 |
| skeletal_muscle | 1 | NST | 4816 | 6178 | 711 | 12 |
| skeletal_muscle | 2 | NST | 3940 | 9358 | 624 | 12 |
| skeletal_muscle | 3 | NST | 4256 | 6147 | 652 | 12 |
| skeletal_muscle | 1 | TST | 4569 | 6045 | 703 | 11 |
| skeletal_muscle | 2 | TST | 2326 | 19463 | 802 | 10 |
| skeletal_muscle | 3 | TST | 4718 | 5875 | 671 | 16 |
| skin | 1 | CST | 1062 | 11795 | 354 | 11 |
| skin | 1 | EZ | 1130 | 6519 | 308 | 11 |
| skin | 1 | NST | 1977 | 18625 | 441 | 14 |
| skin | 1 | TST | 2663 | 33711 | 755 | 15 |
| Colon_muscularis | | CST | Performed multiple times | | | |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of producing a temporally phased single-cell sequencing library comprising cells along a continuous trajectory of adult neurogenesis in the adult brain, the adult dorsal ganglion (DG) or in the adult spinal cord, said method comprising:
   (a) treating more than one population of neurogenic cells of heterogeneous cell types or subtypes, with a nucleoside analogue, wherein the neurogenic cell is selected from the group consisting of: a neuronal stem cell, a neuronal precursor cell, a neuroblast, an immature neuron and a newborn neuron, and wherein the nucleoside analogue is incorporated into replicating DNA and is configured for labeling with a detectable marker;
   (b) isolating a first population of neurogenic cells at one time point and isolating at least one other population of neurogenic cells at a later time point;
   (c) staining the nucleoside analogue incorporated into replicating DNA with the detectable marker within each population of neurogenic cells, wherein the replicating DNA is stained with the detectable marker;
   (d) sorting the stained and/or unstained neurogenic cells; and
   (e) sequencing the RNA from the sorted single neurogenic cells, whereby single cell gene expression data is obtained for neurogenic cells at different stages of neurogenesis.

2. A method of determining an expression profile for a neurogenic cell along a continuous trajectory of adult neurogenesis in the adult brain, the adult dorsal ganglion (DG) or in the adult spinal cord, said method comprising:
   (a) treating more than one population of neurogenic cells of heterogeneous cell types or subtypes, with a nucleoside analogue, wherein the neurogenic cell is selected from the group consisting of: a neuronal stem cell, a neuronal precursor cell, a neuroblast, an immature neuron and a newborn neuron, and wherein the nucleoside analogue is incorporated into replicating DNA and is configured for labeling with a detectable marker;
   (b) isolating a first population of neurogenic cells at one time point and isolating at least one other population of neurogenic cells at a later time point;
   (c) staining the nucleoside analogue incorporated into the replicating DNA with the detectable marker within each population of neurogenic cells, wherein the replicating DNA is stained with the detectable marker;
   (d) sorting the stained and/or unstained neurogenic cells;
   (e) sequencing the RNA from the sorted single neurogenic cells, whereby single cell gene expression data is obtained for neurogenic lineage cells at different stages of maturation; and
   (f) determining an expression profile for each identified cell or cell sub-type based on the gene expression data.

3. The method of claim 2, wherein the expression profile identifies the cell as an adult newborn neuron or immature neuron of the spinal cord and comprises: Gad1, Gad2, Pbx3, Meis2 and Runx1t1.

4. The method of claim 2, wherein the expression profile identifies the cell as a neuronal stem cell, a neuronal precursor cell, a neuroblast, an immature neuron or a newborn neuron and comprises at least one of: Fabp7, Ascl1, Insm1, Notch1, Eomes, Tgfb2, Chd7, Sox5, Sox4, Neurod1, Neurod2, Sema3c, Igfbpl1, Sox11, Slc6a1, Dcx, Grin2b, Gad1, Bhlhe22, Sox8, Sox10, Dip2a, Ncoa3, Rorb, ld3, Sox9, Mndal, Ifi203, Flna, Zeb1, Sox9/2, Fezf2, Pax3, ld3/4, Cdk2, Chd5, Hdac7, Sox2, Sox6, Cdk2ap1, Cdk9, Cdk12, Kif11, Kif21b, Kif17, Kdm5c, Kdm7a, Hdac8, Kdm2b, Hdac5, Chd1, Kdm3b, Rrm2, Gpr56, Draxin, Mfap4, Gfap, Mt1, Aldoc, Clu, Aqp4, Mt2, Cst3, Slc1a2, Pbxip1, Fgfr3, Slc2a1, Slpr1, Fxyd1, Glu1, Slc1a3, Olig2, Aldh1l1, Pre1p, Vim, Pax6, Re1n, Gpr17, Tcf712, Nfib, Dbx2,Emx1, Sox1, Prox1, Dlx1, Foxg1, Slit1, Gad2, Mbp, Meg3, Grm2, St3gal1, Cl13, Kcnc4, Cebpd, Cl12, Trpc6, Pter, Kif26b, Gsgl1, Igfbp5, Fam84a, Lrtm2, Ehd1, Gfra1, Calb1, Doc2b, Lct, Pde1b, Dockl0, Rasll0a, St18, Jun, Dbpht2, Pcdh8, Slc30a3, Mapk3, Sipall2, Gabrd, Sytl7, Stxbp6, Lingo2, Pde7b, Anp32a, Gprin1, Cacng3, Slc39a6, Limd2, Plekha2, Marcks, Rab40b, Npnt, Ppp1r1a, B4galt5, Chst15, Crlf 1, Dsp, Dgkh, Ntng1, Ankrd6, Trp53il1, Gng7, Hlf, Dek, Synpr, Gfod1, Pitpnm2, Ncdn, Gp1bb, Marcksl1, Gpc4, Cplx2, Plk5, Fam163b, Bdnf, Pcp4, Cbfa2t3, Ngef, Rilpl1, Nkain2, Arxes1, Lgi3, Atp2b4, Gfra2, Vav3, Lzts3, Fam3c, Zfpm2, Amer3, 6530402F18Rik, Rragd, Pkig, Acvr1c, Foxo1, Napep1d, Cecr2, Pde8b, Cedc85a, Rps23, Dlg3, Fnip2, Ptchd1, Prkd1, Smad3, Ncam2, Faml9a2, Dgat2, Ptbp3, Htr4, Slitrk2, Thsd7a, Clgtnf4, Lhfpl2, Tmem198, B3galt5, Ncald, Rp132, Rmnd5a, Cdh13, Cyp7bl, Rplpl, Sh3bgrl3, Foxo3, Diap2,Rps15, Sec1412, Spsb1, Btgl, Kcnip4, Nov, Pex51, Ldb2, Cadps2, Fibed1, Fxyd6, Hs6st3, Kcnk9, Cnih3, Lypd1, Mal2, Ramp1, Ankrd33b, A830036E02Rik, Amigo2, Acan, T112, Dock1 1, Krt12, Kcnk2, Ptpn5, Kalrn, Ntsr2, A630077J23Rik, Fat3, Rgsl4, Cacng5, 9130019P16Rik, Gprl2, Itga7, Igfbp4, Kcnv1, Car7, Gcnt4, 5430416009Rik, Serpinala, Drd1a, Map3k15, Zdhhc23, Zfp46, Drap1,Aphlb, ENSMUSG00000095041, Mehrl, Ntf3, Cel21a, Atxn7llos1,Npas4, Myolb, Tac1, Arhgap6, 4930578G10Rik, Lingo3, Sorcs2, Srm, Rara, Tmem154, Igdcc3, Tpsg1, Arap2, Hunk, Slco5a1, 1700024P16Rik, St8sia6, BC046251, Gml1417, 2610042L04Rik, Grip1os3, Kitl, Palm2, Ptplb, Blnk, Abcc4, Fgf5, Arhgef3, Nptx2, Cdh7, Asic2, Lrp12, Cd3d, Adcy 1, Kcnj4, Tiam2, Prdm8, F730043M19Rik, Lphn2, Bell1b, Sponl, Adamts9, Grik4, Car4, Cdh24, Gm20751, Cpne9, Shisa6, Slc22a4, Galnt3, Slco2a1, Efr3b, Homer3, Lnx1, Parp8, 3110047P20Rik, Bok, Tspan17, Eve, Socs2, Gm12296, Tbata, Nkd2, Mapkll, Rerg, 1700017B05Rik, Kent2, Scubel, Asl, Dpf3, Pvrl3, Clmp, 8430431K14Rik, Adamts14, Ptgs2, Traf3, P2rx7, Stac2, Rhebll, Nkain3, Hesl, Ankrd29, Smarcd3, Smoc2, Robo3, Fstl4, Cacnali, Slit2, Ak4, Tbcld1, Ppp4r4, Cpne7, Gukl, Slc26a4, E330009J07Rik, Sema3e, Zdhhe14, Nell1, Lingol, Cpne6, Wasfl, Lmo4, Unc5a, Zfp831, Ywhah, 4930447C04Rik, Cabp7, 1116, Trhde, Kiflc, Arhgef26, Tdrd5, 4921534H16Rik, Cables2, Cpne4, Rasal1, Rprm1, Sstr4, Rltpr, Gpr26, Prkab2, Lrtm1, Ryr3, Fam189a1, Khdrbs3, Hs3st4, Raly1, Golga7b, Specc1, Fam5b, Frmd6, Mdga1, Arc, Egr1, Pkp2, Neurod6, Ptpru, Mgat4c, Robo1, Ankrd27, Cnr1, Thsd4, Raver2, Myadm, Aff3, Cnnm4, Nr4a3, Slc9a1, Gnptab, 3110039M20Rik, Esyt2, Mrpl3, Rab26, Sv2b, Gml1201, Dkk3, Stat2, Pde1a, Cedc88c, Stom11, Ttc8, Actr3b, Map3k7, Gdpdl, Cep78, AI115009, Pip4k2c, Asap2, Msra, Pfkfb3, Kit, Dlx6os1, Grik1, Rbms3, Nxph1, Dlx1as, Dpp10, Grip2, Cntn5, Slc32a1, Coll9a1, Alk, Lhx6, A530058N18Rik, Kenmb2, Kcnip1, Foxred2, Ubash3b, Arx, Zmat4, Gm13629, Sema6c, Galntl6, Pnoc, Sgez, Unc5d, Cntnap4, Grin2d, Tm6sf1, Btbdl1, Arl4c, Pla2g4e, Usp13, Lrrtm3, Dner, Ankl, Rab3b, Adrala, Gabrg3, Hapln1, Hen3, Myol6, Fgf9, Tox2, Gm15881, Zfp57, Cit, Amy 1, Ptprt, Gpsm1, Usp29, Rcan2, Igsfl1, Zcchc12, Sema4g, AI504432, Dlcl, Ece2, E230016M11Rik, Olfm2, Gad1, Tbcld2b, Dpysl5, Spock3, Osbpl3, Impdhl, A230057D06Rik, Erbb4, Coro6, Ptprm, Trim62, Dlx6, Astn2, Plekhh2, Plxdc2, Dchs1, Fam124a, Fmn1, Frmd5, Slc35fl, A330076H08Rik, Rims3, Neb, BC030500, Fam20c, Bend6, Afap1, Nyap2, Hook2, Gria4, Atp8a2, Evl, Sen9a, Rcan3, Dnm3os, Camkl, Hdac9, Slc35e3, Pknox2, Garn13, B930041F14Rik, Ptpn4, Fnbp11, Fchsd2, Inha, Maf, Gm14204, Pam, Eps8, Scrt1, Kcna6, Lin7a, Capn2, Srgap1, Bend4, Grebl1, Pde9a, Hdac6, Cacna2d2, Lama2, Zcchc24, Htra1, Hepacam, Gpr3711, Ttyh1, Ppap2b, Kenj10, Slc6a11, Hif3a, Htr2c, Wdr86, Col9a3, Kcnj13, Ttr, Steap2, Tmem72, Pr1r, Slc4a5, Rbm47, Trpm3, Cab391, Whrn, Enpp2, Car14, Dock6, Lama5, Bad, Ki, Lbp, Eps812, Lrriq1, Psd2, Frem1, Rdh5, Fap, S1c6a20a, Slc2a12, Gmnc, Ppplr1b, F5, Atp2b3, Col4a5, S1c7a10, Mfrp, Carl2, Slc13a4, Ezr, Ccdc108, Sulf 1, Abhd2, Stk39, Ucp2, Dab2, Mitf, S1c6a20b, Col4a3, Prdml6, Otx2, Trpv4, Fras1, Efs, Lrrc23, 1110059M19Rik, Wdr78, Folr1, Ace, Fhad1, Mpp7, Zkscan3, Ccdc135, Vat11, Sh3d19, Spag16, Abca4, Arhgap42, Cpne2, S1c4a10, Slc4a2, Slc12a2, Spata17, Ppfibp2, Phldb2, Calml4, Msx1, Lmx1a, Dnahc6, Myo7a, Neat1, BC021767, Nhs12, Ccdc39, Clic6, Mroh7, Acad8, Col4a4, Ccdc114, Oca2, Dnah11, Stxbp4, Vwa3a, Arsg, Mycbpap, 4932438H23Rik, St6galnac2, Best3, Ifi27, Gm216, 5930403L14Rik, 4632427E13Rik, Cgnl1, Sostdc1, Zfpl85, Lefl, 1500015010Rik, Slcola4, Sned1, Pltp, Arl6ipl, Synm, Fam161a, Igf2, Sytl2, Six3os1, Nwd1, Slc16a8, Ifi2711, Pcolce2, Ccdc141, Kcne2, Dnahc2, Slc38a3, L3mbtl3, Cldn2, Aar2, Dnahc7b, Baiap2l1, Gm26648, Acacb, Gt(ROSA)26Sor, Sgk1, Ttc21a, Tuftl1, Otx2os1, Rfx2, Efcab1, Frrs1, Crb2, Epn3, Mospd1, Acaa2, Ctnnall, Sema3b, Tmem237, Elov17, Pcp411, Esrrb, Mapk4, Zfp280d, Cfap44, Wdr52, Gadd45g, Cldn1, Sgms1, Msx1as, Spag6, Lhb, Rilp, Ccdc24, Ifi35, 6720401G13Rik, Amer1, Zfp119a, Crhr2, Gm17200, Csrp2, Dmpk, Gm7173, Cnst, Ctnna1, Lepr, Intu, Antxr1, Atp10d, E530011L22Rik, Slc39a13, Ccnd3, Spata13, Igfbp2, Top3b, Ephx1, Cish, Vcam1, Tns1, Setd5, Tubb4b, 2010015L04Rik, Igfn1, Krt18, Slco1c1, Myo5c, Apls2, Arhgap28, Frmd4b, Efcab12, Dhrsl1, Tjp3, Spef2, Tinagl1, Tt151, Sgms2, Cf1ar, Stard13, ld1, 4930556M19Rik, Ssfa2, Iqub, Slc5a3, Plekhg3, Klhdc7a, Flcn, Fam86, Bcl211, Spag8, Parp4, Arid5b, Tc2n, Suv420h2, Kif9, Gpr98, Clqtnf5, Foxj1, Zic5, Sgk3, Cob111, Phactr2, Sorbs3, Steap1, Hya11, Armc2, Spint2, Aox1, Serh1, Tsix, Tektl, 1810022K09Rik, C030017K20Rik, Slc12a4, Cfap69, Rail4, Slc3lal, Nek5, Dnah2, Nqol, Col8a1, Tes, Scarf1, Pcbp3, Cd59a, Ccp110, Syne2, Pid1, 9530091C08Rik, Ptgds, D630024D03Rik, Prob 1, Histlh2br, Histlh2bq, Slc16a6, Slc16a2, Slc23a2, Strip2, Fam53b, Esrrg, Heg1, Pikfyve, Lamb2, Sowahc, Pex11a, Gm13139, Trip10, Slc19a1, Brwd3, Mast4, Mapk6, Tspan32os, Cgn, Tbcld9, Cpq, Heatr8, Msi1, Agtrap, Rfwd3, 9830147E19Rik, Shroom3, Slc39a12, Msi2, Col27a1, Mok, Rbbp8, Nckap5, 4930522L14Rik, Cspg4, Tnr, Pcdh15, Matn4, Vcan, Pdgfra, Dscam, Olig1, Hip1r, Ppfibp1, Grin3a, Neu4, Itga9, 3110035E14Rik, Slc1a1, Cacng4, Pllp, Cercam, Rgcc, Traf4, Ugdh, Elfn2, Cask, Cob1, Xylt1, Clq1, Cyth4, Hmha1, Inpp5d, Laptm5, Cd33, Csflr, Mpeg1, Abca9, Pag1, Cldn1 1, Mobp, Mag, Mal, Mog, Qdpr, Csrp1, Efnb3, Ttyh2, Epb4.113, Apod, Slc44a1, Kndc1, Gpr37, Tmeml51a, Cntn2, Itpk1, Car2, Cryab, Tspan2, Tnfaip6, Gm10471, Plekhh1, Gm7347, Hapln2, Arhgap23, Myrf, Arhgefl0, Ugt8a, Dip2a, Asphd1, 5031410I06Rik, Fa2h, Ndrgl, Stmn4, Jam3, Unc5b, Taldo1, Erbb2ip, Tmem63a, Ype12, Wdr54, Tprn, Gm21847, Ado, Kctdl3, Serinc5, Speer7-psl, Adamts4, Tppp3, Gm10220, Pik3c2b, Speer4a, Rcbtbl, Desil, Slain1, Pacs2, Pigz, Opalin, Grb14, Enodol, Scd1, Smad7, Litaf, Pip4k2a, Rtkn, Nkain1, Agpat4, Dusp26, Gjb1, Kctd3, Arrdc3, Dnajb2, Speer8-ps1, Evi2a, Speer4d, Slc6a9, Hid1, Rhob, Galnt6, Gjc2, 1133, Gnail, Mcam, 1700047M11Rik, Plin4, Speer4b, Lparl, Arrdc2, 5031439G07Rik, Dixdcl, Ephbl, Ubxn1, Pgm211, Cpm, Chn2, Gpt, Usp30, 4933400F21Rik, Trim59, Bcas1, Pak7, Adipor2, Gstm7, Inpp5j, Micall1, Sec1415, Tm7sf3, Spock1, Tyro3, Nrsn1, Plc11, Ankrdl3a, Pls1, Ablim2, Thumpd1, Mpp2, Slpr1, Gja1, Sdc4, Farp1, Mlc1, Pla2g7, Adrbk2, Fam107a, Gjb6, Mfge8, Cyp2d22, Sox9, Prex2, Pnpla7, Vcl, Cbs, Ednrb, C4b, Scara3, Mertk, Lcat, Prodh, Igdcc4, Tril, Fam20a, Acsbgl, Atp13a4, Paqr8, F3, Cldn10, Entpd2, Fam213a, Pdgfrb, Slc15a2, Fgd6, Grin2c, Cxc114, Acss1, Tmem47, Gm13872, Rmst, Gpc5, Grm3, Agt, Cyp2j9, Phka1, Lrig1, Thrsp, Cyp4f 15, Phkg1, Gramd3, Lgi4, Sema4b, Dio2, Acot11, Tenm3, Utp14b, Aifm3, Aldh111, Acat3, Bmpr1b, Slc1a4, Arhgefl9, Myol0, Daam2, Gpam, Etnppl, Gli2, Paqr6, Lfng, 4930480K15Rik, Op1ah, Spry2, Paqr7, Chst2, A1dh7a1, Rfx4, Csgalnact1, 1118, Slc13a3, Drp2, Cm13, Mras, Pcdh10, Klfl5, Anks1, Zic2, Ctso, Rgma, Rftn2, Asrgl1, Fndc4, Snta1, Ppargc1a, Slc41a1, Ax1, 2610203C20Rik, Atl2, Glis3, Nt5c2, Rnf31, Npas3, Gnal3, 2310022B05Rik, Utrn, Abhd3, Fbxo2, Hivep1, Stkl6, Dclk2, Lgr4, Kankl, B3galt2, Zfp219, Dbp, Ap3 ml, Coil a2, Trp53bp2, Fbxo44, Kcnt1, Tmem164, Vegfa, Tead1, Aldh2, Tmem44, Mro, Acadv1, Tspan9, Eya1, Rb1, Lix1, Prrx1, Gm16223, 2010300C02Rik, Airn, Lrrtm4, Gm10364, and Gm10662.

5. The method according to claim 1, wherein (b) further comprises isolating single nuclei from each of the isolated populations of neurogenic cells.

6. The method according to claim 2, wherein (b) further comprises isolating single nuclei from each of the isolated populations of cells.

7. The method according to claim 1, wherein neurogenesis occurs in the dorsal ganglion (DG) or in the adult spinal cord.

8. The method according to claim 1, wherein neurogenesis occurs in the dentate gyrus of the hippocampus.

9. The method according to claim 1, wherein neurogenesis occurs in the subventricular zone of the striatum of the adult brain.

10. The method according to claim 2, wherein neurogenesis occurs in the adult brain.

11. The method according to claim 2, wherein neurogenesis occurs in the dorsal ganglion (DG) or in the adult spinal cord.

12. The method according to claim 2, wherein neurogenesis occurs in the dentate gyrus of the hippocampus.

13. The method according to claim 2, wherein neurogenesis occurs in the subventricular zone of the striatum of the adult brain.

\* \* \* \* \*